United States Patent [19]

Levitt

[11] Patent Number: 5,017,214

[45] Date of Patent: May 21, 1991

[54] HERBICIDAL SULFONAMIDES

[76] Inventor: George Levitt, 3218 Romilly Rd., Wilmington, Del. 19810

[21] Appl. No.: 436,581

[22] Filed: Nov. 15, 1989

Related U.S. Application Data

[60] Division of Ser. No. 238,781, Aug. 31, 1988, Pat. No. 4,913,726, which is a division of Ser. No. 114,584, Oct. 30, 1987, Pat. No. 4,786,311, which is a continuation-in-part of Ser. No. 934,118, Nov. 24, 1986, Pat. No. 4,746,353, which is a continuation-in-part of Ser. No. 849,618, Apr. 11, 1986, abandoned, which is a continuation-in-part of Ser. No. 739,214, May 30, 1985, abandoned.

[51] Int. Cl.[5] .................. C07D 401/14; C07D 403/14; C07D 409/14; A01N 43/653

[52] U.S. Cl. .......................................... 71/92; 71/90; 544/130; 544/131; 544/139; 544/140; 544/132; 548/251; 548/253; 546/193; 546/194; 546/210; 546/211; 546/276; 546/278; 546/279

[58] Field of Search ...................... 71/90, 92; 548/251, 548/253; 546/193, 211, 279; 544/130, 140

[56] References Cited

U.S. PATENT DOCUMENTS

| | | | |
|---|---|---|---|
| 4,127,405 | 11/1978 | Levitt | 71/93 |
| 4,169,719 | 10/1979 | Levitt | 71/92 |
| 4,460,401 | 7/1984 | Sauers | 71/92 |
| 4,465,505 | 8/1984 | Wolf | 71/92 |
| 4,475,944 | 10/1984 | Rorer | 71/90 |
| 4,494,980 | 1/1985 | Shapiro | 71/92 |
| 4,511,392 | 4/1985 | Rorer | 71/90 |
| 4,602,936 | 7/1986 | Topfl et al. | 71/90 |
| 4,668,279 | 5/1987 | Rorer | 71/92 |
| 4,669,649 | 10/1987 | Rorer | 71/90 |
| 4,684,393 | 8/1987 | Shapiro | 71/90 |
| 4,705,558 | 11/1987 | Hartzell | 71/92 |

FOREIGN PATENT DOCUMENTS

| | | |
|---|---|---|
| 83975 | 7/1983 | European Pat. Off. . |
| 85476 | 8/1983 | European Pat. Off. . |
| 116518 | 8/1984 | European Pat. Off. . |
| 141777 | 5/1985 | European Pat. Off. . |
| 164268 | 12/1985 | European Pat. Off. . |
| 165753 | 12/1985 | European Pat. Off. . |
| 176304 | 4/1986 | European Pat. Off. . |
| 830441 | 7/1983 | South Africa . |
| 838416 | 5/1984 | South Africa . |
| 852646 | 10/1985 | South Africa . |

*Primary Examiner*—John M. Ford

[57] ABSTRACT

Tetrazole-substituted benzenesulfonamides are useful as agricultural chemicals and, in particular, as growth regulants and herbicides.

57 Claims, No Drawings

HERBICIDAL SULFONAMIDES

RELATED APPLICATIONS

This application is a division of application Ser. No. 238,781, filed on Aug. 31, 1988, now U.S. Pat. No. 4,913,726, which in turn is a division of application Ser. No. 114,584, filed on Oct. 30, 1987, now U.S. Pat. No. 4,786,311, which in turn is a continuation-in-part of copending application U.S. Ser. No. 934,118, filed Nov. 24, 1986, now U.S. Pat. No. 4,746,353, which in turn is a continuation-in-part of copending application U.S. Ser. No. 849,618, filed Apr. 11, 1986, now abandoned, which in turn is a continuation-in-part of copending application U.S. Ser. No. 739,214, filed May 30, 1985, now abandoned.

BACKGROUND OF THE INVENTION

This invention relates to tetrazole-substituted benzene sulfonamides which are useful as agricultural chemicals such as growth regulants and herbicides.

U.S. Pat. No. 4,127,405 and U.S. Pat. No. 4,169,719 disclose herbicidal benzenesulfonylureas.

EP-A-165,753, published Dec. 27, 1985, discloses herbicidal thiophenesulfonamides of formula

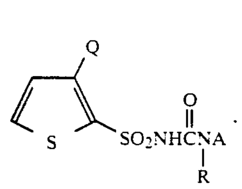

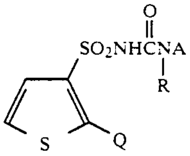

and

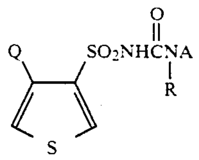

wherein

Q is optionally substituted phenyl or an optionally substituted saturated or unsaturated 5- or 6-membered heterocyclic ring containing one to three heteroatoms.

EP-A-83,975 (published July 20, 1983) discloses herbicidal benzenesulfonamides of formula

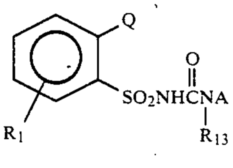

wherein

Q is selected from various five or six-membered aromatic or partially unsaturated heterocyclic rings containing 2 or 3 heteroatoms selected from O, S or NR.

EP-A-85,476 (published Aug. 10, 1983) discloses herbicidal benzenesulfonamides of formulae

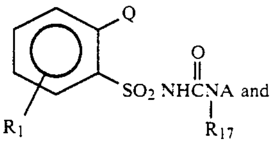

and

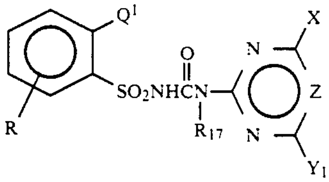

wherein

Q is selected from various 5-membered aromatic heterocycles, and their dihydro and tetrahydro analogs, which contain one heteroatom selected from O, S or NR, or Q is a saturated or partially unsaturated 6-membered ring containing one heteroatom selected from O or S; and $Q^1$ is a 6-membered aromatic heterocycle containing one to three N atoms.

South African Patent Application 83/8416 (published May 12, 1984) discloses herbicidal benzenesulfonamides of formula

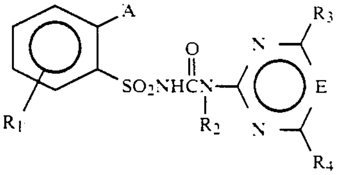

wherein

A is an unsaturated or only partially saturated 5- or 6-membered heterocyclic ring system which is bonded through a carbon atom and contains 1, 2 or 3 heteroatoms.

EP-A-116,518, published Aug. 22, 1984, discloses herbicidal sulfonamides of formula

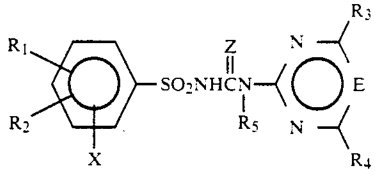

wherein

X is $NR_6R_7$, $N(SO_2R_9)_2$ or

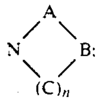

A is CO, $SO_2$, $CONR_{23}$ or $CO_2$;

B is $C_1$–$C_4$ alkyl or $C_2$–$C_4$ alkenyl; and

C is CO, $CR_{21}R_{22}$ or $SO_2$.

U.S. Pat. No. 4,475,944 discloses herbicidal sulfamates, possessing an ortho-heterocyclic ring, such as those of formula

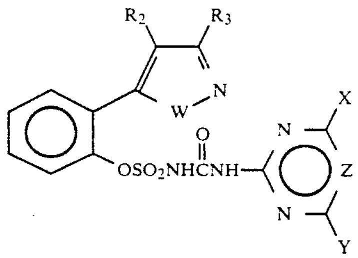

wherein

W is O, S or $NR_1$.

EP-A-164,268, published Dec. 11, 1985, discloses herbicidal benzylsulfonamides of formula

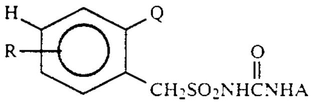

I wherein

Q is a saturated, 5- or 6-membered ring containing 1 to 2 heteroatoms selected from 0–2 S or 0–2 O or an unsaturated 5- or 6-membered ring containing 1 to 3 heteroatoms selected from 0–1 S, 0–1 O or 0–3 N and Q may optionally be substituted by one or more groups selected from $C_1$–$C_4$ alkyl, halogen, $C_1$–$C_3$ alkoxy, $C_1$–$C_3$ alkylthio, $C_1$–$C_2$ haloalkoxy, $C_3$–$C_4$ alkenylthio, $C_1$–$C_2$ haloalkylthio or $SCH_2CN$.

EP-A-165,753, published Dec. 27, 1985, discloses herbicidal pyridinesulfonamides of formula

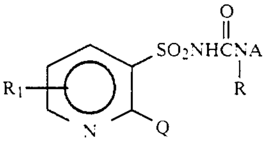

I and

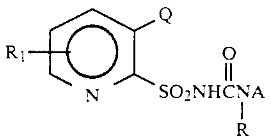

II wherein

Q is phenyl optionally substituted with Cl, $CH_3O$ or $CH_3$, a saturated 5-membered ring containing 1 heteroatom selected from O or S, or an unsaturated 5- or 6-membered ring containing 1 to 3 heteroatoms selected from 0–1 S, 0–1 O or 0–3 N and when Q is an unsaturated 5- or 6-membered ring, it may optionally be substituted by one or more groups selected from $C_1$–$C_4$ alkyl, halogen, $C_1$–$C_3$ alkoxy, $C_1$–$C_3$ alkylthio, $C_3$–$C_4$ alkenylthio, $C_1$–$C_2$ haloalkoxy or $C_1$–$C_{22}$ haloalkylthio.

EP-A-176,304, published Apr. 11, 1986, discloses herbicidal pyrazolesulfonamides such as those of formula

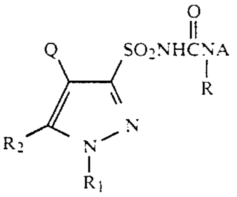

wherein

Q is a saturated 5- or 6-membered ring containing 1 heteroatom selected from 0–1 S or 0–1 O or an unsaturated 5- or 6-membered ring containing 1–3 heteroatoms selected from 0–1 S, 0–1 O or 0–3 N and Q may optionally be substituted by one or more groups selected from $C_1$–$C_4$ alkyl, $C_1$–$C_4$ haloalkyl, halogen, $C_1$–$C_3$ alkoxy, $C_1$–$C_3$ alkylthio, $C_3$–$C_4$ alkenylthio, $C_3$–$C_4$ alkenyloxy, $C_1$–$C_2$ haloalkoxy, $C_1$–$C_2$ haloalkylthio, $C_2$–$C_4$ cyanoalkylthio or $C_1$–$C_2$ alkoxycarbonylmethylthio.

EP-A-141,777, published May 15, 1985, discloses ortho-benzyl-substituted sulfonylureas of the formula

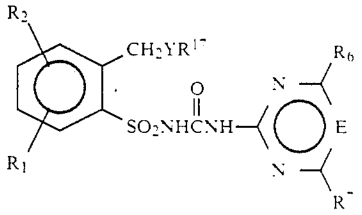

wherein

Y is O or S; and $R^{17}$ is a 5- to 6-membered unsaturated heterocyclic radical including

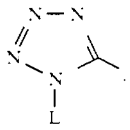

U.S. Pat. No. 4,602,936 carrying part of this disclosure, issued July 29, 1986.

South African Patent Application 83/0441, published July 25, 1983, discloses herbicidal benzenesulfonamides of formula

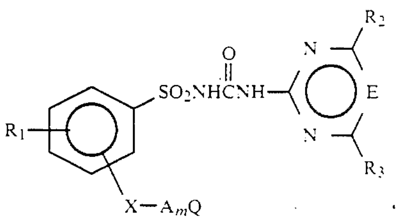

wherein $R_1$ is H, halogen, $NO_2$, $C_1$–$C_4$ alkyl, $C_1$–$C_4$ alkoxy, $C_2$–$C_5$ alkenyl or $C_1$–$C_4$ alkoxycarbonyl;

$R_2$ is $C_1$–$C_3$ alkyl or $C_1$–$C_3$ alkoxy, each unsubstituted or substituted by 1 to 3 halogen atoms;

$R_3$ is halogen, H, $NR_4R_5$, $C_1$–$C_3$ alkyl, unsubstituted or substituted by 1 to 3 alkoxy unsubstituted or substituted by methoxy, ethoxy, or 1 to 3 halogen atoms;

A is $C_1$–$C_4$ alkylene or $C_2$–$C_4$ alkenylene, each unsubstituted or substituted by $C_1$–$C_4$ alkyl;
m is 0 or 1;
E is N or CH;
X is oxygen, sulfur, SO or $SO_2$; and
Q is, in part, a 5- or 6-membered heterocyclic ring bound through carbon or nitrogen, such heterocycles including furan, pyrane, thiophene, triazole, pyridine, pyrroline, oxaxole, isoöxazole, thiazole, isothiazole, thiadiaxole, oxathiole, pyrrole, imidazole, pyrazole, pyrazine, pyrimidine, pyridazine, symmetrical and assymetrical triazines, oxdiazole, oxazine, furazane, pyridine-N-oxide, thiophene-S-oxide, benzthiophene, benzofuran, isobenzofuran, chromene, chromane, indole, isoindole, indazole, quinoline, isoquinoline, phthalazine, quinoxaline, quinazoline, quinoline, benzthiazole and benzimidiazole, and partially or completely hydrogenared and fused homoglogues thereof.

South African Patent Application 85/2646, published Oct. 11, 1985, discloses herbicidal benzenesulfonamides of formula

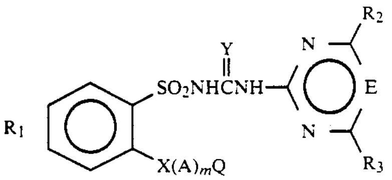

wherein
$R_1$ is H, halogen, $NO_2$, alkyl, alkoxy, alkoxycarbonyl or haloalkyl;
X is O, S, SO or $SO_2$;
Y is O or S;
E is CH or N;
$R_2$ and $R_3$ are independently alkyl, alkoxy or alkoxyalkyl;
A is alkylene or alkenylene;
m is 0 or 1;
Q is, in part,

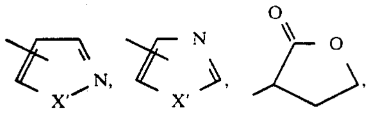

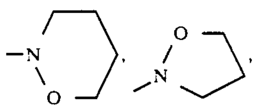

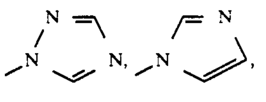

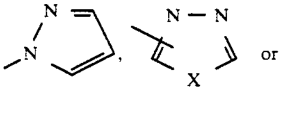

or

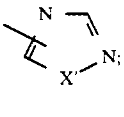

each of which is optionally substituted and/or optionally partially hydrogenated; and
X' is O, S or NR.

The presence of undesired vegetation causes substantial damage to useful crops, especially agricultural products that satisfy man's basic food needs, such as corn, soybeans, wheat and the like. The current population explosion and concomitant world food shortage demand improvements in the efficiency of producing these crops. Prevention or minimization of the loss of a portion of valuable crops by killing or inhibiting the growth of undesired vegetation is one way of improving this efficiency.

A wide variety of materials, useful for killing, or inhibiting (controlling) .he growth of undesired vegetation is available. Such materials are commonly referred to as herbicides. The need exists, however, for still more effective herbicides that destroy or retard weeds without causing signficant damage to useful crops.

SUMMARY OF THE INVENTION

This invention relates to novel compounds of Formula I, agriculturally suitable compositions containing them, and their method-of-use as preemergent or postemergent herbicides or as plant growth regulants.

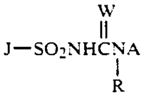

I wherein

J is

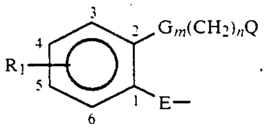

J-1

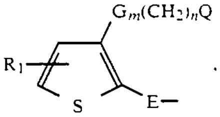

J-2

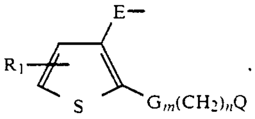

J-3

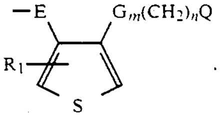

J-4

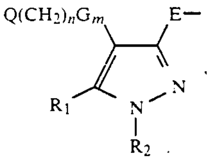

J-5

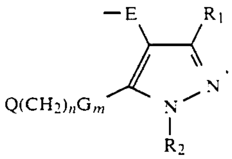

J-6

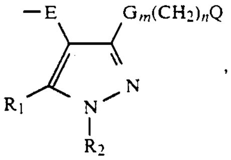

J-7

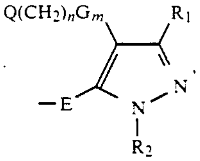

J-8

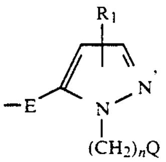

J-9

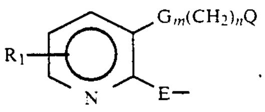

J-10

-continued

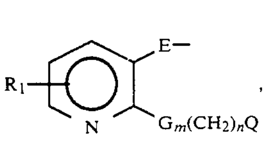

J-11

,

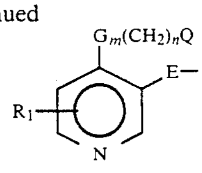

J-12 or

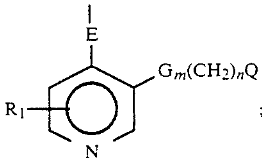

J-13

;

W is O, S or $NR_X$;
$R_X$ is H, OH, $C_1$–$C_3$ alkyl, $C_1$–$C_3$ alkoxy, allyloxy, propargyloxy, $C_1$–$C_3$ haloalkyl, $C_1$–$C_3$ haloalkoxy or $NR_YR_Z$;
$R_Y$ is H or $C_1$–$C_3$ alkyl;
$R_Z$ is $C_1$–$C_3$ alkyl;
G is O, S, SO or $SO_2$;
m is 0 or 1;
n is 0, 1 or 2;
R is H or $CH_3$;
E is a single bond, $CH_2$ or O;

Q is

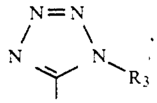

Q-1

,

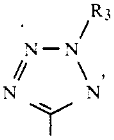

Q-2

,

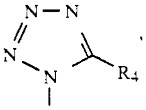

Q-3

,

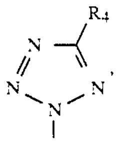

Q-4

,

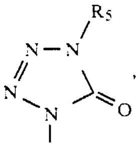

Q-5

,

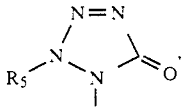

Q-6

,

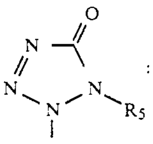

Q-7

;

$R_1$ is H, $C_1$–$C_3$ alkyl, $C_1$–$C_3$ haloalkyl, halogen, nitro, $C_1$–$C_3$ alkoxy, $SO_2NR_aR_b$, $C_1$–$C_3$ alkylthio, $C_1$–$C_3$ alkylsulfinyl, $C_1$–$C_3$ alkylsulfonyl, CN, SCN, $CO_2R_c$, $C_1$–$C_3$ haloalkoxy, $C_1$–$C_3$ haloalkylthio, amino, $C_1$–$C_3$ alkylamino, di($C_1$–$C_3$ alkyl)amino or $C_1$–$C_2$ alkyl substituted with $C_1$–$C_2$ alkoxy, $C_1$–$C_2$ haloalkoxy, $C_1$–$C_2$ alkylthio, $C_1$–$C_2$ haloalkylthio or CN;
$R_2$ is H, $C_1$–$C_3$ alkyl, allyl or phenyl;
$R_3$ is H, $C_1$–$C_6$ alkyl, $C_3$–$C_6$ cycloalkyl, $C_1$–$C_6$ haloalkyl, $CH_2$-($C_2$–$C_5$ alkenyl), $CH_2$($C_2$–$C_5$ haloalkenyl), $CH_2$($C_2$–$C_5$ alkynyl), $CH_2$($C_2$–$C_5$ haloalkynyl), $C_6H_5$ or $C_1$–$C_4$ alkyl substituted with $C_1$–$C_2$ alkoxy, $C_1$–$C_2$ alkylthio, $C_1$–$C_2$ alkylsulfinyl or $C_1$–$C_2$ alkylsulfonyl;
$R_4$ is H, halogen, $C_1$–$C_6$ alkyl, $C_3$–$C_6$ cycloalkyl, $C_1$–$C_6$ haloalkyl, $C_2$–$C_6$ alkenyl, $C_2$–$C_6$ haloalkenyl, $C_2$–$C_6$ alkynyl, $C_3$–$C_6$ haloalkynyl, $C_6H_5$, $C_1$–$C_4$ alkoxy, $C_1$–$C_4$ haloalkoxy, $C_1$–$C_4$ alkylthio, $C_1$–$C_4$ alkylsulfinyl, $C_1$–$C_{44}$ alkylsulfonyl, $OCH_2CH_2O$-($C_1$–$C_2$ alkyl) or di($C_1$–$C_3$ alkyl)amino;

$R_5$ is H, $C_1$–$C_3$ alkyl, $C_1$–$C_3$ haloalkyl, allyl or propargyl;
$R_a$ is H, $C_1$–$C_4$ alkyl, $C_2$–$C_3$ cyanoalkyl methoxy or ethoxy;
$R_b$ is H, $C_1$–$C_4$ alkyl or $C_3$–$C_4$ alkenyl; or
$R_a$ and $R_b$ may be taken together as $-(CH_2)_3-$, $-(CH_2)_4-$, $-(CH_2)_5-$ or $-CH_2CH_2OCH_2CH_2-$;
$R_c$ is $C_1$–$C_4$ alkyl, $C_3$–$C_4$ alkenyl, $C_3$–$C_4$ alkynyl, $C_2$–$C_4$ haloalkyl, $C_1$–$C_2$ cyanoalkyl, $C_5$–$C_6$ cycloalkyl, $C_4$–$C_7$ cycloalkylalkyl or $C_2$–$C_4$ alkoxyalkyl;

A is

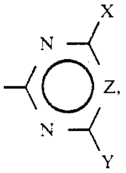

A-1

,

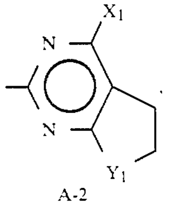

A-2

,

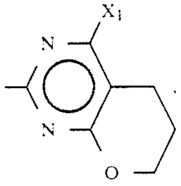

A-3

,

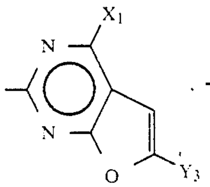

A-4

,

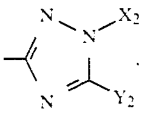

A-5

,

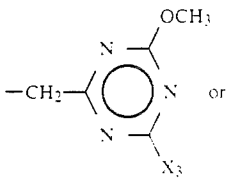

A-6 or

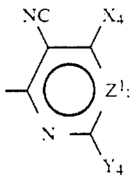

A-7

;

X is H, $C_1$–$C_4$ alkyl, $C_1$–$C_4$ alkoxy, $C_1$–$C_4$ haloalkoxy, $C_1$–$C_4$ haloalkyl, $C_1$–$C_4$ haloalkylthio, $C_1$–$C_4$ alkylthio, halogen, $C_2$–$C_5$ alkoxyalkyl, $C_2$–$C_5$ alkoxyalkoxy, amino, $C_1$–$C_3$ alkylamino, di($C_1$–$C_3$ alkyl)amino or $C_3$–$C_5$ cycloalkyl;
Y is H, $C_1$–$C_4$ alkyl, $C_1$–$C_4$ alkoxy, $C_1$–$C_4$ haloalkoxy, $C_1$–$C_4$ haloalkylthio, $C_1$–$C_4$ alkylthio, $C_2$–$C_5$ alkoxyalkyl, $C_2$–$C_5$ alkoxyalkoxy, amino, $C_1$–$C_3$ alkylamino, di($C_1$–$C_3$ alkyl)amino, $C_3$–$C_4$ alkenyloxy, $C_3$–$C_4$ alkynyloxy, $C_2$–$C_5$ alkylthio alkyl, $C_2$–$C_5$ alkylsulfinylalkyl, $C_2$–$C_5$ alkylsulfinylalkyl, $C_1$–$C_4$ haloalkyl, $C_2$–$C_4$ alkynyl, azido, cyano,

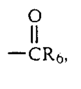

,

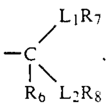

,

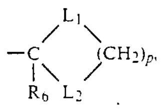

,

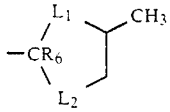

or $-N(OCH_3)CH_3$;

p is 2 or 3;
$L_1$ and $L_2$ are independently O or S;

$R_6$ is H or $CH_3$; $R_7$ and $R_8$ are independently $C_1$–$C_3$ alkyl;

Z is CH, N, $CCH_3$, $CC_2H_5$, CCl or CBr;

$Y_1$ is O or $CH_2$;

$X_1$ is $CH_3$, $OCH_3$, $OC_2H_5$ or $OCF_2H$;

$X_2$ is $CH_3$, $C_2H_5$ or $CH_2CF_3$;

$Y_2$ is $OCH_3$, $OC_2H_5$, $SCH_3$, $SC_2H_5$, $CH_3$ or $CH_2CH_3$;

$X_3$ is $CH_3$ or $OCH_3$;

$Y_3$ is H or $CH_3$;

$X_4$ is $CH_3$, $OCH_3$, $OC_2H_5$, $CH_2OCH_3$ or Cl;

$Y_4$ is $CH_3$, $OCH_3$, $OC_2H_5$ or Cl; and $Z^1$ is CH or N;

and their agriculturally suitable salts; provided that (a) when X is Cl, F, Br or I, then Z is CH and Y is $OCH_3$, $OC_2H_5$, $N(OCH_3)CH_3$, $NHCH_3$, $N(CH_3)_2$ or $OCF_2H$;

(b) when X or Y is $C_1$ haloalkoxy, then Z is CH;

(c) when J is J-9 and n is 0, then Q is Q-1 or Q-2;

(d) when E is 0, then J is J-1;

(e) when W is S, then A is A-1, R is H, and Y is $CH_3$, $OCH_3$, $OC_2H_5$, $CH_2OCH_3$, $C_2H_{54}$, $CF_3$, $SCH_3$, $OCH_2CH{=}CH_2$, $OCH_2C{\equiv}CH$, $OCH_2CH_2OCH_3$, $CH(OCH_3)_2$ or 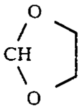 ;

(f) when the total number of carbon atoms in X and Y is greater than 4, then the carbon content of $R_1$, $R_3$, $R_4$ and $R_5$ must each be less than or equal to 2;

(g) $X_4$ and $Y_4$ cannot simultaneously be Cl;

(h) when J is J-1 and m is 0, then n is 0: and (i) when n is 0 and m is 1 then Q is Q-1 or Q-2.

In the above definitions, the term "alkyl" used either alone or in compound words such as "alkylthio" or "haloalkyl", denotes straight chain or branched alkyl, e.g., methyl, ethyl, n-propyl, isopropyl or the different butyl, pentyl or hexyl isomers.

Alkoxy denotes methoxy, ethoxy, n-propoxy, isopropoxy and the different butyl isomers.

Alkenyl denotes straight chain or branched alkenes, e.g., vinyl. 1-propenyl, 2-propenyl, 3-propenyl and the different butenyl, pentenyl or hexenyl isomers.

Alkynyl denotes straight chain or branched alkynes, e.g., ethynyl, 1-propynyl, 2-propynyl and the different butynyl, pentynyl and hexynyl isomers.

Alkylsulfonyl denotes methylsulfonyl, ethylsulfonyl or the different propylsulfonyl isomers.

Alkylthio, alkylsulfinyl, alkylamino, etc. are defined in an analogous manner.

Cycloalkyl denotes cyclopropyl, cyclobutyl, cyclopentyl and cyclohexyl.

The term "halogen", either alone or in compound words such as "haloalkyl", denotes fluorine, chlorine, bromine or iodine.

In terms such as $C_2$–$C_3$ alkylthioalkyl, the specified number of carbon atoms is meant to define the total number of carbon atoms in thaI substituent group. For example, $C_2$–$C_3$ alkylthioalkyl would designate $CH_2SCH_3$, $CH_2SC_2H_5$, $CH_2CH_2SCH_3$ or $CH(CH_3)SCH_3$, and $C_2$–$C_5$ alkoxyalkoxy would represent $OCH_2OCH_3$ through $O(CH_2)_4OCH_3$ or $OCH_2O(CH_2)_3CH_3$ and the various structural isomers embraced therein.

Preferred for reasons of increased ease of synthesis and/or greater herbicidal efficacy are:

(1) Compounds of Formula I where E is a single bond.

(2) Compounds of Formula I where E is $CH_2$.

(3) Compounds of Formula I where E is O.

(4) Compounds of Preferred 1 where
m is O; and
W is O.

(5) Compounds of Preferred 4 where
X is $C_1$–$C_2$ alkyl, $C_1$–$C_2$ alkoxy, cyclopropyl, Cl, F, Br, I, $OCF_2H$. $CH_2F$. $CF_3$, $OCH_2CH_2F$, $OCH_2CHF_2$, $OCH_2CF_3$, $CH_2Cl$ or $CH_2Br$; and
Y is H, $C_1$–$C_2$ alkyl, $C_1$–$C_2$ alkoxy. $CH_2OCH_3$, $CH_2OCH_2CH_3$, $N(OCH_3)CH_3$, $N(CH_3)_2$, $CF_3$, $SCH_3$, $OCH_2CH{=}CH_2$, $OCH_2C{\equiv}CH$, $OCH_2CH_2OCH_3$, $CH_2SCH_3$, $OCF_2H$, $SCF_2H$, $OCF_2Br$, $C{\equiv}CH$ or $C{\equiv}CCH_3$.

(6) Compounds of Preferred 5 where
$R_1$ is H, $CH_3$, F, Cl, Br, $OCH_3$, $SCH_3$, $CH_2CN$, $CH_2OCH_3$, $CF_3$ or $OCF_2H$; and
n is O.

(7) Compounds of Preferred 6 where
$R_3$ is H, $C_1$–$C_3$ alkyl, $C_1$–$C_2$ alkyl substituted with $C_1$–$C_2$ alkoxy, $CH_2CH_2Cl$, $CH_2CH_2F$, $CH_2CHF_2$, $CH_2CF_3$, allyl or propargyl; and
$R_4$ is H, $C_1$–$C_3$ alkyl, $C_1$–$C_2$ alkoxy, $C_1$–$C_2$ alkylthio, $N(CH_3)_2$, allyl, propargyl or $C_1$–$C_2$ alkyl substituted with 1–3 atoms of F, Cl or Br.

(8) Compounds of Preferred 7 where J is J-1.

(9) Compounds of Preferred 8 where
A is A-1;
Z is CH or N;
X is $CH_3$, $OCH_3$, $OCH_2CH_3$, cyclopropyl. Cl or $OCF_2H$;
Y is $CH_3$, $OCH_3$, $C_2H_5$, $CH_2OCH_3$, $NHCH_3$ or $CH(OCH_3)_2$.

(10) Compounds of Preferred 9 where Q is $Q_1$.

(11) Compounds of Preferred 9 where Q is $Q_2$.

(12) Compounds of Preferred 9 where Q is $Q_3$.

(13) Compounds of Preferred 9 where Q is $Q_4$.

(14) Compounds of Preferred 9 where Q is $Q_5$.

(15) Compounds of Preferred 9 where Q is $Q_6$.

(16) Compounds of Preferred 9 where Q is $Q_7$.

(17) Compounds of Preferred 7 where J is J-2.

(18) Compounds of Preferred 17 where
A is A-1;
Z is CH or N;
X is $CH_3$, $OCH_3$, $OCH_2CH_3$, cyclopropyl, Cl or $OCF_2H$;
Y is $CH_3$, $OCH_3$, $C_2H_5$, $CH_2OCH_3$, $NHCH_3$ or $CH(OCH_3)_2$.

(19) Compounds of Preferred 18 where Q is $Q_1$.

(20) Compounds of Preferred 18 where Q is $Q_2$.

(21) Compounds of Preferred 18 where Q is $Q_3$.

(22) Compounds of Preferred 18 where Q is $Q_4$.

(23) Compounds of Preferred 18 where Q is $Q_5$.

(24) Compounds of Preferred 18 where Q is $Q_6$.

(25) Compounds of Preferred 18 where Q is $Q_7$.

(26) Compounds of Preferred 7 where J is J-3.

(27) Compounds of Preferred 26 where
A is A-1;
Z is CH or N;
X is $CH_3$, $OCH_3$, $OCH_2CH_3$, cyclopropyl, Cl or $OCF_2H$;
Y is $CH_3$, $OCH_3$, $C_2H_5$, $CH_2OCH_3$, $NHCH_3$ or $CH(OCH_3)_2$.

(28) Compounds of Preferred 27 where Q is $Q_1$.

(29) Compounds of Preferred 27 where Q is $Q_2$.

(30) Compounds of Preferred 27 where Q is $Q_3$.
(31) Compounds of Preferred 27 where Q is $Q_4$.
(32) Compounds of Preferred 27 where Q is $Q_5$.
(33) Compounds of Preferred 27 where Q is $Q_6$.
(34) Compounds of Preferred 27 where Q is $Q_7$.
(35) Compounds of Preferred 7 where J is J-4.
(36) Compounds of Preferred 35 where
A is A-1;
Z is CH or N;
X is $CH_3$, $OCH_3$, $OCH_2CH_3$, cyclopropyl, Cl or $OCF_2H$;
Y is $CH_3$, $OCH_3$, $C_2H_5$, $CH_2OCH_3$, $NHCH_3$ or $CH(OCH_3)_2$.
(37) Compounds of Preferred 36 where Q is $Q_1$.
(38) Compounds of Preferred 36 where Q is $Q_2$.
(39) Compounds of Preferred 36 where Q is $Q_3$.
(40) Compounds of Preferred 36 where Q is $Q_4$.
(41) Compounds of Preferred 36 where Q is $Q_5$.
(41) Compounds of Preferred 36 where Q is $Q_6$.
(42) Compounds of Preferred 36 where Q is $Q_7$.
(43) Compounds of Preferred 7 where J is J-5.
(45) Compounds of Preferred 44 where
A is A-1;
Z is CH or N;
X is $CH_3$, $OCH_3$, $OCH_2CH_3$, cyclopropyl, Cl or $OCF_2H$;
Y is $CH_3$, $OCH_3$, $C_2H_5$, $CH_2OCH_3$, $NHCH_3$ or $CH(OCH_3)_2$.
(46) Compounds of Preferred 45 where Q is $Q_1$.
(47) Compounds of Preferred 45 where Q is $Q_2$.
(48) Compounds of Preferred 45 where Q is $Q_3$.
(49) Compounds of Preferred 45 where Q is $Q_4$.
(50) Compounds of Preferred 45 where Q is $Q_5$.
(51) Compounds of Preferred 45 where Q is $Q_6$.
(52) Compounds of Preferred 45 where Q is $Q_7$.
(53) Compounds of Preferred 7 where J is J-6.
(54) Compounds of Preferred 53 where
A is A-1;
Z is CH or N;
X is $CH_3$, $OCH_3$, $OCH_2CH_3$, cyclopropyl, Cl or $OCF_2H$;
Y is $CH_3$, $OCH_3$, $C_2H_5$, $CH_2OCH_3$, $NHCH_3$ or $CH(OCH_3)_2$.
(55) Compounds of Preferred 54 where Q is $Q_1$.
(56) Compounds of Preferred 54 where Q is $Q_2$.
(57) Compounds of Preferred 54 where Q is $Q_3$.
(58) Compounds of Preferred 54 where Q is $Q_4$.
(59) Compounds of Preferred 54 where Q is $Q_5$.
(60) Compounds of Preferred 54 where Q is $Q_6$.
(61) Compounds of Preferred 54 where Q is $Q_7$.
(62) Compounds of Preferred 7 where J is J-7.
(63) Compounds of Preferred 62 where
A is A-1;
Z is CH or N;
X is $CH_3$, $OCH_3$, $OCH_2CH_3$, cyclopropyl, Cl or $OCF_2H$;
Y is $CH_3$, $OCH_3$, $C_2H_5$, $CH_2OCH_3$, $NHCH_3$ or $CH(OCH_3)_2$.
(64) Compounds of Preferred 63 where Q is $Q_1$.
(65) Compounds of Preferred 63 where Q is $Q_2$.
(66) Compounds of Preferred 63 where Q is $Q_3$.
(67) Compounds of Preferred 63 where Q is $Q_4$.
(68) Compounds of Preferred 63 where Q is $Q_5$.
(69) Compounds of Preferred 63 where Q is $Q_6$.
(70) Compounds of Preferred 63 where Q is $Q_7$.
(71) Compounds of Preferred 7 where J is J-8.
(72) Compounds of Preferred 71 where
A is A-1;
Z is CH or N;
X is $CH_3$, $OCH_3$, $OCH_2CH_3$, cyclopropyl, Cl or $OCF_2H$;
Y is $CH_3$, $OCH_3$, $C_2H_5$, $CH_2OCH_3$, $NHCH_3$ or $CH(OCH_3)_2$.
(73) Compounds of Preferred 72 where Q is $Q_1$.
(74) Compounds of Preferred 72 where Q is $Q_2$.
(75) Compounds of Preferred 72 where Q is $Q_3$.
(76) Compounds of Preferred 72 where Q is $Q_4$.
(77) Compounds of Preferred 72 where Q is $Q_5$.
(78) Compounds of Preferred 72 where Q is $Q_6$.
(79) Compounds of Preferred 72 where Q is $Q_7$.
(80) Compounds of Preferred 7 where J is J-9.
(81) Compounds of Preferred 80 where
A is A-1;
Z is CH or N;
X is $CH_3$, $OCH_3$, $OCH_2CH_3$, cycloPropyl, Cl or $OCF_2H$;
Y is $CH_3$, $OCH_3$, $C_2H_5$, $CH_2OCH_3$, $NHCH_3$ or $CH(OCH_3)_2$.
(82) Compounds of Preferred 81 where Q is $Q_1$.
(83) Compounds of Preferred 81 where Q is $Q_2$.
(84) Compounds of Preferred 81 where Q is $Q_3$.
(85) Compounds of preferred 81 where Q is $Q_4$.
(86) Compounds of Preferred 81 where Q is $Q_5$.
(87) Compounds of Preferred 81 where Q is $Q_6$.
(88) Compounds of Preferred 81 where Q is $Q_7$.
(89) Compounds of Preferred 7 where J is J-10,
(90) Compounds of Preferred 89 where
A is A-1;
Z is CH or N;
X is $CH_3$, $OCH_3$, $OCH_2CH_3$, cyclopropyl, Cl or $OCF_2H$;
Y is $CH_3$, $OCH_3$, $C_2H_5$, $CH_2OCH_3$, $NHCH_3$ or $CH(OCH_3)_2$.
(91) Compounds of Preferred 90 where Q is $Q_1$.
(92) Compounds of Preferred 90 where Q is $Q_2$.
(93) Compounds of Preferred 90 where Q is $Q_3$.
(94) Compounds of Preferred 90 where Q is $Q_4$.
(95) Compounds of Preferred 90 where Q is $Q_5$.
(96) Compounds of Preferred 90 where Q is $Q_6$.
(97) Compounds of Preferred 90 where Q is $Q_7$.
(98) Compounds of Preferred 7 where J is J-11.
(99) Compounds of Preferred 98 where
A is A-1;
Z is CH or N;
X is $CH_3$, $OCH_3$, $OCH_2CH_3$, cyclopropyl, Cl or $OCF_2H$;
Y is $CH_3$, $OCH_3$, $C_2H_5$, $CH_2OCH_3$, $NHCH_3$ or $CH(OCH_3)_2$.
(100) Compounds of Preferred 99 where Q is $Q_1$.
(101) Compounds of Preferred 99 where Q is $Q_2$.
(102) Compounds of Preferred 99 where Q is $Q_3$.
(103) Compounds of Preferred 99 where Q is $Q_4$.
(104) Compounds of Preferred 99 where Q is $Q_5$.
(105) Compounds of Preferred 99 where Q is $Q_6$.
(106) Compounds of Preferred 99 where Q is $Q_7$.
(107) Compounds of Preferred 7 where J is J-12.
(108) Compounds of Preferred 107 where
A is A-1;
Z is CH or N;
X is CH . $OCH_3$, $OCH_2CH_3$, cyclopropyl, Cl or $OCF_2H$;
Y is $CH_3$, $OCH_3$, $C_2H_5CH_2OCH_3$, $NHCH_3$ or $CH(OCH_3)_2$.
(109) Compounds of Preferred 108 where Q is $Q_1$.
(110) Compounds of Preferred 108 where Q is $Q_2$.
(111) Compounds of Preferred 108 where Q is $Q_3$.

(112) Compounds of Preferred 108 where Q is $Q_4$.
(113) Compounds of Preferred 108 where Q is $Q_5$.
(114) Compounds of Preferred 108 where Q is $Q_6$.
(115) Compounds of Preferred 108 where Q is $Q_7$.
(116) Compounds of Preferred 7 where J is J-13.
(117) Compounds of Preferred 116 where
A is A-1;
Z is CH or N;
X is $CH_3$, $OCH_3$, $OCH_2CH_3$, cyclopropyl, Cl or $OCF_2H$;
Y is $CH_3$, $OCH_3$, $C_2H_5$, $CH_2OCH_3$, $NHCH_3$ or $CH(OCH_3)_2$.
(118) Compounds of Preferred 117 where Q is $Q_1$.
(119) Compounds of Preferred 117 where Q is $Q_2$.
(120) Compounds of Preferred 117 where Q is $Q_3$.
(121) Compounds of Preferred 117 where Q is $Q_4$.
(122) Compounds of Preferred 117 where Q is $Q_5$.
(123) Compounds of Preferred 117 where Q is $Q_6$.
(124) Compounds of Preferred 117 where Q is $Q_7$.
(125) Compounds of Preferred 2 where
m is O;
n is O;
J is J-1, J-2, J-3, J-8, J-10 or J-11;
W is O;
R is H;
$R_1$ is H, $CH_3$, F, Cl, Br, $OCH_3$, $SCH_3$, $CH_2CN$, $CH_2OCH_3$, $CF_3$ or $OCF_2H$;
$R_3$ is H, $C_1$–$C_3$ alkyl, $CH_2CH_2OCH_3$, $CH_2CH_2Cl$, $CH_2CH_2F$, $CH_2CHF_2$, $CH_2CF_3$, allyl or propargyl;
$R_4$ is H or $C_1$–$C_3$ alkyl;
A is A-1;
Z is CH or N;
X is $CH_3$, $OCH_3$, $OCH_2CH_3$, cyclopropyl, Cl or $OCF_2H$; and
Y is $CH_3$, $OCH_3$, $C_2H_5$, $CH_2OCH_3$, $NHCH_3$ or $CH(OCH_3)_2$.
(126) Compounds of Preferred 3 where
m is O;
R is H;
$R_1$ is H;
$R_3$ is H or $C_1$–$C_3$ alkyl;
$R_4$ is H or $C_1$–$C_3$ alkyl;
A is A-1;
Z is CH or N;
X is $CH_3$, $OCH_3$, $OCH_2CH_3$, cyclopropyl, Cl or $OCF_2H$; and
Y is $CH_3$ $OCH_3$ $C_2H_5$, $CH_2OCH_3$, $NHCH_3$ or $CH(OCH_3)_2$.

Specifically preferred for reasons of greatest ease of synthesis and/or greatest herbicidal efficacy are:

N-[(4-chloro-6-methoxypyrimidin-2-yl)aminocarbonyl]-2-(1-ethyl-1H-tetrazol-5-yl)benzenesulfonamide, m.p. 223°–225° C.;

N [(4,6-dimethoxypyrimidin-2-yl)aminocarbonyl]-2-methyl-6-(1-methyl-1H-tetrazol-5-yl)benzenesulfonamide, m.p. 178°–189° C.;

N [(4-chloro-6-methoxypyrimidin-2-yl)aminocarbonyl]-2-(1-methyl )-1H-tetrazol-5-yl)benzenesulfonamide, m.p. 225°–227° C.;

N-[(4,6-dimethoxypyrimidin-2-yl)aminocarbonyl]-2-(1-methyl-1H-tetrazol-5-yl)benzenesulfonamide, m.p. 207°–210° C.;

N-[(4,6-dimethylpyrimidin-2-yl)aminocarbonyl]-2-(1-methyl-1H-tetrazol-5-yl)benzenesulfonamide, m.p. 224°–226° C.;

N-[(4-methoxy-6-methylpyrimidin-2-yl)aminocarbonyl]-1-methyl-4-(2-methyl-2H-tetrazol-5-yl)-1H-pyrazole-5-sulfonamide, m.p. 181°–183° C.;

N-[(4-6-dimethoxypyrimidin-2-yl)aminocarbonyl]-1-methyl-4-(2-methyl-2H-tetrazol-5-yl)-1H-pyrazole-5-sulfonamide, m.p. 171°–173° C.

N-[[N-4,6-dimethoxy-1,3,5-triazin-2-yl)-N-methylamino]carbonyl]-2-(5-methyl-1H-tetrazol-1-yl)benzenesulfonamide, m.p. 180°–182° C.; and N-[[N-(4,6-dimethoxy-1,3,5-triazin-2-yl)-N-methylamino]carbonyl]-2-(5-methyl-1H-tetrazol-1-yl)benzenesulfonamide, sodium salt, NMR ($CDCl_3$) δ 8.4–8.13 (m, 1H), 7.70–7.40 (m, 1H), 7.25–7.00 (m, 1H), 3.85 (s, 6H), 3.19 (s, 3H), 2.32 (s, 3H).

DETAILED DESCRIPTION OF THE INVENTION

Synthesis

Compounds of Formula I can be synthesized by one or both of the methods shown below in Equation 1 and 2.

Equation 1 illustrates the reaction of sulfonyl isocyanates and isothiocyanates of Formula II with the appropriate heterocyclic amines of Formula III to give the desired sulfonylureas and sulfonylthioureas of Formula I.

Equation 1

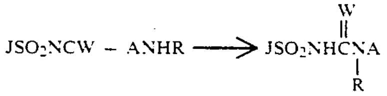

II III I wherein

J, W, R, and A are as previously defined.

The reaction of Equation 1 is best carried out in an inert aprotic solvent such as methylene chloride, tetrahydrofuran or acetonitrile at a temperature between 0° and 82° C. A catalytic amount of 1,4-diazabicyclo[2,2,-2]octane (DABCO®) may be used to accelerate the reaction. In cases in which the products are insoluble in the reaction solvent, they may be isolated by simple filtration. When the products are soluble, they can be isolated by evaporation of the solvent and trituration of the residue with solvents such as 1-chlorobutane, diethyl ether or ethyl acetate, and filtration.

Compounds of Formula I can be prepared as shown below in Equation 2 by the reaction of sulfonamides IV with the phenyl ester of the appropriate carbamic acid or thiocarbamic acid of Formula V. in the presence of an equimolar quantity of a tertiary amine base such as 1,8-diazabicyclo[5,4,0]undec-7-ene (DBU).

Equation 2

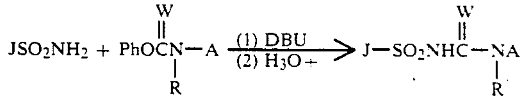

IV V Ia wherein

J, R, W and A are as previously defined.

The reaction shown in Equation 2 is best carried out at 25° C. in a solvent such as dioxane or acetonitrile for 1–2 hours under an inert atmosphere as described in European Patent Application No. 70,804 (published Jan. 26, 1983). The desired products of Formula I can be conveniently isolated by acidifying the reaction solution with aqueous hydrochloric acid. Alternatively, the aqueous layer can be extracted with a solvent such as methylene chloride or ethyl acetate. Drying and evaporation of the solvent affords the desired products.

The phenylcarbamates and phenylthiocarbamates of Formula V can be prepared by methods, or modifications thereof known to those skilled in the art, described in South African Patent Application 82/5671 and South African Patent Application 82/5045.

A judicious choice of the appropriate methods for preparing compounds of Formula I must take into account the nature of the substituents contained within the J values ($J_1$–$J_6$), namely Q and $R_1$, and their chemical compatibility with the reaction conditions of Equations 1 and 2.

Sulfonyl isocyanates of Formula II can be prepared as shown in Equation 3 by the reaction of sulfonamides of the general structure IV with phosgene in the presence of n-butyl isocyanate and a catalytic amount of 1,4-diazabicyclo[2.2.2]octane (DABCO).

Equation 3

$$\underset{IV}{JSO_2NH_2} \xrightarrow[\substack{COCl_2 \\ DABCO \\ xylenes}]{n\text{-}BuNCO} \text{II, where W is O}$$

wherein

J is as previously defined, provided E is not oxygen.

The reaction depicted in Equation 3 is best carried out according to the procedure described in U.S. Pat. No. 4,238,621.

Alternatively, sulfonyl isocyanates II can be prepared via phosgenation of the preformed n-butylureas of Formula VI as represented in Equation 4.

Equation 4

$$IV \xrightarrow[K_2CO_3]{n\text{-}BuNCO} JSO_2NH\underset{\underset{O}{||}}{C}NH\text{-}n\text{-}Bu$$

VI $$VI \xrightarrow[\substack{DABCO \\ xylenes}]{COCl_2} \text{II, where W is O}$$

wherein

J is as previously defined, provided E is not oxygen.

The compounds of Formula VI are conveniently prepared by stirring a mixture of the appropriate sulfonamide IV, anhydrous potassium carbonate, and n-butyl isocyanate in a suitable solvent such as acetone or methyl ethyl ketone at 25° to 80° C. until all of the isocyanate has reacted. The products are isolated by quenching in dilute aqueous acid and recrystallizing the insoluble solid. The n-butylureas VI are then treated with phosgene and a catalytic amount of DABCO in refluxing xylenes or chlorobenzene in a manner analogous to that described in the reference cited for Equation 3.

Alternatively, treatment of the sulfonamides of Formula IV with thionyl chloride gives intermediate N-sulfinylsulfonamides VII, which afford sulfonylisocyanates II (where W is O) upon exposure to phosgene in the presence of a catalytic amount of pyridine.

Equation 5

$$IV \xrightarrow[\Delta]{SOCl_2} \underset{VII}{JSO_2NSO}$$

$$VII \xrightarrow[\substack{Cat.\ Pyridine \\ toluene \\ \Delta}]{COCl_2} \text{II, where W is O}$$

The reaction of Equation 5 can best be performed according to the procedure of H. Ulrich, B. Tucker and A. Sayigh, *J. Org. Chem.*, 34, 3200 (1969).

Sulfonyl isothiocyanates II (where W is S) are known in the art and are prepared from the corresponding sulfonamides (IV) by reaction with carbon disulfide and potassium hydroxide followed by treatment of the resulting dipotassium salt with phosgene. Such a procedure is described in *Arch. Pharm.* 299, 174 (1966).

A judicious choice of (he appropriate method for preparing compounds of Formula II must take into account the nature of the substituents contained within the J values ($J_1$-$J_6$), namely Q and $R_1$, and their chemical compatability with reaction conditions of Equations 3–5.

The required sulfonamides of Formula IV can be synthesized by one or more of the methods shown below.

Equation 6 depicts the reaction of sulfonyl chlorides of Formula VIII with ammonia to give sulfonamides of Formula IVa.

Equation 6

$$\underset{VIII}{JSO_2Cl} \xrightarrow{NH_3} \underset{IVa}{JSO_2NH_2}$$

wherein

J is as previously defined, provided E is not oxygen.

The amination of Equation 6 can be effected by adding at least two molar equivalents of either anhydrous ammonia or concentrated ammonium hydroxide to a solution of the sulfonyl chloride VIII in a solvent such as diethyl ether, methylene chloride, or tetrahydrofuran at temperatures between −30° and 25° C.. The sulfonamides of Formula IVa are isolated either by filtration, in which case the ammonium chloride byproduct is removed by washing with water, or extraction into an organic solvent such as methylene chloride. Drying and evaporation of the solvent affords the sulfonamides IVa, which are usually sufficiently pure to be carried directly on to the next step.

Sulfonyl chlorides of Formula VIII can be prepared by one or more of the methods shown below in Equations 7, 8 and 9.

The reaction of an appropriately substituted N-arylhydroxylamine of Formula IX, as shown in Equation 7, and subsequent displacement with sulfur dioxide in the presence of cupric or cuprous chloride yields the desired sulfonyl chloride of Formula VIII.

Equation 7

$$\underset{IX}{JNHOH} \xrightarrow[\substack{(2)\ SO_2CuCl \\ AcOH}]{(1)\ NaNO_2,\ HCl} \underset{VIII}{JSO_2Cl}$$

The reaction of Equation 7 can be carried out by combining the appropriate arylhydroxylamine with aqueous concentrated hydrochloric acid and acetic acid and adding an aqueous solution of sodium nitrite at −10° to 10° C. After being stirred for 10 minutes to two hours the reaction mixture is added to a mixture of acetic acid, a catalytic amount of cuprous or cupric chloride and excess sulfur dioxide at −5° to 20° C. After being stirred for 0.5 to 24 hours the mixture is diluted with cold water and the product is extracted into a solvent such as methylene chloride or ethyl ether.

The solution of sulfonyl chloride thus obtained can be treated as in Equation 6 to prepare the desired sulfonamide IVa.

Diazotization of appropriately substituted amine derivatives of Formula X, as shown in Equation 8, and subsequent reaction with sulfur dioxide in the presence of either cupric or cuprous chloride gives the desired products of Formula VIII.

Equation 8

$$J{-}NH_2 \xrightarrow[(2)\ SO_2,\ CuCl_2\ or\ CuCl,\ HOAc]{(1)\ NaNO_2,\ HCl} JSO_2Cl$$

X VIII

The reaction of Equation 8 can be effected by methods analogous to those described in EP-A Nos. 83,975 and 85,476 (published Aug. 10, 1983). In Equation 8, a substituted amine X, in concentrated hydrochloric acid is treated with a solution of sodium nitrite in water at −5° to 5° C. After being stirred for 10 minutes to one hour at about 0° C., the solution is added to a mixture of excess sulfur dioxide and a catalytic amount of cupric or cuprous chloride in acetic acid at about 10° C. After being stirred for 0.25 to 24 hours at temperatures between 10° to 25° C., the solution is poured into a large excess of ice water. The sulfonyl chloride VIII can be isolated by filtration, or by extraction into a solvent such as methylene chloride or ether, followed by drying and evaporation of the solvent.

Alternatively, diazotization of appropriately substituted amine hydrochloride salts of Formula Xa can be effected under anhydrous conditions, as shown in Equation 8*a*, and subsequent reaction with sulfur dioxide and cupric chloride gives the desired products of Formula VIII.

Equation 8a $$J{-}NN_3{}^{+}Cl^{-} \xrightarrow[(2)\ SO_2/CuCl_2]{(1)\ RONO/Organic\ solvent} JSO_2Cl$$

Xa VIII

The amine hydrochloride salts Xa are diazotized with an alkylnitrite in a suitable solvent such as acetonitrile or acetone, and the resulting diazonium salts are reacted with sulfur dioxide and cupric chloride to give sulfonyl chlorides VIII. M. Doyle, in *J. Org. Chem.* 42, 2426, 2431 (1977), describes conditions for conducting similar Meerwein reactions.

Sulfonyl chlorides can also be prepared as shown below in Equation 9 by metal halogen exchange or directed lithiation of appropriately substituted aryl or heterocyclic substrates XI, and trapping with sulfuryl chloride.

Equation 9

$$J{-}Br\ (H) \xrightarrow[-78°\ C.\ \ (2)\ SO_2Cl_2/Hexanes]{(1)\ n\text{-}BuLi;\ Et_2O\ or\ THF} JSO_2Cl$$

XI VIIIa wherein

J is as previously described provided that $R_1$ is not $CO_2R_c$, $C_1$–$C_3$ haloalkyl, Br, nitro, $C_1$–$C_3$ alkylsulfonyl or CN.

The lithiation shown in Equation 9 can be performed according to the procedure of S. H. Bhattacharya, et al., *J. Chem. Soc.* (C), 1265 (1968) or by procedures reviewed by H. Gschwind and H. Rodriquez in Organic Reactions, Vol. 26, Wiley, New York, 1979, and references cited within.

Compounds of Formula VIII can be prepared via oxidative chlorination of the appropriate thioethers or mercaptans of Formula XII as represented in Equation 10.

Equation 10

$$J{-}SR_{15} \xrightarrow[H_2O,\ HOAc]{Cl_2} JSO_2Cl$$

XII VIII wherein

J is as previously defined, $R_{15}$ is H, $C_2$–$C_4$ alkyl or benzyl, $R_1$ is not $C_1$–$C_3$ alkylthio or $C_1$–$C_3$ alkysulfinyl, and $R_4$ is not $C_1$–$C_4$ alkylthio or $C_1$–$C_4$ alkylsulfinyl.

The reaction of Equation 10 can be carried out by treating a solution of the thioether XII in a solvent such as acetic acid in the presence of at least 2.5 equivalents of water and at least 3.0 equivalents of chlorine at 0°–30° C. for 0.25 to 5 hours. The reaction is poured into ice-water and the product is isolated by extraction with a suitable solvent such as methylene chloride, dried, and the solvent evaporated to yield a product sufficiently pure to be carried directly on to the next step.

Arylmethanesulfonyl chlorides of Formula VIIIb can be prepared from appropriately substituted benzyl chlorides or bromides of Formula XIII by a simple twostep procedure outlined in Equation 11.

Equation 11

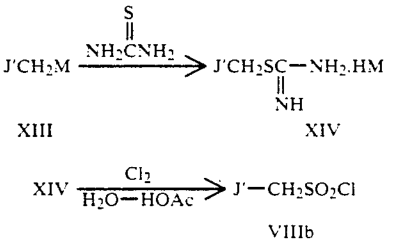

wherein $J'CH_2$ is defined as for J-1 through J-6 where E is $CH_2$; $R_1$, $R_4$ and Q are as previously defined except $R_1$ is not $C_1$–$C_3$ alkylthio or $C_1$–$C_3$ alkylsulfinyl, and $R_4$ is not $C_1$–$C_4$ alkylthio or $C_1$–$C_4$ alkylsulfinyl; and M is Cl or Br.

The conversion of alkyl halides of Formula XIII to isothiouronium salts of Formula XIV can be carried out by the procedure or T. B. Johnson and J. M. Sprague, *J. Am. Chem. Soc.*, 58, 1348 (1936); 59 1837 and 2439 (1937); 61 176 (1939). Oxidative chlorination of isothouronium salts such as XIV to afford sulfonyl chlorides of Formula VIIIb is best carried out according to the procedure of Johnson as described in *J. Am. Chem. Soc.*, 61 2548 (1939).

The requisite tetrazole substituted intermediates can be prepared by various methods depending on the nature of the aromatic ring in J (J-1 to J-6) systems on which the tetrazole is substituted and the nature of the other substituents present on J (J-1 to J-6). These intermediates can be prepared by one skilled in the art by the methods referred to in the following reviews on tetrazole chemistry: F. R. Benson, "Heterocyclic Compounds" (R. C. Elderfield, Ed.) 8, 1-104, John Wiley and Sons, New York, (1967); R. N. Butler, "Advances in Heterocyclic Chem.", 21, 323-436, Academic Press (1977); R. N. Butler, "Comprehensive Heterocyclic Chem.", (K. T. Potts, Ed.) 5, 791,838, Pergamon Press (1984) and F. R. Benson, "High Nitrogen Compounds". John Wiley and Sons, New York (1983).

The heterocyclic amines of Formula III in Equation 1 above can be prepared by methods known in the literature, or simple modifications thereof, by those skilled in the art. For instance, EP-A No. 84,224 (published July 27, 1983) and W. Braker et al., *J. Am. Chem. Soc.*, 69, 3072 (1947) describes methods for preparing aminopyridines and triazines substituted by acetal groups such as dialkoxymethyl or 1,3-dioxolan-2-yl, among other groups. Also, for example, South African Patent application Nos. 82/5045 and 82/5671 describe methods for preparing aminopyrimidines and triazines substituted by haloalkyl or haloalkylthio groups such as $OCH_2CH_2F$, $OCF_2CF_3$, $SCF_2H$, or $OCF_2H$, among other groups. South African patent application No. 83/7434 (published Oct. 5, 1983) describes methods for the synthesis of cycopropylpyrimidines and triazines substituted by such groups as alkyl, haloalkyl, alkoxy, haloalkoxy, alkylamino, dialkylamino or alkoxyalkyl.

The 5,6-dihydrofuro[2,3-d]pyrimidine-2-amines, the cyclopenta[d]pyrimidin-2-amines (III, A is A-2) and the 6,7-dihydro-5H-pyrano[2,3-d]pyrimidin-2-amines (III, A is A-3) can be prepared as described in EP-A No. 15,683. The furo[2,3-d]pyrimidin-2-amines (III, A is A-4) are described in EP-A No. 46,677.

Compounds of Formula III, where A is A-5, are described in EP-A-73,562. Compounds of Formula III, where A is A-6 are described in EP-A-94,260.

In addition, general methods for preparing aminopyrimidines and triazines have been reviewed in the following publications:

"The Chemistry of Heterocyclic Compounds", a series published by Interscience Publishers, Inc., New York and London;

"Pyrimidines", Vol. 16 of the same series by D. J. Brown;

"s-Triazines and Derivatives", Vol. 13 of the same series by E. M. Smolin and L. Rappoport; and F. C. Schaefer, U.S. Pat. No. 3,154,547 and K. R. Huffman and F. C. Schaefer, *J. Org. Chem.*, 28, 1812 (1963), which describes the synthesis of triazines.

Agriculturally suitable salts of compounds of Formula I are also useful herbicides and can be prepared in a number of ways known to the art. For example, metal salts can be made by contacting compounds of Formula I with a solution of an alkali or alkaline earth metal salt having a sufficiently basic anion (e.g., hydroxide, alkoxide or carbonate). Quaternary amine salts can be made by similar techniques.

A particularly useful process for preparing salts of compounds of Formula I involves reaction of a solution of the sulfonylurea in a water-immiscible halogenated hydrocarbon solvent with the appropriate alkali or alkaline earth metal hydroxide as described in copendinq application. U.S. Ser. No. 086,867 filed on Aug. 19, 1987.

Salts of compounds of Formula I can also be prepared by exchange of one cation for another. Cationic exchange can be effected by direct contact of an aqueous solution of a salt of a compound of Formula I (e.g. alkali or quaternary amine salt) with a solution containing the cation to be exchanged. This method is most effective when the desired salt containing the exchange cation is insoluble in water and can be separated by filtration.

Exchange may also be effected by passing an aqueous solution of a salt of a compound of Formula I (e.g., an alkali metal or quaternary amine salt) through a column packed with a cation exchange resin containing the cation to be exchanged for that of the original salt and the desired product is eluted from the column. This method is particularly useful when the desired salt is water-soluble, e.g., a potassium, sodium or calcium salt.

Acid addition salts, useful in this invention, can be obtained by reacting a compound of Formula I with a suitable acid. e.g., p-toluenesulfonic acid. trichloroacetic acid or the like.

The preparation of the compounds of this invention is further illustrated by the following specific examples.

EXAMPLE 1

1-(2-Chlorosulfonylphenyl)-5-methyl-1H-tetrazole

To 5 g of 1-(2-hydroxylaminophenyl)-5-methyl-1H-tetrazole in 12 mL of 37% hydrochloric acid and 5 mL of acetic acid at 0°-5° C. was added 2.3 g of sodium nitrite in 10 mL of water. The resultant solution was stirred at −5° to +5° C. for one hour and then added portionwise, with stirring, to a mixture of 25 mL of acetic acid, 0.5 g of cupric chloride and 5 mL of liquified sulfur dioxide at below 5° C. After stirring for two hours, during which time the mixture was allowed to warm to room temperature, it was poured into 150 mL of ice and water and extracted twice with 150 mL of methylene chloride. The methylene chloride solution was washed three times with 100 mL portions of water, two times with 100 mL of saturated aqueous sodium bicarbonate followed by single washes with 100 mL of saturated aqueous sodium chloride and 100 mL of water. The methylene chloride solution was then dried over magnesium sulfate and filtered to yield a solution containing the desired sulfonylchloride. This solution was used without further work-up to prepare the sulfonamide of Example 2.

EXAMPLE 2

1-(2-Aminosulfonylphenyl)-5-methyl-1H-tetrazole

Twenty-five mL of 28% ammonium hydroxide was added to the methylene chloride solution obtained from Example 2 and the mixture was stirred for two hours and concentrated in vacuo to yield a mixture of an oil and a solid. The solid product was separated by filtration and washed with water to yield 2.2 g of the desired product, which melted at 141°-148° C. Infrared absorption peaks at 3260 and 3360 $cm^{-1}$ were consistent for $NH_2$ and 1160 and 1350 $cm^{-1}$ consistent for the $SO_2$ of the desired product. Elem. anal. calc'd for $C_8H_9N_5O_2S$:C, 40.15; H, 3.79; N, 29.26, S, 13.39. Found: C, 40.43; H, 3.84; N, 29.61; S, 13.04.

EXAMPLE 3

5-(2-Chlorosulfonylphenyl)-2-methyl-2H-tetrazole and 5-(2-chlorosulfonylphenyl)-1-methyl-1H-tetrazole To 5 g of a mixture of 5-(2-hydroxylaminophenyl)-2-methyl-2H-tetrazole and 5-(2-hydroxyaminophenyl)-1-methyl-1H-tetrazole dissolved in 12 mL of 37% hydrochloric acid and 5 mL of acetic acid was added with stirring 2.3 g of sodium nitrite dissolved in 10 mL of water at −5° to 5° C. After one hour this solution was added, at 0°–5° C., portionwise to a mixture of 25 mL of acetic acid, 0.5 g of cupric chloride and 5 mL of liquified sulfur dioxide. After the addition was completed the cooling bath was removed and the reaction mixture was allowed to warm to 31° C. whereupon the cooling bath was reapplied and the stirring was continued until two and one half hours after completion of the addition. The mixture was then poured into ice and worked up as described in Example 1 except that the desired methylene chloride solution was concentrated in vacuo to yield an oil which solidified. This product, (3.28 g) which was a mixture of the desired sulfonylchlorides, was of sufficient purity for the preparation of the sulfonamides of Example 4.

EXAMPLE 4

5-(2-Aminosulfonylphenyl)-2-methyl-2H-tetrazole and 5-(2-aminosulfonylphenyl)-1-methyl-1H-tetrazole The solid product obtained in Example 3 was dissolved in 50 mL of tetrahydrofuran and added portionwise to 20 mL of 28% ammonium hydroxide. The mixture was stirred for one hour and concentrated in vacuo. Water was added to the residue, the mixture filtered and the solid washed with a small amount of cold water to yield 1.3 g of the isomer mixture. Infrared absorption spectra showed peaks at 3260 and 3360 $cm^{-1}$ consistent for $NH_2$ and 1160 and 1330 consistent for the $SO_2$ group of the desired product. Elem. anal. calc'd. for $C_8H_9N_5O_2S$:C, 40.15; H, 3.79; N, 29.26; S. 13.39. Found: C, 40.49; H, 3.86; N, 29.99; S, 13.75.

EXAMPLE 5

5-(2-Aminosulfonylphenyl)-1-methyl-1H-tetrazole

To 4.4 g of 5-(2-ethylthiophenyl)-1-methyl-1H-tetrazole in 40 mL of propionic acid and 1.08 g of water at −10° C. was added slowly, dropwise, 5.2 mL, of liquid chlorine (1.367 g/mL). After the addition the mixture was allowed to warm to room temperature, and was then poured into approximately 100 g of ice. The resultant sulfonyl chloride was extracted with methylene chloride, washed with water and the methylene chloride solution added to 45 mL of concentrated aqueous ammonium hydroxide while maintaining the reaction temperature below 25° C. with ice bath cooling. Evaporation of the methylene chloride yielded a solid product which was removed by filtration from the aqueous residue and washed with water. The product, 3.72 g, melted at 176°–179° C. and showed absorption peaks by infrared spectroscopy at 3210 and 3300 $cm^{-1}$, consistent for the desired sulfonamide.

EXAMPLE 6

5-(2-Aminosulfonyl-4-methylphenyl)-1-methyl-1H-tetrazole

To a mixture of 4.68 g of 5-(4-methyl-2-propylthiophenyl)-1-methyl-1H -tetrazole, 40 mL of propionic acid and 1.08 g of water cooled to −10° C. was added dropwise 5.2 mL (liquified) of chlorine while maintaining the reaction temperature at −10° to 0° C. After one-half hour the reaction mixture was allowed to warm to room temperature and stirred for one hour. It was then poured into 200 mL of ice and water and extracted with methylene chloride. The methylene chloride solution was added to 45 mL of concentrated ammonium hydroxide at 10° C. and stirred overnight. The mixture was concentrated in vacuo to an oil residue which was taken up in 100 mL of methylene chloride washed with three 100 mL portions of water and 100 mL of saturated aqueous sodium hydroxide. The methylene chloride solution was then dried over magnesium sulfate, filtered, and ;he filtrate evaporated to yield 4.1 g of the desired product melting at 161°–171° C.

NMR ($CDCl_3$): δ 2.56 (s, $CH_3$ on phenyl); 3.99 (s, $CH_3$ on tetrazole); 5.6 (s, w, $NH_2$); and 7.3–8.1 (m, 3 CH on phenyl).

EXAMPLE 7

5-(2-Aminosulfonyl-3-methylphenyl)-1-methyl-1H-tetrazole

To a mixture of 14.6 mL of concentrated (12 M) hydrochloric acid, 6.1 mL of acetic acid, 25 mL of ethyl ether and 6.91 g of 5-(2-amino-3-methylphenyl)-1-methyl-1H-tetrazole at 0° C. was added dropwise 2.8 g of sodium nitrite dissolved in 12.2 mL of water while maintaining the reaction temperature at below 10° C. Stirring was continued for one hour after the addition was completed. This mixture was then added slowly to 0.5 mL of acetic acid containing 0.6 g of cupric chloride and 6.1 mL of liquified sulfur dioxide. After stirring for two hours at ambient temperature, the mixture was poured into 200 mL of ice-water and extracted twice with 125 mL of methylene chloride. The organic phase was then washed twice with 200 ml of water, once with 200 mL saturated aqueous sodium chloride, once with 200 mL aqueous sodium bicarbonate followed by 200 mL of water and 200 mL saturated aqueous sodium chloride. The organic phase was then added dropwise to 25 mL of concentrated aqueous ammonium hydroxide and the mixture stirred overnight and evaporated to a solid which was washed with water and dried. The crude product thus obtained melted at 140°–161° C., yield 6.26 g. Mass spectral analysis showed a molecular weight of 253 (calc. 253) for the product.

EXAMPLE 8

N-(4-6-Dimethoxypyrimidin-2-yl)aminocarbonyl]-2-(2-methyl-2H-tetrazol-5-yl)benzenesulfonamide To 25 mL of acetonitrile was added at ambient temperature and pressure 0.48 g of 5-(2-aminosulfonylphenyl)-2-methyl-2H-tetrazole and 0.54 g of phenyl N-(4,6-dimethoxypyrimidin-2-yl)carbamate followed by 0.3 mL of DBU. After being stirred for three hours the reaction mixture was added to 25 g of ice and acidified to PH 3 with hydrochloric acid. The precipitate thus obtained was filtered, washed with water and dried !o yield 0.66 g of the desired product, m.p. 214°–222° C.

Infrared absorptions at 1720, 1600 and 1580 cm were consistent with the desired structure.

NMR($CDCl_3$):δ 3.91 (s, 2×$CH_3O$) 5.82 (s, CH, Pyrimidin) 4.43 (s, CH on N-2 of tetrazole) 4.38 (s. $CH_3$ on N-1 of tetrazole)

Integration of the peaks at 4.43 d and 4.38 d total one $CH_3$ indicating a ratio of 2-methyl-2H-tetrazole to 1-methyl-1H-tetrazole of 2:1. This mixture is suitable for purposes of this invention. If desired, the isomer mixture obtained in Example 6 can be separated by chromatography into its component parts.

EXAMPLE 9

N-[(4-6-Dimethoxypyrimidin-2-yl)aminocarbonyl]-2-(5-methyl-1H-tetrazol-1-yl)benzenesulfonamide To 0.48 g of 1-(2-aminosulfonylphenyl)-5-methyl 1H-tetrazole in 25 mL of acetonitrile was added at ambient temperature and pressure 0.54 g of phenyl N-(4,6-dimethoxypyrimidin-2-yl)carbamate and 0.3 mL of DBU. The reaction mixture was stirred for three hours, added to 25 g of ice and acidified to PH 3 with hydrochloric acid. The precipitate thus obtained was filtered, washed with water and dried to yield 0.74 g of the desired product, melting point at 213°-216° C. Infrared absorption spectra showed peaks at 1710, 1605 and 1570 cm , consistent for the desired product.

NMR($CDCl_3$): δ2.48 (s, $CH_3$ on tetrazole) 3.82 (s, 2×$CH_3O$) 5.81 (s, CH-pyrimidin).

EXAMPLE 10

N-[(4-Methoxy-6-methyl-1,3,5-triazin-2-yl)aminocarbonyl]-2-(5-methyl-1H-tetrazol-1-yl)benzenesulfonamide To 0.48 g of 1-(2-aminosulfonylphenyl)-5-methyl-1H-tetrazole and 0.52 g of phenyl N-(4-methoxy-6-methyl-1,3,5-triazin-2-yl)carbamate in 25 mL of acetonitrile at ambient temperature and pressure was added 0.3 mL of DBU. The mixture was stirred for three hours and then added to 25 g of ice and acidified with hydrochloric acid. The precipitate thus obtained was filtered, washed with water and dried in vacuo to yield 0.65 g of the desired product melting at 207°-209° C. Infrared absorption spectra showed absorption at 1700, 1600 and 1550 $cm^{-1}$ consistent for the desired structure.

EXAMPLE 11

N-[(4-Chloro-6-methoxypyrimidine-2-yl)aminocarbonyl]-2-(1-methyl-1H-tetrazol-5-yl)benzenesulfonamide To 0.48 g of 5-(2-aminosulfonylphenyl)-1-methyl-1H-tetrazole and 0.56 g of phenyl N-(4-chloro-6-methoxypyrimidine-2-yl)carbamate in 20 mL of dry acetonitrile at ambient temperature was added, with stirring, 0.3 mL of DBU. After stirring 16 hours the mixture was then poured into 25 g of ice followed by the addition of 10 mL of 2N hydrochloric acid. The precipitate thus formed was removed by filtration, washed with water and dried to yield 0.74 g of the desired product m.p. 225°-227° C.

NMR ($CDCl_3$): δ 3.88 (s, $CH_3$ on tetrazole); 3.95 (s, $CH_3O$); 6.52 (s, CH of pyrimidine); 7.2-7.5 (m, CH of phenyl and NH); 7.84 (m, 2 CH of phenyl); 8.6 (m, CH of phenyl); and 11.96 (s, NH).

EXAMPLE 12

N-[(4,6-Dimethoxypyrimidin-2-yl)aminocarbonyl]-5-chloro-2-(4-methyl-5-oxo-1H-4H-tetrazol-5-yl)benzenesulfonamide To a stirred solution of 0.29 g of 1-(2-aminosulfonyl-5-chlorophenyl)-4-methyl-1H-tetrazol-5[4H]-one and 0.27 g of phenyl N-(4,6-dimethoxypyrimidin-2-yl)carbamate in 10 mL of acetonitrile at ambient temperature was added 0.1 mL of DBU. The mixture was stirred for two hours, poured into 20 g of ice and acidified with 2N hydrochloric acid. The precipitate was removed by filtration, washed with water and dried to yield 0.37 g of product, m.p. 178°-180° C.

NMR ($CDCl_3$): δ 3.63 (s, $CH_3$ on tetrazole); 3.92 (s, 2×$CH_3O$); 5.81 (s, CH of pyrimidine); 7.4-8.6 (m, 3 CH of phenyl); and 12.6 (s, w, NH).

EXAMPLE 13

3-(2-Methyl-2H-tetrazole-5-yl)-1-phenyl-1H-pyrazole-5-sulfonamide

To a mixture of 3.1 mL of 12N hydrochloric acid, 12.5 mL of acetic acid, 3.7 mL of formic acid and 4.5 g of 5-amino-1-phenyl-3-(2-methyl-2H-tetrazol-5-yl)-1H-pyrazole was added dropwise 1.4 g of sodium nitrite in 2.5 mL of water at −8° to −6° C. The mixture was stirred for 15 minutes and then added to 20 mL of acetic acid containing 3.7 mL (liquid) of sulfur dioxide and 0.75 g of cupric chloride dihydrate. After stirring for thirty minutes and allowing to warm to room temperature, the mixture was poured into an ice and water mixture and the precipitate removed by filtration. After washing with water the solid was dissolved in tetrahydrofuran, cooled to −78° C., and ammonia (liquified, 1.0 mL) was added dropwise. The mixture was allowed to stand overnight at ambient temperature and filtered to yield a brown solid. This solid showed peaks at 3300 and 3200 $cm^{-1}$, consistent for $NH_2$, and 1370, 1185 and 1170 $cm^{-1}$, consistent for $SO_2$.

EXAMPLE 14

N-[[N-(4,6-Dimethoxy-1,3,5-triazin-2-yl)-N-methylamino]carbonyl]-2-(5-methyl-1H-tetrazol-1-yl)benzenesulfonamide To 0.22 g of 2-(5-methyl-1H-tetrazol-1-yl)benzenesulfonamide (compound of Example 2, 0.32 g) and 0.32 g of phenyl (4,6-dimethoxy-1,3,5-triazin-2-yl)(methyl)carbamate in 4 ml of dry acetonitrile was added at room temperature 0.2 ml of DBU. The reaction mixture was allowed to stand for four days, then diluted with 4 ml of water, several ice chips and 4 ml of diethyl ether. After stirring this solution for one minute, the ether layer was removed by pipet and the remaining mixture was acidified by dropwise addition of 1N HCl. The resulting precipitate was filtered, washed with water and dried to give 0.32 g of a white solid, m.p. 180°-182° C. (d).

EXAMPLE 15

Preparation of the sodium salt of N-[[N-(4,6-Dimethoxy-1,3,5-triazin-2-yl)-N-methylamino]carbonyl]-2-(5-methyl-1H-tetrazol-1-yl)-benzenesulfonamide To a stirred suspension of the compound of Example 14.(16.87 g, 38.7 mmol) and sodium carbonate (36 g) in methylene chloride (400 g), was added 1.79 g of sodium hydroxide (powder, 44.7 mmol). The suspension was allowed to stir at ambient temperature (20°-25° C.) for 16 hours before it was filtered. The filtrate was evaporated under reduced pressure using a rotary evaporator. A colorless solid (17.8 g, 38.7 mmol, 100% yield) was isolated;

NMR (90 MHz, $CDCl_3$): δ 8.4-8.13 (m, 1H); 7.70-7.40 (m, 1H); 7.25-7.00 (m, 1H); 3.85 (s, 6H); 3.19 (s, 3H); 2.32 (s, 3H).

By using the procedures described in the foregoing equations and examples or modifications thereof, one skilled in the art can prepare the compounds shown in the following tables.

Compounds

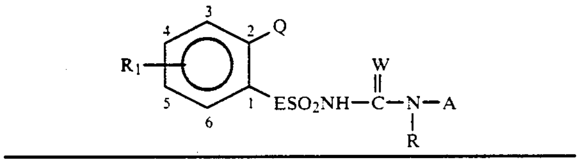

In General Structure 1, A is A-1
In General Structure 2, A is A-2
In General Structure 3, A is A-3
In General Structure 4, A is A-4
In General Structure 5, A is A-5
In General Structure 6, A is A-6
In General Structure 7, A is A-7

General Structure 8

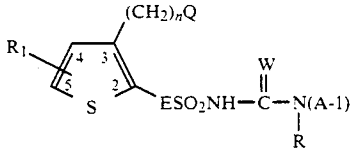

General Structure 9

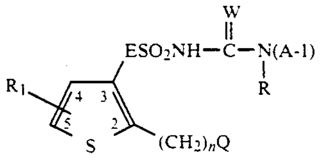

General Structure 10

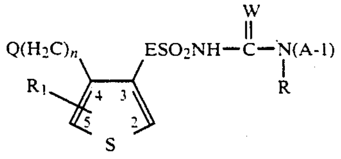

General Structure 11

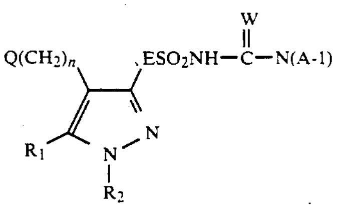

General Structure 12

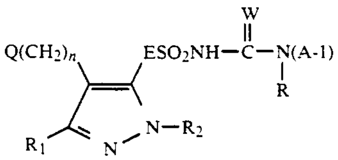

-continued

Compounds

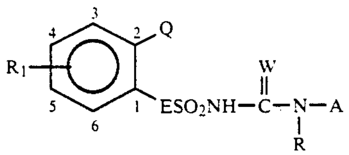

General Structure 13

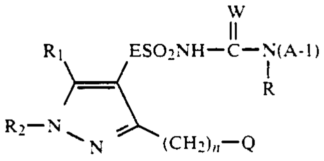

General Structure 14

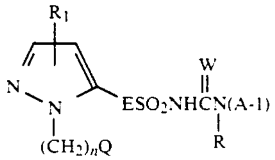

General Structure 15

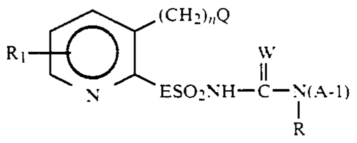

General Structure 16

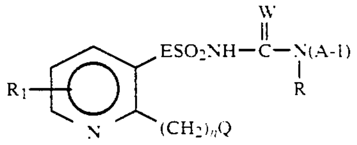

General Structure 17

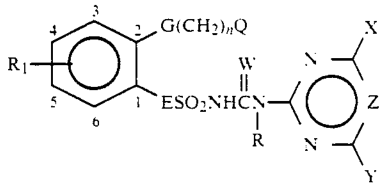

General Structure 18

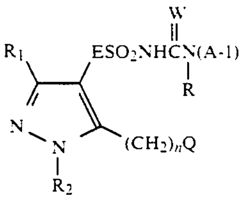

General Structure 19

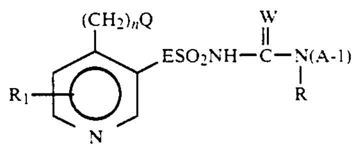

General Structure 20

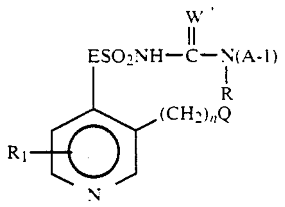

TABLE I

| General Structure 1 | | | | | | | | | |
|---|---|---|---|---|---|---|---|---|---|
| $R_1$ | E | Q | $R_3$ | W | R | X | Y | Z | m.p. (°C.) |
| H | — | Q-1 | $CH_3$ | O | H | $CH_3$ | $CH_3$ | CH | 224-226 |
| H | — | Q-1 | $CH_3$ | O | H | $CH_3$ | $OCH_3$ | CH | 222-224 |
| H | — | Q-1 | $CH_3$ | O | H | $OCH_3$ | $OCH_3$ | CH | 207-210 |
| H | — | Q-1 | $CH_3$ | O | H | Cl | $OCH_3$ | CH | 225-227 |
| H | — | Q-1 | $CH_3$ | O | H | $CH_3$ | $OCH_3$ | N | 196-198 |
| H | — | Q-1 | $CH_3$ | O | H | $OCH_3$ | $OCH_3$ | N | 172-187 |
| H | — | Q-1 | $C_2H_5$ | O | H | $CH_3$ | $CH_3$ | CH | 200-207 |
| H | — | Q-1 | $C_2H_5$ | O | H | $CH_3$ | $OCH_3$ | CH | 203-205 |
| H | — | Q-1 | $C_2H_5$ | O | H | $OCH_3$ | $OCH_3$ | CH | 214-217 |
| H | — | Q-1 | $C_2H_5$ | O | H | Cl | $OCH_3$ | CH | 223-225 |
| H | — | Q-1 | $C_2H_5$ | O | H | $OC_2H_5$ | $NHCH_3$ | N | 193-200 |
| H | — | Q-1 | $C_2H_5$ | O | H | $CH_3$ | $OCH_3$ | N | 192-196 |
| H | — | Q-1 | $C_2H_5$ | O | H | $OCH_3$ | $OCH_3$ | N | 192-195 |
| H | — | Q-1 | $CH(CH_3)_2$ | O | H | $CH_3$ | $CH_3$ | CH | |
| H | — | Q-1 | $CH(CH_3)_2$ | O | H | $CH_3$ | $OCH_3$ | CH | |
| H | — | Q-1 | $CH(CH_3)_2$ | O | H | $OCH_3$ | $OCH_3$ | CH | |
| H | — | Q-1 | $CH(CH_3)_2$ | O | H | Cl | $OCH_3$ | CH | |
| H | — | Q-1 | $CH(CH_3)_2$ | O | H | $CH_3$ | $OCH_3$ | N | |
| H | — | Q-1 | $CH(CH_3)_2$ | O | H | $OCH_3$ | $OCH_3$ | N | |
| H | — | Q-1 | $(CH_2)_4CH_3$ | O | H | $CH_3$ | $CH_3$ | CH | |
| H | — | Q-1 | $(CH_2)_4CH_3$ | O | H | $CH_3$ | $OCH_3$ | CH | |
| H | — | Q-1 | $(CH_2)_4CH_3$ | O | H | $OCH_3$ | $OCH_3$ | CH | |
| H | — | Q-1 | $(CH_2)_4CH_3$ | O | H | Cl | $OCH_3$ | CH | |
| H | — | Q-1 | $(CH_2)_4CH_3$ | O | H | $CH_3$ | $OCH_3$ | N | |
| H | — | Q-1 | $(CH_2)_4CH_3$ | O | H | $OCH_3$ | $OCH_3$ | N | |
| H | — | Q-1 | cyclopentyl | O | H | $CH_3$ | $CH_3$ | CH | |
| H | — | Q-1 | cyclopentyl | O | H | $CH_3$ | $OCH_3$ | CH | |
| H | — | Q-1 | cyclopentyl | O | H | $OCH_3$ | $OCH_3$ | CH | |
| H | — | Q-1 | cyclopentyl | O | H | Cl | $OCH_3$ | CH | |
| H | — | Q-1 | cyclopentyl | O | H | $CH_3$ | $OCH_3$ | N | |
| H | — | Q-1 | cyclopentyl | O | H | $OCH_3$ | $OCH_3$ | N | |
| H | — | Q-1 | $CH_2Cl$ | O | H | $CH_3$ | $CH_3$ | CH | |
| H | — | Q-1 | $CH_2Cl$ | O | H | $CH_3$ | $OCH_3$ | CH | |
| H | — | Q-1 | $CH_2Cl$ | O | H | $OCH_3$ | $OCH_3$ | CH | |
| H | — | Q-1 | $CH_2Cl$ | O | H | Cl | $OCH_3$ | CH | |
| H | — | Q-1 | $CH_2Cl$ | O | H | $CH_3$ | $OCH_3$ | N | |
| H | — | Q-1 | $CH_2Cl$ | O | H | $OCH_3$ | $OCH_3$ | N | |
| H | — | Q-1 | $(CH_2)_2F$ | O | H | $CH_3$ | $CH_3$ | CH | |
| H | — | Q-1 | $(CH_2)_2F$ | O | H | $CH_3$ | $OCH_3$ | CH | |
| H | — | Q-1 | $(CH_2)_2F$ | O | H | $OCH_3$ | $OCH_3$ | CH | |
| H | — | Q-1 | $(CH_2)_2F$ | O | H | Cl | $OCH_3$ | CH | |
| H | — | Q-1 | $(CH_2)_2F$ | O | H | $CH_3$ | $OCH_3$ | N | |
| H | — | Q-1 | $(CH_2)_2F$ | O | H | $OCH_3$ | $OCH_3$ | N | |
| H | — | Q-1 | $—CH_2CH{=}CH_2$ | O | H | $CH_3$ | $CH_3$ | CH | |
| H | — | Q-1 | $—CH_2CH{=}CH_2$ | O | H | $CH_3$ | $OCH_3$ | CH | |
| H | — | Q-1 | $—CH_2CH{=}CH_2$ | O | H | $OCH_3$ | $OCH_3$ | CH | |
| H | — | Q-1 | $—CH_2CH{=}CH_2$ | O | H | Cl | $OCH_3$ | CH | |
| H | — | Q-1 | $—CH_2CH{=}CH_2$ | O | H | $CH_3$ | $OCH_3$ | N | |
| H | — | Q-1 | $—CH_2CH{=}CH_2$ | O | H | $OCH_3$ | $OCH_3$ | N | |
| H | — | Q-1 | $CH_2CH{=}CHCH_2Cl$ | O | H | $CH_3$ | $CH_3$ | CH | |
| H | — | Q-1 | $CH_2CH{=}CHCH_2Cl$ | O | H | $CH_3$ | $OCH_3$ | CH | |
| H | — | Q-1 | $CH_2CH{=}CHCH_2Cl$ | O | H | $OCH_3$ | $OCH_3$ | CH | |
| H | — | Q-1 | $CH_2CH{=}CHCH_2Cl$ | O | H | Cl | $OCH_3$ | CH | |
| H | — | Q-1 | $CH_2CH{=}CHCH_2Cl$ | O | H | $CH_3$ | $OCH_3$ | N | |
| H | — | Q-1 | $CH_2CH{=}CHCH_2Cl$ | O | H | $OCH_3$ | $OCH_C$ | N | |
| H | — | Q-1 | $CH_2—C{\equiv}C—CH_3$ | O | H | $CH_3$ | $CH_3$ | CH | |
| H | — | Q-1 | $CH_2—C{\equiv}C—CH_3$ | O | H | $CH_3$ | $OCH_3$ | CH | |
| H | — | Q-1 | $CH_2—C{\equiv}C—CH_3$ | O | H | $OCH_3$ | $OCH_3$ | CH | |
| H | — | Q-1 | $CH_2—C{\equiv}C—CH_3$ | O | H | Cl | $OCH_3$ | CH | |
| H | — | Q-1 | $CH_2—C{\equiv}C—CH_3$ | O | H | $CH_3$ | $OCH_3$ | N | |
| H | — | Q-1 | $CH_2—C{\equiv}C—CH_3$ | O | H | $OCH_3$ | $OCH_3$ | N | |
| H | — | Q-1 | $C_6H_5$ | O | H | $CH_3$ | $CH_3$ | CH | |
| H | — | Q-1 | $C_6H_5$ | O | H | $CH_3$ | $OCH_3$ | CH | |
| H | — | Q-1 | $C_6H_5$ | O | H | $OCH_3$ | $OCH_3$ | CH | |
| H | — | Q-1 | $C_6H_5$ | O | H | Cl | $OCH_3$ | CH | |
| H | — | Q-1 | $C_6H_5$ | O | H | $CH_3$ | $OCH_3$ | N | |
| H | — | Q-1 | $C_6H_5$ | O | H | $OCH_3$ | $OCH_3$ | N | |
| H | — | Q-1 | $(CH_2)_4OCH_3$ | O | H | $CH_3$ | $CH_3$ | CH | |
| H | — | Q-1 | $(CH_2)_4OCH_3$ | O | H | $CH_3$ | $OCH_3$ | CH | |
| H | — | Q-1 | $(CH_2)_4OCH_3$ | O | H | $OCH_3$ | $OCH_3$ | CH | |
| H | — | Q-1 | $(CH_2)_4OCH_3$ | O | H | Cl | $OCH_3$ | CH | |
| H | — | Q-1 | $(CH_2)_4OCH_3$ | O | H | $CH_3$ | $OCH_3$ | N | |
| H | — | Q-1 | $(CH_2)_4OCH_3$ | O | H | $OCH_3$ | $OCH_3$ | N | |
| H | — | Q-1 | $(CH_2)_2SCH_2CH_3$ | O | H | $CH_3$ | $CH_3$ | CH | |
| H | — | Q-1 | $(CH_2)_2SCH_2CH_3$ | O | H | $CH_3$ | $OCH_3$ | CH | |
| H | — | Q-1 | $(CH_2)_2SCH_2CH_3$ | O | H | $OCH_3$ | $OCH_3$ | CH | |
| H | — | Q-1 | $(CH_2)_2SCH_2CH_3$ | O | H | Cl | $OCH_3$ | CH | |
| H | — | Q-1 | $(CH_2)_2SCH_2CH_3$ | O | H | $CH_3$ | $OCH_3$ | N | |
| H | — | Q-1 | $(CH_2)_2SCH_2CH_3$ | O | H | $OCH_3$ | $OCH_3$ | N | |
| 5-$CH_3$ | — | Q-1 | $CH_3$ | O | H | $CH_3$ | $CH_3$ | CH | 235-238 |

TABLE I-continued

| | | | | General Structure 1 | | | | | |
|---|---|---|---|---|---|---|---|---|---|
| $R_1$ | E | Q | $R_3$ | W | R | X | Y | Z | m.p. (°C.) |
| 5-$CH_3$ | — | Q-1 | $CH_3$ | O | H | $CH_3$ | $OCH_3$ | CH | 233-234 |
| 5-$CH_3$ | — | Q-1 | $CH_3$ | O | H | $OCH_3$ | $OCH_3$ | CH | 213-216 |
| 5-$CH_3$ | — | Q-1 | $CH_3$ | O | H | Cl | $OCH_3$ | CH | 217-219 |
| 5-$CH_3$ | — | Q-1 | $CH_3$ | O | H | $CH_3$ | $OCH_3$ | N | 200-205 |
| 5-$CH_3$ | — | Q-1 | $CH_3$ | O | H | $OCH_3$ | $OCH_3$ | N | 195-198 |
| 3-$CH_3$ | — | Q-1 | $CH_3$ | O | H | $OCH_3$ | OCH | CH | 192-197 |
| 3-$CH_3$ | — | Q-1 | $CH_3$ | O | H | $OCH_3$ | $OCH_3$ | N | 201-206 |
| 3-$CH_3$ | — | Q-1 | $CH_3$ | O | H | $OCH_3$ | $CH_3$ | N | 159-173 |
| 3-$CH_3$ | — | Q-1 | $CH_3$ | O | H | $OCH_3$ | $CH_3$ | CH | 219-222 |
| 3-$CH_3$ | — | Q-1 | $CH_3$ | O | H | $CH_3$ | $CH_3$ | CH | 223-226 |
| 3-$CH_3$ | — | Q-1 | $CH_3$ | O | H | Cl | $OCH_3$ | CH | 181-186 |
| 3-$CH_3$ | — | Q-1 | $CH_3$ | O | H | $OC_2H_5$ | $NHCH_3$ | N | 187-190 |
| 4-$CH_3$ | — | Q-1 | $CH_3$ | O | H | $OCH_3$ | $CH_3$ | N | 179-186 |
| 4-$CH_3$ | — | Q-1 | $CH_3$ | O | H | $OCH_3$ | $OCH_3$ | CH | 214-218 |
| 4-$CH_3$ | — | Q-1 | $CH_3$ | O | H | $OCH_3$ | $CH_3$ | CH | 225-229 |
| 4-$CH_3$ | — | Q-1 | $CH_3$ | O | H | $OCH_3$ | $OCH_3$ | N | 191-196 |
| 4-$CH_3$ | — | Q-1 | $CH_3$ | O | H | $CH_3$ | $CH_3$ | CH | 182-196 |
| 4-$CH_3$ | — | Q-1 | $CH_3$ | O | H | Cl | $OCH_3$ | CH | 140-150 |
| 4-$CH_3$ | — | Q-1 | $CH_3$ | O | H | $OC_2H_5$ | $NHCH_3$ | N | 152-160 |
| 6-$CH_3$ | — | Q-1 | $CH_3$ | O | H | $OCH_3$ | $OCH_3$ | N | 197-200 |
| 6-$CH_3$ | — | Q-1 | $CH_3$ | O | H | $OCH_3$ | $CH_3$ | N | 198-202 |
| 6-$CH_3$ | — | Q-1 | $CH_3$ | O | H | $OCH_3$ | $OCH_3$ | CH | 178-180 |
| 6-$CH_3$ | — | Q-1 | $CH_3$ | O | H | $OCH_3$ | $CH_3$ | CH | 180-183 |
| 6-$CH_3$ | — | Q-1 | $CH_3$ | O | H | $CH_3$ | $CH_3$ | CH | 213-215 |
| 6-$CH_3$ | — | Q-1 | $CH_3$ | O | H | Cl | $OCH_3$ | CH | 196-199 |
| 5-Cl | — | Q-1 | $CH_3$ | O | H | $CH_3$ | $CH_3$ | CH | 221-223 |
| 5-Cl | — | Q-1 | $CH_3$ | O | H | $CH_3$ | $OCH_3$ | CH | 207-210 |
| 5-Cl | — | Q-1 | $CH_3$ | O | H | $OCH_3$ | $OCH_3$ | CH | 214-216 |
| 5-Cl | — | Q-1 | $CH_3$ | O | H | Cl | $OCH_3$ | CH | 203-205 |
| 5-Cl | — | Q-1 | $CH_3$ | O | H | $CH_3$ | $OCH_3$ | N | 191-193 |
| 5-Cl | — | Q-1 | $CH_3$ | O | H | $OCH_3$ | $OCH_3$ | N | 175-180 |
| 5-Cl | — | Q-1 | $CH_3$ | O | H | $OC_2H_5$ | $NHCH_3$ | N | 144-158 |
| 5-Cl | — | Q-1 | $CH_3$ | O | H | $OCH_3$ | $CH(OCH_3)_2$ | CH | 180-183 |
| 5-Br | — | Q-1 | $CH_3$ | O | H | $CH_3$ | $CH_3$ | CH | |
| 5-Br | — | Q-1 | $CH_3$ | O | H | $CH_3$ | $OCH_3$ | CH | |
| 5-Br | — | Q-1 | $CH_3$ | O | H | $OCH_3$ | $OCH_3$ | CH | |
| 5-Br | — | Q-1 | $CH_3$ | O | H | Cl | $OCH_3$ | CH | |
| 5-Br | — | Q-1 | $CH_3$ | O | H | $CH_3$ | $OCH_3$ | N | |
| 5-Br | — | Q-1 | $CH_3$ | O | H | $OCH_3$ | $OCH_3$ | N | |
| 5-$OCF_2H$ | — | Q-1 | $CH_3$ | O | H | $CH_3$ | $CH_3$ | CH | |
| 5-$OCF_2H$ | — | Q-1 | $CH_3$ | O | H | $CH_3$ | $OCH_3$ | CH | |
| 5-$OCF_2H$ | — | Q-1 | $CH_3$ | O | H | $OCH_3$ | $OCH_3$ | CH | |
| 5-$OCF_2H$ | — | Q-1 | $CH_3$ | O | H | Cl | $OCH_3$ | CH | |
| 5-$OCF_2H$ | — | Q-1 | $CH_3$ | O | H | $CH_3$ | $OCH_3$ | N | |
| 5-$OCF_2H$ | — | Q-1 | $CH_3$ | O | H | $OCH_3$ | $OCH_3$ | N | |
| 5-$OCH_3$ | — | Q-1 | $CH_3$ | O | H | $CH_3$ | $CH_3$ | CH | 198-200 |
| 5-$OCH_3$ | — | Q-1 | $CH_3$ | O | H | $CH_3$ | $OCH_3$ | CH | 218-219 |
| 5-$OCH_3$ | — | Q-1 | $CH_3$ | O | H | $OCH_3$ | $OCH_3$ | CH | 205-207 |
| 5-$OCH_3$ | — | Q-1 | $CH_3$ | O | H | Cl | $OCH_3$ | CH | 185-188 |
| 5-$OCH_3$ | — | Q-1 | $CH_3$ | O | H | $CH_3$ | $OCH_3$ | N | |
| 5-$OCH_3$ | — | Q-1 | $CH_3$ | O | H | $OCH_3$ | $OCH_3$ | N | |
| 5-$CF_3$ | — | Q-1 | $CH_3$ | O | H | $CH_3$ | $CH_3$ | CH | |
| 5-$CF_3$ | — | Q-1 | $CH_3$ | O | H | $CH_3$ | $OCH_3$ | CH | |
| 5-$CF_3$ | — | Q-1 | $CH_3$ | O | H | $OCH_3$ | $OCH_3$ | CH | |
| 5-$CF_3$ | — | Q-1 | $CH_3$ | O | H | Cl | $OCH_3$ | CH | |
| 5-$CF_3$ | — | Q-1 | $CH_3$ | O | H | $CH_3$ | $OCH_3$ | N | |
| 5-$CF_3$ | — | Q-1 | $CH_3$ | O | H | $OCH_3$ | $OCH_3$ | N | |
| 5-$CH_2OCH_3$ | — | Q-1 | $CH_3$ | O | H | $CH_3$ | $CH_3$ | CH | |
| 5-$CH_2OCH_3$ | — | Q-1 | $CH_3$ | O | H | $CH_3$ | $OCH_3$ | CH | |
| 5-$CH_2OCH_3$ | — | Q-1 | $CH_3$ | O | H | $OCH_3$ | $OCH_3$ | CH | |
| 5-$CH_2OCH_3$ | — | Q-1 | $CH_3$ | O | H | Cl | $OCH_3$ | CH | |
| 5-$CH_2OCH_3$ | — | Q-1 | $CH_3$ | O | H | $CH_3$ | $OCH_3$ | N | |
| 5-$CH_2OCH_3$ | — | Q-1 | $CH_3$ | O | H | $OCH_3$ | $OCH_3$ | N | |
| 6-Cl | — | Q-1 | $CH_3$ | O | H | $CH_3$ | $CH_3$ | CH | 159-164 |
| 6-Cl | — | Q-1 | $CH_3$ | O | H | $OCH_3$ | $CH_3$ | CH | 196-199 |
| 6-Cl | — | Q-1 | $CH_3$ | O | H | $OCH_3$ | $OCH_3$ | CH | 153-156 |
| 6-Cl | — | Q-1 | $CH_3$ | O | H | Cl | $OCH_3$ | CH | 166-170 |
| 6-Cl | — | Q-1 | $CH_3$ | O | H | $CH_3$ | $OCH_3$ | N | 187-189 |
| 6-Cl | — | Q-1 | $CH_3$ | O | H | $OCH_3$ | $OCH_3$ | N | 202-205 |
| 6-$OCH_3$ | — | Q-1 | $CH_3$ | O | H | $CH_3$ | $CH_3$ | CH | 181-186 |
| 6-$OCH_3$ | — | Q-1 | $CH_3$ | O | H | $OCH_3$ | $CH_3$ | CH | 205-209 |
| 6-$OCH_3$ | — | Q-1 | $CH_3$ | O | H | $OCH_3$ | $OCH_3$ | CH | 174-181 |
| 5-$SCH_3$ | — | Q-1 | $CH_3$ | O | H | $CH_3$ | $CH_3$ | CH | |
| 5-$SCH_3$ | — | Q-1 | $CH_3$ | O | H | $CH_3$ | $OCH_3$ | CH | |
| 5-$SCH_3$ | — | Q-1 | $CH_3$ | O | H | $OCH_3$ | $OCH_3$ | CH | |
| 5-$SCH_3$ | — | Q-1 | $CH_3$ | O | H | Cl | $OCH_3$ | CH | |
| 5-$SCH_3$ | — | Q-1 | $CH_3$ | O | H | $CH_3$ | $OCH_3$ | N | |
| 5-$SCH_3$ | — | Q-1 | $CH_3$ | O | H | $OCH_3$ | $OCH_3$ | N | |
| 5-$SCH_3$ | — | Q-1 | $C_2H_5$ | O | H | $CH_3$ | $CH_3$ | CH | |
| 5-$SCH_3$ | — | Q-1 | $C_2H_5$ | O | H | $CH_3$ | $OCH_3$ | CH | |

TABLE I-continued

| R1 | E | Q | R3 | W | R | X | Y | Z | m.p. (°C.) |
|---|---|---|---|---|---|---|---|---|---|
| | | | | General Structure 1 | | | | | |
| 5-$SCH_3$ | — | Q-1 | $C_2H_5$ | O | H | $OCH_3$ | $OCH_3$ | CH | |
| 5-$SCH_3$ | — | Q-1 | $C_2H_5$ | O | H | Cl | $OCH_3$ | CH | |
| 5-$SCH_3$ | — | Q-1 | $C_2H_5$ | O | H | $CH_3$ | $OCH_3$ | N | |
| 5-$SCH_3$ | — | Q-1 | $C_2H_5$ | O | H | $OCH_3$ | $OCH_3$ | N | |
| H | — | Q-1 | $CH_3$ | O | $CH_3$ | $CH_3$ | $CH_3$ | CH | |
| H | — | Q-1 | $CH_3$ | O | $CH_3$ | $CH_3$ | $OCH_3$ | CH | |
| H | — | Q-1 | $CH_3$ | O | $CH_3$ | $OCH_3$ | $OCH_3$ | CH | |
| H | — | Q-1 | $CH_3$ | O | $CH_3$ | Cl | $OCH_3$ | CH | |
| H | — | Q-1 | $CH_3$ | O | $CH_3$ | $CH_3$ | $OCH_3$ | N | |
| H | — | Q-1 | $CH_3$ | O | $CH_3$ | $OCH_3$ | $OCH_3$ | N | |
| H | — | Q-1 | $CH_3$ | S | H | $CH_3$ | $CH_3$ | CH | |
| H | — | Q-1 | $CH_3$ | S | H | $CH_3$ | $OCH_3$ | CH | |
| H | — | Q-1 | $CH_3$ | S | H | $OCH_3$ | $OCH_3$ | CH | |
| H | — | Q-1 | $CH_3$ | S | H | Cl | $OCH_3$ | CH | |
| H | — | Q-1 | $CH_3$ | S | H | $CH_3$ | $OCH_3$ | N | |
| H | — | Q-1 | $CH_3$ | S | H | $OCH_3$ | $OCH_3$ | N | |
| H | — | Q-1 | $CH_3$ | O | H | H | $OCH_3$ | CH | |
| H | — | Q-1 | $CH_3$ | O | H | H | $OC_2H_5$ | CH | |
| H | — | Q-1 | $CH_3$ | O | H | H | $OCF_2H$ | CH | |
| H | — | Q-1 | $CH_3$ | O | H | $CH_3$ | $CF_3$ | CH | |
| H | — | Q-1 | $CH_3$ | O | H | $CH_3$ | $SCH_3$ | CH | |
| H | — | Q-1 | $CH_3$ | O | H | Cl | $OCH_3$ | CH | |
| H | — | Q-1 | $CH_3$ | O | H | $CH_3$ | $CH_2OCH_3$ | CH | |
| H | — | Q-1 | $CH_3$ | O | H | $CH_3$ | $OCH_2OCH_3$ | CH | |
| H | — | Q-1 | $CH_3$ | O | H | $CH_3$ | $NHCH_3$ | CH | |
| H | — | Q-1 | $CH_3$ | O | H | $CH_3$ | $N(CH_3)_2$ | CH | |
| H | $CH_2$ | Q-1 | $CH_3$ | O | H | $CH_3$ | $CH_3$ | CH | |
| H | $CH_2$ | Q-1 | $CH_3$ | O | H | $CH_3$ | $OCH_3$ | CH | |
| H | $CH_2$ | Q-1 | $CH_3$ | O | H | $OCH_3$ | $OCH_3$ | CH | |
| H | $CH_2$ | Q-1 | $CH_3$ | O | H | Cl | $OCH_3$ | CH | |
| H | $CH_2$ | Q-1 | $CH_3$ | O | H | $CH_3$ | $OCH_3$ | N | |
| H | $CH_2$ | Q-1 | $CH_3$ | O | H | $OCH_3$ | $OCH_3$ | N | |
| H | O | Q-1 | $CH_3$ | O | H | $CH_3$ | $CH_3$ | CH | |
| H | O | Q-1 | $CH_3$ | O | H | $CH_3$ | $OCH_3$ | CH | |
| H | O | Q-1 | $CH_3$ | O | H | $OCH_3$ | $OCH_3$ | CH | |
| H | O | Q-1 | $CH_3$ | O | H | $CH_3$ | $OCH_3$ | N | |
| H | O | Q-1 | $CH_3$ | O | H | $CH_3$ | $CH_3$ | CH | |
| H | O | Q-1 | $CH_3$ | O | H | $CH_3$ | $OCH_3$ | CH | |
| H | O | Q-1 | $CH_3$ | O | H | $OCH_3$ | $OCH_3$ | CH | |
| H | O | Q-1 | $CH_3$ | O | H | Cl | $OCH_3$ | CH | |
| H | O | Q-1 | $CH_3$ | O | H | $CH_3$ | $OCH_3$ | N | |
| H | O | Q-1 | $CH_3$ | O | H | $OCH_3$ | $OCH_3$ | N | |
| H | — | Q-1 | $CH_3$ | O | H | $OC_2H_5$ | $NHCH_3$ | CH | |
| H | — | Q-1 | $CH_3$ | O | H | H | $OCH_3$ | CH | |
| H | — | Q-1 | $CH_3$ | O | H | H | $OC_2H_5$ | CH | |
| H | — | Q-1 | $CH_3$ | O | H | $CH_3$ | $CF_3$ | CH | |
| H | — | Q-1 | $CH_3$ | O | H | $CH_3$ | $SCH_3$ | CH | |
| H | — | Q-1 | $CH_3$ | O | H | $CH_3$ | $CH_2OCH_3$ | CH | |
| H | — | Q-1 | $CH_3$ | O | H | $CH_3$ | $NHCH_3$ | CH | |
| H | — | Q-1 | $CH_3$ | O | H | $CH_3$ | $N(CH_3)_2$ | CH | |
| H | — | Q-1 | $CH_3$ | O | H | H | $OCH_3$ | N | |
| H | — | Q-1 | $CH_3$ | O | H | H | $OC_2H_5$ | N | |
| H | — | Q-1 | $CH_3$ | O | H | H | $OCF_2H$ | N | |
| H | — | Q-1 | $CH_3$ | O | H | $CH_3$ | $CH_2OCH_3$ | N | |
| H | — | Q-1 | $CH_3$ | O | H | $CH_3$ | $NHCH_3$ | N | |
| H | — | Q-1 | $CH_3$ | O | H | $CH_3$ | $N(CH_3)_2$ | N | |
| 3-(n-$C_3H_7$) | — | Q-1 | $CH_3$ | O | H | $CH_3$ | $CH_3$ | CH | |
| 3-(n-$C_3H_7$) | — | Q-1 | $CH_3$ | O | H | $OCH_3$ | $OCH_3$ | CH | |
| 3-(n-$C_3H_7$) | — | Q-1 | $CH_3$ | O | H | $OCH_3$ | $CH_3$ | CH | |
| 5-$CH_2CH_2Cl$ | — | Q-1 | $CH_3$ | O | H | $OCH_3$ | $CH_3$ | CH | |
| 5-$CH_2CH_2Cl$ | — | Q-1 | $CH_3$ | O | H | $OCH_3$ | $OCH_3$ | CH | |
| 5-$OCH_2CH_2CH_3$ | — | Q-1 | $CH_3$ | O | H | $OCH_3$ | $OCH_3$ | CH | |
| 5-$OCH_2CH_2CH_3$ | — | Q-1 | $CH_3$ | O | H | $OCH_3$ | $CH_3$ | CH | |
| 6-$SO_2N(CH_3)_2$ | — | Q-1 | $CH_3$ | O | H | $OCH_3$ | $OCH_3$ | CH | |
| 6-$SO_2N(CH_3)_2$ | — | Q-1 | $CH_3$ | O | H | $OCH_3$ | $CH_3$ | CH | |
| 6-$OCH_2CH_2CH_3$ | — | Q-1 | $CH_3$ | O | H | $OCH_3$ | $CH_3$ | CH | |
| 6-$OCH_2CH_2CH_3$ | — | Q-1 | $CH_3$ | O | H | $OCH_3$ | $OCH_3$ | CH | |
| 6-$SCH_2CH_2CH_3$ | — | Q-1 | $CH_3$ | O | H | $OCH_3$ | $OCH_3$ | CH | |
| 6-$SCH_2CH_2CH_3$ | — | Q-1 | $CH_3$ | O | H | $OCH_3$ | $CH_3$ | CH | |
| 6-$SOCH_3$ | — | Q-1 | $CH_3$ | O | H | $OCH_3$ | $OCH_3$ | CH | |
| 6-$SOCH_3$ | — | Q-1 | $CH_3$ | O | H | $OCH_3$ | $CH_3$ | CH | |
| 6-$SO_2CH_3$ | — | Q-1 | $CH_3$ | O | H | $OCH_3$ | $CH_3$ | CH | |
| 6-$SO_2CH_3$ | — | Q-1 | $CH_3$ | O | H | $OCH_3$ | $OCH_3$ | CH | |
| 5-CN | — | Q-1 | $CH_3$ | O | H | $OCH_3$ | $OCH_3$ | CH | |
| 5-CN | — | Q-1 | $CH_3$ | O | H | $OCH_3$ | $CH_3$ | CH | |
| 5-$CO_2CH_3$ | — | Q-1 | $CH_3$ | O | H | $OCH_3$ | $CH_3$ | CH | |
| 5-$CO_2CH_3$ | — | Q-1 | $CH_3$ | O | H | $OCH_3$ | $OCH_3$ | CH | |
| 5-$OCH_2CH_2Cl$ | — | Q-1 | $CH_3$ | O | H | $OCH_3$ | $OCH_3$ | CH | |
| 5-$OCH_2CH_2Cl$ | — | Q-1 | $CH_3$ | O | H | $OCH_3$ | $CH_3$ | CH | |
| 5-$OCH_2CF_3$ | — | Q-1 | $CH_3$ | O | H | $OCH_3$ | $CH_3$ | CH | |

TABLE I-continued

| | | | | General Structure 1 | | | | | |
|---|---|---|---|---|---|---|---|---|---|
| $R_1$ | E | Q | $R_3$ | W | R | X | Y | Z | m.p. (°C.) |
| 5-$OCH_2CF_3$ | — | Q-1 | $CH_3$ | O | H | $OCH_3$ | $OCH_3$ | CH | |
| 5-$SCH_2CF_3$ | — | Q-1 | $CH_3$ | O | H | $OCH_3$ | $CH_3$ | CH | |
| 5-$SCH_2CF_3$ | — | Q-1 | $CH_3$ | O | H | $OCH_3$ | $OCH_3$ | CH | |
| 5-$NH_2$ | — | Q-1 | $CH_3$ | O | H | $OCH_3$ | $OCH_3$ | CH | |
| 5-$NH_2$ | — | Q-1 | $CH_3$ | O | H | $OCH_3$ | $CH_3$ | CH | |
| 5-$NHC_2H_5$ | — | Q-1 | $CH_3$ | O | H | $OCH_3$ | $CH_3$ | CH | |
| 5-$NHC_2H_5$ | — | Q-1 | $CH_3$ | O | H | $OCH_3$ | $OCH_3$ | CH | |
| 5-$N(CH_3)_2$ | — | Q-1 | $CH_3$ | O | H | $OCH_3$ | $OCH_3$ | CH | |
| 5-$N(CH_3)_2$ | — | Q-1 | $CH_3$ | O | H | $OCH_3$ | $CH_3$ | CH | |
| 5-$CH_2OCH_3$ | — | Q-1 | $CH_3$ | O | H | $OCH_3$ | $CH_3$ | CH | |
| 5-$CH_2OCH_3$ | — | Q-1 | $CH_3$ | O | H | $OCH_3$ | $OCH_3$ | CH | |
| 5-$C_2H_4OCH_3$ | — | Q-1 | $CH_3$ | O | H | $OCH_3$ | $OCH_3$ | CH | |
| 5-$C_2H_4OCH_3$ | — | Q-1 | $CH_3$ | O | H | $OCH_3$ | $CH_3$ | CH | |
| 5-$C_2H_4OC_2H_5$ | — | Q-1 | $CH_3$ | O | H | $OCH_3$ | $CH_3$ | CH | |
| 5-$C_2H_4OC_2H_5$ | — | Q-1 | $CH_3$ | O | H | $OCH_3$ | $OCH_3$ | CH | |
| 5-$CH_2OC_2H_4Cl$ | — | Q-1 | $CH_3$ | O | H | $OCH_3$ | $OCH_3$ | CH | |
| 5-$CH_2OC_2H_4Cl$ | — | Q-1 | $CH_3$ | O | H | $OCH_3$ | $CH_3$ | CH | |
| 5-$CH_2OCH_2CF_3$ | — | Q-1 | $CH_3$ | O | H | $OCH_3$ | $CH_3$ | CH | |
| 5-$CH_2OCH_2CF_3$ | — | Q-1 | $CH_3$ | O | H | $OCH_3$ | $OCH_3$ | CH | |
| 5-$CH_2SCH_3$ | — | Q-1 | $CH_3$ | O | H | $OCH_3$ | $OCH_3$ | CH | |
| 5-$CH_2SCH_3$ | — | Q-1 | $CH_3$ | O | H | $OCH_3$ | $CH_3$ | CH | |
| 5-$CH_2SC_2H_4Cl$ | — | Q-1 | $CH_3$ | O | H | $OCH_3$ | $CH_3$ | CH | |
| 5-$CH_2SC_2H_4Cl$ | — | Q-1 | $CH_3$ | O | H | $OCH_3$ | $OCH_3$ | CH | |
| 5-$CH_2CN$ | — | Q-1 | $CH_3$ | O | H | $OCH_3$ | $OCH_3$ | CH | |
| 5-$CH_2CN$ | — | Q-1 | $CH_3$ | O | H | $OCH_3$ | $CH_3$ | CH | |
| H | — | Q-1 | $CH_3$ | O | H | $OCH_3$ | $OCH_2CH_2CH_2CH_3$ | CH | |
| H | — | Q-1 | $CH_3$ | O | H | $OCH_3$ | $OCH_2CH_2Cl$ | CH | |
| H | — | Q-1 | $CH_3$ | O | H | $OCH_3$ | $OCH_2CH_2$ $CH_2Cl$ | CH | |
| H | — | Q-1 | $CH_3$ | O | H | $OCH_3$ | $SCH_2CH_2Cl$ | CH | |
| H | — | Q.1 | $CH_3$ | O | H | $OCH_3$ | $SCHF_2$ | CH | |
| H | — | Q-1 | $CH_3$ | O | H | $OCH_3$ | $SCH_2CH_3$ | CH | |
| H | — | Q-1 | $CH_3$ | O | H | $OCH_3$ | $CH_2OCH_3$ | CH | |
| H | — | Q-1 | $CH_3$ | O | H | $OCH_3$ | $C_2H_4OC_2H_5$ | CH | |
| H | — | Q-1 | $CH_3$ | O | H | $OCH_3$ | $OC_2H_4OC_2H_5$ | CH | |
| H | — | Q-1 | $CH_3$ | O | H | $OCH_3$ | $OCH_2CH{=}CH_2$ | CH | |
| H | — | Q-1 | $CH_3$ | O | H | $OCH_3$ | $OCH_2C{\equiv}CH$ | CH | |
| H | — | Q-1 | $CH_3$ | O | H | $OCH_3$ | $CH_2SCH_3$ | CH | |
| H | — | Q-1 | $CH_3$ | O | H | $OCH_3$ | $C_2H_4SCH_3$ | CH | |
| H | — | Q-1 | $CH_3$ | O | H | $OCH_3$ | $C_2H_4SC_2H_5$ | CH | |
| H | — | Q-1 | $CH_3$ | O | H | $OCH_3$ | $CH_2SO_2CH_3$ | CH | |
| H | — | Q-1 | $CH_3$ | O | H | $OCH_3$ | $C_2H_4SO_2CH_3$ | CH | |
| H | — | Q-1 | $CH_3$ | O | H | $OCH_3$ | $C_2H_4SOCH_3$ | CH | |
| H | — | Q-1 | $CH_3$ | O | H | $OCH_3$ | $CH_2CH_2CH_2Cl$ | CH | |
| H | — | Q-1 | $CH_3$ | O | H | $OCH_3$ | $CH_2C{\equiv}CH$ | CH | |
| H | — | Q-1 | $CH_3$ | O | H | $OCH_3$ | $N_3$ | CH | |
| H | — | Q-1 | $CH_3$ | O | H | $OCH_3$ | CN | CH | |
| H | — | Q-1 | $CH_3$ | O | H | $OCH_3$ | $COCH_3$ | CH | |
| H | — | Q-1 | $CH_3$ | O | H | $OCH_3$ | $C(CH_3)(OCH_3)_2$ | CH | |
| H | — | Q-1 | $CH_3$ | O | H | $OCH_3$ | 2-methyldi-oxolan-2-yl | CH | |
| H | — | Q-1 | $CH_3$ | O | H | $OCH_3$ | $N(OCH_3)CH_3$ | CH | |
| H | — | Q-1 | $CH_3$ | O | H | $OC_2H_5$ | $NHCH_3$ | N | 204-208 |
| H | — | Q-2 | $CH_3$ | O | H | $CH_3$ | $CH_3$ | CH | |
| H | — | Q-2 | $CH_3$ | O | H | $CH_3$ | $OCH_3$ | CH | |
| H | — | Q-2 | $CH_3$ | O | H | $OCH_3$ | $OCH_3$ | CH | 214-222 |
| H | — | Q-2 | $CH_3$ | O | H | Cl | $OCH_3$ | CH | |
| H | — | Q-2 | $CH_3$ | O | H | $CH_3$ | $OCH_3$ | N | |
| H | — | Q-2 | $CH_3$ | O | H | $OCH_3$ | $OCH_3$ | N | |
| H | — | Q-2 | $C_2H_5$ | O | H | $CH_3$ | $CH_3$ | CH | |
| H | — | Q-2 | $C_2H_5$ | O | H | $CH_3$ | $OCH_3$ | CH | |
| H | — | Q-2 | $C_2H_5$ | O | H | $OCH_3$ | $OCH_3$ | CH | |
| H | — | Q-2 | $C_2H_5$ | O | H | Cl | $OCH_3$ | CH | |
| H | — | Q-2 | $C_2H_5$ | O | H | $CH_3$ | $OCH_3$ | N | |
| H | — | Q-2 | $C_2H_5$ | O | H | $OCH_3$ | $OCH_3$ | N | |
| H | — | Q-2 | $CH(CH_3)_2$ | O | H | $CH_3$ | $CH_3$ | CH | |
| H | — | Q-2 | $CH(CH_3)_2$ | O | H | $CH_3$ | $OCH_3$ | CH | |
| H | — | Q-2 | $CH(CH_3)_2$ | O | H | $OCH_3$ | $OCH_3$ | CH | |
| H | — | Q-2 | $CH(CH_3)_2$ | O | H | Cl | $OCH_3$ | CH | |
| H | — | Q-2 | $CH(CH_3)_2$ | O | H | $CH_3$ | $OCH_3$ | N | |
| H | — | Q-2 | $CH(CH_3)_2$ | O | H | $OCH_3$ | $OCH_3$ | N | |
| H | — | Q-2 | $(CH_2)_2CH_3$ | O | H | $CH_3$ | $CH_3$ | CH | |
| H | — | Q-2 | $(CH_2)_2CH_3$ | O | H | $CH_3$ | $OCH_3$ | CH | |
| H | — | Q-2 | $(CH_2)_2CH_3$ | O | H | $OCH_3$ | $OCH_3$ | CH | |
| H | — | Q-2 | $(CH_2)_2CH_3$ | O | H | Cl | $OCH_3$ | CH | |
| H | — | Q-2 | $(CH_2)_2CH_3$ | O | H | $CH_3$ | $OCH_3$ | N | |
| H | — | Q-2 | $(CH_2)_2CH_3$ | O | H | $OCH_3$ | $OCH_3$ | N | |
| H | — | Q-1 | $CH_2C{\equiv}CH$ | O | H | $CH_3$ | $CH_3$ | CH | |
| H | — | Q-1 | $CH_2C{\equiv}CH$ | O | H | $CH_3$ | $OCH_3$ | CH | |
| H | — | Q-1 | $CH_2C{\equiv}CH$ | O | H | $OCH_3$ | $OCH_3$ | CH | |
| H | — | Q-1 | $CH_2C{\equiv}CH$ | O | H | Cl | $OCH_3$ | CH | |

TABLE I-continued

General Structure 1

| $R_1$ | E | Q | $R_3$ | W | R | X | Y | Z | m.p. (°C.) |
|---|---|---|---|---|---|---|---|---|---|
| H | — | Q-1 | $CH_2C{\equiv}CH$ | O | H | $CH_3$ | $OCH_3$ | N | |
| H | — | Q-1 | $CH_2C{\equiv}CH$ | O | H | $OCH_3$ | $OCH_3$ | N | |
| H | — | Q-1 | $CH_3$ | O | H | $OCH_3$ | $OCF_2H$ | CH | 160-165 |
| H | — | Q-1 | $CH_3$ | O | H | $CH_3$ | $OCF_2H$ | CH | 195-198 |
| 5-$CH_3$ | — | Q-1 | $CH_3$ | O | H | $OCH_3$ | $OCF_2H$ | CH | 168-172 |
| 5-$CH_3$ | — | Q-1 | $CH_3$ | O | H | $CH_3$ | $OCF_2H$ | CH | 90-93 |
| H | — | Q-2 | $CH_2OCH_3$ | O | H | $CH_3$ | $CH_3$ | CH | |
| H | — | Q-2 | $CH_2OCH_3$ | O | H | $CH_3$ | $OCH_3$ | CH | |
| H | — | Q-2 | $CH_2OCH_3$ | O | H | $OCH_3$ | $OCH_3$ | CH | |
| H | — | Q-2 | $CH_2OCH_3$ | O | H | Cl | $OCH_3$ | CH | |
| H | — | Q-2 | $CH_2OCH_3$ | O | H | $CH_3$ | $OCH_3$ | N | |
| H | — | Q-2 | $CH_2OCH_3$ | O | H | $OCH_3$ | $OCH_3$ | N | |
| 5-$OCF_2H$ | — | Q-2 | $CH_3$ | O | H | $CH_3$ | $CH_3$ | CH | |
| 5-$OCF_2H$ | — | Q-2 | $CH_3$ | O | H | $CH_3$ | $OCH_3$ | CH | |
| 5-$OCF_2H$ | — | Q-2 | $CH_3$ | O | H | $OCH_3$ | $OCH_3$ | CH | |
| 5-$OCF_2H$ | — | Q-2 | $CH_3$ | O | H | Cl | $OCH_3$ | CH | |
| 5-$OCF_2H$ | — | Q-2 | $CH_3$ | O | H | $CH_3$ | $OCH_3$ | N | |
| 5-$OCF_2H$ | — | Q-2 | $CH_3$ | O | H | $OCH_3$ | $OCH_3$ | N | |
| 5-$OCH_3$ | — | Q-2 | $CH_3$ | O | H | $CH_3$ | $CH_3$ | CH | |
| 5-$OCH_3$ | — | Q-2 | $CH_3$ | O | H | $CH_3$ | $OCH_3$ | CH | |
| 5-$OCH_3$ | — | Q-2 | $CH_3$ | O | H | $OCH_3$ | $OCH_3$ | CH | |
| 5-$OCH_3$ | — | Q-2 | $CH_3$ | O | H | Cl | $OCH_3$ | CH | |
| 5-$OCH_3$ | — | Q-2 | $CH_3$ | O | H | $CH_3$ | $OCH_3$ | N | |
| 5-$OCH_3$ | — | Q-2 | $CH_3$ | O | H | $OCH_3$ | $OCH_3$ | N | |
| 6-Cl | — | Q-2 | $CH_3$ | O | H | $CH_3$ | $CH_3$ | CH | |
| 6-Cl | — | Q-2 | $CH_3$ | O | H | $OCH_3$ | $CH_3$ | CH | |
| 6-Cl | — | Q-2 | $CH_3$ | O | H | $OCH_3$ | $OCH_3$ | CH | |
| 6-$OCH_3$ | — | Q-2 | $CH_3$ | O | H | $CH_3$ | $CH_3$ | CH | |
| 6-$OCH_3$ | — | Q-2 | $CH_3$ | O | H | $OCH_3$ | $CH_3$ | CH | |
| 6-$OCH_3$ | — | Q-2 | $CH_3$ | O | H | $OCH_3$ | $OCH_3$ | CH | |
| 5-$SCH_3$ | — | Q-2 | $CH_3$ | O | H | $CH_3$ | $CH_3$ | CH | |
| 5-$SCH_3$ | — | Q-2 | $CH_3$ | O | H | $CH_3$ | $OCH_3$ | CH | |
| 5-$SCH_3$ | — | Q-2 | $CH_3$ | O | H | $OCH_3$ | $OCH_3$ | CH | |
| 5-$SCH_3$ | — | Q-2 | $CH_3$ | O | H | Cl | $OCH_3$ | CH | |
| 5-$SCH_3$ | — | Q-2 | $CH_3$ | O | H | $CH_3$ | $OCH_3$ | N | |
| 5-$SCH_3$ | — | Q-2 | $CH_3$ | O | H | $OCH_3$ | $OCH_3$ | N | |
| 5-$SCH_3$ | — | Q-2 | $C_2H_5$ | O | H | $CH_3$ | $CH_3$ | CH | |
| 5-$SCH_3$ | — | Q-2 | $C_2H_5$ | O | H | $CH_3$ | $OCH_3$ | CH | |
| 5-$SCH_3$ | — | Q-2 | $C_2H_5$ | O | H | $OCH_3$ | $OCH_3$ | CH | |
| 5-$SCH_3$ | — | Q-2 | $C_2H_5$ | O | H | Cl | $OCH_3$ | CH | |
| 5-$SCH_3$ | — | Q-2 | $C_2H_5$ | O | H | $CH_3$ | $OCH_3$ | N | |
| 5-$SCH_3$ | — | Q-2 | $C_2H_5$ | O | H | $OCH_3$ | $OCH_3$ | N | |
| H | — | Q-2 | $CH_3$ | O | $CH_3$ | $CH_3$ | $CH_3$ | CH | |
| H | — | Q-2 | $CH_3$ | O | $CH_3$ | $CH_3$ | $OCH_3$ | CH | |
| H | — | Q-2 | $CH_3$ | O | $CH_3$ | $OCH_3$ | $OCH_3$ | CH | |
| H | — | Q-2 | $CH_3$ | O | $CH_3$ | Cl | $OCH_3$ | CH | |
| H | — | Q-2 | $CH_3$ | O | $CH_3$ | $CH_3$ | $OCH_3$ | N | |
| H | — | Q-2 | $CH_3$ | O | $CH_3$ | $OCH_3$ | $OCH_3$ | N | |
| H | — | Q-2 | $CH_3$ | S | H | $CH_3$ | $CH_3$ | CH | |
| H | — | Q-2 | $CH_3$ | S | H | $CH_3$ | $OCH_3$ | CH | |
| H | — | Q-2 | $CH_3$ | S | H | $OCH_3$ | $OCH_3$ | CH | |
| H | — | Q-2 | $CH_3$ | S | H | Cl | $OCH_3$ | CH | |
| H | — | Q-2 | $CH_3$ | S | H | $CH_3$ | $OCH_3$ | N | |
| H | — | Q-2 | $CH_3$ | S | H | $OCH_3$ | $OCH_3$ | N | |
| H | — | Q-2 | $CH_3$ | O | H | $OC_2H_5$ | $NHCH_3$ | N | |
| H | — | Q-2 | $CH_3$ | O | H | H | $OCH_3$ | CH | |
| H | — | Q-2 | $CH_3$ | O | H | H | $OC_2H_5$ | CH | |
| H | — | Q-2 | $CH_3$ | O | H | H | $OCF_2H$ | CH | |
| H | — | Q-2 | $CH_3$ | O | H | $CH_3$ | $SCF_2H$ | CH | |
| H | — | Q-2 | $CH_3$ | O | H | Cl | $OCH_3$ | CH | |
| H | — | Q-2 | $CH_3$ | O | H | $CH_3$ | $CH_2OCH_3$ | CH | |
| H | — | Q-2 | $CH_3$ | O | H | $CH_3$ | $OCH_2OCH_3$ | CH | |
| H | — | Q-2 | $CH_3$ | O | H | $OC_2H_5$ | $NHCH_3$ | N | |
| H | — | Q-2 | $CH_3$ | O | H | H | $OCH_3$ | CH | |
| H | — | Q-2 | $CH_3$ | O | H | H | $OC_2H_5$ | CH | |
| H | — | Q-2 | $CH_3$ | O | H | $CH_3$ | $CF_3$ | CH | |
| H | — | Q-2 | $CH_3$ | O | H | $CH_3$ | $SCH_3$ | CH | |
| H | — | Q-2 | $CH_3$ | O | H | Cl | $OCH_3$ | CH | |
| H | — | Q-2 | $CH_3$ | O | H | $CH_3$ | $CH_2CH_3$ | CH | |
| H | — | Q-2 | $CH_3$ | O | H | $CH_3$ | $OCH_2OCH_3$ | CH | |
| H | — | Q-2 | $CH_3$ | O | H | $OCH_3$ | $OC_2H_5$ | N | |
| H | — | Q-2 | $CH_3$ | O | H | $OCH_3$ | $OCH(CH_3)_2$ | N | |
| H | — | Q-2 | $CH_3$ | O | H | $OCH_3$ | $OCH_2CF_3$ | N | |
| H | — | Q-2 | $CH_3$ | O | H | $OCH_3$ | $CF_3$ | N | |
| H | — | Q-2 | $CH_3$ | O | H | $OCH_3$ | $O(CH_2)_2OCH_3$ | N | |
| H | — | Q-2 | $CH_3$ | O | H | $OCH_3$ | $C{\equiv}C{-}CH_3$ | N | |
| H | — | Q-2 | $CH_3$ | O | H | $OCH_3$ | $N(CH_3)OCH_3$ | N | |
| H | — | Q-2 | $C_2H_5$ | S | H | $CH_3$ | $CH_3$ | CH | |
| H | — | Q-2 | $C_2H_5$ | S | H | $CH_3$ | $OCH_3$ | CH | |
| H | — | Q-2 | $C_2H_5$ | S | H | $OCH_3$ | $OCH_3$ | CH | |

TABLE I-continued

General Structure 1

| $R_1$ | E | Q | $R_3$ | W | R | X | Y | Z | m.p. (°C.) |
|---|---|---|---|---|---|---|---|---|---|
| H | — | Q-2 | $C_2H_5$ | S | H | Cl | $OCH_3$ | CH | |
| H | — | Q-2 | $C_2H_5$ | S | H | $CH_3$ | $OCH_3$ | N | |
| 6-$CH_3$ | — | Q-2 | $CH_3$ | O | H | $CH_3$ | $CH_3$ | CH | |
| 6-$CH_3$ | — | Q-2 | $CH_3$ | O | H | $CH_3$ | $OCH_3$ | CH | |
| 6-$CH_3$ | — | Q-2 | $CH_3$ | O | H | $OCH_3$ | $OCH_3$ | CH | |
| 6-$CH_3$ | — | Q-2 | $CH_3$ | O | H | Cl | $OCH_3$ | CH | |
| 6-$CH_3$ | — | Q-2 | $CH_3$ | O | H | $OCH_3$ | $CH_3$ | N | |
| 6-$CH_3$ | — | Q-1 | $CH_3$ | O | H | Br | $OCH_3$ | CH | 196-198 dec. |
| 6-$CH_3$ | — | Q-1 | $CH_3$ | O | $CH_3$ | $CH_3$ | $OCH_3$ | CH | 199-200 dec. |
| 6-$CH_3$ | — | Q-1 | $CH_3$ | O | $CH_3$ | $CH_3$ | $OCH_3$ | N | 49-56 |
| 6-$CH_3$ | — | Q-1 | $CH_3$ | O | H | H | $CH_3$ | CH | 196-199 dec. |
| 6-$CH_3$ | — | Q-1 | $CH_3$ | O | H | H | $OCH_3$ | CH | 163-166 dec. |
| 6-$CH_3$ | — | Q-1 | $CH_3$ | O | H | $C_2H_5$ | $OCH_3$ | CH | 160-164 |
| 6-$CH_3$ | — | Q-1 | $CH_3$ | O | H | $C_2H_5$ | $OCH_3$ | N | 179-180 dec. |
| 6-$CH_3$ | — | Q-1 | $CH_3$ | O | $CH_3$ | $OCH_3$ | $OCH_3$ | N | |
| 6-$CH_3$ | — | Q-1 | $CH_3$ | O | H | cyclopropyl | $OCH_3$ | N | 222-223 dec. |
| 6-$CH_3$ | — | Q-1 | $CH_3$ | O | H | $CH_3$ | $OC_2H_5$ | CH | |
| 6-$CH_3$ | — | Q-1 | $CH_3$ | O | H | $OCH_3$ | $CH_2OC_2H_5$ | CH | 189-190 dec. |
| 6-$CH_3$ | — | Q-1 | $CH_3$ | O | H | $OCH_3$ | $OCH_2CF_3$ | CH | 140-145 dec. |
| 6-$CH_3$ | — | Q-1 | $CH_3$ | O | H | $OCH_3$ | $OC_2H_5$ | N | 159-164 dec. |
| 6-$CH_3$ | — | Q-1 | $CH_3$ | O | H | $OCH_3$ | $OCF_2H$ | CH | 168-172 |
| 6-$CH_3$ | — | Q-1 | $CH_3$ | O | H | $CH_3$ | $OCF_2H$ | CH | 90-93 |
| H | — | Q-1 | $CH_3$ | NH | H | $OCH_3$ | $OCH_3$ | CH | |
| H | — | Q-1 | $CH_3$ | $NOCH_3$ | H | $CH_3$ | $OCH_3$ | CH | |
| H | — | Q-2 | $CH_3$ | NOH | H | $CH_3$ | $OCH_3$ | CH | |
| H | — | Q-2 | $C_2H_5$ | $NNHCH_3$ | H | $OCH_3$ | $OCH_3$ | CH | |
| 3-Cl | — | Q-1 | $CH_3$ | O | H | $OCH_3$ | $OCH_3$ | N | 199-202 |
| 3-Cl | — | Q-1 | $CH_3$ | O | H | $CH_3$ | $OCH_3$ | N | 206-209 |
| 3-Cl | — | Q-1 | $CH_3$ | O | H | $OCH_3$ | $OCH_3$ | CH | 143-162 |
| 3-Cl | — | Q-1 | $CH_3$ | O | H | $CH_3$ | $OCH_3$ | CH | 226-227 |
| 3-Cl | — | Q-1 | $CH_3$ | O | H | $CH_3$ | $CH_3$ | CH | 221-223 dec. |
| 3-Cl | — | Q-1 | $CH_3$ | O | H | Cl | $OCH_3$ | CH | 189-192 |
| 5-F | — | Q-1 | $CH_3$ | O | H | $OCH_3$ | $OCH_3$ | CH | 209-212 |
| 5-F | — | Q-1 | $CH_3$ | O | H | Cl | $OCH_3$ | CH | 199-201 |
| 5-F | — | Q-1 | $CH_3$ | O | H | $OCH_3$ | $OCH_3$ | N | 187-190 |
| 5-F | — | Q-1 | $CH_3$ | O | H | $CH_3$ | $OCH_3$ | N | 196-201 |
| 5-F | — | Q-1 | $CH_3$ | O | H | $CH_3$ | $CH_3$ | CH | 233-236 |
| 5-F | — | Q-1 | $CH_3$ | O | H | $CH_3$ | $OCH_3$ | CH | 164-168 |
| H | — | Q-1 | $C_2H_5$ | O | H | $OCH_3$ | $OCF_2H$ | CH | 87-94 |
| 6-Cl | — | Q-1 | $CH_3$ | O | H | $OCH_3$ | $OCF_2H$ | CH | 93-95 |
| 6-Cl | — | Q-1 | $CH_3$ | O | H | $CH_3$ | $OCF_2H$ | CH | 118-120 |
| 6-$OCH_3$ | — | Q-1 | $CH_3$ | O | H | $OCH_3$ | $OCH_3$ | N | 194-197 |
| 6-$OCH_3$ | — | Q-1 | $CH_3$ | O | H | $CH_3$ | $OCH_3$ | N | 172-182 |
| 6-$OCH_3$ | — | Q-1 | $CH_3$ | O | H | Cl | $OCH_3$ | CH | 206-209 |
| 6-Cl | — | Q-2 | $CH_3$ | O | H | Cl | $OCH_3$ | CH | |
| 6-Cl | — | Q-2 | $CH_3$ | O | H | $OCH_3$ | $OCH_3$ | N | |
| 6-Cl | — | Q-2 | $CH_3$ | O | H | $CH_3$ | $OCH_3$ | N | |
| 6-$OCH_3$ | — | Q-2 | $CH_3$ | O | H | Cl | $OCH_3$ | CH | |
| 6-$OCH_3$ | — | Q-2 | $CH_3$ | O | H | $OCH_3$ | $OCH_3$ | N | |
| 6-$OCH_3$ | — | Q-2 | $CH_3$ | O | H | $CH_3$ | $OCH_3$ | N | |

TABLE Ia

General Structure 1

| $R_1$ | E | Q | $R_4$ | W | R | X | Y | Z | m.p. (°C.) |
|---|---|---|---|---|---|---|---|---|---|
| H | — | Q-3 | H | O | H | $CH_3$ | $CH_3$ | CH | 214 dec. |
| H | — | Q-3 | H | O | H | $CH_3$ | $OCH_3$ | CH | 204-205 |
| H | — | Q-3 | H | O | H | $OCH_3$ | $OCH_3$ | CH | 187-188 |
| H | — | Q-3 | H | O | H | Cl | $OCH_3$ | CH | 195-196 |
| H | — | Q-3 | H | O | H | $CH_3$ | $OCH_3$ | N | 199-202 |
| H | — | Q-3 | H | O | H | $OCH_3$ | $OCH_3$ | N | 191-192 |
| H | — | Q-3 | $CH_3$ | O | H | $CH_3$ | $CH_3$ | CH | |
| H | — | Q-3 | $CH_3$ | O | H | $OC_2H_5$ | $NHCH_3$ | N | 167-200 dec. |
| H | — | Q-3 | $CH_3$ | O | H | $CH_3$ | $OCH_3$ | CH | 221-223 |
| H | — | Q-3 | $CH_3$ | O | H | $OCH_3$ | $OCH_3$ | CH | 213-216 |
| H | — | Q-3 | $CH_3$ | O | H | Cl | $OCH_3$ | CH | 208-210 |
| H | — | Q-3 | $CH_3$ | O | H | $CH_3$ | $OCH_3$ | N | 207-209 |
| H | — | Q-3 | $CH_3$ | O | H | $OCH_3$ | $OCH_3$ | N | 209-216 |
| H | — | Q-3 | $C_2H_5$ | O | H | $CH_3$ | $CH_3$ | CH | 217-220 |
| H | — | Q-3 | $C_2H_5$ | O | H | $CH_3$ | $OCH_3$ | CH | 224-228 |
| H | — | Q-3 | $C_2H_5$ | O | H | $OCH_3$ | $OCH_3$ | CH | 193-196 |
| H | — | Q-3 | $C_2H_5$ | O | H | Cl | $OCH_3$ | CH | 200-204 |
| H | — | Q-3 | $C_2H_5$ | O | H | $CH_3$ | $OCH_3$ | N | 174-179 |
| H | — | Q-3 | $C_2H_5$ | O | H | $OCH_3$ | $OCH_3$ | N | 194-197 |
| H | — | Q-3 | $CH(CH_3)_2$ | O | H | $CH_3$ | $CH_3$ | CH | |
| H | — | Q-3 | $CH(CH_3)_2$ | O | H | $CH_3$ | $OCH_3$ | CH | |
| H | — | Q-3 | $CH(CH_3)_2$ | O | H | $OCH_3$ | $OCH_3$ | CH | |
| H | — | Q-3 | $CH(CH_3)_2$ | O | H | Cl | $OCH_3$ | CH | |

TABLE Ia-continued

| | | | | General Structure 1 | | | | | |
|---|---|---|---|---|---|---|---|---|---|
| $R_1$ | E | Q | $R_4$ | W | R | X | Y | Z | m.p. (°C.) |
| H | — | Q-3 | $CH(CH_3)_2$ | O | H | $CH_3$ | $OCH_3$ | N | |
| H | — | Q-3 | $CH(CH_3)_2$ | O | H | $OCH_3$ | $OCH_3$ | N | |
| H | — | Q-3 | cyclopropyl | O | H | $CH_3$ | $CH_3$ | CH | |
| H | — | Q-3 | cyclopropyl | O | H | $CH_3$ | $OCH_3$ | CH | |
| H | — | Q-3 | cyclopropyl | O | H | $OCH_3$ | $OCH_3$ | CH | |
| H | — | Q-3 | cyclopropyl | O | H | Cl | $OCH_3$ | CH | |
| H | — | Q-3 | cyclopropyl | O | H | $CH_3$ | $OCH_3$ | N | |
| H | — | Q-3 | cyclopropyl | O | H | $OCH_3$ | $OCH_3$ | N | |
| H | — | Q-3 | $CH_2Cl$ | O | H | $CH_3$ | $CH_3$ | CH | |
| H | — | Q-3 | $CH_2Cl$ | O | H | $CH_3$ | $OCH_3$ | CH | |
| H | — | Q-3 | $CH_2Cl$ | O | H | $OCH_3$ | $OCH_3$ | CH | |
| H | — | Q-3 | $CH_2Cl$ | O | H | Cl | $OCH_3$ | CH | |
| H | — | Q-3 | $CH_2Cl$ | O | H | $CH_3$ | $OCH_3$ | N | |
| H | — | Q-3 | $CH_2Cl$ | O | H | $OCH_3$ | $OCH_3$ | N | |
| H | — | Q-3 | $CF_3$ | O | H | $CH_3$ | $CH_3$ | CH | |
| H | — | Q-3 | $CF_3$ | O | H | $CH_3$ | $OCH_3$ | CH | |
| H | — | Q-3 | $CF_3$ | O | H | $OCH_3$ | $OCH_3$ | CH | |
| H | — | Q-3 | $CF_3$ | O | H | Cl | $OCH_3$ | CH | |
| H | — | Q-3 | $CF_3$ | O | H | $CH_3$ | $OCH_3$ | N | |
| H | — | Q-3 | $CF_3$ | O | H | $OCH_3$ | $OCH_3$ | N | |
| H | — | Q-3 | $OCH_3$ | O | H | $CH_3$ | $CH_3$ | CH | 195-196 |
| H | — | Q-3 | $OCH_3$ | O | H | $CH_3$ | $OCH_3$ | CH | 175-177 |
| H | — | Q-3 | $OCH_3$ | O | H | $OCH_3$ | $OCH_3$ | CH | 188-189 |
| H | — | Q-3 | $OCH_3$ | O | H | Cl | $OCH_3$ | CH | 200-201 |
| H | — | Q-3 | $OCH_3$ | O | H | $CH_3$ | $OCH_3$ | N | 189-190 |
| H | — | Q-3 | $OCH_3$ | O | H | $OCH_3$ | $OCH_3$ | N | 180 |
| H | — | Q-3 | $OC_2H_5$ | O | H | $CH_3$ | $CH_3$ | CH | 199-200 dec. |
| H | — | Q-3 | $OC_2H_5$ | O | H | $CH_3$ | $OCH_3$ | CH | 197-198 dec. |
| H | — | Q-3 | $OC_2H_5$ | O | H | $OCH_3$ | $OCH_3$ | CH | 200-201 dec. |
| H | — | Q-3 | $OC_2H_5$ | O | H | Cl | $OCH_3$ | CH | 184-185 dec. |
| H | — | Q-3 | $OC_2H_5$ | O | H | $CH_3$ | $OCH_3$ | N | 170-173 dec. |
| H | — | Q-3 | $OC_2H_5$ | O | H | $OCH_3$ | $OCH_3$ | N | 178-180 dec. |
| H | — | Q-3 | $SCH_3$ | O | H | $CH_3$ | $CH_3$ | CH | |
| H | — | Q-3 | $SCH_3$ | O | H | $CH_3$ | $OCH_3$ | CH | |
| H | — | Q-3 | $SCH_3$ | O | H | $OCH_3$ | $OCH_3$ | CH | |
| H | — | Q-3 | $SCH_3$ | O | H | Cl | $OCH_3$ | CH | |
| H | — | Q-3 | $SCH_3$ | O | H | $CH_3$ | $OCH_3$ | N | |
| H | — | Q-3 | $SCH_3$ | O | H | $OCH_3$ | $OCH_3$ | N | |
| H | — | Q-3 | $N(CH_3)_2$ | O | H | $CH_3$ | $CH_3$ | CH | |
| H | — | Q-3 | $N(CH_3)_2$ | O | H | $CH_3$ | $OCH_3$ | CH | |
| H | — | Q-3 | $N(CH_3)_2$ | O | H | $OCH_3$ | $OCH_3$ | CH | |
| H | — | Q-3 | $N(CH_3)_2$ | O | H | Cl | $OCH_3$ | CH | |
| H | — | Q-3 | $N(CH_3)_2$ | O | H | $CH_3$ | $OCH_3$ | N | |
| H | — | Q-3 | $N(CH_3)_2$ | O | H | $OCH_3$ | $OCH_3$ | N | |
| 5-$CH_3$ | — | Q-3 | $CH_3$ | O | H | $CH_3$ | $CH_3$ | CH | |
| 5-$CH_3$ | — | Q-3 | $CH_3$ | O | H | $CH_3$ | $OCH_3$ | CH | |
| 5-$CH_3$ | — | Q-3 | $CH_3$ | O | H | $OCH_3$ | $OCH_3$ | CH | 177-186 |
| 5-$CH_3$ | — | Q-3 | $CH_3$ | O | H | Cl | $OCH_3$ | CH | 207-208 |
| 5-$CH_3$ | — | Q-3 | $CH_3$ | O | H | $CH_3$ | $OCH_3$ | N | 200-202 |
| 5-$CH_3$ | — | Q-3 | $CH_3$ | O | H | $OCH_3$ | $OCH_3$ | N | |
| 5-Cl | — | Q-3 | $CH_3$ | O | H | $CH_3$ | $CH_3$ | CH | 227-230 |
| 5-Cl | — | Q-3 | $CH_3$ | O | H | $CH_3$ | $OCH_3$ | CH | 173-180 |
| 5-Cl | — | Q-3 | $CH_3$ | O | H | $OCH_3$ | $OCH_3$ | CH | 216-220 |
| 5-Cl | — | Q-3 | $CH_3$ | O | H | Cl | $OCH_3$ | CH | 227-230 |
| 5-Cl | — | Q-3 | $CH_3$ | O | H | $CH_3$ | $OCH_3$ | N | 188-195 |
| 5-Cl | — | Q-3 | $CH_3$ | O | H | $OCH_3$ | $OCH_3$ | N | 192-194 |
| 5-Cl | — | Q-3 | $CH_3$ | O | H | $OC_2H_5$ | $NHCH_3$ | N | 181-185 |
| 5-Br | — | Q-3 | $CH_3$ | O | H | $CH_3$ | $CH_3$ | CH | |
| 5-Br | — | Q-3 | $CH_3$ | O | H | $CH_3$ | $OCH_3$ | CH | |
| 5-Br | — | Q-3 | $CH_3$ | O | H | $OCH_3$ | $OCH_3$ | CH | |
| 5-Br | — | Q-3 | $CH_3$ | O | H | Cl | $OCH_3$ | CH | |
| 5-Br | — | Q-3 | $CH_3$ | O | H | $CH_3$ | $OCH_3$ | N | |
| 5-Br | — | Q-3 | $CH_3$ | O | H | $OCH_3$ | $OCH_3$ | H | |
| 5-$OCF_2H$ | — | Q-3 | $CH_3$ | O | H | $CH_3$ | $CH_3$ | CH | |
| 5-$OCF_2H$ | — | Q-3 | $CH_3$ | O | H | $CH_3$ | $OCH_3$ | CH | |
| 5-$OCF_2H$ | — | Q-3 | $CH_3$ | O | H | $OCH_3$ | $OCH_3$ | CH | |
| 5-$OCF_2H$ | — | Q-3 | $CH_3$ | O | H | Cl | $OCH_3$ | CH | |
| 5-$OCF_2H$ | — | Q-3 | $CH_3$ | O | H | $CH_3$ | $OCH_3$ | N | |
| 5-$OCF_2H$ | — | Q-3 | $CH_3$ | O | H | $OCH_3$ | $OCH_3$ | N | |
| 5-$OCH_3$ | — | Q-3 | $CH_3$ | O | H | $CH_3$ | $CH_3$ | CH | |
| 5-$OCH_3$ | — | Q-3 | $CH_3$ | O | H | $CH_3$ | $OCH_3$ | CH | |
| 5-$OCH_3$ | — | Q-3 | $CH_3$ | O | H | $OCH_3$ | $OCH_3$ | CH | |
| 5-$OCH_3$ | — | Q-3 | $CH_3$ | O | H | Cl | $OCH_3$ | CH | |
| 5-$OCH_3$ | — | Q-3 | $CH_3$ | O | H | $CH_3$ | $OCH_3$ | N | |
| 5-$OCH_3$ | — | Q-3 | $CH_3$ | O | H | $OCH_3$ | $OCH_3$ | N | |
| 5-$CF_3$ | — | Q-3 | $CH_3$ | O | H | $CH_3$ | $CH_3$ | CH | |
| 5-$CF_3$ | — | Q-3 | $CH_3$ | O | H | $CH_3$ | $OCH_3$ | CH | |
| 5-$CF_3$ | — | Q-3 | $CH_3$ | O | H | $OCH_3$ | $OCH_3$ | CH | |
| 5-$CF_3$ | — | Q-3 | $CH_3$ | O | H | Cl | $OCH_3$ | CH | |
| 5-$CF_3$ | — | Q-3 | $CH_3$ | O | H | $CH_3$ | $OCH_3$ | N | |

TABLE Ia-continued

| | | | | General Structure 1 | | | | | |
|---|---|---|---|---|---|---|---|---|---|
| $R_1$ | E | Q | $R_4$ | W | R | X | Y | Z | m.p. (°C.) |
| 5-$CF_3$ | — | Q-3 | $CH_3$ | O | H | $OCH_3$ | $OCH_3$ | N | |
| 5-$SCH_3$ | — | Q-3 | $CH_3$ | O | H | $CH_3$ | $CH_3$ | CH | |
| 5-$SCH_3$ | — | Q-3 | $CH_3$ | O | H | $CH_3$ | $OCH_3$ | CH | |
| 5-$SCH_3$ | — | Q-3 | $CH_3$ | O | H | $OCH_3$ | $OCH_3$ | CH | |
| 5-$SCH_3$ | — | Q-3 | $CH_3$ | O | H | Cl | $OCH_3$ | CH | |
| 5-$SCH_3$ | — | Q-3 | $CH_3$ | O | H | $CH_3$ | $OCH_3$ | N | |
| 5-$SCH_3$ | — | Q-3 | $CH_3$ | O | H | $OCH_3$ | $OCH_3$ | N | |
| 5-$CH_2OCH_3$ | — | Q-3 | $CH_3$ | O | H | $CH_3$ | $CH_3$ | CH | |
| 5-$CH_2OCH_3$ | — | Q-3 | $CH_3$ | O | H | $CH_3$ | $OCH_3$ | CH | |
| 5-$CH_2OCH_3$ | — | Q-3 | $CH_3$ | O | H | $OCH_3$ | $OCH_3$ | CH | |
| 5-$CH_2OCH_3$ | — | Q-3 | $CH_3$ | O | H | Cl | $OCH_3$ | CH | |
| 5-$CH_2OCH_3$ | — | Q-3 | $CH_3$ | O | H | $CH_3$ | $OCH_3$ | N | |
| 5-$CH_2OCH_3$ | — | Q-3 | $CH_3$ | O | H | $OCH_3$ | $OCH_3$ | N | |
| 5-$OCH_2CH_3$ | — | Q-3 | $CH_3$ | O | H | $CH_3$ | $CH_3$ | CH | |
| 5-$OCH_2CH_3$ | — | Q-3 | $CH_3$ | O | H | $CH_3$ | $OCH_3$ | CH | |
| 5-$OCH_2CH_3$ | — | Q-3 | $CH_3$ | O | H | $OCH_3$ | $OCH_3$ | CH | |
| 5-$OCH_2CH_3$ | — | Q-3 | $CH_3$ | O | H | Cl | $OCH_3$ | CH | |
| 5-$OCH_2CH_3$ | — | Q-3 | $CH_3$ | O | H | $CH_3$ | $OCH_3$ | N | |
| 5-$OCH_2CH_3$ | — | Q-3 | $CH_3$ | O | H | $OCH_3$ | $OCH_3$ | N | |
| H | — | Q-3 | $CH_2OCH_3$ | O | H | $CH_3$ | $CH_3$ | CH | |
| H | — | Q-3 | $CH_2OCH_3$ | O | H | $CH_3$ | $OCH_3$ | CH | |
| H | — | Q-3 | $CH_2OCH_3$ | O | H | $OCH_3$ | $OCH_3$ | CH | |
| H | — | Q-3 | $CH_2OCH_3$ | O | H | Cl | $OCH_3$ | CH | |
| H | — | Q-3 | $CH_2OCH_3$ | O | H | $OCH_3$ | $CH_3$ | N | |
| H | — | Q-3 | $CH_2OCH_3$ | O | H | $OCH_3$ | $OCH_3$ | N | |
| H | — | Q-3 | $CH_3$ | O | H | cyclopropyl | $OCH_3$ | CH | |
| H | — | Q-3 | $CH_3$ | O | H | $OCH_3$ | $N_3$ | CH | |
| H | — | Q-3 | $CH_3$ | O | H | $OCH_3$ | CN | CH | |
| H | — | Q-3 | $CH_3$ | O | H | $OCH_3$ | $C(O)CH_3$ | CH | |
| H | — | Q-3 | $CH_3$ | O | H | $OCH_3$ | $CH(OCH_3)_2$ | CH | |
| H | — | Q-3 | $CH_3$ | O | H | $OCH_3$ | 1,3-dioxo-lan-2-yl | CH | |
| H | — | Q-3 | $CH_3$ | O | H | $OCH_3$ | 1,3-diox-an-2-yl | CH | |
| H | $CH_2$ | Q-3 | $CH_3$ | O | H | $CH_3$ | $CH_3$ | CH | |
| H | $CH_2$ | Q-3 | $CH_3$ | O | H | $CH_3$ | $OCH_3$ | CH | |
| H | $CH_2$ | Q-3 | $CH_3$ | O | H | $OCH_3$ | $OCH_3$ | CH | |
| H | $CH_2$ | Q-3 | $CH_3$ | O | H | Cl | $OCH_3$ | CH | |
| H | $CH_2$ | Q-3 | $CH_3$ | O | H | $CH_3$ | $OCH_3$ | N | |
| H | $CH_2$ | Q-3 | $CH_3$ | O | H | $OCH_3$ | $OCH_3$ | N | |
| H | O | Q-3 | $CH_3$ | O | H | $CH_3$ | $CH_3$ | CH | |
| H | O | Q-3 | $CH_3$ | O | H | $CH_3$ | $OCH_3$ | CH | |
| H | O | Q-3 | $CH_3$ | O | H | $OCH_3$ | $OCH_3$ | CH | |
| H | O | Q-3 | $CH_3$ | O | H | Cl | $OCH_3$ | CH | |
| H | O | Q-3 | $CH_3$ | O | H | $CH_3$ | $OCH_3$ | N | |
| H | O | Q-3 | $CH_3$ | O | H | $OCH_3$ | $OCH_3$ | N | |
| H | — | Q-3 | $CH_3$ | S | H | $CH_3$ | $CH_3$ | CH | |
| H | — | Q-3 | $CH_3$ | S | H | $CH_3$ | $OCH_3$ | CH | |
| H | — | Q-3 | $CH_3$ | S | H | $OCH_3$ | $OCH_3$ | CH | |
| H | — | Q-3 | $CH_3$ | S | H | Cl | $OCH_3$ | CH | |
| H | — | Q-3 | $CH_3$ | S | H | $CH_3$ | $OCH_3$ | N | |
| H | — | Q-3 | $CH_3$ | S | H | $OCH_3$ | $OCH_3$ | N | |
| H | — | Q-3 | $CH_3$ | O | $CH_3$ | $CH_3$ | $CH_3$ | CH | |
| H | — | Q-3 | $CH_3$ | O | $CH_3$ | $CH_3$ | $OCH_3$ | CH | |
| H | — | Q-3 | $CH_3$ | O | $CH_3$ | $OCH_3$ | $OCH_3$ | CH | |
| H | — | Q-3 | $CH_3$ | O | $CH_3$ | Cl | $OCH_3$ | CH | |
| H | — | Q-3 | $CH_3$ | O | $CH_3$ | $CH_3$ | $OCH_3$ | N | |
| H | — | Q-3 | $CH_3$ | O | $CH_3$ | $OCH_3$ | $OCH_3$ | N | 180-182(d) |
| H | — | Q-3 | $CH_3$ | O | H | $OC_2H_5$ | $NHCH_3$ | CH | |
| H | — | Q-3 | $CH_3$ | O | H | H | $OCH_3$ | CH | |
| H | — | Q-3 | $CH_3$ | O | H | H | $OC_2H_5$ | CH | |
| H | — | Q-3 | $CH_3$ | O | H | H | $OCF_2H$ | CH | |
| H | — | Q-3 | $CH_3$ | O | H | $CH_3$ | $SCF_2H$ | CH | |
| H | — | Q-3 | $CH_3$ | O | H | $CH_3$ | $CH_2OCH_3$ | CH | |
| H | — | Q-3 | $CH_3$ | O | H | $OCH_3$ | $OC_2H_5$ | CH | |
| H | — | Q-3 | $CH_3$ | O | H | $OCH_3$ | $CF_3$ | CH | |
| H | — | Q-3 | $CH_3$ | O | H | $OCH_3$ | $O(CH_2)_2OCH_3$ | CH | |
| H | — | Q-3 | $CH_3$ | O | H | $OCH_3$ | $SCF_2H$ | CH | |
| H | — | Q-3 | $CH_3$ | O | H | $OCH_3$ | $C{\equiv}CH$ | CH | |
| H | — | Q-3 | $CH_3$ | O | H | $OCH_3$ | $C{\equiv}C{-}CH_3$ | CH | |
| H | — | Q-3 | $CH_3$ | O | H | $OCH_3$ | $N(OCH_3)CH_3$ | CH | |
| H | — | Q-4 | $CH_3$ | O | H | $CH_3$ | $CH_3$ | CH | |
| H | — | Q-4 | $CH_3$ | O | H | $CH_3$ | $OCH_3$ | CH | |
| H | — | Q-4 | $CH_3$ | O | H | $OCH_3$ | $OCH_3$ | CH | |
| H | — | Q-4 | $CH_3$ | O | H | Cl | $OCH_3$ | CH | |
| H | — | Q-4 | $CH_3$ | O | H | $CH_3$ | $OCH_3$ | N | |
| H | — | Q-4 | $CH_3$ | O | H | $OCH_3$ | $OCH_3$ | N | |
| H | — | Q-4 | $OCH_3$ | O | H | $CH_3$ | $CH_3$ | CH | |
| H | — | Q-4 | $OCH_3$ | O | H | $CH_3$ | $OCH_3$ | CH | |
| H | — | Q-4 | $OCH_3$ | O | H | $OCH_3$ | $OCH_3$ | CH | |

TABLE Ia-continued

| | | | | General Structure 1 | | | | | |
|---|---|---|---|---|---|---|---|---|---|
| $R_1$ | E | Q | $R_4$ | W | R | X | Y | Z | m.p. (°C.) |
| H | — | Q-4 | $OCH_3$ | O | H | Cl | $OCH_3$ | CH | |
| H | — | Q-4 | $OCH_3$ | O | H | $CH_3$ | $OCH_3$ | N | |
| H | — | Q-4 | $OCH_3$ | O | H | $OCH_3$ | $OCH_3$ | N | |
| H | — | Q-4 | $SCH_3$ | O | H | $OCH_3$ | $OCH_3$ | N | |
| H | — | Q-4 | $SCH_3$ | O | H | $CH_3$ | $OCH_3$ | CH | |
| H | — | Q-4 | $SCH_3$ | O | H | $OCH_3$ | $OCH_3$ | CH | |
| H | — | Q-4 | $SCH_3$ | O | H | Cl | $OCH_3$ | CH | |
| H | — | Q-4 | $SCH_3$ | O | H | $CH_3$ | $OCH_3$ | N | |
| H | — | Q-4 | $SCH_3$ | O | H | $OCH_3$ | $OCH_3$ | N | |
| H | — | Q-4 | $N(CH_2)_4$ | O | H | $CH_3$ | $CH_3$ | CH | |
| H | — | Q-4 | $N(CH_2)_4$ | O | H | $CH_3$ | $OCH_3$ | CH | |
| H | — | Q-4 | $N(CH_2)_4$ | O | H | $OCH_3$ | $OCH_3$ | CH | |
| H | — | Q-4 | $N(CH_2)_4$ | O | H | Cl | $OCH_3$ | CH | |
| H | — | Q-4 | $N(CH_2)_4$ | O | H | $CH_3$ | $OCH_3$ | N | |
| H | — | Q-4 | $N(CH_2)_4$ | O | H | $OCH_3$ | $OCH_3$ | N | |
| H | — | Q-4 | $C_6H_5$ | O | M | $OCH_3$ | $OCH_3$ | CH | |
| H | — | Q-4 | $C_6H_5$ | O | H | $OCH_3$ | $CH_3$ | CH | |
| H | — | Q-4 | $C_6H_5$ | O | H | $CH_3$ | $CH_3$ | CH | |
| H | — | Q-4 | $C_6H_5$ | O | H | Cl | $OCH_3$ | CH | |
| H | — | Q-4 | $C_6H_5$ | O | H | $CH_3$ | $OCH_3$ | N | |
| H | — | Q-4 | $CF_3$ | O | H | $CH_3$ | $OCH_3$ | CH | |
| H | — | Q-4 | $CF_3$ | O | H | $CH_3$ | $CH_3$ | CH | |
| H | — | Q-4 | $CF_3$ | O | H | $OCH_3$ | $OCH_3$ | CH | |
| H | — | Q-4 | $CF_3$ | O | H | Cl | $OCH_3$ | CH | |
| H | — | Q-4 | $CF_3$ | O | H | $OCH_3$ | $CH_3$ | N | |
| H | — | Q-4 | $CF_3$ | O | H | $OC_2H_5$ | $NHCH_3$ | N | |
| H | — | Q-4 | $CH_2CH{=}CH_2$ | O | H | $CH_3$ | $CH_3$ | CH | |
| H | — | Q-4 | $CH_2CH{=}CH_2$ | O | H | $CH_3$ | $OCH_3$ | CH | |
| H | — | Q-4 | $CH_2CH{=}CH_2$ | O | H | $OCH_3$ | $OCH_3$ | CH | |
| H | — | Q-4 | $CH_2CH{=}CH_2$ | O | H | $OCH_3$ | $CH_3$ | N | |
| 6-$CH_3$ | — | Q-3 | $CH_3$ | O | H | $CH_3$ | $CH_3$ | CH | |
| 6-$CH_3$ | — | Q-3 | $CH_3$ | O | H | $OCH_3$ | $CH_3$ | CH | |
| 6-$CH_3$ | — | Q-3 | $CH_3$ | O | H | $OCH_3$ | $OCH_3$ | CH | |
| 6-$CH_3$ | — | Q-3 | $CH_3$ | O | H | Cl | $OCH_3$ | CH | |
| 6-$CH_3$ | — | Q-3 | $CH_3$ | O | H | $OCH_3$ | $CH_3$ | N | |
| 6-Cl | — | Q-3 | $CH_3$ | O | H | $CH_3$ | $CH_3$ | CH | |
| 6-Cl | — | Q-3 | $CH_3$ | O | H | $OCH_3$ | $CH_3$ | CH | |
| 6-Cl | — | Q-3 | $CH_3$ | O | H | $OCH_3$ | $OCH_3$ | CH | |
| 6-Cl | — | Q-3 | $CH_3$ | O | H | Cl | $OCH_3$ | CH | |
| H | — | Q-3 | $OC_3H_7$ | O | H | $OCH_3$ | $OCH_3$ | CH | 170-171 |
| H | — | Q-3 | $OC_3H_7$ | O | H | $CH_3$ | $OCH_3$ | CH | 171-173 |
| H | — | Q-3 | $OC_3H_7$ | O | H | $CH_3$ | $CH_3$ | CH | 176-178 |
| H | — | Q-3 | $OC_3H_7$ | O | H | Cl | $OCH_3$ | CH | 163-167 |
| H | — | Q-3 | $OC_3H_7$ | O | H | $OCH_3$ | $OCH_3$ | N | 148-152 |
| H | — | Q-3 | $OC_3H_7$ | O | H | $CH_3$ | $OCH_3$ | N | 158-160 |
| 5-$CH_3$ | — | Q-3 | $OCH_3$ | O | H | $OCH_3$ | $OCH_3$ | CH | 181-184 |
| 5-$CH_3$ | — | Q-3 | $OCH_3$ | O | H | $CH_3$ | $OCH_3$ | CH | 188-190 |
| 5-$CH_3$ | — | Q-3 | $OCH_3$ | O | H | $CH_3$ | $CH_3$ | CH | 166-168 |
| 5-$CH_3$ | — | Q-3 | $OCH_3$ | O | H | Cl | $OCH_3$ | CH | 182-184 |
| 5-$CH_3$ | — | Q-3 | $OCH_3$ | O | H | $OCH_3$ | $OCH_3$ | N | 184-186 |
| 5-$CH_3$ | — | Q-3 | $OCH_3$ | O | H | $CH_3$ | $OCH_3$ | N | 175-178 |
| 5-$CH_3$ | — | Q-3 | $OC_2H_5$ | O | H | $OCH_3$ | $OCH_3$ | CH | 180-181 |
| 5-$CH_3$ | — | Q-3 | $OC_2H_5$ | O | H | $CH_3$ | $OCH_3$ | CH | 188-191 |
| 5-$CH_3$ | — | Q-3 | $OC_2H_5$ | O | H | $CH_3$ | $CH_3$ | CH | 198-199 |
| 5-$CH_3$ | — | Q-3 | $OC_2H_5$ | O | H | Cl | $OCH_3$ | CH | 184-186 |
| 5-$CH_3$ | — | Q-3 | $OC_2H_5$ | O | H | $OCH_3$ | $OCH_3$ | N | 204-206 |
| 5-$CH_3$ | — | Q-3 | $OC_2H_5$ | O | H | $CH_3$ | $OCH_3$ | N | 175-179 |
| 5-$OCH_3$ | — | Q-3 | $OCH_3$ | O | H | $OCH_3$ | $OCH_3$ | CH | 192-193 |
| 5-$OCH_3$ | — | Q-3 | $OCH_3$ | O | H | $CH_3$ | $OCH_3$ | CH | 182-184 |
| 5-$OCH_3$ | — | Q-3 | $OCH_3$ | O | H | $CH_3$ | $CH_3$ | CH | 181-183 |
| 5-$OCH_3$ | — | Q-3 | $OCH_3$ | O | H | Cl | $OCH_3$ | CH | 172-175 |
| 5-$OCH_3$ | — | Q-3 | $OCH_3$ | O | H | $OCH_3$ | $OCH_3$ | N | 167-170 |
| 5-$OCH_3$ | — | Q-3 | $OCH_3$ | O | H | $CH_3$ | $OCH_3$ | N | 174-176 |
| H | — | Q-3 | $OCF_2H$ | O | H | $OCH_3$ | $OCH_3$ | CH | |
| H | — | Q-3 | $OCF_2H$ | O | H | $CH_3$ | $OCH_3$ | CH | |
| H | — | Q-3 | $OCF_2H$ | O | H | $CH_3$ | $CH_3$ | CH | |
| H | — | Q-3 | $OCF_2H$ | O | H | Cl | $OCH_3$ | CH | |
| H | — | Q-3 | $OCF_2H$ | O | H | $OCH_3$ | $OCH_3$ | N | |
| H | — | Q-3 | $OCF_2H$ | O | H | $CH_3$ | $OCH_3$ | N | |
| 3-$CH_3$ | — | Q-3 | $OC_2H_5$ | O | H | $OCH_3$ | $OCH_3$ | CH | |
| 3-$CH_3$ | — | Q-3 | $OC_2H_5$ | O | H | $CH_3$ | $OCH_3$ | CH | |
| 3-$CH_3$ | — | Q-3 | $OC_2H_5$ | O | H | $CH_3$ | $CH_3$ | CH | |
| 3-$CH_3$ | — | Q-3 | $OC_2H_5$ | O | H | Cl | $OCH_3$ | CH | |
| 3-$CH_3$ | — | Q-3 | $OC_2H_5$ | O | H | $OCH_3$ | $OCH_3$ | N | |
| 3-$CH_3$ | — | Q-3 | $OC_2H_5$ | O | H | $CH_3$ | $OCH_3$ | N | |
| 5-$OC_2H_5$ | — | Q-3 | $OCH_3$ | O | H | $OCH_3$ | $OCH_3$ | CH | |
| 5-$OC_2H_5$ | — | Q-3 | $OCH_3$ | O | H | $CH_3$ | $OCH_3$ | CH | |
| 5-$OC_2H_5$ | — | Q-3 | $OCH_3$ | O | H | $CH_3$ | $CH_3$ | CH | |
| 5-$OC_2H_5$ | — | Q-3 | $OCH_3$ | O | H | Cl | $OCH_3$ | CH | |
| 5-$OC_2H_5$ | — | Q-3 | $OCH_3$ | O | H | $OCH_3$ | $OCH_3$ | N | |

TABLE Ia-continued

| R1 | E | Q | R4 | W | R | X | Y | Z | m.p. (°C.) |
|---|---|---|---|---|---|---|---|---|---|
| | | | General Structure 1 | | | | | | |
| 5-$OC_2H_5$ | — | Q-3 | $OCH_3$ | O | H | $CH_3$ | $OCH_3$ | N | |
| 5-$OC_2H_5$ | — | Q-3 | $OC_2H_5$ | O | H | $OCH_3$ | $OCH_3$ | CH | |
| 5-$OC_2H_5$ | — | Q-3 | $OC_2H_5$ | O | H | $CH_3$ | $OCH_3$ | CH | |
| 5-$OC_2H_5$ | — | Q-3 | $OC_2H_5$ | O | H | $CH_3$ | $CH_3$ | CH | |
| 5-$OC_2H_5$ | — | Q-3 | $OC_2H_5$ | O | H | Cl | $OCH_3$ | CH | |
| 5-$OC_2H_5$ | — | Q-3 | $OC_2H_5$ | O | H | $OCH_3$ | $OCH_3$ | N | |
| 5-$OC_2H_5$ | — | Q-3 | $OC_2H_5$ | O | H | $CH_3$ | $OCH_3$ | N | |
| 5-Br | — | Q-3 | $OCH_3$ | O | H | $OCH_3$ | $OCH_3$ | CH | |
| 5-Br | — | Q-3 | $OCH_3$ | O | H | $CH_3$ | $OCH_3$ | CH | |
| 5-Br | — | Q-3 | $OCH_3$ | O | H | $CH_3$ | $CH_3$ | CH | |
| 5-Br | — | Q-3 | $OCH_3$ | O | H | Cl | $OCH_3$ | CH | |
| 5-Br | — | Q-3 | $OCH_3$ | O | H | $OCH_3$ | $OCH_3$ | N | |
| 5-Br | — | Q-3 | $OCH_3$ | O | H | $CH_3$ | $OCH_3$ | N | |
| 5-Br | — | Q-3 | $OC_2H_5$ | O | H | $OCH_3$ | $OCH_3$ | CH | |
| 5-Br | — | Q-3 | $OC_2H_5$ | O | H | $CH_3$ | $OCH_3$ | CH | |
| 5-Br | — | Q-3 | $OC_2H_5$ | O | H | $CH_3$ | $CH_3$ | CH | |
| 5-Br | — | Q-3 | $OC_2H_5$ | O | H | Cl | $OCH_3$ | CH | |
| 5-Br | — | Q-3 | $OC_2H_5$ | O | H | $OCH_3$ | $OCH_3$ | N | |
| 5-Br | — | Q-3 | $OC_2H_5$ | O | H | $CH_3$ | $OCH_3$ | N | |
| H | — | Q-3 | $SOCH_3$ | O | H | $OCH_3$ | $OCH_3$ | CH | |
| H | — | Q-3 | $SOCH_3$ | O | H | $CH_3$ | $OCH_3$ | CH | |
| H | — | Q-3 | $SOCH_3$ | O | H | $CH_3$ | $CH_3$ | CH | |
| H | — | Q-3 | $SOCH_3$ | O | H | Cl | $OCH_3$ | CH | |
| H | — | Q-3 | $SOCH_3$ | O | H | $OCH_3$ | $OCH_3$ | N | |
| H | — | Q-3 | $SOCH_3$ | O | H | $CH_3$ | $OCH_3$ | N | |
| H | — | Q-3 | $SO_2CH_3$ | O | H | $OCH_3$ | $OCH_3$ | CH | |
| H | — | Q-3 | $SO_2CH_3$ | O | H | $CH_3$ | $OCH_3$ | CH | |
| H | — | Q-3 | $SO_2CH_3$ | O | H | $CH_3$ | $CH_3$ | CH | |
| H | — | Q-3 | $SO_2CH_3$ | O | H | Cl | $OCH_3$ | CH | |
| H | — | Q-3 | $SO_2CH_3$ | O | H | $OCH_3$ | $OCH_3$ | N | |
| H | — | Q-3 | $SO_2CH_3$ | O | H | $CH_3$ | $OCH_3$ | N | |
| H | — | Q-3 | $CH_2CH=CH_2$ | O | H | $OCH_3$ | $OCH_3$ | CH | |
| H | — | Q-3 | $CH_2CH=CH_2$ | O | H | $CH_3$ | $OCH_3$ | CH | |
| H | — | Q-3 | $CH_2CH=CH_2$ | O | H | $CH_3$ | $CH_3$ | CH | |
| H | — | Q-3 | $CH_2CH=CH_2$ | O | H | Cl | $OCH_3$ | CH | |
| H | — | Q-3 | $CH_2CH=CH_2$ | O | H | $OCH_3$ | $OCH_3$ | N | |
| H | — | Q-3 | $CH_2CH=CH_2$ | O | H | $CH_3$ | $OCH_3$ | N | |
| 6-$CH_3$ | — | Q-3 | $OCH_3$ | O | H | $OCH_3$ | $OCH_3$ | CH | |
| 6-$CH_3$ | — | Q-3 | $OCH_3$ | O | H | $CH_3$ | $OCH_3$ | CH | |
| 6-$CH_3$ | — | Q-3 | $OCH_3$ | O | H | $CH_3$ | $CH_3$ | CH | |
| 6-$CH_3$ | — | Q-3 | $OCH_3$ | O | H | Cl | $OCH_3$ | CH | |
| 6-$CH_3$ | — | Q-3 | $OCH_3$ | O | H | $OCH_3$ | $OCH_3$ | N | |
| 6-$CH_3$ | — | Q-3 | $OCH_3$ | O | H | $CH_3$ | $OCH_3$ | N | |
| 6-Cl | — | Q-3 | $OCH_3$ | O | H | $OCH_3$ | $OCH_3$ | CH | |
| 6-Cl | — | Q-3 | $OCH_3$ | O | H | $CH_3$ | $OCH_3$ | CH | |
| 6-Cl | — | Q-3 | $OCH_3$ | O | H | $CH_3$ | $CH_3$ | CH | |
| 6-Cl | — | Q-3 | $OCH_3$ | O | H | Cl | $OCH_3$ | CH | |
| 6-Cl | — | Q-3 | $OCH_3$ | O | H | $OCH_3$ | $OCH_3$ | N | |
| 6-Cl | — | Q-3 | $OCH_3$ | O | H | $CH_3$ | $OCH_3$ | N | |
| 6-$CH_3$ | — | Q-3 | $CH_3$ | O | H | $OCH_3$ | $OCH_3$ | N | |
| 6-Cl | — | Q-3 | $CH_3$ | O | H | $CH_3$ | $OCH_3$ | N | |
| 6-Cl | — | Q-3 | $CH_3$ | O | H | $OCH_3$ | $OCH_3$ | N | |
| H | — | Q-4 | $CH_2CH=CH_2$ | O | H | Cl | $OCH_3$ | CH | |
| H | — | Q-4 | $CH_2CH=CH_2$ | O | H | $OCH_3$ | $OCH_3$ | N | |

TABLE Ib

| R1 | E | Q | R5 | W | R | X | Y | Z | m.p. (°C.) |
|---|---|---|---|---|---|---|---|---|---|
| | | | General Structure I | | | | | | |
| H | — | Q-5 | $CH_3$ | O | H | $CH_3$ | $CH_3$ | CH | |
| H | — | Q-5 | $CH_3$ | O | H | $CH_3$ | $OCH_3$ | N | 199-201 |
| H | — | Q-5 | $CH_3$ | O | H | $OCH_3$ | $OCH_3$ | CH | 213-218 |
| H | — | Q-5 | $CH_3$ | O | H | Cl | $OCH_3$ | CH | |
| H | — | Q-5 | $CH_3$ | O | H | $CH_3$ | $OCH_3$ | N | |
| H | — | Q-5 | $CH_3$ | O | H | $OCH_3$ | $OCH_3$ | N | |
| H | — | Q-5 | $CH_2CH_3$ | O | H | $CH_3$ | $CH_3$ | CH | 185-189 |
| H | — | Q-5 | $CH_2CH_3$ | O | H | $CH_3$ | $OCH_3$ | CH | 201-206 |
| H | — | Q-5 | $CH_2CH_3$ | O | H | $OCH_3$ | $OCH_3$ | CH | 191-209 |
| H | — | Q-5 | $CH_2CH_3$ | O | H | Cl | $OCH_3$ | CH | 196-199 |
| H | — | Q-5 | $CH_2CH_3$ | O | H | $CH_3$ | $OCH_3$ | N | 194-198 |
| H | — | Q-5 | $CH_2CH_3$ | O | H | $OCH_3$ | $OCH_3$ | N | 166-169 |
| H | — | Q-6 | $CH_3$ | O | H | $CH_3$ | $CH_3$ | CH | |
| H | — | Q-6 | $CH_3$ | O | H | $CH_3$ | $OCH_3$ | CH | |
| H | — | Q-6 | $CH_3$ | O | H | $OCH_3$ | $OCH_3$ | CH | |
| H | — | Q-6 | $CH_3$ | O | H | Cl | $OCH_3$ | CH | |
| H | — | Q-6 | $CH_3$ | O | H | $CH_3$ | $OCH_3$ | N | |
| H | — | Q-6 | $CH_3$ | O | H | $OCH_3$ | $OCH_3$ | N | |
| H | — | Q-6 | $C_2H_5$ | O | H | $CH_3$ | $CH_3$ | CH | |

TABLE Ib-continued

| General Structure I | | | | | | | | | |
|---|---|---|---|---|---|---|---|---|---|
| $R_1$ | E | Q | $R_5$ | W | R | X | Y | Z | m.p. (°C.) |
| H | — | Q-6 | $C_2H_5$ | O | H | $CH_3$ | $OCH_3$ | CH | |
| H | — | Q-6 | $C_2H_5$ | O | H | $OCH_3$ | $OCH_3$ | CH | |
| H | — | Q-6 | $C_2H_5$ | O | H | Cl | $OCH_3$ | CH | |
| H | — | Q-6 | $C_2H_5$ | O | H | $CH_3$ | $OCH_3$ | N | |
| H | — | Q-6 | $C_2H_5$ | O | H | $OCH_3$ | $OCH_3$ | N | |
| H | — | Q-6 | $CH_2CH{=}CH_2$ | O | H | $CH_3$ | $CH_3$ | CH | |
| H | — | Q-6 | $CH_2CH{=}CH_2$ | O | H | $CH_3$ | $OCH_3$ | CH | |
| H | — | Q-6 | $CH_2CH{=}CH_2$ | O | H | $OCH_3$ | $OCH_3$ | CH | |
| H | — | Q-6 | $CH_2CH{=}CH_2$ | O | H | Cl | $OCH_3$ | CH | |
| H | — | Q-6 | $CH_2CH{=}CH_2$ | O | H | $CH_3$ | $OCH_3$ | N | |
| H | — | Q-6 | $CH_2CH{=}CH_2$ | O | H | $OCH_3$ | $OCH_3$ | N | |
| H | — | Q-7 | $CH_3$ | O | H | $CH_3$ | $CH_3$ | CH | |
| H | — | Q-7 | $CH_3$ | O | H | $CH_3$ | $OCH_3$ | CH | |
| H | — | Q-7 | $CH_3$ | O | H | $OCH_3$ | $OCH_3$ | CH | |
| H | — | Q-7 | $CH_3$ | O | H | Cl | $OCH_3$ | CH | |
| H | — | Q-7 | $CH_3$ | O | H | $CH_3$ | $OCH_3$ | N | |
| H | — | Q-7 | $CH_3$ | O | H | $OCH_3$ | $OCH_3$ | N | |
| H | — | Q-7 | $C_2H_5$ | O | H | $CH_3$ | $CH_3$ | CH | |
| H | — | Q-7 | $C_2H_5$ | O | H | $CH_3$ | $OCH_3$ | CH | |
| H | — | Q-7 | $C_2H_5$ | O | H | $OCH_3$ | $OCH_3$ | CH | |
| H | — | Q-7 | $C_2H_5$ | O | H | Cl | $OCH_3$ | CH | |
| H | — | Q-7 | $C_2H_5$ | O | H | $CH_3$ | $OCH_3$ | N | |
| H | — | Q-7 | $C_2H_5$ | O | H | $OCH_3$ | $OCH_3$ | N | |
| H | — | Q-7 | $CH_2CH{=}CH_2$ | O | H | $CH_3$ | $CH_3$ | CH | |
| H | — | Q-7 | $CH_2CH{=}CH_2$ | O | H | $CH_3$ | $OCH_3$ | CH | |
| H | — | Q-7 | $CH_2CH{=}CH_2$ | O | H | $OCH_3$ | $OCH_3$ | CH | |
| H | — | Q-7 | $CH_2CH{=}CH_2$ | O | H | Cl | $OCH_3$ | CH | |
| H | — | Q-7 | $CH_2CH{=}CH_2$ | O | H | $CH_3$ | $OCH_3$ | N | 202 |
| H | — | Q-7 | $CH_2CH{=}CH_2$ | O | H | $OCH_3$ | $OCH_3$ | N | |
| 5-Cl | — | Q-5 | $CH_3$ | O | H | $OCH_3$ | $OCH_3$ | CH | 178-180 |
| 5-Cl | — | Q-5 | $CH_3$ | O | H | $OCH_3$ | $CH_3$ | CH | 134-140 |
| 5-Cl | — | Q-5 | $CH_3$ | O | H | Cl | $OCH_3$ | CH | |
| 5-Cl | — | Q-5 | $CH_3$ | O | H | $CH_3$ | $CH_3$ | CH | |
| 5-Cl | — | Q-5 | $CH_3$ | O | H | $OCH_3$ | $CH_3$ | N | 202 |
| 5-$CH_3$ | — | Q-5 | $CH_3$ | O | H | $OCH_3$ | $OCH_3$ | CH | |
| 5-$CH_3$ | — | Q-5 | $CH_3$ | O | H | $OCH_3$ | $CH_3$ | CH | |
| 5-$CH_3$ | — | Q-5 | $CH_3$ | O | H | Cl | $OCH_3$ | CH | |
| 5-$CH_3$ | — | Q-5 | $CH_3$ | O | H | $CH_3$ | $CH_3$ | CH | |
| 5-$CH_3$ | — | Q-5 | $CH_3$ | O | H | $OCH_3$ | $CH_3$ | N | |
| 6-$CH_3$ | — | Q-5 | $CH_3$ | O | H | $CH_3$ | $CH_3$ | CH | |
| 6-$CH_3$ | — | Q-5 | $CH_3$ | O | H | $OCH_3$ | $CH_3$ | CH | |
| 6-$CH_3$ | — | Q-5 | $CH_3$ | O | H | $OCH_3$ | $OCH_3$ | CH | |
| 6-$CH_3$ | — | Q-5 | $CH_3$ | O | H | Cl | $OCH_3$ | CH | |
| 6-$CH_3$ | — | Q-5 | $CH_3$ | O | H | $OCH_3$ | $CH_3$ | N | |
| 5-$OCH_3$ | — | Q-5 | $CH_3$ | O | H | $CH_3$ | $CH_3$ | CH | |
| 5-$OCH_3$ | — | Q-5 | $CH_3$ | O | H | $OCH_3$ | $CH_3$ | CH | |
| 5-$OCH_3$ | — | Q-5 | $CH_3$ | O | H | $OCH_3$ | $OCH_3$ | CH | |
| 5-$OCH_3$ | — | Q-5 | $CH_3$ | O | H | Cl | $OCH_3$ | CH | |
| 5-$OCH_3$ | — | Q-5 | $CH_3$ | O | H | $OCH_3$ | $CH_3$ | N | |
| 6-Cl | — | Q-5 | $CH_3$ | O | H | $CH_3$ | $CH_3$ | CH | |
| 6-Cl | — | Q-5 | $CH_3$ | O | H | $OCH_3$ | $CH_3$ | CH | |
| 6-Cl | — | Q-5 | $CH_3$ | O | H | $OCH_3$ | $OCH_3$ | CH | |
| 6-Cl | — | Q-5 | $CH_3$ | O | H | Cl | $OCH_3$ | CH | |
| 6-Cl | — | Q-5 | $CH_3$ | O | H | $OCH_3$ | $CH_3$ | N | |
| 5-$(CH_3)_2N$ | — | Q-5 | $CH_3$ | O | H | $OCH_3$ | $CH_3$ | CH | |
| 5-$(CH_3)_2N$ | — | Q-5 | $CH_3$ | O | H | $OCH_3$ | $OCH_3$ | CH | |
| 5-$(CH_3)_2N$ | — | Q-5 | $CH_3$ | O | H | $CH_3$ | $CH_3$ | CH | |
| 5-$(CH_3)_2N$ | — | Q-5 | $CH_3$ | O | H | Cl | $OCH_3$ | CH | |
| 5-$(CH_3)_2N$ | — | Q-5 | $CH_3$ | O | H | $OCH_3$ | $CH_3$ | N | |
| 5-F | — | Q-5 | $CH_3$ | O | H | $OCH_3$ | $OCH_3$ | CH | |
| 5-F | — | Q-5 | $CH_3$ | O | H | $OCH_3$ | $CH_3$ | CH | |
| 5-F | — | Q-5 | $CH_3$ | O | H | Cl | $OCH_3$ | CH | |
| 5-F | — | Q-5 | $CH_3$ | O | H | $CH_3$ | $CH_3$ | CH | |
| H | — | Q-5 | $CH_3$ | O | H | $CH_3$ | $OCF_2H$ | CH | 196-198 |
| H | — | Q-5 | $CH_3$ | O | H | $OCH_3$ | $OCF_2H$ | CH | 162-166 |
| 5-$CH_3$ | — | Q-5 | $C_2H_5$ | O | H | Cl | $OCH_3$ | CH | 125-128 |
| 5-$CH_3$ | — | Q-5 | $C_2H_5$ | O | H | $OCH_3$ | $OCH_3$ | N | 70-112 |
| 5-$CH_3$ | — | Q-5 | $C_2H_5$ | O | H | $CH_3$ | $OCH_3$ | N | 190-194 |
| 5-$CH_3$ | — | Q-5 | $C_2H_5$ | O | H | $OCH_3$ | $OCH_3$ | CH | 153-157 |
| 5-$CH_3$ | — | Q-5 | $C_2H_5$ | O | H | $CH_3$ | $OCH_3$ | CH | 170-173 |
| 5-$CH_3$ | — | Q-5 | $C_2H_5$ | O | H | $CH_3$ | $CH_3$ | CH | 141-143 |
| 5-Cl | — | Q-5 | $CH_3$ | O | H | $OCH_3$ | $OCH_3$ | N | |
| 5-$CH_3$ | — | Q-5 | $CH_3$ | O | H | $OCH_3$ | $OCH_3$ | N | |
| 6-$CH_3$ | — | Q-5 | $CH_3$ | O | H | $OCH_3$ | $OCH_3$ | N | |
| 5-$OCH_3$ | — | Q-5 | $CH_3$ | O | H | $OCH_3$ | $OCH_3$ | N | |
| 6-Cl | — | Q-5 | $CH_3$ | O | H | $OCH_3$ | $OCH_3$ | N | |
| 5-$(CH_3)_2N$ | — | Q-5 | $CH_3$ | O | H | $OCH_3$ | $OCH_3$ | N | |
| 5-F | — | Q-5 | $CH_3$ | O | H | $CH_3$ | $OCH_3$ | N | |

TABLE Ib-continued

| General Structure I | | | | | | | | | |
|---|---|---|---|---|---|---|---|---|---|
| $R_1$ | E | Q | $R_5$ | W | R | X | Y | Z | m.p. (°C.) |
| 5-F | — | Q-5 | $CH_3$ | O | H | $OCH_3$ | $OCH_3$ | N | |

TABLE II

| General Structure 2 | | | | | | | | |
|---|---|---|---|---|---|---|---|---|
| $R_1$ | E | Q | $R_3$ | W | R | $X_1$ | $Y_1$ | m.p. (°C.) |
| H | — | Q-1 | $CH_3$ | O | H | $CH_3$ | O | |
| H | — | Q-1 | $CH_3$ | O | H | $OCH_3$ | O | |
| H | — | Q-1 | $CH_3$ | O | H | $OC_2H_5$ | O | |
| H | — | Q-1 | $CH_3$ | O | H | $OCF_2H$ | O | |
| H | — | Q-1 | $CH_3$ | O | H | $CH_3$ | $CH_2$ | |
| H | — | Q-1 | $CH_3$ | O | H | $OCH_3$ | $CH_2$ | |
| H | — | Q-1 | $CH_3$ | O | H | $OC_2H_5$ | $CH_2$ | |
| H | — | Q-1 | $CH_3$ | O | H | $OCF_2H$ | $CH_2$ | |
| H | — | Q-1 | $C_2H_5$ | O | H | $CH_3$ | O | |
| H | — | Q-1 | $C_2H_5$ | O | H | $OCH_3$ | O | |
| H | — | Q-1 | $C_2H_5$ | O | H | $OC_2H_5$ | O | |
| H | — | Q-1 | $C_2H_5$ | O | H | $OCF_2H$ | O | |
| H | — | Q-1 | $C_2H_5$ | O | H | $CH_3$ | $CH_2$ | |
| H | — | Q-1 | $C_2H_5$ | O | H | $OCH_3$ | $CH_2$ | |
| H | — | Q-1 | $C_2H_5$ | O | H | $OC_2H_5$ | $CH_2$ | |
| H | — | Q-1 | $C_2H_5$ | O | H | $OCF_2H$ | $CH_2$ | |
| H | — | Q-1 | $(CH_2)_5CH_3$ | O | H | $OCH_3$ | O | |
| H | — | Q-1 | $CH_2CH{=}CH{-}CH_2Cl$ | O | H | $OCH_3$ | O | |
| H | — | Q-1 | $C_2H_5$ | O | H | $OCH_3$ | O | |
| 5-$CH_3$ | — | Q-1 | $CH_3$ | O | H | $OCH_3$ | O | |
| 5-$CH_3$ | — | Q-1 | $CH_3$ | O | H | $OCH_3$ | $CH_2$ | |
| 5-$CH_3$ | — | Q-1 | $CH_3$ | O | H | $OCH_3$ | $CH_2$ | |
| 5-$CH_3$ | — | Q-1 | $CH_3$ | O | H | $OCH_3$ | $CH_2$ | |
| 5-Cl | — | Q-1 | $CH_3$ | O | H | $OCH_3$ | O | |
| 5-$OCH_3$ | — | Q-1 | $CH_3$ | O | H | $OCH_3$ | O | |
| 5-$OCH_3$ | — | Q-1 | $CH_3$ | O | H | $CH_3$ | O | |
| 5-$OC_2H_5$ | — | Q-1 | $CH_3$ | O | H | $OCH_3$ | O | |
| 5-$OC_2H_5$ | — | Q-1 | $CH_3$ | O | H | $CH_3$ | O | |
| 5-$SCH_3$ | — | Q-1 | $CH_3$ | O | H | $OCH_3$ | O | |
| 5-$SCH_3$ | — | Q-1 | $CH_3$ | O | H | $CH_3$ | O | |
| 5-$SC_2H_5$ | — | Q-1 | $CH_3$ | O | H | $OCH_3$ | O | |
| 5-$SC_2H_5$ | — | Q-1 | $CH_3$ | O | H | $CH_3$ | O | |
| 5-CN | — | Q-1 | $CH_3$ | O | H | $OCH_3$ | O | |
| 5-CN | — | Q-1 | $CH_3$ | O | H | $CH_3$ | O | |
| 5-$OCF_2H$ | — | Q-1 | $CH_3$ | O | H | $OCH_3$ | O | |
| 5-$OCF_2H$ | — | Q-1 | $CH_3$ | O | H | $CH_3$ | O | |
| H | — | Q-2 | $CH_3$ | O | H | $CH_3$ | O | |
| H | — | Q-2 | $CH_3$ | O | H | $OCH_3$ | O | |
| H | — | Q-2 | $CH_3$ | O | H | $OC_2H_5$ | O | |
| H | — | Q-2 | $CH_3$ | O | H | $OCF_2H$ | O | |
| H | — | Q-2 | $CH_3$ | O | H | $CH_3$ | $CH_2$ | |
| H | — | Q-2 | $CH_3$ | O | H | $OCH_3$ | $CH_2$ | |
| H | — | Q-2 | $CH_3$ | O | H | $OC_2H_5$ | $CH_2$ | |
| H | — | Q-2 | $C_2H_5$ | O | H | $CH_3$ | O | |
| H | — | Q-2 | $C_2H_5$ | O | H | $OCH_3$ | O | |
| H | — | Q-2 | $C_2H_5$ | O | H | $CH_3$ | $CH_2$ | |
| H | — | Q-2 | $C_2H_5$ | O | H | $OCH_3$ | $CH_2$ | |
| 5-$CH_3$ | — | Q-2 | $CH_3$ | O | H | $OCH_3$ | O | |
| 5-$CH_3$ | — | Q-2 | $CH_3$ | O | H | $OCH_3$ | $CH_2$ | |
| 5-$C_2H_5$ | — | Q-2 | $CH_3$ | O | H | $OCH_3$ | O | |
| 5-$OCH_3$ | — | Q-2 | $CH_3$ | O | H | $OCH_3$ | O | |
| 5-$OCH_3$ | — | Q-2 | $CH_3$ | O | H | $CH_3$ | O | |
| 5-$OC_2H_5$ | — | Q-2 | $CH_3$ | O | H | $OCH_3$ | O | |
| 5-$OC_2H_5$ | — | Q-2 | $CH_3$ | O | H | $CH_3$ | O | |
| 5-$SCH_3$ | — | Q-2 | $CH_3$ | O | H | $OCH_3$ | O | |
| 5-$SCH_3$ | — | Q-2 | $CH_3$ | O | H | $CH_3$ | O | |
| 5-$SC_2H_5$ | — | Q-2 | $CH_3$ | O | H | $OCH_3$ | O | |
| 5-$OCF_2H$ | — | Q-2 | $CH_3$ | O | H | $OCH_3$ | O | |
| 6-$CH_3$ | — | Q-1 | $CH_3$ | O | H | $OCH_3$ | O | |
| 6-$CH_3$ | — | Q-1 | $CH_3$ | O | H | $CH_3$ | O | |
| 6-$CH_3$ | — | Q-1 | $CH_3$ | O | H | $OCH_3$ | $CH_2$ | |
| 6-Cl | — | Q-1 | $CH_3$ | O | H | $OCH_3$ | O | |
| 6-Cl | — | Q-1 | $CH_3$ | O | H | $CH_3$ | O | |
| 6-Cl | — | Q-1 | $CH_3$ | O | H | $OCH_3$ | $CH_2$ | |

TABLE IIa

General Structure 2

| $R_1$ | E | Q | $R_4$ | W | R | $X_1$ | $Y_1$ | m.p. (°C.) |
|---|---|---|---|---|---|---|---|---|
| H | — | Q-3 | $CH_3$ | O | H | $CH_3$ | O | |
| H | — | Q-3 | $CH_3$ | O | H | $OCH_3$ | O | |
| H | — | Q-3 | $CH_3$ | O | H | $OC_2H_5$ | O | |
| H | — | Q-3 | $CH_3$ | O | H | $OCF_2H$ | O | |
| H | — | Q-3 | $CH_3$ | O | H | $CH_3$ | $CH_2$ | |
| H | — | Q-3 | $CH_3$ | O | H | $OCH_3$ | $CH_2$ | |
| H | — | Q-3 | $CH_3$ | O | H | $OC_2H_5$ | $CH_2$ | |
| H | — | Q-3 | $C_2H_5$ | O | H | $CH_3$ | O | |
| H | — | Q-3 | $C_2H_5$ | O | H | $OCH_3$ | O | |
| H | — | Q-3 | $C_2H_5$ | O | H | $OC_2H_5$ | O | |
| H | — | Q-3 | $C_2H_5$ | O | H | $CH_3$ | $CH_2$ | |
| H | — | Q-3 | $C_2H_5$ | O | H | $OCH_3$ | $CH_2$ | |
| H | — | Q-3 | $C_2H_5$ | O | H | $OC_2H_5$ | $CH_2$ | |
| H | — | Q-3 | $C_2H_5$ | O | H | $OCF_2H$ | $CH_2$ | |
| H | — | Q-3 | $C_2H_5$ | O | H | $OCH_3$ | O | |
| H | — | Q-3 | $C_2H_5$ | O | H | $OCH_3$ | O | |
| 5-$CH_3$ | — | Q-3 | $CH_3$ | O | H | $OCH_3$ | O | |
| 5-$CH_3$ | — | Q-3 | $CH_3$ | O | H | $OCH_3$ | $CH_2$ | |
| 5-Cl | — | Q-3 | $CH_3$ | O | H | $OCH_3$ | O | |
| 5-Cl | — | Q-3 | $CH_3$ | O | H | $OCH_3$ | O | |
| 5-Cl | — | Q-3 | $CH_3$ | O | H | $CH_3$ | O | |
| 5-$OCH_3$ | — | Q-3 | $CH_3$ | O | H | $OCH_3$ | O | |
| 5-$OCH_3$ | — | Q-3 | $CH_3$ | O | H | $CH_3$ | O | |
| 5-$OC_2H_5$ | — | Q-3 | $CH_3$ | O | H | $OCH_3$ | O | |
| 5-$OC_2H_5$ | — | Q-3 | $CH_3$ | O | H | $CH_3$ | O | |
| 5-$SCH_3$ | — | Q-3 | $CH_3$ | O | H | $OCH_3$ | O | |
| 5-$SCH_3$ | — | Q-3 | $CH_3$ | O | H | $CH_3$ | O | |
| 5-$SC_2H_5$ | — | Q-3 | $CH_3$ | O | H | $OCH_3$ | O | |
| 5-$SC_2H_5$ | — | Q-3 | $CH_3$ | O | H | $CH_3$ | O | |
| 5-$OCF_2H$ | — | Q-3 | $CH_3$ | O | H | $OCH_3$ | O | |
| 5-$OCF_2H$ | — | Q-3 | $CH_3$ | O | H | $CH_3$ | O | |
| 5-$SCF_2H$ | — | Q-3 | $CH_3$ | O | H | $OCH_3$ | O | |
| 5-$SCF_2H$ | — | Q-3 | $CH_3$ | O | H | $CH_3$ | O | |
| H | — | Q-4 | $CH_3$ | O | H | $CH_3$ | O | |
| H | — | Q-4 | $CH_3$ | O | H | $OCH_3$ | O | |
| H | — | Q-4 | $CH_3$ | O | H | $OC_2H_5$ | O | |
| H | — | Q-4 | $CH_3$ | O | H | $OCF_2H$ | O | |
| H | — | Q-4 | $CH_3$ | O | H | $CH_3$ | $CH_2$ | |
| H | — | Q-4 | $CH_3$ | O | H | $OCH_3$ | $CH_2$ | |
| H | — | Q-4 | $CH_3$ | O | H | $OC_2H_5$ | $CH_2$ | |
| H | — | Q-4 | $CH_3$ | O | H | $OCF_2H$ | $CH_2$ | |
| H | — | Q-4 | $C_2H_5$ | O | H | $CH_3$ | O | |
| H | — | Q-4 | $C_2H_5$ | O | H | $OCH_3$ | O | |
| H | — | Q-4 | $C_2H_5$ | O | H | $OC_2H_5$ | O | |
| H | — | Q-4 | $C_2H_5$ | O | H | $OCF_2H$ | O | |
| H | — | Q-4 | $C_2H_5$ | O | H | $CH_3$ | $CH_2$ | |
| H | — | Q-4 | $C_2H_5$ | O | H | $OCH_3$ | $CH_2$ | |
| H | — | Q-4 | $C_2H_5$ | O | H | $OC_2H_5$ | $CH_2$ | |
| H | — | Q-4 | $C_2H_5$ | O | H | $OCF_2H$ | $CH_2$ | |
| 6-$CH_3$ | — | Q-3 | $CH_3$ | O | H | $OCH_3$ | $CH_2$ | |
| 6-$CH_3$ | — | Q-3 | $CH_3$ | O | H | $OCH_3$ | O | |
| 6-$CH_3$ | — | Q-3 | $CH_3$ | O | H | $CH_3$ | O | |
| 6-Cl | — | Q-3 | $CH_3$ | O | H | $OCH_3$ | $CH_2$ | |
| 6-Cl | — | Q-3 | $CH_3$ | O | H | $OCH_3$ | O | |
| 6-Cl | — | Q-3 | $CH_3$ | O | H | $CH_3$ | O | |
| 6-$CH_3$ | — | Q-4 | $CH_3$ | O | H | $OCH_3$ | $CH_2$ | |
| 6-$CH_3$ | — | Q-4 | $CH_3$ | O | H | $OCH_3$ | O | |
| 6-$CH_3$ | — | Q-4 | $CH_3$ | O | H | $CH_3$ | O | |
| 6-Cl | — | Q-4 | $CH_3$ | O | H | $OCH_3$ | $CH_2$ | |
| 6-Cl | — | Q-4 | $CH_3$ | O | H | $OCH_3$ | O | |
| 6-Cl | — | Q-4 | $CH_3$ | O | H | $CH_3$ | O | |
| H | — | Q-3 | H | O | H | $OCH_3$ | O | |
| H | — | Q-3 | H | O | H | $CH_3$ | O | |
| H | — | Q-3 | H | O | H | $OCH_3$ | $CH_2$ | |
| H | — | Q-3 | H | O | H | $CH_3$ | $CH_2$ | |
| H | — | Q-3 | $OCH_3$ | O | H | $OCH_3$ | O | |
| H | — | Q-3 | $OCH_3$ | O | H | $CH_3$ | O | |
| H | — | Q-3 | $OCH_3$ | O | H | $OCH_3$ | $CH_2$ | |
| H | — | Q-3 | $OCH_3$ | O | H | $CH_3$ | $CH_2$ | |
| H | — | Q-3 | $OC_2H_5$ | O | H | $OCH_3$ | O | |
| H | — | Q-3 | $OC_2H_5$ | O | H | $CH_3$ | O | |
| H | — | Q-3 | $OC_2H_5$ | O | H | $OCH_3$ | $CH_2$ | |
| H | — | Q-3 | $OC_2H_5$ | O | H | $CH_3$ | $CH_2$ | |
| H | — | Q-3 | $SCH_3$ | O | H | $OCH_3$ | O | |
| H | — | Q-3 | $SCH_3$ | O | H | $CH_3$ | O | |
| H | — | Q-3 | $SCH_3$ | O | H | $OCH_3$ | $CH_2$ | |
| H | — | Q-3 | $SCH_3$ | O | H | $CH_3$ | $CH_2$ | |

TABLE IIb

General Structure 2

| $R_1$ | E | Q | $R_5$ | W | R | $X_1$ | $Y_1$ | m.p. (°C.) |
|---|---|---|---|---|---|---|---|---|
| H | — | Q-5 | $CH_3$ | O | H | $OCH_3$ | O | |
| H | — | Q-5 | $CH_3$ | O | H | $OCH_3$ | $CH_2$ | |
| H | — | Q-5 | $CH_3$ | O | H | $CH_3$ | O | |
| H | — | Q-5 | $C_2H_5$ | O | H | $OCH_3$ | O | |
| H | — | Q-5 | $C_2H_5$ | O | H | $OCH_3$ | $CH_2$ | |
| H | — | Q-5 | $C_2H_5$ | O | H | $CH_3$ | O | |
| 5-$CH_3$ | — | Q-5 | $CH_3$ | O | H | $OCH_3$ | O | |
| 5-$CH_3$ | — | Q-5 | $CH_3$ | O | H | $OCH_3$ | $CH_2$ | |
| 5-$CH_3$ | — | Q-5 | $CH_3$ | O | H | $CH_3$ | O | |
| 5-Cl | — | Q-5 | $CH_3$ | O | H | $OCH_3$ | O | |
| 5-Cl | — | Q-5 | $CH_3$ | O | H | $OCH_3$ | $CH_2$ | |
| 5-Cl | — | Q-5 | $CH_3$ | O | H | $CH_3$ | O | |
| 6-$CH_3$ | — | Q-5 | $CH_3$ | O | H | $OCH_3$ | O | |
| 6-$CH_3$ | — | Q-5 | $CH_3$ | O | H | $OCH_3$ | $CH_2$ | |
| 6-$CH_3$ | — | Q-5 | $CH_3$ | O | H | $CH_3$ | O | |
| 6-Cl | — | Q-5 | $CH_3$ | O | H | $OCH_3$ | O | |
| 6-Cl | — | Q-5 | $CH_3$ | O | H | $OCH_3$ | $CH_2$ | |
| 6-Cl | — | Q-5 | $CH_3$ | O | H | $CH_3$ | O | |
| 5-F | — | Q-5 | $CH_3$ | O | H | $OCH_3$ | O | |
| 5-F | — | Q-5 | $CH_3$ | O | H | $OCH_3$ | $CH_2$ | |
| 5-F | — | Q-5 | $CH_3$ | O | H | $CH_3$ | O | |
| 5-$OCH_3$ | — | Q-5 | $CH_3$ | O | H | $OCH_3$ | O | |
| 5-$OCH_3$ | — | Q-5 | $CH_3$ | O | H | $OCH_3$ | $CH_2$ | |
| 5-$OCH_3$ | — | Q-5 | $CH_3$ | O | H | $CH_3$ | O | |

TABLE III

General Structure 3

| $R_1$ | E | Q | $R_3$ | $R_4$ | $R_5$ | W | R | $X_1$ | m.p. (°C.) |
|---|---|---|---|---|---|---|---|---|---|
| H | — | Q-1 | $CH_3$ | — | — | O | H | $CH_3$ | |
| H | — | Q-1 | $CH_3$ | — | — | O | H | $OCH_3$ | |
| H | — | Q-1 | $CH_3$ | — | — | O | H | $OC_2H_5$ | |
| H | — | Q-1 | $CH_3$ | — | — | O | H | $OCF_2H$ | |
| H | — | Q-1 | $C_2H_5$ | — | — | O | H | $CH_3$ | |
| H | — | Q-1 | $C_2H_5$ | — | — | O | H | $OCH_3$ | |
| H | — | Q-1 | $C_2H_5$ | — | — | O | H | $OC_2H_5$ | |
| H | — | Q-2 | $CH_3$ | — | — | O | H | $CH_3$ | |
| H | — | Q-2 | $CH_3$ | — | — | O | H | $OCH_3$ | |
| H | — | Q-2 | $CH_3$ | — | — | O | H | $OC_2H_5$ | |
| H | — | Q-2 | $C_2H_5$ | — | — | O | H | $OCH_3$ | |
| H | — | Q-2 | $C_2H_5$ | — | — | O | H | $CH_3$ | |
| H | — | Q-3 | — | $CH_3$ | — | O | H | $OC_2H_5$ | |
| H | — | Q-3 | — | $CH_3$ | — | O | H | $OCH_3$ | |
| H | — | Q-3 | — | $CH_3$ | — | O | H | $CH_3$ | |
| H | — | Q-3 | — | $C_2H_5$ | — | O | H | $CH_3$ | |
| H | — | Q-3 | — | $C_2H_5$ | — | O | H | $OCH_3$ | |
| 6-$CH_3$ | — | Q-1 | $CH_3$ | — | — | O | H | $OCH_3$ | |
| 6-$CH_3$ | — | Q-1 | $CH_3$ | — | — | O | H | $CH_3$ | |
| 6-Cl | — | Q-1 | $CH_3$ | — | — | O | H | $CH_3$ | |
| 6-Cl | — | Q-1 | $CH_3$ | — | — | O | H | $OCH_3$ | |
| H | — | Q-4 | — | $CH_3$ | — | O | H | $OCH_3$ | |
| H | — | Q-5 | — | — | $CH_3$ | O | H | $OCH_3$ | |
| H | — | Q-5 | — | — | $CH_3$ | O | H | $CH_3$ | |
| H | — | Q-6 | — | — | $CH_3$ | O | H | $OCH_3$ | |
| H | — | Q-7 | — | — | $CH_3$ | O | H | $OCH_3$ | |
| H | — | Q-3 | — | H | — | O | H | $OCH_3$ | |
| H | — | Q-3 | — | H | — | O | H | $CH_3$ | |
| H | — | Q-3 | — | $OCH_3$ | — | O | H | $OCH_3$ | |
| H | — | Q-3 | — | $OCH_3$ | — | O | H | $CH_3$ | |
| H | — | Q-3 | — | $OC_2H_5$ | — | O | H | $OCH_3$ | |
| H | — | Q-3 | — | $OC_2H_5$ | — | O | H | $CH_3$ | |
| H | — | Q-3 | — | $SCH_3$ | — | O | H | $OCH_3$ | |
| H | — | Q-3 | — | $SCH_3$ | — | O | H | $CH_3$ | |

TABLE IV

General Structure 4

| $R_1$ | E | Q | $R_3$ | $R_4$ | $R_5$ | W | R | $X_1$ | $Y_3$ | m.p. (°C.) |
|---|---|---|---|---|---|---|---|---|---|---|
| H | — | Q-1 | $CH_3$ | — | — | O | H | $CH_3$ | H | |
| H | — | Q-1 | $CH_3$ | — | — | O | H | $OCH_3$ | H | |
| H | — | Q-1 | $CH_3$ | — | — | O | H | $O_2C_5H$ | H | |
| H | — | Q-1 | $CH_3$ | — | — | O | H | $CH_3$ | $CH_3$ | |
| H | — | Q-1 | $CH_3$ | — | — | O | H | $OCH_3$ | $CH_3$ | |
| H | — | Q-1 | $CH_3$ | — | — | O | H | $OCF_2H$ | $CH_3$ | |

TABLE IV-continued

General Structure 4

| $R_1$ | E | Q | $R_3$ | $R_4$ | $R_5$ | W | R | $X_1$ | $Y_3$ | m.p. (°C.) |
|---|---|---|---|---|---|---|---|---|---|---|
| H | — | Q-1 | $C_2H_5$ | — | — | O | H | $CH_3$ | H | |
| H | — | Q-1 | $C_2H_5$ | — | — | O | H | $OCH_3$ | H | |
| H | — | Q-1 | $C_2H_5$ | — | — | O | H | $CH_3$ | $CH_3$ | |
| H | — | Q-2 | $CH_3$ | — | — | O | H | $OCH_3$ | $CH_3$ | |
| H | — | Q-2 | $CH_3$ | — | — | O | H | $OCH_3$ | H | |
| H | — | Q-2 | $CH_3$ | — | — | O | H | $CH_3$ | H | |
| H | — | Q-2 | $CH_3$ | — | — | O | H | $OCH_3$ | $CH_3$ | |
| H | — | Q-2 | $CH_3$ | — | — | O | H | $CH_3$ | $CH_3$ | |
| H | — | Q-3 | — | $CH_3$ | — | O | H | $OCH_3$ | $CH_3$ | |
| H | — | Q-3 | — | $CH_3$ | — | O | H | $OCH_3$ | $CH_3$ | |
| H | — | Q-3 | — | $C_2H_5$ | — | O | H | $CH_3$ | $CH_3$ | |
| H | — | Q-3 | — | $C_2H_5$ | — | O | H | $OCH_3$ | H | |
| H | — | Q-4 | — | $CH_3$ | — | O | H | $OCH_3$ | H | |
| H | — | Q-5 | — | — | $CH_3$ | O | H | $OCH_3$ | H | |
| H | — | Q-5 | — | — | $CH_3$ | O | H | $OCH_3$ | $CH_3$ | |
| H | — | Q-5 | — | — | $CH_3$ | O | H | $CH_3$ | H | |
| 5-Cl | — | Q-5 | — | — | $CH_3$ | O | H | $CH_3$ | H | |
| 6-$CH_3$ | — | Q-5 | — | — | $CH_3$ | O | H | $OCH_3$ | H | |
| H | — | Q-3 | — | H | — | O | H | $CH_3$ | H | |
| H | — | Q-3 | — | H | — | O | H | $OCH_3$ | H | |
| H | — | Q-3 | — | $OCH_3$ | — | O | H | $CH_3$ | $CH_3$ | |
| H | — | Q-3 | — | $OCH_3$ | — | O | H | $OCH_3$ | $CH_3$ | |
| H | — | Q-3 | — | $OC_2H_5$ | — | O | H | $CH_3$ | H | |
| H | — | Q-3 | — | $OC_2H_5$ | — | O | H | $OCH_3$ | H | |
| H | — | Q-3 | — | $SCH_3$ | — | O | H | $CH_3$ | $CH_3$ | |
| H | — | Q-3 | — | $SCH_3$ | — | O | H | $OCH_3$ | $CH_3$ | |

TABLE V

General Structure 5

| $R_1$ | E | Q | $R_3$ | $R_4$ | $R_5$ | W | R | $X_2$ | $Y_2$ | m.p. (°C.) |
|---|---|---|---|---|---|---|---|---|---|---|
| H | — | Q-1 | $CH_3$ | — | — | O | H | $CH_3$ | $OCH_3$ | |
| H | — | Q-1 | $CH_3$ | — | — | O | H | $CH_2CF_3$ | $OCH_3$ | |
| H | — | Q-1 | $CH_3$ | — | — | O | H | $CH_3$ | $SC_2H_5$ | |
| H | — | Q-1 | $CH_3$ | — | — | O | H | $CH_3$ | $SCH_3$ | |
| H | — | Q-1 | $CH_3$ | — | — | O | H | $CH_3$ | $OC_2H_5$ | |
| H | — | Q-1 | $C_2H_5$ | — | — | O | H | $CH_3$ | $SCH_3$ | |
| H | — | Q-1 | $C_2H_5$ | — | — | O | H | $CH_3$ | $OCH_3$ | |
| H | — | Q-2 | $CH_3$ | — | — | O | H | $CH_3$ | $OCH_3$ | |
| H | — | Q-2 | $CH(CH_3)_2$ | — | — | O | H | $CH_3$ | $OCH_3$ | |
| H | — | Q-3 | — | $CH_3$ | — | O | H | $CH_3$ | $SCH_3$ | |
| H | — | Q-3 | — | $CH_3$ | — | O | H | $CH_3$ | $SC_2H_5$ | |
| H | — | Q-3 | — | $C_2H_5$ | — | O | H | $CH_3$ | $SCH_3$ | |
| H | — | Q-3 | — | $CF_3$ | — | O | H | $CH_3$ | $SCH_3$ | |
| H | — | Q-4 | — | $CH_3$ | — | O | H | $CH_3$ | $SCH_3$ | |
| 6-$CH_3$ | — | Q-4 | — | $CH_3$ | — | O | H | $CH_3$ | $SCH_3$ | |
| 6-Cl | — | Q-4 | — | $CH_3$ | — | O | H | $CH_3$ | $SCH_3$ | |
| H | — | Q-5 | — | — | $CH_3$ | O | H | $CH_3$ | $SCH_3$ | |
| H | — | Q-6 | — | — | $CH_3$ | O | H | $CH_3$ | $SCH_3$ | |
| H | — | Q-7 | — | — | $CH_3$ | O | H | $CH_3$ | $SCH_3$ | |
| 6-$CH_3$ | — | Q-1 | $CH_3$ | — | — | O | H | $CH_3$ | $SCH_3$ | |
| 5-Cl | — | Q-1 | $CH_3$ | — | — | O | H | $CH_3$ | $SCH_3$ | |
| H | — | Q-3 | — | H | — | O | H | $CH_3$ | $SCH_3$ | |
| H | — | Q-3 | — | H | — | O | H | $C_2H_5$ | $OCH_3$ | |
| H | — | Q-3 | — | $OCH_3$ | — | O | H | $CH_3$ | $OCH_3$ | |
| H | — | Q-3 | — | $OCH_3$ | — | O | H | $CH_3$ | $OC_2H_5$ | |
| H | — | Q-3 | — | $SCH_3$ | — | O | H | $CH_3$ | $OCH_3$ | |
| H | — | Q-3 | — | $SCH_3$ | — | O | H | $CH_3$ | $OC_2H_5$ | |

TABLE VI

General Structure 6

| $R_1$ | E | Q | $R_3$ | $R_4$ | $R_5$ | W | R | $X_3$ | m.p. (°C.) |
|---|---|---|---|---|---|---|---|---|---|
| H | — | Q-1 | $CH_3$ | — | — | O | H | $CH_3$ | |
| H | — | Q-1 | $CH_3$ | — | — | O | H | $OCH_3$ | |
| H | — | Q-1 | $C_2H_5$ | — | — | O | H | $CH_3$ | |
| H | — | Q-1 | $C_2H_5$ | — | — | O | H | $OCH_3$ | |
| H | — | Q-2 | $CH_3$ | — | — | O | H | $CH_3$ | |
| H | — | Q-2 | $C_2H_5$ | — | — | O | H | $CH_3$ | |
| H | — | Q-3 | — | $CH_3$ | — | O | H | $CH_3$ | |
| H | — | Q-3 | — | $CH_3$ | — | O | H | $OCH_3$ | |
| H | — | Q-3 | — | $C_2H_5$ | — | O | H | $CH_3$ | |
| H | — | Q-3 | — | $C_2H_5$ | — | O | H | $OCH_3$ | |
| H | — | Q-3 | — | $CH(CH_3)_2$ | — | O | H | $OCH_3$ | |
| H | — | Q-3 | — | $CH_2Cl$ | — | O | H | $OCH_3$ | |
| H | — | Q-3 | — | $CF_3$ | — | O | H | $OCH_3$ | |
| H | — | Q-4 | — | $CH_3$ | — | O | H | $OCH_3$ | |
| 6-$CH_3$ | — | Q-1 | $CH_3$ | — | — | O | H | $OCH_3$ | |
| 6-Cl | — | Q-1 | $CH_3$ | — | — | O | H | $OCH_3$ | |
| 5-Cl | — | Q-1 | $CH_3$ | — | — | O | H | $OCH_3$ | |
| H | — | Q-5 | — | — | $CH_3$ | O | H | $OCH_3$ | |
| H | — | Q-5 | — | — | $CH_3$ | O | H | $CH_3$ | |
| H | — | Q-6 | — | — | $CH_3$ | O | H | $OCH_3$ | |
| H | — | Q-6 | — | — | $CH_3$ | O | H | $CH_3$ | |
| H | — | Q-7 | — | — | $CH_3$ | O | H | $OCH_3$ | |
| H | — | Q-3 | — | H | — | O | H | $CH_3$ | |
| H | — | Q-3 | — | H | — | O | H | $OCH_3$ | |
| H | — | Q-3 | — | $OCH_3$ | — | O | H | $CH_3$ | |

TABLE VI-continued

General Structure 6

| R1 | E | Q | R3 | R4 | R5 | W | R | X3 | m.p. (°C.) |
|---|---|---|---|---|---|---|---|---|---|
| H | — | Q-3 | — | $OCH_3$ | — | O | H | $OCH_3$ | |
| H | — | Q-3 | — | $OC_2H_5$ | — | O | H | $CH_3$ | |
| H | — | Q-3 | — | $OC_2H_5$ | — | O | H | $OCH_3$ | |
| H | — | Q-3 | — | $SCH_3$ | — | O | H | $CH_3$ | |
| H | — | Q-3 | — | $SCH_3$ | — | O | H | $OCH_3$ | |

TABLE VII

General Structure 7

| $R_1$ | E | Q | $R_3$ | $R_4$ | $R_5$ | W | R | $X_4$ | $Y_4$ | $Z^1$ | m.p. (°C.) |
|---|---|---|---|---|---|---|---|---|---|---|---|
| H | — | Q-1 | $CH_3$ | — | — | O | H | $CH_3$ | $CH_3$ | N | |
| H | — | Q-1 | $CH_3$ | — | — | O | H | $OCH_3$ | $CH_3$ | N | |
| H | — | Q-1 | $CH_3$ | — | — | O | H | $OC_2H_5$ | $CH_3$ | N | |
| H | — | Q-1 | $CH_3$ | — | — | O | H | $CH_2OCH_3$ | $CH_3$ | N | |
| H | — | Q-1 | $CH_3$ | — | — | O | H | Cl | $CH_3$ | N | |
| H | — | Q-1 | $CH_3$ | — | — | O | H | $CH_3$ | $OCH_3$ | N | |
| H | — | Q-1 | $CH_3$ | — | — | O | H | $OCH_3$ | $OCH_3$ | N | |
| H | — | Q-1 | $CH_3$ | — | — | O | H | $OC_2H_5$ | $OCH_3$ | N | |
| H | — | Q-1 | $CH_3$ | — | — | O | H | $CH_2OCH_3$ | $OCH_3$ | N | |
| H | — | Q-1 | $CH_3$ | — | — | O | H | Cl | $OCH_3$ | N | |
| H | — | Q-1 | $CH_3$ | — | — | O | H | $CH_3$ | $CH_3$ | CH | |
| H | — | Q-1 | $CH_3$ | — | — | O | H | $OCH_3$ | $CH_3$ | CH | |
| H | — | Q-1 | $CH_3$ | — | — | O | H | $OC_2H_5$ | $CH_3$ | CH | |
| H | — | Q-1 | $CH_3$ | — | — | O | H | $CH_2OCH_3$ | $CH_3$ | CH | |
| H | — | Q-1 | $CH_3$ | — | — | O | H | Cl | $CH_3$ | CH | |
| H | — | Q-1 | $CH_3$ | — | — | O | H | $CH_3$ | $OCH_3$ | CH | |
| H | — | Q-1 | $CH_3$ | — | — | O | H | $OCH_3$ | $OCH_3$ | CH | |
| H | — | Q-1 | $CH_3$ | — | — | O | H | $OC_2H_5$ | $OCH_3$ | CH | |
| H | — | Q-1 | $CH_3$ | — | — | O | H | $CH_2OCH_3$ | $OCH_3$ | CH | |
| H | — | Q-1 | $CH_3$ | — | — | O | H | Cl | $OCH_3$ | CH | |
| H | — | Q-1 | $CH_3$ | — | — | O | H | $OCH_3$ | $OC_2H_5$ | CH | |
| H | — | Q-1 | $CH_3$. | — | — | O | H | $OCH_3$ | Cl | CH | |
| H | — | Q-1 | $CH_3$ | — | — | O | H | $CH_3$ | $OC_2H_5$ | CH | |
| H | — | Q-1 | $CH_3$ | — | — | O | H | $CH_3$ | Cl | CH | |
| 6-$CH_3$ | — | Q-1 | $CH_3$ | — | — | O | H | $CH_3$ | $CH_3$ | CH | |
| 6-$CH_3$ | — | Q-1 | $CH_3$ | — | — | O | H | $OCH_3$ | $OCH_3$ | CH | |
| 6-$CH_3$ | — | Q.1 | $CH_3$ | — | — | O | H | $CH_3$ | $OCH_3$ | CH | |
| 5 $CH_3$ | — | Q.1 | $CH_3$ | — | — | O | H | $CH_3$ | $OCH_3$ | CH | |
| 5-$CH_3$ | — | Q-1 | $CH_3$ | — | — | O | H | $OCH_3$ | $OCH_3$ | CH | |
| 5-$CH_3$ | — | Q-1 | $CH_3$ | — | — | O | H | $CH_3$ | $CH_3$ | CH | |
| 5-$OCH_3$ | — | Q-1 | $CH_3$ | — | — | O | H | $CH_3$ | $CH_3$ | CH | |
| 5-$OCH_3$ | — | Q-1 | $CH_3$ | — | — | O | H | $OCH_3$ | $CH_3$ | CH | |
| 5-$OCH_3$ | — | Q-1 | $CH_3$ | — | — | O | H | $OCH_3$ | $OCH_3$ | CH | |
| H | — | Q-3 | — | $CH_3$ | — | O | H | $CH_3$ | $CH_3$ | CH | |
| H | — | Q-3 | — | $CH_3$ | — | O | H | $OCH_3$ | $OCH_3$ | CH | |
| H | — | Q-3 | — | $CH_3$ | — | O | H | $CH_3$ | $OCH_3$ | CH | |
| H | — | Q-3 | — | $CH_3$ | — | O | H | $OCH_3$ | $CH_3$ | CH | |
| 6-$CH_3$ | — | Q-3 | — | $CH_3$ | — | O | H | $OCH_3$ | $OCH_3$ | CH | |
| 6-$CH_3$ | — | Q-3 | — | $CH_3$ | — | O | H | $OCH_3$ | $OCH_3$ | N | |
| 5-Cl | — | Q-3 | — | $CH_3$ | — | O | H | $OCH_3$ | $OCH_3$ | CH | |
| 5-Cl | — | Q-3 | — | $CH_3$ | — | O | H | $OCH_3$ | $CH_3$ | CH | |
| 5-$OCH_3$ | — | Q-3 | — | $CH_3$ | — | O | H | $OCH_3$ | $OCH_3$ | CH | |
| 5-$OCH_3$ | — | Q-3 | — | $CH_3$ | — | O | H | $CH_3$ | $OCH_3$ | CH | |
| 5-$OCH_3$ | — | Q-3 | — | $CH_3$ | — | O | H | $OCH_3$ | $CH_3$ | CH | |
| H | — | Q-4 | — | $CH_3$ | — | O | H | $OCH_3$ | $OCH_3$ | CH | |
| H | — | Q-4 | — | $CH_3$ | — | O | H | $CH_3$ | $CH_3$ | CH | |
| H | — | Q-5 | — | — | $CH_3$ | O | H | $CH_3$ | $CH_3$ | CH | |
| H | — | Q-5 | — | — | $CH_3$ | O | H | $CH_3$ | $OCH_3$ | CH | |
| H | — | Q-6 | — | — | $CH_3$ | O | H | $CH_3$ | $OCH_3$ | CH | |
| H | — | Q-7 | — | — | $CH_3$ | O | H | $CH_3$ | $OCH_3$ | CH | |
| H | — | Q-2 | $CH_3$ | — | — | O | H | $CH_3$ | $OCH_3$ | N | |
| H | — | Q-2 | $CH_3$ | — | — | O | H | $OCH_3$ | $OCH_3$ | CH | |
| H | — | Q-2 | $C_2H_5$ | — | — | O | H | $CH_3$ | $CH_3$ | CH | |
| H | — | Q-2 | $C_2H_5$ | — | — | O | H | $OCH_3$ | $CH_3$ | CH | |
| H | — | Q-3 | — | H | — | O | H | $CH_3$ | $OCH_3$ | CH | |
| H | — | Q-3 | — | H | — | O | H | $OCH_3$ | $OCH_3$ | N | |
| H | — | Q-3 | — | $CH_3$ | — | O | H | $CH_3$ | $CH_3$ | CH | |
| H | — | Q-3 | — | $CH_3$ | — | O | H | $OCH_3$ | $CH_3$ | N | |
| H | — | Q-3 | — | $OCH_3$ | — | O | H | $CH_3$ | $OCH_3$ | CH | |
| H | — | Q-3 | — | $OCH_3$ | — | O | H | $OCH_3$ | $OCH_3$ | N | |
| H | — | Q-3 | — | $OC_2H_5$ | — | O | H | $CH_3$ | $CH_3$ | CH | |
| H | — | Q-3 | — | $OC_2H_5$ | — | O | H | $OCH_3$ | $CH_3$ | N | |
| H | — | Q-3 | — | $SCH_3$ | — | O | H | $CH_3$ | $OCH_3$ | CH | |
| H | — | Q-3 | — | $SCH_3$ | — | O | H | $OCH_3$ | $OCH_3$ | N | |

TABLE VIII

| | | | | | | General Structure 8 | | | | | | |
|---|---|---|---|---|---|---|---|---|---|---|---|---|
| $R_1$ | n | E | Q | $R_3$ | $R_4$ | $R_5$ | W | R | X | Y | Z | m.p. (°C.) |
| H | 0 | — | Q-1 | $CH_3$ | — | — | O | H | $CH_3$ | $CH_3$ | CH | |
| H | 0 | — | Q-1 | $CH_3$ | — | — | O | H | $OCH_3$ | $CH_3$ | CH | |
| H | 0 | — | Q-1 | $CH_3$ | — | — | O | H | Cl | $OCH_3$ | CH | |
| H | 0 | — | Q-1 | $CH_3$ | — | — | O | H | $CH_3$ | $OCH_3$ | N | |
| H | 0 | — | Q-1 | $CH_3$ | — | — | O | H | $OCH_3$ | $OCH_3$ | N | |
| H | 0 | — | Q-1 | $C_2H_5$ | — | — | O | H | $OCH_3$ | $CH_3$ | CH | |
| H | 0 | — | Q-1 | $C_2H_5$ | — | — | O | H | $OCH_3$ | $OCH_3$ | CH | |
| H | 0 | — | Q-1 | $C_2H_5$ | — | — | O | H | Cl | $OCH_3$ | CH | |
| H | 0 | — | Q-1 | $C_2H_5$ | — | — | O | H | $CH_3$ | $CH_3$ | CH | |
| H | 0 | — | Q-1 | $C_2H_5$ | — | — | O | H | $CH_3$ | $OCH_3$ | N | |
| H | 0 | — | Q-2 | $CH_3$ | — | — | O | H | $OCH_3$ | $OCH_3$ | N | |
| H | 0 | — | Q-2 | $CH_3$ | — | — | O | H | $OCH_3$ | $OCH_3$ | CH | |
| H | 0 | — | Q-2 | $CH_3$ | — | — | O | H | $OCH_3$ | $CH_3$ | CH | |
| H | 0 | — | Q-2 | $CH_3$ | — | — | O | H | Cl | $OCH_3$ | CH | |
| H | 0 | — | Q-2 | $CH_3$ | — | — | O | H | $CH_3$ | $CH_3$ | CH | |
| H | 0 | — | Q-2 | $CH_3$ | — | — | O | H | $OCH_3$ | $CH_3$ | N | |
| H | 0 | — | Q-2 | $C_2H_5$ | — | — | O | H | $OCH_3$ | $OCH_3$ | N | |
| H | 0 | — | Q-2 | $C_2H_5$ | — | — | O | H | $CH_3$ | $CH_3$ | CH | |
| H | 0 | — | Q-2 | $C_2H_5$ | — | — | O | H | $CH_3$ | $OCH_3$ | CH | |
| H | 0 | — | Q-2 | $C_2H_5$ | — | — | O | H | Cl | $OCH_3$ | CH | |
| H | 0 | — | Q-2 | $C_2H_5$ | — | — | O | H | $CH_3$ | $OCH_3$ | N | |
| H | 0 | — | Q-2 | $C_2H_5$ | — | — | O | H | $OCH_3$ | $OCH_3$ | N | |
| H | 0 | — | Q-3 | — | $CH_3$ | — | O | H | $CH_3$ | $OCH_3$ | CH | |
| H | 0 | — | Q-3 | — | $CH_3$ | — | O | H | Cl | $OCH_3$ | CH | |
| H | 0 | — | Q-3 | — | $CH_3$ | — | O | H | $OCH_3$ | $OCH_3$ | CH | |
| H | 0 | — | Q-3 | — | $CH_3$ | — | O | H | $OCH_3$ | $OCH_3$ | N | |
| H | 0 | — | Q-3 | — | $CH_3$ | — | O | H | $CH_3$ | $OCH_3$ | N | |
| H | 0 | — | Q-3 | — | $C_2H_5$ | — | O | H | $CH_3$ | $CH_3$ | CH | |
| H | 0 | — | Q-3 | — | $C_2H_5$ | — | O | H | $CH_3$ | $OCH_3$ | CH | |
| H | 0 | — | Q-3 | — | $C_2H_5$ | — | O | H | Cl | $OCH_3$ | CH | |
| H | 0 | — | Q-3 | — | $C_2H_5$ | — | O | H | $OCH_3$ | $OCH_3$ | CH | |
| H | 0 | — | Q-3 | — | $C_2H_5$ | — | O | H | $CH_3$ | $OCH_3$ | N | |
| H | 0 | — | Q-3 | — | $CH_2Cl$ | — | O | H | $CH_3$ | $OCH_3$ | CH | |
| H | 0 | — | Q-3 | — | $CH_2Cl$ | — | O | H | $OCH_3$ | $OCH_3$ | CH | |
| H | 0 | — | Q-3 | — | $CH_2Cl$ | — | O | H | Cl | $OCH_3$ | CH | |
| H | 0 | — | Q-3 | — | $CH_2Cl$ | — | O | H | $CH_3$ | $OCH_3$ | N | |
| H | 0 | — | Q-3 | — | $CH_2Cl$ | — | O | H | $OCH_3$ | OCH | N | |
| H | 0 | — | Q-3 | — | $CF_3$ | — | O | H | $CH_3$ | $CH_3$ | CH | |
| H | 0 | — | Q-3 | — | $CF_3$ | — | O | H | $OCH_3$ | $OCH_3$ | CH | |
| H | 0 | — | Q-3 | — | $CF_3$ | — | O | H | $OCH_3$ | $CH_3$ | CH | |
| H | 0 | — | Q-3 | — | $CF_3$ | — | O | H | $CH_3$ | $OCH_3$ | N | |
| H | 0 | — | Q-3 | — | $CH(CH_3)_2$ | — | O | H | $CH_3$ | $OCH_3$ | CH | |
| H | 0 | — | Q-3 | — | $CH(CH_3)_2$ | — | O | H | $OCH_3$ | $OCH_3$ | CH | |
| H | 0 | — | Q-3 | — | $CH(CH_3)_2$ | — | O | H | Cl | $OCH_3$ | CH | |
| H | 0 | — | Q-3 | — | $CH(CH_3)_2$ | — | O | H | $CH_3$ | $OCH_3$ | N | |
| H | 0 | — | Q-3 | — | $OCH_3$ | — | O | H | $OCH_3$ | $OCH_3$ | CH | |
| H | 0 | — | Q-3 | — | $OCH_3$ | — | O | H | $CH_3$ | $OCH_3$ | CH | |
| H | 0 | — | Q-3 | — | $OCH_3$ | — | O | H | Cl | $OCH_3$ | CH | |
| H | 0 | — | Q-3 | — | $OCH_3$ | — | O | H | $OCH_3$ | $OCH_3$ | N | |
| H | 0 | — | Q-3 | — | $SCH_3$ | — | O | H | $CH_3$ | $OCH_3$ | CH | |
| H | 0 | — | Q-3 | — | $SCH_3$ | — | O | H | $OCH_3$ | $OCH_3$ | CH | |
| H | 0 | — | Q-3 | — | $SCH_3$ | — | O | H | $OCH_3$ | $OCH_3$ | N | |
| H | 0 | — | Q-3 | — | $SCH_3$ | — | O | H | $CH_3$ | $OCH_3$ | N | |
| H | 0 | — | Q-3 | — | $N(CH_3)_2$ | — | O | H | $CH_3$ | $CH_3$ | CH | |
| H | 0 | — | Q-3 | — | $N(CH_3)_2$ | — | O | H | $OCH_3$ | $OCH_3$ | CH | |
| H | 0 | — | Q-3 | — | $N(CH_3)_2$ | — | O | H | $OCH_3$ | $CH_3$ | N | |
| H | 0 | — | Q-4 | — | $CH_3$ | — | O | H | $OCH_3$ | $CH_3$ | CH | |
| H | 0 | — | Q-4 | — | $CH_3$ | — | O | H | $OCH_3$ | $OCH_3$ | CH | |
| H | 0 | — | Q-4 | — | $CH_3$ | — | O | H | $CH_3$ | $CH_3$ | CH | |
| H | 0 | — | Q-5 | — | — | $CH_3$ | O | H | $CH_3$ | $CH_3$ | CH | |
| H | 0 | — | Q-5 | — | — | $CH_3$ | O | H | $OCH_3$ | $CH_3$ | CH | |
| H | 0 | — | Q-5 | — | — | $CH_3$ | O | H | $OCH_3$ | $OCH_3$ | CH | |
| H | 0 | — | Q-5 | — | — | $CH_3$ | O | H | Cl | $OCH_3$ | CH | |
| H | 0 | — | Q-5 | — | — | $CH_3$ | O | H | $CH_3$ | $OCH_3$ | N | |
| H | 0 | — | Q-5 | — | — | $C_2H_5$ | O | H | $CH_3$ | $OCH_3$ | CH | |
| H | 0 | — | Q-5 | — | — | $C_2H_5$ | O | H | Cl | $OCH_3$ | CH | |
| H | 0 | — | Q-5 | — | — | $C_2H_5$ | O | H | $CH_3$ | $CH_3$ | CH | |
| H | 0 | — | Q-5 | — | — | $C_2H_5$ | O | H | $OCH_3$ | $OCH_3$ | CH | |
| H | 0 | — | Q-5 | — | — | $C_2H_5$ | O | H | $OCH_3$ | $CH_3$ | N | |
| 4-$CH_3$ | 0 | — | Q-1 | $CH_3$ | — | — | O | H | $OCH_3$ | $CH_3$ | CH | |
| 4-$CH_3$ | 0 | — | Q-1 | $CH_3$ | — | — | O | H | $OCH_3$ | $OCH_3$ | CH | |
| 4-$CH_3$ | 0 | — | Q-1 | $CH_3$ | — | — | O | H | Cl | $OCH_3$ | CH | |
| 4-$CH_3$ | 0 | — | Q-1 | $CH_3$ | — | — | O | H | $CH_3$ | $CH_3$ | CH | |
| 4-$CH_3$ | 0 | — | Q-1 | $CH_3$ | — | — | O | H | $OCH_3$ | $CH_3$ | N | |
| 4-Cl | 0 | — | Q-1 | $CH_3$ | — | — | O | H | $OCH_3$ | $CH_3$ | N | |
| 4-Cl | 0 | — | Q-1 | $CH_3$ | — | — | O | H | $OCH_3$ | $CH_3$ | CH | |
| 4-Cl | 0 | — | Q-1 | $CH_3$ | — | — | O | H | $OCH_3$ | $OCH_3$ | CH | |
| 4-Cl | 0 | — | Q-1 | $CH_3$ | — | — | O | H | Cl | $OCH_3$ | CH | |
| 4-Cl | 0 | — | Q-1 | $CH_3$ | — | — | O | H | $CH_3$ | $CH_3$ | CH | |
| 4-Cl | 0 | — | Q-2 | $CH_3$ | — | — | O | H | $OCH_3$ | $OCH_3$ | CH | |

TABLE VIII-continued

General Structure 8

| $R_1$ | n | E | Q | $R_3$ | $R_4$ | $R_5$ | W | R | X | Y | Z | m.p. (°C.) |
|---|---|---|---|---|---|---|---|---|---|---|---|---|
| 4-Cl | 0 | — | Q-2 | $CH_3$ | — | — | O | H | Cl | $OCH_3$ | CH | |
| H | 1 | — | Q-1 | $CH_3$ | — | — | O | H | Cl | $OCH_3$ | CH | |
| H | 1 | — | Q-1 | $CH_3$ | — | — | O | H | $OCH_3$ | $OCH_3$ | CH | |
| H | 1 | — | Q-1 | $CH_3$ | — | — | O | H | $CH_3$ | $CH_3$ | CH | |
| H | 1 | — | Q-5 | — | — | $CH_3$ | O | H | $CH_3$ | $CH_3$ | CH | |
| H | 1 | — | Q-5 | — | — | $CH_3$ | O | H | $OCH_3$ | $OCH_3$ | CH | |
| H | 1 | — | Q-5 | — | — | $CH_3$ | O | H | Cl | $OCH_3$ | CH | |
| H | 0 | — | Q-1 | $CH_3$ | — | — | O | H | $OCH_3$ | $OCH_3$ | CH | |
| H | 0 | — | Q-1 | $CH_3$ | — | — | O | H | $OC_2H_5$ | $NHCH_3$ | N | |
| H | 0 | — | Q-1 | $C_2H_5$ | — | — | O | H | $OCH_3$ | $OCH_3$ | N | |
| H | 0 | — | Q-2 | $CH_3$ | — | — | O | H | $OC_2H_5$ | $NHCH_3$ | N | |
| H | 0 | — | Q-3 | — | H | — | O | H | $OCH_3$ | $OCH_3$ | CH | |
| H | 0 | — | Q-3 | — | H | — | O | H | $CH_3$ | $OCH_3$ | CH | |
| H | 0 | — | Q-3 | — | H | — | O | H | $CH_3$ | $CH_3$ | CH | |
| H | 0 | — | Q-3 | — | H | — | O | H | Cl | $OCH_3$ | CH | |
| H | 0 | — | Q-3 | — | H | — | O | H | $OCH_3$ | $OCH_3$ | N | |
| H | 0 | — | Q-3 | — | H | — | O | H | $CH_3$ | $OCH_3$ | N | |
| H | 0 | — | Q-3 | — | $CH_3$ | — | O | H | $CH_3$ | $CH_3$ | N | |
| H | 0 | — | Q-3 | — | $C_2H_5$ | — | O | H | $OCH_3$ | $OCH_3$ | N | |
| H | 0 | — | Q-3 | — | $CH_2Cl$ | — | O | H | $CH_3$ | $CH_3$ | CH | |
| H | 0 | — | Q-3 | — | $CF_3$ | — | O | H | Cl | $OCH_3$ | CH | |
| H | 0 | — | Q-3 | — | $CF_3$ | — | O | H | $OCH_3$ | $OCH_3$ | N | |
| H | 0 | — | Q-3 | — | $CH(CH_3)_2$ | — | O | H | $CH_3$ | $CH_3$ | CH | |
| H | 0 | — | Q-3 | — | $CH(CH_3)_2$ | — | O | H | $OCH_3$ | $OCH_3$ | N | |
| H | 0 | — | Q-3 | — | $OCH_3$ | — | O | H | $CH_3$ | $CH_3$ | CH | |
| H | 0 | — | Q-3 | — | $OCH_3$ | — | O | H | $CH_3$ | $OCH_3$ | N | |
| H | 0 | — | Q-3 | — | $SCH_3$ | — | O | H | $CH_3$ | $CH_3$ | CH | |
| H | 0 | — | Q-3 | — | $SCH_3$ | — | O | H | Cl | $OCH_3$ | CH | |
| H | 0 | — | Q-3 | — | $OC_2H_5$ | — | O | H | $OCH_3$ | $OCH_3$ | CH | |
| H | 0 | — | Q-3 | — | $OC_2H_5$ | — | O | H | $CH_3$ | $OCH_3$ | CH | |
| H | 0 | — | Q-3 | — | $OC_2H_5$ | — | O | H | $CH_3$ | $CH_3$ | CH | |
| H | 0 | — | Q-3 | — | $OC_2H_5$ | — | O | H | Cl | $OCH_3$ | CH | |
| H | 0 | — | Q-3 | — | $OC_2H_5$ | — | O | H | $OCH_3$ | $OCH_3$ | N | |
| H | 0 | — | Q-3 | — | $OC_2H_5$ | — | O | H | $CH_3$ | $OCH_3$ | N | |
| H | 0 | — | Q-3 | — | $N(CH_3)_2$ | — | O | H | $CH_3$ | $OCH_3$ | CH | |
| H | 0 | — | Q-3 | — | $N(CH_3)_2$ | — | O | H | Cl | $OCH_3$ | CH | |
| H | 0 | — | Q-3 | — | $N(CH_3)_2$ | — | O | H | $OCH_3$ | $OCH_3$ | N | |
| H | 0 | — | Q-4 | — | $CH_3$ | — | O | H | Cl | $OCH_3$ | CH | |
| H | 0 | — | Q-4 | — | $CH_3$ | — | O | H | $OCH_3$ | $OCH_3$ | N | |
| H | 0 | — | Q-4 | — | $CH_3$ | — | O | H | $OCH_3$ | $OCH_3$ | CH | |
| H | 0 | — | Q-4 | — | $C_2H_5$ | — | O | H | $OCH_3$ | $OCH_3$ | CH | |
| H | 0 | — | Q-4 | — | $C_2H_5$ | — | O | H | $CH_3$ | $OCH_3$ | CH | |
| H | 0 | — | Q-4 | — | $C_2H_5$ | — | O | H | $CH_3$ | $CH_3$ | CH | |
| H | 0 | — | Q-4 | — | $C_2H_5$ | — | O | H | Cl | $OCH_3$ | CH | |
| H | 0 | — | Q-4 | — | $C_2H_5$ | — | O | H | $OCH_3$ | $OCH_3$ | N | |
| H | 0 | — | Q-4 | — | $C_2H_5$ | — | O | H | $CH_3$ | $OCH_3$ | N | |
| H | 0 | — | Q-4 | — | $OCH_3$ | — | O | H | $OCH_3$ | $OCH_3$ | CH | |
| H | 0 | — | Q-4 | — | $OCH_3$ | — | O | H | $CH_3$ | $OCH_3$ | CH | |
| H | 0 | — | Q-4 | — | $OCH_3$ | — | O | H | $CH_3$ | $CH_3$ | CH | |
| H | 0 | — | Q-4 | — | $OCH_3$ | — | O | H | Cl | $OCH_3$ | CH | |
| H | 0 | — | Q-4 | — | $OCH_3$ | — | O | H | $OCH_3$ | $OCH_3$ | N | |
| H | 0 | — | Q-4 | — | $OCH_3$ | — | O | H | $CH_3$ | $OCH_3$ | N | |
| H | 0 | — | Q-5 | — | — | $CH_3$ | O | H | $OCH_3$ | $OCH_3$ | N | |
| H | 0 | — | Q-5 | — | — | $C_2H_5$ | O | H | $OCH_3$ | $OCH_3$ | N | |
| H | 0 | — | Q-6 | — | — | $CH_3$ | O | H | $OCH_3$ | $OCH_3$ | CH | |
| H | 0 | — | Q-6 | — | — | $CH_3$ | O | H | $CH_3$ | $CH_3$ | CH | |
| H | 0 | — | Q-6 | — | — | $CH_3$ | O | H | $OCH_3$ | $OCH_3$ | N | |
| H | 0 | — | Q-6 | — | — | $C_2H_5$ | O | H | Cl | $OCH_3$ | CH | |
| H | 0 | — | Q-6 | — | — | $C_2H_5$ | O | H | $CH_3$ | $OCH_3$ | N | |
| H | 0 | — | Q-6 | — | — | $C_2H_5$ | O | H | $OCH_3$ | $OCH_3$ | N | |
| H | 0 | — | Q-7 | — | — | $CH_3$ | O | H | Cl | $OCH_3$ | CH | |
| H | 0 | — | Q-7 | — | — | $CH_3$ | O | H | $CH_3$ | $OCH_3$ | CH | |
| H | 0 | — | Q-7 | — | — | $CH_3$ | O | H | $CH_3$ | $OCH_3$ | N | |
| H | 0 | — | Q-7 | — | — | $C_2H_5$ | O | H | $OCH_3$ | $OCH_3$ | CH | |
| H | 0 | — | Q-7 | — | — | C2H5 | O | H | $CH_3$ | $CH_3$ | CH | |
| H | 0 | — | Q-7 | — | — | $C_2H_5$ | O | H | $OCH_3$ | $OCH_3$ | N | |
| 4-$CH_3$ | 0 | — | Q-1 | $CH_3$ | — | — | O | H | $OCH_3$ | $OCH_3$ | N | |
| 4-$CH_3$ | 0 | — | Q-2 | $CH_3$ | — | — | O | H | $OCH_3$ | $OCH_3$ | CH | |
| 4-$CH_3$ | 0 | — | Q-2 | $CH_3$ | — | — | O | H | $CH_3$ | $OCH_3$ | CH | |
| 4-$CH_3$ | 0 | — | Q-2 | $CH_3$ | — | — | O | H | $CH_3$ | $CH_3$ | CH | |
| 4-$CH_3$ | 0 | — | Q-2 | $CH_3$ | — | — | O | H | Cl | $OCH_3$ | CH | |
| 4-$CH_3$ | 0 | — | Q-2 | $CH_3$ | — | — | O | H | $OCH_3$ | $OCH_3$ | N | |
| 4-$CH_3$ | 0 | — | Q-2 | $CH_3$ | — | — | O | H | $CH_3$ | $OCH_3$ | N | |
| 4-$CH_3$ | 0 | — | Q-3 | — | $CH_3$ | — | O | H | $OCH_3$ | $OCH_3$ | CH | |
| 4-$CH_3$ | 0 | — | Q-3 | — | $CH_3$ | — | O | H | $CH_3$ | $OCH_3$ | CH | |
| 4-$CH_3$ | 0 | — | Q-3 | — | $CH_3$ | — | O | H | $CH_3$ | $CH_3$ | CH | |
| 4-$CH_3$ | 0 | — | Q-3 | — | $CH_3$ | — | O | H | Cl | $OCH_3$ | CH | |
| 4-$CH_3$ | 0 | — | Q-3 | — | $CH_3$ | — | O | H | $OCH_3$ | $OCH_3$ | N | |
| 4-$CH_3$ | 0 | — | Q-3 | — | $CH_3$ | — | O | H | $CH_3$ | $OCH_3$ | N | |
| 4-$CH_3$ | 0 | — | Q-3 | — | $OCH_3$ | — | O | H | $OCH_3$ | $OCH_3$ | CH | |

TABLE VIII-continued

| | | | | | General Structure 8 | | | | | | | |
|---|---|---|---|---|---|---|---|---|---|---|---|---|
| $R_1$ | n | E | Q | $R_3$ | $R_4$ | $R_5$ | W | R | X | Y | Z | m.p. (°C.) |
| 4-$CH_3$ | 0 | — | Q-3 | — | $OCH_3$ | — | O | H | $CH_3$ | $OCH_3$ | CH | |
| 4-$CH_3$ | 0 | — | Q-3 | — | $OCH_3$ | — | O | H | $CH_3$ | $CH_3$ | CH | |
| 4-$CH_3$ | 0 | — | Q-3 | — | $OCH_3$ | — | O | H | Cl | $OCH_3$ | CH | |
| 4-$CH_3$ | 0 | — | Q-3 | — | $OCH_3$ | — | O | H | $OCH_3$ | $OCH_3$ | N | |
| 4-$CH_3$ | 0 | — | Q-3 | — | $OCH_3$ | — | O | H | $CH_3$ | $OCH_3$ | N | |
| 4-Cl | 0 | — | Q-1 | $CH_3$ | — | — | O | H | $OCH_3$ | $OCH_3$ | N | |
| 4-Cl | 0 | — | Q-2 | $CH_3$ | — | — | O | H | $CH_3$ | $OCH_3$ | CH | |
| 4-Cl | 0 | — | Q-2 | $CH_3$ | — | — | O | H | $CH_3$ | $CH_3$ | CH | |
| 4-Cl | 0 | — | Q-2 | $CH_3$ | — | — | O | H | $OCH_3$ | $OCH_3$ | N | |
| 4-Cl | 0 | — | Q-2 | $CH_3$ | — | — | O | H | $CH_3$ | $OCH_3$ | N | |
| 4-Cl | 0 | — | Q-3 | — | $CH_3$ | — | O | H | $OCH_3$ | $OCH_3$ | CH | |
| 4-Cl | 0 | — | Q-3 | — | $CH_3$ | — | O | H | $CH_3$ | $OCH_3$ | CH | |
| 4-Cl | 0 | — | Q-3 | — | $CH_3$ | — | O | H | $CH_3$ | $CH_3$ | CH | |
| 4-Cl | 0 | — | Q-3 | — | $CH_3$ | — | O | H | Cl | $OCH_3$ | CH | |
| 4-Cl | 0 | — | Q-3 | — | $CH_3$ | — | O | H | $OCH_3$ | $OCH_3$ | N | |
| 4-Cl | 0 | — | Q-3 | — | $CH_3$ | — | O | H | $CH_3$ | $OCH_3$ | N | |
| 4-Cl | 0 | — | Q-3 | — | $OCH_3$ | — | O | H | $OCH_3$ | $OCH_3$ | CH | |
| 4-Cl | 0 | — | Q-3 | — | $OCH_3$ | — | O | H | $CH_3$ | $OCH_3$ | CH | |
| 4-Cl | 0 | — | Q-3 | — | $OCH_3$ | — | O | H | $CH_3$ | $CH_3$ | CH | |
| 4-Cl | 0 | — | Q-3 | — | $OCH_3$ | — | O | H | Cl | $OCH_3$ | CH | |
| 4-Cl | 0 | — | Q-3 | — | $OCH_3$ | — | O | H | $OCH_3$ | $OCH_3$ | N | |
| 4-Cl | 0 | — | Q-3 | — | $OCH_3$ | — | O | H | $CH_3$ | $OCH_3$ | N | |
| 4-Br | 0 | — | Q-1 | $CH_3$ | — | — | O | H | $OCH_3$ | $OCH_3$ | CH | |
| 4-Br | 0 | — | Q-1 | $CH_3$ | — | — | O | H | $CH_3$ | $OCH_3$ | CH | |
| 4-Br | 0 | — | Q-1 | $CH_3$ | — | — | O | H | $CH_3$ | $CH_3$ | CH | |
| 4-Br | 0 | — | Q-1 | $CH_3$ | — | — | O | H | Cl | $OCH_3$ | CH | |
| 4-Br | 0 | — | Q-1 | $CH_3$ | — | — | O | H | $OCH_3$ | $OCH_3$ | N | |
| 4-Br | 0 | — | Q-1 | $CH_3$ | — | — | O | H | $CH_3$ | $OCH_3$ | N | |
| 4-Br | 0 | — | Q-2 | $CH_3$ | — | — | O | H | $OCH_3$ | $OCH_3$ | CH | |
| 4-Br | 0 | — | Q-2 | $CH_3$ | — | — | O | H | $CH_3$ | $OCH_3$ | CH | |
| 4-Br | 0 | — | Q-2 | $CH_3$ | — | — | O | H | $CH_3$ | $CH_3$ | CH | |
| 4-Br | 0 | — | Q-2 | $CH_3$ | — | — | O | H | Cl | $OCH_3$ | CH | |
| 4-Br | 0 | — | Q-2 | $CH_3$ | — | — | O | H | $OCH_3$ | $OCH_3$ | N | |
| 4-Br | 0 | — | Q-2 | $CH_3$ | — | — | O | H | $CH_3$ | $OCH_3$ | N | |
| 4-Br | 0 | — | Q-3 | — | $CH_3$ | — | O | H | $OCH_3$ | $OCH_3$ | CH | |
| 4-Br | 0 | — | Q-3 | — | $CH_3$ | — | O | H | $CH_3$ | $OCH_3$ | CH | |
| 4-Br | 0 | — | Q-3 | — | $CH_3$ | — | O | H | $CH_3$ | $CH_3$ | CH | |
| 4-Br | 0 | — | Q-3 | — | $CH_3$ | — | O | H | Cl | $OCH_3$ | CH | |
| 4-Br | 0 | — | Q-3 | — | $CH_3$ | — | O | H | $OCH_3$ | $OCH_3$ | N | |
| 4-Br | 0 | — | Q-3 | — | $CH_3$ | — | O | H | $CH_3$ | $OCH_3$ | N | |
| 4-Br | 0 | — | Q-3 | — | $OCH_3$ | — | O | H | $OCH_3$ | $OCH_3$ | CH | |
| 4-Br | 0 | — | Q-3 | — | $OCH_3$ | — | O | H | $CH_3$ | $OCH_3$ | CH | |
| 4-Br | 0 | — | Q-3 | — | $OCH_3$ | — | O | H | $CH_3$ | $CH_3$ | CH | |
| 4-Br | 0 | — | Q-3 | — | $OCH_3$ | — | O | H | Cl | $OCH_3$ | CH | |
| 4-Br | 0 | — | Q-3 | — | $OCH_3$ | — | O | H | $OCH_3$ | $OCH_3$ | N | |
| 4-Br | 0 | — | Q-3 | — | $OCH_3$ | — | O | H | $CH_3$ | $OCH_3$ | N | |
| H | 0 | — | Q-1 | $CH_3$ | — | — | S | H | $OCH_3$ | $OCH_3$ | CH | |
| H | 0 | — | Q-1 | $C_2H_5$ | — | — | O | $CH_3$ | $CH_3$ | $OCH_3$ | CH | |
| H | 0 | — | Q-2 | $CH_3$ | — | — | $NCH_3$ | H | $OCH_3$ | $OCH_3$ | CH | |
| H | 0 | — | Q-2 | $CH_3$ | — | — | S | H | $OCH_3$ | $OCH_3$ | CH | |
| H | 0 | — | Q-3 | — | $CH_3$ | — | $NOCH_3$ | H | $OCH_3$ | $OCH_3$ | CH | |
| H | 0 | — | Q-3 | — | $OCH_3$ | — | O | $CH_3$ | $CH_3$ | $CH_3$ | CH | |
| H | 0 | — | Q-5 | — | — | $CH_3$ | S | H | $OCH_3$ | $OCH_3$ | CH | |

TABLE IX

| | | | | | General Structure 9 | | | | | | | |
|---|---|---|---|---|---|---|---|---|---|---|---|---|
| $R_1$ | n | E | Q | $R_3$ | $R_4$ | $R_5$ | W | R | X | Y | Z | m.p. (°C.) |
| H | 0 | — | Q-1 | $CH_3$ | — | — | O | H | $CH_3$ | $CH_3$ | CH | |
| H | 0 | — | Q-1 | $CH_3$ | — | — | O | H | $OCH_3$ | $CH_3$ | CH | |
| H | 0 | — | Q-1 | $CH_3$ | — | — | O | H | Cl | $OCH_3$ | CH | |
| H | 0 | — | Q-1 | $CH_3$ | — | — | O | H | $CH_3$ | $OCH_3$ | N | |
| H | 0 | — | Q-1 | $CH_3$ | — | — | O | H | $OCH_3$ | $OCH_3$ | N | |
| H | 0 | — | Q-1 | $C_2H_5$ | — | — | O | H | $OCH_3$ | $CH_3$ | CH | |
| H | 0 | — | Q-1 | $C_2H_5$ | — | — | O | H | $OCH_3$ | $OCH_3$ | CH | |
| H | 0 | — | Q-1 | $C_2H_5$ | — | — | O | H | Cl | $OCH_3$ | CH | |
| H | 0 | — | Q-1 | $C_2H_5$ | — | — | O | H | $CH_3$ | $CH_3$ | CH | |
| H | 0 | — | Q-1 | $C_2H_5$ | — | — | O | H | $CH_3$ | $OCH_3$ | N | |
| H | 0 | — | Q-2 | $CH_3$ | — | — | O | H | $OCH_3$ | $OCH_3$ | N | |
| H | 0 | — | Q-2 | $CH_3$ | — | — | O | H | $OCH_3$ | $OCH_3$ | CH | |
| H | 0 | — | Q-2 | $CH_3$ | — | — | O | H | $OCH_3$ | $CH_3$ | CH | |
| H | 0 | — | Q-2 | $CH_3$ | — | — | O | H | Cl | $OCH_3$ | CH | |
| H | 0 | — | Q-2 | $CH_3$ | — | — | O | H | $CH_3$ | $CH_3$ | CH | |
| H | 0 | — | Q-2 | $CH_3$ | — | — | O | H | $OCH_3$ | $CH_3$ | N | |
| H | 0 | — | Q-2 | $C_2H_5$ | — | — | O | H | $OCH_3$ | $OCH_3$ | N | |
| H | 0 | — | Q-2 | $C_2H_5$ | — | — | O | H | $CH_3$ | $CH_3$ | CH | |
| H | 0 | — | Q-2 | $C_2H_5$ | — | — | O | H | $CH_3$ | $OCH_3$ | CH | |
| H | 0 | — | Q-2 | $C_2H_5$ | — | — | O | H | Cl | $OCH_3$ | CH | |

TABLE IX-continued

General Structure 9

| $R_1$ | n | E | Q | $R_3$ | $R_4$ | $R_5$ | W | R | X | Y | Z | m.p. (°C.) |
|---|---|---|---|---|---|---|---|---|---|---|---|---|
| H | 0 | — | Q-2 | $C_2H_5$ | — | — | O | H | $CH_3$ | $OCH_3$ | N | |
| H | 0 | — | Q-2 | $C_2H_5$ | — | — | O | H | $OCH_3$ | $OCH_3$ | N | |
| H | 0 | — | Q-3 | — | $CH_3$ | — | O | H | $CH_3$ | $OCH_3$ | CH | |
| H | 0 | — | Q-3 | — | $CH_3$ | — | O | H | Cl | $OCH_3$ | CH | |
| H | 0 | — | Q-3 | — | $CH_3$ | — | O | H | $OCH_3$ | $OCH_3$ | CH | |
| H | 0 | — | Q-3 | — | $CH_3$ | — | O | H | $OCH_3$ | $OCH_3$ | N | |
| H | 0 | — | Q-3 | — | $CH_3$ | — | O | H | $CH_3$ | $OCH_3$ | N | |
| H | 0 | — | Q-3 | — | $C_2H_5$ | — | O | H | $CH_3$ | $CH_3$ | CH | |
| H | 0 | — | Q-3 | — | $C_2H_5$ | — | O | H | $CH_3$ | $OCH_3$ | CH | |
| H | 0 | — | Q-3 | — | $C_2H_5$ | — | O | H | Cl | $OCH_3$ | CH | |
| H | 0 | — | Q-3 | — | $C_2H_5$ | — | O | H | $OCH_3$ | $OCH_3$ | CH | |
| H | 0 | — | Q-3 | — | $C_2H_5$ | — | O | H | $CH_3$ | $OCH_3$ | N | |
| H | 0 | — | Q-3 | — | $CH_2Cl$ | — | O | H | $CH_3$ | $OCH_3$ | CH | |
| H | 0 | — | Q-3 | — | $CH_2Cl$ | — | O | H | $OCH_3$ | $OCH_3$ | CH | |
| H | 0 | — | Q-3 | — | $CH_2Cl$ | — | O | H | Cl | $OCH_3$ | CH | |
| H | 0 | — | Q-3 | — | $CH_2Cl$ | — | O | H | $CH_3$ | $OCH_3$ | N | |
| H | 0 | — | Q-3 | — | $CH_2Cl$ | — | O | H | $OCH_3$ | $OCH_3$ | N | |
| H | 0 | — | Q-3 | — | $CF_3$ | — | O | H | $CH_3$ | $CH_3$ | CH | |
| H | 0 | — | Q-3 | — | $CF_3$ | — | O | H | $OCH_3$ | $OCH_3$ | CH | |
| H | 0 | — | Q-3 | — | $CF_3$ | — | O | H | $OCH_3$ | $CH_3$ | CH | |
| H | 0 | — | Q-3 | — | $CF_3$ | — | O | H | $CH_3$ | $OCH_3$ | N | |
| H | 0 | — | Q-3 | — | $CH(CH_3)_2$ | — | O | H | $CH_3$ | $OCH_3$ | CH | |
| H | 0 | — | Q-3 | — | $CH(CH_3)_2$ | — | O | H | $OCH_3$ | $OCH_3$ | CH | |
| H | 0 | — | Q-3 | — | $CH(CH_3)_2$ | — | O | H | Cl | $OCH_3$ | CH | |
| H | 0 | — | Q-3 | — | $CH(CH_3)_2$ | — | O | H | $CH_3$ | $OCH_3$ | N | |
| H | 0 | — | Q-3 | — | $OCH_3$ | — | O | H | $OCH_3$ | $OCH_3$ | CH | |
| H | 0 | — | Q-3 | — | $OCH_3$ | — | O | H | $CH_3$ | $OCH_3$ | CH | |
| H | 0 | — | Q-3 | — | $OCH_3$ | — | O | H | Cl | $OCH_3$ | CH | |
| H | 0 | — | Q-3 | — | $OCH_3$ | — | O | H | $OCH_3$ | $OCH_3$ | N | |
| H | 0 | — | Q-3 | — | $SCH_3$ | — | O | H | $CH_3$ | $OCH_3$ | CH | |
| H | 0 | — | Q-3 | — | $SCH_3$ | — | O | H | $OCH_3$ | $OCH_3$ | CH | |
| H | 0 | — | Q-3 | — | $SCH_3$ | — | O | H | $OCH_3$ | $OCH_3$ | N | |
| H | 0 | — | Q-3 | — | $SCH_3$ | — | O | H | $CH_3$ | $OCH_3$ | N | |
| H | 0 | — | Q-3 | — | $N(CH_3)_2$ | — | O | H | $CH_3$ | $CH_3$ | CH | |
| H | 0 | — | Q-3 | — | $N(CH_3)_2$ | — | O | H | $OCH_3$ | $OCH_3$ | CH | |
| H | 0 | — | Q-3 | — | $N(CH_3)_2$ | — | O | H | $OCH_3$ | $CH_3$ | N | |
| H | 0 | — | Q-4 | — | $CH_3$ | — | O | H | $OCH_3$ | $CH_3$ | N | |
| H | 0 | — | Q-4 | — | $CH_3$ | — | O | H | $OCH_3$ | $CH_3$ | CH | |
| H | 0 | — | Q-4 | — | $CH_3$ | — | O | H | $OCH_3$ | $OCH_3$ | CH | |
| H | 0 | — | Q-4 | — | $CH_3$ | — | O | H | Cl | $OCH_3$ | CH | |
| H | 0 | — | Q-4 | — | $CH_3$ | — | O | H | $CH_3$ | $CH_3$ | CH | |
| H | 0 | — | Q-5 | — | — | $CH_3$ | O | H | $CH_3$ | $CH_3$ | CH | |
| H | 0 | — | Q-5 | — | — | $CH_3$ | O | H | $OCH_3$ | $CH_3$ | CH | |
| H | 0 | — | Q-5 | — | — | $CH_3$ | O | H | $OCH_3$ | $OCH_3$ | CH | |
| H | 0 | — | Q-5 | — | — | $CH_3$ | O | H | Cl | $OCH_3$ | CH | |
| H | 0 | — | Q-5 | — | — | $CH_3$ | O | H | $CH_3$ | $OCH_3$ | N | |
| 4-$CH_3$ | 0 | — | Q-1 | $CH_3$ | — | — | O | H | $CH_3$ | $CH_3$ | CH | |
| 4-$CH_3$ | 0 | — | Q-1 | $CH_3$ | — | — | O | H | $CH_3$ | $OCH_3$ | CH | |
| 4-$CH_3$ | 0 | — | Q-1 | $CH_3$ | — | — | O | H | $OCH_3$ | $OCH_3$ | CH | |
| 4-$CH_3$ | 0 | — | Q-1 | $CH_3$ | — | — | O | H | Cl | $OCH_3$ | CH | |
| 4-$CH_3$ | 0 | — | Q-1 | $CH_3$ | — | — | O | H | $CH_3$ | $OCH_3$ | N | |
| 4-Br | 0 | — | Q-1 | $CH_3$ | — | — | O | H | $CH_3$ | $CH_3$ | CH | |
| 4-Br | 0 | — | Q-1 | $CH_3$ | — | — | O | H | $CH_3$ | $OCH_3$ | CH | |
| 4-Br | 0 | — | Q-1 | $CH_3$ | — | — | O | H | $OCH_3$ | $OCH_3$ | CH | |
| 4-Br | 0 | — | Q-1 | $CH_3$ | — | — | O | H | Cl | $OCH_3$ | CH | |
| 4-Cl | 0 | — | Q-1 | $CH_3$ | — | — | O | H | $CH_3$ | $OCH_3$ | N | |
| 4-Cl | 0 | — | Q-1 | $CH_3$ | — | — | O | H | $CH_3$ | $OCH_3$ | CH | |
| 4-Cl | 0 | — | Q-1 | $CH_3$ | — | — | O | H | $OCH_3$ | $OCH_3$ | CH | |
| 4-Cl | 0 | — | Q-1 | $CH_3$ | — | — | O | H | Cl | $OCH_3$ | CH | |
| 4-Cl | 0 | — | Q-1 | $CH_3$ | — | — | O | H | $CH_3$ | $CH_3$ | CH | |
| 4-$CH_3$ | 0 | — | Q-2 | $CH_3$ | — | — | O | H | $CH_3$ | $CH_3$ | CH | |
| 4-$CH_3$ | 0 | — | Q-2 | $CH_3$ | — | — | O | H | $CH_3$ | $OCH_3$ | CH | |
| 4-$CH_3$ | 0 | — | Q-2 | $CH_3$ | — | — | O | H | $OCH_3$ | $OCH_3$ | CH | |
| 4-$CH_3$ | 0 | — | Q-2 | $CH_3$ | — | — | O | H | Cl | $OCH_3$ | CH | |
| 4-$CH_3$ | 0 | — | Q-5 | — | — | $CH_3$ | O | H | Cl | $OCH_3$ | CH | |
| 4-$CH_3$ | 0 | — | Q-5 | — | — | $CH_3$ | O | H | $OCH_3$ | $OCH_3$ | CH | |
| 4-$CH_3$ | 0 | — | Q-5 | — | — | $CH_3$ | O | H | $CH_3$ | $OCH_3$ | CH | |
| 4-$CH_3$ | 0 | — | Q-5 | — | — | $CH_3$ | O | H | $CH_3$ | $CH_3$ | CH | |
| H | 0 | — | Q-1 | $CH_3$ | — | — | O | H | $OCH_3$ | $OCH_3$ | CH | |
| H | 0 | — | Q-1 | $C_2H_5$ | — | — | O | H | $OCH_3$ | $OCH_3$ | N | |
| H | 0 | — | Q-3 | — | $CH_3$ | — | O | H | $CH_3$ | $CH_3$ | N | |
| H | 0 | — | Q-3 | — | $C_2H_5$ | — | O | H | $OCH_3$ | $OCH_3$ | N | |
| H | 0 | — | Q-3 | — | $CH_2Cl$ | — | O | H | $CH_3$ | $CH_3$ | CH | |
| H | 0 | — | Q-3 | — | $CF_3$ | — | O | H | Cl | $OCH_3$ | CH | |
| H | 0 | — | Q-3 | — | $CF_3$ | — | O | H | $OCH_3$ | $OCH_3$ | N | |
| H | 0 | — | Q-3 | — | $CH(CH_3)_2$ | — | O | H | $CH_3$ | $CH_3$ | CH | |
| H | 0 | — | Q-3 | — | $CH(CH_3)_2$ | — | O | H | $OCH_3$ | $OCH_3$ | N | |
| H | 0 | — | Q-3 | — | $OCH_3$ | — | O | H | $CH_3$ | $OCH_3$ | CH | |
| H | 0 | — | Q-3 | — | $OCH_3$ | — | O | H | $CH_3$ | $OCH_3$ | N | |
| H | 0 | — | Q-3 | — | $SCH_3$ | — | O | H | $CH_3$ | $CH_3$ | CH | |

TABLE IX-continued

General Structure 9

| $R_1$ | n | E | Q | $R_3$ | $R_4$ | $R_5$ | W | R | X | Y | Z | m.p. (°C.) |
|---|---|---|---|---|---|---|---|---|---|---|---|---|
| H | 0 | — | Q-3 | — | $SCH_3$ | — | O | H | Cl | $OCH_3$ | CH | |
| H | 0 | — | Q-3 | — | $OC_2H_5$ | — | O | H | $OCH_3$ | $OCH_3$ | CH | |
| H | 0 | — | Q-3 | — | $OC_2H_5$ | — | O | H | $CH_3$ | $OCH_3$ | CH | |
| H | 0 | — | Q-3 | — | $OC_2H_5$ | — | O | H | $CH_3$ | $CH_3$ | CH | |
| H | 0 | — | Q-3 | — | $OC_2H_5$ | — | O | H | Cl | $OCH_3$ | CH | |
| H | 0 | — | Q-3 | — | $OC_2H_5$ | — | O | H | $OCH_3$ | $OCH_3$ | N | |
| H | 0 | — | Q-3 | — | $OC_2H_5$ | — | O | H | $CH_3$ | $OCH_3$ | N | |
| H | 0 | — | Q-3 | — | $N(CH_3)_2$ | — | O | H | $CH_3$ | $OCH_3$ | CH | |
| H | 0 | — | Q-3 | — | $N(CH_3)_2$ | — | O | H | Cl | $OCH_3$ | CH | |
| H | 0 | — | Q-3 | — | $N(CH_3)_2$ | — | O | H | $OCH_3$ | $OCH_3$ | N | |
| H | 0 | — | Q-4 | — | $CH_3$ | — | O | H | $OCH_3$ | $OCH_3$ | N | |
| H | 0 | — | Q-5 | — | — | $CH_3$ | O | H | $OCH_3$ | $OCH_3$ | N | |
| H | 0 | — | Q-6 | — | — | $CH_3$ | O | H | $OCH_3$ | $OCH_3$ | CH | |
| H | 0 | — | Q-6 | — | — | $CH_3$ | O | H | $CH_3$ | $OCH_3$ | CH | |
| H | 0 | — | Q-6 | — | — | $CH_3$ | O | H | $CH_3$ | $CH_3$ | CH | |
| H | 0 | — | Q-6 | — | — | $CH_3$ | O | H | Cl | $OCH_3$ | CH | |
| H | 0 | — | Q-6 | — | — | $CH_3$ | O | H | $OCH_3$ | $OCH_3$ | N | |
| H | 0 | — | Q-6 | — | — | $CH_3$ | O | H | $CH_3$ | $OCH_3$ | N | |
| H | 0 | — | Q-7 | — | — | $CH_3$ | O | H | $OCH_3$ | $OCH_3$ | CH | |
| H | 0 | — | Q-7 | — | — | $CH_3$ | O | H | $CH_3$ | $OCH_3$ | CH | |
| H | 0 | — | Q-7 | — | — | $CH_3$ | O | H | $CH_3$ | $CH_3$ | CH | |
| H | 0 | — | Q-7 | — | — | $CH_3$ | O | H | Cl | $OCH_3$ | CH | |
| H | 0 | — | Q-7 | — | — | $CH_3$ | O | H | $OCH_3$ | $OCH_3$ | N | |
| H | 0 | — | Q-7 | — | — | $CH_3$ | O | H | $CH_3$ | $OCH_3$ | N | |
| 4-$CH_3$ | 0 | — | Q-1 | $CH_3$ | — | — | O | H | $OCH_3$ | $OCH_3$ | N | |
| 4-$CH_3$ | 0 | — | Q-2 | $CH_3$ | — | — | O | H | $CH_3$ | $OCH_3$ | N | |
| 4-$CH_3$ | 0 | — | Q-2 | $CH_3$ | — | — | O | H | $OCH_3$ | $OCH_3$ | N | |
| 4-$CH_3$ | 0 | — | Q-3 | — | H | — | O | H | $OCH_3$ | $OCH_3$ | CH | |
| 4-$CH_3$ | 0 | — | Q-3 | — | H | — | O | H | $CH_3$ | $OCH_3$ | CH | |
| 4-$CH_3$ | 0 | — | Q-3 | — | H | — | O | H | $CH_3$ | $CH_3$ | CH | |
| 4-$CH_3$ | 0 | — | Q-3 | — | H | — | O | H | Cl | $OCH_3$ | CH | |
| 4-$CH_3$ | 0 | — | Q-3 | — | H | — | O | H | $OCH_3$ | $OCH_3$ | N | |
| 4-$CH_3$ | 0 | — | Q-3 | — | H | — | O | H | $CH_3$ | $OCH_3$ | N | |
| 4-$CH_3$ | 0 | — | Q-3 | — | $OCH_3$ | — | O | H | $OCH_3$ | $OCH_3$ | CH | |
| 4-$CH_3$ | 0 | — | Q-3 | — | $OCH_3$ | — | O | H | $CH_3$ | $OCH_3$ | CH | |
| 4-$CH_3$ | 0 | — | Q-3 | — | $OCH_3$ | — | O | H | $CH_3$ | $CH_3$ | CH | |
| 4-$CH_3$ | 0 | — | Q-3 | — | $OCH_3$ | — | O | H | Cl | $OCH_3$ | CH | |
| 4-$CH_3$ | 0 | — | Q-3 | — | $OCH_3$ | — | O | H | $OCH_3$ | $OCH_3$ | N | |
| 4-$CH_3$ | 0 | — | Q-3 | — | $OCH_3$ | — | O | H | $CH_3$ | $OCH_3$ | N | |
| 4-Cl | 0 | — | Q-1 | $CH_3$ | — | — | O | H | $OCH_3$ | $OCH_3$ | N | |
| 4-Cl | 0 | — | Q-2 | $CH_3$ | — | — | O | H | $OCH_3$ | $OCH_3$ | CH | |
| 4-Cl | 0 | — | Q-2 | $CH_3$ | — | — | O | H | $CH_3$ | $OCH_3$ | CH | |
| 4-Cl | 0 | — | Q-2 | $CH_3$ | — | — | O | H | $CH_3$ | $CH_3$ | CH | |
| 4-Cl | 0 | — | Q-2 | $CH_3$ | — | — | O | H | Cl | $OCH_3$ | CH | |
| 4-Cl | 0 | — | Q-2 | $CH_3$ | — | — | O | H | $OCH_3$ | $OCH_3$ | N | |
| 4-Cl | 0 | — | Q-2 | $CH_3$ | — | — | O | H | $CH_3$ | $OCH_3$ | N | |
| 4-Cl | 0 | — | Q-3 | — | $CH_3$ | — | O | H | $OCH_3$ | $OCH_3$ | CH | |
| 4-Cl | 0 | — | Q-3 | — | $CH_3$ | — | O | H | $CH_3$ | $OCH_3$ | CH | |
| 4-Cl | 0 | — | Q-3 | — | $CH_3$ | — | O | H | $CH_3$ | $CH_3$ | CH | |
| 4-Cl | 0 | — | Q-3 | — | $CH_3$ | — | O | H | Cl | $OCH_3$ | CH | |
| 4-Cl | 0 | — | Q-3 | — | $CH_3$ | — | O | H | $OCH_3$ | $OCH_3$ | N | |
| 4-Cl | 0 | — | Q-3 | — | $CH_3$ | — | O | H | $CH_3$ | $OCH_3$ | N | |
| 4-Cl | 0 | — | Q-3 | — | $OCH_3$ | — | O | H | $OCH_3$ | $OCH_3$ | CH | |
| 4-Cl | 0 | — | Q-3 | — | $OCH_3$ | — | O | H | $CH_3$ | $OCH_3$ | CH | |
| 4-Cl | 0 | — | Q-3 | — | $OCH_3$ | — | O | H | $CH_3$ | $CH_3$ | CH | |
| 4-Cl | 0 | — | Q-3 | — | $OCH_3$ | — | O | H | Cl | $OCH_3$ | CH | |
| 4-Cl | 0 | — | Q-3 | — | $OCH_3$ | — | O | H | $OCH_3$ | $OCH_3$ | N | |
| 4-Cl | 0 | — | Q-3 | — | $OCH_3$ | — | O | H | $CH_3$ | $OCH_3$ | N | |
| 4-Br | 0 | — | Q-1 | $CH_3$ | — | — | O | H | $OCH_3$ | $OCH_3$ | CH | |
| 4-Br | 0 | — | Q-1 | $CH_3$ | — | — | O | H | $CH_3$ | $OCH_3$ | N | |
| 4-Br | 0 | — | Q-2 | $CH_3$ | — | — | O | H | $OCH_3$ | $OCH_3$ | CH | |
| 4-Br | 0 | — | Q-2 | $CH_3$ | — | — | O | H | $CH_3$ | $OCH_3$ | CH | |
| 4-Br | 0 | — | Q-2 | $CH_3$ | — | — | O | H | $CH_3$ | $CH_3$ | CH | |
| 4-Br | 0 | — | Q-2 | $CH_3$ | — | — | O | H | Cl | $OCH_3$ | CH | |
| 4-Br | 0 | — | Q-2 | $CH_3$ | — | — | O | H | $OCH_3$ | $OCH_3$ | N | |
| 4-Br | 0 | — | Q-2 | $CH_3$ | — | — | O | H | $CH_3$ | $OCH_3$ | N | |
| 4-Br | 0 | — | Q-3 | — | H | — | O | H | $OCH_3$ | $OCH_3$ | CH | |
| 4-Br | 0 | — | Q-3 | — | H | — | O | H | $CH_3$ | $OCH_3$ | CH | |
| 4-Br | 0 | — | Q-3 | — | H | — | O | H | $CH_3$ | $CH_3$ | CH | |
| 4-Br | 0 | — | Q-3 | — | H | — | O | H | Cl | $OCH_3$ | CH | |
| 4-Br | 0 | — | Q-3 | — | H | — | O | H | $OCH_3$ | $OCH_3$ | N | |
| 4-Br | 0 | — | Q-3 | — | H | — | O | H | $CH_3$ | $OCH_3$ | N | |
| 4-Br | 0 | — | Q-3 | — | $OCH_3$ | — | O | H | $OCH_3$ | $OCH_3$ | CH | |
| 4-Br | 0 | — | Q-3 | — | $OCH_3$ | — | O | H | $CH_3$ | $OCH_3$ | CH | |
| 4-Br | 0 | — | Q-3 | — | $OCH_3$ | — | O | H | $CH_3$ | $CH_3$ | CH | |
| 4-Br | 0 | — | Q-3 | — | $OCH_3$ | — | O | H | Cl | $OCH_3$ | CH | |
| 4-Br | 0 | — | Q-3 | — | $OCH_3$ | — | O | H | $OCH_3$ | $OCH_3$ | N | |
| 4-Br | 0 | — | Q-3 | — | $OCH_3$ | — | O | H | $CH_3$ | $OCH_3$ | N | |
| 4-$SCH_3$ | 0 | — | Q-1 | $CH_3$ | — | — | O | H | $OCH_3$ | $OCH_3$ | CH | |
| 4-$SCH_3$ | 0 | — | Q-1 | $CH_3$ | — | — | O | H | $CH_3$ | $CH_3$ | CH | |

TABLE IX-continued

General Structure 9

| R1 | n | E | Q | R3 | R4 | R5 | W | R | X | Y | Z | m.p. (°C.) |
|---|---|---|---|---|---|---|---|---|---|---|---|---|
| 4-SCH3 | 0 | — | Q-1 | CH3 | — | — | O | H | OCH3 | OCH3 | N | |
| 4-SCH3 | 0 | — | Q-2 | CH3 | — | — | O | H | Cl | OCH3 | CH | |
| 4-SCH3 | 0 | — | Q-2 | CH3 | — | — | O | H | CH3 | OCH3 | CH | |
| 4-SCH3 | 0 | — | Q-2 | CH3 | — | — | O | H | CH3 | OCH3 | N | |
| 4-SOCH3 | 0 | — | Q-1 | CH3 | — | — | O | H | Cl | OCH3 | CH | |
| 4-SOCH3 | 0 | — | Q-1 | CH3 | — | — | O | H | CH3 | OCH3 | CH | |
| 4-SOCH3 | 0 | — | Q-1 | CH3 | — | — | O | H | CH3 | OCH3 | N | |
| 4-SOCH3 | 0 | — | Q-2 | CH3 | — | — | O | H | OCH3 | OCH3 | CH | |
| 4-SOCH3 | 0 | — | Q-2 | CH3 | — | — | O | H | CH3 | CH3 | CH | |
| 4-SOCH3 | 0 | — | Q-2 | CH3 | — | — | O | H | OCH3 | OCH3 | N | |
| 4-SO2CH3 | 0 | — | Q-1 | CH3 | — | — | O | H | OCH3 | OCH3 | CH | |
| 4-SO2CH3 | 0 | — | Q-1 | CH3 | — | — | O | H | Cl | OCH3 | CH | |
| 4-SO2CH3 | 0 | — | Q-1 | CH3 | — | — | O | H | CH3 | OCH3 | N | |
| 4-SO2CH3 | 0 | — | Q-2 | CH3 | — | — | O | H | CH3 | OCH3 | CH | |
| 4-SO2CH3 | 0 | — | Q-2 | CH3 | — | — | O | H | CH3 | CH3 | CH | |
| 4-SO2CH3 | 0 | — | Q-2 | CH3 | — | — | O | H | OCH3 | OCH3 | N | |
| 4-SO2N(CH3)2 | 0 | — | Q-1 | CH3 | — | — | O | H | CH3 | OCH3 | CH | |
| 4-SO2N(CH3)2 | 0 | — | Q-1 | CH3 | — | — | O | H | CH3 | CH3 | CH | |
| 4-SO2N(CH3)2 | 0 | — | Q-1 | CH3 | — | — | O | H | OCH3 | OCH3 | N | |
| 4-SO2N(CH3)2 | 0 | — | Q-2 | CH3 | — | — | O | H | OCH3 | OCH3 | CH | |
| 4-SO2N(CH3)2 | 0 | — | Q-2 | CH3 | — | — | O | H | Cl | OCH3 | CH | |
| 4-SO2N(CH3)2 | 0 | — | Q-2 | CH3 | — | — | O | H | CH3 | OCH3 | N | |
| H | 0 | — | Q-1 | CH3 | — | — | S | H | OCH3 | OCH3 | CH | |
| H | 0 | — | Q-2 | CH3 | — | — | O | CH3 | OCH3 | CH3 | CH | |
| H | 0 | — | Q-3 | — | CH3 | — | S | H | CH3 | CH3 | CH | |
| H | 0 | — | Q-3 | — | OCH3 | — | O | CH3 | Cl | OCH3 | CH | |
| H | 0 | — | Q-5 | — | — | CH3 | NH | H | OCH3 | OCH3 | CH | |
| H | 1 | — | Q-1 | CH3 | — | — | O | H | OCH3 | OCH3 | N | |
| H | 1 | — | Q-2 | CH3 | — | — | O | H | CH3 | OCH3 | CH | |

TABLE X

General Structure 10

| R1 | n | E | Q | R3 | R4 | R5 | W | R | X | Y | Z | m.p. (°C.) |
|---|---|---|---|---|---|---|---|---|---|---|---|---|
| H | 0 | — | Q-1 | CH3 | — | — | O | H | CH3 | CH3 | CH | |
| H | 0 | — | Q-1 | CH3 | — | — | O | H | OCH3 | CH3 | CH | |
| H | 0 | — | Q-1 | CH3 | — | — | O | H | Cl | OCH3 | CH | |
| H | 0 | — | Q-1 | CH3 | — | — | O | H | CH3 | OCH3 | N | |
| H | 0 | — | Q-1 | CH3 | — | — | O | H | OCH3 | OCH3 | N | |
| H | 0 | — | Q-1 | C2H5 | — | — | O | H | OCH3 | CH3 | CH | |
| H | 0 | — | Q-1 | C2H5 | — | — | O | H | OCH3 | OCH3 | CH | |
| H | 0 | — | Q-1 | C2H5 | — | — | O | H | Cl | OCH3 | CH | |
| H | 0 | — | Q-1 | C2H5 | — | — | O | H | CH3 | CH3 | CH | |
| H | 0 | — | Q-1 | C2H5 | — | — | O | H | CH3 | OCH3 | N | |
| H | 0 | — | Q-2 | CH3 | — | — | O | H | OCH3 | OCH3 | N | |
| H | 0 | — | Q-2 | CH3 | — | — | O | H | OCH3 | OCH3 | CH | |
| H | 0 | — | Q-2 | CH3 | — | — | O | H | OCH3 | CH3 | CH | |
| H | 0 | — | Q-2 | CH3 | — | — | O | H | Cl | OCH3 | CH | |
| H | 0 | — | Q-2 | CH3 | — | — | O | H | CH3 | CH3 | CH | |
| H | 0 | — | Q-2 | CH3 | — | — | O | H | OCH3 | CH3 | N | |
| H | 0 | — | Q-2 | C2H5 | — | — | O | H | OCH3 | OCH3 | N | |
| H | 0 | — | Q-2 | C2H5 | — | — | O | H | CH3 | CH3 | CH | |
| H | 0 | — | Q-2 | C2H5 | — | — | O | H | CH3 | OCH3 | CH | |
| H | 0 | — | Q-2 | C2H5 | — | — | O | H | Cl | OCH3 | CH | |
| H | 0 | — | Q-2 | C2H5 | — | — | O | H | CH3 | OCH3 | N | |
| H | 0 | — | Q-2 | C2H5 | — | — | O | H | OCH3 | OCH3 | N | |
| H | 0 | — | Q-3 | — | CH3 | — | O | H | CH3 | OCH3 | CH | |
| H | 0 | — | Q-3 | — | CH3 | — | O | H | Cl | OCH3 | CH | |
| H | 0 | — | Q-3 | — | CH3 | — | O | H | OCH3 | OCH3 | CH | |
| H | 0 | — | Q-3 | — | CH3 | — | O | H | OCH3 | OCH3 | N | |
| H | 0 | — | Q-3 | — | CH3 | — | O | H | CH3 | OCH3 | N | |
| H | 0 | — | Q-3 | — | C2H5 | — | O | H | CH3 | CH3 | CH | |
| H | 0 | — | Q-3 | — | C2H5 | — | O | H | CH3 | OCH3 | CH | |
| H | 0 | — | Q-3 | — | C2H5 | — | O | H | Cl | OCH3 | CH | |
| H | 0 | — | Q-3 | — | C2H5 | — | O | H | OCH3 | OCH3 | CH | |
| H | 0 | — | Q-3 | — | C2H5 | — | O | H | CH3 | OCH3 | N | |
| H | 0 | — | Q-3 | — | CH2Cl | — | O | H | CH3 | OCH3 | CH | |
| H | 0 | — | Q-3 | — | CH2Cl | — | O | H | OCH3 | OCH3 | CH | |
| H | 0 | — | Q-3 | — | CH2Cl | — | O | H | Cl | OCH3 | CH | |
| H | 0 | — | Q-3 | — | CH2Cl | — | O | H | CH3 | OCH3 | N | |
| H | 0 | — | Q-3 | — | CH2Cl | — | O | H | OCH3 | OCH3 | N | |
| H | 0 | — | Q-3 | — | CF3 | — | O | H | CH3 | CH3 | CH | |
| H | 0 | — | Q-3 | — | CF3 | — | O | H | OCH3 | OCH3 | CH | |
| H | 0 | — | Q-3 | — | CF3 | — | O | H | OCH3 | CH3 | CH | |
| H | 0 | — | Q-3 | — | CF3 | — | O | H | CH3 | OCH3 | N | |
| H | 0 | — | Q-3 | — | CH(CH3)2 | — | O | H | CH3 | OCH3 | CH | |
| H | 0 | — | Q-3 | — | CH(CH3)2 | — | O | H | OCH3 | OCH3 | CH | |
| H | 0 | — | Q-3 | — | CH(CH3)2 | — | O | H | Cl | OCH3 | CH | |

TABLE X-continued

| | | | | | | General Structure 10 | | | | | | |
|---|---|---|---|---|---|---|---|---|---|---|---|---|
| $R_1$ | n | E | Q | $R_3$ | $R_4$ | $R_5$ | W | R | X | Y | Z | m.p. (°C.) |
| H | 0 | — | Q-3 | — | $CH(CH_3)_2$ | — | O | H | $CH_3$ | $OCH_3$ | N | |
| H | 0 | — | Q-3 | — | $OCH_3$ | — | O | H | $OCH_3$ | $OCH_3$ | CH | |
| H | 0 | — | Q-3 | — | $OCH_3$ | — | O | H | $CH_3$ | $OCH_3$ | CH | |
| H | 0 | — | Q-3 | — | $OCH_3$ | — | O | H | Cl | $CH_3$ | CH | |
| H | 0 | — | Q-3 | — | $OCH_3$ | — | O | H | $OCH_3$ | $OCH_3$ | N | |
| H | 0 | — | Q-3 | — | $SCH_3$ | — | O | H | $CH_3$ | $OCH_3$ | CH | |
| H | 0 | — | Q-3 | — | $SCH_3$ | — | O | H | $OCH_3$ | $OCH_3$ | CH | |
| H | 0 | — | Q-3 | — | $SCH_3$ | — | O | H | $OCH_3$ | $OCH_3$ | N | |
| H | 0 | — | Q-3 | — | $SCH_3$ | — | O | H | $CH_3$ | $OCH_3$ | N | |
| H | 0 | — | Q-3 | — | $N(CH_3)_2$ | — | O | H | $CH_3$ | $CH_3$ | CH | |
| H | 0 | — | Q-3 | — | $N(CH_3)_2$ | — | O | H | $OCH_3$ | $OCH_3$ | CH | |
| H | 0 | — | Q-3 | — | $N(CH_3)_2$ | — | O | H | $OCH_3$ | $CH_3$ | N | |
| H | 0 | — | Q-4 | — | $CH_3$ | — | O | H | $OCH_3$ | $CH_3$ | N | |
| H | 0 | — | Q-4 | — | $CH_3$ | — | O | H | $OCH_3$ | $CH_3$ | CH | |
| H | 0 | — | Q-4 | — | $CH_3$ | — | O | H | $OCH_3$ | $OCH_3$ | CH | |
| H | 0 | — | Q-4 | — | $CH_3$ | — | O | H | Cl | $OCH_3$ | CH | |
| H | 0 | — | Q-4 | — | $CH_3$ | — | O | H | $CH_3$ | $CH_3$ | CH | |
| H | 0 | — | Q-5 | — | — | $CH_3$ | O | H | $CH_3$ | $CH_3$ | CH | |
| H | 0 | — | Q-5 | — | — | $CH_3$ | O | H | $CH_3$ | $OCH_3$ | CH | |
| H | 0 | — | Q-5 | — | — | $CH_3$ | O | H | $OCH_3$ | $OCH_3$ | CH | |
| H | 0 | — | Q-5 | — | — | $CH_3$ | O | H | Cl | $OCH_3$ | CH | |
| H | 0 | — | Q-1 | $CH_3$ | — | — | O | H | $OCH_3$ | $OCH_3$ | CH | |
| H | 0 | — | Q-1 | $C_2H_5$ | — | — | O | H | $OCH_3$ | $OCH_3$ | N | |
| H | 0 | — | Q-3 | — | $CH_3$ | — | O | H | $CH_3$ | $CH_3$ | CH | |
| H | 0 | — | Q-3 | — | $C_2H_5$ | — | O | H | $OCH_3$ | $OCH_3$ | N | |
| H | 0 | — | Q-3 | — | H | — | O | H | $OCH_3$ | $OCH_3$ | CH | |
| H | 0 | — | Q-3 | — | H | — | O | H | $CH_3$ | $OCH_3$ | CH | |
| H | 0 | — | Q-3 | — | H | — | O | H | $CH_3$ | $CH_3$ | CH | |
| H | 0 | — | Q-3 | — | H | — | O | H | Cl | $OCH_3$ | CH | |
| H | 0 | — | Q-3 | — | H | — | O | H | $OCH_3$ | $OCH_3$ | N | |
| H | 0 | — | Q-3 | — | H | — | O | H | $CH_3$ | $OCH_3$ | N | |
| H | 0 | — | Q-3 | — | $CH_2Cl$ | — | O | H | $CH_3$ | $CH_3$ | CH | |
| H | 0 | — | Q-3 | — | $CF_3$ | — | O | H | Cl | $OCH_3$ | CH | |
| H | 0 | — | Q-3 | — | $CF_3$ | — | O | H | $OCH_3$ | $OCH_3$ | CH | |
| H | 0 | — | Q-3 | — | $CH(CH_3)_2$ | — | O | H | $CH_3$ | $CH_3$ | CH | |
| H | 0 | — | Q-3 | — | $CH(CH_3)_2$ | — | O | H | $OCH_3$ | $OCH_3$ | N | |
| H | 0 | — | Q-3 | — | $OCH_3$ | — | O | H | $CH_3$ | $CH_3$ | CH | |
| H | 0 | — | Q-3 | — | $OCH_3$ | — | O | H | $CH_3$ | $OCH_3$ | N | |
| H | 0 | — | Q-3 | — | $SCH_3$ | — | O | H | $CH_3$ | $CH_3$ | CH | |
| H | 0 | — | Q-3 | — | $SCH_3$ | — | O | H | Cl | $OCH_3$ | CH | |
| H | 0 | — | Q-3 | — | $OC_2H_5$ | — | O | H | $OCH_3$ | $OCH_3$ | CH | |
| H | 0 | — | Q-3 | — | $OC_2H_5$ | — | O | H | $CH_3$ | $OCH_3$ | CH | |
| H | 0 | — | Q-3 | — | $OC_2H_5$ | — | O | H | $CH_3$ | $CH_3$ | CH | |
| H | 0 | — | Q-3 | — | $OC_2H_5$ | — | O | H | Cl | $OCH_3$ | CH | |
| H | 0 | — | Q-3 | — | $OC_2H_5$ | — | O | H | $OCH_3$ | $OCH_3$ | N | |
| H | 0 | — | Q-3 | — | $OC_2H_5$ | — | O | H | $CH_3$ | $OCH_3$ | N | |
| H | 0 | — | Q-3 | — | $N(CH_3)_2$ | — | O | H | $CH_3$ | $OCH_3$ | CH | |
| H | 0 | — | Q-3 | — | $N(CH_3)_2$ | — | O | H | Cl | $OCH_3$ | CH | |
| H | 0 | — | Q-3 | — | $N(CH_3)_2$ | — | O | H | $OCH_3$ | $OCH_3$ | N | |
| H | 0 | — | Q-4 | — | $CH_3$ | — | O | H | $OCH_3$ | $OCH_3$ | N | |
| H | 0 | — | Q-4 | — | $C_2H_5$ | — | O | H | $OCH_3$ | $OCH_3$ | CH | |
| H | 0 | — | Q-4 | — | $C_2H_5$ | — | O | H | $CH_3$ | $OCH_3$ | CH | |
| H | 0 | — | Q-4 | — | $C_2H_5$ | — | O | H | $CH_3$ | $CH_3$ | CH | |
| H | 0 | — | Q-4 | — | $C_2H_5$ | — | O | H | Cl | $OCH_3$ | CH | |
| H | 0 | — | Q-4 | — | $C_2H_5$ | — | O | H | $OCH_3$ | $OCH_3$ | N | |
| H | 0 | — | Q-4 | — | $C_2H_5$ | — | O | H | $CH_3$ | $OCH_3$ | N | |
| H | 0 | — | Q-5 | — | — | $CH_3$ | O | H | $OCH_3$ | $OCH_3$ | N | |
| H | 0 | — | Q-5 | — | — | $CH_3$ | O | H | $CH_3$ | $OCH_3$ | N | |
| 2-Cl | 0 | — | Q-1 | $CH_3$ | — | — | O | H | $OCH_3$ | $OCH_3$ | CH | |
| 2-Cl | 0 | — | Q-1 | $CH_3$ | — | — | O | H | $CH_3$ | $OCH_3$ | CH | |
| 2-Cl | 0 | — | Q-1 | $CH_3$ | — | — | O | H | $CH_3$ | $CH_3$ | CH | |
| 2-Cl | 0 | — | Q-1 | $CH_3$ | — | — | O | H | Cl | $OCH_3$ | CH | |
| 2-Cl | 0 | — | Q-1 | $CH_3$ | — | — | O | H | $OCH_3$ | $OCH_3$ | N | |
| 2-Cl | 0 | — | Q-1 | $CH_3$ | — | — | O | H | $CH_3$ | $OCH_3$ | N | |
| 2-Cl | 0 | — | Q-2 | $CH_3$ | — | — | O | H | $OCH_3$ | $OCH_3$ | CH | |
| 2-Cl | 0 | — | Q-2 | $CH_3$ | — | — | O | H | $CH_3$ | $OCH_3$ | CH | |
| 2-Cl | 0 | — | Q-2 | $CH_3$ | — | — | O | H | $CH_3$ | $CH_3$ | CH | |
| 2-Cl | 0 | — | Q-2 | $CH_3$ | — | — | O | H | Cl | $OCH_3$ | CH | |
| 2-Cl | 0 | — | Q-2 | $CH_3$ | — | — | O | H | $OCH_3$ | $OCH_3$ | N | |
| 2-Cl | 0 | — | Q-2 | $CH_3$ | — | — | O | H | $CH_3$ | $OCH_3$ | N | |
| 2-Cl | 0 | — | Q-3 | — | H | — | O | H | $OCH_3$ | $OCH_3$ | CH | |
| 2-Cl | 0 | — | Q-3 | — | H | — | O | H | $CH_3$ | $OCH_3$ | CH | |
| 2-Cl | 0 | — | Q-3 | — | H | — | O | H | $CH_3$ | $CH_3$ | CH | |
| 2-Cl | 0 | — | Q-3 | — | H | — | O | H | Cl | $OCH_3$ | CH | |
| 2-Cl | 0 | — | Q-3 | — | H | — | O | H | $OCH_3$ | $OCH_3$ | N | |
| 2-Cl | 0 | — | Q-3 | — | H | — | O | H | $CH_3$ | $OCH_3$ | N | |
| 2-Cl | 0 | — | Q-3 | — | $OCH_3$ | — | O | H | $OCH_3$ | $OCH_3$ | CH | |
| 2-Cl | 0 | — | Q-3 | — | $OCH_3$ | — | O | H | $CH_3$ | $OCH_3$ | CH | |
| 2-Cl | 0 | — | Q-3 | — | $OCH_3$ | — | O | H | $CH_3$ | $CH_3$ | CH | |
| 2-Cl | 0 | — | Q-3 | — | $OCH_3$ | — | O | H | Cl | $OCH_3$ | CH | |

TABLE X-continued

| General Structure 10 | | | | | | | | | | | | |
|---|---|---|---|---|---|---|---|---|---|---|---|---|
| $R_1$ | n | E | Q | $R_3$ | $R_4$ | $R_5$ | W | R | X | Y | Z | m.p. (°C.) |
| 2-Cl | 0 | — | Q-3 | — | $OCH_3$ | — | O | H | $OCH_3$ | $OCH_3$ | N | |
| 2-Cl | 0 | — | Q-3 | — | $OCH_3$ | — | O | H | $CH_3$ | $OCH_3$ | N | |
| 2-Br | 0 | — | Q-1 | $CH_3$ | — | — | O | H | $OCH_3$ | $OCH_3$ | CH | |
| 2-Br | 0 | — | Q-1 | $CH_3$ | — | — | O | H | $CH_3$ | $OCH_3$ | CH | |
| 2-Br | 0 | — | Q-1 | $CH_3$ | — | — | O | H | $CH_3$ | $CH_3$ | CH | |
| 2-Br | 0 | — | Q-1 | $CH_3$ | — | — | O | H | Cl | $OCH_3$ | CH | |
| 2-Br | 0 | — | Q-1 | $CH_3$ | — | — | O | H | $OCH_3$ | $OCH_3$ | N | |
| 2-Br | 0 | — | Q-1 | $CH_3$ | — | — | O | H | $CH_3$ | $OCH_3$ | N | |
| 2-Br | 0 | — | Q-2 | $CH_3$ | — | — | O | H | $OCH_3$ | $OCH_3$ | CH | |
| 2-Br | 0 | — | Q-2 | $CH_3$ | — | — | O | H | $CH_3$ | $OCH_3$ | CH | |
| 2-Br | 0 | — | Q-2 | $CH_3$ | — | — | O | H | $CH_3$ | $CH_3$ | CH | |
| 2-Br | 0 | — | Q-2 | $CH_3$ | — | — | O | H | Cl | $OCH_3$ | CH | |
| 2-Br | 0 | — | Q-2 | $CH_3$ | — | — | O | H | $OCH_3$ | $OCH_3$ | N | |
| 2-Br | 0 | — | Q-2 | $CH_3$ | — | — | O | H | $CH_3$ | $OCH_3$ | N | |
| 2-Br | 0 | — | Q-3 | — | $OCH_3$ | — | O | H | $OCH_3$ | $OCH_3$ | CH | |
| 2-Br | 0 | — | Q-3 | — | $OCH_3$ | — | O | H | $CH_3$ | $OCH_3$ | CH | |
| 2-Br | 0 | — | Q-3 | — | $OCH_3$ | — | O | H | $CH_3$ | $CH_3$ | CH | |
| 2-Br | 0 | — | Q-3 | — | $OCH_3$ | — | O | H | Cl | $OCH_3$ | CH | |
| 2-Br | 0 | — | Q-3 | — | $OCH_3$ | — | O | H | $OCH_3$ | $OCH_3$ | N | |
| 2-Br | 0 | — | Q-3 | — | $OCH_3$ | — | O | H | $CH_3$ | $OCH_3$ | N | |
| H | 0 | — | Q-1 | $CH_3$ | — | | S | H | $OCH_3$ | $OCH_3$ | CH | |
| H | 0 | — | Q-2 | $CH_3$ | — | | O | $CH_3$ | $CH_3$ | $OCH_3$ | CH | |
| H | 0 | — | Q-3 | — | $OCH_3$ | — | $NNHCH_3$ | H | $OCH_3$ | $OCH_3$ | CH | |
| H | 1 | — | Q-3 | — | H | — | O | H | $CH_3$ | $CH_3$ | CH | |

TABLE XI

| General Structure 11 | | | | | | | | | | | | | |
|---|---|---|---|---|---|---|---|---|---|---|---|---|---|
| $R_1$ | n | E | Q | $R_2$ | $R_3$ | $R_4$ | $R_5$ | W | R | X | Y | Z | m.p. (°C.) |
| H | O | — | Q-1 | $C_6H_5$ | $CH_3$ | — | — | O | H | $CH_3$ | $CH_3$ | CH | |
| H | O | — | Q-1 | $C_6H_5$ | $CH_3$ | — | — | O | H | $OCH_3$ | $CH_3$ | CH | |
| H | O | — | Q-1 | $C_6H_5$ | $CH_3$ | — | — | O | H | Cl | $OCH_3$ | CH | |
| H | O | — | Q-1 | $C_6H_5$ | $CH_3$ | — | — | O | H | $CH_3$ | $OCH_3$ | N | |
| H | O | — | Q-1 | $C_6H_5$ | $CH_3$ | — | — | O | H | $OCH_3$ | $OCH_3$ | N | |
| H | O | — | Q-1 | $C_6H_5$ | $C_2H_5$ | — | — | O | H | $OCH_3$ | $CH_3$ | CH | |
| H | O | — | Q-1 | $C_6H_5$ | $C_2H_5$ | — | — | O | H | $OCH_3$ | $OCH_3$ | CH | |
| H | O | — | Q-1 | $C_6H_5$ | $C_2H_5$ | — | — | O | H | Cl | $OCH_3$ | CH | |
| H | O | — | Q-1 | $C_6H_5$ | $C_2H_5$ | — | — | O | H | $CH_3$ | $CH_3$ | CH | |
| H | O | — | Q-1 | $C_6H_5$ | $C_2H_5$ | — | — | O | H | $CH_3$ | $OCH_3$ | N | |
| H | O | — | Q-2 | $C_6H_5$ | $CH_3$ | — | — | O | H | $OCH_3$ | $OCH_3$ | N | |
| H | O | — | Q-2 | $C_6H_5$ | $CH_3$ | — | — | O | H | $OCH_3$ | $OCH_3$ | CH | |
| H | O | — | Q-2 | $C_6H_5$ | $CH_3$ | — | — | O | H | $OCH_3$ | $CH_3$ | CH | |
| H | O | — | Q-2 | $C_6H_5$ | $CH_3$ | — | — | O | H | Cl | $OCH_3$ | CH | |
| H | O | — | Q-2 | $C_6H_5$ | $CH_3$ | — | — | O | H | $CH_3$ | $CH_3$ | CH | |
| H | O | — | Q-2 | $C_6H_5$ | $CH_3$ | — | — | O | H | $OCH_3$ | $CH_3$ | N | |
| H | O | — | Q-2 | $C_6H_5$ | $C_2H_5$ | — | — | O | H | $OCH_3$ | $OCH_3$ | N | |
| H | O | — | Q-2 | $C\ H_5$ | $C_2H_5$ | — | — | O | H | $CH_3$ | $CH_3$ | CH | |
| H | O | — | Q-2 | $C_6H_5$ | $C_2H_5$ | — | — | O | H | $CH_3$ | $OCH_3$ | CH | |
| H | O | — | Q-2 | $C_6H_5$ | $C_2H_5$ | — | — | O | H | Cl | $OCH_3$ | CH | |
| H | O | — | Q-2 | $C_6H_5$ | $C_2H_5$ | — | — | O | H | $CH_3$ | $OCH_3$ | N | |
| H | O | — | Q-2 | $C_6H_5$ | $C_2H_5$ | — | — | O | H | $OCH_3$ | $OCH_3$ | N | |
| H | O | — | Q-3 | $C_6H_5$ | — | $CH_3$ | — | O | H | $CH_3$ | $OCH_3$ | CH | |
| H | O | — | Q-3 | $C_6H_5$ | — | $CH_3$ | — | O | H | Cl | $OCH_3$ | CH | |
| H | O | — | Q-3 | $C_6H_5$ | — | $CH_3$ | — | O | H | $OCH_3$ | $OCH_3$ | CH | |
| H | O | — | Q-3 | $C_6H_5$ | — | $CH_3$ | — | O | H | $OCH_3$ | $OCH_3$ | N | |
| H | O | — | Q-3 | $C_6H_5$ | — | $CH_3$ | — | O | H | $CH_3$ | $OCH_3$ | N | |
| H | O | — | Q-3 | $C_6H_5$ | — | $C_2H_5$ | — | O | H | $CH_3$ | $CH_3$ | CH | |
| H | O | — | Q-3 | $C_6H_5$ | — | $C_2H_5$ | — | O | H | $CH_3$ | $OCH_3$ | CH | |
| H | O | — | Q-3 | $C_6H_5$ | — | $C_2H_5$ | — | O | H | Cl | $OCH_3$ | CH | |
| H | O | — | Q-3 | $C_6H_5$ | — | $C_2H_5$ | — | O | H | $OCH_3$ | $OCH_3$ | CH | |
| H | O | — | Q-3 | $C_6H_5$ | — | $C_2H_5$ | — | O | H | $CH_3$ | $OCH_3$ | N | |
| H | O | — | Q-3 | $C_6H_5$ | — | $CH_2Cl$ | — | O | H | $CH_3$ | $OCH_3$ | CH | |
| H | O | — | Q-3 | $C_6H_5$ | — | $CH_2Cl$ | — | O | H | $OCH_3$ | $OCH_3$ | CH | |
| H | O | — | Q-3 | $C_6H_5$ | — | $CH_2Cl$ | — | O | H | Cl | $OCH_3$ | CH | |
| H | O | — | Q-3 | $C_6H_5$ | — | $CH_2Cl$ | — | O | H | $CH_3$ | $OCH_3$ | N | |
| H | O | — | Q-3 | $C_6H_5$ | — | $CH_2Cl$ | — | O | H | $OCH_3$ | $OCH_3$ | N | |
| H | O | — | Q-3 | $C_6H_5$ | — | $CF_3$ | — | O | H | $CH_3$ | $CH_3$ | CH | |
| H | O | — | Q-3 | $C_6H_5$ | — | $CF_3$ | — | O | H | $OCH_3$ | $OCH_3$ | CH | |
| H | O | — | Q-3 | $C_6H_5$ | — | $CF_3$ | — | O | H | $OCH_3$ | $CH_3$ | CH | |
| H | O | — | Q-3 | $C_6H_5$ | — | $CF_3$ | — | O | H | $CH_3$ | $OCH_3$ | N | |
| H | O | — | Q-3 | $C_6H_5$ | — | $CH(CH_3)_2$ | — | O | H | $CH_3$ | $OCH_3$ | CH | |
| H | O | — | Q-3 | $C_6H_5$ | — | $CH(CH_3)_2$ | — | O | H | $OCH_3$ | $OCH_3$ | CH | |
| H | O | — | Q-3 | $C_6H_5$ | — | $CH(CH_3)_2$ | — | O | H | Cl | $OCH_3$ | CH | |
| H | O | — | Q-3 | $C_6H_5$ | — | $CH(CH_3)_2$ | — | O | H | $CH_3$ | $OCH_3$ | N | |
| H | O | — | Q-3 | $C_6H_5$ | — | $OCH_3$ | — | O | H | $OCH_3$ | $OCH_3$ | CH | |
| H | O | — | Q-3 | $C_6H_5$ | — | $OCH_3$ | — | O | H | $CH_3$ | $OCH_3$ | CH | |
| H | O | — | Q-3 | $C_6H_5$ | — | $OCH_3$ | — | O | H | Cl | $CH_3$ | CH | |
| H | O | — | Q-3 | $C_6H_5$ | — | $OCH_3$ | — | O | H | $OCH_3$ | $OCH_3$ | N | |

TABLE XI-continued

| $R_1$ | n | E | Q | $R_2$ | $R_3$ | $R_4$ (General Structure 11) | $R_5$ | W | R | X | Y | Z | m.p. (°C.) |
|---|---|---|---|---|---|---|---|---|---|---|---|---|---|
| H | 0 | — | Q-3 | $C_6H_5$ | — | $SCH_3$ | — | O | H | $CH_3$ | $OCH_3$ | CH | |
| H | 0 | — | Q-3 | $C_6H_5$ | — | $SCH_3$ | — | O | H | $OCH_3$ | $OCH_3$ | CH | |
| H | 0 | — | Q-3 | $C_6H_5$ | — | $SCH_3$ | — | O | H | $OCH_3$ | $OCH_3$ | N | |
| H | 0 | — | Q-3 | $C_6H_5$ | — | $SCH_3$ | — | O | H | $CH_3$ | $OCH_3$ | N | |
| H | 0 | — | Q-3 | $C_6H_5$ | — | $N(CH_3)_2$ | — | O | H | $CH_3$ | $CH_3$ | CH | |
| H | 0 | — | Q-3 | $C_6H_5$ | — | $N(CH_3)_2$ | — | O | H | $OCH_3$ | $OCH_3$ | CH | |
| H | 0 | — | Q-3 | $C_6H_5$ | — | $N(CH_3)_2$ | — | O | H | $OCH_3$ | $CH_3$ | N | |
| H | 0 | — | Q-5 | $C_6H_5$ | — | — | $CH_3$ | O | H | $OCH_3$ | $CH_3$ | N | |
| H | 0 | — | Q-5 | $C_6H_5$ | — | — | $CH_3$ | O | H | $OCH_3$ | $CH_3$ | CH | |
| H | 0 | — | Q-5 | $C_6H_5$ | — | — | $CH_3$ | O | H | $OCH_3$ | $OCH_3$ | CH | |
| H | 0 | — | Q-5 | $C_6H_5$ | — | — | $CH_3$ | O | H | Cl | $OCH_3$ | CH | |
| H | 0 | — | Q-5 | $C_6H_5$ | — | — | $CH_3$ | O | H | $CH_3$ | $CH_3$ | CH | |
| H | 0 | — | Q-1 | $CH_3$ | $CH_3$ | — | — | O | H | $CH_3$ | $CH_3$ | CH | |
| H | 0 | — | Q-1 | $CH_3$ | $CH_3$ | — | — | O | H | $OCH_3$ | $CH_3$ | CH | |
| H | 0 | — | Q-1 | $CH_3$ | $CH_3$ | — | — | O | H | Cl | $OCH_3$ | CH | |
| H | 0 | — | Q-1 | $CH_3$ | $CH_3$ | — | — | O | H | $CH_3$ | $OCH_3$ | N | |
| H | 0 | — | Q-1 | $CH_3$ | $CH_3$ | — | — | O | H | $OCH_3$ | $OCH_3$ | N | |
| H | 0 | — | Q-1 | $CH_3$ | $C_2H_5$ | — | — | O | H | $OCH_3$ | $CH_3$ | CH | |
| H | 0 | — | Q-1 | $CH_3$ | $C_2H_5$ | — | — | O | H | $OCH_3$ | $OCH_3$ | CH | |
| H | 0 | — | Q-1 | $CH_3$ | $C_2H_5$ | — | — | O | H | Cl | $OCH_3$ | CH | |
| H | 0 | — | Q-1 | $CH_3$ | $C_2H_5$ | — | — | O | H | $CH_3$ | $CH_3$ | CH | |
| H | 0 | — | Q-1 | $CH_3$ | $C_2H_5$ | — | — | O | H | $CH_3$ | $OCH_3$ | N | |
| H | 0 | — | Q-2 | $CH_3$ | $CH_3$ | — | — | O | H | $OCH_3$ | $OCH_3$ | N | |
| H | 0 | — | Q-2 | $CH_3$ | $CH_3$ | — | — | O | H | $OCH_3$ | $OCH_3$ | CH | |
| H | 0 | — | Q-2 | $CH_3$ | $CH_3$ | — | — | O | H | $OCH_3$ | $CH_3$ | CH | |
| H | 0 | — | Q-2 | $CH_3$ | $CH_3$ | — | — | O | H | Cl | $OCH_3$ | CH | |
| H | 0 | — | Q-2 | $CH_3$ | $CH_3$ | — | — | O | H | $CH_3$ | $CH_3$ | CH | |
| H | 0 | — | Q-2 | $CH_3$ | $CH_3$ | — | — | O | H | $OCH_3$ | $CH_3$ | N | |
| H | 0 | — | Q-2 | $CH_3$ | $C_2H_5$ | — | — | O | H | $OCH_3$ | $OCH_3$ | N | |
| H | 0 | — | Q-2 | $CH_3$ | $C_2H_5$ | — | — | O | H | $CH_3$ | $CH_3$ | CH | |
| H | 0 | — | Q-2 | $CH_3$ | $C_2H_5$ | — | — | O | H | $CH_3$ | $OCH_3$ | CH | |
| H | 0 | — | Q-2 | $CH_3$ | $C_2H_5$ | — | — | O | H | Cl | $OCH_3$ | CH | |
| H | 0 | — | Q-2 | $CH_3$ | $C_2H_5$ | — | — | O | H | $CH_3$ | $OCH_3$ | N | |
| H | 0 | — | Q-2 | $CH_3$ | $C_2H_5$ | — | — | O | H | $OCH_3$ | $OCH_3$ | N | |
| H | 0 | — | Q-3 | $CH_3$ | — | $CH_3$ | — | O | H | $CH_3$ | $OCH_3$ | CH | |
| H | 0 | — | Q-3 | $CH_3$ | — | $CH_3$ | — | O | H | Cl | $OCH_3$ | CH | |
| H | 0 | — | Q-3 | $CH_3$ | — | $CH_3$ | — | O | H | $OCH_3$ | $OCH_3$ | CH | |
| H | 0 | — | Q-3 | $CH_3$ | — | $CH_3$ | — | O | H | $OCH_3$ | $OCH_3$ | N | |
| H | 0 | — | Q-3 | $CH_3$ | — | $CH_3$ | — | O | H | $CH_3$ | $OCH_3$ | N | |
| H | 0 | — | Q-3 | $CH_3$ | — | $C_2H_5$ | — | O | H | $CH_3$ | $CH_3$ | CH | |
| H | 0 | — | Q-3 | $CH_3$ | — | $C_2H_5$ | — | O | H | $CH_3$ | $OCH_3$ | CH | |
| H | 0 | — | Q-3 | $CH_3$ | — | $C_2H_5$ | — | O | H | Cl | $OCH_3$ | CH | |
| H | 0 | — | Q-3 | $CH_3$ | — | $C_2H_5$ | — | O | H | $OCH_3$ | $OCH_3$ | CH | |
| H | 0 | — | Q-3 | $CH_3$ | — | $C_2H_5$ | — | O | H | $CH_3$ | $OCH_3$ | N | |
| H | 0 | — | Q-3 | $CH_3$ | — | $CH_2Cl$ | — | O | H | $CH_3$ | $OCH_3$ | CH | |
| H | 0 | — | Q-3 | $CH_3$ | — | $CH_2Cl$ | — | O | H | $OCH_3$ | $OCH_3$ | CH | |
| H | 0 | — | Q-3 | $CH_3$ | — | $CH_2Cl$ | — | O | H | Cl | $OCH_3$ | CH | |
| H | 0 | — | Q-3 | $CH_3$ | — | $CH_2Cl$ | — | O | H | $CH_3$ | $OCH_3$ | N | |
| H | 0 | — | Q-3 | $CH_3$ | — | $CH_2Cl$ | — | O | H | $OCH_3$ | $OCH_3$ | N | |
| H | 0 | — | Q-3 | $CH_3$ | — | $CF_3$ | — | O | H | $CH_3$ | $CH_3$ | CH | |
| H | 0 | — | Q-3 | $CH_3$ | — | $CF_3$ | — | O | H | $OCH_3$ | $OCH_3$ | CH | |
| H | 0 | — | Q-3 | $CH_3$ | — | $CF_3$ | — | O | H | $OCH_3$ | $CH_3$ | CH | |
| H | 0 | — | Q-3 | $CH_3$ | — | $CF_3$ | — | O | H | $CH_3$ | $OCH_3$ | N | |
| H | 0 | — | Q-3 | $CH_3$ | — | $CH(CH_3)_2$ | — | O | H | $CH_3$ | $OCH_3$ | CH | |
| H | 0 | — | Q-3 | $CH_3$ | — | $CH(CH_3)_2$ | — | O | H | $OCH_3$ | $OCH_3$ | CH | |
| H | 0 | — | Q-3 | $CH_3$ | — | $CH(CH_3)_2$ | — | O | H | Cl | $OCH_3$ | CH | |
| H | 0 | — | Q-3 | $CH_3$ | — | $CH(CH_3)_2$ | — | O | H | $CH_3$ | $OCH_3$ | N | |
| H | 0 | — | Q-3 | $CH_3$ | — | $OCH_3$ | — | O | H | $OCH_3$ | $OCH_3$ | CH | |
| H | 0 | — | Q-3 | $CH_3$ | — | $OCH_3$ | — | O | H | $CH_3$ | $OCH_3$ | CH | |
| H | 0 | — | Q-3 | $CH_3$ | — | $OCH_3$ | — | O | H | Cl | $CH_3$ | CH | |
| H | 0 | — | Q-3 | $CH_3$ | — | $OCH_3$ | — | O | H | $OCH_3$ | $OCH_3$ | N | |
| H | 0 | — | Q-3 | $CH_3$ | — | $SCH_3$ | — | O | H | $CH_3$ | $OCH_3$ | CH | |
| H | 0 | — | Q-3 | $CH_3$ | — | $SCH_3$ | — | O | H | $OCH_3$ | $OCH_3$ | CH | |
| H | 0 | — | Q-3 | $CH_3$ | — | $SCH_3$ | — | O | H | $OCH_3$ | $OCH_3$ | N | |
| H | 0 | — | Q-3 | $CH_3$ | — | $SCH_3$ | — | O | H | $CH_3$ | $OCH_3$ | N | |
| H | 0 | — | Q-3 | $CH_3$ | — | $N(CH_3)_2$ | — | O | H | $CH_3$ | $CH_3$ | CH | |
| H | 0 | — | Q-3 | $CH_3$ | — | $N(CH_3)_2$ | — | O | H | $OCH_3$ | $OCH_3$ | CH | |
| H | 0 | — | Q-3 | $CH_3$ | — | $N(CH_3)_2$ | — | O | H | $OCH_3$ | $CH_3$ | N | |
| H | 0 | — | Q-5 | $CH_3$ | — | — | $CH_3$ | O | H | $OCH_3$ | $CH_3$ | N | |
| Cl | 0 | — | Q-2 | $CH_3$ | $CH_3$ | — | — | O | H | $CH_3$ | $CH_3$ | CH | |
| Cl | 0 | — | Q-2 | $CH_3$ | $CH_3$ | — | — | O | H | $CH_3$ | $OCH_3$ | CH | |
| Cl | 0 | — | Q-2 | $CH_3$ | $CH_3$ | — | — | O | H | $OCH_3$ | $OCH_3$ | CH | |
| Cl | 0 | — | Q-2 | $CH_3$ | $CH_3$ | — | — | O | H | Cl | $OCH_3$ | CH | |
| Cl | 0 | — | Q-2 | $CH_3$ | $CH_3$ | — | — | O | H | $CH_3$ | $OCH_3$ | N | |
| Cl | 0 | — | Q-2 | $CH_3$ | $CH_3$ | — | — | O | H | $OCH_3$ | $OCH_3$ | N | |
| Cl | 0 | — | Q-2 | $CH_3$ | $CH_3$ | — | — | O | $CH_3$ | $OCH_3$ | $CH_3$ | N | |
| Cl | 0 | — | Q-2 | $CH_3$ | $CH_2CH_3$ | — | — | O | H | $CH_3$ | $CH_3$ | CH | |
| Cl | 0 | — | Q-2 | $CH_3$ | $CH_2CH_3$ | — | — | O | H | $CH_3$ | $OCH_3$ | CH | |
| Cl | 0 | — | Q-2 | $CH_3$ | $CH_2CH_3$ | — | — | O | H | $OCH_3$ | $OCH_3$ | CH | |
| Cl | 0 | — | Q-2 | $CH_3$ | $CH_2CH_3$ | — | — | O | H | Cl | $OCH_3$ | CH | |

TABLE XI-continued

| | | | | | | General Structure 11 | | | | | | | |
|---|---|---|---|---|---|---|---|---|---|---|---|---|---|
| $R_1$ | n | E | Q | $R_2$ | $R_3$ | $R_4$ | $R_5$ | W | R | X | Y | Z | m.p. (°C.) |
| Cl | O | — | Q-2 | $CH_3$ | $CH_2CH_3$ | — | — | O | H | $OCH_3$ | $CH_3$ | N | |
| Cl | O | — | Q-2 | $CH_3$ | $CH_2CH_3$ | — | — | O | H | $OCH_3$ | $OCH_3$ | N | |
| H | O | — | Q-2 | $CH_2CH_3$ | $CH_3$ | — | — | O | H | $CH_3$ | CH | CH | |
| H | O | — | Q-2 | $CH_2CH_3$ | $CH_3$ | — | — | O | H | $CH_3$ | $OCH_3$ | CH | |
| H | O | — | Q-2 | $CH_2CH_3$ | $CH_3$ | — | — | O | H | $OCH_3$ | $OCH_3$ | CH | |
| H | O | — | Q-2 | $CH_2CH_3$ | $CH_3$ | — | — | O | H | Cl | $OCH_3$ | CH | |
| H | O | — | Q-2 | $CH_2CH_3$ | $CH_3$ | — | — | O | H | $OCH_3$ | $CH_3$ | N | |
| H | O | — | Q-2 | $CH_2CH_3$ | $CH_3$ | — | — | O | H | $OCH_3$ | $OCH_3$ | N | |
| Cl | O | — | Q-1 | $CH_3$ | $CH_3$ | — | — | O | H | $OCH_3$ | $CH_3$ | CH | |
| Cl | O | — | Q-1 | $CH_3$ | $CH_3$ | — | — | O | H | $OCH_3$ | $OCH_3$ | CH | |
| Cl | O | — | Q-1 | $CH_3$ | $CH_3$ | — | — | O | H | $OCH_3$ | $CH_3$ | N | |
| Cl | O | — | Q-1 | $CH_3$ | $CH_3$ | — | — | O | H | $OCH_3$ | $OCH_3$ | N | |
| Cl | O | — | Q-3 | $CH_3$ | — | $CH_3$ | — | O | H | $CH_3$ | $CH_3$ | CH | |
| Cl | O | — | Q-3 | $CH_3$ | — | $CH_3$ | — | O | H | $OCH_3$ | $CH_3$ | CH | |
| Cl | O | — | Q-3 | $CH_3$ | — | $CH_3$ | — | O | H | $OCH_3$ | $OCH_3$ | CH | |
| Cl | O | — | Q-3 | $CH_3$ | — | $CH_3$ | — | O | H | Cl | $OCH_3$ | CH | |
| Cl | O | — | Q-3 | $CH_3$ | — | $CH_3$ | — | O | H | $OCH_3$ | $CH_3$ | N | |
| Cl | O | — | Q-3 | $CH_3$ | — | $CH_3$ | — | O | H | $OCH_3$ | $OCH_3$ | N | |
| Br | O | — | Q-2 | $CH_3$ | $CH_3$ | — | — | O | H | $CH_3$ | $OCH_3$ | CH | |
| Br | O | — | Q-2 | $CH_3$ | $CH_3$ | — | — | O | H | $OCH_3$ | $OCH_3$ | CH | |
| Br | O | — | Q-2 | $CH_3$ | $CH_3$ | — | — | O | H | Cl | $OCH_3$ | CH | |
| Br | O | — | Q-2 | $CH_3$ | $CH_3$ | — | — | O | H | $OCH_3$ | $CH_3$ | N | |
| Br | O | — | Q-2 | $CH_3$ | $CH_3$ | — | — | O | H | $OCH_3$ | $OCH_3$ | N | |
| Br | O | — | Q-2 | $CH_3$ | $CH_2CH_3$ | — | — | O | H | $CH_3$ | $OCH_3$ | CH | |
| Br | O | — | Q-2 | $CH_3$ | $CH_2CH_3$ | — | — | O | H | $OCH_3$ | $OCH_3$ | CH | |
| Br | O | — | Q-2 | $CH_3$ | $CH_2CH_3$ | — | — | O | H | Cl | $OCH_3$ | CH | |
| Br | O | — | Q-2 | $CH_3$ | $CH_2CH_3$ | — | — | O | H | $OCH_3$ | $OCH_3$ | N | |
| Br | O | — | Q-2 | $CH_3$ | $CH_2CH_3$ | — | — | O | H | $OCH_3$ | $CH_3$ | N | |
| Br | O | — | Q-1 | $CH_3$ | $CH_3$ | — | — | O | H | $OCH_3$ | $CH_3$ | CH | |
| Br | O | — | Q-1 | $CH_3$ | $CH_3$ | — | — | O | H | $OCH_3$ | $OCH_3$ | CH | |
| Br | O | — | Q-1 | $CH_3$ | $CH_3$ | — | — | O | H | $OCH_3$ | $OCH_3$ | N | |
| Br | O | — | Q-1 | $CH_3$ | $CH_3$ | — | — | O | H | $OCH_3$ | $CH_3$ | N | |
| Br | O | — | Q-4 | $CH_3$ | — | $CH_3$ | — | O | H | $OCH_3$ | $CH_3$ | CH | |
| Br | O | — | Q-4 | $CH_3$ | — | $CH_3$ | — | O | H | $OCH_3$ | $OCH_3$ | CH | |
| Br | O | — | Q-4 | $CH_3$ | — | $CH_3$ | — | O | H | $OCH_3$ | $OCH_3$ | N | |
| Br | O | — | Q-4 | $CH_3$ | — | $CH_3$ | — | O | H | $OCH_3$ | $CH_3$ | N | |
| F | O | — | Q-2 | $CH_3$ | $CH_3$ | — | — | O | H | $OCH_3$ | $CH_3$ | CH | |
| F | O | — | Q-2 | $CH_3$ | $CH_3$ | — | — | O | H | $OCH_3$ | $OCH_3$ | CH | |
| F | O | — | Q-2 | $CH_3$ | $CH_3$ | — | — | O | H | $OCH_3$ | $CH_3$ | N | |
| F | O | — | Q-2 | $CH_3$ | $CH_3$ | — | — | O | H | $OCH_3$ | $OCH_3$ | N | |
| F | O | — | Q-2 | $CH_3$ | $CH_3$ | — | — | O | H | Cl | $OCH_3$ | CH | |
| F | O | — | Q-1 | $CH_3$ | $CH_3$ | — | — | O | H | $OCH_3$ | $CH_3$ | CH | |
| F | O | — | Q-1 | $CH_3$ | $CH_3$ | — | — | O | H | $OCH_3$ | $OCH_3$ | CH | |
| F | O | — | Q-1 | $CH_3$ | $CH_3$ | — | — | O | H | $OCH_3$ | $OCH_3$ | N | |
| F | O | — | Q-1 | $CH_3$ | $CH_3$ | — | — | O | H | $OCH_3$ | $CH_3$ | N | |
| F | O | — | Q-3 | $CH_3$ | — | $CH_3$ | — | O | H | $OCH_3$ | $CH_3$ | CH | |
| F | O | — | Q-3 | $CH_3$ | — | $CH_3$ | — | O | H | $OCH_3$ | $OCH_3$ | CH | |
| F | O | — | Q-3 | $CH_3$ | — | $CH_3$ | — | O | H | $OCH_3$ | $CH_3$ | N | |
| F | O | — | Q-3 | $CH_3$ | — | $CH_3$ | — | O | H | $OCH_3$ | $OCH_3$ | N | |
| $OCH_3$ | O | — | Q-2 | $CH_3$ | $CH_3$ | — | — | O | H | $CH_3$ | $OCH_3$ | CH | |
| $OCH_3$ | O | — | Q-2 | $CH_3$ | $CH_3$ | — | — | O | H | $OCH_3$ | $OCH_3$ | CH | |
| $OCH_3$ | O | — | Q-2 | $CH_3$ | $CH_3$ | — | — | O | H | Cl | $OCH_3$ | CH | |
| $OCH_3$ | O | — | Q-2 | $CH_3$ | $CH_3$ | — | — | O | H | $OCH_3$ | $CH_3$ | N | |
| $OCH_3$ | O | — | Q-2 | $CH_3$ | $CH_3$ | — | — | O | H | $OCH_3$ | $OCH_3$ | N | |
| $OCH_3$ | O | — | Q-2 | $CH_3$ | $CH_2CH_3$ | — | — | O | H | $OCH_3$ | $CH_3$ | CH | |
| $OCH_3$ | O | — | Q-2 | $CH_3$ | $CH_2CH_3$ | — | — | O | H | $OCH_3$ | $OCH_3$ | CH | |
| $OCH_3$ | O | — | Q-2 | $CH_3$ | $CH_2CH_3$ | — | — | O | H | $OCH_3$ | $CH_3$ | N | |
| $OCH_3$ | O | — | Q-2 | $CH_3$ | $CH_2CH_3$ | — | — | O | H | $OCH_3$ | $OCH_3$ | N | |
| $OCH_3$ | O | — | Q-1 | $CH_3$ | $CH_3$ | — | — | O | H | $OCH_3$ | $CH_3$ | CH | |
| $OCH_3$ | O | — | Q-1 | $CH_3$ | $CH_3$ | — | — | O | H | $OCH_3$ | $OCH_3$ | CH | |
| $OCH_3$ | O | — | Q-1 | $CH_3$ | $CH_3$ | — | — | O | H | $OCH_3$ | $OCH_3$ | N | |
| $OCH_3$ | O | — | Q-1 | $CH_3$ | $CH_3$ | — | — | O | H | $OCH_3$ | $CH_3$ | CH | |
| $OCH_3$ | O | — | Q-1 | $CH_3$ | $CH_3$ | — | — | O | H | Cl | $OCH_3$ | CH | |
| $OCH_3$ | O | — | Q-1 | $CH_3$ | $CH_2CH_3$ | — | — | O | H | $OCH_3$ | $OCH_3$ | CH | |
| $OCH_3$ | O | — | Q-1 | $CH_3$ | $CH_2CH_3$ | — | — | O | H | $OCH_3$ | $CH_3$ | CH | |
| $OCH_3$ | O | — | Q-1 | $CH_3$ | $CH_2CH_3$ | — | — | O | H | $OCH_3$ | $OCH_3$ | N | |
| $OCH_3$ | O | — | Q-3 | $CH_3$ | — | $CH_3$ | — | O | H | $OCH_3$ | $OCH_3$ | CH | |
| $OCH_3$ | O | — | Q-3 | $CH_3$ | — | $CH_3$ | — | O | H | $OCH_3$ | $CH_3$ | CH | |
| $OCH_3$ | O | — | Q 3 | $CH_3$ | — | $CH_3$ | — | O | H | $OCH_3$ | $CH_3$ | N | |
| $OCH_3$ | O | — | Q-3 | $CH_3$ | — | $CH_3$ | — | O | H | $OCH_3$ | $OCH_3$ | N | |
| $OCH_3$ | O | — | Q-3 | $CH_3$ | — | $CH_3$ | — | O | H | $CH_3$ | $CH_3$ | CH | |
| $CF_3$ | O | — | Q-2 | $CH_3$ | $CH_3$ | — | — | O | H | $CH_3$ | $OCH_3$ | CH | |
| $CF_3$ | O | — | Q-2 | $CH_3$ | $CH_3$ | — | — | O | H | $CH_3$ | $OCH_3$ | N | |
| $CF_3$ | O | — | Q-2 | $CH_3$ | $CH_3$ | — | — | O | H | $OCH_3$ | $OCH_3$ | N | |
| $CF_3$ | O | — | Q-2 | $CH_3$ | $CH_3$ | — | — | O | H | $OCH_3$ | $OCH_3$ | CH | |
| $CF_3$ | O | — | Q-1 | $CH_3$ | $CH_3$ | — | — | O | H | $CH_3$ | $OCH_3$ | CH | |
| $CF_3$ | O | — | Q-1 | $CH_3$ | $CH_3$ | — | — | O | H | $OCH_3$ | $OCH_3$ | CH | |
| $CF_3$ | O | — | Q-1 | $CH_3$ | $CH_3$ | — | — | O | H | $OCH_3$ | $OCH_3$ | N | |
| $CF_3$ | O | — | Q-1 | $CH_3$ | $CH_3$ | — | — | O | H | $OCH_3$ | $CH_3$ | N | |
| $CF_3$ | O | — | Q-3 | $CH_3$ | — | $CH_3$ | — | O | H | $OCH_3$ | $CH_3$ | CH | |

TABLE XI-continued

| General Structure 11 | | | | | | | | | | | | | |
|---|---|---|---|---|---|---|---|---|---|---|---|---|---|
| $R_1$ | n | E | Q | $R_2$ | $R_3$ | $R_4$ | $R_5$ | W | R | X | Y | Z | m.p. (°C.) |
| $CF_3$ | O | — | Q-3 | $CH_3$ | — | $CH_3$ | — | O | H | $OCH_3$ | $OCH_3$ | CH | |
| $CF_3$ | O | — | Q-3 | $CH_3$ | — | $CH_3$ | — | O | H | $OCH_3$ | $CH_3$ | N | |
| $CF_3$ | O | — | Q 3 | $CH_3$ | — | $CH_3$ | — | O | H | $OCH_3$ | $OCH_3$ | N | |
| $OCF_2H$ | O | — | Q-2 | $CH_3$ | $CH_3$ | — | — | O | H | $OCH_3$ | $CH_3$ | CH | |
| $OCF_2H$ | O | — | Q-2 | $CH_3$ | $CH_3$ | — | — | O | H | $OCH_3$ | $OCH_3$ | CH | |
| $OCF_2H$ | O | — | Q-2 | $CH_3$ | $CH_3$ | — | — | O | H | $OCH_3$ | $OCH_3$ | N | |
| Cl | O | — | Q-3 | $CH_3$ | — | $OCH_3$ | — | O | H | $OCH_3$ | $CH_3$ | CH | |
| Cl | O | — | Q-3 | $CH_3$ | — | $OCH_3$ | — | O | H | $OCH_3$ | $OCH_3$ | CH | |
| Cl | O | — | Q-3 | $CH_3$ | — | $OCH_3$ | — | O | H | $OCH_3$ | $OCH_3$ | N | |
| Cl | O | — | Q-3 | $CH_3$ | — | $OCH_3$ | — | O | H | $OCH_3$ | $CH_3$ | N | |
| Br | O | — | Q-3 | $CH_3$ | — | $OCH_3$ | — | O | H | $OCH_3$ | $CH_3$ | CH | |
| Br | O | — | Q-3 | $CH_3$ | — | $OCH_3$ | — | O | H | $OCH_3$ | $OCH_3$ | CH | |
| Br | O | — | Q-3 | $CH_3$ | — | $OCH_3$ | — | O | H | $OCH_3$ | $OCH_3$ | N | |
| F | O | — | Q-3 | $CH_3$ | — | $OCH_3$ | — | O | H | $OCH_3$ | $OCH_3$ | N | |
| F | O | — | Q-3 | $CH_3$ | — | $OCH_3$ | — | O | H | $OCH_3$ | $OCH_3$ | CH | |
| F | O | — | Q-3 | $CH_3$ | — | $OCH_3$ | — | O | H | $OCH_3$ | $CH_3$ | CH | |
| $OCH_3$ | O | — | Q-3 | $CH_3$ | — | $OCH_3$ | — | O | H | $OCH_3$ | $CH_3$ | CH | |
| $OCH_3$ | O | — | Q-3 | $CH_3$ | — | $OCH_3$ | — | O | H | $OCH_3$ | $OCH_3$ | CH | |
| $OCH_3$ | O | — | Q-3 | $CH_3$ | — | $OCH_3$ | — | O | H | $OCH_3$ | $OCH_3$ | N | |
| $OCH_3$ | O | — | Q-3 | $CH_3$ | — | $OCH_3$ | — | O | H | $OCH_3$ | $CH_3$ | N | |
| $CF_3$ | O | — | Q-3 | $CH_3$ | — | $OCH_3$ | — | O | H | $OCH_3$ | $CH_3$ | CH | |
| $CF_3$ | O | — | Q-3 | $CH_3$ | — | $OCH_3$ | — | O | H | $OCH_3$ | $OCH_3$ | CH | |
| $CF_3$ | O | — | Q-3 | $CH_3$ | — | $OCH_3$ | — | O | H | $OCH_3$ | $CH_3$ | N | |
| $CF_3$ | O | — | Q-3 | $CH_3$ | — | $OCH_3$ | — | O | H | $OCH_3$ | $OCH_3$ | N | |
| Cl | O | — | Q-3 | $CH_3$ | — | $SCH_3$ | — | O | H | $OCH_3$ | $CH_3$ | CH | |
| Cl | O | — | Q-3 | $CH_3$ | — | $SCH_3$ | — | O | H | $OCH_3$ | $OCH_3$ | CH | |
| Cl | O | — | Q-3 | $CH_3$ | — | $SCH_3$ | — | O | H | $OCH_3$ | $OCH_3$ | N | |
| Br | O | — | Q-3 | $CH_3$ | — | $SCH_3$ | — | O | H | $OCH_3$ | $OCH_3$ | CH | |
| Br | O | — | Q-3 | $CH_3$ | — | $SCH_3$ | — | O | H | $OCH_3$ | $CH_3$ | CH | |
| F | O | — | Q-3 | $CH_3$ | — | $SCH_3$ | — | O | H | $OCH_3$ | $OCH_3$ | N | |
| F | O | — | Q-3 | $CH_3$ | — | $SCH_3$ | — | O | H | $OCH_3$ | $CH_3$ | CH | |
| $OCH_3$ | O | — | Q-3 | $CH_3$ | — | $SCH_3$ | — | O | H | $OCH_3$ | $OCH_3$ | N | |
| $OCH_3$ | O | — | Q-3 | $CH_3$ | — | $SCH_3$ | — | O | H | $OCH_3$ | $CH_3$ | CH | |
| $OCH_3$ | O | — | Q-3 | $CH_3$ | — | $SCH_3$ | — | O | H | $OCH_3$ | $OCH_3$ | CH | |
| $CH_3$ | O | — | Q-1 | $CH_3$ | $CH_3$ | — | — | O | H | $CH_3$ | $CH_3$ | CH | |
| $CH_3$ | O | — | Q-1 | $CH_3$ | $CH_3$ | — | — | O | H | $OCH_3$ | $CH_3$ | CH | |
| $CH_3$ | O | — | Q-1 | $CH_3$ | $CH_3$ | — | — | O | H | $OCH_3$ | $OCH_3$ | CH | |
| $CH_3$ | O | — | Q-1 | $CH_3$ | $CH_3$ | — | — | O | H | Cl | $OCH_3$ | CH | |
| $CH_3$ | O | — | Q-1 | $CH_3$ | $CH_3$ | — | — | O | H | $OCH_3$ | $CH_3$ | N | |
| $CH_3$ | O | — | Q-1 | $CH_3$ | $CH_3$ | — | — | O | H | $OCH_3$ | $OCH_3$ | N | |
| $CH_3$ | O | — | Q-3 | $CH_3$ | — | $OCH_3$ | — | O | H | $OCH_3$ | $CH_3$ | CH | |
| $CH_3$ | O | — | Q-3 | $CH_3$ | — | $OCH_3$ | — | O | H | $OCH_3$ | $OCH_3$ | CH | |
| $CH_3$ | O | — | Q-3 | $CH_3$ | — | $OCH_3$ | — | O | H | Cl | $OCH_3$ | CH | |
| $CH_3$ | O | — | Q-3 | $CH_3$ | — | $OCH_3$ | — | O | H | $OCH_3$ | $CH_3$ | N | |
| $CH_3$ | O | — | Q-3 | $CH_3$ | — | $OCH_3$ | — | O | H | $OCH_3$ | $OCH_3$ | N | |
| Cl | O | — | Q-2 | $CH_3$ | $CH_3$ | — | — | O | $CH_3$ | $OCH_3$ | $OCH_3$ | CH | |
| Br | O | — | Q-2 | $CH_3$ | $CH_3$ | — | — | O | $CH_3$ | $OCH_3$ | $OCH_3$ | CH | |
| F | O | — | Q-2 | $CH_3$ | $CH_3$ | — | — | O | $CH_3$ | $OCH_3$ | $OCH_3$ | CH | |
| Cl | O | — | Q-5 | $CH_3$ | — | — | $CH_3$ | O | H | $CH_3$ | $OCH_3$ | CH | |
| Cl | O | — | Q-5 | $CH_3$ | — | — | $CH_3$ | O | H | $OCH_3$ | $OCH_3$ | CH | |
| Br | O | — | Q-5 | $CH_3$ | — | — | $CH_3$ | O | H | $OCH_3$ | $CH_3$ | CH | |
| Br | O | — | Q-5 | $CH_3$ | — | — | $CH_3$ | O | H | $OCH_3$ | $OCH_3$ | CH | |
| F | O | — | Q-5 | $CH_3$ | — | — | $CH_3$ | O | H | $OCH_3$ | $OCH_3$ | CH | |
| F | O | — | Q-5 | $CH_3$ | — | — | $CH_3$ | O | H | $CH_3$ | $OCH_3$ | CH | |
| $OCH_3$ | O | — | Q-5 | $CH_3$ | — | — | $CH_3$ | O | H | $CH_3$ | $OCH_3$ | CH | |
| $OCH_3$ | O | — | Q-5 | $CH_3$ | — | — | $CH_3$ | O | H | $OCH_3$ | $OCH_3$ | CH | |
| $OCH_3$ | O | — | Q-5 | $CH_3$ | — | — | $CH_3$ | O | H | $OCH_3$ | $OCH_3$ | N | |
| Cl | O | — | Q 5 | $CH_3$ | — | — | $CH_3$ | O | H | $OCH_3$ | $CH_3$ | N | |
| Cl | O | — | Q-5 | $CH_3$ | — | — | $CH_3$ | O | H | $OCH_3$ | $OCH_3$ | N | |

TABLE XII

| General Structure 12 | | | | | | | | | | | | | |
|---|---|---|---|---|---|---|---|---|---|---|---|---|---|
| $R_1$ | n | E | Q | $R_2$ | $R_3$ | $R_4$ | $R_5$ | W | R | X | Y | Z | m.p. (°C.) |
| H | O | — | Q-1 | $C_6H_5$ | $CH_3$ | — | — | O | H | $CH_3$ | $CH_3$ | CH | |
| H | O | — | Q-1 | $C_6H_5$ | $CH_3$ | — | — | O | H | $OCH_3$ | $CH_3$ | CH | |
| H | O | — | Q-1 | $C_6H_5$ | $CH_3$ | — | — | O | H | Cl | $OCH_3$ | CH | |
| H | O | — | Q-1 | $C_6H_5$ | $CH_3$ | — | — | O | H | $CH_3$ | $OCH_3$ | N | |
| H | O | — | Q-1 | $C_6H_5$ | $CH_3$ | — | — | O | H | $OCH_3$ | $OCH_3$ | N | |
| H | O | — | Q-1 | $C_6H_5$ | $C_2H_5$ | — | — | O | H | $OCH_3$ | $CH_3$ | CH | |
| H | O | — | Q-1 | $C_6H_5$ | $C_2H_5$ | — | — | O | H | $OCH_3$ | $OCH_3$ | CH | |
| H | O | — | Q-1 | $C_6H_5$ | $C_2H_5$ | — | — | O | H | Cl | $OCH_3$ | CH | |
| H | O | — | Q-1 | $C_6H_5$ | $C_2H_5$ | — | — | O | H | $CH_3$ | $CH_3$ | CH | |
| H | O | — | Q-1 | $C_6H_5$ | $C_2H_5$ | — | — | O | H | $CH_3$ | $OCH_3$ | N | |
| H | O | — | Q-2 | $C_6H_5$ | $CH_3$ | — | — | O | H | $OCH_3$ | $OCH_3$ | N | |
| H | O | — | Q-2 | $C_6H_5$ | $CH_3$ | — | — | O | H | $OCH_3$ | $OCH_3$ | CH | 232-233 |
| H | O | — | Q-2 | $C_6H_5$ | $CH_3$ | — | — | O | H | $OCH_3$ | $CH_3$ | CH | 193-195 |
| H | O | — | Q-2 | $C_6H_5$ | $CH_3$ | — | — | O | H | Cl | $OCH_3$ | CH | 195-198 |

TABLE XII-continued

| | | | | | | General Structure 12 | | | | | | | |
|---|---|---|---|---|---|---|---|---|---|---|---|---|---|
| $R_1$ | n | E | Q | $R_2$ | $R_3$ | $R_4$ | $R_5$ | W | R | X | Y | Z | m.p. (°C.) |
| H | O | — | Q-2 | $C_6H_5$ | $CH_3$ | — | — | O | H | $CH_3$ | $CH_3$ | CH | 165-170 |
| H | O | — | Q-2 | $C_6H_5$ | $CH_3$ | — | — | O | H | $OCH_3$ | $CH_3$ | N | 140-145 |
| H | O | — | Q-2 | $C_6H_5$ | $C_2H_5$ | — | — | O | H | $OCH_3$ | $OCH_3$ | N | 195-196 |
| H | O | — | Q-2 | C $H_5$ | $C_2H_5$ | — | — | O | H | $CH_3$ | $CH_3$ | CH | |
| H | O | — | Q-2 | $C_6H_5$ | $C_2H_5$ | — | — | O | H | $CH_3$ | $OCH_3$ | CH | |
| H | O | — | Q-2 | $C_6H_5$ | $C_2H_5$ | — | — | O | H | Cl | $OCH_3$ | CH | |
| H | O | — | Q-2 | $C_6H_5$ | $C_2H_5$ | — | — | O | H | $CH_3$ | $OCH_3$ | N | |
| H | O | — | Q-2 | $C_6H_5$ | $C_2H_5$ | — | — | O | H | $OCH_3$ | $OCH_3$ | N | |
| H | O | — | Q-3 | $C_6H_5$ | — | $CH_3$ | — | O | H | $CH_3$ | $OCH_3$ | CH | |
| H | O | — | Q-3 | $C_6H_5$ | — | $CH_3$ | — | O | H | Cl | $OCH_3$ | CH | |
| H | O | — | Q-3 | $C_6H_5$ | — | $CH_3$ | — | O | H | $OCH_3$ | $OCH_3$ | CH | |
| H | O | — | Q-3 | $C_6H_5$ | — | $CH_3$ | — | O | H | $OCH_3$ | $OCH_3$ | N | |
| H | O | — | Q-3 | $C_6H_5$ | — | $CH_3$ | — | O | H | $CH_3$ | $OCH_3$ | N | |
| H | O | — | Q-3 | $C_6H_5$ | — | $C_2H_5$ | — | O | H | $CH_3$ | $CH_3$ | CH | |
| H | O | — | Q-3 | $C_6H_5$ | — | $C_2H_5$ | — | O | H | $CH_3$ | $OCH_3$ | CH | |
| H | O | — | Q-3 | $C_6H_5$ | — | $C_2H_5$ | — | O | H | Cl | $OCH_3$ | CH | |
| H | O | — | Q-3 | $C_6H_5$ | — | $C_2H_5$ | — | O | H | $OCH_3$ | $OCH_3$ | CH | |
| H | O | — | Q-3 | $C_6H_5$ | — | $C_2H_5$ | — | O | H | $CH_3$ | $OCH_3$ | N | |
| H | O | — | Q-3 | $C_6H_5$ | — | $CH_2Cl$ | — | O | H | $CH_3$ | $OCH_3$ | CH | |
| H | O | — | Q-3 | $C_6H_5$ | — | $CH_2Cl$ | — | O | H | $OCH_3$ | $OCH_3$ | CH | |
| H | O | — | Q-3 | $C_6H_5$ | — | $CH_2Cl$ | — | O | H | Cl | $OCH_3$ | CH | |
| H | O | — | Q-3 | $C_6H_5$ | — | $CH_2Cl$ | — | O | H | $CH_3$ | $OCH_3$ | N | |
| H | O | — | Q-3 | $C_6H_5$ | — | $CH_2Cl$ | — | O | H | $OCH_3$ | $OCH_3$ | N | |
| H | O | — | Q-3 | $C_6H_5$ | — | $CF_3$ | — | O | H | $CH_3$ | $CH_3$ | CH | |
| H | O | — | Q-3 | $C_6H_5$ | — | $CF_3$ | — | O | H | $OCH_3$ | $OCH_3$ | CH | |
| H | O | — | Q-3 | $C_6H_5$ | — | $CF_3$ | — | O | H | $OCH_3$ | $CH_3$ | CH | |
| H | O | — | Q-3 | $C_6H_5$ | — | $CF_3$ | — | O | H | $CH_3$ | $OCH_3$ | N | |
| H | O | — | Q-3 | $C_6H_5$ | — | $CH(CH_3)_2$ | — | O | H | $CH_3$ | $OCH_3$ | CH | |
| H | O | — | Q-3 | $C_6H_5$ | — | $CH(CH_3)_2$ | — | O | H | $OCH_3$ | $OCH_3$ | CH | |
| H | O | — | Q-3 | $C_6H_5$ | — | $CH(CH_3)_2$ | — | O | H | Cl | $OCH_3$ | CH | |
| H | O | — | Q-3 | $C_6H_5$ | — | $CH(CH_3)_2$ | — | O | H | $CH_3$ | $OCH_3$ | N | |
| H | O | — | Q-3 | $C_6H_5$ | — | $OCH_3$ | — | O | H | $OCH_3$ | $OCH_3$ | CH | |
| H | O | — | Q-3 | $C_6H_5$ | — | $OCH_3$ | — | O | H | $CH_3$ | $OCH_3$ | CH | |
| H | O | — | Q-3 | $C_6H_5$ | — | $OCH_3$ | — | O | H | Cl | $CH_3$ | CH | |
| H | O | — | Q-3 | $C_6H_5$ | — | $OCH_3$ | — | O | H | $OCH_3$ | $OCH_3$ | N | |
| H | O | — | Q-3 | $C_6H_5$ | — | $SCH_3$ | — | O | H | $CH_3$ | $OCH_3$ | CH | |
| H | O | — | Q-3 | $C_6H_5$ | — | $SCH_3$ | — | O | H | $OCH_3$ | $OCH_3$ | CH | |
| H | O | — | Q-3 | $C_6H_5$ | — | $SCH_3$ | — | O | H | $OCH_3$ | $OCH_3$ | N | |
| H | O | — | Q-3 | $C_6H_5$ | — | $SCH_3$ | — | O | H | $CH_3$ | $OCH_3$ | N | |
| H | O | — | Q-3 | $C_6H_5$ | — | $N(CH_3)_2$ | — | O | H | $CH_3$ | $CH_3$ | CH | |
| H | O | — | Q-3 | $C_6H_5$ | — | $N(CH_3)_2$ | — | O | H | $OCH_3$ | $OCH_3$ | CH | |
| H | O | — | Q-3 | $C_6H_5$ | — | $N(CH_3)_2$ | — | O | H | $OCH_3$ | $CH_3$ | N | |
| H | O | — | Q-1 | $CH_3$ | $CH_3$ | — | — | O | H | $CH_3$ | $CH_3$ | CH | 165-167 |
| H | O | — | Q-1 | $CH_3$ | $CH_3$ | — | — | O | H | $OCH_3$ | $CH_3$ | CH | 125-127 |
| H | O | — | Q-1 | $CH_3$ | $CH_3$ | — | — | O | H | Cl | $OCH_3$ | CH | 189-191 |
| H | O | — | Q-1 | $CH_3$ | $CH_3$ | — | — | O | H | $CH_3$ | $OCH_3$ | N | 166-170 |
| H | O | — | Q-1 | $CH_3$ | $CH_3$ | — | — | O | H | $OCH_3$ | $OCH_3$ | N | 160-172 |
| H | O | — | Q-1 | $CH_3$ | $C_2H_5$ | — | — | O | H | $OCH_3$ | $CH_3$ | CH | |
| H | O | — | Q-1 | $CH_3$ | $C_2H_5$ | — | — | O | H | $OCH_3$ | $OCH_3$ | CH | |
| H | O | — | Q-1 | $CH_3$ | $C_2H_5$ | — | — | O | H | Cl | $OCH_3$ | CH | |
| H | O | — | Q-1 | $CH_3$ | $C_2H_5$ | — | — | O | H | $CH_3$ | $CH_3$ | CH | |
| H | O | — | Q-1 | $CH_3$ | $C_2H_5$ | — | — | O | H | $CH_3$ | $OCH_3$ | N | |
| H | O | — | Q-2 | $CH_3$ | $CH_3$ | — | — | O | H | $OCH_3$ | $OCH_3$ | N | 180-183 |
| H | O | — | Q-2 | $CH_3$ | $CH_3$ | — | — | O | H | $OCH_3$ | $OCH_3$ | CH | 171-173 |
| H | O | — | Q-2 | $CH_3$ | $CH_3$ | — | — | O | H | $OCH_3$ | $CH_3$ | CH | 181-183 |
| H | O | — | Q-2 | $CH_3$ | $CH_3$ | — | — | O | H | Cl | $OCH_3$ | CH | 178-180 |
| H | O | — | Q-2 | $CH_3$ | $CH_3$ | — | — | O | H | $CH_3$ | $CH_3$ | CH | 200-202 |
| H | O | — | Q-2 | $CH_3$ | $CH_3$ | — | — | O | H | $OCH_3$ | $CH_3$ | N | 179-180 |
| H | O | — | Q-2 | $CH_3$ | $C_2H_5$ | — | — | O | H | $OCH_3$ | $OCH_3$ | CH | 195 |
| H | O | — | Q-2 | $CH_3$ | $C_2H_5$ | — | — | O | H | $CH_3$ | $CH_3$ | CH | 172-173 |
| H | O | — | Q-2 | $CH_3$ | $C_2H_5$ | — | — | O | H | $CH_3$ | $OCH_3$ | CH | 152-156 |
| H | O | — | Q-2 | $CH_3$ | $C_2H_5$ | — | — | O | H | Cl | $OCH_3$ | CH | 170-171 |
| H | O | — | Q-2 | $CH_3$ | $C_2H_5$ | — | — | O | H | $CH_3$ | $OCH_3$ | N | 173-174 |
| H | O | — | Q-2 | $CH_3$ | $C_2H_5$ | — | — | O | H | $OCH_3$ | $OCH_3$ | N | 168-170 |
| H | O | — | Q-3 | $CH_3$ | — | $CH_3$ | — | O | H | $CH_3$ | $OCH_3$ | CH | |
| H | O | — | Q-3 | $CH_3$ | — | $CH_3$ | — | O | H | Cl | $OCH_3$ | CH | |
| H | O | — | Q-3 | $CH_3$ | — | $CH_3$ | — | O | H | $OCH_3$ | $OCH_3$ | CH | |
| H | O | — | Q-3 | $CH_3$ | — | $CH_3$ | — | O | H | $OCH_3$ | $OCH_3$ | N | |
| H | O | — | Q-3 | $CH_3$ | — | $CH_3$ | — | O | H | $CH_3$ | $OCH_3$ | N | |
| H | O | — | Q-3 | $CH_3$ | — | $C_2H_5$ | — | O | H | $CH_3$ | $CH_3$ | CH | |
| H | O | — | Q-3 | $CH_3$ | — | $C_2H_5$ | — | O | H | $CH_3$ | $OCH_3$ | CH | |
| H | O | — | Q-3 | $CH_3$ | — | $C_2H_5$ | — | O | H | Cl | $OCH_3$ | CH | |
| H | O | — | Q-3 | $CH_3$ | — | $C_2H_5$ | — | O | H | $OCH_3$ | $OCH_3$ | CH | |
| H | O | — | Q-3 | $CH_3$ | — | $C_2H_5$ | — | O | H | $CH_3$ | $OCH_3$ | N | |
| H | O | — | Q-3 | $CH_3$ | — | $CH_2Cl$ | — | O | H | $CH_3$ | $OCH_3$ | CH | |
| H | O | — | Q-3 | $CH_3$ | — | $CH_2Cl$ | — | O | H | $OCH_3$ | $OCH_3$ | CH | |
| H | O | — | Q-3 | $CH_3$ | — | $CH_2Cl$ | — | O | H | Cl | $OCH_3$ | CH | |
| H | O | — | Q-3 | $CH_3$ | — | $CH_2Cl$ | — | O | H | $CH_3$ | $OCH_3$ | N | |
| H | O | — | Q-3 | $CH_3$ | — | $CH_2Cl$ | — | O | H | $OCH_3$ | $OCH_3$ | N | |
| H | O | — | Q-3 | $CH_3$ | — | $CF_3$ | — | O | H | $CH_3$ | $CH_3$ | CH | |

TABLE XII-continued

General Structure 12

| $R_1$ | n | E | Q | $R_2$ | $R_3$ | $R_4$ | $R_5$ | W | R | X | Y | Z | m.p. (°C.) |
|---|---|---|---|---|---|---|---|---|---|---|---|---|---|
| H | O | — | Q-3 | $CH_3$ | — | $CF_3$ | — | O | H | $OCH_3$ | $OCH_3$ | CH | |
| H | O | — | Q-3 | $CH_3$ | — | $CF_3$ | — | O | H | $OCH_3$ | $CH_3$ | CH | |
| H | O | — | Q-3 | $CH_3$ | — | $CF_3$ | — | O | H | $CH_3$ | $OCH_3$ | N | |
| H | O | — | Q-3 | $CH_3$ | — | $CH(CH_3)_2$ | — | O | H | $CH_3$ | $OCH_3$ | CH | |
| H | O | — | Q-3 | $CH_3$ | — | $CH(CH_3)_2$ | — | O | H | $OCH_3$ | $OCH_3$ | CH | |
| H | O | — | Q-3 | $CH_3$ | — | $CH(CH_3)_2$ | — | O | H | Cl | $OCH_3$ | CH | |
| H | O | — | Q-3 | $CH_3$ | — | $CH(CH_3)_2$ | — | O | H | $CH_3$ | $OCH_3$ | N | |
| H | O | — | Q-3 | $CH_3$ | — | $OCH_3$ | — | O | H | $OCH_3$ | $OCH_3$ | CH | |
| H | O | — | Q-3 | $CH_3$ | — | $OCH_3$ | — | O | H | $CH_3$ | $OCH_3$ | CH | |
| H | O | — | Q-3 | $CH_3$ | — | $OCH_3$ | — | O | H | Cl | $CH_3$ | CH | |
| H | O | — | Q-3 | $CH_3$ | — | $OCH_3$ | — | O | H | $OCH_3$ | $OCH_3$ | N | |
| H | O | — | Q-3 | $CH_3$ | — | $SCH_3$ | — | O | H | $CH_3$ | $OCH_3$ | CH | |
| H | O | — | Q-3 | $CH_3$ | — | $SCH_3$ | — | O | H | $OCH_3$ | $OCH_3$ | CH | |
| H | O | — | Q-3 | $CH_3$ | — | $SCH_3$ | — | O | H | $OCH_3$ | $OCH_3$ | N | |
| H | O | — | Q-3 | $CH_3$ | — | $SCH_3$ | — | O | H | $CH_3$ | $OCH_3$ | N | |
| H | O | — | Q-3 | $CH_3$ | — | $N(CH_3)_2$ | — | O | H | $CH_3$ | $CH_3$ | CH | |
| H | O | — | Q-3 | $CH_3$ | — | $N(CH_3)_2$ | — | O | H | $OCH_3$ | $OCH_3$ | CH | |
| H | O | — | Q-3 | $CH_3$ | — | $N(CH_3)_2$ | — | O | H | $OCH_3$ | $CH_3$ | N | |
| H | O | — | Q-5 | $CH_3$ | — | — | $CH_3$ | O | H | $OCH_3$ | $CH_3$ | N | |
| H | O | — | Q-5 | $CH_3$ | — | — | $CH_3$ | O | H | $OCH_3$ | $CH_3$ | CH | |
| H | O | — | Q-5 | $CH_3$ | — | — | $CH_3$ | O | H | $OCH_3$ | $OCH_3$ | CH | |
| H | O | — | Q-5 | $CH_3$ | — | — | $CH_3$ | O | H | Cl | $OCH_3$ | CH | |
| H | O | — | Q-5 | $CH_3$ | — | — | $CH_3$ | O | H | $CH_3$ | $CH_3$ | CH | |
| Cl | O | — | Q-2 | $CH_3$ | $CH_3$ | — | — | O | H | $CH_3$ | $CH_3$ | CH | |
| Cl | O | — | Q-2 | $CH_3$ | $CH_3$ | — | — | O | H | $CH_3$ | $OCH_3$ | CH | |
| Cl | O | — | Q-2 | $CH_3$ | $CH_3$ | — | — | O | H | $OCH_3$ | $OCH_3$ | CH | |
| Cl | O | — | Q-2 | $CH_3$ | $CH_3$ | — | — | O | H | Cl | $OCH_3$ | CH | |
| Cl | O | — | Q-2 | $CH_3$ | $CH_3$ | — | — | O | H | $CH_3$ | $OCH_3$ | N | |
| Cl | O | — | Q-2 | $CH_3$ | $CH_3$ | — | — | O | H | $OCH_3$ | $OCH_3$ | N | |
| Cl | O | — | Q-2 | $CH_3$ | $CH_3$ | — | — | O | $CH_3$ | $OCH_3$ | $CH_3$ | N | |
| Cl | O | — | Q-2 | $CH_3$ | $CH_2CH_3$ | — | — | O | H | $CH_3$ | $CH_3$ | CH | |
| Cl | O | — | Q-2 | $CH_3$ | $CH_2CH_3$ | — | — | O | H | $CH_3$ | $OCH_3$ | CH | |
| Cl | O | — | Q-2 | $CH_3$ | $CH_2CH_3$ | — | — | O | H | $OCH_3$ | $OCH_3$ | CH | |
| Cl | O | — | Q-2 | $CH_3$ | $CH_2CH_3$ | — | — | O | H | Cl | $OCH_3$ | CH | |
| Cl | O | — | Q-2 | $CH_3$ | $CH_2CH_3$ | — | — | O | H | $OCH_3$ | $CH_3$ | N | |
| Cl | O | — | Q-2 | $CH_3$ | $CH_2CH_3$ | — | — | O | H | $OCH_3$ | $OCH_3$ | N | |
| H | O | — | Q-2 | $CH_2CH_3$ | $CH_3$ | — | — | O | H | $CH_3$ | $CH_3$ | CH | |
| H | O | — | Q-2 | $CH_2CH_3$ | $CH_3$ | — | — | O | H | $CH_3$ | $OCH_3$ | CH | |
| H | O | — | Q-2 | $CH_2CH_3$ | $CH_3$ | — | — | O | H | $OCH_3$ | $OCH_3$ | CH | |
| H | O | — | Q-2 | $CH_2CH_3$ | $CH_3$ | — | — | O | H | Cl | $OCH_3$ | CH | |
| H | O | — | Q-2 | $CH_2CH_3$ | $CH_3$ | — | — | O | H | $OCH_3$ | $CH_3$ | N | |
| H | O | — | Q-2 | $CH_2CH_3$ | $CH_3$ | — | — | O | H | $OCH_3$ | $OCH_3$ | N | |
| Cl | O | — | Q-1 | $CH_3$ | $CH_3$ | — | — | O | H | $OCH_3$ | $CH_3$ | CH | |
| Cl | O | — | Q-1 | $CH_3$ | $CH_3$ | — | — | O | H | $OCH_3$ | $OCH_3$ | CH | |
| Cl | O | — | Q-1 | $CH_3$ | $CH_3$ | — | — | O | H | $OCH_3$ | $CH_3$ | N | |
| Cl | O | — | Q-1 | $CH_3$ | $CH_3$ | — | — | O | H | $OCH_3$ | $OCH_3$ | N | |
| Cl | O | — | Q-3 | $CH_3$ | — | $CH_3$ | — | O | H | $CH_3$ | $CH_3$ | CH | |
| Cl | O | — | Q-3 | $CH_3$ | — | $CH_3$ | — | O | H | $OCH_3$ | $CH_3$ | CH | |
| Cl | O | — | Q-3 | $CH_3$ | — | $CH_3$ | — | O | H | $OCH_3$ | $OCH_3$ | CH | |
| Cl | O | — | Q-3 | $CH_3$ | — | $CH_3$ | — | O | H | Cl | $OCH_3$ | CH | |
| Cl | O | — | Q-3 | $CH_3$ | — | $CH_3$ | — | O | H | $OCH_3$ | $CH_3$ | N | |
| Cl | O | — | Q-3 | $CH_3$ | — | $CH_3$ | — | O | H | $OCH_3$ | $OCH_3$ | N | |
| Br | O | — | Q-2 | $CH_3$ | $CH_3$ | — | — | O | H | $CH_3$ | $OCH_3$ | CH | |
| Br | O | — | Q-2 | $CH_3$ | $CH_3$ | — | — | O | H | $OCH_3$ | $OCH_3$ | CH | |
| Br | O | — | Q-2 | $CH_3$ | $CH_3$ | — | — | O | H | Cl | $OCH_3$ | CH | |
| Br | O | — | Q-2 | $CH_3$ | $CH_3$ | — | — | O | H | $OCH_3$ | $CH_3$ | N | |
| Br | O | — | Q-2 | $CH_3$ | $CH_3$ | — | — | O | H | $OCH_3$ | $OCH_3$ | N | |
| Br | O | — | Q-2 | $CH_3$ | $CH_2CH_3$ | — | — | O | H | $CH_3$ | $OCH_3$ | CH | |
| Br | O | — | Q-2 | $CH_3$ | $CH_2CH_3$ | — | — | O | H | $OCH_3$ | $OCH_3$ | CH | |
| Br | O | — | Q-2 | $CH_3$ | $CH_2CH_3$ | — | — | O | H | Cl | $OCH_3$ | CH | |
| Br | O | — | Q-2 | $CH_3$ | $CH_2CH_3$ | — | — | O | H | $OCH_3$ | $OCH_3$ | N | |
| Br | O | — | Q-2 | $CH_3$ | $CH_2CH_3$ | — | — | O | H | $OCH_3$ | $CH_3$ | N | |
| Br | O | — | Q-1 | $CH_3$ | $CH_3$ | — | — | O | H | $OCH_3$ | $CH_3$ | CH | |
| Br | O | — | Q-1 | $CH_3$ | $CH_3$ | — | — | O | H | $OCH_3$ | $OCH_3$ | CH | |
| Br | O | — | Q-1 | $CH_3$ | $CH_3$ | — | — | O | H | $OCH_3$ | $OCH_3$ | N | |
| Br | O | — | Q-1 | $CH_3$ | $CH_3$ | — | — | O | H | $OCH_3$ | $CH_3$ | N | |
| Br | O | — | Q-4 | $CH_3$ | — | $CH_3$ | — | O | H | $OCH_3$ | $CH_3$ | CH | |
| Br | O | — | Q-4 | $CH_3$ | — | $CH_3$ | — | O | H | $OCH_3$ | $OCH_3$ | CH | |
| Br | O | — | Q-4 | $CH_3$ | — | $CH_3$ | — | O | H | $OCH_3$ | $OCH_3$ | N | |
| Br | O | — | Q-4 | $CH_3$ | — | $CH_3$ | — | O | H | $OCH_3$ | $CH_3$ | N | |
| F | O | — | Q-2 | $CH_3$ | $CH_3$ | — | — | O | H | $OCH_3$ | $CH_3$ | CH | |
| F | O | — | Q-2 | $CH_3$ | $CH_3$ | — | — | O | H | $OCH_3$ | $OCH_3$ | CH | |
| F | O | — | Q-2 | $CH_3$ | $CH_3$ | — | — | O | H | $OCH_3$ | $CH_3$ | N | |
| F | O | — | Q-2 | $CH_3$ | $CH_3$ | — | — | O | H | $OCH_3$ | $OCH_3$ | N | |
| F | O | — | Q-2 | $CH_3$ | $CH_3$ | — | — | O | H | Cl | $OCH_3$ | CH | |
| F | O | — | Q-1 | $CH_3$ | $CH_3$ | — | — | O | H | $OCH_3$ | $CH_3$ | CH | |
| F | O | — | Q-1 | $CH_3$ | $CH_3$ | — | — | O | H | $OCH_3$ | $OCH_3$ | CH | |
| F | O | — | Q-1 | $CH_3$ | $CH_3$ | — | — | O | H | $OCH_3$ | $OCH_3$ | N | |
| F | O | — | Q-1 | $CH_3$ | $CH_3$ | — | — | O | H | $OCH_3$ | $CH_3$ | N | |
| F | O | — | Q-3 | $CH_3$ | — | $CH_3$ | — | O | H | $OCH_3$ | $CH_3$ | CH | |

TABLE XII-continued

| R1 | n | E | Q | R2 | R3 | R4 | R5 | W | R | X | Y | Z | m.p. (°C.) |
|---|---|---|---|---|---|---|---|---|---|---|---|---|---|
| | | | | | | General Structure 12 | | | | | | | |
| F | O | — | Q-3 | $CH_3$ | — | $CH_3$ | — | O | H | $OCH_3$ | $OCH_3$ | CH | |
| F | O | — | Q-3 | $CH_3$ | — | $CH_3$ | — | O | H | $OCH_3$ | $CH_3$ | N | |
| F | O | — | Q-3 | $CH_3$ | — | $CH_3$ | — | O | H | $OCH_3$ | $OCH_3$ | N | |
| $OCH_3$ | O | — | Q-2 | $CH_3$ | $CH_3$ | — | — | O | H | $CH_3$ | $OCH_3$ | CH | |
| $OCH_3$ | O | — | Q-2 | $CH_3$ | $CH_3$ | — | — | O | H | $OCH_3$ | $OCH_3$ | CH | |
| $OCH_3$ | O | — | Q-2 | $CH_3$ | $CH_3$ | — | — | O | H | Cl | $OCH_3$ | CH | |
| $OCH_3$ | O | — | Q-2 | $CH_3$ | $CH_3$ | — | — | O | H | $OCH_3$ | $CH_3$ | N | |
| $OCH_3$ | O | — | Q-2 | $CH_3$ | $CH_3$ | — | — | O | H | $OCH_3$ | $OCH_3$ | N | |
| $OCH_3$ | O | — | Q-2 | $CH_3$ | $CH_2CH_3$ | — | — | O | H | $OCH_3$ | $CH_3$ | CH | |
| $OCH_3$ | O | — | Q-2 | $CH_3$ | $CH_2CH_3$ | — | — | O | H | $OCH_3$ | $OCH_3$ | CH | |
| $OCH_3$ | O | — | Q-2 | $CH_3$ | $CH_2CH_3$ | — | — | O | H | $OCH_3$ | $CH_3$ | N | |
| $OCH_3$ | O | — | Q-2 | $CH_3$ | $CH_2CH_3$ | — | — | O | H | $OCH_3$ | $OCH_3$ | N | |
| $OCH_3$ | O | — | Q-1 | $CH_3$ | $CH_3$ | — | — | O | H | $OCH_3$ | $CH_3$ | CH | |
| $OCH_3$ | O | — | Q-1 | $CH_3$ | $CH_3$ | — | — | O | H | $OCH_3$ | $OCH_3$ | CH | |
| $OCH_3$ | O | — | Q-1 | $CH_3$ | $CH_3$ | — | — | O | H | $OCH_3$ | $OCH_3$ | N | |
| $OCH_3$ | O | — | Q-1 | $CH_3$ | $CH_3$ | — | — | O | H | $OCH_3$ | $CH_3$ | CH | |
| $OCH_3$ | O | — | Q-1 | $CH_3$ | $CH_3$ | — | — | O | H | Cl | $OCH_3$ | CH | |
| $OCH_3$ | O | — | Q-1 | $CH_3$ | $CH_2CH_3$ | — | — | O | H | $OCH_3$ | $OCH_3$ | CH | |
| $OCH_3$ | O | — | Q-1 | $CH_3$ | $CH_2CH_3$ | — | — | O | H | $OCH_3$ | $CH_3$ | CH | |
| $OCH_3$ | O | — | Q-1 | $CH_3$ | $CH_2CH_3$ | — | — | O | H | $OCH_3$ | $OCH_3$ | N | |
| $OCH_3$ | O | — | Q-3 | $CH_3$ | — | $CH_3$ | — | O | H | $OCH_3$ | $OCH_3$ | CH | |
| $OCH_3$ | O | — | Q-3 | $CH_3$ | — | $CH_3$ | — | O | H | $OCH_3$ | $CH_3$ | CH | |
| $OCH_3$ | O | — | Q-3 | $CH_3$ | — | $CH_3$ | — | O | H | $OCH_3$ | $CH_3$ | N | |
| $OCH_3$ | O | — | Q-3 | $CH_3$ | — | $CH_3$ | — | O | H | $OCH_3$ | $OCH_3$ | N | |
| $OCH_3$ | O | — | Q-3 | $CH_3$ | — | $CH_3$ | — | O | H | $CH_3$ | $CH_3$ | CH | |
| $CF_3$ | O | — | Q-2 | $CH_3$ | $CH_3$ | — | — | O | H | $CH_3$ | $OCH_3$ | CH | |
| $CF_3$ | O | — | Q-2 | $CH_3$ | $CH_3$ | — | — | O | H | $CH_3$ | $OCH_3$ | N | |
| $CF_3$ | O | — | Q-2 | $CH_3$ | $CH_3$ | — | — | O | H | $OCH_3$ | $OCH_3$ | N | |
| $CF_3$ | O | — | Q-2 | $CH_3$ | $CH_3$ | — | — | O | H | $OCH_3$ | $OCH_3$ | CH | |
| $CF_3$ | O | — | Q-1 | $CH_3$ | $CH_3$ | — | — | O | H | $CH_3$ | $OCH_3$ | CH | |
| $CF_3$ | O | — | Q-1 | $CH_3$ | $CH_3$ | — | — | O | H | $OCH_3$ | $OCH_3$ | CH | |
| $CF_3$ | O | — | Q-1 | $CH_3$ | $CH_3$ | — | — | O | H | $OCH_3$ | $OCH_3$ | N | |
| $CF_3$ | O | — | Q-1 | $CH_3$ | $CH_3$ | — | — | O | H | $OCH_3$ | $CH_3$ | N | |
| $CF_3$ | O | — | Q-3 | $CH_3$ | — | $CH_3$ | — | O | H | $OCH_3$ | $CH_3$ | CH | |
| $CF_3$ | O | — | Q-3 | $CH_3$ | — | $CH_3$ | — | O | H | $OCH_3$ | $OCH_3$ | CH | |
| $CF_3$ | O | — | Q-3 | $CH_3$ | — | $CH_3$ | — | O | H | $OCH_3$ | $CH_3$ | N | |
| $CF_3$ | O | — | Q-3 | $CH_3$ | — | $CH_3$ | — | O | H | $OCH_3$ | $OCH_3$ | N | |
| $OCF_2H$ | O | — | Q-2 | $CH_3$ | $CH_3$ | — | — | O | H | $OCH_3$ | $CH_3$ | CH | |
| $OCF_2H$ | O | — | Q-2 | $CH_3$ | $CH_3$ | — | — | O | H | $OCH_3$ | $OCH_3$ | CH | |
| $OCF_2H$ | O | — | Q-2 | $CH_3$ | $CH_3$ | — | — | O | H | $OCH_3$ | $OCH_3$ | N | |
| Cl | O | — | Q-3 | $CH_3$ | — | $OCH_3$ | — | O | H | $OCH_3$ | $CH_3$ | CH | |
| Cl | O | — | Q-3 | $CH_3$ | — | $OCH_3$ | — | O | H | $OCH_3$ | $OCH_3$ | CH | |
| Cl | O | — | Q-3 | $CH_3$ | — | $OCH_3$ | — | O | H | $OCH_3$ | $OCH_3$ | N | |
| Cl | O | — | Q-3 | $CH_3$ | — | $OCH_3$ | — | O | H | $OCH_3$ | $CH_3$ | N | |
| Br | O | — | Q-3 | $CH_3$ | — | $OCH_3$ | — | O | H | $OCH_3$ | $CH_3$ | CH | |
| Br | O | — | Q-3 | $CH_3$ | — | $OCH_3$ | — | O | H | $OCH_3$ | $OCH_3$ | CH | |
| Br | O | — | Q-3 | $CH_3$ | — | $OCH_3$ | — | O | H | $OCH_3$ | $OCH_3$ | N | |
| F | O | — | Q-3 | $CH_3$ | — | $OCH_3$ | — | O | H | $OCH_3$ | $OCH_3$ | N | |
| F | O | — | Q-3 | $CH_3$ | — | $OCH_3$ | — | O | H | $OCH_3$ | $OCH_3$ | CH | |
| F | O | — | Q-3 | $CH_3$ | — | $OCH_3$ | — | O | H | $OCH_3$ | $CH_3$ | CH | |
| $OCH_3$ | O | — | Q-3 | $CH_3$ | — | $OCH_3$ | — | O | H | $OCH_3$ | $CH_3$ | CH | |
| $OCH_3$ | O | — | Q-3 | $CH_3$ | — | $OCH_3$ | — | O | H | $OCH_3$ | $OCH_3$ | CH | |
| $OCH_3$ | O | — | Q-3 | $CH_3$ | — | $OCH_3$ | — | O | H | $OCH_3$ | $OCH_3$ | N | |
| $OCH_3$ | O | — | Q-3 | $CH_3$ | — | $OCH_3$ | — | O | H | $OCH_3$ | $CH_3$ | N | |
| $CF_3$ | O | — | Q-3 | $CH_3$ | — | $OCH_3$ | — | O | H | $OCH_3$ | $CH_3$ | CH | |
| $CF_3$ | O | — | Q-3 | $CH_3$ | — | $OCH_3$ | — | O | H | $OCH_3$ | $OCH_3$ | CH | |
| $CF_3$ | O | — | Q-3 | $CH_3$ | — | $OCH_3$ | — | O | H | $OCH_3$ | $CH_3$ | N | |
| $CF_3$ | O | — | Q-3 | $CH_3$ | — | $OCH_3$ | — | O | H | $OCH_3$ | $OCH_3$ | N | |
| Cl | O | — | Q-3 | $CH_3$ | — | $SCH_3$ | — | O | H | $OCH_3$ | $CH_3$ | CH | |
| Cl | O | — | Q-3 | $CH_3$ | — | $SCH_3$ | — | O | H | $OCH_3$ | $OCH_3$ | CH | |
| Cl | O | — | Q-3 | $CH_3$ | — | $SCH_3$ | — | O | H | $OCH_3$ | $OCH_3$ | N | |
| Br | O | — | Q-3 | $CH_3$ | — | $SCH_3$ | — | O | H | $OCH_3$ | $OCH_3$ | CH | |
| Br | O | — | Q-3 | $CH_3$ | — | $SCH_3$ | — | O | H | $OCH_3$ | $CH_3$ | CH | |
| F | O | — | Q-3 | $CH_3$ | — | $SCH_3$ | — | O | H | $OCH_3$ | $OCH_3$ | N | |
| F | O | — | Q-3 | $CH_3$ | — | $SCH_3$ | — | O | H | $OCH_3$ | $CH_3$ | CH | |
| $OCH_3$ | O | — | Q-3 | $CH_3$ | — | $SCH_3$ | — | O | H | $OCH_3$ | $OCH_3$ | N | |
| $OCH_3$ | O | — | Q-3 | $CH_3$ | — | $SCH_3$ | — | O | H | $OCH_3$ | $CH_3$ | CH | |
| $OCH_3$ | O | — | Q-3 | $CH_3$ | — | $SCH_3$ | — | O | H | $OCH_3$ | $OCH_3$ | CH | |
| $CH_3$ | O | — | Q-1 | $CH_3$ | $CH_3$ | — | — | O | H | $CH_3$ | $CH_3$ | CH | |
| $CH_3$ | O | — | Q-1 | $CH_3$ | $CH_3$ | — | — | O | H | $OCH_3$ | $CH_3$ | CH | |
| $CH_3$ | O | — | Q-1 | $CH_3$ | $CH_3$ | — | — | O | H | $OCH_3$ | $OCH_3$ | CH | |
| $CH_3$ | O | — | Q-1 | $CH_3$ | $CH_3$ | — | — | O | H | Cl | $OCH_3$ | CH | |
| $CH_3$ | O | — | Q-1 | $CH_3$ | $CH_3$ | — | — | O | H | $OCH_3$ | $CH_3$ | N | |
| $CH_3$ | O | — | Q-1 | $CH_3$ | $CH_3$ | — | — | O | H | $OCH_3$ | $OCH_3$ | N | |
| $CH_3$ | O | — | Q-3 | $CH_3$ | — | $OCH_3$ | — | O | H | $OCH_3$ | $CH_3$ | CH | |
| $CH_3$ | O | — | Q-3 | $CH_3$ | — | $OCH_3$ | — | O | H | $OCH_3$ | $OCH_3$ | CH | |
| $CH_3$ | O | — | Q-3 | $CH_3$ | — | $OCH_3$ | — | O | H | Cl | $OCH_3$ | CH | |
| $CH_3$ | O | — | Q-3 | $CH_3$ | — | $OCH_3$ | — | O | H | $OCH_3$ | $CH_3$ | N | |
| $CH_3$ | O | — | Q-3 | $CH_3$ | — | $OCH_3$ | — | O | H | $OCH_3$ | $OCH_3$ | N | |
| Cl | O | — | Q-2 | $CH_3$ | $CH_3$ | — | — | O | $CH_3$ | $OCH_3$ | $OCH_3$ | CH | |

TABLE XII-continued

General Structure 12

| $R_1$ | n | E | Q | $R_2$ | $R_3$ | $R_4$ | $R_5$ | W | R | X | Y | Z | m.p. (°C.) |
|---|---|---|---|---|---|---|---|---|---|---|---|---|---|
| Br | O | — | Q-2 | $CH_3$ | $CH_3$ | — | — | O | $CH_3$ | $OCH_3$ | $OCH_3$ | CH | |
| F | O | — | Q-2 | $CH_3$ | $CH_3$ | — | — | O | $CH_3$ | $OCH_3$ | $OCH_3$ | CH | |
| Cl | O | — | Q-5 | $CH_3$ | — | — | $CH_3$ | O | H | $CH_3$ | $OCH_3$ | CH | |
| Cl | O | — | Q-5 | $CH_3$ | — | — | $CH_3$ | O | H | $OCH_3$ | $OCH_3$ | CH | |
| Br | O | — | Q-5 | $CH_3$ | — | — | $CH_3$ | O | H | $OCH_3$ | $CH_3$ | CH | |
| Br | O | — | Q-5 | $CH_3$ | — | — | $CH_3$ | O | H | $OCH_3$ | $OCH_3$ | CH | |
| F | O | — | Q-5 | $CH_3$ | — | — | $CH_3$ | O | H | $OCH_3$ | $OCH_3$ | CH | |
| F | O | — | Q-5 | $CH_3$ | — | — | $CH_3$ | O | H | $CH_3$ | $OCH_3$ | CH | |
| $OCH_3$ | O | — | Q-5 | $CH_3$ | — | — | $CH_3$ | O | H | $CH_3$ | $OCH_3$ | CH | |
| $OCH_3$ | O | — | Q-5 | $CH_3$ | — | — | $CH_3$ | O | H | $OCH_3$ | $OCH_3$ | CH | |
| $OCH_3$ | O | — | Q-5 | $CH_3$ | — | — | $CH_3$ | O | H | $OCH_3$ | $OCH_3$ | N | |
| Cl | O | — | Q-5 | $CH_3$ | — | — | $CH_3$ | O | H | $OCH_3$ | $CH_3$ | N | |
| Cl | O | — | Q-5 | $CH_3$ | — | — | $CH_3$ | O | H | $OCH_3$ | $OCH_3$ | N | |
| $CH_3$ | O | — | Q-2 | $CH_3$ | $CH_3$ | — | — | O | H | $CH_3$ | $CH_3$ | CH | 213-216 |
| $CH_3$ | O | — | Q-2 | $CH_3$ | $CH_3$ | — | — | O | H | $CH_3$ | $OCH_3$ | CH | 186-189 |
| $CH_3$ | O | — | Q-2 | $CH_3$ | $CH_3$ | — | — | O | H | $OCH_3$ | $OCH_3$ | CH | 207-208 |
| $CH_3$ | O | — | Q-2 | $CH_3$ | $CH_3$ | — | — | O | H | Cl | $OCH_3$ | CH | 170-173 |
| $CH_3$ | O | — | Q-2 | $CH_3$ | $CH_3$ | — | — | O | H | $OC_2H_5$ | $NHCH_3$ | N | 186-191 |
| $CH_3$ | O | — | Q-2 | $CH_3$ | $CH_3$ | — | — | O | H | $CH_3$ | $OCH_3$ | N | 141-144 |
| $CH_3$ | O | — | Q-2 | $CH_3$ | $CH_3$ | — | — | O | H | $OCH_3$ | $OCH_3$ | N | 191-193 |
| H | O | — | Q-2 | $CH_3$ | $CH_3$ | — | — | O | H | $OC_2H_5$ | $NHCH_3$ | N | 179-183 |
| H | O | — | Q-1 | $CH_3$ | $CH_3$ | — | — | O | H | $OCH_3$ | $OCH_3$ | CH | 165-167 |

TABLE XIII

General Structure 13

| $R_1$ | n | E | Q | $R_2$ | $R_3$ | $R_4$ | $R_5$ | W | R | X | Y | Z | m.p. (°C.) |
|---|---|---|---|---|---|---|---|---|---|---|---|---|---|
| H | O | — | Q-1 | $C_6H_5$ | $CH_3$ | — | — | O | H | $CH_3$ | $CH_3$ | CH | |
| H | O | — | Q-1 | $C_6H_5$ | $CH_3$ | — | — | O | H | $OCH_3$ | $CH_3$ | CH | |
| H | O | — | Q-1 | $C_6H_5$ | $CH_3$ | — | — | O | H | Cl | $OCH_3$ | CH | |
| H | O | — | Q-1 | $C_6H_5$ | $CH_3$ | — | — | O | H | $CH_3$ | $OCH_3$ | N | |
| H | O | — | Q-1 | $C_6H_5$ | $CH_3$ | — | — | O | H | $OCH_3$ | $OCH_3$ | N | |
| H | O | — | Q-1 | $C_6H_5$ | $C_2H_5$ | — | — | O | H | $OCH_3$ | $CH_3$ | CH | |
| H | O | — | Q-1 | $C_6H_5$ | $C_2H_5$ | — | — | O | H | $OCH_3$ | $OCH_3$ | CH | |
| H | O | — | Q-1 | $C_6H_5$ | $C_2H_5$ | — | — | O | H | Cl | $OCH_3$ | CH | |
| H | O | — | Q-1 | $C_6H_5$ | $C_2H_5$ | — | — | O | H | $CH_3$ | $CH_3$ | CH | |
| H | O | — | Q-1 | $C_6H_5$ | $C_2H_5$ | — | — | O | H | $CH_3$ | $OCH_3$ | N | |
| H | O | — | Q-2 | $C_6H_5$ | $CH_3$ | — | — | O | H | $OCH_3$ | $OCH_3$ | N | |
| H | O | — | Q-2 | $C_6H_5$ | $CH_3$ | — | — | O | H | $OCH_3$ | $OCH_3$ | CH | |
| H | O | — | Q-2 | $C_6H_5$ | $CH_3$ | — | — | O | H | $OCH_3$ | $CH_3$ | CH | |
| H | O | — | Q-2 | $C_6H_5$ | $CH_3$ | — | — | O | H | Cl | $OCH_3$ | CH | |
| H | O | — | Q-2 | $C_6H_5$ | $CH_3$ | — | — | O | H | $CH_3$ | $CH_3$ | CH | |
| H | O | — | Q-2 | $C_6H_5$ | $CH_3$ | — | — | O | H | $OCH_3$ | $CH_3$ | N | |
| H | O | — | Q-2 | $C_6H_5$ | $C_2H_5$ | — | — | O | H | $OCH_3$ | $OCH_3$ | N | |
| H | O | — | Q-2 | C $H_5$ | $C_2H_5$ | — | — | O | H | $CH_3$ | $CH_3$ | CH | |
| H | O | — | Q-2 | $C_6H_5$ | $C_2H_5$ | — | — | O | H | $CH_3$ | $OCH_3$ | CH | |
| H | O | — | Q-2 | $C_6H_5$ | $C_2H_5$ | — | — | O | H | Cl | $OCH_3$ | CH | |
| H | O | — | Q-2 | $C_6H_5$ | $C_2H_5$ | — | — | O | H | $CH_3$ | $OCH_3$ | N | |
| H | O | — | Q-2 | $C_6H_5$ | $C_2H_5$ | — | — | O | H | $OCH_3$ | $OCH_3$ | N | |
| H | O | — | Q-3 | $C_6H_5$ | — | $CH_3$ | — | O | H | $CH_3$ | $OCH_3$ | CH | |
| H | O | — | Q-3 | $C_6H_5$ | — | $CH_3$ | — | O | H | Cl | $OCH_3$ | CH | |
| H | O | — | Q-3 | $C_6H_5$ | — | $CH_3$ | — | O | H | $OCH_3$ | $OCH_3$ | CH | |
| H | O | — | Q-3 | $C_6H_5$ | — | $CH_3$ | — | O | H | $OCH_3$ | $OCH_3$ | N | |
| H | O | — | Q-3 | $C_6H_5$ | — | $CH_3$ | — | O | H | $CH_3$ | $OCH_3$ | N | |
| H | O | — | Q-3 | $C_6H_5$ | — | $C_2H_5$ | — | O | H | $CH_3$ | $CH_3$ | CH | |
| H | O | — | Q-3 | $C_6H_5$ | — | $C_2H_5$ | — | O | H | $CH_3$ | $OCH_3$ | CH | |
| H | O | — | Q-3 | $C_6H_5$ | — | $C_2H_5$ | — | O | H | Cl | $OCH_3$ | CH | |
| H | O | — | Q-3 | $C_6H_5$ | — | $C_2H_5$ | — | O | H | $OCH_3$ | $OCH_3$ | CH | |
| H | O | — | Q-3 | $C_6H_5$ | — | $C_2H_5$ | — | O | H | $CH_3$ | $OCH_3$ | N | |
| H | O | — | Q-3 | $C_6H_5$ | — | $CH_2Cl$ | — | O | H | $CH_3$ | $OCH_3$ | CH | |
| H | O | — | Q-3 | $C_6H_5$ | — | $CH_2Cl$ | — | O | H | $OCH_3$ | $OCH_3$ | CH | |
| H | O | — | Q-3 | $C_6H_5$ | — | $CH_2Cl$ | — | O | H | Cl | $OCH_3$ | CH | |
| H | O | — | Q-3 | $C_6H_5$ | — | $CH_2Cl$ | — | O | H | $CH_3$ | $OCH_3$ | N | |
| H | O | — | Q-3 | $C_6H_5$ | — | $CH_2Cl$ | — | O | H | $OCH_3$ | $OCH_3$ | N | |
| H | O | — | Q-3 | $C_6H_5$ | — | $CF_3$ | — | O | H | $CH_3$ | $CH_3$ | CH | |
| H | O | — | Q-3 | $C_6H_5$ | — | $CF_3$ | — | O | H | $OCH_3$ | $OCH_3$ | CH | |
| H | O | — | Q-3 | $C_6H_5$ | — | $CF_3$ | — | O | H | $OCH_3$ | $CH_3$ | CH | |
| H | O | — | Q-3 | $C_6H_5$ | — | $CF_3$ | — | O | H | $CH_3$ | $OCH_3$ | N | |
| H | O | — | Q-3 | $C_6H_5$ | — | $CH(CH_3)_2$ | — | O | H | $CH_3$ | $OCH_3$ | CH | |
| H | O | — | Q-3 | $C_6H_5$ | — | $CH(CH_3)_2$ | — | O | H | $OCH_3$ | $OCH_3$ | CH | |
| H | O | — | Q-3 | $C_6H_5$ | — | $CH(CH_3)_2$ | — | O | H | Cl | $OCH_3$ | CH | |
| H | O | — | Q-3 | $C_6H_5$ | — | $CH(CH_3)_2$ | — | O | H | $CH_3$ | $OCH_3$ | N | |
| H | O | — | Q-3 | $C_6H_5$ | — | $OCH_3$ | — | O | H | $OCH_3$ | $OCH_3$ | CH | |
| H | O | — | Q-3 | $C_6H_5$ | — | $OCH_3$ | — | O | H | $CH_3$ | $OCH_3$ | CH | |
| H | O | — | Q-3 | $C_6H_5$ | — | $OCH_3$ | — | O | H | Cl | $CH_3$ | CH | |
| H | O | — | Q-3 | $C_6H_5$ | — | $OCH_3$ | — | O | H | $OCH_3$ | $OCH_3$ | N | |
| H | O | — | Q-3 | $C_6H_5$ | — | $SCH_3$ | — | O | H | $CH_3$ | $OCH_3$ | CH | |
| H | O | — | Q-3 | $C_6H_5$ | — | $SCH_3$ | — | O | H | $OCH_3$ | $OCH_3$ | CH | |

TABLE XIII-continued

General Structure 13

| R1 | n | E | Q | R2 | R3 | R4 | R5 | W | R | X | Y | Z | m.p. (°C.) |
|---|---|---|---|---|---|---|---|---|---|---|---|---|---|
| H | O | — | Q-3 | $C_6H_5$ | — | $SCH_3$ | — | O | H | $OCH_3$ | $OCH_3$ | N | |
| H | O | — | Q-3 | $C_6H_5$ | — | $SCH_3$ | — | O | H | $CH_3$ | $OCH_3$ | N | |
| H | O | — | Q-3 | $C_6H_5$ | — | $N(CH_3)_2$ | — | O | H | $CH_3$ | $CH_3$ | CH | |
| H | O | — | Q-3 | $C_6H_5$ | — | $N(CH_3)_2$ | — | O | H | $OCH_3$ | $OCH_3$ | CH | |
| H | O | — | Q-3 | $C_6H_5$ | — | $N(CH_3)_2$ | — | O | H | $OCH_3$ | $CH_3$ | N | |
| H | O | — | Q-5 | $C_6H_5$ | — | — | $CH_3$ | O | H | $OCH_3$ | $CH_3$ | N | |
| Cl | O | — | Q-2 | $CH_3$ | $CH_3$ | — | — | O | H | $CH_3$ | $CH_3$ | CH | |
| Cl | O | — | Q-2 | $CH_3$ | $CH_3$ | — | — | O | H | $CH_3$ | $OCH_3$ | CH | |
| Cl | O | — | Q-2 | $CH_3$ | $CH_3$ | — | — | O | H | $OCH_3$ | $OCH_3$ | CH | |
| Cl | O | — | Q-2 | $CH_3$ | $CH_3$ | — | — | O | H | Cl | $OCH_3$ | CH | |
| Cl | O | — | Q-2 | $CH_3$ | $CH_3$ | — | — | O | H | $CH_3$ | $OCH_3$ | N | |
| Cl | O | — | Q-2 | $CH_3$ | $CH_3$ | — | — | O | H | $OCH_3$ | $OCH_3$ | N | |
| Cl | O | — | Q-2 | $CH_3$ | $CH_3$ | — | — | O | $CH_3$ | $OCH_3$ | $CH_3$ | N | |
| Cl | O | — | Q-2 | $CH_3$ | $CH_2CH_3$ | — | — | O | H | $CH_3$ | $CH_3$ | CH | |
| Cl | O | — | Q-2 | $CH_3$ | $CH_2CH_3$ | — | — | O | H | $CH_3$ | $OCH_3$ | CH | |
| Cl | O | — | Q-2 | $CH_3$ | $CH_2CH_3$ | — | — | O | H | $OCH_3$ | $OCH_3$ | CH | |
| Cl | O | — | Q-2 | $CH_3$ | $CH_2CH_3$ | — | — | O | H | Cl | $OCH_3$ | CH | |
| Cl | O | — | Q-2 | $CH_3$ | $CH_2CH_3$ | — | — | O | H | $OCH_3$ | $CH_3$ | N | |
| Cl | O | — | Q-2 | $CH_3$ | $CH_2CH_3$ | — | — | O | H | $OCH_3$ | $OCH_3$ | N | |
| H | O | — | Q-2 | $CH_2CH_3$ | $CH_3$ | — | — | O | H | $CH_3$ | $CH_3$ | CH | |
| H | O | — | Q-2 | $CH_2CH_3$ | $CH_3$ | — | — | O | H | $CH_3$ | $OCH_3$ | CH | |
| H | O | — | Q-2 | $CH_2CH_3$ | $CH_3$ | — | — | O | H | $OCH_3$ | $OCH_3$ | CH | |
| H | O | — | Q-2 | $CH_2CH_3$ | $CH_3$ | — | — | O | H | Cl | $OCH_3$ | CH | |
| H | O | — | Q-2 | $CH_2CH_3$ | $CH_3$ | — | — | O | H | $OCH_3$ | $CH_3$ | N | |
| H | O | — | Q-2 | $CH_2CH_3$ | $CH_3$ | — | — | O | H | $OCH_3$ | $OCH_3$ | N | |
| Cl | O | — | Q-1 | $CH_3$ | $CH_3$ | — | — | O | H | $OCH_3$ | $CH_3$ | CH | |
| Cl | O | — | Q-1 | $CH_3$ | $CH_3$ | — | — | O | H | $OCH_3$ | $OCH_3$ | CH | |
| Cl | O | — | Q-1 | $CH_3$ | $CH_3$ | — | — | O | H | $OCH_3$ | $CH_3$ | N | |
| Cl | O | — | Q-1 | $CH_3$ | $CH_3$ | — | — | O | H | $OCH_3$ | $OCH_3$ | N | |
| Cl | O | — | Q-3 | $CH_3$ | — | $CH_3$ | — | O | H | $CH_3$ | $CH_3$ | CH | |
| Cl | O | — | Q-3 | $CH_3$ | — | $CH_3$ | — | O | H | $OCH_3$ | $CH_3$ | CH | |
| Cl | O | — | Q-3 | $CH_3$ | — | $CH_3$ | — | O | H | $OCH_3$ | $OCH_3$ | CH | |
| Cl | O | — | Q-3 | $CH_3$ | — | $CH_3$ | — | O | H | Cl | $OCH_3$ | CH | |
| Cl | O | — | Q-3 | $CH_3$ | — | $CH_3$ | — | O | H | $OCH_3$ | $CH_3$ | N | |
| Cl | O | — | Q-3 | $CH_3$ | — | $CH_3$ | — | O | H | $OCH_3$ | $OCH_3$ | N | |
| Br | O | — | Q-2 | $CH_3$ | $CH_3$ | — | — | O | H | $CH_3$ | $OCH_3$ | CH | |
| Br | O | — | Q-2 | $CH_3$ | $CH_3$ | — | — | O | H | $OCH_3$ | $OCH_3$ | CH | |
| Br | O | — | Q-2 | $CH_3$ | $CH_3$ | — | — | O | H | Cl | $OCH_3$ | CH | |
| Br | O | — | Q-2 | $CH_3$ | $CH_3$ | — | — | O | H | $OCH_3$ | $CH_3$ | N | |
| Br | O | — | Q-2 | $CH_3$ | $CH_3$ | — | — | O | H | $OCH_3$ | $OCH_3$ | N | |
| Br | O | — | Q-2 | $CH_3$ | $CH_2CH_3$ | — | — | O | H | $CH_3$ | $OCH_3$ | CH | |
| Br | O | — | Q-2 | $CH_3$ | $CH_2CH_3$ | — | — | O | H | $OCH_3$ | $OCH_3$ | CH | |
| Br | O | — | Q-2 | $CH_3$ | $CH_2CH_3$ | — | — | O | H | Cl | $OCH_3$ | CH | |
| Br | O | — | Q-2 | $CH_3$ | $CH_2CH_3$ | — | — | O | H | $OCH_3$ | $OCH_3$ | N | |
| Br | O | — | Q-2 | $CH_3$ | $CH_2CH_3$ | — | — | O | H | $OCH_3$ | $CH_3$ | N | |
| Br | O | — | Q-1 | $CH_3$ | $CH_3$ | — | — | O | H | $OCH_3$ | $CH_3$ | CH | |
| Br | O | — | Q-1 | $CH_3$ | $CH_3$ | — | — | O | H | $OCH_3$ | $OCH_3$ | CH | |
| Br | O | — | Q-1 | $CH_3$ | $CH_3$ | — | — | O | H | $OCH_3$ | $OCH_3$ | N | |
| Br | O | — | Q-1 | $CH_3$ | $CH_3$ | — | — | O | H | $OCH_3$ | $CH_3$ | N | |
| Br | O | — | Q-4 | $CH_3$ | — | $CH_3$ | — | O | H | $OCH_3$ | $CH_3$ | CH | |
| Br | O | — | Q-4 | $CH_3$ | — | $CH_3$ | — | O | H | $OCH_3$ | $OCH_3$ | CH | |
| Br | O | — | Q-4 | $CH_3$ | — | $CH_3$ | — | O | H | $OCH_3$ | $OCH_3$ | N | |
| Br | O | — | Q-4 | $CH_3$ | — | $CH_3$ | — | O | H | $OCH_3$ | $CH_3$ | N | |
| F | O | — | Q-2 | $CH_3$ | $CH_3$ | — | — | O | H | $OCH_3$ | $CH_3$ | CH | |
| F | O | — | Q-2 | $CH_3$ | $CH_3$ | — | — | O | H | $OCH_3$ | $OCH_3$ | CH | |
| F | O | — | Q-2 | $CH_3$ | $CH_3$ | — | — | O | H | $OCH_3$ | $CH_3$ | N | |
| F | O | — | Q-2 | $CH_3$ | $CH_3$ | — | — | O | H | $OCH_3$ | $OCH_3$ | N | |
| F | O | — | Q-2 | $CH_3$ | $CH_3$ | — | — | O | H | Cl | $OCH_3$ | CH | |
| F | O | — | Q-1 | $CH_3$ | $CH_3$ | — | — | O | H | $OCH_3$ | $CH_3$ | CH | |
| F | O | — | Q-1 | $CH_3$ | $CH_3$ | — | — | O | H | $OCH_3$ | $OCH_3$ | CH | |
| F | O | — | Q-1 | $CH_3$ | $CH_3$ | — | — | O | H | $OCH_3$ | $OCH_3$ | N | |
| F | O | — | Q-1 | $CH_3$ | $CH_3$ | — | — | O | H | $OCH_3$ | $CH_3$ | N | |
| F | O | — | Q-3 | $CH_3$ | — | $CH_3$ | — | O | H | $OCH_3$ | $CH_3$ | CH | |
| F | O | — | Q-3 | $CH_3$ | — | $CH_3$ | — | O | H | $OCH_3$ | $OCH_3$ | CH | |
| F | O | — | Q-3 | $CH_3$ | — | $CH_3$ | — | O | H | $OCH_3$ | $CH_3$ | N | |
| F | O | — | Q-3 | $CH_3$ | — | $CH_3$ | — | O | H | $OCH_3$ | $OCH_3$ | N | |
| $OCH_3$ | O | — | Q-2 | $CH_3$ | $CH_3$ | — | — | O | H | $CH_3$ | $OCH_3$ | CH | |
| $OCH_3$ | O | — | Q-2 | $CH_3$ | $CH_3$ | — | — | O | H | $OCH_3$ | $OCH_3$ | CH | |
| $OCH_3$ | O | — | Q-2 | $CH_3$ | $CH_3$ | — | — | O | H | Cl | $OCH_3$ | CH | |
| $OCH_3$ | O | — | Q-2 | $CH_3$ | $CH_3$ | — | — | O | H | $OCH_3$ | $CH_3$ | N | |
| $OCH_3$ | O | — | Q-2 | $CH_3$ | $CH_3$ | — | — | O | H | $OCH_3$ | $OCH_3$ | N | |
| $OCH_3$ | O | — | Q-2 | $CH_3$ | $CH_2CH_3$ | — | — | O | H | $OCH_3$ | $CH_3$ | CH | |
| $OCH_3$ | O | — | Q-2 | $CH_3$ | $CH_2CH_3$ | — | — | O | H | $OCH_3$ | $OCH_3$ | CH | |
| $OCH_3$ | O | — | Q-2 | $CH_3$ | $CH_2CH_3$ | — | — | O | H | $OCH_3$ | $CH_3$ | N | |
| $OCH_3$ | O | — | Q-2 | $CH_3$ | $CH_2CH_3$ | — | — | O | H | $OCH_3$ | $OCH_3$ | N | |
| $OCH_3$ | O | — | Q-1 | $CH_3$ | $CH_3$ | — | — | O | H | $OCH_3$ | $CH_3$ | CH | |
| $OCH_3$ | O | — | Q-1 | $CH_3$ | $CH_3$ | — | — | O | H | $OCH_3$ | $OCH_3$ | CH | |
| $OCH_3$ | O | — | Q-1 | $CH_3$ | $CH_3$ | — | — | O | H | $OCH_3$ | $OCH_3$ | N | |
| $OCH_3$ | O | — | Q-1 | $CH_3$ | $CH_3$ | — | — | O | H | $OCH_3$ | $CH_3$ | CH | |
| $OCH_3$ | O | — | Q-1 | $CH_3$ | $CH_3$ | — | — | O | H | Cl | $OCH_3$ | CH | |

TABLE XIII-continued

General Structure 13

| $R_1$ | n | E | Q | $R_2$ | $R_3$ | $R_4$ | $R_5$ | W | R | X | Y | Z | m.p. (°C.) |
|---|---|---|---|---|---|---|---|---|---|---|---|---|---|
| $OCH_3$ | O | — | Q-1 | $CH_3$ | $CH_2CH_3$ | — | — | O | H | $OCH_3$ | $OCH_3$ | CH | |
| $OCH_3$ | O | — | Q-1 | $CH_3$ | $CH_2CH_3$ | — | — | O | H | $OCH_3$ | $CH_3$ | CH | |
| $OCH_3$ | O | — | Q-1 | $CH_3$ | $CH_2CH_3$ | — | — | O | H | $OCH_3$ | $OCH_3$ | N | |
| $OCH_3$ | O | — | Q-3 | $CH_3$ | — | $CH_3$ | — | O | H | $OCH_3$ | $OCH_3$ | CH | |
| $OCH_3$ | O | — | Q-3 | $CH_3$ | — | $CH_3$ | — | O | H | $OCH_3$ | $CH_3$ | CH | |
| $OCH_3$ | O | — | Q 3 | $CH_3$ | — | $CH_3$ | — | O | H | $OCH_3$ | $CH_3$ | N | |
| $OCH_3$ | O | — | Q-3 | $CH_3$ | — | $CH_3$ | — | O | H | $OCH_3$ | $OCH_3$ | N | |
| $OCH_3$ | O | — | Q-3 | $CH_3$ | — | $CH_3$ | — | O | H | $CH_3$ | $CH_3$ | CH | |
| $CF_3$ | O | — | Q-2 | $CH_3$ | $CH_3$ | — | — | O | H | $CH_3$ | $OCH_3$ | CH | |
| $CF_3$ | O | — | Q-2 | $CH_3$ | $CH_3$ | — | — | O | H | $CH_3$ | $OCH_3$ | N | |
| $CF_3$ | O | — | Q-2 | $CH_3$ | $CH_3$ | — | — | O | H | $OCH_3$ | $OCH_3$ | N | |
| $CF_3$ | O | — | Q-2 | $CH_3$ | $CH_3$ | — | — | O | H | $OCH_3$ | $OCH_3$ | CH | |
| $CF_3$ | O | — | Q-1 | $CH_3$ | $CH_3$ | — | — | O | H | $CH_3$ | $OCH_3$ | CH | |
| $CF_3$ | O | — | Q-1 | $CH_3$ | $CH_3$ | — | — | O | H | $OCH_3$ | $OCH_3$ | CH | |
| $CF_3$ | O | — | Q-1 | $CH_3$ | $CH_3$ | — | — | O | H | $OCH_3$ | $OCH_3$ | N | |
| $CF_3$ | O | — | Q-1 | $CH_3$ | $CH_3$ | — | — | O | H | $OCH_3$ | $CH_3$ | N | |
| $CF_3$ | O | — | Q-3 | $CH_3$ | — | $CH_3$ | — | O | H | $OCH_3$ | $CH_3$ | CH | |
| $CF_3$ | O | — | Q-3 | $CH_3$ | — | $CH_3$ | — | O | H | $OCH_3$ | $OCH_3$ | CH | |
| $CF_3$ | O | — | Q-3 | $CH_3$ | — | $CH_3$ | — | O | H | $OCH_3$ | $CH_3$ | N | |
| $CF_3$ | O | — | Q-3 | $CH_3$ | — | $CH_3$ | — | O | H | $OCH_3$ | $OCH_3$ | N | |
| $OCF_2H$ | O | — | Q-2 | $CH_3$ | $CH_3$ | — | — | O | H | $OCH_3$ | $CH_3$ | CH | |
| $OCF_2H$ | O | — | Q-2 | $CH_3$ | $CH_3$ | — | — | O | H | $OCH_3$ | $OCH_3$ | CH | |
| $OCF_2H$ | O | — | Q-2 | $CH_3$ | $CH_3$ | — | — | O | H | $OCH_3$ | $OCH_3$ | N | |
| Cl | O | — | Q-3 | $CH_3$ | — | $OCH_3$ | — | O | H | $OCH_3$ | $CH_3$ | CH | |
| Cl | O | — | Q-3 | $CH_3$ | — | $OCH_3$ | — | O | H | $OCH_3$ | $OCH_3$ | CH | |
| Cl | O | — | Q-3 | $CH_3$ | — | $OCH_3$ | — | O | H | $OCH_3$ | $OCH_3$ | N | |
| Cl | O | — | Q-3 | $CH_3$ | — | $OCH_3$ | — | O | H | $OCH_3$ | $CH_3$ | N | |
| Br | O | — | Q-3 | $CH_3$ | — | $OCH_3$ | — | O | H | $OCH_3$ | $CH_3$ | CH | |
| Br | O | — | Q-3 | $CH_3$ | — | $OCH_3$ | — | O | H | $OCH_3$ | $OCH_3$ | CH | |
| Br | O | — | Q-3 | $CH_3$ | — | $OCH_3$ | — | O | H | $OCH_3$ | $OCH_3$ | N | |
| F | O | — | Q-3 | $CH_3$ | — | $OCH_3$ | — | O | H | $OCH_3$ | $OCH_3$ | N | |
| F | O | — | Q-3 | $CH_3$ | — | $OCH_3$ | — | O | H | $OCH_3$ | $OCH_3$ | CH | |
| F | O | — | Q-3 | $CH_3$ | — | $OCH_3$ | — | O | H | $OCH_3$ | $CH_3$ | CH | |
| $OCH_3$ | O | — | Q-3 | $CH_3$ | — | $OCH_3$ | — | O | H | $OCH_3$ | $CH_3$ | CH | |
| $OCH_3$ | O | — | Q-3 | $CH_3$ | — | $OCH_3$ | — | O | H | $OCH_3$ | $OCH_3$ | CH | |
| $OCH_3$ | O | — | Q-3 | $CH_3$ | — | $OCH_3$ | — | O | H | $OCH_3$ | $OCH_3$ | N | |
| $OCH_3$ | O | — | Q-3 | $CH_3$ | — | $OCH_3$ | — | O | H | $OCH_3$ | $CH_3$ | N | |
| $CF_3$ | O | — | Q-3 | $CH_3$ | — | $OCH_3$ | — | O | H | $OCH_3$ | $CH_3$ | CH | |
| $CF_3$ | O | — | Q-3 | $CH_3$ | — | $OCH_3$ | — | O | H | $OCH_3$ | $OCH_3$ | CH | |
| $CF_3$ | O | — | Q-3 | $CH_3$ | — | $OCH_3$ | — | O | H | $OCH_3$ | $CH_3$ | N | |
| $CF_3$ | O | — | Q-3 | $CH_3$ | — | $OCH_3$ | — | O | H | $OCH_3$ | $OCH_3$ | N | |
| Cl | O | — | Q-3 | $CH_3$ | — | $SCH_3$ | — | O | H | $OCH_3$ | $CH_3$ | CH | |
| Cl | O | — | Q-3 | $CH_3$ | — | $SCH_3$ | — | O | H | $OCH_3$ | $OCH_3$ | CH | |
| Cl | O | — | Q-3 | $CH_3$ | — | $SCH_3$ | — | O | H | $OCH_3$ | $OCH_3$ | N | |
| Br | O | — | Q-3 | $CH_3$ | — | $SCH_3$ | — | O | H | $OCH_3$ | $OCH_3$ | CH | |
| Br | O | — | Q-3 | $CH_3$ | — | $SCH_3$ | — | O | H | $OCH_3$ | $CH_3$ | CH | |
| F | O | — | Q-3 | $CH_3$ | — | $SCH_3$ | — | O | H | $OCH_3$ | $OCH_3$ | N | |
| F | O | — | Q-3 | $CH_3$ | — | $SCH_3$ | — | O | H | $OCH_3$ | $CH_3$ | CH | |
| $OCH_3$ | O | — | Q-3 | $CH_3$ | — | $SCH_3$ | — | O | H | $OCH_3$ | $OCH_3$ | N | |
| $OCH_3$ | O | — | Q-3 | $CH_3$ | — | $SCH_3$ | — | O | H | $OCH_3$ | $CH_3$ | CH | |
| $OCH_3$ | O | — | Q-3 | $CH_3$ | — | $SCH_3$ | — | O | H | $OCH_3$ | $OCH_3$ | CH | |
| $CH_3$ | O | — | Q-1 | $CH_3$ | $CH_3$ | — | — | O | H | $CH_3$ | $CH_3$ | CH | |
| $CH_3$ | O | — | Q-1 | $CH_3$ | $CH_3$ | — | — | O | H | $OCH_3$ | $CH_3$ | CH | |
| $CH_3$ | O | — | Q-1 | $CH_3$ | $CH_3$ | — | — | O | H | $OHC_3$ | $OCH_3$ | CH | |
| $CH_3$ | O | — | Q-1 | $CH_3$ | $CH_3$ | — | — | O | H | Cl | $OCH_3$ | CH | |
| $CH_3$ | O | — | Q-1 | $CH_3$ | $CH_3$ | — | — | O | H | $OCH_3$ | $CH_3$ | N | |
| $CH_3$ | O | — | Q-1 | $CH_3$ | $CH_3$ | — | — | O | H | $OCH_3$ | $OCH_3$ | N | |
| $CH_3$ | O | — | Q-3 | $CH_3$ | — | $OCH_3$ | — | O | H | $OCH_3$ | $CH_3$ | CH | |
| $CH_3$ | O | — | Q-3 | $CH_3$ | — | $OCH_3$ | — | O | H | $OCH_3$ | $OCH_3$ | CH | |
| $CH_3$ | O | — | Q-3 | $CH_3$ | — | $OCH_3$ | — | O | H | Cl | $OCH_3$ | CH | |
| $CH_3$ | O | — | Q-3 | $CH_3$ | — | $OCH_3$ | — | O | H | $OCH_3$ | $CH_3$ | N | |
| $CH_3$ | O | — | Q-3 | $CH_3$ | — | $OCH_3$ | — | O | H | $OCH_3$ | $OCH_3$ | N | |
| Cl | O | — | Q-2 | $CH_3$ | $CH_3$ | — | — | O | $CH_3$ | $OCH_3$ | $OCH_3$ | CH | |
| Br | O | — | Q-2 | $CH_3$ | $CH_3$ | — | — | O | $CH_3$ | $OCH_3$ | $OCH_3$ | CH | |
| F | O | — | Q-2 | $CH_3$ | $CH_3$ | — | — | O | $CH_3$ | $OCH_3$ | $OCH_3$ | CH | |
| Cl | O | — | Q-5 | $CH_3$ | — | — | $CH_3$ | O | H | $CH_3$ | $OCH_3$ | CH | |
| Cl | O | — | Q-5 | $CH_3$ | — | — | $CH_3$ | O | H | $OCH_3$ | $OCH_3$ | CH | |
| Br | O | — | Q-5 | $CH_3$ | — | — | $CH_3$ | O | H | $OCH_3$ | $CH_3$ | CH | |
| Br | O | — | Q-5 | $CH_3$ | — | — | $CH_3$ | O | H | $OCH_3$ | $OCH_3$ | CH | |
| F | O | — | Q-5 | $CH_3$ | — | — | $CH_3$ | O | H | $OCH_3$ | $OCH_3$ | CH | |
| F | O | — | Q-5 | $CH_3$ | — | — | $CH_3$ | O | H | $CH_3$ | $OCH_3$ | CH | |
| $OCH_3$ | O | — | Q-5 | $CH_3$ | — | — | $CH_3$ | O | H | $CH_3$ | $OCH_3$ | CH | |
| $OCH_3$ | O | — | Q-5 | $CH_3$ | — | — | $CH_3$ | O | H | $OCH_3$ | $OCH_3$ | CH | |
| $OCH_3$ | O | — | Q-5 | $CH_3$ | — | — | $CH_3$ | O | H | $OCH_3$ | $OCH_3$ | N | |
| Cl | O | — | Q 5 | $CH_3$ | — | — | $CH_3$ | O | H | $OCH_3$ | $CH_3$ | N | |
| Cl | O | — | Q-5 | $CH_3$ | — | — | $CH_3$ | O | H | $OCH_3$ | $OCH_3$ | N | |

TABLE XIV

| | | | | | General Structure 14 | | | | | | |
|---|---|---|---|---|---|---|---|---|---|---|---|
| $R_1$ | n | E | Q | $R_3$ | $R_4$ | W | R | X | Y | Z | m.p. (°C.) |
| H | O | — | Q-1 | $CH_3$ | — | O | H | $CH_3$ | $CH_3$ | CH | |
| H | O | — | Q-1 | $CH_3$ | — | O | H | $OCH_3$ | $CH_3$ | CH | |
| H | O | — | Q-1 | $CH_3$ | — | O | H | Cl | $OCH_3$ | CH | |
| H | O | — | Q-1 | $CH_3$ | — | O | H | $CH_3$ | $OCH_3$ | N | |
| H | O | — | Q-1 | $CH_3$ | — | O | H | $OCH_3$ | $OCH_3$ | N | |
| H | O | — | Q-1 | $C_2H_5$ | — | O | H | $OCH_3$ | $CH_3$ | CH | |
| H | O | — | Q-1 | $C_2H_5$ | — | O | H | $OCH_3$ | $OCH_3$ | CH | |
| H | O | — | Q-1 | $C_2H_5$ | — | O | H | Cl | $OCH_3$ | CH | |
| H | O | — | Q-1 | $C_2H_5$ | — | O | H | $CH_3$ | $CH_3$ | CH | |
| H | O | — | Q-1 | $C_2H_5$ | — | O | H | $CH_3$ | $OCH_3$ | N | |
| H | O | — | Q-2 | $CH_3$ | — | O | H | $OCH_3$ | $OCH_3$ | N | |
| H | O | — | Q-2 | $CH_3$ | — | O | H | $OCH_3$ | $OCH_3$ | CH | |
| H | O | — | Q-2 | $CH_3$ | — | O | H | $OCH_3$ | $CH_3$ | CH | |
| H | O | — | Q-2 | $CH_3$ | — | O | H | Cl | $OCH_3$ | CH | |
| H | O | — | Q-2 | $CH_3$ | — | O | H | $CH_3$ | $CH_3$ | CH | |
| H | O | — | Q-2 | $CH_3$ | — | O | H | $OCH_3$ | $CH_3$ | N | |
| H | O | — | Q-2 | $C_2H_5$ | — | O | H | $OCH_3$ | $OCH_3$ | N | |
| H | O | — | Q-2 | $C_2H_5$ | — | O | H | $CH_3$ | $CH_3$ | CH | |
| H | O | — | Q-2 | $C_2H_5$ | — | O | H | $CH_3$ | $OCH_3$ | CH | |
| H | O | — | Q-2 | $C_2H_5$ | — | O | H | Cl | $OCH_3$ | CH | |
| H | O | — | Q-2 | $C_2H_5$ | — | O | H | $CH_3$ | $OCH_3$ | N | |
| H | O | — | Q-2 | $C_2H_5$ | — | O | H | $OCH_3$ | $OCH_3$ | N | |

TABLE XV

| | | | | | | General Structure 15 | | | | | | |
|---|---|---|---|---|---|---|---|---|---|---|---|---|
| $R_1$ | n | E | Q | $R_3$ | $R_4$ | $R_5$ | W | R | X | Y | Z | m.p. (°C.) |
| H | O | — | Q-1 | $CH_3$ | — | — | O | H | $CH_3$ | $CH_3$ | CH | |
| H | O | — | Q-1 | $CH_3$ | — | — | O | H | $OCH_3$ | $CH_3$ | CH | |
| H | O | — | Q-1 | $CH_3$ | — | — | O | H | Cl | $OCH_3$ | CH | |
| H | O | — | Q-1 | $CH_3$ | — | — | O | H | $CH_3$ | $OCH_3$ | N | |
| H | O | — | Q-1 | $CH_3$ | — | — | O | H | $OCH_3$ | $OCH_3$ | N | |
| H | O | — | Q-1 | $C_2H_5$ | — | — | O | H | $OCH_3$ | $CH_3$ | CH | |
| H | O | — | Q-1 | $C_2H_5$ | — | — | O | H | $OCH_3$ | $OCH_3$ | CH | |
| H | O | — | Q-1 | $C_2H_5$ | — | — | O | H | Cl | $OCH_3$ | CH | |
| H | O | — | Q-1 | $C_2H_5$ | — | — | O | H | $CH_3$ | $CH_3$ | CH | |
| H | O | — | Q-1 | $C_2H_5$ | — | — | O | H | $CH_3$ | $OCH_3$ | N | |
| H | O | — | Q-2 | $CH_3$ | — | — | O | H | $OCH_3$ | $OCH_3$ | CH | 138-143 |
| H | O | — | Q-2 | $CH_3$ | — | — | O | H | $OCH_3$ | $CH_3$ | CH | 155-159 |
| H | O | — | Q-2 | $CH_3$ | — | — | O | H | Cl | $OCH_3$ | CH | 157-158 |
| H | O | — | Q-2 | $CH_3$ | — | — | O | H | $CH_3$ | $CH_3$ | CH | 135-140 |
| H | O | — | Q-2 | $CH_3$ | — | — | O | H | $OCH_3$ | $CH_3$ | N | |
| H | O | — | Q-2 | $CH_3$ | — | — | O | H | $OCH_3$ | $OCH_3$ | N | 75-78 |
| H | O | — | Q-2 | $C_2H_5$ | — | — | O | H | $CH_3$ | $CH_3$ | CH | |
| H | O | — | Q-2 | $C_2H_5$ | — | — | O | H | $CH_3$ | $OCH_3$ | CH | |
| H | O | — | Q-2 | $C_2H_5$ | — | — | O | H | Cl | $OCH_3$ | CH | |
| H | O | — | Q-2 | $C_2H_5$ | — | — | O | H | $CH_3$ | $OCH_3$ | N | |
| H | O | — | Q-2 | $C_2H_5$ | — | — | O | H | $OCH_3$ | $OCH_3$ | N | |
| H | O | — | Q-3 | — | $CH_3$ | — | O | H | $CH_3$ | $OCH_3$ | CH | |
| H | O | — | Q-3 | — | $CH_3$ | — | O | H | Cl | $OCH_3$ | CH | |
| H | O | — | Q-3 | — | $CH_3$ | — | O | H | $OCH_3$ | $OCH_3$ | CH | |
| H | O | — | Q-3 | — | $CH_3$ | — | O | H | $OCH_3$ | $OCH_3$ | N | |
| H | O | — | Q-3 | — | $CH_3$ | — | O | H | $CH_3$ | $OCH_3$ | N | |
| H | O | — | Q-3 | — | $C_2H_5$ | — | O | H | $CH_3$ | $CH_3$ | CH | |
| H | O | — | Q-3 | — | $C_2H_5$ | — | O | H | $CH_3$ | $OCH_3$ | CH | |
| H | O | — | Q-3 | — | $C_2H_5$ | — | O | H | Cl | $OCH_3$ | CH | |
| H | O | — | Q-3 | — | $C_2H_5$ | — | O | H | $OCH_3$ | $OCH_3$ | CH | |
| H | O | — | Q-3 | — | $C_2H_5$ | — | O | H | $CH_3$ | $OCH_3$ | N | |
| H | O | — | Q-3 | — | $CH_2Cl$ | — | O | H | $CH_3$ | $OCH_3$ | CH | |
| H | O | — | Q-3 | — | $CH_2Cl$ | — | O | H | $OCH_3$ | $OCH_3$ | CH | |
| H | O | — | Q-3 | — | $CH_2Cl$ | — | O | H | Cl | $OCH_3$ | CH | |
| H | O | — | Q-3 | — | $CH_2Cl$ | — | O | H | $CH_3$ | $OCH_3$ | N | |
| H | O | — | Q-3 | — | $CH_2Cl$ | — | O | H | $OCH_3$ | $OCH_3$ | N | |
| H | O | — | Q-3 | — | $CF_3$ | — | O | H | $CH_3$ | $CH_3$ | CH | |
| H | O | — | Q-3 | — | $CF_3$ | — | O | H | $OCH_3$ | $OCH_3$ | CH | |
| H | O | — | Q-3 | — | $CF_3$ | — | O | H | $OCH_3$ | $CH_3$ | CH | |
| H | O | — | Q-3 | — | $CF_3$ | — | O | H | $CH_3$ | $OCH_3$ | N | |
| H | O | — | Q-3 | — | $CH(CH_3)_2$ | — | O | H | $CH_3$ | $OCH_3$ | CH | |
| H | O | — | Q-3 | — | $CH(CH_3)_2$ | — | O | H | $OCH_3$ | $OCH_3$ | CH | |
| H | O | — | Q-3 | — | $CH(CH_3)_2$ | — | O | H | Cl | $OCH_3$ | CH | |
| H | O | — | Q-3 | — | $CH(CH_3)_2$ | — | O | H | $CH_3$ | $OCH_3$ | N | |
| H | O | — | Q-3 | — | $OCH_3$ | — | O | H | $OCH_3$ | $OCH_3$ | CH | |
| H | O | — | Q-3 | — | $OCH_3$ | — | O | H | $CH_3$ | $OCH_3$ | CH | |
| H | O | — | Q-3 | — | $OCH_3$ | — | O | H | Cl | $OCH_3$ | CH | |
| H | O | — | Q-3 | — | $OCH_3$ | — | O | H | $OCH_3$ | $OCH_3$ | N | |
| H | O | — | Q-3 | — | $SCH_3$ | — | O | H | $CH_3$ | $OCH_3$ | CH | |
| H | O | — | Q-3 | — | $SCH_3$ | — | O | H | $OCH_3$ | $OCH_3$ | CH | |
| H | O | — | Q-3 | — | $SCH_3$ | — | O | H | $OCH_3$ | $OCH_3$ | N | |

TABLE XV-continued

General Structure 15

| R1 | n | E | Q | R3 | R4 | R5 | W | R | X | Y | Z | m.p. (°C.) |
|---|---|---|---|---|---|---|---|---|---|---|---|---|
| H | O | — | Q-3 | — | $SCH_3$ | — | O | H | $CH_3$ | $OCH_3$ | N | |
| H | O | — | Q-3 | — | $N(CH_2)_2$ | — | O | H | $CH_3$ | $CH_3$ | CH | |
| H | O | — | Q-3 | — | $N(CH_2)_2$ | — | O | H | $OCH_3$ | $OCH_3$ | CH | |
| H | O | — | Q-3 | — | $N(CH_2)_2$ | — | O | H | $OCH_3$ | $CH_3$ | N | |
| H | O | — | Q-4 | — | $CH_3$ | — | O | H | $OCH_3$ | $CH_3$ | N | |
| H | O | — | Q-4 | — | $CH_3$ | — | O | H | $OCH_3$ | $CH_3$ | CH | |
| H | O | — | Q-4 | — | $CH_3$ | — | O | H | $OCH_3$ | $OCH_3$ | CH | |
| H | O | — | Q-4 | — | $CH_3$ | — | O | H | Cl | $OCH_3$ | CH | |
| H | O | — | Q-4 | — | $CH_3$ | — | O | H | $CH_3$ | $CH_3$ | CH | |
| H | O | — | Q-5 | — | — | $CH_3$ | O | H | $CH_3$ | $CH_3$ | CH | |
| H | O | — | Q-5 | — | — | $CH_3$ | O | H | $OCH_3$ | $CH_3$ | CH | |
| H | O | — | Q-5 | — | — | $CH_3$ | O | H | $OCH_3$ | $OCH_3$ | CH | |
| H | O | — | Q-5 | — | — | $CH_3$ | O | H | Cl | $OCH_3$ | CH | |
| H | O | — | Q-1 | $CH_3$ | — | — | O | H | $OCH_3$ | $OCH_3$ | CH | |
| H | O | — | Q-1 | $C_2H_5$ | — | — | O | H | $OCH_3$ | $OCH_3$ | N | |
| H | O | — | Q-2 | $C_2H_5$ | — | — | O | H | $OCH_3$ | $OCH_3$ | CH | |
| H | O | — | Q-3 | — | H | — | O | H | $OCH_3$ | $OCH_3$ | CH | |
| H | O | — | Q-3 | — | H | — | O | H | $CH_3$ | $OCH_3$ | CH | |
| H | O | — | Q-3 | — | H | — | O | H | $CH_3$ | $CH_3$ | CH | |
| H | O | — | Q-3 | — | H | — | O | H | Cl | $OCH_3$ | CH | |
| H | O | — | Q-3 | — | H | — | O | H | $OCH_3$ | $OCH_3$ | N | |
| H | O | — | Q-3 | — | H | — | O | H | $CH_3$ | $OCH_3$ | N | |
| H | O | — | Q-3 | — | $CH_3$ | — | O | H | $CH_3$ | $CH_3$ | CH | |
| H | O | — | Q-3 | — | $C_2H_5$ | — | O | H | $OCH_3$ | $OCH_3$ | N | |
| H | O | — | Q-3 | — | $CH_2Cl$ | — | O | H | $CH_3$ | $CH_3$ | CH | |
| H | O | — | Q-3 | — | $CF_3$ | — | O | H | Cl | $OCH_3$ | CH | |
| H | O | — | Q-3 | — | $CF_3$ | — | O | H | $OCH_3$ | $OCH_3$ | N | |
| H | O | — | Q-3 | — | $CH(CH_3)_2$ | — | O | H | $CH_3$ | $CH_3$ | CH | |
| H | O | — | Q-3 | — | $CH(CH_3)_2$ | — | O | H | $OCH_3$ | $OCH_3$ | N | |
| H | O | — | Q-3 | — | $OCH_3$ | — | O | H | $CH_3$ | $CH_3$ | CH | |
| H | O | — | Q-3 | — | $OCH_3$ | — | O | H | $CH_3$ | $OCH_3$ | N | |
| H | O | — | Q-3 | — | $OC_2H_5$ | — | O | H | $OCH_3$ | $OCH_3$ | CH | |
| H | O | — | Q-3 | — | $OC_2H_5$ | — | O | H | $CH_3$ | $OCH_3$ | CH | |
| H | O | — | Q-3 | — | $OC_2H_5$ | — | O | H | $CH_3$ | $CH_3$ | CH | |
| H | O | — | Q-3 | — | $OC_2H_5$ | — | O | H | Cl | $OCH_3$ | CH | |
| H | O | — | Q-3 | — | $OC_2H_5$ | — | O | H | $OCH_3$ | $OCH_3$ | N | |
| H | O | — | Q-3 | — | $OC_2H_5$ | — | O | H | $CH_3$ | $OCH_3$ | N | |
| H | O | — | Q-3 | — | $SCH_3$ | — | O | H | $CH_3$ | $CH_3$ | CH | |
| H | O | — | Q-3 | — | $SCH_3$ | — | O | H | Cl | $OCH_3$ | CH | |
| H | O | — | Q-3 | — | $N(CH_3)_2$ | — | O | H | $CH_3$ | $OCH_3$ | CH | |
| H | O | — | Q-3 | — | $N(CH_3)_2$ | — | O | H | Cl | $OCH_3$ | CH | |
| H | O | — | Q-3 | — | $N(CH_3)_2$ | — | O | H | $OCH_3$ | $OCH_3$ | N | |
| H | O | — | Q-4 | — | $CH_3$ | — | O | H | $OCH_3$ | $OCH_3$ | N | |
| H | O | — | Q-5 | — | — | $CH_3$ | O | H | $OCH_3$ | $OCH_3$ | CH | |
| H | O | — | Q-5 | — | — | $CH_3$ | O | H | $CH_3$ | $OCH_3$ | CH | |
| H | O | — | Q-5 | — | — | $C_2H_5$ | O | H | $OCH_3$ | $OCH_3$ | CH | |
| H | O | — | Q-5 | — | — | $C_2H_5$ | O | H | $CH_3$ | $OCH_3$ | CH | |
| H | O | — | Q-5 | — | — | $C_2H_5$ | O | H | $CH_3$ | $CH_3$ | CH | |
| H | O | — | Q-5 | — | — | $C_2H_5$ | O | H | Cl | $OCH_3$ | CH | |
| H | O | — | Q-5 | — | — | $C_2H_5$ | O | H | $OCH_3$ | $OCH_3$ | N | |
| H | O | — | Q-5 | — | — | $C_2H_5$ | O | H | $CH_3$ | $OCH_3$ | N | |

TABLE XVI

General Structure 16

| R1 | n | E | Q | R3 | R4 | R5 | W | R | X | Y | Z | m.p. (°C.) |
|---|---|---|---|---|---|---|---|---|---|---|---|---|
| H | O | — | Q-1 | $CH_3$ | — | — | O | H | $CH_3$ | $CH_3$ | CH | |
| H | O | — | Q-1 | $CH_3$ | — | — | O | H | $OCH_3$ | $CH_3$ | CH | |
| H | O | — | Q-1 | $CH_3$ | — | — | O | H | Cl | $OCH_3$ | CH | |
| H | O | — | Q-1 | $CH_3$ | — | — | O | H | $CH_3$ | $OCH_3$ | N | |
| H | O | — | Q-1 | $CH_3$ | — | — | O | H | $OCH_3$ | $OCH_3$ | N | |
| H | O | — | Q-1 | $C_2H_5$ | — | — | O | H | $OCH_3$ | $CH_3$ | CH | |
| H | O | — | Q-1 | $C_2H_5$ | — | — | O | H | $OCH_3$ | $OCH_3$ | CH | |
| H | O | — | Q-1 | $C_2H_5$ | — | — | O | H | Cl | $OCH_3$ | CH | |
| H | O | — | Q-1 | $C_2H_5$ | — | — | O | H | $CH_3$ | $CH_3$ | CH | |
| H | O | — | Q-1 | $C_2H_5$ | — | — | O | H | $CH_3$ | $OCH_3$ | N | |
| H | O | — | Q-2 | $CH_3$ | — | — | O | H | $OCH_3$ | $OCH_3$ | N | |
| H | O | — | Q-2 | $CH_3$ | — | — | O | H | $OCH_3$ | $OCH_3$ | CH | |
| H | O | — | Q-2 | $CH_3$ | — | — | O | H | $OCH_3$ | $CH_3$ | CH | |
| H | O | — | Q-2 | $CH_3$ | — | — | O | H | Cl | $OCH_3$ | CH | |
| H | O | — | Q-2 | $CH_3$ | — | — | O | H | $CH_3$ | $CH_3$ | CH | |
| H | O | — | Q-2 | $CH_3$ | — | — | O | H | $OCH_3$ | $CH_3$ | N | |
| H | O | — | Q-2 | $C_2H_5$ | — | — | O | H | $OCH_3$ | $OCH_3$ | CH | |
| H | O | — | Q-2 | $C_2H_5$ | — | — | O | H | $CH_3$ | $CH_3$ | CH | |
| H | O | — | Q-2 | $C_2H_5$ | — | — | O | H | $CH_3$ | $OCH_3$ | CH | |
| H | O | — | Q-2 | $C_2H_5$ | — | — | O | H | Cl | $OCH_3$ | CH | |
| H | O | — | Q-2 | $C_2H_5$ | — | — | O | H | $CH_3$ | $OCH_3$ | N | |
| H | O | — | Q-2 | $C_2H_5$ | — | — | O | H | $OCH_3$ | $OCH_3$ | N | |

TABLE XVI-continued

General Structure 16

| $R_1$ | n | E | Q | $R_3$ | $R_4$ | $R_5$ | W | R | X | Y | Z | m.p. (°C.) |
|---|---|---|---|---|---|---|---|---|---|---|---|---|
| H | O | — | Q-3 | — | $CH_3$ | — | O | H | $CH_3$ | $OCH_3$ | CH | |
| H | O | — | Q-3 | — | $CH_3$ | — | O | H | Cl | $OCH_3$ | CH | |
| H | O | — | Q-3 | — | $CH_3$ | — | O | H | $OCH_3$ | $OCH_3$ | CH | |
| H | O | — | Q-3 | — | $CH_3$ | — | O | H | $OCH_3$ | $OCH_3$ | N | |
| H | O | — | Q-3 | — | $CH_3$ | — | O | H | $CH_3$ | $OCH_3$ | N | |
| H | O | — | Q-3 | — | $C_2H_5$ | — | O | H | $CH_3$ | $CH_3$ | CH | |
| H | O | — | Q-3 | — | $C_2H_5$ | — | O | H | $CH_3$ | $OCH_3$ | CH | |
| H | O | — | Q-3 | — | $C_2H_5$ | — | O | H | Cl | $OCH_3$ | CH | |
| H | O | — | Q-5 | — | — | $CH_3$ | O | H | Cl | $OCH_3$ | CH | |
| H | O | — | Q-5 | — | — | $CH_3$ | O | H | $CH_3$ | $OCH_3$ | CH | |
| H | O | — | Q-5 | — | — | $CH_3$ | O | H | $OCH_3$ | $OCH_3$ | CH | |
| H | O | — | Q-5 | — | — | $CH_3$ | O | H | $CH_3$ | $CH_3$ | CH | |
| H | O | — | Q-5 | — | — | $CH_3$ | O | H | $OCH_3$ | $CH_3$ | N | |
| H | O | — | Q-1 | $CH_3$ | — | — | O | H | $OCH_3$ | $OCH_3$ | CH | |
| H | O | — | Q-1 | $C_2H_5$ | — | — | O | H | $OCH_3$ | $OCH_3$ | N | |
| H | O | — | Q-3 | — | $CH_3$ | — | O | H | $CH_3$ | $CH_3$ | CH | |
| H | O | — | Q-3 | — | $C_2H_5$ | — | O | H | $OCH_3$ | $OCH_3$ | CH | |
| H | O | — | Q-3 | — | $C_2H_5$ | — | O | H | $OCH_3$ | $OCH_3$ | N | |
| H | O | — | Q-3 | — | $C_2H_5$ | — | O | H | $CH_3$ | $OCH_3$ | N | |
| H | O | — | Q-3 | — | $OCH_3$ | — | O | H | $OCH_3$ | $OCH_3$ | CH | |
| H | O | — | Q-3 | — | $OCH_3$ | — | O | H | $CH_3$ | $OCH_3$ | CH | |
| H | O | — | Q-3 | — | $OCH_3$ | — | O | H | $CH_3$ | $CH_3$ | CH | |
| H | O | — | Q-3 | — | $OCH_3$ | — | O | H | Cl | $OCH_3$ | CH | |
| H | O | — | Q-3 | — | $OCH_3$ | — | O | H | $OCH_3$ | $OCH_3$ | N | |
| H | O | — | Q-3 | — | $OCH_3$ | — | O | H | $CH_3$ | $OCH_3$ | N | |
| H | O | — | Q-4 | — | $CH_3$ | — | O | H | $OCH_3$ | $OCH_3$ | CH | |
| H | O | — | Q-4 | — | $CH_3$ | — | O | H | $CH_3$ | $OCH_3$ | CH | |
| H | O | — | Q-4 | — | $CH_3$ | — | O | H | $CH_3$ | $CH_3$ | CH | |
| H | O | — | Q-4 | — | $CH_3$ | — | O | H | Cl | $OCH_3$ | CH | |
| H | O | — | Q-4 | — | $CH_3$ | — | O | H | $OCH_3$ | $OCH_3$ | N | |
| H | O | — | Q-4 | — | $CH_3$ | — | O | H | $CH_3$ | $OCH_3$ | N | |
| H | O | — | Q-5 | — | — | $CH_3$ | O | H | $OCH_3$ | $OCH_3$ | N | |

TABLE XVII

General Structure 17

| $R_1$ | E | Q | G | n | $R_3$ | W | R | X | Y | Z | m.p. (°C.) |
|---|---|---|---|---|---|---|---|---|---|---|---|
| H | — | Q-1 | O | 0 | $CH_3$ | O | H | $OCH_3$ | $OCH_3$ | CH | |
| H | — | Q-1 | S | 0 | $CH_3$ | O | H | $CH_3$ | $OCH_3$ | CH | |
| H | — | Q-1 | SO | 0 | $CH_3$ | O | H | $CH_3$ | $CH_3$ | CH | |
| H | — | Q-1 | $SO_2$ | 0 | $CH_3$ | O | H | $OCH_3$ | $OCH_3$ | N | |
| H | — | Q-1 | O | 1 | $CH_3$ | O | H | $CH_3$ | $OCH_3$ | N | |
| H | — | Q-1 | S | 1 | $CH_3$ | O | H | $OCH_3$ | $OCH_3$ | CH | |
| H | — | Q-1 | SO | 1 | $CH_3$ | O | H | $OCH_3$ | $OCH_3$ | CH | |
| H | — | Q-1 | $SO_2$ | 1 | $CH_3$ | O | H | $CH_3$ | $OCH_3$ | CH | |
| H | — | Q-1 | O | 2 | $CH_3$ | O | H | $CH_3$ | $OCH_3$ | N | |
| H | — | Q-1 | S | 2 | $CH_3$ | O | H | $OCH_3$ | $OCH_3$ | N | |
| H | — | Q-1 | SO | 2 | $CH_3$ | O | H | $OCH_3$ | $OCH_3$ | CH | |
| H | — | Q-1 | $SO_2$ | 2 | $CH_3$ | O | H | $OCH_3$ | $OCH_3$ | CH | |
| 6-$CH_3$ | — | Q-1 | O | 0 | $CH_3$ | O | H | $OCH_3$ | $OCH_3$ | CH | |
| 6-$CH_3$ | — | Q-1 | S | 1 | $CH_3$ | O | H | $CH_3$ | $OCH_3$ | CH | |
| 6-$CH_3$ | — | Q-1 | SO | 2 | $CH_3$ | O | H | $OCH_3$ | $OCH_3$ | N | |
| 6-$CH_3$ | — | Q-1 | $SO_2$ | 1 | $CH_3$ | O | H | $CH_3$ | $OCH_3$ | N | |
| 5-Cl | — | Q-1 | O | 1 | $CH_3$ | O | H | $OCH_3$ | $OCH_3$ | CH | |
| 5-Cl | — | Q-1 | S | 2 | $CH_3$ | O | H | $CH_3$ | $OCH_3$ | CH | |
| 5-Cl | — | Q-1 | SO | 1 | $CH_3$ | O | H | $OCH_3$ | $OCH_3$ | N | |
| 5-Cl | — | Q-1 | $SO_2$ | 2 | $CH_3$ | O | H | $CH_3$ | $OCH_3$ | N | |
| H | — | Q-2 | O | 0 | $CH_3$ | O | H | $CH_3$ | $OCH_3$ | CH | |
| H | — | Q-2 | S | 0 | $CH_3$ | O | H | $OCH_3$ | $OCH_3$ | CH | |
| H | — | Q-2 | SO | 0 | $CH_3$ | O | H | $CH_3$ | $OCH_3$ | N | |
| H | — | Q-2 | $SO_2$ | 0 | $CH_3$ | O | H | $OCH_3$ | $OCH_3$ | N | |
| H | — | Q-2 | O | 1 | $CH_3$ | O | H | $CH_3$ | $OCH_3$ | CH | |
| H | — | Q-2 | S | 1 | $CH_3$ | O | H | $OCH_3$ | $OCH_3$ | CH | |
| H | — | Q-2 | SO | 1 | $CH_3$ | O | H | $CH_3$ | $OCH_3$ | N | |
| H | — | Q-2 | $SO_2$ | 1 | $CH_3$ | O | H | $OCH_3$ | $OCH_3$ | N | |
| H | — | Q-2 | O | 2 | $CH_3$ | O | H | $CH_3$ | $CH_3$ | CH | |
| H | — | Q-2 | S | 2 | $CH_3$ | O | H | $OCH_3$ | $OCH_3$ | CH | |
| H | — | Q-2 | SO | 2 | $CH_3$ | O | H | $CH_3$ | $CH_3$ | N | |
| H | — | Q-2 | $SO_2$ | 2 | $CH_3$ | O | H | $OCH_3$ | $OCH_3$ | N | |

TABLE XVIIa

| General Structure 17 | | | | | | | | | | | |
|---|---|---|---|---|---|---|---|---|---|---|---|
| $R_1$ | E | Q | G | n | $R_4$ | W | R | X | Y | Z | m.p. (°C.) |
| H | — | Q-3 | O | 1 | $CH_3$ | O | H | $CH_3$ | $OCH_3$ | N | |
| H | — | Q-3 | S | 1 | $CH_3$ | O | H | $OCH_3$ | $OCH_3$ | CH | |
| H | — | Q-3 | SO | 1 | $CH_3$ | O | H | $CH_3$ | $OCH_3$ | CH | |
| H | — | Q-3 | $SO_2$ | 1 | $CH_3$ | O | H | $OCH_3$ | $OCH_3$ | N | |
| H | — | Q-3 | O | 2 | $CH_3$ | O | H | $CH_3$ | $OCH_3$ | CH | |
| H | — | Q-3 | S | 2 | $CH_3$ | O | H | $OCH_3$ | $OCH_3$ | N | |
| H | — | Q-3 | SO | 2 | $CH_3$ | O | H | $CH_3$ | $OCH_3$ | N | |
| H | — | Q-3 | $SO_2$ | 2 | $CH_3$ | O | H | $OCH_3$ | $OCH_3$ | CH | |
| H | — | Q-4 | O | 1 | $CH_3$ | O | H | $CH_3$ | $OCH_3$ | N | |
| H | — | Q-4 | S | 1 | $CH_3$ | O | H | $OCH_3$ | $OCH_3$ | CH | |
| H | — | Q-4 | SO | 1 | $CH_3$ | O | H | $CH_3$ | $OCH_3$ | CH | |
| H | — | Q-4 | $SO_2$ | 1 | $CH_3$ | O | H | $OCH_3$ | $OCH_3$ | N | |
| H | — | Q-4 | O | 2 | $CH_3$ | O | H | $CH_3$ | $OCH_3$ | N | |
| H | — | Q-4 | S | 2 | $CH_3$ | O | H | $OCH_3$ | $OCH_3$ | CH | |
| H | — | Q-4 | SO | 2 | $CH_3$ | O | H | $CH_3$ | $OCH_3$ | CH | |
| H | — | Q-4 | $SO_2$ | 2 | $CH_3$ | O | H | $OCH_3$ | $OCH_3$ | N | |

TABLE XVIIb

| General Structure 17 | | | | | | | | | | | |
|---|---|---|---|---|---|---|---|---|---|---|---|
| $R_1$ | E | Q | G | n | $R_5$ | W | R | X | Y | Z | m.p. (°C.) |
| H | — | Q-5 | O | 1 | $CH_3$ | O | H | $CH_3$ | $OCH_3$ | CH | |
| H | — | Q-5 | S | 1 | $CH_3$ | O | H | $OCH_3$ | $OCH_3$ | N | |
| H | — | Q-5 | SO | 1 | $CH_3$ | O | H | $CH_3$ | $OCH_3$ | N | |
| H | — | Q-5 | $SO_2$ | 1 | $CH_3$ | O | H | $OCH_3$ | $OCH_3$ | CH | |
| H | — | Q-5 | O | 2 | $CH_3$ | O | H | $CH_3$ | $OCH_3$ | N | |
| H | — | Q-5 | S | 2 | $CH_3$ | O | H | $OCH_3$ | $OCH_3$ | CH | |
| H | — | Q-5 | SO | 2 | $CH_3$ | O | H | $CH_3$ | $OCH_3$ | CH | |
| H | — | Q-5 | $SO_2$ | 2 | $CH_3$ | O | H | $OCH_3$ | $OCH_3$ | N | |
| H | — | Q-6 | O | 1 | $CH_3$ | O | H | $CH_3$ | $OCH_3$ | N | |
| H | — | Q-6 | S | 1 | $CH_3$ | O | H | $OCH_3$ | $OCH_3$ | CH | |
| H | — | Q-6 | SO | 1 | $CH_3$ | O | H | $CH_3$ | $OCH_3$ | CH | |
| H | — | Q-6 | $SO_2$ | 1 | $CH_3$ | O | H | $OCH_3$ | $OCH_3$ | N | |
| H | — | Q-6 | O | 2 | $CH_3$ | O | H | $CH_3$ | $OCH_3$ | CH | |
| H | — | Q-6 | S | 2 | $CH_3$ | O | H | $OCH_3$ | $OCH_3$ | N | |
| H | — | Q 6 | SO | 2 | $CH_3$ | O | H | $CH_3$ | $OCH_3$ | N | |
| H | — | Q-6 | $SO_2$ | 2 | $CH_3$ | O | H | $OCH_3$ | $OCH_3$ | CH | |
| H | — | Q-7 | O | 1 | $CH_3$ | O | H | $CH_3$ | $OCH_3$ | CH | |
| H | — | Q-7 | S | 1 | $CH_3$ | O | H | $OCH_3$ | $OCH_3$ | N | |
| H | — | Q-7 | SO | 1 | $CH_3$ | O | H | $CH_3$ | $OCH_3$ | N | |
| H | — | Q 7 | $SO_2$ | 1 | $CH_3$ | O | H | $OCH_3$ | $OCH_3$ | CH | |
| H | — | Q-7 | O | 2 | $CH_3$ | O | H | $CH_3$ | $OCH_3$ | CH | |
| H | — | Q-7 | S | 2 | $CH_3$ | O | H | $OCH_3$ | $OCH_3$ | N | |
| H | — | Q-7 | SO | 2 | $CH_3$ | O | H | $CH_3$ | $OCH_3$ | N | |
| H | — | Q-7 | $SO_2$ | 2 | $CH_3$ | O | H | $OCH_3$ | $OCH_3$ | CH | |

TABLE XVIII

| General Structure 18 | | | | | | | | | | | | | |
|---|---|---|---|---|---|---|---|---|---|---|---|---|---|
| $R_1$ | n | E | Q | $R_2$ | $R_3$ | $R_4$ | $R_5$ | W | R | X | Y | Z | m.p. (°C.) |
| H | O | — | Q-1 | $C_6H_5$ | $CH_3$ | — | — | O | H | $CH_3$ | $CH_3$ | CH | |
| H | O | — | Q-1 | $C_6H_5$ | $CH_3$ | — | — | O | H | $OCH_3$ | $CH_3$ | CH | |
| H | O | — | Q-1 | $C_6H_5$ | $CH_3$ | — | — | O | H | Cl | $OCH_3$ | CH | |
| H | O | — | Q-1 | $C_6H_5$ | $CH_3$ | — | — | O | H | $CH_3$ | $OCH_3$ | N | |
| H | O | — | Q-1 | $C_6H_5$ | $CH_3$ | — | — | O | H | $OCH_3$ | $OCH_3$ | N | |
| H | O | — | Q-1 | $C_6H_5$ | $C_2H_5$ | — | — | O | H | $OCH_3$ | $CH_3$ | CH | |
| H | O | — | Q-1 | $C_6H_5$ | $C_2H_5$ | — | — | O | H | $OCH_3$ | $OCH_3$ | CH | |
| H | O | — | Q-1 | $C_6H_5$ | $C_2H_5$ | — | — | O | H | Cl | $OCH_3$ | CH | |
| H | O | — | Q-1 | $C_6H_5$ | $C_2H_5$ | — | — | O | H | $CH_3$ | $CH_3$ | CH | |
| H | O | — | Q-1 | $C_6H_5$ | $C_2H_5$ | — | — | O | H | $CH_3$ | $OCH_3$ | N | |
| H | O | — | Q-2 | $C_6H_5$ | $CH_3$ | — | — | O | H | $OCH_3$ | $OCH_3$ | N | |
| H | O | — | Q-2 | $C_6H_5$ | $CH_3$ | — | — | O | H | $OCH_3$ | $OCH_3$ | CH | |
| H | O | — | Q-2 | $C_6H_5$ | $CH_3$ | — | — | O | H | $OCH_3$ | $CH_3$ | CH | |
| H | O | — | Q-2 | $C_6H_5$ | $CH_3$ | — | — | O | H | Cl | $OCH_3$ | CH | |
| H | O | — | Q-2 | $C_6H_5$ | $CH_3$ | — | — | O | H | $CH_3$ | $CH_3$ | CH | |
| H | O | — | Q-2 | $C_6H_5$ | $CH_3$ | — | — | O | H | $OCH_3$ | $CH_3$ | N | |
| H | O | — | Q-2 | $C_6H_5$ | $C_2H_5$ | — | — | O | H | $OCH_3$ | $OCH_3$ | N | |
| H | O | — | Q-2 | $C_6H_5$ | $C_2H_5$ | — | — | O | H | $CH_3$ | $CH_3$ | CH | |
| H | O | — | Q-2 | $C_6H_5$ | $C_2H_5$ | — | — | O | H | $CH_3$ | $OCH_3$ | CH | |
| H | O | — | Q-2 | $C_6H_5$ | $C_2H_5$ | — | — | O | H | Cl | $OCH_3$ | CH | |
| H | O | — | Q-2 | $C_6H_5$ | $C_2H_5$ | — | — | O | H | $CH_3$ | $OCH_3$ | N | |
| H | O | — | Q-2 | $C_6H_5$ | $C_2H_5$ | — | — | O | H | $OCH_3$ | $OCH_3$ | N | |
| H | O | — | Q-3 | $C_6H_5$ | — | $CH_3$ | — | O | H | $CH_3$ | $OCH_3$ | CH | |
| H | O | — | Q-3 | $C_6H_5$ | — | $CH_3$ | — | O | H | Cl | $OCH_3$ | CH | |

TABLE XVIII-continued

General Structure 18

| R1 | n | E | Q | R2 | R3 | R4 | R5 | W | R | X | Y | Z | m.p. (°C.) |
|---|---|---|---|---|---|---|---|---|---|---|---|---|---|
| H | O | — | Q-3 | $C_6H_5$ | — | $CH_3$ | — | O | H | $OCH_3$ | $OCH_3$ | CH | |
| H | O | — | Q-3 | $C_6H_5$ | — | $CH_3$ | — | O | H | $OCH_3$ | $OCH_3$ | N | |
| H | O | — | Q-3 | $C_6H_5$ | — | $CH_3$ | — | O | H | $CH_3$ | $OCH_3$ | N | |
| H | O | — | Q-3 | $C_6H_5$ | — | $C_2H_5$ | — | O | H | $CH_3$ | $CH_3$ | CH | |
| H | O | — | Q-3 | $C_6H_5$ | — | $C_2H_5$ | — | O | H | $CH_3$ | $OCH_3$ | CH | |
| H | O | — | Q-3 | $C_6H_5$ | — | $C_2H_5$ | — | O | H | Cl | $OCH_3$ | CH | |
| H | O | — | Q-3 | $C_6H_5$ | — | $C_2H_5$ | — | O | H | $OCH_3$ | $OCH_3$ | CH | |
| H | O | — | Q-3 | $C_6H_5$ | — | $C_2H_5$ | — | O | H | $CH_3$ | $OCH_3$ | N | |
| H | O | — | Q-3 | $C_6H_5$ | — | $CH_2Cl$ | — | O | H | $CH_3$ | $OCH_3$ | CH | |
| H | O | — | Q-3 | $C_6H_5$ | — | $CH_2Cl$ | — | O | H | $OCH_3$ | $OCH_3$ | CH | |
| H | O | — | Q-3 | $C_6H_5$ | — | $CH_2Cl$ | — | O | H | Cl | $OCH_3$ | CH | |
| H | O | — | Q-3 | $C_6H_5$ | — | $CH_2Cl$ | — | O | H | $CH_3$ | $OCH_3$ | N | |
| H | O | — | Q-3 | $C_6H_5$ | — | $CH_2Cl$ | — | O | H | $OCH_3$ | $OCH_3$ | N | |
| H | O | — | Q-3 | $C_6H_5$ | — | $CF_3$ | — | O | H | $CH_3$ | $CH_3$ | CH | |
| H | O | — | Q-3 | $C_6H_5$ | — | $CF_3$ | — | O | H | $OCH_3$ | $OCH_3$ | CH | |
| H | O | — | Q-3 | $C_6H_5$ | — | $CF_3$ | — | O | H | $OCH_3$ | $CH_3$ | CH | |
| H | O | — | Q-3 | $C_6H_5$ | — | $CF_3$ | — | O | H | $CH_3$ | $OCH_3$ | N | |
| H | O | — | Q-3 | $C_6H_5$ | — | $CH(CH_3)_2$ | — | O | H | $CH_3$ | $OCH_3$ | CH | |
| H | O | — | Q-3 | $C_6H_5$ | — | $CH(CH_3)_2$ | — | O | H | $OCH_3$ | $OCH_3$ | CH | |
| H | O | — | Q-3 | $C_6H_5$ | — | $CH(CH_3)_2$ | — | O | H | Cl | $OCH_3$ | CH | |
| H | O | — | Q-3 | $C_6H_5$ | — | $CH(CH_3)_2$ | — | O | H | $CH_3$ | $OCH_3$ | N | |
| H | O | — | Q-3 | $C_6H_5$ | — | $OCH_3$ | — | O | H | $OCH_3$ | $OCH_3$ | CH | |
| H | O | — | Q-3 | $C_6H_5$ | — | $OCH_3$ | — | O | H | $CH_3$ | $OCH_3$ | CH | |
| H | O | — | Q-3 | $C_6H_5$ | — | $OCH_3$ | — | O | H | Cl | $OCH_3$ | CH | |
| H | O | — | Q-3 | $C_6H_5$ | — | $OCH_3$ | — | O | H | $OCH_3$ | $OCH_3$ | N | |
| H | O | — | Q-3 | $C_6H_5$ | — | $SCH_3$ | — | O | H | $CH_3$ | $OCH_3$ | CH | |
| H | O | — | Q-3 | $C_6H_5$ | — | $SCH_3$ | — | O | H | $OCH_3$ | $OCH_3$ | CH | |
| H | O | — | Q-3 | $C_6H_5$ | — | $SCH_3$ | — | O | H | $OCH_3$ | $OCH_3$ | N | |
| H | O | — | Q-3 | $C_6H_5$ | — | $SCH_3$ | — | O | H | $CH_3$ | $OCH_3$ | N | |
| H | O | — | Q-3 | $C_6H_5$ | — | $N(CH_3)_2$ | — | O | H | $CH_3$ | $CH_3$ | CH | |
| H | O | — | Q-3 | $C_6H_5$ | — | $N(CH_3)_2$ | — | O | H | $OCH_3$ | $OCH_3$ | CH | |
| H | O | — | Q-3 | $C_6H_5$ | — | $N(CH_3)_2$ | — | O | H | $OCH_3$ | $CH_3$ | N | |
| H | O | — | Q-1 | $CH_3$ | $CH_3$ | — | — | O | H | $CH_3$ | $CH_3$ | CH | |
| H | O | — | Q-1 | $CH_3$ | $CH_3$ | — | — | O | H | $OCH_3$ | $CH_3$ | CH | |
| H | O | — | Q-1 | $CH_3$ | $CH_3$ | — | — | O | H | Cl | $OCH_3$ | CH | |
| H | O | — | Q-1 | $CH_3$ | $CH_3$ | — | — | O | H | $CH_3$ | $OCH_3$ | N | |
| H | O | — | Q-1 | $CH_3$ | $CH_3$ | — | — | O | H | $OCH_3$ | $OCH_3$ | N | |
| H | O | — | Q-1 | $CH_3$ | $C_2H_5$ | — | — | O | H | $OCH_3$ | $CH_3$ | CH | |
| H | O | — | Q-1 | $CH_3$ | $C_2H_5$ | — | — | O | H | $OCH_3$ | $OCH_3$ | CH | |
| H | O | — | Q-1 | $CH_3$ | $C_2H_5$ | — | — | O | H | Cl | $OCH_3$ | CH | |
| H | O | — | Q-1 | $CH_3$ | $C_2H_5$ | — | — | O | H | $CH_3$ | $CH_3$ | CH | |
| H | O | — | Q-1 | $CH_3$ | $C_2H_5$ | — | — | O | H | $CH_3$ | $OCH_3$ | N | |
| H | O | — | Q-2 | $CH_3$ | $CH_3$ | — | — | O | H | $OCH_3$ | $OCH_3$ | N | |
| H | O | — | Q-2 | $CH_3$ | $CH_3$ | — | — | O | H | $OCH_3$ | $OCH_3$ | CH | |
| H | O | — | Q-2 | $CH_3$ | $CH_3$ | — | — | O | H | $OCH_3$ | $CH_3$ | CH | |
| H | O | — | Q-2 | $CH_3$ | $CH_3$ | — | — | O | H | Cl | $OCH_3$ | CH | |
| H | O | — | Q-2 | $CH_3$ | $CH_3$ | — | — | O | H | $CH_3$ | $CH_3$ | CH | |
| H | O | — | Q-2 | $CH_3$ | $CH_3$ | — | — | O | H | $OCH_3$ | $CH_3$ | N | |
| H | O | — | Q-2 | $CH_3$ | $C_2H_5$ | — | — | O | H | $OCH_3$ | $OCH_3$ | CH | |
| H | O | — | Q-2 | $CH_3$ | $C_2H_5$ | — | — | O | H | $CH_3$ | $CH_3$ | CH | |
| H | O | — | Q-2 | $CH_3$ | $C_2H_5$ | — | — | O | H | $CH_3$ | $OCH_3$ | CH | |
| H | O | — | Q-2 | $CH_3$ | $C_2H_5$ | — | — | O | H | Cl | $OCH_3$ | CH | |
| H | O | — | Q-2 | $CH_3$ | $C_2H_5$ | — | — | O | H | $CH_3$ | $OCH_3$ | N | |
| H | O | — | Q-2 | $CH_3$ | $C_2H_5$ | — | — | O | H | $OCH_3$ | $OCH_3$ | N | |
| H | O | — | Q-3 | $CH_3$ | — | $CH_3$ | — | O | H | $CH_3$ | $OCH_3$ | CH | |
| H | O | — | Q-3 | $CH_3$ | — | $CH_3$ | — | O | H | Cl | $OCH_3$ | CH | |
| H | O | — | Q-3 | $CH_3$ | — | $CH_3$ | — | O | H | $OCH_3$ | $OCH_3$ | CH | |
| H | O | — | Q-3 | $CH_3$ | — | $CH_3$ | — | O | H | $OCH_3$ | $OCH_3$ | N | |
| H | O | — | Q-3 | $CH_3$ | — | $CH_3$ | — | O | H | $CH_3$ | $OCH_3$ | N | |
| H | O | — | Q-3 | $CH_3$ | — | $C_2H_5$ | — | O | H | $CH_3$ | $CH_3$ | CH | |
| H | O | — | Q-3 | $CH_3$ | — | $C_2H_5$ | — | O | H | $CH_3$ | $OCH_3$ | CH | |
| H | O | — | Q-3 | $CH_3$ | — | $C_2H_5$ | — | O | H | Cl | $OCH_3$ | CH | |
| H | O | — | Q-3 | $CH_3$ | — | $C_2H_5$ | — | O | H | $OCH_3$ | $OCH_3$ | CH | |
| H | O | — | Q-3 | $CH_3$ | — | $C_2H_5$ | — | O | H | $CH_3$ | $OCH_3$ | N | |
| H | O | — | Q-3 | $CH_3$ | — | $CH_2Cl$ | — | O | H | $CH_3$ | $OCH_3$ | CH | |
| H | O | — | Q-3 | $CH_3$ | — | $CH_2Cl$ | — | O | H | $OCH_3$ | $OCH_3$ | CH | |
| H | O | — | Q-3 | $CH_3$ | — | $CH_2Cl$ | — | O | H | Cl | $OCH_3$ | CH | |
| H | O | — | Q-3 | $CH_3$ | — | $CH_2Cl$ | — | O | H | $CH_3$ | $OCH_3$ | N | |
| H | O | — | Q-3 | $CH_3$ | — | $CH_2Cl$ | — | O | H | $OCH_3$ | $OCH_3$ | N | |
| H | O | — | Q-3 | $CH_3$ | — | $CF_3$ | — | O | H | $CH_3$ | $CH_3$ | CH | |
| H | O | — | Q-3 | $CH_3$ | — | $CF_3$ | — | O | H | $OCH_3$ | $OCH_3$ | CH | |
| H | O | — | Q-3 | $CH_3$ | — | $CF_3$ | — | O | H | $OCH_3$ | $CH_3$ | CH | |
| H | O | — | Q-3 | $CH_3$ | — | $CF_3$ | — | O | H | $CH_3$ | $OCH_3$ | N | |
| H | O | — | Q-3 | $CH_3$ | — | $CH(CH_3)_2$ | — | O | H | $CH_3$ | $OCH_3$ | CH | |
| H | O | — | Q-3 | $CH_3$ | — | $CH(CH_3)_2$ | — | O | H | $OCH_3$ | $OCH_3$ | CH | |
| H | O | — | Q-3 | $CH_3$ | — | $CH(CH_3)_2$ | — | O | H | Cl | $OCH_3$ | CH | |
| H | O | — | Q-3 | $CH_3$ | — | $CH(CH_3)_2$ | — | O | H | $CH_3$ | $OCH_3$ | N | |
| H | O | — | Q-3 | $CH_3$ | — | $OCH_3$ | — | O | H | $OCH_3$ | $OCH_3$ | CH | |
| H | O | — | Q-3 | $CH_3$ | — | $OCH_3$ | — | O | H | $CH_3$ | $OCH_3$ | CH | |
| H | O | — | Q-3 | $CH_3$ | — | $OCH_3$ | — | O | H | Cl | $CH_3$ | CH | |

TABLE XVIII-continued

| General Structure 18 | | | | | | | | | | | | | |
|---|---|---|---|---|---|---|---|---|---|---|---|---|---|
| $R_1$ | n | E | Q | $R_2$ | $R_3$ | $R_4$ | $R_5$ | W | R | X | Y | Z | m.p. (°C.) |
| H | O | — | Q-3 | $CH_3$ | — | $OCH_3$ | — | O | H | $OCH_3$ | $OCH_3$ | N | |
| H | O | — | Q-3 | $CH_3$ | — | $SCH_3$ | — | O | H | $CH_3$ | $OCH_3$ | CH | |
| H | O | — | Q-3 | $CH_3$ | — | $SCH_3$ | — | O | H | $OCH_3$ | $OCH_3$ | CH | |
| H | O | — | Q-3 | $CH_3$ | — | $SCH_3$ | — | O | H | $OCH_3$ | $OCH_3$ | N | |
| H | O | — | Q-3 | $CH_3$ | — | $SCH_3$ | — | O | H | $CH_3$ | $OCH_3$ | N | |
| H | O | — | Q-3 | $CH_3$ | — | $N(CH_3)_2$ | — | O | H | $CH_3$ | $CH_3$ | CH | |
| H | O | — | Q-3 | $CH_3$ | — | $N(CH_3)_2$ | — | O | H | $OCH_3$ | $OCH_3$ | CH | |
| H | O | — | Q-3 | $CH_3$ | — | $N(CH_3)_2$ | — | O | H | $OCH_3$ | $CH_3$ | N | |
| H | O | — | Q-5 | $CH_3$ | — | — | $CH_3$ | O | H | $OCH_3$ | $CH_3$ | N | |
| H | O | — | Q-5 | $CH_3$ | — | — | $CH_3$ | O | H | $OCH_3$ | $CH_3$ | CH | |
| H | O | — | Q-5 | $CH_3$ | — | — | $CH_3$ | O | H | $OCH_3$ | $OCH_3$ | CH | |
| H | O | — | Q-5 | $CH_3$ | — | — | $CH_3$ | O | H | Cl | $OCH_3$ | CH | |
| H | O | — | Q-5 | $CH_3$ | — | — | $CH_3$ | O | H | $CH_3$ | $CH_3$ | CH | |
| Cl | O | — | Q-2 | $CH_3$ | $CH_3$ | — | — | O | H | $CH_3$ | $CH_3$ | CH | |
| Cl | O | — | Q-2 | $CH_3$ | $CH_3$ | — | — | O | H | $CH_3$ | $OCH_3$ | CH | |
| Cl | O | — | Q-2 | $CH_3$ | $CH_3$ | — | — | O | H | $OCH_3$ | $OCH_3$ | CH | |
| Cl | O | — | Q-2 | $CH_3$ | $CH_3$ | — | — | O | H | Cl | $OCH_3$ | CH | |
| Cl | O | — | Q-2 | $CH_3$ | $CH_3$ | — | — | O | H | $CH_3$ | $OCH_3$ | N | |
| Cl | O | — | Q-2 | $CH_3$ | $CH_3$ | — | — | O | H | $OCH_3$ | $OCH_3$ | N | |
| Cl | O | — | Q-2 | $CH_3$ | $CH_3$ | — | — | O | $CH_3$ | $OCH_3$ | $CH_3$ | N | |
| Cl | O | — | Q-2 | $CH_3$ | $CH_2CH_3$ | — | — | O | H | $CH_3$ | $CH_3$ | CH | |
| Cl | O | — | Q-2 | $CH_3$ | $CH_2CH_3$ | — | — | O | H | $CH_3$ | $OCH_3$ | CH | |
| Cl | O | — | Q-2 | $CH_3$ | $CH_2CH_3$ | — | — | O | H | $OCH_3$ | $OCH_3$ | CH | |
| Cl | O | — | Q-2 | $CH_3$ | $CH_2CH_3$ | — | — | O | H | Cl | $OCH_3$ | CH | |
| Cl | O | — | Q-2 | $CH_3$ | $CH_2CH_3$ | — | — | O | H | $OCH_3$ | $CH_3$ | N | |
| Cl | O | — | Q-2 | $CH_3$ | $CH_2CH_3$ | — | — | O | H | $OCH_3$ | $OCH_3$ | N | |
| H | O | — | Q-2 | $CH_2CH_3$ | $CH_3$ | — | — | O | H | $CH_3$ | $CH_3$ | CH | |
| H | O | — | Q-2 | $CH_2CH_3$ | $CH_3$ | — | — | O | H | $CH_3$ | $OCH_3$ | CH | |
| H | O | — | Q-2 | $CH_2CH_3$ | $CH_3$ | — | — | O | H | $OCH_3$ | $OCH_3$ | CH | |
| H | O | — | Q-2 | $CH_2CH_3$ | $CH_3$ | — | — | O | H | Cl | $OCH_3$ | CH | |
| H | O | — | Q-2 | $CH_2CH_3$ | $CH_3$ | — | — | O | H | $OCH_3$ | $CH_3$ | N | |
| H | O | — | Q-2 | $CH_2CH_3$ | $CH_3$ | — | — | O | H | $OCH_3$ | $OCH_3$ | N | |
| Cl | O | — | Q-1 | $CH_3$ | $CH_3$ | — | — | O | H | $OCH_3$ | $CH_3$ | CH | |
| Cl | O | — | Q-1 | $CH_3$ | $CH_3$ | — | — | O | H | $OCH_3$ | $OCH_3$ | CH | |
| Cl | O | — | Q-1 | $CH_3$ | $CH_3$ | — | — | O | H | $OCH_3$ | $CH_3$ | N | |
| Cl | O | — | Q-1 | $CH_3$ | $CH_3$ | — | — | O | H | $OCH_3$ | $OCH_3$ | N | |
| Cl | O | — | Q-3 | $CH_3$ | — | $CH_3$ | — | O | H | $CH_3$ | $CH_3$ | CH | |
| Cl | O | — | Q-3 | $CH_3$ | — | $CH_3$ | — | O | H | $OCH_3$ | $CH_3$ | CH | |
| Cl | O | — | Q-3 | $CH_3$ | — | $CH_3$ | — | O | H | $OCH_3$ | $OCH_3$ | CH | |
| Cl | O | — | Q-3 | $CH_3$ | — | $CH_3$ | — | O | H | Cl | $OCH_3$ | CH | |
| Cl | O | — | Q-3 | $CH_3$ | — | $CH_3$ | — | O | H | $OCH_3$ | $CH_3$ | N | |
| Cl | O | — | Q-3 | $CH_3$ | — | $CH_3$ | — | O | H | $OCH_3$ | $OCH_3$ | N | |
| Br | O | — | Q-2 | $CH_3$ | $CH_3$ | — | — | O | H | $CH_3$ | $OCH_3$ | CH | |
| Br | O | — | Q-2 | $CH_3$ | $CH_3$ | — | — | O | H | $OCH_3$ | $OCH_3$ | CH | |
| Br | O | — | Q-2 | $CH_3$ | $CH_3$ | — | — | O | H | Cl | $OCH_3$ | CH | |
| Br | O | — | Q-2 | $CH_3$ | $CH_3$ | — | — | O | H | $OCH_3$ | $CH_3$ | N | |
| Br | O | — | Q-2 | $CH_3$ | $CH_3$ | — | — | O | H | $OCH_3$ | $OCH_3$ | N | |
| Br | O | — | Q-2 | $CH_3$ | $CH_2CH_3$ | — | — | O | H | $CH_3$ | $OCH_3$ | CH | |
| Br | O | — | Q-2 | $CH_3$ | $CH_2CH_3$ | — | — | O | H | $OCH_3$ | $OCH_3$ | CH | |
| Br | O | — | Q-2 | $CH_3$ | $CH_2CH_3$ | — | — | O | H | Cl | $OCH_3$ | CH | |
| Br | O | — | Q-2 | $CH_3$ | $CH_2CH_3$ | — | — | O | H | $OCH_3$ | $OCH_3$ | N | |
| Br | O | — | Q-2 | $CH_3$ | $CH_2CH_3$ | — | — | O | H | $OCH_3$ | $CH_3$ | N | |
| Br | O | — | Q-1 | $CH_3$ | $CH_3$ | — | — | O | H | $OCH_3$ | $CH_3$ | CH | |
| Br | O | — | Q-1 | $CH_3$ | $CH_3$ | — | — | O | H | $OCH_3$ | $OCH_3$ | CH | |
| Br | O | — | Q-1 | $CH_3$ | $CH_3$ | — | — | O | H | $OCH_3$ | $OCH_3$ | N | |
| Br | O | — | Q-1 | $CH_3$ | $CH_3$ | — | — | O | H | $OCH_3$ | $CH_3$ | N | |
| Br | O | — | Q-4 | $CH_3$ | — | $CH_3$ | — | O | H | $OCH_3$ | $CH_3$ | CH | |
| Br | O | — | Q-4 | $CH_3$ | — | $CH_3$ | — | O | H | $OCH_3$ | $OCH_3$ | CH | |
| Br | O | — | Q-4 | $CH_3$ | — | $CH_3$ | — | O | H | $OCH_3$ | $OCH_3$ | N | |
| Br | O | — | Q-4 | $CH_3$ | — | $CH_3$ | — | O | H | $OCH_3$ | $CH_3$ | N | |
| F | O | — | Q-2 | $CH_3$ | $CH_3$ | — | — | O | H | $OCH_3$ | $CH_3$ | CH | |
| F | O | — | Q-2 | $CH_3$ | $CH_3$ | — | — | O | H | $OCH_3$ | $OCH_3$ | CH | |
| F | O | — | Q-2 | $CH_3$ | $CH_3$ | — | — | O | H | $OCH_3$ | $CH_3$ | N | |
| F | O | — | Q-2 | $CH_3$ | $CH_3$ | — | — | O | H | $OCH_3$ | $OCH_3$ | N | |
| F | O | — | Q-2 | $CH_3$ | $CH_3$ | — | — | O | H | Cl | $OCH_3$ | CH | |
| F | O | — | Q-1 | $CH_3$ | $CH_3$ | — | — | O | H | $OCH_3$ | $CH_3$ | CH | |
| F | O | — | Q-1 | $CH_3$ | $CH_3$ | — | — | O | H | $OCH_3$ | $OCH_3$ | CH | |
| F | O | — | Q-1 | $CH_3$ | $CH_3$ | — | — | O | H | $OCH_3$ | $OCH_3$ | N | |
| F | O | — | Q-1 | $CH_3$ | $CH_3$ | — | — | O | H | $OCH_3$ | $CH_3$ | N | |
| F | O | — | Q-3 | $CH_3$ | — | $CH_3$ | — | O | H | $OCH_3$ | $CH_3$ | CH | |
| F | O | — | Q-3 | $CH_3$ | — | $CH_3$ | — | O | H | $OCH_3$ | $OCH_3$ | CH | |
| F | O | — | Q-3 | $CH_3$ | — | $CH_3$ | — | O | H | $OCH_3$ | $CH_3$ | N | |
| F | O | — | Q-3 | $CH_3$ | — | $CH_3$ | — | O | H | $OCH_3$ | $OCH_3$ | N | |
| $OCH_3$ | O | — | Q-2 | $CH_3$ | $CH_3$ | — | — | O | H | $CH_3$ | $OCH_3$ | CH | |
| $OCH_3$ | O | — | Q-2 | $CH_3$ | $CH_3$ | — | — | O | H | $OCH_3$ | $OCH_3$ | CH | |
| $OCH_3$ | O | — | Q-2 | $CH_3$ | $CH_3$ | — | — | O | H | Cl | $OCH_3$ | CH | |
| $OCH_3$ | O | — | Q-2 | $CH_3$ | $CH_3$ | — | — | O | H | $OCH_3$ | $CH_3$ | N | |
| $OCH_3$ | O | — | Q-2 | $CH_3$ | $CH_3$ | — | — | O | H | $OCH_3$ | $OCH_3$ | N | |
| $OCH_3$ | O | — | Q-2 | $CH_3$ | $CH_2CH_3$ | — | — | O | H | $OCH_3$ | $CH_3$ | CH | |
| $OCH_3$ | O | — | Q-2 | $CH_3$ | $CH_2CH_3$ | — | — | O | H | $OCH_3$ | $OCH_3$ | CH | |

TABLE XVIII-continued

| | | | | | | General Structure 18 | | | | | | | |
|---|---|---|---|---|---|---|---|---|---|---|---|---|---|
| $R_1$ | n | E | Q | $R_2$ | $R_3$ | $R_4$ | $R_5$ | W | R | X | Y | Z | m.p. (°C.) |
| $OCH_3$ | O | — | Q-2 | $CH_3$ | $CH_2CH_3$ | — | — | O | H | $OCH_3$ | $CH_3$ | N | |
| $OCH_3$ | O | — | Q-2 | $CH_3$ | $CH_2CH_3$ | — | — | O | H | $OCH_3$ | $OCH_3$ | N | |
| $OCH_3$ | O | — | Q-1 | $CH_3$ | $CH_3$ | — | — | O | H | $OCH_3$ | $CH_3$ | CH | |
| $OCH_3$ | O | — | Q-1 | $CH_3$ | $CH_3$ | — | — | O | H | $OCH_3$ | $OCH_3$ | CH | |
| $OCH_3$ | O | — | Q-1 | $CH_3$ | $CH_3$ | — | — | O | H | $OCH_3$ | $OCH_3$ | N | |
| $OCH_3$ | O | — | Q-1 | $CH_3$ | $CH_3$ | — | — | O | H | $OCH_3$ | $CH_3$ | CH | |
| $OCH_3$ | O | — | Q-1 | $CH_3$ | $CH_3$ | — | — | O | H | Cl | $OCH_3$ | CH | |
| $OCH_3$ | O | — | Q-1 | $CH_3$ | $CH_2CH_3$ | — | — | O | H | $OCH_3$ | $OCH_3$ | CH | |
| $OCH_3$ | O | — | Q-1 | $CH_3$ | $CH_2CH_3$ | — | — | O | H | $OCH_3$ | $CH_3$ | CH | |
| $OCH_3$ | O | — | Q-1 | $CH_3$ | $CH_2CH_3$ | — | — | O | H | $OCH_3$ | $OCH_3$ | N | |
| $OCH_3$ | O | — | Q-3 | $CH_3$ | — | $CH_3$ | — | O | H | $OCH_3$ | $OCH_3$ | CH | |
| $OCH_3$ | O | — | Q-3 | $CH_3$ | — | $CH_3$ | — | O | H | $OCH_3$ | $CH_3$ | CH | |
| $OCH_3$ | O | — | Q-3 | $CH_3$ | — | $CH_3$ | — | O | H | $OCH_3$ | $CH_3$ | N | |
| $OCH_3$ | O | — | Q-3 | $CH_3$ | — | $CH_3$ | — | O | H | $OCH_3$ | $OCH_3$ | N | |
| $OCH_3$ | O | — | Q-3 | $CH_3$ | — | $CH_3$ | — | O | H | $CH_3$ | $CH_3$ | CH | |
| $CF_3$ | O | — | Q-2 | $CH_3$ | $CH_3$ | — | — | O | H | $CH_3$ | $OCH_3$ | CH | |
| $CF_3$ | O | — | Q-2 | $CH_3$ | $CH_3$ | — | — | O | H | $CH_3$ | $OCH_3$ | N | |
| $CF_3$ | O | — | Q-2 | $CH_3$ | $CH_3$ | — | — | O | H | $OCH_3$ | $OCH_3$ | N | |
| $CF_3$ | O | — | Q-2 | $CH_3$ | $CH_3$ | — | — | O | H | $OCH_3$ | $OCH_3$ | CH | |
| $CF_3$ | O | — | Q-1 | $CH_3$ | $CH_3$ | — | — | O | H | $CH_3$ | $OCH_3$ | CH | |
| $CF_3$ | O | — | Q-1 | $CH_3$ | $CH_3$ | — | — | O | H | $OCH_3$ | $OCH_3$ | CH | |
| $CF_3$ | O | — | Q-1 | $CH_3$ | $CH_3$ | — | — | O | H | $OCH_3$ | $OCH_3$ | N | |
| $CF_3$ | O | — | Q-1 | $CH_3$ | $CH_3$ | — | — | O | H | $OCH_3$ | $CH_3$ | N | |
| $CF_3$ | O | — | Q-3 | $CH_3$ | — | $CH_3$ | — | O | H | $OCH_3$ | $CH_3$ | CH | |
| $CF_3$ | O | — | Q-3 | $CH_3$ | — | $CH_3$ | — | O | H | $OCH_3$ | $OCH_3$ | CH | |
| $CF_3$ | O | — | Q-3 | $CH_3$ | — | $CH_3$ | — | O | H | $OCH_3$ | $CH_3$ | N | |
| $CF_3$ | O | — | Q-3 | $CH_3$ | — | $CH_3$ | — | O | H | $OCH_3$ | $OCH_3$ | N | |
| $OCF_2H$ | O | — | Q-2 | $CH_3$ | $CH_3$ | — | — | O | H | $OCH_3$ | $CH_3$ | CH | |
| $OCF_2H$ | O | — | Q-2 | $CH_3$ | $CH_3$ | — | — | O | H | $OCH_3$ | $OCH_3$ | CH | |
| $OCF_2H$ | O | — | Q-2 | $CH_3$ | $CH_3$ | — | — | O | H | $OCH_3$ | $OCH_3$ | N | |
| Cl | O | — | Q-3 | $CH_3$ | — | $OCH_3$ | — | O | H | $OCH_3$ | $CH_3$ | CH | |
| Cl | O | — | Q-3 | $CH_3$ | — | $OCH_3$ | — | O | H | $OCH_3$ | $OCH_3$ | CH | |
| Cl | O | — | Q-3 | $CH_3$ | — | $OCH_3$ | — | O | H | $OCH_3$ | $OCH_3$ | N | |
| Cl | O | — | Q-3 | $CH_3$ | — | $OCH_3$ | — | O | H | $OCH_3$ | $CH_3$ | N | |
| Br | O | — | Q-3 | $CH_3$ | — | $OCH_3$ | — | O | H | $OCH_3$ | $CH_3$ | CH | |
| Br | O | — | Q-3 | $CH_3$ | — | $OCH_3$ | — | O | H | $OCH_3$ | $OCH_3$ | CH | |
| Br | O | — | Q-3 | $CH_3$ | — | $OCH_3$ | — | O | H | $OCH_3$ | $OCH_3$ | N | |
| F | O | — | Q-3 | $CH_3$ | — | $OCH_3$ | — | O | H | $OCH_3$ | $OCH_3$ | N | |
| F | O | — | Q-3 | $CH_3$ | — | $OCH_3$ | — | O | H | $OCH_3$ | $OCH_3$ | CH | |
| F | O | — | Q-3 | $CH_3$ | — | $OCH_3$ | — | O | H | $OCH_3$ | $CH_3$ | CH | |
| $OCH_3$ | O | — | Q-3 | $CH_3$ | — | $OCH_3$ | — | O | H | $OCH_3$ | $CH_3$ | CH | |
| $OCH_3$ | O | — | Q-3 | $CH_3$ | — | $OCH_3$ | — | O | H | $OCH_3$ | $OCH_3$ | CH | |
| $OCH_3$ | O | — | Q-3 | $CH_3$ | — | $OCH_3$ | — | O | H | $OCH_3$ | $OCH_3$ | N | |
| $OCH_3$ | O | — | Q-3 | $CH_3$ | — | $OCH_3$ | — | O | H | $OCH_3$ | $CH_3$ | N | |
| $CF_3$ | O | — | Q-3 | $CH_3$ | — | $OCH_3$ | — | O | H | $OCH_3$ | $CH_3$ | CH | |
| $CF_3$ | O | — | Q-3 | $CH_3$ | — | $OCH_3$ | — | O | H | $OCH_3$ | $OCH_3$ | CH | |
| $CF_3$ | O | — | Q-3 | $CH_3$ | — | $OCH_3$ | — | O | H | $OCH_3$ | $CH_3$ | N | |
| $CF_3$ | O | — | Q-3 | $CH_3$ | — | $OCH_3$ | — | O | H | $OCH_3$ | $OCH_3$ | N | |
| Cl | O | — | Q-3 | $CH_3$ | — | $SCH_3$ | — | O | H | $OCH_3$ | $CH_3$ | CH | |
| Cl | O | — | Q-3 | $CH_3$ | — | $SCH_3$ | — | O | H | $OCH_3$ | $OCH_3$ | CH | |
| Cl | O | — | Q-3 | $CH_3$ | — | $SCH_3$ | — | O | H | $OCH_3$ | $OCH_3$ | N | |
| Br | O | — | Q-3 | $CH_3$ | — | $SCH_3$ | — | O | H | $OCH_3$ | $OCH_3$ | CH | |
| Br | O | — | Q-3 | $CH_3$ | — | $SCH_3$ | — | O | H | $OCH_3$ | $CH_3$ | CH | |
| F | O | — | Q-3 | $CH_3$ | — | $SCH_3$ | — | O | H | $OCH_3$ | $OCH_3$ | N | |
| F | O | — | Q-3 | $CH_3$ | — | $SCH_3$ | — | O | H | $OCH_3$ | $CH_3$ | CH | |
| $OCH_3$ | O | — | Q-3 | $CH_3$ | — | $SCH_3$ | — | O | H | $OCH_3$ | $OCH_3$ | N | |
| $OCH_3$ | O | — | Q-3 | $CH_3$ | — | $SCH_3$ | — | O | H | $OCH_3$ | $CH_3$ | CH | |
| $OCH_3$ | O | — | Q-3 | $CH_3$ | — | $SCH_3$ | — | O | H | $OCH_3$ | $OCH_3$ | CH | |
| $CH_3$ | O | — | Q-1 | $CH_3$ | $CH_3$ | — | — | O | H | $CH_3$ | $CH_3$ | CH | |
| $CH_3$ | O | — | Q-1 | $CH_3$ | $CH_3$ | — | — | O | H | $OCH_3$ | $CH_3$ | CH | |
| $CH_3$ | O | — | Q-1 | $CH_3$ | $CH_3$ | — | — | O | H | $OCH_3$ | $OCH_3$ | CH | |
| $CH_3$ | O | — | Q-1 | $CH_3$ | $CH_3$ | — | — | O | H | Cl | $OCH_3$ | CH | |
| $CH_3$ | O | — | Q-1 | $CH_3$ | $CH_3$ | — | — | O | H | $OCH_3$ | $CH_3$ | N | |
| $CH_3$ | O | — | Q-1 | $CH_3$ | $CH_3$ | — | — | O | H | $OCH_3$ | $OCH_3$ | N | |
| $CH_3$ | O | — | Q-3 | $CH_3$ | — | $OCH_3$ | — | O | H | $OCH_3$ | $CH_3$ | CH | |
| $CH_3$ | O | — | Q-3 | $CH_3$ | — | $OCH_3$ | — | O | H | $OCH_3$ | $OCH_3$ | CH | |
| $CH_3$ | O | — | Q-3 | $CH_3$ | — | $OCH_3$ | — | O | H | Cl | $OCH_3$ | CH | |
| $CH_3$ | O | — | Q-3 | $CH_3$ | — | $OCH_3$ | — | O | H | $OCH_3$ | $CH_3$ | N | |
| $CH_3$ | O | — | Q-3 | $CH_3$ | — | $OCH_3$ | — | O | H | $OCH_3$ | $OCH_3$ | N | |
| Cl | O | — | Q-2 | $CH_3$ | $CH_3$ | — | — | O | $CH_3$ | $OCH_3$ | $OCH_3$ | CH | |
| Br | O | — | Q-2 | $CH_3$ | $CH_3$ | — | — | O | $CH_3$ | $OCH_3$ | $OCH_3$ | CH | |
| F | O | — | Q-2 | $CH_3$ | $CH_3$ | — | — | O | $CH_3$ | $OCH_3$ | $OCH_3$ | CH | |
| Cl | O | — | Q-5 | $CH_3$ | — | — | $CH_3$ | O | H | $CH_3$ | $OCH_3$ | CH | |
| Cl | O | — | Q-5 | $CH_3$ | — | — | $CH_3$ | O | H | $OCH_3$ | $OCH_3$ | CH | |
| Br | O | — | Q-5 | $CH_3$ | — | — | $CH_3$ | O | H | $OCH_3$ | $CH_3$ | CH | |
| Br | O | — | Q-5 | $CH_3$ | — | — | $CH_3$ | O | H | $OCH_3$ | $OCH_3$ | CH | |
| F | O | — | Q-5 | $CH_3$ | — | — | $CH_3$ | O | H | $OCH_3$ | $OCH_3$ | CH | |
| F | O | — | Q-5 | $CH_3$ | — | — | $CH_3$ | O | H | $CH_3$ | $OCH_3$ | CH | |
| $OCH_3$ | O | — | Q-5 | $CH_3$ | — | — | $CH_3$ | O | H | $CH_3$ | $OCH_3$ | CH | |
| $OCH_3$ | O | — | Q-5 | $CH_3$ | — | — | $CH_3$ | O | H | $OCH_3$ | $OCH_3$ | CH | |

TABLE XVIII-continued

General Structure 18

| R1 | n | E | Q | R2 | R3 | R4 | R5 | W | R | X | Y | Z | m.p. (°C.) |
|---|---|---|---|---|---|---|---|---|---|---|---|---|---|
| $OCH_3$ | O | — | Q-5 | $CH_3$ | — | — | $CH_3$ | O | H | $OCH_3$ | $OCH_3$ | N | |
| Cl | O | — | Q-5 | $CH_3$ | — | — | $CH_3$ | O | H | $OCH_3$ | $CH_3$ | N | |
| Cl | O | — | Q-5 | $CH_3$ | — | — | $CH_3$ | O | H | $OCH_3$ | $OCH_3$ | N | |

TABLE XIX

General Structure 19

| R1 | n | E | Q | R3 | R4 | R5 | W | R | X | Y | Z | m.p. (°C.) |
|---|---|---|---|---|---|---|---|---|---|---|---|---|
| H | O | — | Q-1 | $CH_3$ | — | — | O | H | $CH_3$ | $CH_3$ | CH | |
| H | O | — | Q-1 | $CH_3$ | — | — | O | H | $OCH_3$ | $CH_3$ | CH | |
| H | O | — | Q-1 | $CH_3$ | — | — | O | H | Cl | $OCH_3$ | CH | |
| H | O | — | Q-1 | $CH_3$ | — | — | O | H | $CH_3$ | $OCH_3$ | N | |
| H | O | — | Q-1 | $CH_3$ | — | — | O | H | $OCH_3$ | $OCH_3$ | N | |
| H | O | — | Q-1 | $C_2H_5$ | — | — | O | H | $OCH_3$ | $CH_3$ | CH | |
| H | O | — | Q-1 | $C_2H_5$ | — | — | O | H | $OCH_3$ | $OCH_3$ | CH | |
| H | O | — | Q-1 | $C_2H_5$ | — | — | O | H | Cl | $OCH_3$ | CH | |
| H | O | — | Q-1 | $C_2H_5$ | — | — | O | H | $CH_3$ | $CH_3$ | CH | |
| H | O | — | Q-1 | $C_2H_5$ | — | — | O | H | $CH_3$ | $OCH_3$ | N | |
| H | O | — | Q-2 | $CH_3$ | — | — | O | H | $OCH_3$ | $OCH_3$ | N | |
| H | O | — | Q-2 | $CH_3$ | — | — | O | H | $OCH_3$ | $OCH_3$ | CH | |
| H | O | — | Q-2 | $CH_3$ | — | — | O | H | $OCH_3$ | $CH_3$ | CH | |
| H | O | — | Q-2 | $CH_3$ | — | — | O | H | Cl | $OCH_3$ | CH | |
| H | O | — | Q-2 | $CH_3$ | — | — | O | H | $CH_3$ | $CH_3$ | CH | |
| H | O | — | Q-2 | $CH_3$ | — | — | O | H | $OCH_3$ | $CH_3$ | N | |
| H | O | — | Q-2 | $C_2H_5$ | — | — | O | H | $OCH_3$ | $OCH_3$ | CH | |
| H | O | — | Q-2 | $C_2H_5$ | — | — | O | H | $CH_3$ | $CH_3$ | CH | |
| H | O | — | Q-2 | $C_2H_5$ | — | — | O | H | $CH_3$ | $OCH_3$ | CH | |
| H | O | — | Q-2 | $C_2H_5$ | — | — | O | H | Cl | $OCH_3$ | CH | |
| H | O | — | Q-2 | $C_2H_5$ | — | — | O | H | $CH_3$ | $OCH_3$ | N | |
| H | O | — | Q-2 | $C_2H_5$ | — | — | O | H | $OCH_3$ | $OCH_3$ | N | |
| H | O | — | Q-3 | — | $CH_3$ | — | O | H | $CH_3$ | $OCH_3$ | CH | |
| H | O | — | Q-3 | — | $CH_3$ | — | O | H | Cl | $OCH_3$ | CH | |
| H | O | — | Q-3 | — | $CH_3$ | — | O | H | $OCH_3$ | $OCH_3$ | CH | |
| H | O | — | Q-3 | — | $CH_3$ | — | O | H | $OCH_3$ | $OCH_3$ | N | |
| H | O | — | Q-3 | — | $CH_3$ | — | O | H | $CH_3$ | $OCH_3$ | N | |
| H | O | — | Q-3 | — | $C_2H_5$ | — | O | H | $CH_3$ | $CH_3$ | CH | |
| H | O | — | Q-3 | — | $C_2H_5$ | — | O | H | $CH_3$ | $OCH_3$ | CH | |
| H | O | — | Q-3 | — | $C_2H_5$ | — | O | H | Cl | $OCH_3$ | CH | |
| H | O | — | Q-5 | — | — | $CH_3$ | O | H | Cl | $OCH_3$ | CH | |
| H | O | — | Q-5 | — | — | $CH_3$ | O | H | $CH_3$ | $OCH_3$ | CH | |
| H | O | — | Q-5 | — | — | $CH_3$ | O | H | $OCH_3$ | $OCH_3$ | CH | |
| H | O | — | Q-5 | — | — | $CH_3$ | O | H | $CH_3$ | $CH_3$ | CH | |
| H | O | — | Q-5 | — | — | $CH_3$ | O | H | $OCH_3$ | $CH_3$ | N | |
| H | O | — | Q-1 | $CH_3$ | — | — | O | H | $OCH_3$ | $OCH_3$ | CH | |
| H | O | — | Q-1 | $C_2H_5$ | — | — | O | H | $OCH_3$ | $OCH_3$ | N | |
| H | O | — | Q-3 | — | $CH_3$ | — | O | H | $CH_3$ | $CH_3$ | CH | |
| H | O | — | Q-3 | — | $C_2H_5$ | — | O | H | $OCH_3$ | $OCH_3$ | CH | |
| H | O | — | Q-3 | — | $C_2H_5$ | — | O | H | $OCH_3$ | $OCH_3$ | N | |
| H | O | — | Q-3 | — | $C_2H_5$ | — | O | H | $CH_3$ | $OCH_3$ | N | |
| H | O | — | Q-3 | — | $OCH_3$ | — | O | H | $OCH_3$ | $OCH_3$ | CH | |
| H | O | — | Q-3 | — | $OCH_3$ | — | O | H | $CH_3$ | $OCH_3$ | CH | |
| H | O | — | Q-3 | — | $OCH_3$ | — | O | H | $CH_3$ | $CH_3$ | CH | |
| H | O | — | Q-3 | — | $OCH_3$ | — | O | H | Cl | $OCH_3$ | CH | |
| H | O | — | Q-3 | — | $OCH_3$ | — | O | H | $OCH_3$ | $OCH_3$ | N | |
| H | O | — | Q-3 | — | $OCH_3$ | — | O | H | $CH_3$ | $OCH_3$ | N | |
| H | O | — | Q-4 | — | $CH_3$ | — | O | H | $OCH_3$ | $OCH_3$ | CH | |
| H | O | — | Q-4 | — | $CH_3$ | — | O | H | $CH_3$ | $OCH_3$ | CH | |
| H | O | — | Q-4 | — | $CH_3$ | — | O | H | $CH_3$ | $CH_3$ | CH | |
| H | O | — | Q-4 | — | $CH_3$ | — | O | H | Cl | $OCH_3$ | CH | |
| H | O | — | Q-4 | — | $CH_3$ | — | O | H | $OCH_3$ | $OCH_3$ | N | |
| H | O | — | Q-4 | — | $CH_3$ | — | O | H | $CH_3$ | $OCH_3$ | N | |
| H | O | — | Q-5 | — | — | $CH_3$ | O | H | $OCH_3$ | $OCH_3$ | N | |

TABLE XX

General Structure 20

| R1 | n | E | Q | R3 | R4 | R5 | W | R | X | Y | Z | m.p. (°C.) |
|---|---|---|---|---|---|---|---|---|---|---|---|---|
| H | O | — | Q-1 | $CH_3$ | — | — | O | H | $CH_3$ | $CH_3$ | CH | |
| H | O | — | Q-1 | $CH_3$ | — | — | O | H | $OCH_3$ | $CH_3$ | CH | |
| H | O | — | Q-1 | $CH_3$ | — | — | O | H | Cl | $OCH_3$ | CH | |
| H | O | — | Q-1 | $CH_3$ | — | — | O | H | $CH_3$ | $OCH_3$ | N | |
| H | O | — | Q-1 | $CH_3$ | — | — | O | H | $OCH_3$ | $OCH_3$ | N | |
| H | O | — | Q-1 | $C_2H_5$ | — | — | O | H | $OCH_3$ | $CH_3$ | CH | |
| H | O | — | Q-1 | $C_2H_5$ | — | — | O | H | $OCH_3$ | $OCH_3$ | CH | |
| H | O | — | Q-1 | $C_2H_5$ | — | — | O | H | Cl | $OCH_3$ | CH | |
| H | O | — | Q-1 | $C_2H_5$ | — | — | O | H | $CH_3$ | $CH_3$ | CH | |

TABLE XX-continued

| General Structure 20 | | | | | | | | | | | | | |
|---|---|---|---|---|---|---|---|---|---|---|---|---|---|
| $R_1$ | n | E | Q | $R_3$ | $R_4$ | $R_5$ | W | R | X | Y | Z | m.p. (°C.) |
| H | O | — | Q-1 | $C_2H_5$ | — | — | O | H | $CH_3$ | $OCH_3$ | N | |
| H | O | — | Q-2 | $CH_3$ | — | — | O | H | $OCH_3$ | $OCH_3$ | N | |
| H | O | — | Q-2 | $CH_3$ | — | — | O | H | $OCH_3$ | $OCH_3$ | CH | |
| H | O | — | Q-2 | $CH_3$ | — | — | O | H | $OCH_3$ | $CH_3$ | CH | |
| H | O | — | Q-2 | $CH_3$ | — | — | O | H | Cl | $OCH_3$ | CH | |
| H | O | — | Q-2 | $CH_3$ | — | — | O | H | $CH_3$ | $CH_3$ | CH | |
| H | O | — | Q-2 | $CH_3$ | — | — | O | H | $OCH_3$ | $CH_3$ | N | |
| H | O | — | Q-2 | $C_2H_5$ | — | — | O | H | $OCH_3$ | $OCH_3$ | CH | |
| H | O | — | Q-2 | $C_2H_5$ | — | — | O | H | $CH_3$ | $CH_3$ | CH | |
| H | O | — | Q-2 | $C_2H_5$ | — | — | O | H | $CH_3$ | $OCH_3$ | CH | |
| H | O | — | Q-2 | $C_2H_5$ | — | — | O | H | Cl | $OCH_3$ | CH | |
| H | O | — | Q-2 | $C_2H_5$ | — | — | O | H | $CH_3$ | $OCH_3$ | N | |
| H | O | — | Q-2 | $C_2H_5$ | — | — | O | H | $OCH_3$ | $OCH_3$ | N | |
| H | O | — | Q-3 | — | $CH_3$ | — | O | H | $CH_3$ | $OCH_3$ | CH | |
| H | O | — | Q-3 | — | $CH_3$ | — | O | H | Cl | $OCH_3$ | CH | |
| H | O | — | Q-3 | — | $CH_3$ | — | O | H | $OCH_3$ | $OCH_3$ | CH | |
| H | O | — | Q-3 | — | $CH_3$ | — | O | H | $OCH_3$ | $OCH_3$ | N | |
| H | O | — | Q-3 | — | $CH_3$ | — | O | H | $CH_3$ | $OCH_3$ | N | |
| H | O | — | Q-3 | — | $C_2H_5$ | — | O | H | $CH_3$ | $CH_3$ | CH | |
| H | O | — | Q-3 | — | $C_2H_5$ | — | O | H | $CH_3$ | $OCH_3$ | CH | |
| H | O | — | Q-3 | — | $C_2H_5$ | — | O | H | Cl | $OCH_3$ | CH | |
| H | O | — | Q-5 | — | — | $CH_3$ | O | H | Cl | $OCH_3$ | CH | |
| H | O | — | Q-5 | — | — | $CH_3$ | O | H | $CH_3$ | $OCH_3$ | CH | |
| H | O | — | Q-5 | — | — | $CH_3$ | O | H | $OCH_3$ | $OCH_3$ | CH | |
| H | O | — | Q-5 | — | — | $CH_3$ | O | H | $CH_3$ | $CH_3$ | CH | |
| H | O | — | Q-5 | — | — | $CH_3$ | O | H | $OCH_3$ | $CH_3$ | N | |
| H | O | — | Q-1 | $CH_3$ | — | — | O | H | $OCH_3$ | $OCH_3$ | CH | |
| H | O | — | Q-1 | $C_2H_5$ | — | — | O | H | $OCH_3$ | $OCH_3$ | N | |
| H | O | — | Q-3 | — | $CH_3$ | — | O | H | $CH_3$ | $CH_3$ | CH | |
| H | O | — | Q-3 | — | $C_2H_5$ | — | O | H | $OCH_3$ | $OCH_3$ | CH | |
| H | O | — | Q-3 | — | $C_2H_5$ | — | O | H | $OCH_3$ | $OCH_3$ | N | |
| H | O | — | Q-3 | — | $C_2H_5$ | — | O | H | $CH_3$ | $OCH_3$ | N | |
| H | O | — | Q-3 | — | $OCH_3$ | — | O | H | $OCH_3$ | $OCH_3$ | CH | |
| H | O | — | Q-3 | — | $OCH_3$ | — | O | H | $CH_3$ | $OCH_3$ | CH | |
| H | O | — | Q-3 | — | $OCH_3$ | — | O | H | $CH_3$ | $CH_3$ | CH | |
| H | O | — | Q-3 | — | $OCH_3$ | — | O | H | Cl | $OCH_3$ | CH | |
| H | O | — | Q-3 | — | $OCH_3$ | — | O | H | $OCH_3$ | $OCH_3$ | N | |
| H | O | — | Q-3 | — | $OCH_3$ | — | O | H | $CH_3$ | $OCH_3$ | N | |
| H | O | — | Q-4 | — | $CH_3$ | — | O | H | $OCH_3$ | $OCH_3$ | CH | |
| H | O | — | Q-4 | — | $CH_3$ | — | O | H | $CH_3$ | $OCH_3$ | CH | |
| H | O | — | Q-4 | — | $CH_3$ | — | O | H | $CH_3$ | $CH_3$ | CH | |
| H | O | — | Q-4 | — | $CH_3$ | — | O | H | Cl | $OCH_3$ | CH | |
| H | O | — | Q-4 | — | $CH_3$ | — | O | H | $OCH_3$ | $OCH_3$ | N | |
| H | O | — | Q-4 | — | $CH_3$ | — | O | H | $CH_3$ | $OCH_3$ | N | |
| H | O | — | Q-5 | — | — | $CH_3$ | O | H | $OCH_3$ | $OCH_3$ | N | |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid inert diluent(s). More specifically, they will contain these ingredients in the following approximate proportions:

| | Active Ingredient | Weight Percent* | |
|---|---|---|---|
| | | Diluent(s) | Surfactant(s) |
| Wettable Powders | 20-90 | 0-74 | 1-10 |
| Oil Suspensions, Emulsions, Solutions, (including Emulsifiable Concentrates) | 3-50 | 40-95 | 0-15 |
| Aqueous Suspension | 10-50 | 40-84 | 1-20 |
| Dusts | 1-25 | 70-99 | 0-5 |
| Granules and Pellets | 0.1-95 | 5-99.9 | 0-15 |
| High Strength Compositions | 90-99 | 0-10 | 0-2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are somtimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 5th Ed., McGraw-Hill, New York, 1973, pp. 8-57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7 line and Examples 8, 12, 15, 39, 41, 52, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley & Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE 16

| Wettable Powder | |
|---|---|
| N-[(4,6-dimethoxypyrimidin-2-yl)aminocarbonyl]-2-(1-methyl-1H-tetrazol-5-yl)benzenesulfonamide | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 17

| Wettable Powder | |
|---|---|
| N-[(4,6-dimethoxypyrimidin-2-yl)aminocarbonyl]-2-(5-methyl-1H-tetrazol-1-yl)benzenesulfonamide | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 18

| Granule | |
|---|---|
| Wettable Powder of Example 17 (above) | 5% |
| attapulgite granules (U.S.S. 20–40 mesh; 0.84–0.42 mm) | 95% |

A slurry of wettable powder containing 25% solids is sprayed on the surface of attapulgite granules while tumbling in a double-cone blender. The granules are dried and packaged.

EXAMPLE 19

| Extruded Pellet | |
|---|---|
| N-[(4,6-dimethoxypyrimidin-2-yl)aminocarbonyl]-2-(5-methyl-1H-tetrazol-1-yl)benzenesulfonamide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 20

| Oil Suspension | |
|---|---|
| N-[(4,6-dimethoxypyrimidin-2-yl)aminocarbonyl]-2-(1-methyl-1H-tetrazol-5-yl)benzenesulfonamide | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 21

| Wettable Powder | |
|---|---|
| N-[(4,6-dimethoxypyrimidin-2-yl)aminocarbonyl]-2-(5-methyl-1H-tetrazol-1-yl)benzenesulfonamide | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 22

| Low Strength Granule | |
|---|---|
| N-[(4,6-dimethoxypyrimidin-2-yl)aminocarbonyl]-2-(1- | 1% |

-continued

| Low Strength Granule | |
|---|---|
| methyl-1H-tetrazol-5-yl)benzenesulfonamide | |
| N,N-dimethylformamide | 9% |
| attapulgite granules (U.S.S. 20-40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 23

| Aqueous Suspension | |
|---|---|
| N-[(4,6-dimethoxypyrimidin-2-yl)aminocarbonyl]-2-(1-methyl-1H-tetrazol-5-yl)benzenesulfonamide | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 24

| Solution | |
|---|---|
| N-[(4,6-dimethoxypyrimidin-2-yl)aminocarbonyl]-2-(1-methyl-1H-tetrazol-5-yl)benzenesulfonamide, Sodium Salt | 5% |
| water | 95% |

The salt is added directly to the water with stirring to produce the solution, which may then be packaged for use.

EXAMPLE 25

| Low Strength Granule | |
|---|---|
| N-[(4,6-dimethoxypyrimidin-2-yl)aminocarbonyl]-2-(1-methyl-1H-tetrazol-5-yl)benzenesulfonamide | 0.1% |
| attapulgite granules (U.S.S. 20-40 mesh) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 26

| Granule | |
|---|---|
| N-[(4,6-dimethoxypyrimidin-2-yl)aminocarbonyl]-2-(1-methyl-1H-tetrazol-5-yl)benzenesulfonamide | 80% |
| wetting agent | 1% |
| crude ligninsulfonate salt (containing 5-20% of the natural sugars) | 10% |
| attapulgite clay | 9% |

The ingredients are blended and milled to pass through a 100 mesh screen. This material is then added to a fluid bed granulator, the air flow is adjusted to gently fluidize the material and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14-100 mesh (1410-149 microns), and packaged for use.

EXAMPLE 27

| High Strength Concentrate | |
|---|---|
| N-[(4,6-dimethoxypyrimidin-2-yl)aminocarbonyl]-2-(1-methyl-1H-tetrazol-5-yl)benzenesulfonamide | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE 28

| Wettable powder | |
|---|---|
| N-[(4,6-dimethoxypyrimidin-2-yl)aminocarbonyl]-2-(1-methyl-1H-tetrazol-5-yl)benzenesulfonamide | 90% |
| dioctyl sodium sulfosuccinate | 0.1% |
| synthetic fine silica | 9.9% |

The ingredients are blended and ground in a hammer-mill to produce particles essentially all below 100 microns. The material is sifted through a U.S.S. No. 50 screen and then packaged.

EXAMPLE 29

| Wettable Powder | |
|---|---|
| N-[(4,6-dimethoxypyrimidin-2-yl)aminocarbonyl]-2-(1-methyl-1H-tetrazol-5-yl)benzenesulfonamide | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 30

| Oil Suspension | |
|---|---|
| N-[(4,6-dimethoxypyrimidin-2-yl)aminocarbonyl]-2-(1-methyl-1H-tetrazol-5-yl)benzenesulfonamide | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

EXAMPLE 31

| Dust | |
|---|---|
| N-[(4,6-dimethoxypyrimidin-2-yl)aminocarbonyl]-2-(1-methyl-1H-tetrazol-5-yl)benzenesulfonamide | 10% |
| attapulgite | 10% |
| Pyrophyllite | 80% |

The active ingredient is blended with attapulgite and then passed through a hammer-mill to produce particles substantially all below 200 microns. The ground concentrate is then blended with powdered pyrophyllite until homogeneous.

EXAMPLE 32

| Wettable Powder | |
|---|---|
| N-[[N-(4,6-dimethoxy-1,3,5-triazin-2-yl)-N-methyl-amino]carbonyl]-2-(5-methyl-1H-tetrazol-1-yl)-benzenesulfonamide | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 33

| Granule | |
|---|---|
| Wettable Powder of Example 32 (above) | 5% |
| attapulgite granules (U.S.S. 20-40 mesh; 0.84-0.42 mm) | 95% |
| A slurry of wettable powder containing | 25% |

A slurry of wettable powder containing 25% solids is sprayed on the surface of attapulgite granules while tumbling in a double-cone blender. The granules are dried and packaged.

EXAMPLE 34

| Extruded Pellet | |
|---|---|
| N-[[N-(4,6-dimethoxy-1,3,5-triazin-2-yl)-N-methyl-amino]carbonyl]-2-(5-methyl-1H-tetrazol-1-yl)-benzenesulfonamide | 25% |
| anhydrous sodium sulfate | 10% |
| crude calcium ligninsulfonate | 5% |
| sodium alkyulnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 35

| Oil Suspension | |
|---|---|
| N-[[N-(4,6-dimethoxy-1,3,5-triazin-2-yl)-N-methyl-amino]carbonyl]-2-(5-methyl-1H-tetrazol-1-yl)-benzenesulfonamide | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 36

| Wettable Powder | |
|---|---|
| N-[[N-(4,6-dimethoxy-1,3,5-triazin-2-yl)-N-methyl-amino]carbonyl]-2-(5-methyl-1H-tetrazol-1-yl)-benzenesulfonamide | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 37

| Low Strength Granule | |
|---|---|
| N-[[N-(4,6-dimethoxy-1,3,5-triazin-2-yl)-N-methyl-amino]carbonyl]-2-(5-methyl-1H-tetrazol-1-yl)-benzenesulfonamide | 1% |
| N,N-dimethylformamide | 9% |
| attapulgite granules | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 38

| Aqueous Suspension | |
|---|---|
| N-[[N-(4,6-dimethoxy-1,3,5-triazin-2-yl)-N-methyl-amino]carbonyl]-2-(5-methyl-1H-tetrazol-1-yl)-benzenesulfonamide | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mil to produce particles essentially all under 5 microns in size.

EXAMPLE 39

| Solution | |
|---|---|
| N-[[N-(4,6-dimethoxy-1,3,5-triazin-2-yl)-N-methylamino]carbonyl]-2-(5-methyl-1H-tetrazol-1-yl)-benzenesulfonamide, sodium salt | 5% |
| water | 95% |

The salt is added directly to the water with stirring to produce the solution, which may then be packaged for use.

EXAMPLE 40

| Low Strength Granule | |
|---|---|
| N-[[N-(4,6-dimethoxy-1,3,5-triazin-2-yl)-N-methylamino]carbonyl]-2-(5-methyl-1H-tetrazol-1-yl)-benzenesulfonamide | 0.1% |
| attapulgite granules (U.S.S. 20–40 mesh) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 41

| Granule | |
|---|---|
| N-[[N-(4,6-dimethoxy-1,3,5-triazin-2-yl)-N-methylamino]carbonyl]-2-(5-methyl-1H-tetrazol-1-yl)-benzenesulfonamide | 80% |
| wetting agent | 1% |
| crude ligninsulfonate salt (containing 5–20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14–100 mesh (1410–149 microns), and packaged for use.

EXAMPLE 42

| High Strength Concentrate | |
|---|---|
| N-[[N-(4,6-dimethoxy-1,3,5-triazin-2-yl)-N-methylamino]carbonyl]-2-(5-methyl-1H-tetrazol-1-yl)-benzenesulfonamide | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE 43

| Example 43<br>Wettable Powder | |
|---|---|
| N-[[N-(4,6-dimethoxy-1,3,5-triazin-2-yl)-N-methylamino]carbonyl]-2-(5-methyl-1H-tetrazol-1-yl)-benzenesulfonamide | 90% |
| dioctyl sodium sulfosuccinate | 0.1% |
| synthetic fine silica | 9.9% |

The ingredients are blended and ground in a hammer-mill to produce particles essentially all below 100 microns. The material is sifted through a U.S.S. No. 50 screen and then packaged.

EXAMPLE 44

| Example 44<br>Wettable Powder | |
|---|---|
| N-[[N-(4,6-dimethoxy-1,3,5-triazin-2-yl)-N-methylamino]carbonyl]-2-(5-methyl-1H-tetrazol-1-yl)-benzenesulfonamide | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 45

| Example 45<br>Oil Suspension | |
|---|---|
| N-[[N-(4,6-dimethoxy-1,3,5-triazin-2-yl)-N-methylamino]carbonyl]-2-(5-methyl-1H-tetrazol-1-yl)-benzenesulfonamide | 35% |
| blend of Polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

EXAMPLE 46

| Example 46<br>Dust | |
|---|---|
| N-[(4,6-dimethoxypyrimidin-2-yl)aminocarbonyl]-2-(1-methyl-1H-tetrazol-5-yl)benzenesulfonamide | 10% |
| attapulgite | 10% |
| Pyrophyllite | 80% |

The active ingredient is blended with attapulgite and then passed through a hammer-mill to produce particles substantially all below 200 microns. The ground concentrate is then blended with powdered pyrophyllite until homogeneous.

Utility

Test results indicate that the compounds of the present invention are highly active preemergent or postemergent herbicides or plant growth regulants. They haVe utility for broad-spectrum pre- and/or post-emergence weed control in areas where complete control of all vegetation is desired, such as around fuel storage tanks, industrial storage areas, parking lots, drive-in theaters, around billboards, highway and railroad structures. Some of the compounds have utility for selective weed control in crops such as corn, rice, wheat, barley, soybean and rape. Alternatively, many of the subject compounds are useful to modify plant growth.

The rates of application for the compounds of the invention are determined by a number of factors, including their use as plant growth modifiers or as herbicides, the crop species involved, the types of weeds to be controlled, weather and climate, formulations selected, mode of application, amount of foliage present, etc. In general terms, the subject compounds should be applied at levels of about 0.001 to 10 kg/ha, the lower rates being suggested for use on lighter soils and/or those having a low organic matter content, for plant growth modification or for situations where only short-term persistence is required.

The compounds of the invention may be used in combination with any other commercial herbicide, examples of which are those of the triazine, triazole, uracil, urea, amide, diphenylether, carbamate, phenoxyacetic acid and bipyridylium types, as well as other sulfonylureas. They are particularly useful in combination with the following herbicides.

| | Chemical Name |
|---|---|
| Common Name | |
| alachlor | 2-chloro 2',6'-diethyl-N-(methoxymethyl)-acetanilide |
| atrazine | 2-chloro-4-(ethylamino)-6-(isopropyl-amino)-s-triazine |
| butylate | S-ethyl-diisobutylthiocarbamate |
| cyanazine | 2-[[4-chloro-6-(ethylamino)-s-triazin-2-yl]amino]-2-ethylpropionitrile |
| dicamba | 3,6-dichloro-o-anisic acid |
| EPTC | S-ethyl dipropylthiocarbamate |
| glyphosate | N-(phosphonomethyl)glycine |
| linuron | 3-(3,4-dichlorophenyl)-1-methoxy-1-methylurea |
| metolachlor | 2-chloro-N-(2-ethyl-6-methylphenyl)-N-(2-methoxy-1-methylethyl)acetamide |
| metribuzin | 4-amino-6-tert-butyl-3-(methylthio)-as-triazine-5(4H)-one |
| tridiphane | 2-(3,5-dichlorophenyl)-2-(2,2,2-tri-chloroethyl)oxirane |
| 2,4-D | (2,4-dichlorophenoxy)acetic acid |
| thiobencarb | S-4-chlorobenzyldiethylthiocarbamate |
| molinate | S-ethyl N,N-hexamethylenethiocarbamate |
| butachlor | N-(butoxymethyl)-2-chloro-2',6'-di-ethylacetanilide |
| naproanilide | N-phenyl-2-(1-naphthyloxy)propionamide |
| paraquat | 1,1'-dimethyl-4,4'-bipyridinium ion |
| pyrazolate | 4-(2,4-dichlorobenzoyl)-1,3-dimethyl-pyrazol-5-yl-4-toluenesulfonate |
| pretilachlor | 2-chloro 2',6'-diethyl-N-(n-propoxy-ethyl)acetanilide |
| oxidazon | 3-[2,4-dichloro-5-(1-methylethoxy)-phenyl]-5-(1,1-dimethylethyl)-1,3,4-oxadiazol-2(3H)-one |
| Trade Name or Code Number | |
| Harmony ® | 3-[[(4-methoxy-6-methyl-1,3,5-triazin-2-yl)aminocarbonyl]aminosulfonyl]-2-thiophenecarboxylic acid, methyl ester |
| Cinch ® | exo-1-methyl-4-(1-methylethyl)-2-[(2-methylphenyl)methoxy]-7-oxabicyclo-[2.2.1]heptane |
| MY-93 | S-(1-methyl-1-phenethyl)piperidine-1-carbothioate |
| CH-83 | S-(2-methylpropyl)-hexanhydro-1H-azepine-1-carbothioic acid, ester |
| X-52 | 2,4-dichlorophenyl-3-methoxy-4-nitro-phenyl ether |
| SC-2957 | S-benzyl-N-ethyl-N-propylthiocarbamate |
| HW-52 | N-(2,3-dichlorophenyl)-4-(ethoxy-methoxy)benzamide |
| NTN-801 | 2-(benzothiazol-2-yl)-N-methyl-N-phenylacetamide |
| SL-49 | 2-[4-[(2,4-dichlorophenyl)carbonyl]-1,3-dimethyl-1H-pyrazol-5-yloxy]-1-phenylethanone |
| BAS-514 | 3,7-dichloro-8-quinoline carboxylic acid |
| Assure ® | ethyl 2-[4-(6-chloro-2-quinoxalinyloxy)-phenoxy]-propionate |
| DPX-L5300 (Express ®) | 2-[[N-(4-methoxy-6-methyl-1,3,5-triazine-2-yl)-N-methylaminocarbonyl)]-aminosulfonyl]benzoic acid, methyl ester |

| Common Name | Tradename | Chemical Name |
|---|---|---|
| acifluorfen | Blazer ® | 5-[2-chloro-4-(trifluoro-methyl)phenoxy]-2-ni-trobenzoic acid |
| alachlor | Lasso ® | 2-chloro-2',6'-diethyl-N-(methoxymethyl)acet-anilide |
| bentazon | Basagran ® | 3-isopropyl-1H-2,1,3-benzothiadiazin-4(3H)-one 2,2-dioxide |
| chloramben | Amiben ® | 3-amino-2,5-dichloro-benzoic acid |
| fluazifop-butyl | Fusilade ® | butyl 2-4-[5-(trifluoro-methyl)-2-pyridinyl-oxy]phenoxy] propanoate |
| linuron | Lorox ® | 3-(3,4-dichlorophenyl)-1-methoxy-1-methylurea |
| metolachlor | Dual ® | 2-chloro-N-(2-ethyl-6-methylphenyl)-N-(2-methoxy-1-methylethyl)-acetamide |
| metribuzin | Lexone ® | 4-amino-6-tert-butyl-3-(methylthio)-as-tri-azin-5(4H)one |
| pendimethalin | Prowl ® | N-(1-ethylpropyl)-3,4-dimethyl-2,6-dinitro-benzeneamine |
| sethoxydim | Poast ® | 2-[1-(ethoxyimino)butyl]-5-[2-(ethylthio)-propyl]-3-hydroxy-2-cyclohexene-1-one |
| trifluralin | Treflan ® | α,α,α-trifluoro-2-6-di-nitro-N-N-dipropyl-p-toluidine |
| AC 252,214 | — | 2-(4-5-dihydro-4-methyl-4-(1-methylethyl)-5-oxo-1H-imidazol-2-yl)-3-quinolinecarboxylic acid |
| FMC 57020 | — | 2-(2'-chlorophenyl)-methyl-4,4-dimethyl-3-isoxazolidinone |
| fomesafen | Flex ® | 5-(2-chloro-4-trifluoro-methylphenoxy)-N-methylsulfonyl-2-nitro-benzamide |
| lactofen | — | 1'-(carboethoxy)ethyl-5-(2-chloro-4-(trifluoro-methyl)phenoxy)-2-nitrobenzoate |
| DOWCO 453 ME | | 2-(4-(3-chloro-5-tri-fluoromethylpyridin-2-yloxy)phenoxy)propanoic acid, methyl ester |
| fenoxaprop ethyl | Whip ® | ethyl 2-(4-(6-chloro-2-benzoxazolyloxy)phen-oxy)propanoate |
| CGA 82725 | Topik ® | 2-(4-(3,5-dichloropyri-din-2-yloxy)phenoxy- |

-continued

| Common Name | Tradename | Chemical Name |
| --- | --- | --- |
| | | propanoic acid, propynyl ester |
| chlorimuron ethyl | Classic ® | 2-[[(4-chloro-6-methoxypyrimidin-2-yl)aminocarbonyl]aminosulfonyl]benzoic acid ethyl ester |
| cinmethylin | Cinch ® | exo-1-methyl-4-(1-methylethyl)-2-[(2-methylphenyl)methoxy]-7-oxabicyclo[2.2.1]heptane |
| AC 263,499 | Pursuit ® | 2-[4,5-dihydro-4-methyl-4-(1-methylethyl)-5-oxo-1H-imidazol-2-yl)]-5-ethyl-3-pyridinecarboxylic acid |
| AC 252,214 | Scepter ® | 2-[4,5-dihydro-4-methyl-4-(1-methylethyl)-5-oxo-1H-imidazol-2-yl]-3-quinolinecarboxylic acid |

The herbicidal properties of the subject compounds were discovered in a number of greenhouse tests. The test procedures and results follow.

COMPOUNDS

General Structures for Compounds 1-58

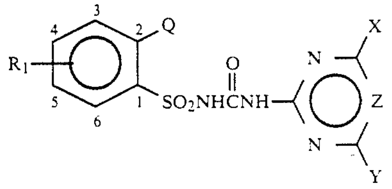

Q is

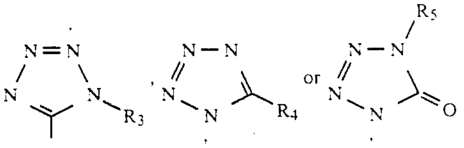

Q-1, Q-3 or Q-5

| Compound | Q | $R_1$ | $R_3$ | $R_4$ | $R_5$ | X | Y | Z |
| --- | --- | --- | --- | --- | --- | --- | --- | --- |
| 1 | Q-3 | H | — | $CH_3$ | — | $OCH_3$ | $CH_3$ | N |
| 2 | Q-3 | H | — | $CH_3$ | — | $OCH_3$ | $OCH_3$ | CH |
| 3 | Q-1 | H | $CH_3$ | — | — | $OCH_3$ | $OCH_3$ | CH |
| 4 | Q-3 | H | — | $CH_3$ | — | $CH_3$ | $OCH_3$ | CH |
| 5 | Q-3 | H | — | $CH_3$ | — | Cl | $OCH_3$ | CH |
| 6 | Q-3 | H | — | $CH_3$ | — | $OCH_3$ | $OCH_3$ | N |
| 7 | Q-3 | H | — | $CH_3$ | — | $NHCH_3$ | $OCH_2CH_3$ | N |
| 8 | Q-3 | H | — | H | — | $OCH_3$ | $OCH_3$ | N |
| 9 | Q-3 | H | — | H | — | Cl | $OCH_3$ | CH |
| 10 | Q-3 | H | — | H | — | $CH_3$ | $OCH_3$ | CH |
| 11 | Q-3 | H | — | H | — | $CH_3$ | $CH_3$ | CH |
| 12 | Q-3 | H | — | H | — | $CH_3$ | $OCH_3$ | N |
| 13 | Q-3 | H | — | H | — | $OCH_3$ | $OCH_3$ | CH |
| 14 | Q-3 | 5-$CH_3$ | — | $CH_3$ | — | $OCH_3$ | $OCH_3$ | CH |
| 15 | Q-3 | 5-$CH_3$ | — | $CH_3$ | — | $CH_3$ | $OCH_3$ | N |
| 16 | Q-3 | 5-$CH_3$ | — | $CH_3$ | — | Cl | $OCH_3$ | CH |
| 17 | Q-3 | H | — | $CH_2CH_3$ | — | $CH_3$ | $OCH_3$ | CH |
| 18 | Q-3 | H | — | $CH_2CH_3$ | — | $OCH_3$ | $OCH_3$ | CH |
| 19 | Q-3 | H | — | $CH_2CH_3$ | — | $CH_3$ | $CH_3$ | CH |
| 20 | Q-3 | H | — | $CH_2CH_3$ | — | Cl | $OCH_3$ | CH |
| 21 | Q-3 | H | — | $CH_2CH_3$ | — | $OCH_3$ | $OCH_3$ | N |
| 22 | Q-3 | H | — | $CH_2CH_3$ | — | $CH_3$ | $OCH_3$ | N |
| 23 | Q-3 | 5-Cl | — | $CH_3$ | — | $OCH_3$ | $OCH_3$ | CH |
| 24 | Q-3 | 5-Cl | — | $CH_3$ | — | $CH_3$ | $OCH_3$ | CH |
| 25 | Q-3 | 5-Cl | — | $CH_3$ | — | $OCH_3$ | $OCH_3$ | N |
| 26 | Q-3 | 5-Cl | — | $CH_3$ | — | $CH_3$ | $OCH_3$ | N |
| 27 | Q-3 | 5-Cl | — | $CH_3$ | — | $CH_3$ | $CH_3$ | CH |
| 28 | Q-3 | 5-Cl | — | $CH_3$ | — | Cl | $OCH_3$ | CH |
| 29 | Q-3 | 5-Cl | — | $CH_3$ | — | $NHCH_3$ | $OCH_2CH_3$ | N |
| 30 | Q-1 | H | $CH_2CH_3$ | — | — | $OCH_3$ | $OCH_3$ | N |
| 31 | Q-1 | H | $CH_2CH_3$ | — | — | $CH_3$ | $OCH_3$ | N |
| 32 | Q-1 | H | $CH_2CH_3$ | — | — | $OCH_3$ | $OCH_3$ | CH |
| 33 | Q-1 | H | $CH_2CH_3$ | — | — | $CH_3$ | $OCH_3$ | CH |
| 34 | Q-1 | H | $CH_2CH_3$ | — | — | $CH_3$ | $CH_3$ | CH |
| 35 | Q-1 | H | $CH_2CH_3$ | — | — | Cl | $OCH_3$ | CH |
| 36 | Q-1 | H | $CH_2CH_3$ | — | — | $NHCH_3$ | $OCH_2CH_3$ | N |
| 37 | Q-1 | 3-$CH_3$ | $CH_3$ | — | — | $OCH_3$ | $OCH_3$ | N |
| 38 | Q-1 | 3-$CH_3$ | $CH_3$ | — | — | $CH_3$ | $OCH_3$ | N |
| 39 | Q-1 | 3-$CH_3$ | $CH_3$ | — | — | $OCH_3$ | $OCH_3$ | CH |
| 40 | Q-1 | 3-$CH_3$ | $CH_3$ | — | — | $CH_3$ | $OCH_3$ | CH |
| 41 | Q-1 | 3-$CH_3$ | $CH_3$ | — | — | $CH_3$ | $CH_3$ | CH |
| 42 | Q-1 | 3-$CH_3$ | $CH_3$ | — | — | Cl | $OCH_3$ | CH |
| 43 | Q-1 | 3-$CH_3$ | $CH_3$ | — | — | $NHCH_3$ | $OCH_2CH_3$ | N |

-continued

General Structures for Compounds 1-58

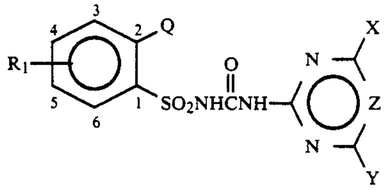

Q is

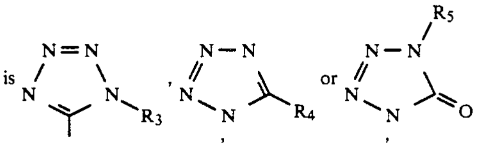

Q-1, Q-3 or Q-5

| Compound | Q | $R_1$ | $R_3$ | $R_4$ | $R_5$ | X | Y | Z |
|---|---|---|---|---|---|---|---|---|
| 44 | Q-1 | 4-$CH_3$ | $CH_3$ | — | — | $OCH_3$ | $OCH_3$ | N |
| 45 | Q-1 | 4-$CH_3$ | $CH_3$ | — | — | $CH_3$ | $OCH_3$ | N |
| 46 | Q-1 | 4-$CH_3$ | $CH_3$ | — | — | $OCH_3$ | $OCH_3$ | CH |
| 47 | Q-1 | 4-$CH_3$ | $CH_3$ | — | — | $CH_3$ | $OCH_3$ | CH |
| 48 | Q-1 | 4-$CH_3$ | $CH_3$ | — | — | $CH_3$ | $CH_3$ | CH |
| 49 | Q-1 | 4-$CH_3$ | $CH_3$ | — | — | Cl | $OCH_3$ | CH |
| 50 | Q-1 | 4-$CH_3$ | $CH_3$ | — | — | $NHCH_3$ | $OCH_2CH_3$ | N |
| 51 | Q-1 | 6-$CH_3$ | $CH_3$ | — | — | $OCH_3$ | $OCH_3$ | N |
| 52 | Q-1 | 6-$CH_3$ | $CH_3$ | — | — | $CH_3$ | $OCH_3$ | N |
| 53 | Q-1 | 6-$CH_3$ | $CH_3$ | — | — | $OCH_3$ | $OCH_3$ | CH |
| 54 | Q-1 | 6-$CH_3$ | $CH_3$ | — | — | $CH_3$ | $OCH_3$ | CH |
| 55 | Q-1 | 6-$CH_3$ | $CH_3$ | — | — | $CH_3$ | $CH_3$ | CH |
| 56 | Q-1 | 6-$CH_3$ | $CH_3$ | — | — | Cl | $OCH_3$ | CH |
| 57 | Q-5 | H | — | — | $CH_3$ | $OCH_3$ | $OCH_3$ | CH |
| 58 | Q-5 | H | — | — | $CH_3$ | $CH_3$ | $OCH_3$ | N |

General Structures for Compounds 59-63

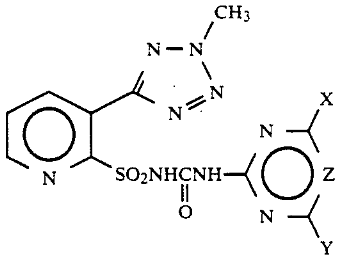

| Compound | X | Y | Z |
|---|---|---|---|
| 59 | $OCH_3$ | $OCH_3$ | CH |
| 60 | $CH_3$ | $OCH_3$ | CH |
| 61 | $CH_3$ | $CH_3$ | CH |

-continued

General Structures for Compounds 59-63

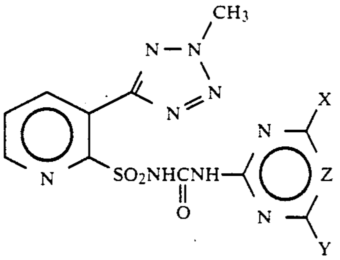

| Compound | X | Y | Z |
|---|---|---|---|
| 62 | $OCH_3$ | $OCH_3$ | N |
| 63 | Cl | $OCH_3$ | CH |

General Structures for Compounds 64–179

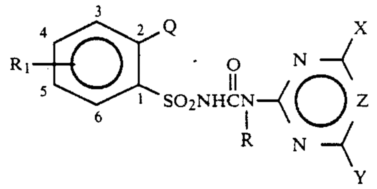

Q is 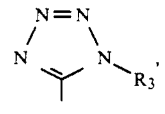, 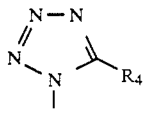 or 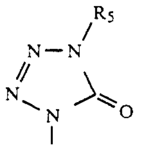

Q-1 Q-3 Q-5

| Compound | Q | R | $R_1$ | $R_3$ | $R_4$ | $R_5$ | X | Y | Z |
|---|---|---|---|---|---|---|---|---|---|
| 64 | Q-1 | H | 6-Cl | $CH_3$ | — | — | $OCH_3$ | $OCH_3$ | N |
| 65 | Q-1 | H | 6-Cl | $CH_3$ | — | — | $CH_3$ | $OCH_3$ | N |
| 66 | Q-1 | H | 6-Cl | $CH_3$ | — | — | $OCH_3$ | $OCH_3$ | CH |
| 67 | Q-1 | H | 6-Cl | $CH_3$ | — | — | $CH_3$ | $OCH_3$ | CH |
| 68 | Q-1 | H | 6-Cl | $CH_3$ | — | — | $CH_3$ | $CH_3$ | CH |
| 69 | Q-1 | H | 6-Cl | $CH_3$ | — | — | Cl | $OCH_3$ | CH |
| 70 | Q-1 | H | 3-Cl | $CH_3$ | — | — | $OCH_3$ | $OCH_3$ | N |
| 71 | Q-1 | H | 3-Cl | $CH_3$ | — | — | $CH_3$ | $OCH_3$ | N |
| 72 | Q-1 | H | 3-Cl | $CH_3$ | — | — | $OCH_3$ | $OCH_3$ | CH |
| 73 | Q-1 | H | 3-Cl | $CH_3$ | — | — | $CH_3$ | $OCH_3$ | CH |
| 74 | Q-1 | H | 3-Cl | $CH_3$ | — | — | $CH_3$ | $CH_3$ | CH |
| 75 | Q-1 | H | 3-Cl | $CH_3$ | — | — | Cl | $OCH_3$ | CH |
| 76 | Q-3 | H | H | — | $OCH_2CH_3$ | — | $OCH_3$ | $OCH_3$ | CH |
| 77 | Q-3 | H | H | — | $OCH_2CH_3$ | — | $CH_3$ | $OCH_3$ | CH |
| 78 | Q-3 | H | H | — | $OCH_2CH_3$ | — | $CH_3$ | $CH_3$ | CH |
| 79 | Q-3 | H | H | — | $OCH_2CH_3$ | — | Cl | $OCH_3$ | CH |
| 80 | Q-3 | H | H | — | $OCH_2CH_3$ | — | $OCH_3$ | $OCH_3$ | N |
| 81 | Q-3 | H | H | — | $OCH_2CH_3$ | — | $CH_3$ | $OCH_3$ | N |
| 82 | Q-3 | H | H | — | $OCH_3$ | — | $OCH_3$ | $OCH_3$ | CH |
| 83 | Q-3 | H | H | — | $OCH_3$ | — | $CH_3$ | $OCH_3$ | CH |
| 84 | Q-3 | H | H | — | $OCH_3$ | — | $CH_3$ | $CH_3$ | CH |
| 85 | Q-3 | H | H | — | $OCH_3$ | — | Cl | $OCH_3$ | CH |
| 86 | Q-3 | H | H | — | $OCH_3$ | — | $OCH_3$ | $OCH_3$ | N |
| 87 | Q-3 | H | H | — | $OCH_3$ | — | $CH_3$ | $OCH_3$ | N |
| 88 | Q-3 | H | H | — | $OCH_2CH_2CH_3$ | — | $OCH_3$ | $OCH_3$ | CH |
| 89 | Q-3 | H | H | — | $OCH_2CH_2CH_3$ | — | $CH_3$ | $OCH_3$ | CH |
| 90 | Q-3 | H | H | — | $OCH_2CH_2CH_3$ | — | $CH_3$ | $CH_3$ | CH |
| 91 | Q-3 | H | H | — | $OCH_2CH_2CH_3$ | — | Cl | $OCH_3$ | CH |
| 92 | Q-3 | H | H | — | $OCH_2CH_2CH_3$ | — | $OCH_3$ | $OCH_3$ | N |
| 93 | Q-3 | H | H | — | $OCH_2CH_2CH_3$ | — | $CH_3$ | $OCH_3$ | N |
| 94 | Q-1 | H | 6-Cl | $CH_3$ | — | — | $OCF_2H$ | $OCH_3$ | CH |
| 95 | Q-1 | H | 6-Cl | $CH_3$ | — | — | $OCF_2H$ | $CH_3$ | CH |
| 96 | Q-1 | H | H | $CH_2CH_3$ | — | — | $OCF_2H$ | $OCH_3$ | CH |
| 97 | Q-1 | H | 5-F | $CH_3$ | — | — | $OCH_3$ | $OCH_3$ | CH |
| 98 | Q-1 | H | 5-F | $CH_3$ | — | — | Cl | $OCH_3$ | CH |
| 99 | Q-5 | H | 5-$CH_3$ | — | — | $CH_2CH_3$ | $OCH_3$ | $OCH_3$ | CH |
| 100 | Q-5 | H | 5-$CH_3$ | — | — | $CH_2CH_3$ | Cl | $OCH_3$ | CH |
| 101 | Q-5 | H | 5-$CH_3$ | — | — | $CH_2CH_3$ | $CH_3$ | $CH_3$ | CH |
| 102 | Q-5 | H | 5-$CH_3$ | — | — | $CH_2CH_3$ | $CH_3$ | $OCH_3$ | CH |
| 103 | Q-1 | H | 5-$OCH_3$ | $CH_3$ | — | — | Cl | $OCH_3$ | CH |
| 104 | Q-1 | H | 5-$OCH_3$ | $CH_3$ | — | — | $OCH_3$ | $OCH_3$ | CH |
| 105 | Q-1 | H | 5-$OCH_3$ | $CH_3$ | — | — | $CH_3$ | $OCH_3$ | CH |
| 106 | Q-1 | H | 5-$OCH_3$ | $CH_3$ | — | — | $CH_3$ | $CH_3$ | CH |
| 107 | Q-3 | H | 5-$CH_3$ | — | $OCH_3$ | — | $OCH_3$ | $OCH_3$ | CH |
| 108 | Q-3 | H | 5-$CH_3$ | — | $OCH_3$ | — | $CH_3$ | $OCH_3$ | CH |
| 109 | Q-3 | H | 5-$CH_3$ | — | $OCH_3$ | — | $CH_3$ | $CH_3$ | CH |
| 110 | Q-3 | H | 5-$CH_3$ | — | $OCH_3$ | — | Cl | $OCH_3$ | CH |
| 111 | Q-3 | H | 5-$CH_3$ | — | $OCH_3$ | — | $OCH_3$ | $OCH_3$ | N |
| 112 | Q-3 | H | 5-$CH_3$ | — | $OCH_3$ | — | $CH_3$ | $OCH_3$ | N |
| 113 | Q-1 | H | 5-F | $CH_3$ | — | — | $OCH_3$ | $OCH_3$ | N |
| 114 | Q-1 | H | 5-F | $CH_3$ | — | — | $CH_3$ | $OCH_3$ | N |
| 115 | Q-1 | H | 5-F | $CH_3$ | — | — | $CH_3$ | $CH_3$ | CH |
| 116 | Q-1 | H | 5-F | $CH_3$ | — | — | $CH_3$ | $OCH_3$ | CH |
| 117 | Q-5 | H | 5-$CH_3$ | — | — | $CH_2CH_3$ | $OCH_3$ | $OCH_3$ | N |
| 118 | Q-5 | H | 5-$CH_3$ | — | — | $CH_2CH_3$ | $CH_3$ | $OCH_3$ | N |
| 119 | Q-1 | H | 6-$OCH_3$ | $CH_3$ | — | — | $OCH_3$ | $OCH_3$ | CH |
| 120 | Q-1 | H | 6-$OCH_3$ | $CH_3$ | — | — | $OCH_3$ | $OCH_3$ | N |
| 121 | Q-1 | H | 6-$OCH_3$ | $CH_3$ | — | — | $CH_3$ | $OCH_3$ | CH |
| 122 | Q-1 | H | 6-$OCH_3$ | $CH_3$ | — | — | $CH_3$ | $OCH_3$ | N |
| 123 | Q-1 | H | 6-$OCH_3$ | $CH_3$ | — | — | Cl | $OCH_3$ | CH |

-continued

General Structures for Compounds 64-179

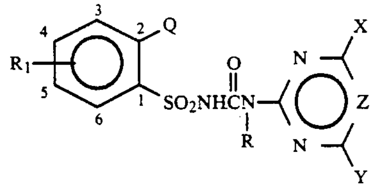

Q is 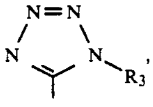, 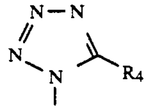 or 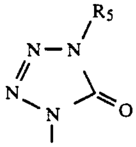

Q-1 Q-3 Q-5

| Compound | Q | R | $R_1$ | $R_3$ | $R_4$ | $R_5$ | X | Y | Z |
|---|---|---|---|---|---|---|---|---|---|
| 124 | Q-1 | H | 6-$OCH_3$ | $CH_3$ | — | — | $CH_3$ | $CH_3$ | CH |
| 125 | Q-5 | H | H | — | — | $CH_2CH_3$ | $OCH_3$ | $OCH_3$ | CH |
| 126 | Q-5 | H | H | — | — | $CH_2CH_3$ | $OCH_3$ | $OCH_3$ | N |
| 127 | Q-5 | H | H | — | — | $CH_2CH_3$ | $CH_3$ | $OCH_3$ | CH |
| 128 | Q-5 | H | H | — | — | $CH_2CH_3$ | $CH_3$ | $OCH_3$ | N |
| 129 | Q-5 | H | H | — | — | $CH_2CH_3$ | Cl | $OCH_3$ | CH |
| 130 | Q-5 | H | H | — | — | $CH_2CH_3$ | $CH_3$ | $CH_3$ | CH |
| 131 | Q-3 | H | 5-$OCH_3$ | — | $OCH_3$ | — | $OCH_3$ | $OCH_3$ | CH |
| 132 | Q-3 | H | 5-$OCH_3$ | — | $OCH_3$ | — | $CH_3$ | $OCH_3$ | CH |
| 133 | Q-3 | H | 5-$OCH_3$ | — | $OCH_3$ | — | $CH_3$ | $CH_3$ | CH |
| 134 | Q-3 | H | 5-$OCH_3$ | — | $OCH_3$ | — | Cl | $OCH_3$ | CH |
| 135 | Q-3 | H | 5-$OCH_3$ | — | $OCH_3$ | — | $OCH_3$ | $OCH_3$ | N |
| 136 | Q-3 | H | 5-$OCH_3$ | — | $OCH_3$ | — | $CH_3$ | $OCH_3$ | N |
| 137 | Q-1 | H | 6-$CH_3$ | $CH_3$ | — | — | Br | $OCH_3$ | CH |
| 138 | Q-1 | $CH_3$ | 6-$CH_3$ | $CH_3$ | — | — | $CH_3$ | $OCH_3$ | CH |
| 139 | Q-1 | $CH_3$ | 6-$CH_3$ | $CH_3$ | — | — | $CH_3$ | $OCH_3$ | N |
| 140 | Q-1 | H | 6-$CH_3$ | $CH_3$ | — | — | $CH_3$ | H | CH |
| 141 | Q-1 | H | 6-$CH_3$ | $CH_3$ | — | — | $OCH_3$ | H | CH |
| 142 | Q-1 | H | 6-$CH_3$ | $CH_3$ | — | — | $CH_2CH_3$ | $OCH_3$ | CH |
| 143 | Q-1 | H | 6-$CH_3$ | $CH_3$ | — | — | $CH_2CH_3$ | $OCH_3$ | N |
| 144 | Q-1 | $CH_3$ | 6-$CH_3$ | $CH_3$ | — | — | $OCH_3$ | $OCH_3$ | N |
| 145 | Q-1 | H | 6-$CH_3$ | $CH_3$ | — | — | cyclopropyl | $OCH_3$ | N |
| 146 | Q-1 | H | 6-$CH_3$ | $CH_3$ | — | — | $CH_3$ | $OCH_2CH_3$ | CH |
| 147 | Q-1 | H | 6-$CH_3$ | $CH_3$ | — | — | $OCH_3$ | $CH_2OCH_2CH_3$ | CH |
| 148 | Q-1 | H | 6-$CH_3$ | $CH_3$ | — | — | $OCH_3$ | $OCH_2CF_3$ | N |
| 149 | Q-1 | H | 6-$CH_3$ | $CH_3$ | — | — | $OCH_3$ | $OCH_2CH_3$ | N |
| 150 | Q-1 | H | 5-Cl | $CH_3$ | — | — | $OCH_3$ | $OCH_3$ | N |
| 151 | Q-1 | H | 5-Cl | $CH_3$ | — | — | $CH_3$ | $OCH_3$ | N |
| 152 | Q-1 | H | 5-Cl | $CH_3$ | — | — | $OCH_3$ | $OCH_3$ | CH |
| 153 | Q-1 | H | 5-Cl | $CH_3$ | — | — | $CH_3$ | $OCH_3$ | CH |
| 154 | Q-1 | H | 5-Cl | $CH_3$ | — | — | $CH_3$ | $CH_3$ | CH |
| 155 | Q-1 | H | 5-Cl | $CH_3$ | — | — | Cl | $OCH_3$ | CH |
| 156 | Q-1 | H | 5-Cl | $CH_3$ | — | — | $OCH_2CH_3$ | $NHCH_3$ | N |
| 157 | Q-1 | H | 5-Cl | $CH_3$ | — | — | $OCH_3$ | $CH(OCH_3)_2$ | CH |
| 158 | Q-5 | H | 5-Cl | — | — | $CH_3$ | $OCH_3$ | $OCH_3$ | CH |
| 159 | Q-5 | H | 5-Cl | — | — | $CH_3$ | $CH_3$ | $OCH_3$ | CH |
| 160 | Q-5 | H | 5-Cl | — | — | $CH_3$ | $CH_3$ | $OCH_3$ | N |
| 161 | Q-1 | H | 6-$CH_3$ | $CH_3$ | — | — | $OCF_2H$ | $OCH_3$ | CH |
| 162 | Q-1 | H | 6-$CH_3$ | $CH_3$ | — | — | $OCF_2H$ | $CH_3$ | CH |
| 163 | Q-1 | H | H | $CH_3$ | — | — | $CH_3$ | $CH_3$ | CH |
| 164 | Q-1 | H | H | $CH_3$ | — | — | $CH_3$ | $OCH_3$ | CH |
| 165 | Q-1 | H | H | $CH_3$ | — | — | $OCH_3$ | $OCH_3$ | CH |
| 166 | Q-1 | H | H | $CH_3$ | — | — | Cl | $OCH_3$ | CH |
| 167 | Q-1 | H | H | $CH_3$ | — | — | $CH_3$ | $OCH_3$ | N |
| 168 | Q-1 | H | H | $CH_3$ | — | — | $OCH_3$ | $OCH_3$ | N |
| 169 | Q-1 | H | H | $CH_3$ | — | — | $OCH_2CH_3$ | $NHCH_3$ | N |
| 170 | Q-1 | H | H | $CH_3$ | — | — | $OCF_2H$ | $OCH_3$ | CH |
| 171 | Q-5 | H | H | — | — | $CH_3$ | $OCF_2H$ | $OCH_3$ | CH |
| 172 | Q-5 | H | H | — | — | $CH_3$ | $OCF_2H$ | $CH_3$ | CH |
| 173 | Q-1 | H | H | $CH_3$ | — | — | $OCF_2H$ | $CH_3$ | CH |
| 174 | Q-1 | H | 5-$CH_3$ | $CH_3$ | — | — | $OCH_3$ | $OCH_3$ | N |
| 175 | Q-1 | H | 5-$CH_3$ | $CH_3$ | — | — | $CH_3$ | $OCH_3$ | N |
| 176 | Q-1 | H | 5-$CH_3$ | $CH_3$ | — | — | $OCH_3$ | $OCH_3$ | CH |
| 177 | Q-1 | H | 5-$CH_3$ | $CH_3$ | — | — | $CH_3$ | $OCH_3$ | CH |
| 178 | Q-1 | H | 5-$CH_3$ | $CH_3$ | — | — | $CH_3$ | $CH_3$ | CH |
| 179 | Q-1 | H | 5-$CH_3$ | $CH_3$ | — | — | Cl | $OCH_3$ | CH |

General Structure for Compounds 180–205

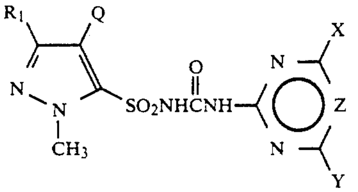

Q is 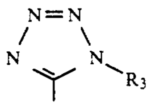 or 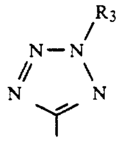

Q-1 Q-2

| Compound | Q | $R_1$ | $R_3$ | X | Y | Z |
|---|---|---|---|---|---|---|
| 180 | Q-2 | $CH_3$ | $CH_3$ | $CH_3$ | $CH_3$ | CH |
| 181 | Q-2 | $CH_3$ | $CH_3$ | $CH_3$ | $OCH_3$ | CH |
| 182 | Q-2 | $CH_3$ | $CH_3$ | $OCH_3$ | $OCH_3$ | CH |
| 183 | Q-2 | $CH_3$ | $CH_3$ | Cl | $OCH_3$ | CH |
| 184 | Q-2 | $CH_3$ | $CH_3$ | $OCH_2CH_3$ | $NHCH_3$ | N |
| 185 | Q-2 | $CH_3$ | $CH_3$ | $CH_3$ | $OCH_3$ | N |
| 186 | Q-2 | $CH_3$ | $CH_3$ | $OCH_3$ | $OCH_3$ | N |
| 187 | Q-2 | H | $CH_3$ | $CH_3$ | $CH_3$ | CH |
| 188 | Q-2 | H | $CH_3$ | $CH_3$ | $OCH_3$ | CH |
| 189 | Q-2 | H | $CH_3$ | $OCH_3$ | $OCH_3$ | CH |
| 190 | Q-2 | H | $CH_3$ | Cl | $OCH_3$ | CH |
| 191 | Q-2 | H | $CH_3$ | $CH_3$ | $OCH_3$ | N |
| 192 | Q-2 | H | $CH_3$ | $OCH_3$ | $OCH_3$ | N |
| 193 | Q-2 | H | $CH_3$ | $OCH_2CH_3$ | $NHCH_3$ | N |
| 194 | Q-1 | H | $CH_3$ | $CH_3$ | $OCH_3$ | CH |
| 195 | Q-1 | H | $CH_3$ | $OCH_3$ | $OCH_3$ | CH |
| 196 | Q-1 | H | $CH_3$ | $CH_3$ | $CH_3$ | CH |
| 197 | Q-1 | H | $CH_3$ | Cl | $OCH_3$ | CH |
| 198 | Q-1 | H | $CH_3$ | $CH_3$ | $OCH_3$ | N |
| 199 | Q-1 | H | $CH_3$ | $OCH_3$ | $OCH_3$ | N |
| 200 | Q-2 | H | $CH_2CH_3$ | $CH_3$ | $CH_3$ | CH |
| 201 | Q-2 | H | $CH_2CH_3$ | $CH_3$ | $OCH_3$ | CH |
| 202 | Q-2 | H | $CH_2CH_3$ | $OCH_3$ | $OCH_3$ | CH |
| 203 | Q-2 | H | $CH_2CH_3$ | Cl | $OCH_3$ | CH |
| 204 | Q-2 | H | $CH_2CH_3$ | $CH_3$ | $OCH_3$ | N |
| 205 | Q-2 | H | $CH_2CH_3$ | $OCH_3$ | $OCH_3$ | N |

General Structure for Compounds 206–207

| Compound | |
|---|---|
| 206 | 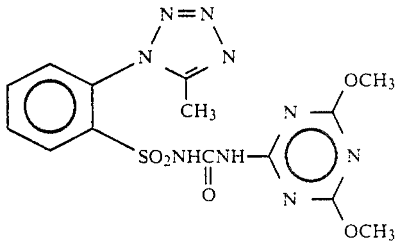 |
| 207 | sodium salt of compound 206 |

TEST A

Seeds of crabgrass (*Digitaria* spp.). giant foxtail (*Setaria faberii*) (in some cases), barnyardgrass (*Echinochloa crus-galli*), cheatgrass (*Bromus secalinus*), wild oats (*Avena fatua*), velvetleaf (*Abutilon theo- phrasti*), morningglory (*Ipomoea* spp.). cocklebur (*Xanthium pensylvanicum*) sorghum, corn, soybean, sugarbeet, cotton, rice, barley (in some cases), wheat and purple nutsedge (*Cyperus rotundus*) tubers were planted and treated preemergence with the test chemicals dissolved in a nonphytotoxic solvent. At the same time, these crop and weed species were treated with a soil/foliage application. At the time of treatment the plants ranged in height from 2 to 18 cm. Treated plants and controls were maintained in a greenhouse for sixteen days, after which all species were compared to controls and visually rated for response to treatment. The ratings, summarized in Table A, are based on a numerical scale extending from 0=no injury, to 10=complete kill. The accompanying descriptive symbols have the following meanings:

C=chlorosis/necrosis;
B=burn;
D=defoliation;
E=emergence inhibition;
G=growth retardation;
H=formative effect;
U=unusual pigmentation;
X=axillary stimulation;
S=albinism; and
6Y=abscised buds or flowers.

TABLE A

POSTEMERGENCE

| Rate kg/ha | Compound 1 0.05 | Compound 2 0.05 | Compound 3 0.05 | Compound 4 0.05 | Compound 4 0.01 | Compound 5 0.05 | Compound 5 0.01 | Compound 6 0.05 | Compound 6 0.01 | Compound 7 0.05 | Compound 7 0.01 | Compound 8 0.05 | Compound 8 0.05 | Compound 8 0.01 | Compound 9 0.05 | Compound 9 0.01 |
|---|---|---|---|---|---|---|---|---|---|---|---|---|---|---|---|---|
| Morningglory | 3C,8G | 10C | 10C | 10C | 10C | 10C | 9C | 1C,1H | 1C | 6C,9G | 4C,9H | 1H | 3H | 0 | 5C,9G | 2C,5G |
| Cocklebur | 3C,7H | 9C | 9C | 9C | 9C | 10C | 9C | 1H | 0 | 8G | 2G | 0 | 2H | 0 | 9C | 3C,9H |
| Velvetleaf | 2C,4G | 10C | 9C | 9C | 9C | 9C | 4C,9H | 0 | 0 | 4C,8H | 3C,5G | 2G | 0 | 0 | 4C,8G | 1C |
| Nutsedge | 8G | 9C | 9C | 4C,9G | 3C,9G | 9C | 4C,9G | 0 | 0 | 6G | 0 | 0 | 0 | 0 | 4C,9G | 3C,9G |
| Crabgrass | 5G | 5C,9G | 9C | 5C,9G | 3C,8G | 4C,8G | 3C,5G | 0 | 0 | 4C,8G | 2C,5G | 0 | 0 | 0 | 2G | 0 |
| Giant Foxtail | | | | — | — | — | — | — | — | — | — | 0 | — | — | — | — |
| Barnyardgrass | 5C,9G | 9C | 5C,9G | 9C | 9C | 9C | 9C | 4C,9H | 0 | 5C,9H | 3C,9H | 1H | 2H | 0 | 9H | 2C,5H |
| Cheatgrass | 0 | 7G | 9C | 3C,9G | 6G | 4G | 0 | 0 | 0 | 6G | 2G | 0 | 0 | 0 | 7G | 0 |
| Wild Oats | 3C,8G | 9C | 9C | 5C,9G | 5C,9G | 4C,9G | 3C,9G | 2G | 0 | 5C,9G | 4C,9G | 0 | 0 | 0 | 0 | 0 |
| Wheat | 4C,9G | 9C | 9C | 5C,9G | 2C,9G | 4C,9H | 8G | 3G | 0 | 4C,9G | 2C,9G | 0 | 0 | 0 | 0 | 0 |
| Corn | 9C | 9C | 9C | 5C,9G | 3C,9H | 5C,9G | 9H | 4C,9H | 3C,7H | 6C,9G | 4C,9H | 5H | 5H | 2G | 7H | 1C,3G |
| Barley | | | | — | — | — | — | — | — | — | — | 0 | — | — | — | — |
| Soybean | 5C,9G | 9C | 9C | 5C,9G | 5C,9G | 4C,9G | 4C,9H | 4C,8H | 1C,1H | 3C,7G | 3G | 2G | 3H | 0 | 5G | 0 |
| Rice | 6C,9G | 9C | 9C | 9C | 9C | 6C,9G | 9C | 5C,9G | 5G | 9C | 9C | 2G | 2G | 0 | 4C,8G | 0 |
| Sorghum | 6C,9H | 9C | 9C | 5C,9G | 6C,9G | 9C | 9C | 4C,8H | 3G | 5C,9G | 4C,9H | 5G | 0 | 0 | 5C,9H | 3C,8H |
| Sugar beet | 6C,9H | 9C | 9C | 8G | 10C | 9C | 9C | 4C,6G | 0 | 5C,9H | 4C,6H | 2C,3H | 3C,5H | 0 | 10C | 4C,9H |
| Cotton | 6C,9H | 9C | 9C | 9C | 9C | 9C | 4C,9G | 4C,6G | 3C,4G | 3C,5G | 3C,5G | 2G | 0 | 0 | 9C | 3C,8H |

| Rate kg/ha | Compound 10 0.05 | Compound 10 0.01 | Compound 11 0.05 | Compound 11 0.01 | Compound 12 0.01 | Compound 13 0.01 | Compound 14 0.05 | Compound 14 0.01 | Compound 15 0.05 | Compound 15 0.01 | Compound 16 0.05 | Compound 16 0.01 | Compound 17 0.05 | Compound 17 0.01 | Compound 18 0.05 | Compound 18 0.01 |
|---|---|---|---|---|---|---|---|---|---|---|---|---|---|---|---|---|
| Morningglory | 10C | 9C | 2C,6G | 2H | 2G | 10C | 5C,9G | 4G | 3C,8H | 0 | 10C | 5C,9G | 10C | 10C | 10C | 9C |
| Cocklebur | 9C | 9C | 9C | 5C,9G | 0 | 10C | 10C | 10C | 2C,4G | 0 | 10C | 8G | 10C | 10C | 10C | 10C |
| Velvetleaf | 9C | 4C,8G | 5C,9H | 4C,9H | 0 | 9C | 10C | 10C | 2C,4H | 0 | 9C | 3C,8G | 9C | 9C | 10C | 9C |
| Nutsedge | 9C | 9C | 4C,9G | 3C,9G | 0 | 9C | 9C | 5C,9G | 0 | 0 | 5C,9G | 2C,8G | 5C,9G | 3C,9G | 10C | 10C |
| Crabgrass | 3C,7G | 2H | 3C,5G | 1H | 0 | 4G | 2C,7G | 1C | 0 | 0 | 5G | 0 | 3C,8G | 3C,5G | 9C | 3C,7G |
| Giant Foxtail | — | — | — | — | — | — | — | — | — | — | — | — | 9C | 9C | 9C | 5C,9H |
| Barnyardgrass | 9H | 3C,7H | 5C,9H | 2C,3H | 0 | 5C,9H | 9C | 9C | 3C,8H | 3G | 9C | 3C,8H | 9C | 9C | 9C | 9C |
| Cheatgrass | 9C | 3C,9G | 9C | 8G | 0 | 4C,9G | 3G | 0 | 0 | 0 | 0 | 0 | 5C,9G | 3C,8G | 9C | 2C,8G |
| Wild Oats | 5C,9G | 2C,7H | 9C | 9H | 0 | 3C,5G | 5C,9G | 3C,9G | 2C,9G | 2C,2G | 3C,9G | 2C,5G | 9C | 5C,9G | 5C,9G | 4C,9G |
| Wheat | 9G | 3G | 9G | 5G | 0 | 0 | 5C,9G | 2C,9G | 0 | 0 | 8G | 5G | 4C,9G | 9G | 9C | 3C,9G |
| Corn | 9C | 3C,9H | 5C,9G | 3C,9H | 0 | 9H | 9C | 5C,9H | 1C,5G | 2G | 4G | 2G | 9C | 5C,9G | 10C | 3C,9H |
| Barley | — | — | — | — | — | — | — | — | — | — | — | — | 5C,9G | 3C,8H | 6C,9G | 3C,8G |
| Soybean | 5C,9G | 3C,8H | 3C,7H | 2H | 1H | 9C | 9C | 9C | 4C,9G | 3H | 3C,9G | 2H,7G | 9C | 9C | 9C | 9C |
| Rice | 9C | 2C,7G | 9C | 5C,9G | 0 | 2C,8G | 9C | 9C | 5G | 0 | 5C,9G | 7G | 9C | 9C | 9C | 9C |
| Sorghum | 9C | 3C,9H | 9C | 4C,9H | 0 | 9H | 9C | 5C,9H | 3C,9H | 0 | 9C | 3C,9H | 9C | 9C | 9C | 9C |
| Sugar beet | 10C | 10C | 9C | 9C | 1C,1H | 5C,9G | 5C,9G | 9C | 3C,6G | 2C,3G | 9C | 4C,8G | 10C | 5C,9G | 10C | 9C |
| Cotton | 9C | 9C | 9C | 9H | 1C | 9C | 9C | 5C,9G | 3C,9H | 1H | 2C,9G | 8G | 9C | 5C,9G | 9C | 10C |

| Rate kg/ha | Compound 19 0.05 | Compound 19 0.01 | Compound 20 0.05 | Compound 20 0.01 | Compound 21 0.05 | Compound 21 0.01 | Compound 22 0.05 | Compound 22 0.01 | Compound 23 0.05 | Compound 23 0.01 | Compound 24 0.01 | Compound 25 0.05 | Compound 25 0.01 | Compound 26 0.05 | Compound 26 0.01 | Compound 27 0.05 | Compound 27 0.01 |
|---|---|---|---|---|---|---|---|---|---|---|---|---|---|---|---|---|---|
| Morningglory | 10C | 4C,9G | 10C | 9C | 4C,9G | 3C,7H | 4C,8H | 3C,7H | 10C | 8G | 5G | 0 | 0 | 3C,5G | 0 | 2C,6G | 2G |
| Cocklebur | 9C | 7G | 10C | 9C | 4C,9H | 5H | 5C,9G | 3C,7H | 10C | 10C | 10C | 3H | 2H | 4C,8H | 2H | 10C | 5C,9G |
| Velvetleaf | 9C | 9C | 9C | 2C,7G | 3C,6G | 1H | 3C,7H | 3C,5H | 10C | 5C,9G | 5C,9G | 0 | 0 | 2C,5G | 0 | 9C | 3C,7G |
| Nutsedge | 5C,9G | 3C,8G | 5C,9G | 4C,3G | 4G | 3C,8G | 5G | 0 | 10C | 10C | 5C,9G | 0 | 0 | 3C,6G | 0 | 10C | 3C,8G |
| Crabgrass | 4C,8G | 3C,4G | 5C,9H | 4C,8G | 3C,5G | 2G | 3C,7H | 3C,6G | 5G | 3G | 0 | 0 | 0 | 3C,4H | 0 | 2G | 2G |
| Giant Foxtail | 9C | 5C,9G | 5C,9H | 4C,8G | 9C | 4C,9G | 9C | 4C,9H | 5C,9G | 3C,8G | 3C,7G | 3C,8H | 2H | 4C,9H | 3C,5G | 4C,9G | 4G |
| Barnyardgrass | 9C | 9C | 9C | 9C | 9C | 9C | 9C | 9C | 9C | 3C,9H | 3C,7G | 5C,9H | 0 | 5C,9H | 2C,5G | 4C,9H | 4C,8H |
| Cheatgrass | 3C,7G | 5G | 5G | 2G | 0 | 0 | 2C | 0 | 5G | 2G | 2G | 0 | 0 | 3G | 0 | 4G | 0 |
| Wild Oats | 9C | 9C | 3C,9G | 3C,7G | 2C | 0 | 2C,6G | 0 | 5G | 2G | 0 | 4C,8G | 0 | 4C,9G | 3C,4G | 9G | 3C,6G |

TABLE A-continued

| | | | | | | | | | | | | | | | | | |
|---|---|---|---|---|---|---|---|---|---|---|---|---|---|---|---|---|---|
| Wheat | 9C | 5C,9G | 3C,9G | 9G | 5G | 0 | 8G | 0 | 8G | 6G | 5G | 5C,9G | 0 | 3C,9G | 7G | 5C,9G | 2C,6G |
| Corn | 9C | 4C,9H | 4C,9H | 3C,9H | 10C | 9C | 10C | 9C | 9H | 6H | 0 | 3C,9H | 2H | 9H | 0 | 2G | 0 |
| Barley | 9C | 4C,9G | 2C,8G | 3C,7G | 0 | 0 | 2G | 0 | 3C,9H | 6G | 3G | 9G | 2G | 8G | 0 | 9G | 3G |
| Soybean | 9C | 4C,9G | 9C | 4C,9G | 5C,9G | 4C,9G | 9C | 5C,9G | 9C | 9C | 9C | 2H,4G | 0 | 3C,8G | 2H | 5C,9G | 4C,9H |
| Rice | 9C | 9C | 9C | 5C,9G | 5C,9G | 7G | 9C | 6G | 9C | 4C,9G | 3C,7G | 9C | 2G | 9C | 8G | 9C | 5C,9G |
| Sorghum | 10C | 9C | 9C | 9C | 9C | 4C,9G | 9C | 9C | 9C | 9C | 4C,9H | 4C,9H | 3G | 5C,9G | 3C,7H | 9C | 4C,9G |
| Sugar beet | 10C | 4C,8G | 9C | 4C,9G | 3C,6H | 3C,5G | 9C | 3C,8G | 10C | 10C | 10C | 5G | 0 | 9C | 2H | 10C | 9C |
| Cotton | 9C | 4C,9G | 5C,9G | 9C | 4C,9H | 4C,9H | 4C,9H | 3C,8H | 9C | 9C | 4C,9G | 0 | 0 | 3C,7G | 0 | 9C | 9H |

| | Compound 28 | | Compound 29 | | Compound 30 | | Compound 31 | | Compound 32 | | Compound 33 | | Compound 34 | | Compound 35 | | Compound 36 | |
|---|---|---|---|---|---|---|---|---|---|---|---|---|---|---|---|---|---|---|
| Rate kg/ha | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| Morningglory | 10C | 3C,8G | 3C,9G | 3C,7H | 10C | 4C,8H | 10C | 3C,8H | 10C | 10C | 10C | 10C | 10C | 5C,9G | 10C | 10C | 9C | 10C |
| Cocklebur | 10C | 9C | 3H | 0 | 9C | 4C,9G | 10C | 9C | 10C | 10C | 10C | 9C | 10C | 5C,9G | 10C | 10C | 9C | 3C,8H |
| Velvetleaf | 4C,9G | 3C,9G | 3C,7H | 0 | 9C | 7G | 9C | 4C,8H | 10C | 10C | 10C | 9C | 10C | 5C,9G | 10C | 4C,9G | 9C | 9C |
| Nutsedge | 10C | 4C,9G | 0 | 0 | 4C,8G | 4G | 7G | 0 | 10C | 9C | 9C | 5C,9G | 5C,9G | 5C,9G | 10C | 4C,9G | 3C,7G | 3G |
| Crabgrass | 3G | 0 | 3C,5G | 0 | 6C,9H | 4C,6G | 9C | 3C,8G | 5C,8G | 7G | 3C,7G | 2G | 2C,9G | 2C,4G | 3C,7H | 3G | 9C | 3C,7G |
| Giant Foxtail | 7G | 2G | 5C,9G | 3C,7G | 9C | 10C | 10C | 9C | 9C | 9C | 9C | 4C,9H | 10C | 9C | 9C | 4C,9G | 9C | 9C |
| Barnyardgrass | 3C,7H | 1C,4G | 3C,8H | 2H | 10C | 9C | 10C | 9C | 9C | 9C | 10C | 9C | 10C | 4C,9H | 10C | 10C | 9C | 10C |
| Cheatgrass | 0 | 0 | 0 | 0 | 3G | 0 | 3G | 0 | 7G | 5G | 7G | 5G | 6G | 2G | 6G | 2G | 7G | 3G |
| Wild Oats | 2G | 0 | 4C,9G | 7G | 4G | 3G | 7G | 4G | 4C,9G | 9G | 5C,9G | 3C,7G | 9C | 4C,9G | 3C,9G | 3C,6G | 9C | 9C |
| Wheat | 4G | 0 | 9G | 7G | 4G | 0 | 2C,6G | 3G | 10C | 6C,9G | 9C | 4C,9G | 9C | 3C,9G | 5C,9G | 2C,8G | 9C | 5C,9G |
| Corn | 0 | 0 | 4C,8H | 5H | 10C | 10C | 10C | 9C | 10C | 2C,7H | 3C,9H | 3C,7H | 4C,9H | 1H | 4G | 0 | 9C | 9C |
| Barley | 2G | 0 | 9C | 9G | 0 | 0 | 1C,4G | 0 | 9C | 8G | 3C,9G | 4C,9G | 9C | 2C,8G | 9C | 6C | 9C | 4C,9G |
| Soybean | 3H,8G | 3H,8G | 3C,7H | 4H | 9C | 5C,9G | 9C | 4C,9G | 9C | 9C | 10C | 5C,9G | 9C | 4C,9G | 4C,9G | 4C,9G | 5C,9G | 4C,9G |
| Rice | 2C,8G | 6G | 9C | 3C,8G | 5C,9G | 4C,9G | 9C | 4C,9G | 9C | 9C | 9C | 9C | 9C | 9C | 9C | 5C,9G | 9C | 9C |
| Sorghum | 4C,9H | 4C,9G | 5C,9G | 4C,9G | 9C | 9C | 10C | 9C | 10C | 9C | 10C | 10C | 9C | 4C,9H | 9C | 9C | 9C | 9C |
| Sugar beet | 9C | 9C | 3C,7H | 4H | 10C | 5C,9G | 10C | 9C | 10C | 10C | 9C | 5C,9G | 10C | 9C | 10C | 10C | 9C | 10C |
| Cotton | 9H | 9G | 5H | 0 | 9C | 9H | 9C | 9C | 9C | 10C | 9C | 9C | 10C | 9C | 10C | 10C | 9C | 9C |

| | Compound 37 | | Compound 38 | | Compound 39 | | Compound 40 | | Compound 41 | | Compound 42 | | Compound 43 | | Compound 44 | | Compound 45 | |
|---|---|---|---|---|---|---|---|---|---|---|---|---|---|---|---|---|---|---|
| Rate kg/ha | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| Morningglory | 3C,8H | 3C,5H | 3C,8H | 1C | 10C | 10C | 10C | 9C | 4C,8H | 2C,4G | 2C,8G | 2C,7G | 3C,8H | 3C,7H | 3C,7H | 3C,3H | 4C,9H | 2C,5G |
| Cocklebur | 2C,2G | 0 | 3C,7H | 0 | 9C | 9C | 9C | 9C | 5C,9H | 2C,4G | 5C,9H | 3C,8G | 3G | 0 | 2C,5G | 2C | 4C,9H | 1C |
| Velvetleaf | 2C,4G | 0 | 2C,5G | 1C | 9C | 10C | 10C | 5C,9H | 4C,8H | 3C,5H | 4C,8H | 5G | 7G | 2C,5G | 3C,6H | 0 | 3C,7H | 3C,3G |
| Nutsedge | 0 | 0 | 0 | 0 | 9C | 5C,9G | 2C,8G | 5G | 0 | 0 | 3G | 4G | 0 | 0 | 0 | 0 | 3G | 0 |
| Crabgrass | 2C,3G | 0 | 2G | 0 | 5C,9G | 3C,7G | 3C,7G | 4G | 2G | 0 | 0 | 0 | 3G | 0 | 0 | 0 | 2G | 0 |
| Giant Foxtail | 4C,8G | 4G | 3C,8H | 2G | 5C,9G | 3C,7G | 3C,7G | 2G | 5G | 0 | 4G | 0 | 2G | 0 | 1C | 0 | 2G | 0 |
| Barnyardgrass | 9C | 3C,7H | 5C,9G | 4H | 9C | 9C | 9C | 3C,7H | 2C,7H | 3H | 4C,9H | 4G | 4G | 3G | 3C,7H | 2C,5G | 3C,9H | 2C,5H |
| Cheatgrass | 2C,6G | 2G | 2G | 0 | 10C | 9C | 9C | 4C,9G | 3C,8G | 4G | 7G | 0 | 8G | 7G | 0 | 0 | 3G | 0 |
| Wild Oats | 2C,6G | 0 | 2C,5G | 0 | 5C,9G | 9G | 4C,9G | 3C,6G | 7G | 3G | 2C,7G | 0 | 4C,9G | 5C,9G | 0 | 0 | 2G | 0 |
| Wheat | 0 | 0 | 4G | 0 | 3C,9G | 9G | 9G | 9G | 4G | 2G | 2G | 0 | 9G | 9G | 0 | 0 | 2G | 0 |
| Corn | 4C,9G | 3C,8H | 3C,9H | 3C,7H | 3C,9G | 2U,9G | 3C,8H | 1C,3G | 0 | 0 | 2G | 0 | 0 | 0 | 3C,7G | 0 | 2C,6G | 0 |
| Barley | 0 | 0 | 0 | 0 | 4C,9G | 9G | 5G | 2G | 0 | 0 | 0 | 0 | 9G | 9G | 2C | 0 | 0 | 0 |
| Soybean | 4C,9G | 3C,3G | 3C,8G | 2C,4H | 6C,9G | 5C,9G | 9C | 4C,9G | 4C,8H | 3C,5H | 2C,7G | 1H | 3H, 8G | 2H,5G | 2C,7H | 3H | 3C,8G | 2C,6H |
| Rice | 5C,9G | 4C,9G | 5C,9G | 5G | 9C | 5C,9G | 9C | 4C,9G | 5C,9G | 3C,5G | 2C,9G | 5G | 4C,9G | 4C,9G | 4C,9G | 4G | 5C,9G | 5G |
| Sorghum | 4C,9G | 4C,9G | 4C,9G | 2C,6G | 3U,9G | 9G | 4C,9H | 3C,8G | 2C,6G | 2C,4G | 9G | 7G | 4C,8G | 2C,5G | 5C,9H | 5G | 4C,9H | 2C,8G |
| Sugar beet | 3C,7H | 2H | 3C,7H | 3C,4H | 10C | 9C | 10C | 3C,8H | 3C,6H | 2C,3G | 3C,8G | 2C,6G | 3C,7G | 2C,5G | 3C,7H | 3C,6G | 5C,9G | 3C,7H |
| Cotton | 3C,8H | 2C,3G | 3C,7H | 2C,2G | 9C | 4C,9G | 4C,9G | 4C,9H | 4C,9H | 2C,3G | 2C,8G | 5G | 5G | 0 | 3C,6G | 1C | 3C,8H | 2C,4G |

| | Compound 46 | | Compound 47 | | Compound 48 | | Compound 49 | | Compound 50 | | Compound 51 | | Compound 52 | | Compound 53 | | Compound 54 | |
|---|---|---|---|---|---|---|---|---|---|---|---|---|---|---|---|---|---|---|
| Rate kg/ha | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| Morningglory | 10C | 10C | 9C | 4C,9H | 4C,9H | 2C,2H | 4C,8G | 2C,5G | 2C,5H | 0 | 4C,8H | 1C | 5C,9G | 4C,9H | 9C | 10C | 10C | 10C |
| Cocklebur | 10C | 8H | 7H | 2G | 1H | 1H | 4C,9H | 5G | 0 | 0 | 3C,6G | 0 | 4C,9H | 3C,4G | 9C | 9C | 10C | 10C |

TABLE A-continued

| | | | | | | | | | | | | | | | | | | |
|---|---|---|---|---|---|---|---|---|---|---|---|---|---|---|---|---|---|---|
| Velvetleaf | 10C | 9C | 5C,9G | 3C,8G | 3C,7H | 3G | 3C,8H | 3H | 2C,5G | 0 | 2G | 0 | 3C,8H | 3C,4G | 9C | 10C | 10C | 10C |
| Nutsedge | 2C,9G | 4C,8G | 7G | 3G | 4G | 0 | 5G | 0 | 0 | 0 | 8G | 0 | 9G | 2C,7G | 9C | 9C | 9C | 5C,9G |
| Crabgrass | 7G | 5G | 4G | 0 | 0 | 0 | 0 | 0 | 0 | 0 | 2C,2G | 0 | 3C,7G | 2C | 8G | 3G | 6G | 3G |
| Giant Foxtail | 5C,9G | 3C,8G | 5G | 2G | 0 | 0 | 3C,6G | 0 | 2C,4G | 0 | 6C,9H | 3C,7H | 9C | 4C,8G | 9C | 3C,8G | 5C,9G | 3C,9G |
| Barnyardgrass | 10C | 5C,9G | 3C,9H | 3C,8H | 3C,7H | 1H | 3C,8H | 3H | 3C,7H | 0 | 9C | 3C,8H | 9C | 9H | 9C | 9C | 10C | 9C |
| Cheatgrass | 9G | 8G | 2C,6G | 4G | 2G | 0 | 0 | 0 | 0 | 0 | 8G | 0 | 3C,8G | 5G | 9C | 9G | 9C | 4C,9G |
| Wild Oats | 2C,9G | 9G | 3C,8G | 3G | 2G | 0 | 0 | 0 | 0 | 0 | 4C,9G | 0 | 4C,9G | 3C,7G | 2G | 0 | 3C,5G | 0 |
| Wheat | 5C,9G | 9G | 8G | 2G | 2G | 0 | 2G | 0 | 0 | 0 | 8G | 2G | 8G | 4G | 9G | 7G | 3C,9G | 9G |
| Corn | 2C,9G | 9H | 3C,8H | 2G | 1H | 0 | 1H | 0 | 2G | 0 | 4C,9H | 2C,5G | 3C,8H | 0 | 3H | 0 | 2H | 0 |
| Barley | 3C,9G | 9G | 3C,8G | 4G | 2G | 0 | 1C | 0 | 0 | 0 | 3G | 0 | 3C,7G | 2G | 3C,9G | 2C,6G | 8G | 5G |
| Soybean | 9C | 5C,9G | 4C,9G | 3C,8G | 2C,7G | 2H | 2H | 1H | 0 | 0 | 3C,7H | 2C,5G | 4C,9G | 2C,8H | 9C | 5C,9G | 9C | 4C,9G |
| Rice | 9C | 9C | 4C,9G | 4C,9G | 4C,9G | 2G | 4C,9G | 4C,9G | 6G | 0 | 9C | 5C,9G | 9C | 4C,9G | 9C | 5C,9G | 9C | 9C |
| Sorghum | 9C | 5C,9G | 4C,9G | 4C,9G | 4C,8G | 6G | 4C,9G | 4C,9H | 8G | 4G | 9C | 4C,9H | 9C | 5C,9G | 9C | 10C | 9C | 9C |
| Sugar beet | 10C | 9C | 9C | 9C | 4C,8H | 2C,6G | 3C,8H | 2C,5G | 3C,7G | 0 | 9C | 3C,7H | 9C | 4C,8H | 9C | 10C | 10C | 9C |
| Cotton | 10C | 2C,8G | 8H | 3C,8G | 6H | 0 | 7G | 3G | 2G | 0 | 8H | 7H | 4C,9G | 3C,8H | 9C | 9C | 9C | 5C,9G |

| | Compound 55 | | Compound 56 | | Compound 57 | | Compound 58 | | Compound 59 | | Compound 60 | | Compound 61 | | Compound 62 | | Compound 63 | |
|---|---|---|---|---|---|---|---|---|---|---|---|---|---|---|---|---|---|---|
| Rate kg/ha | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| Morningglory | 10C | 8C | 10C | 10C | 10C | 2C,8G | 1C,7G | 0 | 10C | 10C | 3C,8G | 1C,1H | 1C,1H | 0 | 0 | 0 | 10C | 4C,8G |
| Cocklebur | 10C | 9C | 10C | 4C,9G | 10C | 10C | 0 | 0 | 10C | 10C | 2C,8G | 2H | 3H | 0 | 0 | 0 | 4C,9H | 3C,7H |
| Velvetleaf | 10C | 9C | 10C | 3C,8G | 10C | 2C,9H | 2G | 0 | 10C | 9C | 3C,9G | 4G | 4H | 0 | 0 | 0 | 4C,8H | 3C,7H |
| Nutsedge | 9C | 9G | 5C,9G | 4C,9G | 5C,9G | 2C,9G | 0 | 0 | 10C | 10C | 2C,5G | 0 | 0 | 0 | 0 | 0 | 9G | 2C,8G |
| Crabgrass | 3C,6G | 2C,5G | 6G | 2G | 7G | 0 | 0 | 0 | 3C,9G | 7G | 0 | 0 | 0 | 0 | 0 | 0 | 3C,6G | 5G |
| Giant Foxtail | 9C | 3C,8G | 4C,9G | 7G | 3C,9G | 2C,7G | 0 | 0 | 9C | 9C | 3C,8G | 4G | 5G | 2G | 2G | 0 | 9C | 2C,8G |
| Barnyardgrass | 9C | 10C | 9C | 9H | 2C,9G | 2C,5H | 0 | 0 | 9C | 9C | 3C,7H | 2H | 2C,5G | 3G | 2C,5G | 0 | 9C | 3C,9G |
| Cheatgrass | 9C | 5C,9G | 4C,9G | 9G | 8C | 2C,9G | 2G | 0 | 9C | 10C | 9G | 3G | 6G | 0 | 6G | 0 | 5C,9G | 9G |
| Wild Oats | 5C,9G | 3C,3G | 3G | 0 | 2C,9G | 2C,6G | 0 | 0 | 9C | 5C,9G | 2C,7G | 0 | 2C,5G | 2G | 2C,5G | 0 | 3C,8G | 2C,5G |
| Wheat | 9G | 9G | 8G | 3G | 1C,6G | 0 | 0 | 0 | 9C | 4C,9G | 9G | 0 | 9G | 8G | 6G | 0 | 9G | 7G |
| Corn | 2H | 0 | 0 | 0 | 1C,8H | 3C,8H | 0 | 0 | 9C | 10C | 3C,8H | 0 | 2C,7G | 3G | 3G | 0 | 5C,9G | 3C,9G |
| Barley | 9G | 3C,7G | 2G | 0 | 5C,9G | 3C,9G | 0 | 0 | 9C | 5C,9G | 2C,4G | 0 | 2C,5G | 3G | 4G | 0 | 9G | 8G |
| Soybean | 5C,9G | 4C,8G | 3C,8G | 3C,5H | 5C,8H | 2C,6H | 0 | 0 | 9C | 9C | 3G | 2H | 2C,6H | 3H | 0 | 0 | 3C,8H | 3C,4H |
| Rice | 5C,9G | 5C,9G | 9C | 5C,9G | 5C,9G | 2C,8G | 3C | 0 | 9C | 9C | 5C,9G | 0 | 3C,9G | 3G | 7G | 0 | 6C,9G | 4C,9G |
| Sorghum | 5C,9G | 5C,9G | 9C | 3C,9G | 3C,9G | 3C,9G | 1C,5G | 0 | 9C | 9C | 2C,9G | 5G | 4G | 2G | 7G | 0 | 3C,9G | 4C,9G |
| Sugar beet | 9C | 9C | 10C | 9C | 9C | 10C | 2C,4H | 0 | 9C | 9C | 9C | 3G | 2C,4G | 0 | 2C | 0 | 9C | 5C,9G |
| Cotton | 9G | 9G | 10C | 3C,8G | 10C | 2C,8H | 2G | 0 | 10C | 9C | 3C,8G | 0 | 0 | 0 | 0 | 0 | 4C,9G | 3C,8H |

| | Compound 64* | | Compound 65* | | Compound 66 | | Compound 67 | | Compound 68 | | Compound 69 | | Compound 70 | | Compound 71 | | Compound 72 | |
|---|---|---|---|---|---|---|---|---|---|---|---|---|---|---|---|---|---|---|
| Rate kg/ha | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| Cotton | 0 | 0 | 0 | 0 | 10C | 4C,9G | 9C | 4C,9H | 4C,9G | 4C,9H | 4C,8G | 4C,9H | 3C,8H | 0 | 4C,9H | 3C,8H | 9C | 4C,9G |
| Morningglory | 0 | 0 | 0 | 0 | 10C | 10C | 10C | 10C | 9C | 5C,9G | 10C | 4C,9H | 3C,8G | 3C,7G | 4C,9H | 3C,8H | 10C | 4C,9G |
| Cocklebur | 0 | 0 | 0 | 0 | 10C | 10C | 10C | 9C | 10C | 5C,9G | 9C | 4C,9H | 2G | 0 | 4C,9H | 2C,2H | 10C | 5C,9G |
| Nutsedge | 0 | 0 | 0 | 0 | 6C,9G | 5C,9G | 5C,9G | 4C,8G | 5C,9G | 7C | 2C,8G | 5G | 0 | 0 | 4G | 0 | 5C,9G | 5C,9G |
| Crabgrass | 0 | 0 | 0 | 0 | 2C,6G | 4G | 4G | 3H | 6G | 3G | 3H | 2H | 0 | 0 | 0 | 0 | 2H | 0 |
| Barnyardgrass | 0 | 0 | 0 | 0 | 9C | 9C | 9C | 9C | 9C | 3C,9H | 9C | 4C,9H | 5C,9H | 5G | 5C,9H | 9C | 10C | 9C |
| Wild Oats | 0 | 0 | 0 | 0 | 2G | 0 | 2C,6G | 2G | 4C,9G | 2C,3G | 3G | 0 | 4C,8G | 2G | 3C,8G | 3G | 5C,9G | 3C,7G |
| Wheat | 0 | 0 | 0 | 0 | 9G | 8G | 9G | 7G | 9G | 9G | 6G | 0 | 3C,8G | 3G | 3G | 0 | 5C,9G | 8G |
| Corn | 0 | 0 | 0 | 0 | 4G | 2G | 0 | 0 | 2H | 0 | 0 | 0 | 5C,9G | 6G | 6G | 3G | 4C,9G | 4G |
| Soybean | 0 | 0 | 0 | 0 | 9C | 9C | 9C | 5C,9G | 4C,9G | 5C,9G | 5C,9G | 3C,7H | 4C,9G | 3C,7H | 4C,9G | 3C,8G | 9C | 5C,9G |
| Rice | 0 | 0 | 0 | 0 | 9C | 9C | 9C | 9C | 9C | 9C | 9C | 4C,9G | 4C,9G | 5G | 8G | 2C,5G | 9C | 5C,9G |
| Sorghum | 0 | 0 | 0 | 0 | 9C | 9C | 9C | 5C,9G | 9C | 4C,9G | 9C | 4C,9G | 3C,9H | 4C,8H | 5C,9H | 3C,9H | 10C | 9C |
| Cheatgrass | 0 | 0 | 0 | 0 | 9C | 4C,9G | 9C | 4C,9G | 10C | 4C,9G | 4C,9G | 4C,9G | 3C,8G | 2C,5G | 3C,6G | 4G | 9C | 9C |
| Sugar beet | 0 | 0 | 0 | 0 | 9C | 10C | 10C | 9C | 10C | 9C | 9C | 5C,9G | 3C,7H | 2C,2H | 4C,8H | 3C,6H | 10C | 10C |
| Velvetleaf | 0 | 0 | 0 | 0 | 10C | 9C | 10C | 4C,9H | 9C | 5C,9G | 3C,7H | 2C | 0 | 0 | 4C,6H | 0 | 10C | 10C |

TABLE A-continued

| | | | | | | | | | | | | | | | | | | |
|---|---|---|---|---|---|---|---|---|---|---|---|---|---|---|---|---|---|---|
| Corn | 0 | 0 | 3C,7H | 0 | 2C,7H | 0 | 0 | 0 | 0 | 0 | 2G | 0 | 2C,7G | 2G | 0 | 0 | 10C | 10C |
| Soybean | 0 | 0 | 3C,9G | 2C,6H | 3C,8H | 2C,7H | 4C,9G | 3C,7H | 0 | 0 | 4C,9G | 4C,9G | 9C | 9C | 4C,9G | 4C,9G | 9C | 4C,9G |
| Rice | 2G | 0 | 4G | 0 | 4G | 3G | 2C,5G | 0 | 0 | 0 | 9C | 4C,8G | 9C | 5C,9G | 4C,9G | 5G | 4C,9G | 8G |
| Sorghum | 3G | 0 | 2C,8H | 1C,5G | 2C,8H | 2C,7G | 4C,9G | 3C,9G | 0 | 0 | 9C | 9C | 10C | 10C | 10C | 9C | 5C,9G | 10C |
| Cheatgrass | 0 | 0 | 7G | 0 | 5G | 0 | 10C | 4G | 0 | 0 | 2C,5G | 0 | 4C,9G | 6G | 3c,7G | 0 | 9C | 3C,8G |
| Sugar beet | 0 | 0 | 4C,8G | 2C,7G | 5C,8G | 3C,7G | 9C | 2C,3H | 0 | 0 | 4C,9G | 2C,3G | 10C | 10C | 10C | 4c,8G | 10C | 9C |
| Velvetleaf | 0 | 0 | 2C,4H | 2G | 3C,7H | 2C,2H | 4C,9H | 2C,4H | 3G | 2G | 10C | 5C,9G | 10C | 10C | 4C,9H | 4C,8H | 10C | 10C |
| Giant Foxtail | 0 | 0 | 4G | 0 | 6G | 2G | 2C,7G | 2G | 0 | 0 | 4C,9G | 3C,9G | 5C,9G | 6G | 3C,8G | 2C,6G | 2C,7G | 3G |
| Barley | 0 | 0 | 2G | 0 | 0 | 0 | 2G | 0 | 0 | 0 | 9G | 6G | 9G | 5G | 2C,2G | 0 | 9C | 8G |
| | Compound 100 | | Compound 101 | | Compound 102 | | Compound 103 | | Compound 104 | | Compound 105 | | Compound 106 | | Compound 107 | | Compound 108 | |
| Rate kg/ha | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| Cotton | 4C,9H | 2C,7G | 3C,9G | 2C,4G | 4C,9H | 3C,8H | 9C | 4C,9H | 9C | 4C,9G | 5C,9G | 4C,9H | 4C,9G | 4C,9H | 10C | 5C,9G | 5C,9G | 10C |
| Morningglory | 3C,5G | 2H | 4C,9G | 3C,8H | 10C | 5C,9G | 10C | 4C,9G | 10C | 10C | 10C | 3C,8G | 10C | 0 | 10C | 2H | 10C | 9C |
| Cocklebur | 3C,9H | 6G | 5C,9G | 3C,8H | 9C | 4C,9G | 10C | 10C | 10C | 10C | 9C | 10C | 10C | 10C | 10C | 10C | 10C | 10C |
| Nutsedge | 3C,9G | 3G | 3C,8G | 0 | 5C,9G | 4C,9G | 9C | 5C,9G | 9C | 9C | 5C,9G | 8G | 9C | 4C,8G | 5C,9G | 3C,8G | 3C,8G | 2C,7G |
| Crabgrass | 0 | 0 | 2G | 0 | 0 | 0 | 0 | 0 | 3G | 0 | 3G | 0 | 5G | 0 | 3C,7G | 2G | 3C,7G | 5G |
| Barnyardgrass | 2H | 0 | 2C,5H | 0 | 3C,8H | 1H | 3C,9H | 7H | 10C | 9C | 9C | 3C,8H | 10C | 5C,9H | 10C | 9C | 9C | 9C |
| Wild Oats | 0 | 0 | 2C,5G | 0 | 3C,6G | 3G | 2C,5G | 2G | 3C,9G | 3C,7G | 3C,7G | 3C,5G | 3C,9G | 3C,8G | 3C,9G | 3C,8G | 4C,9G | 3C,7G |
| Wheat | 0 | 0 | 2C,7G | 3G | 5C,9G | 7G | 7G | 2G | 2C,9G | 3C,9G | 6C,9G | 2C,8G | 3C,9G | 5C,9G | 5C,9G | 3C,9G | 9C | 5C,9G |
| Corn | 3G | 0 | 3C,9H | 4G | 4C,9H | 2C,7G | 1H | 0 | 0 | 0 | 0 | 0 | 0 | 0 | 9C | 3C,9G | 4C,9G | 4C,9H |
| Soybean | 3H | 0 | 3C,7H | 2C,5H | 5C,9G | 4C,9G | 3C,9G | 8H | 9C | 9C | 9C | 5C,9G | 5C,9G | 5C,9G | 9C | 5C,9G | 5C,9G | 9C |
| Rice | 2G | 0 | 7G | 0 | 8G | 0 | 5C,9G | 7G | 9C | 3C,9G | 5C,9G | 4C,9G | 5C,9G | 5C,9G | 9C | 5C,9G | 9C | 9C |
| Sorghum | 4C,9G | 7H | 2C,9G | 3C,8H | 9C | 4C,9H | 9C | 9C | 9C | 9C | 9C | 5C,9G | 10C | 3C,9H | 9C | 9C | 10C | 9C |
| Cheatgrass | 2C,5G | 0 | 8G | 2G | 4C,9G | 3C,7G | 8G | 3G | 7G | 3G | 7G | 5G | 5C,9G | 5C,9H | 10C | 2C,8G | 5C,9G | 3C,8G |
| Sugar beet | 3C,5G | 1C | 10C | 3C,7G | 9C | 3C,7G | 10C | 10C | 10C | 10C | 10C | 4C,9H | 10C | 10C | 10C | 9C | 10C | 10C |
| Velvetleaf | 3C,8H | 3C,7G | 4C,8H | 3C,7H | 9C | 4C,9G | 10C | 5C,9G | 10C | 10C | 10C | 4C,8G | 9C | 4C,9H | 10C | 9C | 9C | 10C |
| Giant Foxtail | 2G | 0 | 2C,7G | 2G | 4C,9G | 4G | 6G | 3G | 3C,7H | 3C,6G | 4C,8G | 7G | 4C,8G | 3C,8G | 5C,9G | 3C,8G | 5C,9G | 4C,8G |
| Barley | 2G | 0 | 2C,6G | 0 | 2C,9G | 2C,6G | 7G | 2G | 3C,9G | 3C,8G | 8G | 6G | 2C,9G | 3C,8G | 4C,8G | 9G | 3C,9G | 8G |
| | Compound 109 | | Compound 110 | | Compound 111 | | Compound 112 | | Compound 113 | | Compound 114 | | Compound 115 | | Compound 116 | | Compound 117 | |
| Rate kg/ha | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| Cotton | 9C | 5C,9G | 6C,9G | 3C,9G | 4C,8H | 3C,7H | 4C,9H | 4C,8G | 1H | 0 | 2C,3H | 2G | 4C,9G | 9H | 5C,9G | 10C | 5C,9G | 4C,8G |
| Morningglory | 2C,7G | 5G | 10C | 10C | 4C,8H | 3C,7G | 10C | 4C,9G | 0 | 0 | 1H | 0 | 10C | 5C,9G | 10C | 10C | 5C,9G | 4C,9H |
| Cocklebur | 10C | 10C | 10C | 10C | 4C,9H | 2C,4G | 10C | 4C,8H | 1H | 0 | 2H | 2H | 8G | 2G | 10C | 2C,3H | 4C,9H | 3C,5H |
| Nutsedge | 4C,9G | 6C,9G | 5C,9G | 3C,8G | 2C,4G | 0 | 3C,9G | 0 | 0 | 0 | 4C,9G | 0 | 10C | 4C,8G | 9C | 3C,8G | 9G | 8G |
| Crabgrass | 3C,6G | 5G | 3C,5G | 3G | 0 | 0 | 2G | 0 | 2G | 0 | 3C,6G | 3G | 6G | 2G | 3C,6G | 2C | 0 | 0 |
| Barnyardgrass | 10C | 9C | 9C | 4C,9H | 3C,7H | 2C,5H | 9C | 3C,7G | 5C,9H | 3C,6G | 9C | 3C,8H | 9C | 5C,9G | 9C | 9C | 2H | 0 |
| Wild Oats | 4C,9G | 4C,9G | 3C,9G | 2C,3G | 0 | 0 | 3C,5G | 0 | 3C,5G | 2G | 9C | 3C,6H | 5C,9G | 3G | 3C,7G | 3G | 0 | 0 |
| Wheat | 9C | 2C,9G | 3C,9G | 3G | 0 | 0 | 4G | 0 | 9C | 8G | 9C | 3C,7H | 9G | 2C,9G | 5C,9G | 9G | 2G | 0 |
| Corn | 3C,8H | 3C,7H | 3C,8H | 2G | 3C,7G | 0 | 9G | 3C,6G | 2C,9G | 2C,5H | 4H | 0 | 2G | 0 | 6H | 0 | 0 | 0 |
| Soybean | 9C | 4C,9G | 4C,9G | 3C,6G | 4C,9G | 3C,8G | 4C,9G | 4C,8G | 2G | 0 | 3C,8G | 0 | 5C,9G | 4C,9G | 9C | 5C,9G | 4C,9G | 3C,7H |
| Rice | 9C | 9C | 9C | 4C,9G | 3G | 0 | 4G | 0 | 9C | 8G | 5C,9G | 9G | 9C | 9C | 9C | 3C,8G | 2G | 0 |
| Sorghum | 9C | 9C | 9C | 4C,9H | 3C,7H | 0 | 3C,9G | 3C,8H | 4C,9G | 3C,7H | 9C | 4C,9G | 9C | 9C | 9C | 9C | 3C,3H | 0 |
| Cheatgrass | 5C,9G | 8G | 4C,8G | 6G | 0 | 0 | 0 | 0 | 3C,9G | 0 | 9C | 3C,7G | 8G | 6G | 3C,8G | 3C,6G | 0 | 0 |
| Sugar beet | 10C | 9C | 9C | 9C | 3C,5H | 3C,8H | 10C | 4C,8H | 3C,8G | 3G | 3C,7H | 3C,6G | 9C | 9C | 10C | 9C | 9C | 3C,7G |
| Velvetleaf | 9C | 4C,8H | 9C | 9C | 3C,7H | 0 | 4C,9G | 3C,6H | 4G | 0 | 2H | 0 | 9C | 9C | 10C | 9C | 3C,8H | 3C,4H |
| Giant Foxtail | 4C,8G | 2C,6G | 3C,8G | 3G | 2G | 0 | 3C,7G | 2C,2G | 3C,8H | 2G | 9C | 3C,8H | 9C | 4C,9G | 4C,9H | 3C,7G | 0 | 0 |
| Barley | 4C,9G | 2C,8G | 9G | 5G | 0 | 0 | 3G | 0 | 2C,9G | 9G | 10C | 2C,8G | 3C,8G | 3C,6G | 3C,8G | 3G | 0 | 0 |
| | Compound 118 | | Compound 119 | | Compound 120 | | Compound 121 | | Compound 122 | | Compound 123 | | Compound 124 | | Compound 125 | | Compound 126 | |
| Rate kg/ha | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.05 | 0.05 | 0.01 |
| Cotton | 9H | 8H | 9C | 9C | 1C | 0 | 10C | 4C,9G | 0 | — | 4C,9H | 4C,9H | 4C,9H | 3C,8H | 5C,9G | 9C | 9H | — |

TABLE A-continued

| | | | | | | | | | | | | | | | | | | |
|---|---|---|---|---|---|---|---|---|---|---|---|---|---|---|---|---|---|---|
| Giant Foxtail | 0 | 0 | 0 | 0 | 9C | 4C,9G | 9C | 5C,9G | 9C | 5C,9G | 5C,9G | 7G | 4C,9H | 3G | 4C,9H | 3C,7G | 3C,8G | 3G |
| Barley | 0 | 0 | 0 | 0 | 7G | 3G | 3G | 0 | 2G | 0 | 0 | 0 | 2G | 0 | 5G | 0 | 9G | 4G |

| | Compound 73 | | Compound 74 | | Compound 75 | | Compound 76 | | Compound 77 | | Compound 78 | | Compound 79 | | Compound 80 | | Compound 81 | |
|---|---|---|---|---|---|---|---|---|---|---|---|---|---|---|---|---|---|---|
| Rate kg/ha | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| Cotton | 4C,9H | 9G | 9G | 9G | 9G | 9C | 9C | 9C | 5C,9G | 3C,9G | 9G | 10C | 9C | 9C | 2C,8H | 9C | 2C,8H | |
| Morningglory | 10C | 9C | 4C,9G | 3C,8H | 9C | 2C,9G | 10C | 7G | 10C | 10C | 10C | 3C,8H | 10C | 9C | 3C,8H | 4C,8H | 10C | 4C,8H |
| Cocklebur | 10C | 4C,9G | 4C,9G | 3C,8H | 5C,9G | 3C,8H | 10C | 10C | 10C | 10C | 9C | 3C,8H | 10C | 9C | 5C,9H | 4C,8H | 10C | 10C |
| Nutsedge | 5C,9G | 3C,9G | 4C,9G | 2C,5G | 3C,9G | 5C,9G | 10C | 10C | 10C | 5C,9G | 4C,9G | 2C,9G | 10C | 4C,9G | 8G | 6G | 3C,8G | 0 |
| Crabgrass | 0 | 2H | 0 | 0 | 0 | 0 | 2C,7G | 7G | 2C,6G | 3G | 6G | 0 | 6G | 2G | 5G | 0 | 2C,5G | 0 |
| Barnyardgrass | 4C,9H | 3C,7H | 3C,8H | 4G | 3C,8H | 3C,5H | 10C | 9C | 9C | 9C | 9C | 4C,9H | 3C,9G | 2C,8G | 9C | 2C,9H | 10C | 3C,9G |
| Wild Oats | 6C,9G | 2C,2G | 9C | 3C,7G | 2C,3G | 0 | 2C,9G | 2C,6G | 3C,9G | 2C,7G | 3C,9G | 3C,9G | 6C | 2C,6G | 3C,7G | 2C,5G | 5C,9G | 3C,8G |
| Wheat | 4C,9G | 2C,5G | 4C,8G | 3G | 2C,3G | 0 | 4C,9G | 10C | 2C,9G | 9C | 3C,9G | 9G | 2C,9G | 9G | 4G | 0 | 2G | 0 |
| Corn | 3C,5G | 3G | 1C | 0 | 0 | 0 | 6U,9C | 3U,8G | 4U,9G | 2C,9G | 3C,8H | 1C,4G | 3C,9G | 2C,7H | 6U,9C | 3U,9G | 6U,9C | 3U,9C |
| Soybean | 5C,9G | 4C,8G | 4C,9G | 4C,9G | 3C,8G | 4H | 10C | 9C | 6C,9G | 5C,9G | 5C,9G | 3C,9G | 3C,8H | 2H,7G | 5C,9H | 4C,8H | 4C,9G | 3C,9G |
| Rice | 5C,9G | 3G | 5C,9G | 2C,8G | 3C,8G | 2G | 6C,9G | 9C | 9C | 5C,9G | 9C | 3C,9G | 5C,9G | 2C,9G | 9C | 8G | 4C,9G | 8G |
| Sorghum | 9C | 4C,9H | 9H | 2C,5G | 10C | 9G | 9C | 3U,9G | 9C | 9C | 10C | 2C,9G | 5C,9G | 5C,9G | 9C | 2C,9G | 9C | 9C |
| Cheatgrass | 9C | 4C,9G | 4C,9G | 2C,7G | 3C,8G | 2C,5G | 10C | 10C | 10C | 9C | 10C | 5C,9G | 9C | 9G | 9G | 5G | 3C,9G | 6G |
| Sugar beet | 10C | 3C,8H | 3C,8H | 3C,8G | 4C,9G | 1C,2G | 10C | 10C | 10C | 10C | 10C | 10C | 10C | 10C | 10C | 5C,9H | 10C | 3C,9H |
| Velvetleaf | 10C | 4C,9H | 9G | 3C,7H | 5C,9G | 3C,5G | 10C | 10C | 10C | 9C | 10C | 5C,9H | 10C | 5C,9H | 5C,9H | 3C,6H | 9C | 3C,8H |
| Giant Foxtail | 3C,7H | 2G | 3G | 2G | 1C | 0 | 4C,9G | 2C,9G | 9C | 4C,9G | 10C | 3C,9G | 9G | 6G | 9C | 2C,8G | 10C | 9C |
| Barley | 3G | 0 | 3C,7G | 0 | 0 | 0 | 3C,9G | 9G | 9C | 9G | 4C,9G | 9G | 9G | 9G | 2C,6G | 5G | 6G | 2G |

| | Compound 82 | | Compound 83 | | Compound 84 | | Compound 85 | | Compound 86 | | Compound 87 | | Compound 88 | | Compound 89 | | Compound 90 | |
|---|---|---|---|---|---|---|---|---|---|---|---|---|---|---|---|---|---|---|
| Rate kg/ha | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| Cotton | 9C | 5C,9G | 9C | 9C | 9C | 4C,9G | 9C | 4C,9G | 4C,9H | 3C,4G | 4C,9H | 4C,8H | — | — | — | — | — | — |
| Morningglory | 10C | 10C | 10C | 10C | 10C | 10C | 10C | 10C | 3C,8H | 3C,6H | 5C,9G | 3C,9G | 2C | 0 | 3C,8H | 2C,7G | 2C,4H | 0 |
| Cocklebur | 10C | 10C | 10C | 10C | 10C | 10C | 10C | 10C | 4G | 0 | 9C | 3C,8H | 4C,9H | 3C,8H | 5C,9H | 4C,8H | 4C,9H | 0 |
| Nutsedge | 9C | 9C | 9C | 4C,8G | 9C | 9C | 9C | 5C,9G | 3C,5G | 0 | 4C,9G | 3C,5G | 2C,6G | 6G | 2C,8G | 3G | 0 | 0 |
| Crabgrass | 6C,9G | 4C,6G | 4C,8G | 4G | 4C,9G | 7G | 3C,6G | 2G | 3C,5G | 0 | 5C,9G | 4G | 0 | 0 | 0 | 0 | 0 | 0 |
| Barnyardgrass | 9C | 9C | 9C | 9C | 9C | 9C | 10C | 9C | 9C | 5C,9H | 9C | 9C | 3C,6G | 4G | 3C,8H | 0 | 2G | 0 |
| Wild Oats | 9C | 3C,9G | 5C,9G | 4C,9G | 9C | 4C,9G | 5C,9G | 4C,9G | 5C,9G | 5C,9G | 6C,9G | 4C,9G | 2C,2G | 2G | 2C,5G | 2C,3G | 3C,5G | 2G |
| Wheat | 9C | 3C,9G | 6C,9G | 4C,9G | 9C | 4C,9G | 4C,9G | 8G | 5C,9G | 4C,9G | 3C,9G | 3C,7G | 6G | 3G | 3C,9G | 2C,7G | 2C,4G | 2G |
| Corn | 10C | 3C,9G | 9C | 9C | 6C,9G | 3C,9G | 5C,9G | 9G | 9C | 9G | 9C | 9C | 2C,6H | 2G | 3C,8H | 3G | 0 | 0 |
| Soybean | 5C,9G | 5C,9G | 9C | 4C,9G | 6C,9G | 4C,9G | 5C,9G | 3C,9G | 4C,9G | 4C,9G | 5C,9G | 4C,9G | 4C,9G | 4C,8G | 5C,9G | 3C,9H | 3C,7H | 0 |
| Rice | 6C,9G | 9C | 9C | 9C | 9C | 9C | 9C | 5C,9G | 5C,9G | 3C,8G | 4C,9G | 4C,9G | 3C,8G | 7G | 2C,8G | 2C,5G | 4G | 0 |
| Sorghum | 9C | 9C | 9C | 9C | 9C | 5C,9G | 9C | 9C | 5C,9G | 3C,8H | 9C | 9C | 3C,8H | 6G | 3C,9H | 2C,8H | 2C,7H | 0 |
| Cheatgrass | 9C | 9C | 9C | 9C | 9C | 9C | 9C | 3C,9G | 4C,8G | 4C,8G | 6C,9G | 2C,9G | 2C,9G | 2C,8G | 9G | 2C,9G | 9G | 4G |
| Sugar beet | 9C | 10C | 10C | 10C | 10C | 10C | 10C | 9C | 10C | 3C,7H | 10C | 5C,9G | 10C | 1C,3G | 3C,9G | 0 | 2C,5G | 0 |
| Velvetleaf | 10C | 9C | 10C | 9C | 10C | 10C | 10C | 9C | 3C,5H | 1C | 9C | 3C,4H | 3C,9H | 2C,7G | 4C,9G | 2C,7G | 2C,7G | 5G |
| Giant Foxtail | 10C | 9C | 10C | 10C | 9C | 9C | 9C | 9C | 9C | 3C,7H | 10C | 9C | 4G | 0 | 5G | 2G | 2G | 0 |
| Barley | 4C,9G | 4C,9G | 5C,9G | 3C,9G | 9C | 4C,9G | 4C,9G | 3C,7G | 2C | 0 | 3C,6G | 0 | 5G | 0 | 5G | 5G | 3G | 0 |

| | Compound 91 | | Compound 92 | | Compound 93 | | Compound 94 | | Compound 95 | | Compound 96 | | Compound 97 | | Compound 98 | | Compound 99 | |
|---|---|---|---|---|---|---|---|---|---|---|---|---|---|---|---|---|---|---|
| Rate kg/ha | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| Cotton | — | — | — | — | — | — | 4C,9G | 1C,5G | 0 | 0 | 4C,9G | 4C,9G | 9C | 4C,9H | 4C,9G | 3C,9H | 9C | 3C,9G |
| Morningglory | 2C,4G | 2G | 2C,7G | 2H | 3C,8H | 2C,6H | 5C,9G | 5C,9G | 0 | 0 | 10C | 10C | 10C | 10C | 9C | 9C | 10C | 10C |
| Cocklebur | 3C,8H | 1C,5G | 4C,8H | 2C,7H | 3C,8H | 2C | 4C,9H | 3C,8H | 4G | 3G | 10C | 10C | 10C | 4G | 10C | 5C,9G | 10C | 10C |
| Nutsedge | 0 | 0 | 0 | 0 | 0 | 0 | 6G | 0 | 0 | 0 | 5C,9G | 3C,8G | 10C | 9C | 4C,9G | 4C,8G | 10C | 9C |
| Crabgrass | 0 | 0 | 0 | 0 | 0 | 0 | 0 | 0 | 0 | 0 | 7G | 2G | 4C,8G | 5G | 1C | 0 | 2G | 0 |
| Barnyardgrass | 0 | 0 | 3C,6H | 0 | 2C,7G | 3G | 4C,9H | 2C,7H | 0 | 0 | 10C | 10C | 10C | 10C | 9C | 3C,8H | 3C,9H | 1C,4H |
| Wild Oats | 0 | 0 | 0 | 0 | 4G | 0 | 2G | 0 | 0 | 0 | 9G | 2C,5G | 4C,9G | 3C,6G | 5G | 0 | 3C,7G | 0 |
| Wheat | 0 | 0 | 0 | 0 | 2G | 0 | 4G | 3G | 0 | 0 | 9G | 2C,6G | 3C,9G | 8G | 2C,7G | 3G | 2C,8G | 7G |

TABLE A-continued

| | | | | | | | | | | | | | | | | | | |
|---|---|---|---|---|---|---|---|---|---|---|---|---|---|---|---|---|---|---|
| Morningglory | 9C | 3C,8H | 10C | 10C | 3H | 0 | 10C | 10C | 0 | — | 10C | 9C | 4C,9G | 4C,9H | 10C | 10C | 4C,9G | — |
| Cocklebur | 4C,9G | 3C,7H | 10C | 10C | 1H | 0 | 10C | 9C | 2H | — | 9C | 4C,9H | 5C,9G | 4C,9H | 10C | 10C | 4C,9G | — |
| Nutsedge | 9C | 4C,8G | 5C,9G | 4C,9G | 0 | 0 | 9G | 8G | 0 | — | 3C,8G | 2C,5G | 9G | 3C,9G | 10C | 5C,9G | 8G | — |
| Crabgrass | 0 | 0 | 3C,5G | 2G | 0 | 0 | 3C,5G | 2G | 0 | — | 2C,5G | 2G | 3C,4G | 2G | 3C,8G | 5G | 0 | — |
| Barnyardgrass | 4H | 0 | 9C | 9C | 4H | 0 | 9C | 9C | 1H | — | 9C | 4C,9H | 5C,9H | 4C,8H | 5C,9H | 3C,6H | 0 | — |
| Wild Oats | 0 | 0 | 4C,8G | 3C,5G | 3C,7G | 0 | 4C,9G | 3C,5G | 2C,5G | — | 4C,9G | 5G | 4C,9G | 7G | 8G | 4G | 0 | — |
| Wheat | 0 | 0 | 9C | 4C,9G | 8G | 0 | 5C,9G | 8G | 6G | — | 9G | 8G | 3C,9G | 9G | 8G | 4G | 0 | — |
| Corn | 0 | 0 | 2C,7H | 3H | 0 | 0 | 0 | 0 | 0 | — | 0 | 0 | 0 | 0 | 3C,9G | 9G | 2H | — |
| Soybean | 3C,7H | 3C,7H | 5C,9G | 5C,9G | 3C,4G | 0 | 5C,9G | 4C,9G | 2G | — | 4C,9G | 3C,8G | 5C,9G | 4C,9G | 4C,9G | 4C,9G | 3C,5G | — |
| Rice | 2G | 0 | 9C | 9C | 8G | 0 | 9C | 9C | 3G | — | 9C | 5C,9G | 9C | 5C,9G | 5C,9G | 3C,9G | 0 | — |
| Sorghum | 6H | 0 | 9C | 9C | 4C,9H | 0 | 9C | 4C,9G | 2C,5G | — | 9C | 4C,9G | 5C,9G | 3C,9G | 5C,9G | 3C,9G | 3C,6G | — |
| Cheatgrass | 0 | 0 | 5C,9G | 4C,8G | 3C,8G | 0 | 4C,9G | 4C,9G | 3C,8G | — | 9C | 9G | 6C,9G | 3C,9G | 9C | 9C | 5G | — |
| Sugar beet | 9C | 3C,7H | 10C | 9C | 1H | 0 | 10C | 10C | 0 | — | 10C | 4C,8H | 9C | 4C,9H | 10C | 10C | 3C,8G | — |
| Velvetleaf | 4C,8H | 3C,6H | 10C | 9C | 1C | 0 | 10C | 9C | 1C | — | 9C | 3C,7H | 9C | 4C,8H | 10C | 10C | 3C,6G | — |
| Giant Foxtail | 1C | 2G | 9C | 9C | 2C,5G | 0 | 9C | 4C,9G | 0 | — | 5C,9G | 3C,7H | 6C,9G | 4C,8G | 3C,7G | 5G | 0 | — |
| Barley | 0 | 0 | 5C,9G | 4C,9G | 7G | 0 | 4C,9G | 3C,8G | 8G | — | 3C,8G | 3C,6G | 5C,9G | 2C,9G | 8G | 5G | 0 | — |

| | Compound 127 | | Compound 128 | | Compound 129 | | Compound 130 | | Compound 131 | | Compound 132 | | Compound 133 | | Compound 134 | | Compound 135 | |
|---|---|---|---|---|---|---|---|---|---|---|---|---|---|---|---|---|---|---|
| Rate kg/ha | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| Cotton | 10C | 3C,9G | 2C,9H | 2C,5H | 3C,9H | 2C,8H | 2C,8H | 3C,6H | 10C | 5C,9G | 9C | 10C | 9C | 7G | 9C | 3C,8H | 2C,3G | 1C |
| Morningglory | 10C | 9C | 6C,9G | 4C,8H | 3C,8H | 2C,8G | 6C,9G | 4C,8H | 10C | 4C,9G | 10C | 9C | 9C | 7G | 10C | 9C | 4C,8H | 3C,4H |
| Cocklebur | 10C | 5C,9H | 3C,9H | 3C,4H | 9C | 4C,9H | 10C | 2C,3H | 10C | 10C | 10C | 10C | 10C | 5C,9G | 10C | 10C | 3C,5H | 3G |
| Nutsedge | 2C,8G | 8G | 2C,6G | 0 | 6G | 2C,7G | 3C,8G | 2C,4G | 9C | 3C,8G | 4C,9G | 2C,9G | 9C | 3C,9G | 9C | 9G | 0 | 2C,4G |
| Crabgrass | 0 | 0 | 0 | 0 | 0 | 0 | 0 | 0 | 4C,8G | 2G | 4C,8G | 3G | 5C,9G | 5G | 3G | 0 | 2G | 0 |
| Barnyardgrass | 3C,9H | 2C,7H | 2C,5H | 0 | 2G | 3G | 2C,6H | 2C,6G | 9C | 9C | 10C | 9C | 10C | 10C | 9C | 5C,9H | 3C,8H | 3C,7H |
| Wild Oats | 2C,6G | 2C | 2C | 0 | 2G | 0 | 2C,5G | 3G | 3C,9G | 5G | 4C,9G | 3C,6G | 4C,9G | 4C,9G | 4C,9G | 2G | 0 | 0 |
| Wheat | 9G | 9G | 2C | 0 | 2G | 0 | 2C,9G | 2G | 3C,9G | 9G | 3C,9G | 9G | 4C,9G | 9C | 9G | 4G | 2G | 0 |
| Corn | 3C,9G | 3C,7H | 2C,8H | 2C,3G | 2C | 0 | 3C,8H | 2C,2H | 10C | 3C,9G | 5C,9G | 4G | 3C,9H | 2H | 0 | 3G | 3C,9G | 3C,7H |
| Soybean | 3C,8H | 3C,8G | 3C,8H | 2C,3H | 2H | 0 | 4C,8H | 3C,4H | 9C | 9C | 5C,9G | 9C | 9C | 4C,9G | 4C,9G | 3C,8H | 3C,8G | 4H |
| Rice | 2C,9G | 6G | 4G | 0 | 2C,5G | 0 | 3C,9G | 2C,4G | 9C | 9C | 9C | 9C | 9C | 5C,9G | 9C | 7G | 3G | 0 |
| Sorghum | 5C,9G | 2C,9G | 9H | 2C,7H | 9G | 3C,8H | 2C,9G | 2C,9G | 10C | 9C | 9C | 9C | 10C | 2C,7H | 9C | 3C,8H | 3C,9H | 3C,7H |
| Cheatgrass | 10C | 3C,9G | 5G | 3G | 2C,8G | 5G | 8G | 8G | 9C | 9C | 10C | 9C | 10C | 9C | 9C | 9G | 8G | 6G |
| Sugar beet | 10C | 6C,9G | 3C,9H | 2C,3G | 3C,6G | 2C,7G | 3C,9G | 3C,5H | 9C | 10C | 10C | 10C | 10C | 9C | 9C | 9C | 8H | 5H |
| Velvetleaf | 9C | 9C | 3C,7H | 2C,4G | 2C,8G | 2C,7G | 5C,9H | 3C,7G | 10C | 10C | 10C | 5C,9G | 10C | 10C | 9C | 5C,9G | 2G | 2G |
| Giant Foxtail | 2C,9G | 6G | 3G | 2G | 2G | 3G | 2C,7G | 3G | 9C | 4C,9G | 9C | 3C,8G | 9C | 4C,8G | 5C,9G | 3C,7G | 2C,8G | 7G |
| Barley | 9G | 6G | 4G | 0 | 0 | 0 | 7G | 0 | 4C,9G | 5G | 9C | 7G | 4C,9G | 8G | 7G | 0 | 0 | 0 |

| | Compound 136 | | Compound 137 | | Compound 138 | | Compound 139 | | Compound 140 | | Compound 141 | | Compound 142 | | Compound 143 | | Compound 144 | |
|---|---|---|---|---|---|---|---|---|---|---|---|---|---|---|---|---|---|---|
| Rate kg/ha | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| Cotton | 8H | 2C,2G | 10C | 4C,9G | 3C,7G | 0 | 4C,9G | 3C,8G | 9C | 3C,9G | 5C,9H | 4C,8H | 10C | 5G | 5C,9G | 4C,8H | 3C,7G | 2C,2G |
| Morningglory | 4C,8H | 3C,8H | 10C | 4C,8G | 10C | 3C,7H | 4C,9G | 4C,8G | 9C | 5C,9G | 9C | 4C,8H | 10C | 5C,9G | 10C | 5C,9G | 3C,8G | 3C,6G |
| Cocklebur | 4C,8H | 3C,5G | 10C | 10C | 2H | 0 | 4C,9G | 4C,9G | 10C | 8H | 10C | 4C,9H | 9C | 3C,7H | 10C | 9C | 4C,8H | 2H |
| Nutsedge | 3C,7G | 3C,5G | 3C,9G | 3C,8G | 0 | 0 | 3C,5G | 2C,4G | 4C,9G | 9G | 2C,5G | 3G | 4C,9G | 4C,9G | 4C,8G | 2C,5G | 0 | — |
| Crabgrass | 3G | 0 | 4G | 0 | 0 | 0 | 5G | 0 | 5G | 0 | 0 | 0 | 3G | 0 | 3G | 3G | 0 | 0 |
| Barnyardgrass | 9C | 4C,9H | 9C | 3C,9H | 9H | 4C,9H | 9C | 3C,8H | 9C | 5C,9H | 4C,9H | 3C,7H | 4C,9H | 3C,7H | 9C | 3C,8H | 3C,6H | 0 |
| Wild Oats | 2C,3G | 2G | 0 | 0 | 0 | 0 | 2C | 0 | 1C | 0 | 1C | 0 | 0 | 0 | 2C,5G | 0 | 0 | 0 |
| Wheat | 0 | 0 | 2G | 0 | 7G | 0 | 9G | 3G | 5G | 0 | 2G | 0 | 4G | 0 | 7G | 3G | 0 | 0 |
| Corn | 9C | 3C,8H | 0 | 0 | 0 | 0 | 0 | 0 | 3G | 0 | 0 | 0 | 1C | 0 | 3C,7G | 2G | 0 | 0 |
| Soybean | 4C,9G | 4C,8H | 3C,9G | 1H | 3C,5H | 2H | 4C,9G | 4C,8G | 5C,9G | 3C,5H | 4C,9G | 1H | 4C,9G | 5C,9G | 5C,9G | 4C,9G | 3C,6H | 2C,2H |
| Rice | 2C,3G | 0 | 5C,9G | 3C,6G | 3C,7G | 3G | 5C,9G | 2C,5G | 6C,9G | 6G | 5G | 0 | 5C,9G | 8G | 9C | 6C,9G | 2C | 0 |
| Sorghum | 9C | 3C,9G | 9C | 9G | 5C,9G | 4C,9H | 4C,9G | 2C,5G | 6C,9G | 4C,9H | 5C,9H | 3C,6G | 5C,9H | 3C,9H | 9C | 6C,9G | 3C,7G | 2G |
| Cheatgrass | 5C,9G | 7G | 8G | 5G | 3C,8G | 6G | 5G | 0 | 9C | 3C,9G | 9G | 8G | 3C,9G | 8G | 3C,9G | 2G | 0 | 0 |
| Sugar beet | 9C | 3C,7G | 9C | 3C,8G | 3C,4H | 2H | 5C,9H | 4C,9H | 10C | 9C | 9C | 9C | 9C | 9G | 10C | 9C | 3C,8G | 0 |

TABLE A-continued

| | | | | | | | | | | | | | | | | | | |
|---|---|---|---|---|---|---|---|---|---|---|---|---|---|---|---|---|---|---|
| Velvetleaf | 3C,7G | 1C | 10C | 3C,8G | 3C,7H | 2G | 10C | 3C,8H | 10C | 9C | 9C | 4C,7G | 10C | 9C | 10C | 4C,8H | 3C,7G | 0 |
| Giant Foxtail | 9C | 3C,7G | 3C,9G | 3C,7G | 3C,7G | 5G | 5C,9G | 3C,5G | 3C,8G | 3C,5G | 3C,7G | 3G | 3C,7G | 3C,5G | 9C | 5C,9G | 3G | 0 |
| Barley | 2G | 0 | 0 | 0 | 0 | 0 | 2G | 0 | 0 | 0 | 0 | 0 | 2C,3G | 0 | 8G | 0 | 0 | 0 |
| | Compound 145 | | Compound 146 | | Compound 147 | | Compound 148 | | Compound 149 | | Compound 150 | | Compound 151 | | Compound 152 | | Compound 153 | |
| Rate kg/ha | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| Cotton | 4C,9H | 4C,9H | 10C | 4C,8G | 3C,8H | 0 | 8H | 0 | 9G | 4C,8H | 0 | 0 | 3C,7G | 0 | 10C | 9C | 10C | 10C |
| Morningglory | 9C | 5C,9H | 10C | 4C,8G | 3C,5G | 0 | 3C,4H | 0 | 4C,9G | 3C,8H | 2C,3G | 0 | 4C,8H | 0 | 10C | 10C | 10C | 9C |
| Cocklebur | 10C | 3C,9G | 10C | 4C,9H | 5C,9G | 2H | 3C,3H | 0 | 4C,9G | 3C,3H | 2C | 0 | 4C,8H | 0 | 10C | 10C | 10C | 10C |
| Nutsedge | — | — | 4C,9G | 4C,9G | — | — | — | 0 | — | 2G | 0 | 0 | 0 | 0 | 4C,9G | 4C,9G | 4C,9G | 9G |
| Crabgrass | 5G | 0 | 5G | 4G | 2G | 0 | 3G | 0 | 5G | 3G | 0 | 0 | 3C,5G | 3G | 3C,7G | 3C,6G | 3C,7G | 3G |
| Barnyardgrass | 5C,9H | 3C,7H | 9C | 4C,8H | 4C,8H | 2H | 5C,9H | 3C,7H | 9C | 3C,8H | 3C,9H | 5G | 9C | 3C,9H | 9C | 9C | 9C | 4C,8H |
| Wild Oats | 2G | 0 | 0 | 0 | 1C | 0 | 3C,7G | 0 | 3C,8G | 2G | 2C,9G | 3C,4G | 5C,9G | 3C,8G | 4C,9G | 2C,6G | 3C,7G | 2C,3G |
| Wheat | — | — | 7G | — | 3G | 0 | — | 0 | — | — | 9G | 9G | 9G | 9G | 2C,9G | 9G | 4C,9G | 8G |
| Corn | 3C,9H | 2C,5G | 3C,7H | 1H | 2H | 0 | 5C,9G | 3C,3G | 9C | 3C,8H | 3G | 0 | 0 | 0 | 0 | 0 | 0 | 0 |
| Soybean | 5C,9G | 3C,9H | 5C,9G | 4C,8G | 3C,8G | 0 | 3C,7G | 2G | 5C,9G | 3C,7G | 3C,7H | 1H | 3C,8G | 3C,6G | 5C,9G | 9C | 9C | 9C |
| Rice | 9C | 3C,8G | 5C,9G | 3C,5G | 4C,9G | 0 | 8G | 2G | 9C | 5C,9G | 3C,9G | 5G | 4C,9G | 6G | 5C,9G | 5C,9G | 5C,9G | 6C,9H |
| Sorghum | 9C | 5C,9G | 9C | 4C,9H | 4C,9G | 3G | 4C,9H | 3C,6G | 9C | 4C,9G | 3C,8H | 3G | 5C,9G | 3C,9G | 9C | 9C | 9C | 6C,9G |
| Cheatgrass | 3C,7G | 2G | 9C | 9G | 3C,5G | 0 | 4C,9G | 6G | 8G | 6G | 5G | 0 | 8G | 2C,5G | 9G | 8G | 4C,9G | 7G |
| Sugar beet | 9C | 9C | 10C | 5C,9H | 3C,7G | 3G | 3C,7H | 2H | 9C | 4C,8H | 3C,7H | 5H | 4C,8G | 4C,5G | 10C | 9C | 9C | 6C,9G |
| Velvetleaf | 6C,9G | 3C,6G | 10C | 5C,9H | 3C,6G | 0 | 0 | — | 4C,8G | 2C | 3G | 0 | 1C | 0 | 10C | 5C,9G | 10C | 9C |
| Giant Foxtail | 5C,9G | 5C,9G | 5C,9G | 3C,8G | 3C,7G | 0 | 4C,8G | 3G | 5C,9G | 3C,8G | 2G | 0 | 5C,9G | 2C,5G | 4C,8G | 3C,7G | 3C,8G | 5G |
| Barley | 7G | 0 | 5G | 0 | 3C,7G | 0 | 0 | 0 | 6G | 0 | 8G | 7G | 8G | 6G | 8G | 8G | 8G | 5G |
| | Compound 154 | | Compound 155 | | Compound 156 | | Compound 157 | | Compound 158 | | Compound 159 | | Compound 160 | | Compound 161 | | Compound 162 | |
| Rate kg/ha | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| Cotton | 10C | 3C,8H | 10C | 9C | 2G | 2H | 2G | 0 | 10C | 10C | 10C | 4C,9G | 3C,7H | 1C | 9C | 3C,8G | 6G | 0 |
| Morningglory | 4C,9H | 2C,6G | 10C | 10C | 4C,9G | 3C,7H | 2C,5G | 0 | 9C | 10C | 9C | 9C | 4C,8H | 1H | 10C | 9C | 1C | 0 |
| Cocklebur | 9C | 4C,9H | 10C | 10C | 7H | 2H | 3C,8H | 2C,3H | 10C | 10C | 10C | 10C | 1H | 1H | 10C | 10C | 7H | 0 |
| Nutsedge | 9G | 2C,9G | 9G | 9G | 0 | 0 | 0 | 0 | 9C | 2C,9G | 3C,8G | 2C,9G | 4G | 0 | 2C,9G | 9G | 0 | 0 |
| Crabgrass | 5G | 3G | 3C,6G | 5G | 3C,6G | 2C,4G | 5G | 0 | 1H | 0 | 4G | 0 | 4G | 0 | 5G | 0 | 0 | 0 |
| Barnyardgrass | 4C,8H | 3C,7H | 3C,7H | 3C,8H | 6C,9H | 3C,8H | 3C,4G | 2C,3H | 9C | 4C,9H | 3C,8H | 9C | 4C,9H | 3C,7H | 9C | 4C,9H | 3C,5H | 0 |
| Wild Oats | 3C,8G | 2C,5G | 3C,5G | 0 | 9C | 4C,9G | 2C,5G | 0 | 3C,6G | 2C,2H | 3C,8G | 2C,5G | 2C,9G | 4C,9G | 4G | 0 | 0 | 0 |
| Wheat | 8G | 4G | 7G | 3G | 3C,9G | 9G | 7G | 4G | 9G | 5G | 9G | 2C,9G | 7G | 3G | 5G | 0 | 0 | 0 |
| Corn | 2G | 2G | 0 | 0 | 0 | 0 | 0 | 0 | 5G | 2G | 3C,8H | 3G | 2C,5H | 0 | 2G | 0 | 0 | 0 |
| Soybean | 4C,9G | 4C,9G | 4C,9G | 3C,9G | 8G | 3C,7G | 3C,8G | 2C,3H | 9C | 5C,9G | 9C | 4C,9G | 3C,6H | 2H | 9C | 9C | 3H | 0 |
| Rice | 5C,9G | 5C,9G | 4C,9G | 2C,8G | 6C,9G | 4C,9G | 6G | 4G | 9G | 3C,8G | 2C,8G | 4G | 4C,9G | 4G | 2C,9G | 7G | 2G | 0 |
| Sorghum | 4C,9G | 5C,9H | 5C,9G | 5C,9H | 5C,9G | 3C,8H | 3C,6G | 2C,4G | 2C,9G | 5C,9G | 4C,9G | 4C,9G | 3C,9H | 2C,5G | 9C | 5C,9G | 7G | 0 |
| Cheatgrass | 8G | 3C,5G | 2C,5G | 2G | 3C,8G | 2C,7G | 3C,4G | 2G | 5C,9G | 3C,6G | 9C | 5C,9G | 4C,9G | 3C,8G | 3C,9G | 2C,8G | 5G | 0 |
| Sugar beet | 9C | 4C,9G | 5C,9G | 3C,7H | 3C,7H | 3C,7H | 3C,3G | 0 | 10C | 9C | 9C | 5C,9G | 3C,7H | 4H | 4C,9G | 3C,7H | 2C,5G | 0 |
| Velvetleaf | 4C,9H | 3C,7H | 4C,8H | 3C,6H | 2C,5G | 3C,3G | 2G | 3G | 10C | 10C | 10C | 10C | 2C,2G | 0 | 10C | 6C,9G | 2C,5G | 0 |
| Giant Foxtail | 3C,7G | 3G | 3C,7G | 2C,5G | 4C,9G | 3C,8G | 2C,7G | 3G | 2C,8G | 4G | 4C,9G | 7G | 4C,9G | 3C,6G | 3C,9G | 3C,8G | 3C,6G | 0 |
| Barley | 7G | 5G | 8G | 5G | 7G | 4C,9G | 4C,9G | 5G | 9G | 3C,4G | 2C,9G | 3G | 4C,9G | 2C,5G | 3C,9G | 2C,5G | 2C,5G | 0 |
| | Compound 163 | | Compound 164 | | Compound 165 | | Compound 166 | | Compound 167 | | Compound 168 | | Compound 169 | | Compound 170 | | Compound 171 | |
| Rate kg/ha | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| Cotton | 9C | 5C,9G | 10C | 10C | 10C | 10C | 10C | 9C | 4C,9H | 3C,8G | 3C,6G | 0 | 10C | 3C,7H | 9C | 4C,9G | 5C,9H | 4C,9H |
| Morningglory | 10C | 10C | 10C | 10C | 10C | 10C | 10C | 10C | 4C,8H | 4C,8H | 4C,8H | 3C,7H | 9C | 4C,8H | 10C | 9C | 5C,9H | 3C,6G |
| Cocklebur | 9C | 2G | 10C | 9H | 9C | 6H | 10C | 10C | 5C,9H | 1H | 1H | 0 | 1H | 0 | 10C | 10C | 10C | 4C,9H |
| Nutsedge | 5C,9G | 5C,9G | 5C,9G | 4C,9G | 9C | 5C,9G | 9C | 2C,9G | 5G | 0 | 0 | 0 | 3G | 0 | 10C | 4C,9G | 8G | 3C,7G |
| Crabgrass | 4C,9G | 3C,6G | 3C,7H | 2C,5G | 6C,9G | 2C,8G | 3C,7G | 3G | 3C,7G | 2C,5G | 4G | 0 | 4C,9H | 2C,8G | 4C,8G | 2C,6G | 2G | 0 |
| Barnyardgrass | 9C | 9C | 9C | 9C | 10C | 9C | 9C | 9C | 9C | 4C,8G | 10C | 0 | 9C | 9C | 9C | 9C | 4G | 2H |
| Wild Oats | 6C,9G | 5C,9G | 9C | 3C,8G | 5C,9G | 4C,9G | 4C,9G | 2C,6G | 3C,6G | 2C | 3G | 0 | 5C,9G | 5C,9G | 5C,9G | 3C,8G | 2C,5G | 0 |

TABLE A-continued

| | | | | | | | | | | | | | | | | | | |
|---|---|---|---|---|---|---|---|---|---|---|---|---|---|---|---|---|---|---|
| Wheat | 9C | 9C | 9C | 3C,9G | 9C | 4C,9G | 2C,9G | 6G | 4C,9G | 2G | 3G | 0 | 9G | 9G | 9G | 6G | 4G | 0 |
| Corn | 1H | 0 | 3C,7H | 1H | 3H,7G | 3G | 0 | 0 | 2C,4H | 2H | 10C | 5H | 2C,8H | 3H | 3C,7H | 0 | 0 | 0 |
| Soybean | 4C,9G | 6C,9G | 9C | 9C | 9C | 9C | 5C,9G | 4C,9G | 5C,9G | 4C,9G | 5C,9G | 2C,7G | 3C,8H | 5H | 9C | 9C | 3C,9G | 4C,8G |
| Rice | 5C,9G | 9C | 9C | 9C | 9C | 9C | 9C | 9C | 9C | 3C,6G | 4C,9G | 3G | 9C | 9C | 9C | 4C,9G | 4C,9G | 2C,6G |
| Sorghum | 10C | 9C | 10C | 9C | 10C | 9C | 9C | 9C | 9C | 4C,9H | 4C,9G | 2C,3G | 9C | 4C,9G | 9C | 9C | 4C,9H | 3C,8G |
| Cheatgrass | 5C,9G | 2C,9G | 9C | 4C,9G | 9C | 4C,9G | 3C,9G | 6G | 2C,8G | 2C,5G | 4G | 0 | 4C,9G | 9G | 9C | 3C,9G | 2C,8G | 8G |
| Sugar beet | 9C | 9C | 9C | 9C | 10C | 10C | 9C | 10C | 10C | 9C | 9C | 2C,5G | 9C | 3C,7H | 10C | 5C,9G | 9C | 5C,9H |
| Velvetleaf | 10C | 10C | 10C | 10C | 10C | 10C | 10C | 10C | 5C,8H | 3C,5H | 2C,4G | 0 | 9C | 4C,8H | 10C | 10C | 5C,9H | 4C,8H |
| Giant Foxtail | 9C | 9C | 9C | 9C | 9C | 6C,9G | 9C | 9C | 9C | 4C,8H | 9C | 0 | 9C | 9C | 9C | 4C,9G | 5G | 2H |
| Barley | 3C,9G | 9G | 4C,9G | 3C,8G | 4C,9G | 9G | 9G | 7G | 2G | 0 | 0 | 0 | 9C | 4C,9G | 3C,8G | 7G | 2C,4G | 0 |

| | Compound 172 | | Compound 173 | | Compound 174 | | Compound 175 | | Compound 176 | | Compound 177 | | Compound 178 | | Compound 179 | | Compound 180 | |
|---|---|---|---|---|---|---|---|---|---|---|---|---|---|---|---|---|---|---|
| Rate kg/ha | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| Cotton | 0 | — | 3C,9G | 10C | 5C,9G | 3G | 9C | 4C,9G | 9C | 10C | 9C | 10C | 9C | 4C,9H | 10C | 4C,9H | 10C | 4C,8H |
| Morningglory | 0 | — | 0 | 0 | 3C,8H | 2C,4H | 5C,9G | 4C,8H | 10C | 9C | 10C | 5C,9G | 10C | 2C,7G | 10C | 5C,9G | 3C,8H | 6C,9G |
| Cocklebur | 2G | — | 8G | 2C,6G | 4C,9G | 2G | 10C | 4C,8H | 10C | 10C | 10C | 10C | 10C | 9C | 10C | 10C | 9C | 5C,9H |
| Nutsedge | 3G | — | 0 | 0 | 0 | 0 | 2C,8G | 0 | 9G | 9G | 9G | 3C,9G | 8G | 2C,4G | 9C | 3C,9G | 5C,9G | 2C,9G |
| Crabgrass | 0 | — | 0 | 0 | 0 | 0 | 3G | 0 | 3C,8G | 5G | 3C,7G | 2G | 3G | 0 | 5G | 0 | 6G | 4G |
| Barnyardgrass | 0 | — | 2C,5H | 0 | 7H | 3G | 9H | 5G | 9C | 4C,9H | 5C,9H | 3C,9H | 9H | 3C,7H | 4C,9H | 3C,7H | 10C | 3C,7H |
| Wild Oats | 0 | — | 0 | 0 | 0 | 0 | 3C,8G | 5G | 4C,9G | 9G | 5C,9G | 3C,7G | 4C,9G | 4C,9G | 3C,5G | 2C,3G | 3C,8G | 2C,7G |
| Wheat | 0 | — | 5G | 0 | 0 | 0 | 3G | 0 | 9G | 9G | 9G | 9G | 9G | 9G | 9G | 5G | 2C,9G | 9G |
| Corn | 0 | — | 0 | 0 | 2G | 0 | 0 | 0 | 2H | 0 | 1H | 0 | 0 | 0 | 1H | 0 | 4U,8G | 2C,7G |
| Soybean | 0 | — | 0 | 0 | 4C,9G | 7H | 5C,9G | 4C,9G | 9C | 9C | 9C | 5C,9G | 5C,9G | 4C,9G | 3C,8H | 2C,5H | 5C,9G | 5C,8H |
| Rice | 0 | — | 0 | 0 | 7G | 0 | 9G | 4G | 9C | 9C | 9C | 5C,9G | 4C,9G | 4C,9G | 4C,9G | 4C,9G | 5C,9G | 6C,8G |
| Sorghum | 0 | — | 3G | 0 | 2G | 0 | 3C,9G | 3C,7G | 5C,9G | 4C,9G | 5C,9G | 3C,9G | 3C,9G | 3C,8G | 3C,9G | 4C,9H | 10C | 3U,8G |
| Cheatgrass | 0 | — | 3G | 0 | 0 | 0 | 3G | 0 | 6G | 4G | 8G | 0 | 0 | 0 | 3G | 0 | 5C,9G | 4C,8G |
| Sugar beet | 3G | — | 3H | 2G | 9C | 4C,8H | 9C | 10C | 10C | 10C | 10C | 9C | 10C | 10C | 10C | 9C | 9C | 9C |
| Velvetleaf | 0 | — | 3G | 2C,3G | 3C,7H | 0 | 4C,9H | 3C,6H | 10C | 10C | 10C | 6C,9G | 10C | 4C,9H | 10C | 4C,9G | 9C | 6C,9H |
| Giant Foxtail | 0 | — | 2C,6G | 0 | 2G | 0 | 3C,6G | 3G | 4C,9G | 3C,7G | 4C,9G | 3C,6G | 2C,4G | 3G | 3C,7H | 3C,6G | 10C | 3C,9G |
| Barley | 0 | — | 0 | 0 | 0 | 0 | 6G | 0 | 3C,9G | 9G | 3C,9G | 3C,9G | 9G | 7G | 9G | 5G | 6C,9G | 3C,8G |

| | Compound 181 | | Compound 182 | | Compound 183 | | Compound 184 | | Compound 185 | | Compound 186 | | Compound 187 | | Compound 188 | | Compound 189 | |
|---|---|---|---|---|---|---|---|---|---|---|---|---|---|---|---|---|---|---|
| Rate kg/ha | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| Cotton | 10C | 9C | 10C | 10C | 10C | 4C,8H | 4C,8H | 3C,7H | 3C,8H | 2C,8H | 2C,8H | 3C,8H | 2C,7H | 2C,6H | 9C | 5C,9H | 10C | 5C,9G |
| Morningglory | 10C | 10C | 10C | 10C | 10C | 2C,8H | 10C | 5C,9H | 5C,9G | 4C,8H | 4C,9G | 3C,8H | 4C,9H | 4C,8H | 10C | 10C | 10C | 10C |
| Cocklebur | 10C | 10C | 10C | 10C | 10C | 3C,7H | 2C,9H | 7G | 5C,9G | 5C,9H | 4C,9H | 4C,8H | 3C,8H | 2C,7H | 10C | 10C | 10C | 10C |
| Nutsedge | 9C | 6C,8G | 10C | 9C | 9C | 9G | 3G | 2G | 2C,8G | 3G | 6G | 3C | 2C,9G | 2C,7G | 9C | 9C | 10C | 9C |
| Crabgrass | 2C,7G | 4G | 2C,9G | 5G | 2C,4G | 2G | 6G | 2G | 2G | 0 | 0 | 0 | 0 | 0 | 2G | 0 | 5G | 0 |
| Barnyardgrass | 9C | 4C,9G | 10C | 10C | 9C | 5C,8G | 9C | 5C,9G | 10C | 10C | 10C | 3C,8H | 2C,7G | 3G | 9C | 4C,9H | 10C | 4C,9H |
| Wild Oats | 2C,8G | 7G | 2C,6G | 2G | 2C,8G | 0 | 3C,9G | 2C,8G | 3C,9G | 2C,5G | 2C,7G | 2C,8G | 0 | 0 | 2C,4G | 0 | 2G | 0 |
| Wheat | 9G | 8G | 3C,9G | 7G | 2C,9G | 3G | 3C,9G | 2C,8G | 9G | 2C,6G | 9G | 9G | 0 | 0 | 2C,5G | 0 | 8G | 0 |
| Corn | 6U,9G | 3U,8G | 10C | 6U,9G | 6U,9G | 3C,7G | 4U,9C | 2U,9G | 5U,9C | 2U,9G | 10C | 4U,9C | 3C,7G | 3C,3G | 9C | 5C,9G | 9C | 4C,9G |
| Soybean | 6C,9G | 6C,9G | 6C,9G | 9C | 4C,8H | 2C,6H | 5C,8H | 4C,9H | 4C,9H | 4C,7H | 4C,9H | 3C,8H | 2C,8G | 7H | 5C,9G | 4C,9G | 4C,9G | 3C,9G |
| Rice | 3C,7G | 3G | 5C,8G | 2C,8G | 3C,8G | 3G | 9C | 9C | 9C | 4C,9G | 9C | 4C,9G | 4G | 0 | 7G | 0 | 4C,9G | 2G |
| Sorghum | 6C,9G | 3C,8G | 6C,9G | 5C,9G | 6C,9G | 2C,8G | 10C | 5C,9G | 9C | 3C,9G | 5C,9G | 4C,9G | 2C,8G | 2C,6G | 9C | 3C,9G | 5C,9G | 9G |
| Cheatgrass | 10C | 9C | 10C | 9C | 9C | 3C,8G | 5C,9G | 3C,9G | 5C,9G | 5C,9G | 9C | 4C,9G | 2C,8G | 7G | 9C | 4C,8G | 5C,9G | 9C |
| Sugar beet | 10C | 10C | 10C | 9C | 6C,9G | 5C,9G | 2C,7G | 0 | 4C,9G | 5C,9H | 9C | 5C,9G | 9C | 3C,7H | 9C | 10C | 9C | 10C |
| Velvetleaf | 10C | 10C | 10C | 10C | 10C | 6C,9H | 5C,9G | 4C,8H | 4C,9H | 3C,8H | 4C,8H | 3C,5H | 4C,8H | 4C,7H | 10C | 10C | 10C | 9C |
| Giant Foxtail | 9C | 4C,9G | 10C | 6C,9G | 3C,9G | 2C,7G | 9C | 5C,9G | 10C | 5C,9G | 9C | 3C,9G | 6G | 2G | 3C,8G | 3G | 4C,9G | 6G |
| Barley | 2C,8G | 7G | 8G | 5G | 8G | 2C,4G | 4C,9G | 3C,9G | 4C,9G | 2C,8G | 3C,9G | 2C,8G | 2C,6G | 3G | 2G | 0 | 7G | 0 |

| | Compound 190 | | Compound 191 | | Compound 192 | | Compound 193 | | Compound 194 | | Compound 195 | | Compound 196 | | Compound 197 | | Compound 198* | |
|---|---|---|---|---|---|---|---|---|---|---|---|---|---|---|---|---|---|---|
| Rate kg/ha | 0.05 | 0.01 | 0.05 | 0.01 | 0.05 | 0.01 | 0.05 | 0.01 | 0.05 | 0.01 | 0.05 | 0.01 | 0.05 | 0.01 | 0.0 | 0.01 | 0.05 | 0.01 |

TABLE A-continued

| | | | | | | | | | | | | | | | | | | |
|---|---|---|---|---|---|---|---|---|---|---|---|---|---|---|---|---|---|---|
| Cotton | 3C,9H | 8H | 6H | 0 | 1H | 0 | 7H | 3G | 4C,8H | 2C,4H | 4C,9G | 2C,9G | 0 | 0 | 5H | 0 | 0 | 0 |
| Morningglory | 4C,9G | 3C,5G | 3C,6H | 0 | 8H | 5G | 4C,9H | 3C,7H | 4C,9G | 4C,8H | 9C | 3C,8H | 1H | 0 | 0 | 0 | 0 | 0 |
| Cocklebur | 3C,8G | 6H | 3C,7H | 0 | 7H | 0 | 5G | 2G | 4C,9H | 3C,5G | 5C,9G | 4C,9H | 2C,3G | 0 | 0 | 0 | 0 | 0 |
| Nutsedge | 9G | 3C,9G | 7G | 0 | 0 | 0 | 0 | 0 | 2G | 0 | 8G | 3C,5G | 0 | — | 0 | 0 | 0 | 0 |
| Crabgrass | 0 | 0 | 0 | 0 | 0 | 0 | 3C,5G | 4G | 0 | 0 | 0 | 3G | 0 | 0 | 0 | 0 | 0 | 0 |
| Barnyardgrass | 3C,5G | 1H | 9H | 3H | 5C,9H | 4H | 9C | 3C,8H | 3H | 0 | 5H | 3C,5H | 0 | 0 | 0 | 0 | 0 | 0 |
| Wild Oats | 0 | 0 | 0 | 0 | 0 | 0 | 4C,8G | 3C,6G | 0 | 0 | 0 | 0 | 0 | 0 | 0 | 0 | 0 | 0 |
| Wheat | 0 | 0 | 0 | 0 | 0 | 0 | 9G | 3C,7G | 2G | 0 | 0 | 0 | 0 | 0 | 0 | 0 | 0 | 0 |
| Corn | 2C,5G | 1H | 2C,9G | 3C,8H | 3C,9G | 5H | 4U,9G | 3C,9G | 9G | 7H | 1C | 1C | 0 | 0 | 0 | 0 | 0 | 0 |
| Soybean | 1H | 0 | 3C,7H | 0 | 3C,5H | 1H | 5C,9G | 4C,8G | 8H | 4H | 4C,9G | 3C,7H | 0 | 0 | 0 | 0 | 0 | 0 |
| Rice | 0 | 0 | 6G | 5G | 5C,9G | 7G | 9C | 9C | 7G | 4G | 3G | 2G | 4G | 0 | 0 | 0 | 0 | 0 |
| Sorghum | 9G | 3C,6G | 3C,9H | 4G | 3C,8H | 2G | 9C | 3C,9G | 3C,8H | 2G | 4C,9G | 4C,9H | 0 | 0 | 0 | 0 | 0 | 0 |
| Cheatgrass | 7G | 0 | 8G | 2G | 8G | 0 | 5C,9G | 9G | 5C,9G | 5G | 2C,8G | 8G | 0 | 0 | 0 | 0 | 0 | 0 |
| Sugar beet | 9C | 3C,7G | 7H | 3G | 3C,8H | 4H | 6G | 3H | 4C,8G | 2C,3G | 9C | 5C,8H | 0 | 0 | 0 | 0 | 0 | 0 |
| Velvetleaf | 3C,8G | 0 | 0 | 0 | 1C | 0 | 4C,7H | 6G | 1C | 0 | 3C,7H | 3C,3G | 0 | 0 | 0 | 0 | 0 | 0 |
| Giant Foxtail | 0 | 0 | 0 | 0 | 0 | 0 | 5C,9G | 3C,7G | 1H | 0 | 0 | 1H | 0 | 0 | 0 | 0 | 0 | 0 |
| Barley | 0 | 0 | 0 | 0 | 0 | 0 | 2G | 0 | 2G | 0 | 0 | 0 | 0 | 0 | 0 | 0 | 0 | 0 |

| | Compound 199 | | Compound 200 | | Compound 201 | | Compound 202 | | Compound 203 | | Compound 204 | | Compound 205 | | Compound 206 | |
|---|---|---|---|---|---|---|---|---|---|---|---|---|---|---|---|---|
| Rate kg/ha | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| Cotton | 0 | 0 | 3C,9G | 3C,8H | 5C,9G | 5C,9G | 9C | 10C | 9C | 9H | 3C,8G | 3C,5G | 4C,9H | 3C,9H | 9C | 4C,9H |
| Morningglory | 0 | 0 | 4C,9G | 4C,9G | 10C | 10C | 10C | 10C | 4C,9G | 3C,8H | 5C,9G | 3C,8G | 4C,9G | 3C,8H | 10C | 9C |
| Cocklebur | 0 | 0 | 5C,9G | 4C,9G | 10C | 10C | 10C | 10C | 5C,9G | 3C,8G | 5C,9G | 3C,8H | 4C,9H | 3C,8H | 10C | 4C,9G |
| Nutsedge | 0 | 0 | 0 | 0 | 3C,9G | 3C,7G | 9C | 10C | 2C,8G | 8G | 0 | 0 | 5G | 0 | 2C,8G | — |
| Crabgrass | 0 | 0 | 0 | 0 | 0 | 0 | 0 | 0 | 0 | 0 | 0 | 0 | 2G | 0 | 2C,8G | 4G |
| Barnyardgrass | 0 | 0 | 2G | 0 | 3C,9H | 6H | 3C,9H | 6H | 1C,2H | 0 | 2C,8H | 5H | 3C,8H | 2C,7H | 4C,9G | 3C,7H |
| Wild Oats | 0 | 0 | 0 | 0 | 1C | 0 | 0 | 0 | 0 | 0 | 2G | 0 | 1C | 0 | 4G | 0 |
| Wheat | 0 | 0 | 0 | 0 | 2G | 0 | 2G | 0 | 0 | 0 | 0 | 0 | 0 | 0 | 5G | 0 |
| Corn | 0 | 0 | 2G | 0 | 4C,9G | 3C,9H | 10C | 4C,9G | 2C,4G | 0 | 3G | 0 | 0 | 0 | 4C,9G | 3C,7H |
| Soybean | 0 | 0 | 3C,8G | 3C,4H | 4C,8G | 3C,8H | 5C,9G | 4C,9G | 3H | 1H | 4C,9G | 3C,8G | 4C,9G | 3C,5G | 3C,4H | 1C,1H |
| Rice | 0 | 0 | 0 | 0 | 3G | 0 | 7G | 2G | 0 | 0 | 6G | 1C | 9G | 2C,4G | 7G | 3G |
| Sorghum | 0 | 0 | 3C,6G | 3G | 9G | 4C,9G | 4C,9G | 4C,9G | 3C,8G | 2G | 3C,7G | 1C | 3C,9H | 3G | 3G,7G | 5G |
| Cheatgrass | 0 | 0 | 6G | 3G | 4C,9G | 7G | 9C | 9G | 6G | 0 | 8G | 5G | 5C,9G | 7G | 0 | 0 |
| Sugar beet | 2G | 0 | 9C | 5C,9G | 10C | 10C | 10C | 9C | 3C,9H | 4C,9G | 4C,9G | 9C | 9C | 3C,8H | 10C | 9C |
| Velvetleaf | 0 | 0 | 9C | 3C,8H | 10C | 10C | 10C | 10C | 5C,9H | 3C,8H | 4C,8H | 3C,6H | 3C,8H | 3C,5H | 10C | 4C,8H |
| Giant Foxtail | 0 | 0 | 0 | 0 | 3G | 0 | 3G | 2G | 1C | 0 | 2C,5G | 0 | 3C,4G | 0 | 5C,9G | 4C,9G |
| Barley | 0 | 0 | 0 | 0 | 2C,2G | 0 | 0 | 0 | 0 | 0 | 0 | 0 | 0 | 0 | 0 | 0 |

| PREEMERGENCE | Compound 1 | Compound 2 | Compound 3 | Compound 4 | | Compound 5 | | Compound 6 | | Compound 7 | | Compound 8 | | | Compound 9 | |
|---|---|---|---|---|---|---|---|---|---|---|---|---|---|---|---|---|
| Rate kg/ha | 0.05 | 0.05 | 0.05 | 0.05 | 0.01 | 0.05 | 0.01 | 0.05 | 0.01 | 0.05 | 0.01 | 0.05 | 0.05 | 0.01 | 0.05 | 0.01 |
| Morningglory | 3G | 9H | 9G | 9G | 9G | 9G | 9G | 0 | 0 | 9G | 7G | 0 | 0 | 0 | 9G | 4C,8H |
| Cocklebur | 0 | 9H | 9H | 9H | 9H | 9H | 9H | 0 | 0 | 8G | 7G | 0 | 0 | 0 | 8H | 2C,5G |
| Velvetleaf | 0 | 10C | 10C | 9C | 9C | 9C | 4C,8G | 0 | 0 | 4C,9G | 0 | 0 | 0 | 0 | 7H | 4G |
| Nutsedge | 0 | 10E | 10E | 10E | 4C,8G | 10E | 10E | 0 | 0 | 0 | 0 | 0 | 0 | 0 | 10E | 3G |
| Crabgrass | 0 | 3C,8G | 8G | 5C,9G | 5C,9G | 4C,9G | 7G | 0 | 0 | 4C,8G | 0 | 0 | 0 | 0 | 2C | 0 |
| Giant Foxtail | | | | — | — | — | — | — | — | — | — | 0 | — | — | — | — |
| Barnyardgrass | 0 | 4C,9H | 9H | 5C,9H | 5C,9H | 4C,9H | 4C,9H | 0 | 0 | 9H | 3G | 0 | 0 | 0 | 3C,7G | 0 |
| Cheatgrass | 0 | 7G | 9H | 9G | 7G | 5G | 3G | 0 | 0 | 5G | 0 | 0 | 0 | 0 | 3C,7H | 4G |
| Wild Oats | 0 | 5C,9G | 5C,9G | 6C,9H | 4C,8H | 5C,9G | 3C,7G | 0 | 0 | 5C,9H | 3C,6G | 0 | 1C | 0 | 2C,7G | 0 |
| Wheat | 5G | 10E | 10E | 10E | 5C,9H | 4C,9H | 9G | 4G | 0 | 4C,9H | 2C,6G | 0 | 0 | 0 | 6G | 0 |
| Corn | 3C,8G | 4C,9G | 3C,9H | 9H | 5C,9H | 3C,9G | 8G | 2G | 0 | 9G | 3C,7G | 0 | 4G | 0 | 3C,8H | 0 |
| Barley | | | | — | — | — | — | — | — | — | — | 0 | — | — | — | — |
| Soybean | 5G | 9H | 9H | 9H | 4C,7G | 3C,8H | 4C,6G | 0 | 0 | 2G | 0 | 0 | 2G | 0 | 3G | 0 |
| Rice | 1C | 10E | 10E | 10E | 10E | 10E | 10E | 3G | 0 | 10E | 4C,8H | 0 | 5G | 0 | 10E | 7G |
| Sorghum | 3C,6G | 5C,9H | 10H | 10E | 5C,9H | 10E | 9H | 0 | 0 | 10E | 4C,9H | 0 | 0 | 0 | 4C,9H | 4C,8G |
| Sugar beet | 0 | 5C,9G | 9C | 5C,9G | 5C,9G | 5C,9G | 5C,9G | 0 | 0 | 5C,9G | 4C,8G | 0 | 4G | 3H | 9C | 4C,8G |
| Cotton | 0 | 3C,9G | 9C | 3C,9G | 3C,9G | 3C,9G | 3C,9G | 0 | 0 | 2C,5G | 0 | 0 | 0 | 0 | 9G | 8G |

| | Compound 10 | | Compound 11 | | Compound 12 | Compound 13 | Compound 14 | | Compound 15 | | Compound 16 | | Compound 17 | | Compound 18 | |
|---|---|---|---|---|---|---|---|---|---|---|---|---|---|---|---|---|
| Rate kg/ha | 0.05 | 0.01 | 0.05 | 0.01 | 0.01 | 0.01 | 0.05 | 0.01 | 0.05 | 0.01 | 0.05 | 0.01 | 0.05 | 0.01 | 0.05 | 0.01 |
| Morningglory | 9G | 8G | 8G | 3C,5H | 0 | 9G | 9G | 8G | 5H | 3H | 9C | 9H | 9C | 7H | 9G | 8G |
| Cocklebur | — | 9H | 9H | 8H | 0 | 9H | 9H | 9H | 7H | 0 | 9H | 9H | 9H | 9H | 9H | 9H |
| Velvetleaf | 9C | 6C,9G | 9C | 3C,7H | 0 | 5C,9G | 10C | 9C | 6G | 0 | 9C | 2C,4G | 9C | 3C,8G | 9C | 9C |
| Nutsedge | 10E | 9G | 10E | 4G | 0 | 10E | 10E | 4C,9G | 0 | 0 | 10E | 3C,9G | 10E | 10E | 10E | 10E |
| Crabgrass | 4C,7G | 2C,4G | 2C,3G | 0 | 0 | 3G | 2C,7G | 3G | 0 | 0 | 4G | 2G | 4C,8G | 3C,7G | 8G | 4G |
| Giant Foxtail | — | — | — | — | — | — | — | — | — | — | — | — | 4C,9H | 3C,8H | 9H | 3C,6G |
| Barnyardgrass | 4C,9H | 2C,6G | 3C,5G | 0 | 0 | 3C,8H | 5C,9H | 3C,8H | 1C | 0 | 3C,9H | 3C,3G | 5C,9H | 4C,9H | 5C,9H | 3C,9H |
| Cheatgrass | 10E | 4C,9H | 5C,9H | 5G | 0 | 8G | 6G | 2G | 0 | 0 | 0 | 0 | 4C,8H | 3G | 7H | 6G |
| Wild Oats | 9C | 4C,9G | 9C | 3C,7G | 0 | 5G | 9C | 5C,9G | 2C,5G | 0 | 5C,9G | 3C,6G | 5C,9G | 4C,9G | 5C,9G | 2C,9G |
| Wheat | 4C,9G | 7G | 9G | 5G | 0 | 0 | 4C,9G | 3C,8G | 0 | 0 | 8G | 3G | 10H | 3C,8G | 10H | 9G |
| Corn | 9H | 4C,9H | 2C,9H | 3C,7H | 2G | 8G | 3C,9G | 7G | 6G | 0 | 6G | 2G | 10H | 4C,9H | 4C,9H | 8G |
| Barley | — | — | — | — | — | — | — | — | — | — | — | — | 9G | 3C,9G | 3C,9G | 9G |
| Soybean | 9H | 4C,8H | 2C,7G | 2C,3G | 2C | 3C,8H | 3C,9H | 2C,7G | 2C,2H | 1C | 3C,7G | 3C,3H | 9H | 4C,8H | 9H | 4C,8H |
| Rice | 10E | 4C,9H | 10E | 3C,8G | 0 | 2C,9H | 10E | 3C,8G | 5G | 1C | 10E | 2C,8G | 10E | 9H | 10E | 10E |
| Sorghum | 10E | 5C,9H | 9H | 3C,8H | 1C | 3C,9H | 10E | 3C,9H | 3C,6G | 0 | 10H | 3C,9H | 10H | 6C,9H | 10H | 10H |
| Sugar beet | 5C,9G | 5C,9G | 9C | 5C,9G | 3H | 10C | 5C,9G | 5C,9G | 3C,7H | 0 | 10E | 5C,9G | 10E | 9C | 5C,9G | 5C,9G |
| Cotton | 9C | 9G | 9G | 9G | 0 | 9G | 9G | 9G | 2C | 0 | 9G | 2C,5G | 9C | 2C,9G | 4C,9G | 4C,9G |

| | Compound 19 | | Compound 20 | | Compound 21 | | Compound 22 | | Compound 23 | | Compound 24 | Compound 25 | | Compound 26 | | Compound 27 | |
|---|---|---|---|---|---|---|---|---|---|---|---|---|---|---|---|---|---|
| Rate kg/ha | 0.05 | 0.01 | 0.05 | 0.01 | 0.05 | 0.01 | 0.05 | 0.01 | 0.05 | 0.01 | 0.01 | 0.05 | 0.01 | 0.05 | 0.01 | 0.05 | 0.01 |
| Morningglory | 8H | 3C,7G | 9G | 7H | 5H | 0 | 3C,8H | 2H | 9H | 7H | 7H | 0 | 0 | 2H | 1H | 6G | 0 |
| Cocklebur | 8H | — | 9H | 9H | 9H | — | 9H | 2C | 9H | 9H | 9H | 0 | 0 | 2C | 0 | 8H | 6H |
| Velvetleaf | 9C | 3C,7H | 5C,9G | 7G | 7G | 0 | 8H | 5G | 10C | 9G | 9C | 3G | 0 | 0 | 0 | 3C,8H | 7G |
| Nutsedge | 9G | 7G | 10E | 9G | 0 | 0 | 0 | 0 | 10E | 9G | 3C,7G | 0 | 0 | 0 | 0 | 5G | 0 |
| Crabgrass | 5G | 0 | 9C | 2G | 2C,5G | 0 | 2C,5G | 4G | 0 | 0 | 2G | 0 | 0 | 0 | 0 | 0 | 0 |
| Giant Foxtail | 9H | 5G | 4C,8G | 4G | 2C,5G | 2G | 3C,7G | 3G | 4C,9H | 1C | 3C,5G | 3G | 0 | 0 | 0 | 3C,6G | 3C |
| Barnyardgrass | 3C,8H | 3C,6G | 9H | 3C,8H | 3C,6G | 0 | 3C,8G | 0 | 5C,9H | 3C,8H | 3C,6G | 0 | 0 | 7C | 0 | 4C,9H | 3C,3G |
| Cheatgrass | 2G | 0 | 3G | 0 | 0 | 0 | 0 | 0 | 4G | 0 | 0 | 0 | 0 | 0 | 0 | 0 | 0 |
| Wild Oats | 5C,9G | 3C,8H | 3C,9H | 2C,5G | 2G | 0 | 2C | 0 | 6G | 0 | 2C | 0 | 0 | 0 | 0 | 3C,7G | 2C |
| Wheat | 5C,9H | 3C,8H | 3C,9H | 7G | 0 | 0 | 3G | 0 | 4C,9G | 4G | 5G | 0 | 0 | 0 | 0 | 7G | 2G |

-continued

| | | | | | | | | | | | | | | | | | |
|---|---|---|---|---|---|---|---|---|---|---|---|---|---|---|---|---|---|
| Corn | 4C,9H | 3C,7H | 3C,9H | 9H | 4C,9H | 2C,6G | 9H | 3C,8H | 3C,8G | 2C,5G | 0 | 3G | 0 | 0 | 0 | 2C | 0 |
| Barley | 4C,9G | 9G | 3C,9G | 8G | 0 | 0 | 7G | 0 | 3C,9G | 2C,8G | 2C,8G | 5G | 0 | 5G | 3G | 9G | 6G |
| Soybean | 9H | 3C,6H | 3C,8H | 3C,5G | 3C,7H | 0 | 3C,7H | 2C,3G | 3C,8H | 3C,8H | 3C,7H | 0 | 0 | 0 | 0 | 2C,7G | 2C,2H |
| Rice | 10E | 4C,8H | 10E | 9H | 8G | 2G | 9H | 0 | 9H | 4C,9G | 3C,6H | 5G | 0 | 3C,5G | 2C | 9H | 3C,7H |
| Sorghum | 5C,9H | 6C,9H | 10H | 10H | 5C,9H | 3C,6G | 4C,9H | 3C,8H | 10E | 3C,9H | 4C,8H | 2C | 0 | 3C,5G | 2G | 9H | 2C,6G |
| Sugar beet | 9C | 5G | 9C | 5C,9G | 5G | 3G | 4C,7H | 5G | 5C,9G | 5C,9G | 5C,9G | 0 | 0 | 2H | 3G | 4C,8G | 3C,7H |
| Cotton | 9G | 2C,8G | 9G | 8G | 5G | 0 | 2C,5G | 1C | 10C | 9C | 2C,7H | — | 0 | 1C | 0 | 4C,8G | 2C,3G |

| | Compound 28 | | Compound 29 | | Compound 30 | | Compound 31 | | Compound 3 | | Compound 33 | | Compound 34 | | Compound 35 | | Compound 36 | |
|---|---|---|---|---|---|---|---|---|---|---|---|---|---|---|---|---|---|---|
| Rate kg/ha | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| Morningglory | 3C,9G | 5H | 5H | 1C | 9C | 4C,4H | 4C,8H | 3C,5H | 9C | 8H | 9C | 9G | 9H | 8H | 9C | 8H | 2C,9H | 3C,7H |
| Cocklebur | 9H | 3C,4H | 0 | 0 | 9H | 3C | 9H | 2C,5G | 9H | 8H | 9H | — | 8H | 9H | 9H | 7H | 9H | 3H |
| Velvetleaf | 5C,9H | 2G | 0 | 0 | 9C | 9C | 9C | 0 | 10C | 10C | 4C,9G | 9G | 9H | 3C,9G | 9G | 8G | 9G | 3C,5H |
| Nutsedge | 10E | 0 | 0 | 0 | 4G | 0 | 4G | 0 | 10E | 10E | 10E | 3C,5G | 4C,8G | 2C,3G | 10E | 9G | 5G | 0 |
| Crabgrass | 0 | 0 | 0 | 0 | 3C,7G | 3C,4G | 3C,5G | 0 | 7G | 4G | 3C,7G | 2C,4G | 3C,5G | 1C | 2C,5G | 3C,4G | 4C,9G | 3C,6G |
| Giant Foxtail | 3C,3H | 3G | 5G | 0 | 9H | 3G | 3C,6G | 1C | 5C,9G | 4C,7G | 4C,8H | 3C,4G | 4C,8G | 2G | 3C,6G | 4G | 4C,9H | 3C,5G |
| Barnyardgrass | 5C,9H | 3C,3G | 3C,5G | 0 | 5C,9H | 3C,7G | 9C | 3C,4H | 9C | 9H | 4C,9H | 2C,2H | 3C,7H | 0 | 4C,9H | 3C,7G | 3C,9H | 3C,7H |
| Cheatgrass | 3G | 3G | 0 | 0 | 3G | 0 | 2G | 0 | 7G | 0 | 8G | 2G | 6G | 0 | 0 | 0 | 8G | 0 |
| Wild Oats | 2C | 0 | 3C,6G | 0 | 2C | 0 | 2C,4G | 0 | 5C,9G | 3C,8G | 4C,9H | 6C,9G | 4C,9H | 4C,8G | 3C,8G | 3C,5G | 6C,9H | 3C,8G |
| Wheat | 6G | 0 | 9H | 2G | 2G | 0 | 2G | 0 | 10E | 4C,9G | 9C | 4C,9G | 4C,8G | 8G | 5C,9H | 7G | 6C,9H | 5G |
| Corn | 2G | 0 | 2C,5G | 0 | 5C,9H | 9H | 9H | 0 | 3C,9H | 3C,7G | 3C,8H | 1C,5G | 4C,8H | 2G | 2C,8G | 4G | 10H | 4C,9H |
| Barley | 8G | 5G | 2C,8G | 2G | 5G | 0 | 5G | 0 | 5C,9G | 4C,9G | 5C,9G | 9G | 5C,9G | 9G | 9G | 9G | 9C | 5C,9G |
| Soybean | 3C,5G | 3C,4G | 2C,2H | 0 | 3C,8H | 3C,7H | 3C,8H | 2H | 9H | 3C,7H | 9H | 9H | 9H | 3C,7H | 3C,8H | 3C,7H | 9H | 3C,7H |
| Rice | 5C,9H | 4C,8H | 3C,8H | 2C | 9H | 3C,6H | 4C,9H | 2C,4G | 10E | 10E | 10E | 10E | 10E | 3C,8H | 10E | 10E | 10E | 3C,9H |
| Sorghum | 5C,9H | 5C,9H | 3C,8H | 1C | 6C,9H | 4C,8H | 10H | 4C,7G | 6C,9H | 9C | 10H | 7C,9H | 6C,9H | 4C,8H | 10H | 10H | 10H | 6C,9H |
| Sugar beet | 10C | 3C,7G | 3G | 4H | 10E | 5H | 5C,9G | 5H | 4C,8G | 9C | 9C | 9C | 9C | 4C,8H | 4C,9G | 3C,8G | 10C | 4C,9G |
| Cotton | 3C,7G | 2C,4G | 0 | 2H | 4C,9G | 2C,2H | 4C,8H | 2C | 9C | 9G | 9G | 8G | 4C,8G | 2G | 9G | 4C,9G | 8G | 1C |

| | Compound 37 | | Compound 38 | | Compound 39 | | Compound 40 | | Compound 41 | | Compound 42 | | Compound 43 | | Compound 44 | | Compound 45 | |
|---|---|---|---|---|---|---|---|---|---|---|---|---|---|---|---|---|---|---|
| Rate kg/ha | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| Morningglory | 0 | 0 | 1C | 0 | 9C | 8G | 3C,8H | 2C,3H | 1C | 2G | 2C,4H | 1H | 3H | 0 | 2C | 5G | 4H | 4H |
| Cocklebur | — | 0 | 0 | 0 | 9H | 8H | 3C,7H | 2C,3H | 3C,3G | — | 3C,7H | 7H | 8G | 0 | 1H | 0 | 6H | 4H |
| Velvetleaf | 5G | 0 | 0 | 0 | 3C,9G | 4C,9G | 3C,8H | 3C,5H | 1H | 0 | 0 | 2G | 0 | 0 | 7G | 0 | 2G | 3G |
| Nutsedge | 2G | 0 | 3G | 0 | 10E | 8G | 4G | 0 | 0 | 0 | 0 | 0 | 0 | 0 | 0 | 0 | 0 | 0 |
| Crabgrass | 0 | 0 | — | 0 | 3C,3G | 2G | 2C,5G | 0 | 0 | 0 | 6G | 0 | 0 | 0 | 0 | 0 | 0 | 0 |
| Giant Foxtail | 0 | 0 | 0 | 0 | 4C,9H | 3C,6G | 3C,7G | 2G | 0 | 0 | 2C,7G | 0 | 5G | 0 | 3G | 0 | 0 | 0 |
| Barnyardgrass | 1C | 0 | 3G | 0 | 5C,9H | 4C,9H | 3C,8H | 2C,3G | 0 | 0 | 9H | 6G | 0 | 0 | 3G | 0 | 4G | 0 |
| Cheatgrass | 0 | 0 | 2G | 0 | 5C,9H | 9H | 9H | 3C,6G | 0 | 0 | 8G | 4G | 7G | 3G | 0 | 0 | 0 | 0 |
| Wild Oats | 0 | 0 | 0 | 0 | 4C,9H | 3C,8H | 3C,8G | 3C,5G | 0 | 0 | 2G | 0 | 2C,6G | 0 | 0 | 0 | 0 | 0 |
| Wheat | 0 | 0 | 0 | 0 | 5C,9H | 3C,9G | 3C,8G | 5G | 0 | 0 | 2G | 0 | 6G | 0 | 0 | 0 | 0 | 0 |
| Corn | 3C,7H | 2C | 2C,5G | 0 | 3C,9H | 2C,8G | 3C,5G | 2C,2G | 2G | 0 | 2G | 0 | 2C,6G | 0 | 3C,7H | 0 | 3C,8H | 0 |
| Barley | 0 | 0 | 0 | 0 | 9G | 9G | 3C,9G | 8G | 2G | 0 | 5G | 0 | 9G | 7G | 0 | 0 | 0 | 0 |
| Soybean | 3C,3H | 1C | 3C,3H | 0 | 9H | 3C,6H | 4C,6H | 3C,4H | 3C,3H | 1C | 7G | 0 | 1C | 0 | 0 | 0 | 2C,2H | 0 |
| Rice | 3C,6H | 3C,3G | 2C,7G | 2G | 10E | 5C,9H | 4C,9H | 2C,6G | 0 | 0 | 8H | 7G | 9H | 4G | 3C,8H | 2C,4G | 3C,7H | 0 |
| Sorghum | 3C,8G | 3C,4G | 3C,8G | 2C | 4C,9G | 4C,8H | 4C,9G | 3C,6G | 3C,3G | 0 | 8G | 2C,7G | 3C,6H | 0 | 3C,8H | 2C | 3C,8G | 2C,4G |
| Sugar beet | 3C,5G | 7G | 5H | 3G | 9G | 8G | 5C,9G | 4C,8G | 6G | 3H | 8G | 0 | 9G | 2G | 7G | 5G | 4G | 4G |
| Cotton | 2C,4G | 1C | 2G | 0 | 9G | 9G | 8G | 2C,6G | 2C,3G | 0 | 5G | 2G | 0 | 0 | 2C | 0 | 5G | 2C |

| | Compound 46 | | Compound 47 | | Compound 48 | | Compound 49 | | Compound 50 | | Compound 51 | | Compound 52 | | Compound 53 | | Compound 54 | |
|---|---|---|---|---|---|---|---|---|---|---|---|---|---|---|---|---|---|---|
| Rate kg/ha | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| Morningglory | 9G | 9G | 9G | 7G | 2G | 3G | 8G | 7G | 0 | 0 | 5G | 7G | 8G | 0 | 9C | 9G | 9G | 9G |
| Cocklebur | 9H | 8G | 8H | — | 0 | — | 9H | 7H | 8G | — | 4H | — | 7H | 0 | 9H | — | 9H | 9H |
| Velvetleaf | 9C | 9G | 4C,9G | 7H | 0 | — | 3H | 0 | 7G | — | 0 | 5G | 5G | 0 | 9C | 9C | 5C,9G | 5C,9G |

-continued

| | | | | | | | | | | | | | | | | | | |
|---|---|---|---|---|---|---|---|---|---|---|---|---|---|---|---|---|---|---|
| Nutsedge | 4C,9G | 0 | 4G | 0 | 0 | 0 | 4G | 0 | 0 | 0 | 0 | 0 | 5G | 0 | 10E | 10E | 10E | 10E |
| Crabgrass | 3G | 0 | 2G | 0 | 0 | 0 | 0 | 0 | 0 | 0 | 0 | 0 | 0 | 0 | 2G | 0 | 3G | 0 |
| Giant Foxtail | 9H | 7G | 8G | 2C | 0 | 0 | 3C,4G | 2G | 0 | 0 | 4G | 2G | 6G | 2G | 9H | 8H | 9H | 3C,8H |
| Barnyardgrass | 9H | 3C,9H | 8H | 2C | 0 | 0 | 3C,8H | 2G | 0 | 0 | 2G | 2G | 5G | 0 | 9H | 9H | 9H | 9H |
| Cheatgrass | 7G | 3G | 6G | 0 | 0 | 0 | 0 | 0 | 0 | 0 | 2G | 0 | 5G | 0 | 10H | 9H | 9H | 10E |
| Wild Oats | 4C,9H | 8H | 2C,8G | 2G | 0 | 0 | 2G | 0 | 0 | 0 | 0 | 0 | 2G | 0 | 0 | 0 | 8G | 2C,5G |
| Wheat | 10H | 3C,9H | 8G | 3G | 0 | 0 | 3G | 0 | 0 | 0 | 2G | 0 | 7G | 0 | 9H | 7H | 10H | 4C,9H |
| Corn | 10H | 3C,9H | 2C,9G | 2C,6G | 0 | 0 | 4G | 0 | 0 | 0 | 2C,8G | 0 | 3C,8H | 2G | 2C,7G | 4G | 7G | 6G |
| Barley | 9G | 9H | 9G | 2C,7G | 2G | 0 | 8G | 0 | 0 | 0 | 6G | 0 | 8G | 3G | 9G | 9G | 9G | 9G |
| Soybean | 9H | 8H | 3C,7H | 7H | 2C | 0 | 4G | 0 | 0 | 0 | 2C,5G | 1H | 8H | 5H | 9H | 9H | 9H | 3C,8H |
| Rice | 10E | 10E | 5C,9H | 6G | 0 | 3G | 3C,8H | 4G | 2C | 0 | 9H | 2G | 9H | 5H | 10E | 10E | 10E | 10E |
| Sorghum | 10H | 5C,9H | 5C,9H | 2C,8G | 2C | — | 10H | 3C,8H | 2C,5G | 0 | 2C,9H | 2C,5G | 3C,9H | 3C,8G | 5C,9H | 9H | 10H | 5C,9H |
| Sugar beet | 5C,9G | 5C,9G | 4C,9G | 7G | — | 2G | 3C,8G | 8G | 4G | 0 | 5G | 5G | 9G | 8G | 9C | 9C | 9C | 5C,9G |
| Cotton | 9G | 9G | 9G | 2C,5G | 2G | — | 2C,7G | 1C | 0 | 0 | 7G | 0 | 2C,7G | 2G | 9G | 9G | 4C,9G | 9G |

| | Compound 55 | | Compound 56 | | Compound 57 | | Compound 58 | | Compound 59 | | Compound 60 | | Compound 61 | | Compound 62 | | Compound 63 | |
|---|---|---|---|---|---|---|---|---|---|---|---|---|---|---|---|---|---|---|
| Rate kg/ha | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| Morningglory | 9G | 8G | 9G | 9G | 8H | 3C,7H | 0 | 0 | 9G | 9G | 0 | 0 | 0 | 0 | 0 | 0 | 3H | 0 |
| Cocklebur | 9H | 9H | 9H | 5H | 2C,8H | 2C,7H | 0 | 0 | 9H | 9H | 2H | 0 | 0 | 0 | 0 | 0 | 4G | 1H |
| Velvetleaf | 4C,9G | 8G | 8H | 6H | 2C,7H | 2C,5H | 0 | 0 | 9C | 3C,9G | 0 | 0 | 0 | 0 | 0 | 0 | 0 | 0 |
| Nutsedge | 10E | 9G | 10E | 4G | 10E | 9G | 0 | 0 | 10E | 10E | 0 | 0 | 0 | 0 | 0 | 0 | 7G | 0 |
| Crabgrass | 2G | 0 | 2G | 0 | 1C,5G | 2C,4G | 0 | 0 | 3C,7G | 3G | 0 | 0 | 0 | 0 | 0 | 0 | 3G | 0 |
| Giant Foxtail | 9H | 3C,8G | 3C,7G | 6G | 2C,7H | 2C,6G | 0 | 0 | 5C,9H | 3C,7G | 0 | 0 | 0 | 0 | 0 | 0 | 3G | 2G |
| Barnyardgrass | 9H | 3C,8H | 9H | 8H | 2C,6H | 2C,4H | 0 | 0 | 5C,9H | 4C,9H | 0 | 0 | 0 | 0 | 0 | 0 | 4G | 2G |
| Cheatgrass | 9H | 8G | 8H | 6G | 3C,9H | 2C,9H | 0 | 0 | 10E | 9H | 0 | 0 | 0 | 0 | 0 | 0 | 5G | 0 |
| Wild Oats | 8G | 0 | 0 | 0 | 2C,6G | 2C,6G | 0 | 0 | 4C,9H | 3C,6G | 0 | 0 | 0 | 0 | 0 | 0 | 2C | 0 |
| Wheat | 9G | 2G | 8G | 5G | 4G | 0 | 0 | 0 | 10H | 4C,9H | 0 | 0 | 0 | 0 | 0 | 0 | 3G | 0 |
| Corn | 3G | 1C,2G | 1C | 0 | 2C,7G | 3C,4G | 0 | 0 | 5C,9H | 4C,9H | 0 | 0 | 0 | 0 | 0 | 0 | 3C,3G | 0 |
| Barley | 9G | 8G | 4C,8G | 5G | 6G | 6G | 0 | 0 | 4C,9G | 3C,9G | 0 | 0 | 0 | 0 | 0 | 0 | 3C,9G | 4G |
| Soybean | 3C,8H | 2C,6G | 7H | 2H | 2C,5G | 1C,2G | 0 | 0 | 9H | 9H | 0 | 0 | 0 | 0 | 0 | 0 | 1C | 0 |
| Rice | 10E | 9H | 10E | 8H | 3C,9H | 2C,8H | 0 | 0 | 10E | 10E | 0 | 0 | 0 | 0 | 0 | 0 | 4C,8H | 3G |
| Sorghum | 10H | 9H | 9H | 5C,9H | 2C,9H | 2C,8H | 0 | 0 | 10H | 4C,9H | 0 | 0 | 0 | 0 | 0 | 0 | 4C,9H | 3C,5G |
| Sugar beet | 9G | 9G | 4C,9G | 8G | 9C | 4C,8G | 1C | 0 | 5C,9G | 4C,9G | 0 | 0 | 0 | 0 | 0 | 0 | 7G | 3C,5G |
| Cotton | 9G | 9G | 9G | 7G | 2C,8G | 2C,8G | 0 | 0 | 9G | 9G | 0 | 0 | 0 | 0 | 0 | 0 | 3C,6G | 5G |

| | Compound 64* | | Compound 65* | | Compound 66 | | Compound 67 | | Compound 68 | | Compound 69 | | Compound 70 | | Compound 71 | | Compound 72 | |
|---|---|---|---|---|---|---|---|---|---|---|---|---|---|---|---|---|---|---|
| Rate kg/ha | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| Cotton | 0 | 0 | 0 | 0 | 4C,9G | 2C,8G | 3C,7H | 6G | 3C,8H | 2G | 2C,6G | 2C | 0 | 0 | 0 | 0 | 8G | 3G |
| Morningglory | 0 | 0 | 0 | 0 | 9H | 2C,9H | 8H | 2C,6H | 9G | 3H | 8G | 2C,2H | 2G | 0 | 3H | 0 | 7H | 4H |
| Cocklebur | 0 | 0 | 0 | 0 | 9H | 7H | 3C,7H | 2C,5G | 3C,7H | 1C | 3C,7H | 2C | 0 | 0 | 0 | — | 8H | 2C |
| Nutsedge | 0 | 0 | 0 | 0 | 10E | 9G | 5G | 5G | 10E | 0 | 2C,5G | 3G | 0 | 0 | 0 | 0 | 10E | 3C,7G |
| Crabgrass | 0 | 0 | 0 | 0 | 4G | 0 | 0 | 0 | 2G | 0 | 2G | 0 | 0 | 0 | 0 | 0 | 0 | 0 |
| Barnyardgrass | 0 | 0 | 0 | 0 | 9H | 3C,9H | 3C,9H | 2G | 3C,9H | 1C | 3C,7H | 0 | 2C,5G | 0 | 0 | 0 | 9H | 2C,5G |
| Wild oats | 0 | 0 | 0 | 0 | 2G | 0 | 2C | 0 | 2C,4G | 0 | 0 | 0 | 0 | 0 | 0 | 0 | 3C,7G | 2G |
| Wheat | 0 | 0 | 0 | 0 | 4C,9H | 2C,8H | 3C,8H | 5G | 8G | 6G | 5G | 0 | 0 | 0 | 0 | 0 | 8G | 2G |
| Corn | 0 | 0 | 0 | 0 | 4C,8H | 6G | 4G | 0 | 2G | 2G | 0 | 0 | 3G | 0 | 2C,4G | 0 | 3C,8H | 3G |
| Soybeans | 0 | 0 | 0 | 0 | 9H | 9H | 9H | 3C,7H | 3C,9H | 3C,6H | 3C,7H | 2C,4G | 0 | 0 | 0 | 0 | 7H | 3C,5H |
| Rice | 0 | 0 | 0 | 0 | 9H | 9H | 3C,9H | 3C,7G | 5C,9H | 3C,7G | 9H | 7G | 6G | 0 | 0 | 0 | 10E | 9H |
| Sorghum | 0 | 0 | 0 | 0 | 10H | 5C,9H | 3C,9H | 3C,9H | 5C,9H | 3C,7H | 3C,9H | 2C,8H | 2G | 0 | 3C,5G | 0 | 10H | 9H |
| Cheatgrass | 0 | 0 | 0 | 0 | 9H | 8G | 9G | 8G | 3C,9G | 8G | 9H | 8G | 5G | 0 | 0 | 0 | 9H | 3C,9H |
| Sugar beet | 0 | 0 | 0 | 0 | 5C,9G | 4C,9G | 9G | 7G | 4C,8H | 3C,8G | 3C,7H | 2C,5G | 2G | 0 | 3G | 0 | 9G | 9G |
| Velvetleaf | 0 | 0 | 0 | 0 | 5C,9G | 2C,7G | 3C,7H | 0 | 3C,5H | 1C | 2H | 2C,2G | 1C | 0 | 0 | 0 | 5H | 0 |
| Giant Foxtail | 0 | 0 | 0 | 0 | 9H | 2C,8H | 3C,8G | 3G | 3C,9H | 2C,5G | 9H | 3C,5G | 2C,2G | 0 | 2G | 0 | 3C,8H | 2C,2G |

-continued

| Barley | 0 | 0 | 0 | 0 | 9G | 2C,6G | 2G | 2G | 3C,7G | 0 | 2G | 0 | 0 | 0 | 0 | 0 | 8G | 5G |
|---|---|---|---|---|---|---|---|---|---|---|---|---|---|---|---|---|---|---|
| | Compound 73 | | Compound 74 | | Compound 75 | | Compound 76 | | Compound 77 | | Compound 78 | | Compound 79 | | Compound 80 | | Compound 81 | |
| Rate kg/ha | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| Cotton | 2G | 0 | 1C | 0 | 2G | 0 | 9G | 9G | 3C,9G | 8G | 9G | 5G | 9G | 8G | 9G | 0 | 3C,9G | 0 |
| Morningglory | 2G | 0 | 0 | 0 | 3C,8H | 6G | 9G | 8G | 9G | 9G | 9G | 2C,7H | 9G | 9G | 2C,8H | 2C,6H | 9G | 2C,4H |
| Cocklebur | 0 | 0 | 0 | 0 | 2C,2H | 1C | 9H | 9H | 9H | 8H | 9H | 2C,3H | 9H | — | 8H | 2C,4G | 9H | 1C,2G |
| Nutsedge | 5G | 0 | 10E | 0 | 3C,8G | 0 | 10E | 10E | 10E | 9G | 9G | 6G | 10E | 9G | 4C,9G | 4G | 9G | 2G |
| Crabgrass | 0 | 0 | 0 | 0 | 0 | 0 | 7G | 6G | 3C,8G | 2C,7G | 10E | 0 | 5G | 0 | 3C,7H | 0 | 3C,7H | 0 |
| Barnyardgrass | 3C,7G | 0 | 2G | 0 | 3C,8H | 0 | 9H | 9H | 9H | 3C,9H | 3C,9H | 3G | 3C,9H | 2C,7H | 5C,9H | 5G | 9H | 0 |
| Wild Oats | 3C,5G | 0 | 0 | 0 | 0 | 0 | 7G | 7G | 3C,8G | 2C,7G | 2C,8H | 2C,7G | 2C,8G | 0 | 7G | 4G | 8G | 2C,4G |
| Wheat | 7G | 0 | 0 | 0 | 0 | 0 | 3C,9G | 2C,9G | 10C | 4C,9H | 10H | 8H | 3C,9H | 7G | 5G | 0 | 6G | 0 |
| Corn | 2G | 0 | 0 | 0 | 0 | 0 | 9G | 9G | 10C | 9G | 9G | 2C,7G | 9G | 2C,7G | 9G | 8G | 9G | 9G |
| Soybeans | 3C,4H | 1C,1H | 1H | 0 | 2C | 0 | 9H | 9H | 9H | 8H | 9H | 2C,6G | 3C,8H | 2C,7G | 4C,8H | 3C,7H | 9H | 2C,6G |
| Rice | 9H | 3G | 7H | 0 | 7H | 6H | 10E | 10E | 10E | 10H | 10E | 9H | 10E | 10E | 9H | 3C,8H | 10E | 2C,8H |
| Sorghum | 9H | 3C,3G | 3C,7G | 0 | 9H | 3C,7G | 10C | 10C | 10E | 10E | 9H | 9H | 10H | 10H | 10H | 9H | 10E | 3C,8H |
| Cheatgrass | 9H | 0 | 5G | 0 | 8H | 0 | 10E | 10H | 10H | 9H | 9H | 8H | 9H | 9H | 9H | 1C,4G | 9H | 4G |
| Sugar beet | 7G | 1H | 5H | 0 | 5H | 2G | 9G | 9G | 5C,9G | 5C,9G | 4C,9G | 3C,8G | 3C,9G | 2C,6G | 4C,9G | 5G | 9G | 2C,6G |
| Velvetleaf | 2G | 0 | 2G | 0 | 2G | 4G | 9G | 9G | 3C,9G | 3C,9G | 2C,8G | 2C,7H | 9G | 9G | 2C,7H | 3C | 3C,8H | 2C |
| Giant Foxtail | 3C,3G | 0 | 0 | 0 | 2C | 0 | 9H | 8G | 3C,9H | 3C,9H | 2C,9H | 2C,5H | 8G | 5G | 7G | 2G | 9H | 5G |
| Barley | 2G | 0 | 0 | 0 | 0 | 0 | 9G | 9G | 10C | 9G | 9C | 8G | 9G | 9G | 7G | 6G | 9G | 6G |

| | Compound 82 | | Compound 83 | | Compound 84 | | Compound 85 | | Compound 86 | | Compound 87 | | Compound 88 | | Compound 89 | | Compound 90 | |
|---|---|---|---|---|---|---|---|---|---|---|---|---|---|---|---|---|---|---|
| Rate kg/ha | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| Cotton | 9G | 9G | 9G | 9G | 9G | 9G | 9G | 9G | 4C,8G | 7G | 5G | 4G | 0 | 0 | 0 | 0 | 0 | 0 |
| Morningglory | 9G | 9G | 9G | 9G | 9G | 9G | 9G | 9G | 8H | 2H | 9G | 8H | 0 | 0 | 2C,3G | 0 | 0 | 0 |
| Cocklebur | 9G | 9H | 9H | 9H | 9H | — | 9H | 9H | 4G | — | 8H | 8G | — | 2G | 3C,8H | 0 | 0 | 0 |
| Nutsedge | 10E | 10E | 10E | 10E | 10E | 10E | 10E | 10E | 3G | 5G | 7G | 4G | 4G | 0 | 2G | 0 | 0 | 0 |
| Crabgrass | 8G | 7G | 4C,8G | 4C,8H | 10E | 2G | 8H | 0 | 9G | 0 | 5G | — | 2G | 0 | 2G | 0 | 0 | 0 |
| Barnyardgrass | 9H | 9H | 9H | 9H | 9H | 9H | 9H | 9H | 3C,9H | 3G | 9H | 7H | 0 | 0 | 2G | 0 | 0 | 0 |
| Wild Oats | 3C,9G | 4C,8G | 6C,9H | 4C,8G | 6C,9H | 4C,9G | 3C,9H | 3C,5G | 2C,3G | 0 | 2C,4G | 0 | 0 | 0 | 2G | 0 | 0 | 0 |
| Wheat | 4C,9H | 3C,9G | 5C,9H | 8G | 10H | 4C,8G | 2C,9H | 3C,8H | 3G | 0 | 5G | 0 | 7G | 0 | 4G | 0 | 0 | 0 |
| Corn | 2U,9G | 2U,9G | 9H | 9G | 9H | 9H | 9H | 9H | 3C,9H | 4C,8G | 9H | 3C,9G | 2C,3H | 0 | 3C,6G | 2G | 0 | 0 |
| Soybean | 9H | 9H | 9H | 9H | 9H | 9H | 9H | 9H | 9H | 2H | 9H | 3C,6H | 2C,3G | 0 | 3C,5G | 1C,3G | 0 | 0 |
| Rice | 10E | 10E | 10E | 10E | 10E | 10E | 10E | 10E | 9H | 7H | 9H | 5G | 3C,8H | 0 | 2C,3H | 0 | 0 | 0 |
| Sorghum | 9H | 4C,9H | 10E | 10H | 10E | 10E | 10E | 10H | 3C,9H | 4C,9G | 10H | 4C,9H | 2C,9H | 0 | 3C,7H | 2C,3H | 0 | 0 |
| Cheatgrass | 9H | 9H | 9H | 9H | 9H | 9H | 9H | 8H | 7G | 6G | 9H | 5G | 8G | 2G | 8H | 3G | 0 | 0 |
| Sugar beet | 9G | 9G | 9G | 9C | 9C | 9G | 3C,9G | 9G | 4C,8G | 4H | 4C,9G | 3G | 6G | 0 | 2C,4G | 4G | 0 | 0 |
| Velvetleaf | 4C,9G | 8G | 5C,9G | 8G | 4C,9G | 4C,9G | 9C | 7H | 2C | 2G | 7H | 3G | 0 | 0 | 2C,3H | 0 | 0 | 0 |
| Giant Foxtail | 9H | 9H | 9H | 9H | 9H | 9H | 9H | 10H | 3C,8H | 3G | 4C,9H | 4C,8G | 0 | 0 | 3G | 0 | 0 | 0 |
| Barley | 3C,9G | 2C,9G | 4C,9H | 4C,9H | 9H | 9H | 3C,9H | 4C,9H | 4C,8G | 0 | 9G | 0 | 8G | 0 | 2C,7H | 2G | 0 | 0 |

| | Compound 91 | | Compound 92 | | Compound 93 | | Compound 94 | | Compound 95 | | Compound 96 | | Compound 97 | | Compound 98 | | Compound 99 | |
|---|---|---|---|---|---|---|---|---|---|---|---|---|---|---|---|---|---|---|
| Rate kg/ha | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| Cotton | 0 | 0 | 0 | 0 | 2G | 0 | 5G | 0 | 0 | 0 | 2C,8G | 6G | 9G | 9G | 3C,8G | 2C,4G | 7H | 6G |
| Morningglory | 0 | 0 | 0 | 0 | 0 | 0 | 3C,8G | 5G | 0 | 0 | 9G | 8G | 9G | 9G | 9H | 4H | 9G | 6H |
| Cocklebur | 0 | — | 2C | 0 | 0 | — | 2C,4H | 0 | 0 | — | 9H | 3C,8H | 3G | 5G | 2C,7G | 0 | 8H | 8H |
| Nutsedge | 0 | 0 | 0 | 0 | 0 | 0 | 0 | 0 | 10E | 4G | 10E | 3C,9G | 10E | 10E | 10E | 10E | 10E | 9G |
| Crabgrass | 0 | 0 | 9G | 8G | 0 | 0 | 2C,5G | 2G | 0 | 0 | 2C,7G | 5G | 10E | 2C,5G | 2C,3G | 2G | 10E | 6G |
| Barnyardgrass | 0 | 0 | 0 | 0 | 0 | 0 | 4C,9H | 5G | 0 | 0 | 9H | 2C,7H | 9H | 9H | 9H | 3C,7H | 7H | 0 |
| Wild Oats | 0 | 0 | 0 | 0 | 0 | 0 | 0 | 0 | 0 | 0 | 7G | 0 | 3C,8G | 2C,6G | 2C | 0 | 7G | 5G |
| Wheat | 0 | 0 | 0 | 0 | 0 | 0 | 7G | 0 | 0 | 0 | 9G | 9G | 10H | 9H | 7G | 0 | 9G | 8G |
| Corn | 0 | 0 | 0 | 0 | 1C | 0 | 2C,3G | 0 | 0 | 0 | 4C,7G | 1C,3G | 3C,8G | 3G | 0 | 0 | 3C,9G | 7G |

-continued

| | | | | | | | | | | | | | | | | | | |
|---|---|---|---|---|---|---|---|---|---|---|---|---|---|---|---|---|---|---|
| Soybean | 0 | 0 | 1C,2G | 0 | 2C,4G | 0 | 2C,3G | 0 | 0 | 0 | 9G | 3C,7H | 9H | 9H | 3C,8H | 3C,4G | 3C,8H | 6H |
| Rice | 0 | 0 | 0 | 0 | 0 | 0 | 5G | 0 | 6G | 0 | 10E | 8G | 10E | 9H | 10H | 3C,7G | 9H | 9H |
| Sorghum | 0 | 0 | 2C,5G | 1C | 3C,7H | 0 | 4C,9H | 3C,8H | 4G | 0 | 10E | 6C,9G | 10E | 5C,9H | 10H | 10H | 10H | 9H |
| Cheatgrass | 0 | 0 | 0 | 0 | 0 | 0 | 8G | 0 | 0 | 0 | 7G | 7G | 9G | 7G | 9G | 2G | 9G | 8H |
| Sugar beet | 0 | 0 | 4G | 2G | 2H | 0 | 4C,8G | 5G | 6G | 0 | 4C,9G | 8G | 9G | 9G | 4C,9G | 8H | 4C,9G | 6H |
| Velvetleaf | 0 | 0 | 0 | 0 | 2G | 0 | 3G | 0 | 0 | 0 | 4C,9G | 2C,8G | 5C,9G | 7H | 2C,7H | 2C,3H | 4C,9G | 8G |
| Giant Foxtail | 0 | 0 | 0 | 0 | 0 | 0 | 3C,8H | 4G | 0 | 0 | 2C,9G | 8G | 2C,7G | 2C,5G | 2C,9H | 3G | 4G | 0 |
| Barley | 0 | 0 | 0 | 0 | 0 | 0 | 3G | 0 | 0 | 0 | 9G | 7G | 9G | 9G | 2C,8G | 7G | 9G | 8G |

| | Compound 100 | | Compound 101 | | Compound 102 | | Compound 103 | | Compound 104 | | Compound 105 | | Compound 106 | | Compound 107 | | Compound 108 | |
|---|---|---|---|---|---|---|---|---|---|---|---|---|---|---|---|---|---|---|
| Rate kg/ha | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| Cotton | 1C | 0 | 0 | 0 | 8G | 2C,3G | 9G | 2G | 9H | 5G | 2C,8H | 0 | 2C,4G | 2G | 9G | 9G | 3C,8G | 7G |
| Morningglory | 2G | 0 | 3C,4H | 0 | 8H | 3C,4H | 9G | 6H | 9G | 2C,5G | 3H | 0 | 2C,5G | 0 | 5G | 2G | 9H | 3G |
| Cocklebur | 5G | 0 | 2C,2G | 0 | 8H | 3C,3H | 9G | 9H | — | 1H | 8H | 2H | 2C,5G | 3C,7H | 9H | 9H | 9H | 9H |
| Nutsedge | 9G | 0 | 3G | 0 | 10E | 0 | 10E | 10E | 9G | 10E | 9G | 0 | 8G | 0 | 10E | 10E | 10E | 4C,9G |
| Crabgrass | 5G | 0 | 0 | 0 | 0 | 0 | 2G | 0 | 4G | 0 | 0 | 0 | 10H | 0 | 8G | 2C,5G | 4C,8G | 3C,7G |
| Barnyardgrass | 0 | 0 | 0 | 0 | 6H | 2G | 8H | 4G | 9H | 2G | 4C,9H | 0 | 0 | 0 | 5C,9H | 9H | 9H | 3C,9H |
| Wild Oats | 0 | 0 | 0 | 0 | 3C,8G | 0 | 5G | 0 | 7G | 0 | 2C,6G | 0 | 0 | 2G | 8G | 5G | 5C,9G | 3C,8G |
| Wheat | 0 | 0 | 5G | 0 | 9H | 3C,8G | 7G | 2G | 9H | 5G | 8H | 0 | 5G | 5G | 9H | 7G | 9H | 3C,9G |
| Corn | 0 | 0 | 0 | 0 | 3C,9H | 3C,6G | 0 | 0 | 3G | 0 | 0 | 3G | 0 | 0 | 9G | 7G | 3C,9H | 3C,8G |
| Soybean | 2C | 0 | 2C | 0 | 3C,6H | 3C,5H | 8H | 3C,7H | 9H | 6H | 3C,7H | 3C,3H | 9H | 3C,4H | 9H | 3C,6H | 3C,8H | 3C,7H |
| Rice | 6G | 0 | 4G | 0 | 8H | 0 | 10H | 3C,7G | 9H | 7G | 10H | 0 | 8H | 3C,6G | 10E | 9H | 10E | 4C,9H |
| Sorghum | 3C,8G | 2G | 2C,6G | 0 | 10H | 4C,8H | 10E | 9H | 6C,9H | 9H | 9H | 2C | 4C,9H | 3C,8H | 10H | 9H | 10E | 4C,9H |
| Cheatgrass | 0 | 0 | 5G | 0 | 8G | 7G | 8G | 5G | 8G | 0 | 8G | 0 | 8G | 5G | 10E | 4C,9G | 10E | 3C,8G |
| Sugar beet | 2H | 2G | 7G | 0 | 4C,9G | 4C,8H | 9G | 9G | 5C,9G | 8G | 5C,9G | 7G | 3C,8G | 7H | 9C | 10C | 10C | 4C,9G |
| Velvetleaf | 3H | 0 | 3C,5G | 0 | 4C,8H | 1H | 7H | 1H | 4C,8G | 3G | 6H | 2G | 2C,2H | 2H | 5C,9G | 8H | 5C,9G | 3C,5H |
| Giant Foxtail | 0 | 0 | 3G | 0 | 8G | 2G | 7G | 1C | 3G | 0 | 3G | 0 | 0 | 0 | 9H | 3C,7G | 9H | 3C,7G |
| Barley | 0 | 0 | 5G | 0 | 9G | 3C,7G | 9G | 6G | 8G | 4G | 8G | 3G | 9G | 3C,7H | — | — | — | 2C,8G |

| | Compound 109 | | Compound 110 | | Compound 111 | | Compound 112 | | Compound 113 | | Compound 114 | | Compound 115 | | Compound 116 | | Compound 117 | |
|---|---|---|---|---|---|---|---|---|---|---|---|---|---|---|---|---|---|---|
| Rate kg/ha | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| Cotton | 8H | 3G | 8G | 7G | 0 | 0 | 2G | 0 | 0 | 0 | 2H | 0 | 3C,5G | 6G | 3C,5G | 0 | 2G | 0 |
| Morningglory | 5G | 1H | 9G | 7H | 2C,3H | 0 | 8G | 0 | 0 | 0 | 0 | 0 | 7H | 0 | 2C,6G | 0 | 7H | 0 |
| Cocklebur | — | 3C,8H | 9H | 8H | 0 | — | 7H | 2C,5G | 0 | — | 0 | 0 | 3G | 0 | — | 3G | 3C,5G | 1C |
| Nutsedge | 10E | 10E | 10E | 10E | 10E | 0 | 10E | 0 | 0 | 0 | 0 | 0 | 9G | 0 | 8G | 0 | 4G | 0 |
| Crabgrass | 4C,8G | 2C,2G | 3C,5G | 3G | 2G | 0 | 2G | 0 | 2G | 0 | 7G | 3G | 4G | 0 | 9G | 0 | 0 | 0 |
| Barnyardgrass | 5C,9H | 2C,7H | 9H | 3C,9H | 7H | 0 | 9H | 6H | 4G | 0 | 6G | 0 | 8H | 2G | 3C,9H | 2G | 0 | 0 |
| Wild Oats | 4C,8H | 3C,7G | 3C,8G | 3G | 0 | 0 | 0 | 0 | 0 | 0 | 0 | 0 | 2C | 0 | 1C | 0 | 0 | 0 |
| Wheat | 3C,9H | 6G | 3C,7G | 3G | 0 | 0 | 0 | 0 | 2G | 0 | 7G | 0 | 2G | 0 | 3C,7H | 0 | 0 | 0 |
| Corn | 3C,7G | 2C,3G | 3C,7G | 2C,2G | 3C,3G | 0 | 2G | 3G | 2G | 0 | 0 | 0 | 0 | 0 | 3G | 0 | 0 | 0 |
| Soybean | 9H | 3C,6G | 4C,8H | 3c,6H | 2C,4H | 0 | 3C,7G | 3C,4G | 0 | 0 | 0 | 0 | 3C,6H | 2C | 8H | 3C,6H | 3C,5G | 2C |
| Rice | 10E | 10H | 10E | 9H | 2C,5G | 0 | 3C,7H | 3G | 2C,5G | 0 | 2C,5G | 0 | 9H | 3C,5G | 10H | 5G | 0 | 0 |
| Sorghum | 10H | 9H | 5C,9H | 5C,9H | 3C,6G | 0 | 8H | 3C,5G | 3C,5G | 0 | 3C,7G | 0 | 9H | 3C,7G | 10E | 8G | 0 | 0 |
| Cheatgrass | 5C,9G | 8H | 9G | 3C,7G | 0 | 0 | 4G | 0 | 0 | 0 | 0 | 0 | 7G | 0 | 9H | 2G | 0 | 0 |
| Sugar beet | 9C | 9G | 9C | 9C | 5G | 2G | 3C,9H | 7H | 1H | 0 | 4H | 0 | 4C,9G | 7H | 4C,9G | 6H | 3C,7G | 2H |
| Velvetleaf | 5C,9G | 3C,7G | 4C,8H | 5H | 2G | 0 | 2C,2H | 0 | 2G | 0 | 0 | 0 | 3C,5H | 0 | 3C,8H | 1C | 2C | 0 |
| Giant Foxtail | 3C,8G | 3C,5G | 3C,8G | 3C,6G | 1H | 0 | 7G | 0 | 2G | 0 | 3G | 0 | 7G | 0 | 3C,8G | 0 | 0 | 0 |
| Barley | 8G | 7G | — | 2C,5G | 0 | 0 | 0 | 3G | 9G | 0 | 9G | 2G | 2C,9G | 3G | 9G | 0 | 0 | 0 |

| | Compound 118 | | Compound 119 | | Compound 120 | | Compound 121 | | Compound 122 | | Compound 123 | | Compound 124 | | Compound 125 | | Compound 126 | |
|---|---|---|---|---|---|---|---|---|---|---|---|---|---|---|---|---|---|---|
| Rate kg/ha | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| Cotton | 2G | 0 | 4C,8G | 6G | 0 | 0 | 3C,7H | 0 | 0 | — | 5G | 0 | 2G | 0 | 9G | 8G | 0 | — |
| Morningglory | 8H | 0 | 9G | 3C,7H | 0 | 0 | 3C,7H | 3C,3H | 0 | — | 3C,8H | 2C,6H | 7H | 1H | 9G | 9G | 1H | — |

-continued

| | | | | | | | | | | | | | | | | | | |
|---|---|---|---|---|---|---|---|---|---|---|---|---|---|---|---|---|---|---|
| Cocklebur | 3C,3H | 0 | 9H | 2C,2H | 0 | 0 | 3C,8H | 3C,3G | 0 | — | 3C,6H | — | 2H | 1H | 9H | 9H | 7G | — |
| Nutsedge | 9G | 0 | 10E | 3C,9G | 0 | 0 | 4C,8G | 0 | 0 | — | 9G | 10E | 3G | 0 | 10E | 10E | 0 | — |
| Crabgrass | 0 | 0 | 3C,4G | 3C,5G | 0 | 0 | 3C,6G | 3G | 0 | — | 7G | 0 | 0 | 0 | 5G | 0 | 0 | — |
| Barnyardgrass | 3G | 0 | 4C,9H | 3C,7H | 0 | 0 | 4C,9H | 4G | 0 | — | 3C,9H | 3C,8H | 5G | 0 | 9H | 3C,7G | 0 | — |
| Wild Oats | 0 | 0 | 3C,6G | 0 | 0 | 0 | 2G | 0 | 0 | — | 3G | 0 | 2G | 0 | 6G | 3G | 0 | — |
| Wheat | 0 | 0 | 3C,9H | 3G | 0 | 0 | 8G | 6G | 0 | — | 8G | 0 | 3G | 0 | 7G | 2G | 0 | — |
| Corn | 7G | 0 | 3C,6H | 0 | 0 | 0 | 2H | 0 | 0 | — | 1H | 0 | 0 | 0 | 9H | 2C,9G | 0 | — |
| Soybean | 2C,6H | 0 | 4C,8H | 3C,6H | 0 | 0 | 3C,7H | 0 | 0 | — | 3C,5H | 2C,3H | 3C,6G | 0 | 2C,7H | 3C,2H | 2G | — |
| Rice | 4G | 0 | 10E | 3C,8H | 0 | 0 | 3C,8H | 4G | 0 | — | 9H | 3C,8G | 3C,6G | 0 | 9H | 9H | 4G | — |
| Sorghum | 3G | 0 | 5C,9H | 3C,8H | 0 | 0 | 4C,9H | 2C,6G | 0 | — | 5C,9H | 3C,9H | 3C,7G | 2C | 9H | 5C,9H | 2C | — |
| Cheatgrass | 0 | 0 | 5C,9G | 3C,9G | 0 | 0 | 9H | 7G | 0 | — | 5C,9G | 8G | 8G | 0 | 9H | 8G | 0 | — |
| Sugar beet | 7G | 0 | 9C | 9C | 3G | 0 | 9C | 4C,8H | 2G | — | 9C | 5G | 9G | 4G | 10C | 9C | 8G | — |
| Velvetleaf | 3C,4G | 0 | 4C,8H | 3C,6H | 0 | 0 | 3C,7H | 1C | 0 | — | 5G | 0 | 2C,3G | 2H | 5C,9G | 4C,8H | 0 | — |
| Giant Foxtail | 0 | 0 | 4C,9H | 3C,8G | 0 | 0 | 3C,8H | 0 | 0 | — | 9H | 2G | 0 | 0 | 8G | 2C,5G | 0 | — |
| Barley | 4G | 0 | 3C,9G | 3C,8G | 0 | 0 | 8G | 0 | 0 | — | 7G | 3C,7G | 7G | — | 8G | 8G | 0 | — |

| | Compound 127 | | Compound 128 | | Compound 129 | | Compound 130 | | Compound 131 | | Compound 132 | | Compound 133 | | Compound 134 | | Compound 135 | |
|---|---|---|---|---|---|---|---|---|---|---|---|---|---|---|---|---|---|---|
| Rate kg/ha | 0.05 | 0.01 | 0.05 | 0.01 | 0.0 | 0.01 | 0.05 | 0.01 | 0.05 | 0.01 | 0.05 | 0.01 | 0.05 | 0.01 | 0.05 | 0.01 | 0.05 | 0.01 |
| Cotton | 2C,8G | 4G | 0 | 0 | 2G | 0 | 4G | 0 | 9G | 6G | 8G | 3H | 9G | 2G | 7H | 1H | 0 | 0 |
| Morningglory | 9G | 3C,9H | 2C,3H | 0 | 2C,6H | 0 | 0 | 0 | 9G | 3G | 2C,3G | 2G | 7G | 0 | 9G | 7G | 1H | 0 |
| Cocklebur | 3C,8H | 3C,7H | 2H | 0 | 3C,8H | 0 | 0 | 0 | 8H | 9H | 9H | 2C,2H | 8H | 2C,8H | 8H | — | 4H | — |
| Nutsedge | 10E | 2C,9G | 8G | 0 | 9G | 0 | 0 | 0 | 10E | 10E | 9G | 3C,9G | 10E | 10E | 10E | 9G | 10E | 0 |
| Crabgrass | 2C | 0 | 2G | 0 | 2G | 0 | 0 | 0 | 5G | 0 | 3C,9G | 5G | 8G | 0 | 3G | 0 | 0 | — |
| Barnyardgrass | 4C,8H | 2C,3G | 5G | 0 | 6G | 0 | 3G | 0 | 9H | 5G | 3C,9H | 3C,7G | 9H | 8G | 9H | 7H | 5G | 0 |
| Wild Oats | 4C,7G | 3G | 0 | 0 | 2G | 0 | 0 | 0 | 3C,6G | 0 | 3C,5G | 0 | 3C,7G | 2C,3G | 6G | 0 | 0 | 0 |
| Wheat | 8G | 3G | 0 | 0 | 0 | 0 | 0 | 0 | 9H | 0 | 3C,9H | 0 | 3C,9H | 5G | 7G | 0 | 0 | 0 |
| Corn | 4C,8H | 2C,3G | 0 | 0 | 3G | 0 | 0 | 0 | 3C,9H | 2G | 3C,8H | 3G | 3C,9H | 3C,5G | 3C,7G | 5G | 6H | 0 |
| Soybean | 3C,5G | 2C | 2C | 0 | 2C | 0 | 0 | 0 | 9H | 3C,4G | 3C,7G | 3C,5H | 9H | 3C,6H | 3C,7H | 3C,4H | 0 | 0 |
| Rice | 9H | 3C | 0 | 0 | 2C,8H | 0 | 5G | 0 | 10E | 8G | 10E | 9H | 10E | 9H | 10E | 9H | 2G | 0 |
| Sorghum | 5C,9H | 3C,8H | 2,3G | 0 | 3C,9H | 0 | 2C,5G | 2G | 5C,9H | 3C,8G | 5C,9H | 3C,9H | 10H | 3C,9H | 10H | 5C,9H | 3C,7G | 0 |
| Cheatgrass | 4C,9H | 3C,8H | 0 | 0 | 4G | 0 | 3C,7G | 2G | 9H | 8G | 8G | 8H | 9H | 8H | 9H | 8G | 6G | 0 |
| Sugar beet | 3C,9G | 3C,9G | 0 | 0 | 3C,8G | 0 | 9C | 0 | 5C,9G | 9C | 5C,9G | 7H | 4C,9G | 4C,9G | 9G | 8G | 7G | 2H |
| Velvetleaf | 4C,8H | 3C,6G | 0 | 0 | 3G | 0 | 0 | 0 | 8H | 7G | 2C,6H | 2C,2H | 7H | 3G | 7H | 5G | 0 | 2G |
| Giant Foxtail | 3C,8H | 6G | 0 | 0 | 3G | 0 | 2G | 0 | 9H | 6G | 3C,9H | 4G | 9H | 6G | 9H | 6G | 2G | 2G |
| Barley | 8G | 2G | 0 | 0 | 2G | 0 | 7G | 0 | 9G | 2C,4G | 3C,8G | 2C,8G | 9G | 9G | 9G | 7G | 0 | 0 |

| | Compound 136 | | Compound 137 | | Compound 138 | | Compound 139 | | Compound 140 | | Compound 141 | | Compound 142 | | Compound 143 | | Compound 144 | |
|---|---|---|---|---|---|---|---|---|---|---|---|---|---|---|---|---|---|---|
| Rate kg/ha | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| Cotton | 0 | 0 | 6G | 0 | 0 | 0 | 0 | 0 | 2C | 0 | 1C | 0 | 2C | 0 | 3C,5G | 0 | 0 | 0 |
| Morningglory | 3C,7H | 0 | 9G | 4G | 0 | 0 | 0 | 0 | 8H | 0 | 3C,3H | 0 | 2C,2H | 0 | 8G | 0 | 0 | 0 |
| Cocklebur | 3C,5G | 2C | 3C,5H | 2C,5G | — | 0 | 0 | 0 | 8G | 0 | 2C | 0 | 2C | 0 | 3C,3H | 0 | 0 | 0 |
| Nutsedge | 7G | 0 | 9G | 0 | 0 | 0 | 0 | 0 | 9G | 0 | 0 | 0 | 10E | 0 | 0 | 0 | 0 | 0 |
| Crabgrass | 3C,7G | 0 | 3G | 0 | 0 | 0 | 0 | 0 | 4G | 0 | 0 | 0 | 2G | 0 | 0 | 0 | 0 | 0 |
| Barnyardgrass | 4C,8H | 0 | 9H | 0 | 0 | 0 | 0 | 0 | 3C,7G | 0 | 1C | 0 | 3C,7H | 0 | 7G | 0 | 0 | 0 |
| Wild Oats | 0 | 0 | 0 | 0 | 0 | 0 | 0 | 0 | 0 | 0 | 0 | 0 | 1C | 0 | 0 | 0 | 0 | 0 |
| Wheat | 0 | 0 | 3G | 0 | 0 | 0 | 0 | 0 | 0 | 0 | 0 | 0 | 6G | 0 | 6G | 0 | 0 | 0 |
| Corn | 3C,8H | 2C | 2G | 0 | 0 | 0 | 0 | 0 | 0 | 0 | 0 | 0 | 2C,3G | 0 | 3C,7G | 0 | 0 | 0 |
| Soybean | 3C,3G | 0 | 3C,3H | 2G | 0 | 0 | 0 | 0 | 3C,3H | 0 | 2G | 0 | 3C,5H | 0 | 3C,7G | 3C,4H | 0 | 0 |
| Rice | 4G | 0 | 9G | 9G | 0 | 0 | 0 | 0 | 9H | 0 | 0 | 0 | 3C,9H | 0 | 10E | 2C,5G | 0 | 0 |
| Sorghum | 5C,9H | 3C,6G | 10H | 9H | 0 | 0 | 0 | 0 | 4C,8G | 3C | 4C,7G | 0 | 3C,9H | 0 | 9H | 3C,9H | 0 | 0 |
| Cheatgrass | 8H | 0 | 9G | 0 | 0 | 0 | 0 | 0 | 8G | 0 | 2G | 0 | 9H | 0 | 4G | 0 | 0 | 0 |
| Sugar beet | 4C,8H | 1H | 9H | 8H | 4G | 0 | 0 | 0 | 9G | 4G | 4C,7H | 0 | 9G | 0 | 4C,9G | 7H | 0 | 0 |
| Velvetleaf | 0 | 0 | 5H | 0 | 0 | 0 | 0 | 0 | 7H | 0 | 2C | 0 | 2H | 0 | 3C,6H | 0 | 0 | 0 |

-continued

| | | | | | | | | | | | | | | | | | | |
|---|---|---|---|---|---|---|---|---|---|---|---|---|---|---|---|---|---|---|
| Giant Foxtail | 3C,8G | 0 | 9H | 0 | 0 | 0 | 0 | 0 | 3C,4G | 0 | 3G | 0 | 2C,5G | 0 | 8G | 0 | 0 | 0 |
| Barley | 4G | 0 | 2C,3G | 0 | 0 | 0 | 0 | 0 | 0 | 0 | 0 | 0 | 2C,3G | 0 | 2C,4G | 2G | 0 | 0 |

| | Compound 145 | | Compound 146 | | Compound 147 | | Compound 148 | | Compound 149 | | Compound 150 | | Compound 151 | | Compound 152 | | Compound 153 | |
|---|---|---|---|---|---|---|---|---|---|---|---|---|---|---|---|---|---|---|
| Rate kg/ha | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| Cotton | 1C | 0 | 2G | 0 | 0 | 0 | 0 | 0 | 2C,2G | 0 | 0 | 0 | 1C | 0 | 9G | 8G | 8G | 3G |
| Morningglory | 3C,3H | 0 | 0 | 0 | 0 | 0 | 0 | 0 | 3C,5H | 0 | 0 | 0 | 0 | 0 | 9G | 6G | 8H | 7H |
| Cocklebur | 1C | 0 | 0 | 0 | 0 | — | 0 | — | 2C | 0 | 0 | 0 | 6G | 2H | 9H | — | — | — |
| Nutsedge | 0 | 0 | 8G | 0 | 0 | 0 | 0 | 0 | 2G | 0 | 0 | 0 | 0 | 0 | 10E | 9G | 10E | 9G |
| Crabgrass | 0 | 0 | 1C | 0 | 0 | 0 | 0 | 0 | 0 | 0 | 0 | 0 | 0 | 0 | 8G | 6G | 7G | 2G |
| Barnyardgrass | 5G | 0 | 3C,8H | 0 | 2C | 0 | 0 | 0 | 3C,7G | 0 | 0 | 0 | 2H | 0 | 9H | 8H | 3C,8H | 0 |
| Wild Oats | 0 | 0 | 1C | 0 | 0 | 0 | 0 | 0 | 0 | 0 | 0 | 0 | 2C,5G | 0 | 7G | 3G | 4C,8G | 2C,3G |
| Wheat | 0 | 0 | 5G | 0 | 0 | 0 | 0 | 0 | 2G | 0 | 8G | 0 | 3C,9H | 0 | 9H | 9G | 4C,9H | 8G |
| Corn | 3C,5G | 0 | 3C,4G | 1C | 0 | 0 | 0 | 0 | 3C,6G | 1C | 1C,1H | 0 | 0 | 0 | 3G | 0 | 0 | 0 |
| Soybean | 3C,5G | 0 | 2C,2H | 0 | 0 | 0 | 0 | 0 | 3C,2H | 2C | 0 | 0 | 0 | 0 | 9H | 8H | 9H | 3C,6H |
| Rice | 4C,9H | 0 | 9H | 0 | 2C | 0 | 0 | 0 | 3C,9H | 2C,3G | 7H | 0 | 10H | 0 | 10E | 9H | 9H | 9H |
| Sorghum | 4C,9H | 3C,7G | 3C,9H | 3C,5G | 3C,3G | 0 | 3C,6G | 0 | 3C,9H | 3C,8H | 3C,4G | 0 | 9H | 0 | 10H | 9H | 10H | 9H |
| Cheatgrass | 0 | 0 | 2C,8G | 0 | 0 | 0 | 0 | 0 | 0 | 0 | 0 | 0 | 0 | 0 | 8G | 6G | 9H | 3C,7G |
| Sugar beet | 4C | 6H | 9G | 2H | 4H | 0 | 3G | 4G | 5H | 3H | 5G | 0 | 5G | 1H | 9C | 3C,7G | 9G | 3C,8H |
| Velvetleaf | 2C | 0 | 0 | 0 | 0 | 0 | 0 | 0 | 2C | 0 | 0 | 0 | 0 | 0 | 5C,9G | 4C,6H | 4C,8H | 3C,4H |
| Giant Foxtail | 3G | 0 | 4C,9H | 0 | 0 | 0 | 0 | 0 | 4C,8G | 0 | 0 | 0 | 5G | 0 | 6G | 2G | 6G | 0 |
| Barley | 2C | 0 | 2C | 0 | 2C | 0 | 0 | 0 | 2G | 0 | 7H | 0 | 4C,9G | 0 | 9G | 8G | 9G | 6G |

| | Compound 154 | | Compound 155 | | Compound 156 | | Compound 157 | | Compound 158 | | Compound 159 | | Compound 160 | | Compound 161 | | Compound 162 | |
|---|---|---|---|---|---|---|---|---|---|---|---|---|---|---|---|---|---|---|
| Rate kg/ha | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| Cotton | 2G | 4G | 3C,7G | 1C | 0 | 0 | 0 | 0 | 5C,9G | 4C,8G | 8G | 2C,4G | 0 | 0 | 8G | 2C,3G | 2G | 0 |
| Morningglory | 7H | 0 | 4C,8H | 5H | 2C | 1H | 0 | 0 | 7H | 6H | 9H | 5H | 2C,3G | 0 | 9G | 3C,8H | 5G | 0 |
| Cocklebur | 8H | 8H | 3C,8H | 3C,5H | 3H | 3H | 0 | 0 | — | — | 9H | 3C,3H | 2H | 0 | 3C,8H | 3C,3H | 2C,4G | 0 |
| Nutsedge | 3C,8G | 0 | 10E | 9G | 0 | 0 | 0 | 0 | 9G | 9G | 10E | 5G | 0 | 0 | 7G | 3C,8G | 0 | 0 |
| Crabgrass | 3G | 0 | 7G | 3G | 3G | 0 | 3G | 0 | 0 | 0 | 4G | 0 | 0 | 0 | 5G | 0 | 0 | 0 |
| Barnyardgrass | 3C,7H | 0 | 6H | 3G | 4G | 0 | 2G | 0 | 8G | 6G | 3C,8H | 0 | 2C | 0 | 4C,9H | 4C,9H | 3G | 0 |
| Wild Oats | 2C,3G | 0 | 0 | 0 | 3C,6G | 3G | 0 | 0 | 2C,3G | 2G | 4C,8H | 2C,4G | 6G | 0 | 0 | 2G | 0 | 0 |
| Wheat | 2C,6G | 0 | 8G | 0 | 2C,8H | 5G | 0 | 0 | 2C,8G | 6G | 4C,9H | 8H | 4G | 0 | 8G | 2G | 0 | 0 |
| Corn | 0 | 0 | 0 | 0 | 0 | 0 | 0 | 0 | 3C,3G | 0 | 3C,7H | 2G | 0 | 0 | 3C,7G | 2C,5G | 0 | 0 |
| Soybean | 3C,6H | 2C,2H | 3C,8H | 3C,4H | 1C,1H | 0 | 0 | 0 | 3C,6H | 5G | 3C,7H | 3C,3H | 0 | 0 | 4C,8H | 3C,6H | 0 | 0 |
| Rice | 9H | 8G | 10E | 9H | 9H | 0 | 2G | 0 | 5C,9H | 8H | 10E | 7G | 3C,6C | 0 | 5C,9H | 4C,9H | 6G | 0 |
| Sorghum | 9H | 3C,5G | 9H | 4C,9H | 3C,9G | 2C,5G | 2G | 0 | 5C,9H | 4C,9H | 3C,7H | 3C,7H | 0 | 0 | 9H | 4C,9H | 3G | 0 |
| Cheatgrass | 7G | 0 | 5G | 0 | 4G | 0 | 0 | 0 | 9G | 6G | 9H | 8G | 6G | 0 | 3C,9G | 8G | 0 | 0 |
| Sugar beet | 4G | 5G | 7H | 3H | 5H | 6G | 0 | 0 | 9C | 4C,9G | 5C,9G | 3C,8G | 6H | 0 | 9G | 3C,7G | 3G | 0 |
| Velvetleaf | 3C,5H | 1C | 3C,5H | 3G | 2H | 1H | 0 | 0 | 9G | 8H | 8H | 3G | 2H | 0 | 3C,7G | 2H | 2G | 0 |
| Giant Foxtail | 5G | 0 | 6G | 2G | 2C,5H | 0 | 2H | 0 | 7G | 0 | 4C,8H | 5G | 2C,5G | 0 | 4C,9G | 3C,9H | 2G | 0 |
| Barley | 8G | 2G | 8G | 4G | 9G | 2G | 2G | 0 | 9H | 6G | 3C,9G | 2G | 2C,8G | 0 | 3C,9G | 4G | 0 | 0 |

| | Compound 163 | | Compound 164 | | Compound 165 | | Compound 166 | | Compound 167 | | Compound 168 | | Compound 169 | | Compound 170 | | Compound 171 | |
|---|---|---|---|---|---|---|---|---|---|---|---|---|---|---|---|---|---|---|
| Rate kg/ha | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| Cotton | 3C,8H | 2G | 4C,9G | 2C,5G | 5C,9G | 9G | 2C,8H | 5G | 3G | 0 | 0 | 0 | 3G | 0 | 4C,8H | 3C,8G | 2C,6G | 0 |
| Morningglory | 8H | 5H | 9C | 3C,9H | 9C | 9C | 9G | 3C,8H | 2H | 1H | 0 | 0 | 8H | 0 | 9H | 8H | 8H | 3C,3H |
| Cocklebur | 0 | 0 | 5G | 0 | 6G | 3G | 7H | 3H | 2G | 1H | 0 | 0 | 0 | 0 | 9H | 8H | — | 2C,2H |
| Nutsedge | 10E | 8G | 9G | 10E | 10E | 10E | 10E | 10E | 0 | 0 | 0 | 0 | 0 | 0 | 10E | 8G | 0 | 0 |
| Crabgrass | 4C,8G | 2C,8G | 4C,7G | 3C,6G | 4C,9G | 3C,6G | 2C,6G | 3C,6G | 0 | 0 | 0 | 0 | 4C,8G | 0 | 3C,7G | 0 | 0 | 0 |
| Barnyardgrass | 3C,8H | 2C,4G | 9H | 4C,8H | 9H | 9H | 9H | 3C,9H | 2C,6G | 3G | 0 | 0 | 4C,9H | 3G | 9H | 6H | 3G | 0 |
| Wild Oats | 3C,9H | 2C,3G | 4C,9H | 2C | 4C,8G | 2C,6G | 2C,8G | 1C | 0 | 0 | 0 | 0 | 2C,8H | 2G | 3C,9G | 3G | 1C | 0 |
| Wheat | 3C,9H | 8G | 4C,9H | 2C,8H | 4C,9H | 2C,8H | 9H | 7H | 7G | 0 | 0 | 0 | 9H | 4G | 3C,9G | 5G | 0 | 0 |

-continued

| | | | | | | | | | | | | | | | | | | |
|---|---|---|---|---|---|---|---|---|---|---|---|---|---|---|---|---|---|---|
| Corn | 0 | 0 | 3C,9H | 0 | 4C,9H | 4G | 2G | 0 | 6H | 0 | 2C,3G | 0 | 4C,9H | 0 | 3C,8H | 2G | 1C,2G | 0 |
| Soybean | 8H | 7H | 9H | 7H | 9H | 9H | 9H | 3C,8H | 2C,6H | 2C,2H | 2G | 0 | 3G | 0 | 9H | 8H | 2C,6G | 0 |
| Rice | 10E | 9H | 10E | 9H | 10E | 10E | 10E | 10E | 8H | 2C,5G | 0 | 0 | 10E | 9H | 5C,9H | 2C,8G | 4G | 2G |
| Sorghum | 5C,9H | 9H | 10E | 5C,9H | 10H | 4C,9H | 10E | 10E | 4C,9H | 2C,4G | 2C,5G | 0 | 10H | 9H | 5C,9H | 9H | 3C,9G | 3G |
| Cheatgrass | 9H | 8G | 9H | 9H | 9H | 9H | 9G | 7G | 3G | 0 | 0 | 0 | 9H | 0 | 5C,9G | 8G | 5G | 0 |
| Sugar beet | 5C,9G | 8G | 5C,9G | 8H | 5C,9G | 9G | 4C,9G | 9G | 6G | 0 | 0 | 0 | 0 | 0 | 5C,9G | 4C,9G | 5C,9G | 5G |
| Velvetleaf | 8H | 3C,5H | 5C,9H | 2C,5H | 5C,9G | 2C,8H | 5C,9G | 3G | 0 | 0 | 0 | 0 | 2G | 0 | 5C,9G | 5G | 3C,7H | 2C,2G |
| Giant Foxtail | 4C,9H | 2C,5G | 4C,9H | 3C,8H | 9H | 4C,9H | 9H | 2C,6G | 2C,5G | 0 | 0 | 0 | 9H | 3C,8G | 5C,9H | 4C,8H | 3G | 0 |
| Barley | 9G | 2C,7G | 3C,9G | 4G | 9G | 9G | 9G | 2C,8G | 7G | 0 | 0 | 0 | 2C,9H | 2C | 3C,9G | 8G | 5G | 0 |
| | Compound 172 | | Compound 173 | | Compound 174 | | Compound 175 | | Compound 176 | | Compound 177 | | Compound 178 | | Compound 179 | | Compound 180 | |
| Rate kg/ha | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| Cotton | 0 | — | 2G | 0 | 3G | 0 | 2G | 0 | 2C,9G | 8G | 3C,6G | 1C | 2G | 0 | 9G | 2C,6G | 2C,6G | 0 |
| Morningglory | 0 | — | 0 | 0 | 5H | 0 | 6H | 1H | 9H | 4G | 7G | 0 | 2H | 0 | 3C,8G | 3C,7H | 7H | 3G |
| Cocklebur | 0 | — | 3G | 0 | 2C,6H | 0 | 2C,5G | 0 | 9H | 7H | — | 3C,4G | 2C,3H | 0 | 9H | 8H | — | 3C |
| Nutsedge | 0 | — | 0 | 0 | 0 | 0 | 0 | 0 | 9G | 5G | 8G | 3G | 2C,5G | 0 | 10E | 10E | 7G | 0 |
| Crabgrass | 0 | — | 0 | 0 | 0 | 0 | 0 | 0 | 9G | 0 | 2C | 0 | 0 | 0 | 2G | 0 | 0 | 2G |
| Barnyardgrass | 0 | — | 0 | 0 | 2H | 0 | 0 | 0 | 9G | 1H | 3H | 0 | 1C | 0 | 8H | 7H | 0 | 0 |
| Wild Oats | 0 | — | 0 | 0 | 0 | 0 | 0 | 0 | 3C,7G | 2C,5G | 3C,5G | 0 | 3C,4G | 0 | 2C,5G | 0 | 2C,4G | 0 |
| Wheat | 0 | — | 0 | 0 | 0 | 0 | 0 | 0 | 9H | 9H | 9H | 0 | 6G | 0 | 8H | 3G | 2C,8H | 4G |
| Corn | 0 | — | 0 | 0 | 6G | 0 | 0 | 0 | 5G | 0 | 0 | 0 | 0 | 0 | 0 | 0 | 9H | 0 |
| Soybean | 0 | — | 0 | 0 | 2C,5G | 0 | 3C,6H | 1C,1H | 9H | 3C,6H | 3C,7H | 2C,4G | 2C,5G | 0 | 3C,7H | 5G | 2C,8H | 5G |
| Rice | 0 | — | 2G | 0 | 8H | 0 | 8G | 2G | 10E | 10H | 9H | 1C | 2C,3G | 0 | 10E | 9H | 3C,9H | 2C |
| Sorghum | 0 | — | 4G | 0 | 2G | 0 | 2C,8H | 2G | 4C,9H | 9H | 9H | 3C,5G | 3C,7G | 0 | 9H | 9H | 3C,9H | 3C,6G |
| Cheatgrass | 0 | — | 0 | 0 | 0 | 0 | 0 | 0 | 5G | 0 | 4G | 0 | 0 | 0 | 0 | 0 | 2C,8H | 2G |
| Sugar beet | 0 | — | 7G | 5G | 4G | 0 | 7H | 2G | 9G | 9G | 9G | 7G | 4C,9G | 3C,6H | 9G | 9G | 4C,8G | 3G |
| Velvetleaf | 0 | — | 0 | 0 | 2G | 0 | 0 | 0 | 4C,9G | 3H | 6G | 3C,3H | 3C,3H | 0 | 3C,7H | 3C,3H | 4C,7H | 2H |
| Giant Foxtail | 0 | — | 2G | 0 | 0 | 0 | 0 | 0 | 2C,9G | 0 | 4G | 1C | 0 | 0 | 5G | 3G | 0 | 2G |
| Barley | 0 | — | 5G | 0 | 0 | 0 | 8G | 0 | 9G | 2C,6H | 3C,9G | 0 | 2C,8G | 0 | 9G | 4G | 2C,9H | 4G |
| | Compound 181 | | Compound 182 | | Compound 183 | | Compound 184 | | Compound 185 | | Compound 186 | | Compound 187 | | Compond 188 | | Compound 189 | |
| Rate kg/ha | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| Cotton | 3C,7G | 3G | 3C,9G | 3C,8G | 2C,8G | 4G | 1C,3G | 0 | 1C,3G | 2G | 1C,4G | 0 | 0 | 0 | 1C | 0 | 9G | 9G |
| Morningglory | 9G | 6G | 9H | 9C | 9H | 3C,8H | 9G | 2C,7G | 2C,8H | 2C,5G | 3C,8H | 2G | 0 | 0 | 2C,2H | 0 | 9G | 8G |
| Cocklebur | 8H | 2G | 2c,9H | — | 8H | 4C,8G | 8G | 0 | 3C,7G | — | 2C,9H | 0 | 0 | 0 | 2C,5G | 1C | 9H | 9H |
| Nutsedge | 9G | 0 | 10E | 9G | 10E | 3C,8G | 0 | 0 | 5G | 0 | 0 | 0 | 0 | 0 | 0 | 0 | 10E | 9G |
| Crabgrass | 0 | 3G | 2C,4G | 6G | 2C | 0 | 2C | 0 | 0 | 0 | 0 | 0 | 0 | 0 | 0 | 0 | 3G | 0 |
| Barnyardgrass | 3C,7G | 0 | 9H | 2C,7H | 9H | 7G | 3C,9H | 0 | 2C,4G | 0 | 2C,4G | 0 | 0 | 0 | 0 | 0 | 3C,9H | 5G |
| Wild Oats | 2C,6G | 0 | 2C,7G | 3G | 2C,4G | 0 | 2C,8G | 2C | 2C,4G | 3G | 2C,7G | 3G | 0 | 0 | 0 | 0 | 3C,4G | 0 |
| Wheat | 2C,8G | 7G | 2C,8H | 7G | 2C,8H | 4G | 2C,9H | 7G | 2C,8H | 6G | 8H | 5G | 0 | 0 | 0 | 0 | 5G | 0 |
| Corn | 2C,9H | 3C,7H | 9H | 2C,9H | 9H | 9H | 9H | 3C,8G | 9H | 2C,8G | 9H | 3C,9G | 0 | 0 | 3C,4G | 0 | 5C,9H | 3C,7G |
| Soybean | 3C,8H | 2C,4G | 2C,8H | 3C,8H | 2C,7H | 3H | 3C,7H | 2C,5G | 1C,6G | 4G | 2C,8H | 1C,3G | 2G | 0 | 5G | 2C,2H | 9H | 6H |
| Rice | 2C,7G | 0 | 3C,8H | 2C,6G | 2C,9H | 3C,8H | 10E | 7G | 10E | 2C,7G | 10H | 2C,4G | 2C | 0 | 0 | 2G | 8H | 0 |
| Sorghum | 3C,7H | 3C,7G | 10H | 2C,9H | 10H | 10H | 9C | 3C,9H | 10C | 3C,9H | 10C | 4C,9G | 0 | 0 | 3C,7G | 3C,3G | 9G | 9H |
| Cheatgrass | 3C,9H | 3G | 9H | 2C,9H | 2C,9H | 9H | 9H | 2C,9H | 9H | 6G | 9H | 6G | 0 | 0 | 7G | 0 | 9H | 7G |
| Sugar beet | 4C,9G | 2C,8G | 3C,9G | 4C,9G | 4C,8G | 4C,8H | 5G | 5G | 5G | 0 | 3C,7G | 1C,3G | 0 | 0 | 7H | 2H | 9H | 9G |
| Velvetleaf | 4C,8H | 7G | 4C,9H | 2C,8H | 4C,8H | 2C,4G | 3C,7H | 0 | 0 | 0 | 4G | 0 | 4G | 2H | 2C | 2G | 4C,9G | 3G |
| Giant Foxtail | 3G | 3G | 2C,9H | 3C,9H | 2C,7G | 2C | 2C,8H | 0 | 2C,5G | 0 | 2C,5G | 0 | 0 | 0 | 0 | 0 | 9G | 0 |
| Barley | 2C,8G | 2C,5G | 8G | 8G | 8G | 5G | 9H | 7G | 9G | 2C,8H | 4C,9G | 2C,8G | 0 | 0 | 0 | 0 | 3C,9G | 2G |
| | Compound 190 | | Compound 191 | | Compound 192 | | Compound 193 | | Compound 194 | | Compound 195 | | Compound 196 | | Compound 197 | | Compound 198* | |
| Rate kg/ha | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| Cotton | 2C,7H | 3G | 0 | 0 | 0 | 0 | 1C | 0 | 0 | 0 | 3C,5G | 0 | 0 | 0 | 0 | 0 | 0 | 0 |

-continued

| | | | | | | | | | | | | | | | | | | |
|---|---|---|---|---|---|---|---|---|---|---|---|---|---|---|---|---|---|---|
| Morningglory | 3H | 0 | 2H | 4H | 0 | 0 | 3H | 0 | 0 | 0 | 6H | 0 | 0 | 0 | 0 | 0 | 0 | 0 |
| Cocklebur | 2C | 0 | 0 | 0 | 0 | 0 | 1C | — | 0 | 0 | 0 | 2C | 0 | 0 | 0 | 0 | 0 | 0 |
| Nutsedge | 5G | 0 | 0 | 0 | 0 | 0 | 0 | 0 | 0 | 0 | 0 | 0 | 0 | 0 | 0 | 0 | 0 | 0 |
| Crabgrass | 0 | 0 | 0 | 0 | 0 | 0 | 0 | 0 | 0 | 0 | 0 | 0 | 0 | 0 | 0 | 0 | 0 | 0 |
| Barnyardgrass | 7H | 0 | 0 | 0 | 0 | 0 | 0 | 0 | 0 | 0 | 1C | 0 | 0 | 0 | 0 | 0 | 0 | 0 |
| Wild Oats | 2G | 0 | 0 | 0 | 0 | 0 | 2C,4G | 0 | 0 | 0 | 0 | 0 | 0 | 0 | 0 | 0 | 0 | 0 |
| Wheat | 0 | 0 | 0 | 0 | 0 | 0 | 3C,8G | 0 | 0 | 0 | 0 | 0 | 0 | 0 | 0 | 0 | 0 | 0 |
| Corn | 3C,6G | 0 | 2C,6G | 0 | 5G | 0 | 3C,8H | 0 | 0 | 0 | 0 | 0 | 0 | 0 | 0 | 0 | 0 | 0 |
| Soybean | 3H | 0 | 0 | 0 | 0 | 0 | 3C,8H | 2G | 0 | 0 | 3C,5G | 1C | 0 | 0 | 0 | 0 | 0 | 0 |
| Rice | 7G | 0 | 0 | 0 | 5G | 0 | 8G | 0 | 0 | 0 | 2C,4G | 0 | 0 | 0 | 0 | 0 | 0 | 0 |
| Sorghum | 2C,8G | 3C,5G | 6G | 0 | 3C,3G | 0 | 9H | 3C,3G | 0 | 0 | 3C,7G | 3G | 0 | 0 | 0 | 0 | 0 | 0 |
| Cheatgrass | 7G | 0 | 0 | 0 | 0 | 0 | 6G | 0 | 0 | 0 | 7G | 3G | 0 | 0 | 0 | 0 | 0 | 0 |
| Sugar beet | 7H | 0 | 0 | 0 | 2H | 0 | 3H | 2H | 0 | 0 | 4C,8G | 5G | 0 | 0 | 0 | 0 | 0 | 0 |
| Velvetleaf | 0 | 0 | 0 | 0 | 0 | 0 | 0 | 0 | 0 | 0 | 2C | 0 | 0 | 0 | 0 | 0 | 0 | 0 |
| Giant Foxtail | 2G | 0 | 0 | 0 | 0 | 0 | 0 | 0 | 0 | 0 | 0 | 0 | 0 | 0 | 0 | 0 | 0 | 0 |
| Barley | 0 | 0 | 0 | 0 | 0 | 0 | 7H | 0 | 0 | 0 | 0 | 0 | 0 | 0 | 0 | 0 | 0 | 0 |

| | Compound 199 | | Compound 200 | | Compound 201 | | Compound 202 | | Compound 203 | | Compound 204 | | Compound 205 | | Compond 206 | |
|---|---|---|---|---|---|---|---|---|---|---|---|---|---|---|---|---|
| Rate kg/ha | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| Cotton | 0 | 0 | 2G | 0 | 3C,6G | 0 | 3C,9G | 7H | 6G | 0 | 1C | 0 | 2G | 0 | 9G | 2C,4G |
| Morningglory | 0 | 0 | 0 | 0 | 3C,8G | 2C | 9G | 7H | 2C,2H | 0 | 0 | 0 | 3C,6H | 0 | 7G | 6H |
| Cocklebur | 0 | 0 | 0 | 0 | 3C,6H | 2C,6H | 8H | 7H | 2C,2H | 0 | 0 | 0 | 2C | 6G | 3C,6H | 6G |
| Nutsedge | 0 | 0 | 0 | 0 | 9G | 5G | 10E | 10E | 7G | 0 | 0 | 0 | 0 | 0 | 7G | — |
| Crabgrass | 0 | 0 | 0 | 0 | 0 | 0 | 0 | 0 | 0 | 0 | 0 | 0 | 0 | 0 | 2C | 0 |
| Barnyardgrass | 0 | 0 | 0 | 0 | 3C,7H | 3C,2G | 3C,8H | 1H | 1C | 0 | 3G | 0 | 3C,4G | 0 | 5G | 2G |
| Wild Oats | 0 | 0 | 2G | 0 | 2G | 0 | 3G | 0 | 0 | 0 | 0 | 0 | 0 | 0 | 0 | 0 |
| Wheat | 0 | 0 | 0 | 0 | 0 | 0 | 4G | 0 | 0 | 0 | 0 | 0 | 0 | 0 | 0 | 0 |
| Corn | 0 | 0 | 0 | 0 | 4C,8G | 3C,5G | 3C,9G | 3C,8G | 2C,3G | 0 | 3C,5G | 0 | 3C,7G | 1C | 3C,6G | 2G |
| Soybean | 0 | 0 | 0 | 0 | 2C,3H | 1C,2H | 4C,8H | 3H | 1C | 0 | 1C | 0 | 2C,2H | 1H | 0 | 0 |
| Rice | 0 | 0 | 0 | 0 | 5G | 0 | 8G | 2G | 2G | 0 | 6G | 0 | 9H | 3G | 2C,7G | 0 |
| Sorghum | 0 | 0 | 2C,3G | 0 | 4C,9H | 3C,6G | 3C,9H | 3C,8H | 2C,6G | 0 | 3C,9H | 3C,3G | 4C,9G | 3C,3G | 2C,3G | 0 |
| Cheatgrass | 0 | 0 | 5G | 0 | 8G | 3C,5G | 9G | 6G | 3G | 0 | 4G | 0 | 8H | 0 | 0 | 0 |
| Sugar beet | 0 | 0 | 3C,8G | 0 | 5C,9G | 3C,8G | 5C,9G | 8G | 3C,8G | 3H | 3C,8H | 2H | 4C,9G | 3H | 4C,9G | 3C,7G |
| Velvetleaf | 0 | 0 | 0 | 0 | 3C,5H | 3C | 3C,8G | 3C,3G | 2G | 0 | 0 | 0 | 1C | 0 | 3C,6H | 3C,3H |
| Giant Foxtail | 0 | 0 | 0 | 0 | 2G | 0 | 2G | 0 | 0 | 0 | 2G | 0 | 0 | 0 | 2C,8G | 3G |
| Barley | 0 | 0 | 0 | 0 | 2G | 0 | 2C,4G | 0 | 2G | 0 | 0 | 0 | 2C,2G | 0 | 0 | 0 |

*It is noted that Compounds 64 and 65 were inactive at the levels tested. However, it is believed that at higher levels, herbicidal activity would be present.
*It is noted that Compound 198 was inactive at the levels tested. However, it is believed that at higher levels, herbicidal activity would be present.

Test B

Postemergence

Two round pans (25 cm diameter by 12.5 cm deep) were filled with Sassafras sandy loam soil. One pan was planted with blackgrass,(*Alopecurus myosuroides*), sugar beets, nutsedge (*Cyperus rotundus*) tubers, rape (*Brassica napus*), crabgrass (*Dioitaria sanguinalis*), sicklepod (*Cassia obtusifolia*), teaweed (*Sida spinosa*), jimsonweed (*Datura stramonium*), velvetleaf (*Abutilon theophrasti*), and giant foxtail (*Setaria faberii*). The other pan was planted with wheat, barley, cotton, rice, corn, soybean, wild oats (*Avena fatua*), cocklebur (*Xanthium pensylvanicum*), morningglory (*Ipomoea hederacea*), johnsongrass (*Sorghum halepense*) and barnyardgrass (*Echinochloa crusgalli*). The plants were grown for approximately fourteen days, then sprayed postemergence with the chemicals dissolved in a non-phytotoxic solvent.

Preemergence

Two round pans (25 cm diameter by 12.5 cm deep) were filled with Sassafras sandy loam soil. One pan was planted with blackgrass, sugar beets, nutsedge, rape, crabgrass, sicklepod, teaweed, jimsonweed, velvetleaf, and giant foxtail. The other pan was planted with wheat, barley, cotton, rice, corn, soybeans, wild oats, cocklebur, morningglory, johnsongrass, and barnyardgrass. The two pans were sprayed preemergence with the chemicals dissolved in a non-phytotoxic solvent.

Treated plants and controls were maintained in the greenhouse for 28 days, then all treated plants were compared to controls and visually rated for plant response. Response ratings are based on a scale of 0 to 100 where 0=no effect, and 100=complete control. A dash (-) response means no test.

Response ratings are contained in Table B.

TABLE B

POSTEMERGENCE

| | Compound 2 | | | | | | | Compound 3 | | | | | | | | | | Compound 4 | | | | | Compound 5 | | | |
|---|---|---|---|---|---|---|---|---|---|---|---|---|---|---|---|---|---|---|---|---|---|---|---|---|---|---|
| Rate g/ha | 62 | 16 | 16 | 4 | 4 | 1 | .25 | 62 | 16 | 16 | 16 | 4 | 4 | 4 | 1 | 1 | .25 | .25 | 62 | 16 | 4 | 1 | 62 | 16 | 4 | 1 |
| Corn | 100 | 100 | 100 | 100 | 100 | 60 | 40 | 100 | 100 | 100 | 100 | 100 | 90 | 100 | 80 | 70 | 60 | 0 | 100 | 100 | 80 | 40 | 100 | 90 | 60 | 40 |
| Wheat | 100 | 100 | 100 | 60 | 100 | 40 | 0 | 100 | 100 | 30 | 70 | 40 | 0 | 20 | 0 | 0 | 0 | 0 | 100 | 100 | 40 | 0 | 70 | 40 | 0 | 0 |
| Barley | — | — | — | — | — | — | — | — | — | — | — | — | — | — | — | — | — | — | — | — | — | — | — | — | — | — |
| Rice | 100 | 100 | 100 | 90 | 70 | 50 | 30 | 100 | 100 | 80 | 100 | 90 | 60 | 100 | 50 | 30 | 30 | 0 | 100 | 100 | 60 | 30 | 100 | 90 | 30 | 0 |
| Soybean | 100 | 100 | 100 | 100 | 90 | 90 | 60 | 100 | 100 | 100 | 100 | 100 | 90 | 90 | 80 | 70 | 80 | 0 | 100 | 100 | 100 | 60 | 90 | 90 | 60 | 40 |
| Cotton | 100 | 100 | 60 | 70 | 20 | 40 | 0 | 100 | 100 | 100 | 100 | 100 | 80 | 100 | 70 | 40 | 30 | 0 | 100 | 90 | 70 | 30 | 100 | 90 | 60 | 30 |
| Sugar beet | 100 | 100 | 100 | 100 | 100 | 100 | 100 | 100 | 100 | 100 | 100 | 100 | 100 | 100 | 100 | 100 | 100 | 0 | 100 | 100 | 100 | 100 | 100 | 100 | 100 | 90 |
| Rape | 100 | 100 | 100 | 100 | 100 | 100 | 100 | 100 | 100 | 100 | 100 | 100 | 100 | 100 | 100 | 100 | 100 | 0 | 100 | 100 | 100 | 100 | 100 | 100 | 100 | 100 |
| Crabgrass | 100 | 80 | 100 | 50 | 60 | 40 | 0 | 100 | 90 | 50 | 70 | 70 | 30 | 30 | 50 | 0 | 30 | 0 | 100 | 80 | 50 | 30 | 70 | 50 | 40 | 30 |
| Johnsongrass | 100 | 100 | 100 | 100 | 90 | 60 | 40 | 100 | 100 | 100 | 100 | 100 | 70 | 90 | 70 | 30 | 30 | 0 | 100 | 100 | 70 | 30 | 100 | 100 | 80 | 40 |
| Blackgrass | 100 | 100 | 100 | 100 | 90 | 50 | 30 | 100 | 100 | 100 | 100 | 100 | 60 | 100 | 80 | 30 | 70 | 0 | 100 | 100 | 60 | 30 | 100 | 100 | 60 | 30 |
| Barnyardgrass | 100 | 100 | 100 | 100 | 100 | 60 | 40 | 100 | 100 | 100 | 100 | 100 | 70 | 100 | 100 | 30 | 40 | 0 | 100 | 100 | 60 | 30 | 100 | 100 | 80 | 40 |
| Nutsedge | 100 | 100 | 100 | 100 | 80 | 90 | 80 | 100 | 100 | 100 | 100 | 100 | 100 | 100 | 100 | 100 | 100 | 0 | 100 | 90 | 50 | 30 | 100 | 100 | 80 | 70 |
| Giant Foxtail | 100 | 100 | 100 | 90 | 90 | 50 | 30 | 100 | 100 | 80 | 60 | 60 | 30 | 30 | 30 | 0 | 0 | 0 | 100 | 90 | 60 | 30 | 100 | 80 | 30 | 0 |
| Green Foxtail | | | | | | | | | | | | | | | | | | | | | | | | | | |
| Cheatgrass | | | | | | | | | | | | | | | | | | | | | | | | | | |
| Wild Oats | 90 | 100 | 80 | 60 | 70 | 40 | 0 | 100 | 100 | 50 | 100 | 40 | 0 | 80 | 0 | 0 | 0 | 0 | 100 | 90 | 30 | 0 | 70 | 40 | 0 | 0 |
| Wild Buckwheat | | | | | | | | | | | | | | | | | | | | | | | | | | |
| Viola | | | | | | | | | | | | | | | | | | | | | | | | | | |
| Lambsquarter | | | | | | | | | | | | | | | | | | | | | | | | | | |
| Cocklebur | 100 | 100 | 90 | 70 | 60 | 30 | 0 | 100 | 100 | 90 | 100 | 100 | 70 | 90 | 60 | 60 | 30 | 0 | 100 | 90 | 50 | 30 | 100 | 100 | 60 | 30 |
| Morningglory | 100 | 100 | 90 | 100 | 70 | 90 | 60 | 100 | 100 | 100 | 100 | 100 | 100 | 100 | 100 | 80 | 70 | 0 | 100 | 100 | 80 | 50 | 100 | 90 | 80 | 60 |
| Teaweed | 100 | 100 | 90 | 70 | 30 | 40 | 0 | 100 | 100 | 60 | 90 | 80 | 30 | 60 | 50 | 0 | 30 | 0 | 100 | 80 | 60 | 40 | 90 | 70 | 50 | 30 |
| Sicklepod | 100 | 100 | 100 | 90 | 70 | 60 | 0 | 100 | 100 | 100 | 100 | 100 | 100 | 100 | 90 | 100 | 80 | 0 | 100 | 80 | 60 | 30 | 70 | 60 | 40 | 30 |
| Jimsonweed | 100 | 100 | 100 | 90 | 70 | 70 | 40 | 100 | 100 | 90 | 100 | 90 | 60 | 100 | 70 | 30 | 40 | 0 | 100 | 100 | 70 | 40 | 100 | 90 | 60 | 30 |
| Velvetleaf | 100 | 100 | 100 | 100 | 80 | 80 | 50 | 100 | 100 | 90 | 100 | 100 | 80 | 100 | 90 | 50 | 50 | 0 | 100 | 100 | 100 | 60 | 100 | 100 | 60 | 30 |

POSTEMERGENCE

| | Compound 8 | | | | Compound 13 | | | | Compound 14 | | | | Compound 16 | | | | Compound 20 | | | Compound 21 | | | Compound 22 | | | Compound 23 | | | |
|---|---|---|---|---|---|---|---|---|---|---|---|---|---|---|---|---|---|---|---|---|---|---|---|---|---|---|---|---|---|
| Rate g/ha | 62 | 16 | 4 | 1 | 62 | 16 | 4 | 1 | 16 | 4 | 1 | .25 | 62 | 16 | 4 | 1 | 62 | 16 | 4 | 62 | 16 | 4 | 62 | 16 | 4 | 62 | 16 | 4 | 1 |
| Corn | 100 | 80 | 50 | 30 | 100 | 100 | 70 | 40 | 100 | 80 | 60 | 40 | 0 | 0 | 0 | 0 | 100 | 90 | 40 | 100 | 90 | 70 | 100 | 100 | 70 | 50 | 30 | 0 | 0 |
| Wheat | 30 | 0 | 0 | 0 | 30 | 0 | 0 | 0 | 30 | 0 | 0 | 0 | 0 | 0 | 0 | 0 | 90 | 60 | 20 | 0 | 0 | 0 | 70 | 20 | 0 | 40 | 0 | 0 | 0 |
| Barley | — | — | — | — | — | — | — | — | — | — | — | — | — | — | — | — | — | — | — | 0 | 0 | 0 | 0 | 0 | 0 | — | — | — | — |
| Rice | 90 | 70 | 0 | 0 | 90 | 30 | 0 | 0 | 60 | 30 | 0 | 0 | 60 | 0 | 0 | 0 | 95 | 90 | 85 | 80 | 20 | 0 | 90 | 50 | 20 | 70 | 40 | 0 | 0 |
| Soybean | 100 | 80 | 70 | 0 | 100 | 100 | 100 | 70 | 100 | 100 | 70 | 60 | 100 | 70 | 40 | 0 | 95 | 90 | 80 | 100 | 90 | 50 | 100 | 100 | 80 | 100 | 100 | 80 | 60 |
| Cotton | 100 | 90 | 60 | 40 | 100 | 100 | 90 | 50 | 100 | 70 | 50 | 30 | 90 | 70 | 50 | 30 | 100 | 100 | 90 | 60 | 0 | 0 | 80 | 70 | 20 | 100 | 100 | 70 | 40 |
| Sugar beet | 100 | 100 | 100 | 90 | 100 | 100 | 100 | 100 | 100 | 100 | 90 | 70 | 100 | 100 | 90 | 70 | 95 | 90 | 90 | 90 | 80 | 0 | 100 | 90 | 70 | 100 | 100 | 100 | 100 |
| Rape | 100 | 100 | 100 | 90 | 100 | 100 | 100 | 100 | 100 | 100 | 90 | 60 | 100 | 100 | 90 | 60 | 100 | 100 | 100 | 100 | 90 | 30 | 100 | 100 | 70 | 100 | 100 | 100 | 100 |
| Crabgrass | 90 | 50 | 30 | 0 | 90 | 60 | 50 | 30 | 30 | 0 | 0 | 0 | 30 | 0 | 0 | 0 | 60 | 30 | 20 | 40 | 0 | 0 | 60 | 30 | 0 | 60 | 40 | 30 | 0 |
| Johnsongrass | 90 | 50 | 0 | 0 | 100 | 90 | 60 | 30 | 100 | 80 | 60 | 30 | 90 | 70 | 30 | 0 | 100 | 100 | 85 | 100 | 70 | 20 | 100 | 100 | 70 | 100 | 100 | 80 | 60 |
| Blackgrass | 100 | 90 | 30 | 0 | 100 | 70 | 40 | 0 | 70 | 30 | 0 | 0 | 70 | 30 | 0 | 0 | 100 | 95 | 85 | 80 | 60 | 0 | 100 | 70 | 50 | 100 | 70 | 30 | 0 |
| Barnyardgrass | 90 | 50 | 0 | 0 | 100 | 90 | 60 | 30 | 100 | 80 | 50 | 30 | 90 | 50 | 0 | 0 | 100 | 95 | 80 | 100 | 70 | 30 | 100 | 100 | 50 | 100 | 100 | 80 | 60 |
| Nutsedge | 100 | 70 | 70 | 40 | 100 | 100 | 90 | 80 | 90 | 70 | 50 | 30 | 90 | 70 | 60 | 40 | 100 | 80 | 60 | 0 | 0 | 0 | 0 | 0 | 0 | 100 | 100 | 70 | 50 |
| Giant Foxtail | 90 | 50 | 0 | 0 | 100 | 80 | 30 | 0 | 70 | 30 | 0 | 0 | 0 | 0 | 0 | 0 | 90 | 85 | 60 | 100 | 60 | 20 | 100 | 100 | 50 | 70 | 50 | 30 | 0 |
| Green Foxtail | | | | | | | | | | | | | | | | | | | | 70 | 20 | 0 | 100 | 80 | 50 | | | | |
| Cheatgrass | | | | | | | | | | | | | | | | | | | | 0 | 0 | 0 | 0 | 0 | 0 | | | | |
| Wild Oats | 30 | 0 | 0 | 0 | 60 | 30 | 0 | 0 | 40 | 0 | 0 | 0 | 0 | 0 | 0 | 0 | 85 | 70 | 30 | 0 | 0 | 0 | 60 | 20 | 0 | 40 | 0 | 0 | 0 |
| Wild Buckwheat | | | | | | | | | | | | | | | | | | | | 100 | 80 | 0 | 80 | 80 | 50 | | | | |
| Viola | | | | | | | | | | | | | | | | | | | | 40 | 20 | 0 | 80 | — | 20 | | | | |

TABLE B-continued

| | | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| Lambsquarter | | | | | | | | | | | | | | | | | | | 90 | 50 | 0 | 80 | 60 | 50 | | | | |
| Cocklebur | 100 | 90 | 50 | 30 | 100 | 70 | 50 | 30 | 100 | 90 | 60 | 30 | 90 | 80 | 50 | 30 | 100 | 95 | 85 | 60 | 0 | 0 | 100 | 60 | 20 | 100 | 100 | 100 | 100 |
| Morningglory | 100 | 90 | 60 | 30 | 100 | 100 | 100 | 50 | 90 | 70 | 50 | 30 | 90 | 80 | 60 | 30 | 100 | 100 | 90 | 50 | 0 | 50 | 70 | 60 | 20 | 100 | 80 | 60 | 30 |
| Teaweed | 100 | 70 | 30 | 30 | 100 | 90 | 60 | 40 | 90 | 50 | 30 | 0 | 70 | 30 | 30 | 0 | 90 | 95 | 90 | 40 | 20 | 0 | 70 | 50 | 20 | 90 | 70 | 50 | 30 |
| Sicklepod | 90 | 50 | 30 | 0 | 100 | 100 | 80 | 40 | 80 | 50 | 0 | 0 | 50 | 30 | 0 | 0 | 70 | 25 | 30 | 50 | 0 | 0 | 80 | 50 | 20 | 100 | 70 | 50 | 30 |
| Jimsonweed | 100 | 100 | 60 | 30 | 100 | 100 | 60 | 30 | 90 | 90 | 50 | 30 | 100 | 80 | 50 | 30 | 95 | 90 | 30 | 80 | 70 | 20 | 90 | 70 | 50 | 100 | 100 | 70 | 50 |
| Velvetleaf | 100 | 100 | 70 | 50 | 100 | 100 | 100 | 70 | 100 | 90 | 50 | 30 | 100 | 80 | 30 | 0 | 100 | 100 | 90 | 30 | 0 | 0 | 70 | 30 | 20 | 100 | 100 | 100 | 90 |

POSTEMERGENCE

| | Compound 24 | | | | Compound 27 | | | | Compound 28 | | | Compound 31 | | | | Compound 32 | | | | Compound 33 | | | Compound 34 | | | |
|---|---|---|---|---|---|---|---|---|---|---|---|---|---|---|---|---|---|---|---|---|---|---|---|---|---|---|
| Rate g/ha | 62 | 16 | 4 | 1 | 250 | 62 | 16 | 4 | 250 | 62 | 16 | 62 | 16 | 4 | 1 | 62 | 16 | 4 | 1 | 62 | 16 | 4 | 62 | 16 | 4 | 1 |
| Corn | 0 | 0 | 0 | 0 | 0 | 0 | 0 | 0 | 0 | 0 | 0 | 100 | 70 | 50 | 30 | 80 | 40 | 0 | 0 | 80 | 40 | 30 | 70 | 30 | 0 | 0 |
| Wheat | 30 | 0 | 0 | 0 | 40 | 20 | 0 | 0 | 30 | 0 | 0 | 0 | 0 | 0 | 0 | 80 | 60 | 40 | 20 | 90 | 70 | 30 | 60 | 30 | 0 | 0 |
| Barley | — | — | — | — | — | — | — | — | | | | — | — | — | — | — | — | — | — | — | — | — | — | — | — | — |
| Rice | 30 | 0 | 0 | 0 | 90 | 70 | 50 | 30 | 50 | 30 | 0 | 70 | 30 | 0 | 0 | 100 | 70 | 50 | 30 | 80 | 70 | 30 | 90 | 70 | 50 | 30 |
| Soybean | 100 | 100 | 80 | 60 | 90 | 80 | 70 | 50 | 80 | 60 | 40 | 100 | 90 | 70 | 40 | 100 | 100 | 90 | 70 | 90 | 90 | 70 | 90 | 90 | 80 | 60 |
| Cotton | 100 | 90 | 70 | 40 | 100 | 90 | 60 | 30 | 100 | 70 | 30 | 80 | 60 | 30 | 0 | 100 | 100 | 100 | 80 | 90 | 90 | 50 | 90 | 80 | 50 | 30 |
| Sugar beet | 100 | 100 | 100 | 90 | 100 | 100 | 100 | 100 | 100 | 100 | 100 | 100 | 100 | 60 | 30 | 100 | 100 | 70 | 50 | 100 | 100 | 80 | 100 | 100 | 70 | 50 |
| Rape | 100 | 100 | 100 | 100 | 100 | 100 | 100 | 100 | 100 | 100 | 100 | 100 | 100 | 100 | 100 | 100 | 100 | 100 | 100 | 100 | 100 | 100 | 100 | 100 | 100 | 100 |
| Crabgrass | 30 | 0 | 0 | 0 | 70 | 50 | 30 | 0 | 50 | 30 | 0 | 90 | 70 | 50 | 30 | 90 | 70 | 50 | 30 | 60 | 30 | 0 | 80 | 50 | 30 | 0 |
| Johnsongrass | 100 | 70 | 50 | 30 | 100 | 90 | 70 | 50 | 90 | 70 | 50 | 100 | 100 | 60 | 30 | 100 | 100 | 100 | 80 | 100 | 100 | 60 | 100 | 90 | 70 | 30 |
| Blackgrass | 100 | 100 | 70 | 40 | 90 | 60 | 30 | 0 | 100 | 90 | 70 | 100 | 100 | 60 | 30 | 100 | 100 | 90 | 70 | 90 | 70 | 30 | 100 | 70 | 30 | 0 |
| Barnyardgrass | 80 | 60 | 30 | 0 | 100 | 90 | 70 | 50 | 90 | 60 | 30 | 100 | 100 | 70 | 30 | 100 | 100 | 100 | 90 | 100 | 70 | 50 | 100 | 70 | 50 | 0 |
| Nutsedge | 100 | 90 | 70 | 50 | 100 | 100 | 70 | 50 | 70 | 50 | 30 | 30 | 0 | 0 | 0 | 100 | 100 | 100 | 90 | 100 | 60 | 50 | 90 | 70 | 50 | 30 |
| Giant Foxtail | 70 | 30 | 0 | 0 | 70 | 50 | 30 | 0 | 80 | 60 | 30 | 100 | 100 | 70 | 40 | 100 | 90 | 70 | 50 | 90 | 70 | 50 | 90 | 70 | 60 | 0 |
| Green Foxtail | | | | | | | | | | | | | | | | | | | | | | | | | | |
| Cheatgrass | | | | | | | | | | | | | | | | | | | | | | | | | | |
| Wild Oats | 30 | 0 | 0 | 0 | 60 | 40 | 20 | 0 | 30 | 0 | 0 | 70 | 40 | 20 | 0 | 80 | 60 | 40 | 20 | 80 | 40 | 30 | 70 | 50 | 30 | 0 |
| Wild Buckwheat | | | | | | | | | | | | | | | | | | | | | | | | | | |
| Viola | | | | | | | | | | | | | | | | | | | | | | | | | | |
| Lambsquarter | | | | | | | | | | | | | | | | | | | | | | | | | | |
| Cocklebur | 100 | 100 | 100 | 90 | 100 | 90 | 70 | 50 | 90 | 70 | 50 | 90 | 70 | 50 | 30 | 100 | 100 | 100 | 70 | 100 | 80 | 60 | 90 | 70 | 30 | 0 |
| Morningglory | 100 | 90 | 70 | 50 | 90 | 80 | 70 | 50 | 100 | 100 | 70 | 90 | 70 | 50 | 30 | 100 | 100 | 90 | 70 | 100 | 100 | 50 | 90 | 80 | 60 | 40 |
| Teaweed | 70 | 50 | 30 | 0 | 80 | 60 | 40 | 20 | 80 | 60 | 40 | 80 | 60 | 30 | 0 | 100 | 80 | 60 | 30 | 80 | 50 | 30 | 80 | 50 | 30 | 0 |
| Sicklepod | 70 | 50 | 30 | 0 | 80 | 60 | 30 | 0 | 50 | 30 | 0 | 80 | 60 | 30 | 0 | 100 | 100 | 90 | 80 | 90 | 50 | 30 | 90 | 50 | 30 | 0 |
| Jimsonweed | 100 | 70 | 50 | 30 | 100 | 70 | 50 | 30 | 100 | 80 | 60 | 100 | 80 | 60 | 40 | 100 | 90 | 80 | 70 | 90 | 80 | 60 | 100 | 80 | 70 | 50 |
| Velvetleaf | 100 | 100 | 70 | 50 | 100 | 100 | 80 | 50 | 100 | 80 | 50 | 100 | 80 | 60 | 40 | 100 | 100 | 100 | 90 | 100 | 100 | 90 | 100 | 100 | 80 | 60 |

POSTEMERGENCE

| | Compound 35 | | | | Compound 36 | | | | Compound 39 | | | | Compound 40 | | | | Compound 46 | | | | Compound 53 | | | | Compound 54 | | | |
|---|---|---|---|---|---|---|---|---|---|---|---|---|---|---|---|---|---|---|---|---|---|---|---|---|---|---|---|---|
| Rate g/ha | 62 | 16 | 4 | 1 | 62 | 16 | 4 | 1 | 62 | 16 | 4 | 1 | 62 | 16 | 4 | 1 | 62 | 16 | 4 | 1 | 62 | 16 | 4 | 1 | 62 | 16 | 4 | 1 |
| Corn | 30 | 0 | 0 | 0 | 90 | 70 | 30 | 0 | 100 | 100 | 70 | 30 | 80 | 20 | 0 | 0 | 100 | 80 | 50 | 0 | 0 | 0 | 0 | 0 | 0 | 0 | 0 | 0 |
| Wheat | 40 | 0 | 0 | 0 | 80 | 50 | 30 | 0 | 100 | 100 | 80 | 50 | 90 | 80 | 20 | 0 | 80 | 70 | 20 | 0 | 60 | 30 | 0 | 0 | 80 | 60 | 40 | 20 |
| Barley | — | — | — | — | — | — | — | — | 100 | 80 | 40 | 0 | 20 | 0 | 0 | 0 | 90 | 80 | 50 | 0 | 60 | 30 | 0 | 0 | 60 | 30 | 0 | 0 |
| Rice | 100 | 70 | 30 | 0 | 90 | 70 | 50 | 30 | 100 | 100 | 80 | 30 | 90 | 60 | 30 | 0 | 100 | 100 | 70 | 20 | 90 | 60 | 30 | 0 | 90 | 60 | 30 | 0 |
| Soybean | 90 | 80 | 60 | 50 | 100 | 80 | 60 | 40 | 100 | 100 | 90 | 70 | 100 | 80 | 80 | 50 | 100 | 90 | 80 | 60 | 100 | 90 | 80 | 70 | 100 | 90 | 70 | 50 |
| Cotton | 100 | 80 | 40 | 0 | 90 | 70 | 40 | 0 | 70 | 30 | 30 | 0 | 70 | 60 | 30 | 0 | 100 | 60 | 50 | 0 | 90 | 60 | 20 | 0 | 90 | 70 | 20 | 0 |
| Sugar beet | 100 | 100 | 100 | 70 | 100 | 100 | 100 | 70 | 100 | 90 | 40 | 20 | 70 | 50 | 0 | 0 | 100 | 100 | 60 | 20 | 100 | 100 | 100 | 90 | 100 | 100 | 90 | 70 |
| Rape | 100 | 100 | 100 | 100 | 0 | 0 | 0 | 0 | 100 | 100 | 100 | 80 | 100 | 100 | 70 | 50 | 100 | 100 | 90 | 50 | 100 | 100 | 100 | 100 | 100 | 100 | 100 | 90 |
| Crabgrass | 60 | 30 | 0 | 0 | 90 | 60 | 30 | 0 | 90 | 50 | 20 | 0 | 40 | 0 | 0 | 0 | 60 | 30 | 0 | 0 | 70 | 50 | 30 | 0 | 60 | 30 | 0 | 0 |
| Johnsongrass | 100 | 100 | 70 | 40 | 100 | 90 | 60 | 30 | 100 | 100 | 70 | 50 | 80 | 50 | 20 | 0 | 90 | 100 | 80 | 20 | 100 | 90 | 70 | 50 | 100 | 90 | 70 | 50 |
| Blackgrass | 100 | 80 | 30 | 0 | 100 | 100 | 70 | 30 | 90 | 100 | 70 | 60 | 80 | 50 | 20 | 0 | 100 | 90 | 60 | 0 | 100 | 90 | 60 | 30 | 100 | 90 | 70 | 50 |

TABLE B-continued

| | | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| Barnyardgrass | 100 | 100 | 70 | 30 | 100 | 90 | 70 | 30 | 100 | 100 | 90 | 60 | 90 | 60 | 20 | 0 | 100 | 100 | 80 | 20 | 100 | 100 | 90 | 60 | 100 | 90 | 70 | 50 |
| Nutsedge | 90 | 70 | 50 | 30 | 0 | 0 | 0 | 0 | 70 | 80 | 30 | 0 | 50 | 0 | 0 | 0 | 30 | — | — | 0 | — | — | — | — | — | — | — | — |
| Giant Foxtail | 90 | 80 | 50 | 30 | 90 | 70 | 50 | 30 | 90 | 40 | 20 | 0 | 60 | 30 | 0 | 0 | 100 | 80 | 40 | 0 | 100 | 90 | 70 | 50 | 90 | 70 | 50 | 30 |
| Green Foxtail | | | | | | | | | 100 | 70 | 50 | 0 | 60 | 30 | 20 | 0 | 100 | 80 | 60 | 0 | 90 | 70 | 50 | 30 | 90 | 70 | 50 | 30 |
| Cheatgrass | | | | | | | | | 100 | 100 | 60 | 50 | 80 | 70 | 50 | 0 | 40 | 20 | 0 | 0 | 100 | 90 | 70 | 50 | 100 | 70 | 50 | 30 |
| Wild Oats | 50 | 0 | 0 | 0 | 90 | 60 | 30 | 0 | 100 | 100 | 90 | 40 | 100 | 40 | 0 | 0 | 90 | 90 | 30 | 0 | 30 | 0 | 0 | 0 | 30 | 0 | 0 | 0 |
| Wild Buckwheat | | | | | | | | | 100 | 90 | 70 | 0 | 70 | 0 | 0 | 0 | 100 | 100 | 80 | 0 | 100 | 90 | 70 | 50 | 90 | 70 | 50 | 30 |
| Viola | | | | | | | | | 70 | 80 | 80 | 30 | 80 | — | — | — | 90 | 70 | 30 | 30 | 100 | 90 | 70 | 50 | 90 | 70 | 50 | 30 |
| Lambsquarter | | | | | | | | | 100 | 90 | 50 | 20 | 90 | 70 | 20 | 0 | 100 | 100 | 80 | 50 | 100 | 90 | 70 | 50 | 100 | 90 | 70 | 50 |
| Cocklebur | 100 | 90 | 50 | 30 | 30 | 0 | 0 | 0 | 100 | 100 | 100 | 30 | 100 | 90 | 80 | 0 | 100 | 70 | 20 | 0 | 100 | 90 | 70 | 50 | 100 | 90 | 70 | 50 |
| Morningglory | 100 | 90 | 50 | 30 | 100 | 90 | 70 | 50 | 100 | 100 | 90 | 30 | 100 | 100 | 70 | 30 | 100 | 100 | 80 | 60 | 100 | 100 | 90 | 60 | 100 | 70 | 50 | 30 |
| Teaweed | 90 | 60 | 30 | 0 | 70 | 50 | 30 | 0 | 90 | 50 | 20 | 0 | 60 | 50 | 30 | 0 | 80 | 60 | 40 | 0 | 90 | 70 | 50 | 30 | 90 | 70 | 50 | 30 |
| Sicklepod | 90 | 40 | 0 | 0 | 90 | 60 | 30 | 0 | 100 | 100 | 50 | 0 | 100 | 30 | 30 | 20 | 100 | 90 | 70 | 0 | 100 | 100 | 70 | 50 | 100 | 70 | 50 | 30 |
| Jimsonweed | 100 | 80 | 50 | 30 | 80 | 60 | 40 | 0 | 100 | 100 | 70 | 50 | 90 | 70 | 50 | 0 | 100 | 90 | 80 | 20 | 100 | 90 | 70 | 50 | 100 | 90 | 70 | 50 |
| Velvetleaf | 100 | 100 | 70 | 30 | 80 | 60 | 40 | 0 | 100 | 90 | 60 | 20 | 100 | 80 | 60 | 0 | 100 | 90 | 60 | 20 | 100 | 100 | 80 | 60 | 100 | 90 | 70 | 50 |

POSTEMERGENCE

| | Compound 55 | | | | Compound 56 | | | | | Compound 206 | | | |
|---|---|---|---|---|---|---|---|---|---|---|---|---|---|
| Rate g/ha | 62 | 16 | 4 | 1 | 62 | 16 | 4 | 1 | Rate g/ha | 62 | 16 | 4 | 1 |
| Corn | 0 | 0 | 0 | 0 | 0 | 0 | 0 | 0 | Giant foxtail | 50 | 30 | 0 | 0 |
| Wheat | 90 | 60 | 30 | 0 | 40 | 20 | 0 | 0 | Velvetleaf | 100 | 100 | 90 | 70 |
| Barley | 70 | 40 | 0 | 0 | 20 | 0 | 0 | 0 | Sugarbeet | 100 | 100 | 90 | 70 |
| Rice | 90 | 60 | 30 | 0 | 80 | 60 | 30 | 0 | Large crabgrass | 50 | 30 | 0 | 0 |
| Soybean | 90 | 80 | 70 | 50 | 70 | 30 | 0 | 0 | Prikley sida | 80 | 70 | 50 | 30 |
| Cotton | 90 | 60 | 0 | 0 | 40 | 0 | 0 | 0 | Jimsonweed | 100 | 70 | 50 | 30 |
| Sugar beet | 100 | 100 | 90 | 70 | 100 | 90 | 70 | 50 | Rice dry seeded | 70 | 50 | 30 | 0 |
| Rape | 100 | 100 | 100 | 80 | 100 | 100 | 90 | 80 | Cocklebur | 90 | 60 | 30 | 0 |
| Crabgrass | 80 | 60 | 40 | 20 | 50 | 30 | 0 | 0 | Cotton | 80 | 70 | 60 | 30 |
| Johnsongrass | 100 | 90 | 70 | 50 | 90 | 70 | 50 | 30 | Soybeans | 30 | 0 | 0 | 0 |
| Blackgrass | 100 | 90 | 70 | 50 | 90 | 70 | 50 | 30 | Barnyardgrass | 100 | 60 | 30 | 0 |
| Barnyardgrass | 100 | 100 | 70 | 50 | 90 | 70 | 50 | 30 | Wild oats | 0 | 0 | 0 | 0 |
| Nutsedge | — | — | — | — | — | — | — | — | Ivy morningglory | 90 | 80 | 70 | 50 |
| Giant Foxtail | 90 | 80 | 70 | 30 | 90 | 60 | 30 | 0 | Wheat | 30 | 0 | 0 | 0 |
| Green Foxtail | 90 | 70 | 50 | 30 | 90 | 70 | 50 | 30 | Sicklepod | 70 | 50 | 30 | 0 |
| Cheatgrass | 100 | 90 | 70 | 50 | 90 | 70 | 50 | 30 | Johnsongrass | 50 | 30 | 0 | 0 |
| Wild Oats | 70 | 30 | 0 | 0 | 0 | 0 | 0 | 0 | Purple nutsedge | 70 | 30 | 0 | 0 |
| Wild Buckwheat | 100 | 90 | 80 | 60 | 90 | 70 | 50 | 30 | Corn | 60 | 30 | 0 | 0 |
| Viola | 100 | 90 | 70 | 50 | — | 70 | 50 | 30 | Wild buckwheat | 70 | 50 | 30 | 0 |
| Lambsquarter | 100 | 90 | 70 | 50 | 90 | 70 | 50 | 30 | Blackgrass | 70 | 50 | 30 | 0 |
| Cocklebur | 100 | 90 | 70 | 50 | 90 | 70 | 50 | 30 | Rape | 100 | 100 | 90 | 70 |
| Morningglory | 100 | 80 | 60 | 30 | 100 | 60 | 30 | 0 | Barley | 0 | 0 | 0 | 0 |
| Teaweed | 90 | 70 | 50 | 30 | 90 | 70 | 50 | 30 | Green foxtail | 80 | 50 | 30 | 0 |
| Sicklepod | 100 | 70 | 50 | 30 | 70 | 50 | 30 | 0 | Cheat grass | 0 | 0 | 0 | 0 |
| Jimsonweed | 90 | 80 | 60 | 30 | 90 | 70 | 50 | 30 | Lambsquarter | 100 | 90 | 70 | 50 |
| Velvetleaf | 100 | 90 | 70 | 40 | 100 | 70 | 50 | 30 | Chickweed spp. | 100 | 90 | 60 | 30 |

PREEMERGENCE

| | Compound 2 | | | | | | | Compound 3 | | | | | | | | | | Compound 4 | | | | Compound 5 | | | |
|---|---|---|---|---|---|---|---|---|---|---|---|---|---|---|---|---|---|---|---|---|---|---|---|---|---|
| Rate g/ha | 250 | 62 | 62 | 16 | 16 | 4 | 1 | 250 | 62 | 62 | 16 | 16 | 16 | 4 | 4 | 1 | 1 | 250 | 62 | 16 | 4 | 250 | 62 | 16 | 4 |
| Corn | 100 | 100 | 100 | 80 | 90 | 20 | 0 | 100 | 100 | 100 | 70 | 70 | 100 | 20 | 40 | 0 | 0 | 100 | 100 | 90 | 60 | 100 | 100 | 90 | 30 |
| Wheat | 100 | 90 | 100 | 80 | 100 | 30 | 0 | 100 | 100 | 100 | 20 | 0 | 40 | 0 | 0 | 0 | 0 | 100 | 100 | 90 | 70 | 100 | 100 | 50 | 0 |
| Barley | — | — | — | — | — | — | — | — | — | — | — | — | — | — | — | — | — | — | — | — | — | — | — | — | — |

TABLE B-continued

| | | | | | | | | | | | | | | | | | | | | | | | | |
|---|---|---|---|---|---|---|---|---|---|---|---|---|---|---|---|---|---|---|---|---|---|---|---|---|
| Rice | 100 | 100 | 100 | 100 | 100 | 90 | 70 | 100 | 100 | 100 | 100 | 100 | 100 | 100 | 100 | 90 | 0 | 100 | 100 | 100 | 100 | 100 | 100 | 100 | 100 |
| Soybean | 100 | 100 | 100 | 80 | 100 | 40 | 20 | 100 | 100 | 100 | 70 | 70 | 90 | 40 | 40 | 0 | 0 | 100 | 100 | 90 | 60 | 100 | 90 | 80 | 60 |
| Cotton | 100 | 80 | 100 | 80 | 80 | 30 | 0 | 100 | 100 | 100 | 70 | 70 | 100 | 30 | 0 | 0 | 0 | 100 | 90 | 60 | 30 | 100 | 80 | 50 | 30 |
| Sugar beet | 100 | 100 | 100 | 100 | 100 | 100 | 30 | 100 | 100 | 100 | 100 | 100 | 100 | 100 | 90 | 80 | 0 | 100 | 100 | 100 | 90 | 100 | 100 | 100 | 80 |
| Rape | 100 | 100 | 100 | 90 | 100 | 20 | 0 | 100 | 100 | 100 | 90 | 90 | 100 | 90 | 80 | 20 | 0 | 100 | 100 | 100 | 50 | 100 | 100 | 80 | 60 |
| Crabgrass | 100 | 100 | 100 | 90 | 90 | 30 | 0 | 100 | 90 | 100 | 60 | 30 | 80 | 30 | 0 | 0 | 0 | 100 | 90 | 50 | 30 | 90 | 70 | 50 | 30 |
| Johnsongrass | 100 | 100 | 100 | 100 | 100 | 90 | 30 | 100 | 100 | 100 | 90 | 70 | 100 | 80 | 30 | 50 | 0 | 100 | 100 | 100 | 70 | 100 | 100 | 100 | 100 |
| Blackgrass | 100 | 90 | 100 | 100 | 100 | 70 | 20 | 100 | 100 | 100 | 100 | 90 | 100 | 100 | 70 | 50 | 0 | 100 | 100 | 100 | 90 | 100 | 100 | 100 | 90 |
| Barnyardgrass | 100 | 100 | 100 | 90 | 100 | 80 | 20 | 100 | 100 | 100 | 80 | 50 | 100 | 30 | 0 | 0 | 0 | 100 | 100 | 100 | 60 | 100 | 100 | 90 | 70 |
| Nutsedge | 100 | 100 | 100 | 100 | 100 | 70 | 20 | 100 | 100 | 100 | 100 | 90 | 100 | 90 | 50 | 50 | 0 | 100 | 90 | 80 | 60 | 100 | 100 | 100 | 90 |
| Giant Foxtail | 100 | 100 | 100 | 90 | 100 | 80 | 50 | 100 | 100 | 100 | 80 | 30 | 100 | 50 | 0 | 0 | 0 | 100 | 100 | 100 | 60 | 100 | 100 | 90 | 60 |
| Green Foxtail | | | | | | | | | | | | | | | | | | | | | | | | | |
| Cheatgrass | | | | | | | | | | | | | | | | | | | | | | | | | |
| Wild Oats | 100 | 90 | 100 | 90 | 90 | 20 | 0 | 100 | 100 | 100 | 70 | 90 | 80 | 0 | 40 | 0 | 0 | 100 | 90 | 70 | 70 | 90 | 80 | 50 | 30 |
| Wild Buckwheat | | | | | | | | | | | | | | | | | | | | | | | | | |
| Viola | | | | | | | | | | | | | | | | | | | | | | | | | |
| Lambsquarter | | | | | | | | | | | | | | | | | | | | | | | | | |
| Cocklebur | 100 | 90 | 100 | 80 | 90 | 20 | 0 | 100 | 100 | 100 | 50 | 80 | 80 | 50 | 40 | 20 | 0 | 100 | 100 | 80 | 50 | 100 | 90 | 70 | 50 |
| Morningglory | 100 | 50 | 100 | 40 | 70 | 0 | 0 | 100 | 100 | 100 | 40 | 80 | 100 | 30 | 40 | 0 | 0 | 100 | 90 | 50 | 30 | 100 | 80 | 70 | 30 |
| Teaweed | 100 | 100 | 100 | 80 | 90 | 50 | 20 | 100 | 100 | 100 | 80 | 70 | 90 | 70 | 30 | 0 | 0 | 100 | 90 | 70 | 30 | 90 | 70 | 50 | 30 |
| Sicklepod | 100 | 90 | 100 | 80 | 80 | 60 | 20 | 100 | 90 | 100 | 90 | 50 | 90 | 80 | 30 | 20 | 0 | 100 | 90 | 60 | 30 | 90 | 70 | 50 | 50 |
| Jimsonweed | 100 | 100 | 100 | 90 | 90 | 60 | 20 | 100 | 100 | 100 | 100 | 80 | 100 | 80 | 30 | 50 | 0 | 100 | 90 | 80 | 50 | 100 | 90 | 60 | 30 |
| Velvetleaf | 100 | 100 | 100 | 100 | 100 | 60 | 0 | 100 | 100 | 100 | 100 | 80 | 100 | 90 | 30 | 60 | 0 | 100 | 100 | 80 | 50 | 100 | 90 | 60 | 30 |

PREEMERGENCE

| | Compound 8 | | | | Compound 13 | | | | Compound 14 | | | | Compound 16 | | | | Compound 20 | | | Compound 21 | | | Compound 22 | | | Compound 23 | | | |
|---|---|---|---|---|---|---|---|---|---|---|---|---|---|---|---|---|---|---|---|---|---|---|---|---|---|---|---|---|---|
| Rate g/ha | 250 | 62 | 16 | 4 | 250 | 62 | 16 | 4 | 62 | 16 | 4 | 1 | 250 | 62 | 16 | 4 | 250 | 62 | 16 | 250 | 62 | 16 | 250 | 62 | 16 | 250 | 62 | 16 | 4 |
| Corn | 100 | 90 | 30 | 0 | 100 | 90 | 90 | 20 | 90 | 70 | 50 | 30 | 80 | 50 | 30 | 0 | 100 | 95 | 90 | 90 | 60 | 20 | 90 | 80 | 0 | 70 | 50 | 30 | 0 |
| Wheat | 80 | 30 | 0 | 0 | 30 | 0 | 0 | 0 | 80 | 40 | 0 | 0 | 90 | 40 | 0 | 0 | 95 | 95 | 80 | 40 | 0 | 0 | 50 | 0 | 0 | 80 | 60 | 40 | 0 |
| Barley | — | — | — | — | — | — | — | — | — | — | — | — | — | — | — | — | — | — | — | 0 | 0 | 0 | 60 | 20 | 0 | — | — | — | — |
| Rice | 100 | 100 | 100 | 20 | 100 | 100 | 100 | 70 | 100 | 100 | 70 | 40 | 100 | 100 | 90 | 60 | 100 | 100 | 100 | — | — | — | — | — | — | 100 | 100 | 80 | 50 |
| Soybean | 100 | 80 | 40 | 0 | 100 | 100 | 90 | 70 | 100 | 90 | 70 | 60 | 100 | 80 | 60 | 30 | 95 | 95 | 85 | 80 | 80 | 30 | 90 | 80 | 30 | 100 | 80 | 60 | 40 |
| Cotton | 100 | 60 | 20 | 0 | 100 | 80 | 80 | 20 | 80 | 70 | 50 | 30 | 90 | 70 | 50 | 30 | 95 | 90 | 80 | 90 | 20 | 0 | 90 | 80 | 20 | 90 | 70 | 40 | 0 |
| Sugar beet | 100 | 100 | 100 | 50 | 100 | 100 | 100 | 90 | 100 | 100 | 100 | 80 | 100 | 100 | 100 | 100 | 100 | 95 | 90 | 90 | 70 | 50 | 80 | 70 | 80 | 100 | 100 | 100 | 80 |
| Rape | 100 | 100 | 90 | 40 | 100 | 100 | 90 | 90 | 100 | 100 | 60 | 60 | 100 | 90 | 60 | 0 | 100 | 95 | 80 | 80 | 60 | 0 | 90 | 80 | 70 | 100 | 90 | 70 | 50 |
| Crabgrass | 80 | 70 | 40 | 20 | 90 | 70 | 50 | 0 | 90 | 70 | 50 | 30 | 90 | 70 | 50 | 40 | 90 | 30 | 10 | 90 | 0 | 0 | 70 | 70 | 20 | 90 | 70 | 50 | 30 |
| Johnsongrass | 100 | 90 | 60 | 20 | 100 | 100 | 100 | 60 | 100 | 80 | 50 | 30 | 100 | 80 | 50 | 30 | 95 | 95 | 90 | 100 | 80 | 0 | 100 | 90 | 80 | 100 | 90 | 80 | 60 |
| Blackgrass | 100 | 90 | 70 | 30 | 100 | 90 | 80 | 50 | 100 | 90 | 60 | 30 | 100 | 90 | 60 | 30 | 100 | 95 | 80 | 100 | 50 | 0 | 90 | 70 | 70 | 100 | 100 | 80 | 50 |
| Barnyardgrass | 100 | 90 | 20 | 0 | 100 | 100 | 90 | 60 | 100 | 70 | 50 | 0 | 100 | 80 | 40 | 0 | 100 | 95 | 90 | 100 | 50 | 0 | 100 | 90 | 50 | 100 | 80 | 60 | 40 |
| Nutsedge | 100 | 100 | 80 | 60 | 100 | 100 | 100 | 90 | 100 | 100 | 90 | 80 | 100 | 100 | 100 | 90 | 100 | 100 | 100 | 0 | 0 | 0 | 0 | 0 | 0 | 100 | 100 | 80 | 60 |
| Giant Foxtail | 100 | 90 | — | 0 | 100 | 90 | 70 | 50 | 100 | 60 | 40 | 0 | 80 | 60 | 30 | 0 | 100 | 95 | 90 | 90 | 70 | 0 | 100 | 90 | 70 | 100 | 100 | 90 | 70 |
| Green Foxtail | | | | | | | | | | | | | | | | | | | | 90 | 90 | 30 | 100 | 90 | 50 | | | | |
| Cheatgrass | | | | | | | | | | | | | | | | | | | | 50 | 0 | 0 | 60 | 0 | 0 | | | | |
| Wild Oats | 100 | 90 | 80 | 0 | — | — | — | — | 80 | 40 | 0 | 0 | 90 | 40 | 0 | 0 | 90 | 85 | 65 | 60 | 20 | 0 | 50 | 50 | 20 | 70 | 50 | 30 | 0 |
| Wild Buckwheat | | | | | | | | | | | | | | | | | | | | 100 | 50 | 50 | 90 | 60 | 20 | | | | |
| Viola | | | | | | | | | | | | | | | | | | | | 100 | — | 20 | 90 | 50 | 30 | | | | |
| Lambsquarter | | | | | | | | | | | | | | | | | | | | 90 | 70 | 0 | 90 | 60 | 0 | | | | |
| Cocklebur | 100 | 80 | 20 | 0 | 100 | 70 | 80 | 20 | 100 | 90 | 70 | 50 | 100 | 80 | 70 | 30 | 95 | 90 | 90 | 30 | 20 | 0 | — | 30 | 0 | 90 | 80 | 70 | 50 |
| Morningglory | 100 | 60 | 20 | 0 | 100 | 90 | 80 | 30 | 90 | 70 | 50 | 30 | 100 | 80 | 50 | 30 | 95 | 90 | 80 | 70 | 0 | 0 | 80 | 60 | 20 | 70 | 50 | 30 | 0 |
| Teaweed | 100 | 90 | 90 | 20 | 100 | 90 | 90 | 20 | 90 | 80 | 50 | 30 | 90 | 80 | 50 | 30 | 90 | 80 | 50 | 80 | 30 | 0 | 70 | 40 | 0 | 90 | 70 | 50 | — |
| Sicklepod | 100 | 90 | 30 | 0 | 100 | 100 | 80 | 20 | 90 | 70 | 50 | 30 | 90 | 70 | 50 | 30 | 90 | 50 | 10 | 50 | 0 | 0 | 70 | 30 | 0 | 90 | 70 | 40 | 0 |
| Jimsonweed | 100 | 100 | 80 | 30 | 100 | 100 | 90 | 50 | 90 | 70 | 50 | 30 | 90 | 70 | 50 | 30 | 100 | 90 | 60 | 60 | 0 | 0 | 70 | 30 | 0 | 100 | 80 | &0 | 40 |

TABLE B-continued

| Velvetleaf | 100 | 100 | 60 | 20 | 100 | 100 | 90 | 80 | 90 | 70 | 50 | 30 | 90 | 70 | 50 | 30 | 100 | 95 | 70 | 30 | 0 | 0 | 60 | 30 | 0 | 100 | 80 | 60 | 40 |
|---|---|---|---|---|---|---|---|---|---|---|---|---|---|---|---|---|---|---|---|---|---|---|---|---|---|---|---|---|---|

PREEMERGENCE

| | Compound 24 | | | | Compound 27 | | | | Compound 28 | | | | Compound 31 | | | | Compound 32 | | | | Compound 33 | | | | Compound 34 | | | |
|---|---|---|---|---|---|---|---|---|---|---|---|---|---|---|---|---|---|---|---|---|---|---|---|---|---|---|---|---|
| Rate g/ha | 250 | 62 | 16 | 4 | 250 | 62 | 16 | 4 | 250 | 62 | 16 | 4 | 250 | 62 | 16 | 4 | 250 | 62 | 16 | 4 | 250 | 62 | 16 | 4 | 250 | 62 | 16 | 4 |
| Corn | 30 | 0 | 0 | 0 | 0 | 0 | 0 | 0 | 0 | 0 | 0 | 0 | 90 | 60 | 0 | 0 | 90 | 80 | 70 | 40 | 40 | 0 | 0 | 0 | 60 | 0 | 0 | 0 |
| Wheat | 70 | 30 | 0 | 0 | 70 | 50 | 30 | 0 | 70 | 30 | 0 | 0 | 60 | 30 | 0 | 0 | 80 | 60 | 40 | 20 | 90 | 40 | 0 | 0 | 70 | 30 | 0 | 0 |
| Barley | — | — | — | — | — | — | — | — | 70 | 30 | 0 | 0 | — | — | — | — | — | — | — | — | — | — | — | — | — | — | — | — |
| Rice | 90 | 70 | 50 | 30 | 100 | 90 | 70 | 50 | 100 | 90 | 60 | 30 | 100 | 100 | 90 | 70 | 100 | 100 | 100 | 100 | 100 | 100 | 30 | 0 | 100 | 100 | 40 | 0 |
| Soybean | 90 | 70 | 50 | 30 | 70 | 50 | 30 | 0 | 90 | 60 | 30 | 0 | 90 | 70 | 50 | 30 | 100 | 80 | 60 | 40 | 90 | 60 | 30 | 0 | 90 | 50 | 0 | 0 |
| Cotton | 70 | 50 | 30 | 0 | 50 | 30 | 0 | 0 | 70 | 30 | 0 | 0 | 80 | 40 | 0 | 0 | 90 | 70 | 50 | 30 | 80 | 60 | 30 | 0 | 60 | 30 | 0 | 0 |
| Sugar beet | 100 | 100 | 90 | 80 | 100 | 90 | 70 | 50 | 90 | 70 | 50 | 30 | 100 | 90 | 70 | 50 | 100 | 100 | 90 | 70 | 100 | 80 | 40 | 0 | 100 | 90 | 70 | 50 |
| Rape | 100 | 90 | 70 | 50 | 90 | 70 | 50 | 30 | 90 | 70 | 50 | 30 | 90 | 70 | 50 | 20 | 100 | 90 | 70 | 50 | 90 | 70 | 50 | 30 | 90 | 70 | 40 | 0 |
| Crabgrass | 90 | 60 | 30 | 0 | 80 | 70 | 60 | 30 | 70 | 50 | 30 | 0 | 90 | 60 | 30 | 0 | 90 | 80 | 70 | 60 | 70 | 50 | 30 | 0 | 70 | 50 | 40 | 30 |
| Johnsongrass | 90 | 80 | 70 | 50 | 90 | 80 | 70 | 40 | 100 | 90 | 70 | 50 | 100 | 80 | 60 | 40 | 100 | 100 | 90 | 70 | 100 | 90 | 70 | 50 | 90 | 70 | 40 | 0 |
| Blackgrass | 90 | 80 | 70 | 40 | 90 | 70 | 50 | 30 | 90 | 70 | 50 | 30 | 100 | 90 | 70 | 50 | 90 | 80 | 70 | 50 | 90 | 70 | 30 | 0 | 100 | 80 | 40 | 0 |
| Barnyardgrass | 90 | 80 | 60 | 30 | 90 | 60 | 30 | 0 | 90 | 70 | 50 | 30 | 90 | 80 | 60 | 30 | 100 | 90 | 70 | 40 | 100 | 70 | 30 | 0 | | | | |
| Nutsedge | 100 | 80 | 60 | 40 | 90 | 70 | 50 | 30 | 100 | 70 | 50 | 30 | 80 | 60 | 40 | 20 | 100 | 90 | 80 | 70 | 90 | 70 | 50 | 30 | 90 | 70 | 50 | 30 |
| Giant Foxtail | 100 | 90 | 70 | 40 | 90 | 60 | 40 | 0 | 90 | 70 | 50 | 30 | 100 | 80 | 60 | 30 | 100 | 100 | 80 | 60 | 100 | 80 | 50 | 30 | 90 | 50 | 0 | 0 |
| Green Foxtail | 90 | 70 | 50 | 30 | | | | | | | | | | | | | | | | | | | | | | | | |
| Cheatgrass | 60 | 30 | 0 | 0 | | | | | | | | | | | | | | | | | | | | | | | | |
| Wild Oats | 70 | 40 | 30 | 0 | 80 | 60 | 30 | 0 | 30 | 0 | 0 | 0 | 60 | 30 | 0 | 0 | 90 | 70 | 50 | 30 | 80 | 30 | 0 | 0 | 70 | 30 | 0 | 0 |
| Wild Buckwheat | 90 | 70 | 50 | 30 | | | | | | | | | | | | | | | | | | | | | | | | |
| Viola | 90 | 70 | 50 | 30 | | | | | | | | | | | | | | | | | | | | | | | | |
| Lambsquarter | 100 | 70 | 50 | 30 | | | | | | | | | | | | | | | | | | | | | | | | |
| Cocklebur | 90 | 70 | 50 | 30 | 90 | 70 | 50 | 30 | 90 | 70 | 50 | 30 | 90 | 60 | 30 | 0 | 90 | 50 | 30 | 0 | | | | | | | | |
| Morningglory | 80 | 60 | 40 | 20 | 30 | 0 | 0 | 0 | 90 | 60 | 30 | 0 | 80 | 60 | 40 | 20 | 100 | 90 | 60 | 30 | 90 | 60 | 30 | 0 | 80 | 50 | 30 | 0 |
| Teaweed | 90 | 70 | 50 | 30 | 90 | 70 | 50 | 30 | | | | | 70 | 50 | 30 | 0 | 100 | 80 | 60 | 40 | 60 | 30 | 0 | 0 | 80 | 50 | 30 | 0 |
| Sicklepod | 90 | 70 | 40 | 0 | 90 | 70 | 40 | 0 | 40 | 0 | 0 | 0 | 80 | 60 | 40 | 0 | 100 | 80 | 40 | 0 | 90 | 60 | 30 | 0 | 70 | 30 | 0 | 0 |
| Jimsonweed | 90 | 70 | 50 | 30 | 90 | 70 | 50 | 30 | 90 | 70 | 50 | 30 | 90 | 70 | 50 | 30 | 90 | 80 | 70 | 50 | 90 | 70 | 50 | 30 | 90 | 70 | 50 | 30 |
| Velvetleaf | 90 | 70 | 50 | 30 | 90 | 70 | 50 | 30 | 90 | 70 | 50 | 30 | 90 | 70 | 50 | 30 | 90 | 80 | 70 | 50 | 80 | 60 | 40 | 20 | 80 | 70 | 50 | 30 |

PREEMERGENCE

| | Compound 35 | | | | Compound 36 | | | | Compound 39 | | | | Compound 40 | | | | Compound 46 | | | | Compound 53 | | | | Compound 54 | | | |
|---|---|---|---|---|---|---|---|---|---|---|---|---|---|---|---|---|---|---|---|---|---|---|---|---|---|---|---|---|
| Rate g/ha | 250 | 62 | 16 | 4 | 250 | 62 | 16 | 4 | 250 | 62 | 16 | 4 | 250 | 62 | 16 | 4 | 250 | 62 | 16 | 4 | 250 | 62 | 16 | 4 | 250 | 62 | 16 | 4 |
| Corn | 30 | 0 | 0 | 0 | 70 | 30 | 0 | 0 | 100 | 80 | 70 | 20 | 80 | 20 | 0 | 0 | 90 | 80 | 0 | 0 | 0 | 0 | 0 | 0 | 0 | 0 | 0 | 0 |
| Wheat | 80 | 60 | 30 | 0 | 60 | 30 | 0 | 0 | 90 | 70 | 60 | 0 | 80 | 60 | 0 | 0 | 90 | 70 | 40 | 20 | 70 | 40 | 20 | 0 | 80 | 50 | 30 | 0 |
| Barley | — | — | — | — | — | — | — | | 90 | 80 | 20 | 0 | 0 | 0 | 0 | 0 | 90 | 90 | 50 | 0 | 60 | 40 | 20 | 0 | 50 | 30 | 0 | 0 |
| Rice | 100 | 100 | 100 | 70 | 100 | 100 | 100 | 90 | 100 | 100 | 90 | 60 | 100 | 80 | 50 | 0 | 100 | 100 | 90 | 80 | 90 | 80 | 70 | 30 | 90 | 70 | 50 | 30 |
| Soybean | 90 | 80 | 70 | 30 | 80 | 40 | 0 | 0 | 100 | 100 | 60 | 60 | 100 | 50 | 30 | 0 | 90 | 80 | 40 | 0 | 90 | 80 | 60 | 30 | 80 | 60 | 30 | 0 |
| Cotton | 90 | 70 | 50 | 30 | 40 | 0 | 0 | 0 | 80 | 70 | 20 | 0 | 30 | 0 | 0 | 0 | 90 | 70 | 40 | 0 | 60 | 50 | 30 | 0 | 80 | 40 | 0 | 0 |
| Sugar beet | 100 | 100 | 90 | 70 | 100 | 90 | 70 | 50 | 100 | 100 | 60 | 20 | 90 | 80 | 60 | 0 | 100 | 90 | 70 | 50 | 100 | 90 | 80 | 70 | 100 | 90 | 80 | 70 |
| Rape | 100 | 90 | 60 | 30 | 80 | 60 | 40 | 0 | 100 | 100 | 90 | 20 | 100 | 90 | 40 | 0 | 100 | 100 | 80 | 50 | 100 | 90 | 70 | 50 | 90 | 80 | 70 | 50 |
| Crabgrass | 80 | 60 | 50 | 30 | 100 | 70 | 50 | 30 | 100 | 90 | 70 | 20 | 100 | 80 | 20 | 0 | 90 | 50 | 30 | 0 | 90 | 70 | 50 | 30 | 70 | 50 | 30 | 0 |
| Johnsongrass | 100 | 100 | 90 | 70 | 100 | 90 | 70 | 40 | 100 | 100 | 90 | 80 | 100 | 100 | 90 | 80 | 100 | 70 | 50 | 30 | 90 | 80 | 70 | 30 | 90 | 70 | 50 | 30 |
| Blackgrass | 100 | 100 | 90 | 50 | 100 | 100 | 80 | 60 | 100 | 90 | 90 | 50 | 100 | 90 | 70 | 50 | 90 | 90 | 50 | 0 | 100 | 70 | 50 | 30 | 90 | 80 | 70 | 50 |
| Barnyardgrass | 100 | 90 | 80 | 50 | 100 | 80 | 40 | 0 | 100 | 90 | 70 | 30 | 100 | 90 | 80 | 0 | 90 | 70 | 40 | 0 | 90 | 80 | 70 | 30 | 90 | 80 | 70 | 40 |
| Nutsedge | 100 | 100 | 70 | 50 | 70 | 50 | 30 | 0 | 100 | — | — | — | — | — | 0 | — | 90 | 70 | 50 | 30 | 90 | 80 | 70 | 50 | 100 | 90 | 70 | 50 |
| Giant Foxtail | 100 | 90 | 80 | 50 | 100 | 90 | 70 | 40 | 100 | 90 | 70 | 30 | 100 | 90 | 70 | 0 | 90 | 80 | 50 | 30 | 90 | 80 | 70 | 30 | 90 | 80 | 70 | 40 |
| Green Foxtail | | | | | | | | | 100 | 90 | 80 | 70 | 100 | 100 | 40 | 0 | 90 | 80 | 50 | 30 | 90 | 70 | 50 | 30 | 90 | 80 | 70 | 50 |
| Cheatgrass | | | | | | | | | 100 | 100 | 90 | 70 | 100 | 90 | 70 | 60 | 90 | 80 | 30 | 20 | 90 | 80 | 70 | 30 | 90 | 80 | 70 | 50 |
| Wild Oats | 80 | 60 | 30 | 0 | 70 | 40 | 0 | 0 | 90 | 90 | 60 | 20 | 90 | 30 | 0 | 0 | 70 | 60 | 30 | 0 | 40 | 20 | 0 | 0 | 40 | 0 | 0 | 0 |

TABLE B-continued

| | | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| Wild Buckwheat | | | | | | | | | 100 | 90 | 80 | 70 | 100 | 70 | 60 | 20 | 100 | 80 | 60 | 30 | 90 | 80 | 70 | 50 | 90 | 80 | 70 | 50 |
| Viola | | | | | | | | | 100 | 100 | 90 | 20 | 90 | 80 | 20 | 0 | 100 | 100 | 100 | 90 | 100 | 90 | 70 | 50 | 100 | 100 | 90 | 70 |
| Lambsquarter | | | | | | | | | 100 | 100 | 90 | 60 | 100 | 100 | 80 | 70 | 100 | 100 | 70 | 50 | 90 | 70 | 50 | 30 | 90 | 80 | 70 | 50 |
| Cocklebur | 90 | 80 | 50 | 40 | — | 0 | 0 | 0 | 100 | 80 | 70 | 0 | 90 | — | — | — | 40 | 0 | 0 | 0 | 90 | 70 | 50 | 30 | 90 | 70 | 50 | 30 |
| Morningglory | 90 | 80 | 60 | 30 | 80 | 60 | 30 | 0 | 100 | 90 | 40 | 0 | 90 | 70 | 20 | 0 | 90 | 80 | 70 | 50 | 90 | 80 | 70 | 60 | 90 | 80 | 70 | 50 |
| Teaweed | 90 | 70 | 40 | 0 | 90 | 70 | 50 | 20 | 100 | 90 | 60 | 30 | 90 | 90 | 50 | 0 | 90 | 70 | 50 | 30 | 90 | 70 | 50 | 30 | 90 | 70 | 50 | 30 |
| Sicklepod | 50 | 30 | 0 | 0 | 90 | 70 | 50 | 30 | 100 | 80 | 30 | 0 | 80 | 0 | 0 | 0 | 50 | 30 | 0 | 0 | 90 | 80 | 70 | 60 | 90 | 70 | 50 | 30 |
| Jimsonweed | 100 | 80 | 50 | 30 | 90 | 70 | 40 | 20 | 100 | 90 | 70 | 50 | 100 | 40 | 20 | 0 | 90 | 70 | 50 | 30 | 90 | 80 | 70 | 50 | 100 | 70 | 50 | 30 |
| Velvetleaf | 90 | 80 | 50 | 30 | 90 | 70 | 50 | 20 | 100 | 90 | 50 | 20 | 90 | 30 | 0 | 0 | 90 | 70 | 50 | 30 | 90 | 70 | 50 | 30 | 90 | 70 | 50 | 30 |

PREEMERGENCE

| | Compound 55 | | | | Compound 56 | | | | | Compound 206 | | | |
|---|---|---|---|---|---|---|---|---|---|---|---|---|---|
| Rate g/ha | 250 | 62 | 16 | 4 | 250 | 62 | 16 | 4 | Rate g/ha | 250 | 62 | 16 | 4 |
| Corn | 0 | 0 | 0 | 0 | 0 | 0 | 0 | 0 | Giant foxtail | 80 | 70 | 50 | 30 |
| Wheat | 80 | 40 | 0 | 0 | 80 | 40 | 0 | 0 | Velvetleaf | 90 | 70 | 50 | — |
| Barley | 80 | 30 | 0 | 0 | 0 | 0 | 0 | 0 | Sugarbeet | 90 | 70 | 50 | — |
| Rice | 100 | 70 | 50 | 30 | 90 | 80 | 70 | 40 | Large crabgrass | 60 | 30 | 0 | 0 |
| Soybean | 90 | 70 | 30 | 0 | 80 | 60 | 30 | 0 | Prikley sida | 70 | 50 | 30 | 20 |
| Cotton | 90 | 60 | 30 | 0 | 70 | 0 | 0 | 0 | Jimsonweed | 70 | 50 | 30 | 0 |
| Sugar beet | 100 | 90 | 80 | 70 | 100 | 90 | 80 | 70 | Rice dry seeded | 80 | 60 | 40 | 20 |
| Rape | 90 | 80 | 70 | 40 | 100 | 90 | 80 | 70 | Cocklebur | 40 | 20 | 0 | 0 |
| Crabgrass | 70 | 50 | 30 | 0 | 70 | 50 | 30 | 0 | Cotton | 30 | 0 | 0 | 0 |
| Johnsongrass | 90 | 80 | 70 | 50 | 100 | 90 | 80 | 60 | Soybeans | 0 | 0 | 0 | 0 |
| Blackgrass | 100 | 100 | 90 | 80 | 90 | 80 | 70 | 50 | Barnyardgrass | 70 | 30 | 0 | 0 |
| Barnyardgrass | 90 | 80 | 70 | 40 | 100 | 80 | 70 | 50 | Wild oats | 0 | 0 | 0 | — |
| Nutsedge | 90 | 80 | 70 | 50 | 90 | 80 | 70 | 50 | Ivy morningglory | 80 | 50 | 30 | 0 |
| Giant Foxtail | 90 | 80 | 60 | 30 | 90 | 80 | 70 | 40 | Wheat | 0 | 0 | 0 | 0 |
| Green Foxtail | 90 | 80 | 70 | 50 | 90 | 80 | 70 | 50 | Sicklepod | 30 | 20 | 0 | 0 |
| Cheatgrass | 90 | 80 | 70 | 40 | 90 | 80 | 70 | 50 | Johnsongrass | 80 | 50 | 30 | 0 |
| Wild Oats | 50 | 30 | 0 | 0 | 30 | 0 | 0 | 0 | Purple nutsedge | 30 | 0 | 0 | 0 |
| Wild Buckwheat | 90 | 80 | 70 | 50 | 90 | 70 | 60 | 40 | Corn | 100 | 30 | 0 | 0 |
| Viola | 100 | 100 | 90 | 70 | 100 | 100 | 90 | 80 | Wild buckwheat | 80 | 50 | 30 | — |
| Lambsquarter | 90 | 70 | 50 | 30 | 90 | 70 | 50 | 30 | Blackgrass | 60 | 30 | 0 | — |
| Cocklebur | 100 | 70 | 50 | 30 | 100 | 70 | 50 | 30 | Rape | 90 | 90 | 60 | — |
| Morningglory | 100 | 90 | 60 | 30 | 90 | 70 | 50 | 30 | Barley | 0 | 0 | 0 | — |
| Teaweed | 90 | 70 | 50 | 30 | 90 | 70 | 50 | 30 | Green foxtail | 100 | 50 | 30 | 0 |
| Sicklepod | 90 | 70 | 50 | 30 | 100 | 70 | 50 | 30 | Cheat grass | 0 | 0 | 0 | — |
| Jimsonweed | 90 | 70 | 50 | 30 | 90 | 70 | 50 | 30 | Lambsquarter | 90 | 70 | 50 | 30 |
| Velvetleaf | 90 | 70 | 50 | 30 | 90 | 70 | 60 | 50 | Chickweed spp. | 60 | 30 | 0 | — |

Test C

The Corn and Sorghum Herbicide Test included the following species in both the preemergence and postemergence evaluations:

| | SPECIES | |
|---|---|---|
| Category | Common Name | Scientific Name |
| Crops | Corn | *Zea mays* |
| | Soybean | *Glycine max* |
| | Sorghum | *Sorghum bicolor* |
| Grasses | Green foxtail | *Setaria viridis* |
| | Giant foxtail | *Setaria faberii* |
| | Johnsongrass | *Sorghum halepense* |
| | Barnyardgrass | *Echinochloa crus-galli* |
| | Fall panicum | *Panicum dichotomiflorum* |
| | Crabgrass | *Digitaria sanguinalis* |
| | Nutsedge | *Cyperus rotundus* |
| Broadleaves | Cocklebur | *Xanthium pensylvanicum* |
| | Morningglory | *Ipomoea hederacea* |
| | Velvetleaf | *Abutilon theophrasti* |
| | Jimsonweed | *Datura stramonium* |
| | Lambsquarters | *Chenopodium album* |
| | Pigweed | *Amaranthus retroflexus* |
| | Smartweed | *Polygonum persicaris* |

Postemergence

Postemergence plants were grown in Sassafras sandy loam soil. Corn and soybeans were grown in separate 25 cm diameter containers. Sorghum and the seven grass weed species were grown in two 18 cm diameter containers, 4 species per container. The seven broadleaf weed species were also grown in two 18 cm diameter containers, 4 species in one container, 3 species in the second container. One additional planting of corn in an 18 cm diameter container was made. The soil surface of this additional container of corn was covered with the absorbent, perlite, before spray treatment so that test chemicals would enter the plant only via the foliage. The plants were grown 10-21 days, dependent upon the species and then sprayed postemergence with the test chemicals dissolved in a non-phytotoxic solvent.

PREEMERGENCE

Preemergence plantings were grown in fertilized Tama silt loam soil. These plants are identical to those described in the postemergence section, with the exception of the corn planting having perlite covering the soil surface. These plantings were made the day of or the day before spraying the test chemicals dissolved in a non-phytotoxic solvent.

EVALUATION

Treated plants and controls were maintained in the greenhouse for 2 to 4 weeks. Visual planting response ratings were made on a percentage scale of 0 to 100 in comparison with a control where 0=no injury, and 100=death.

TABLE C

| RATE RATE GM | 0004 | 0008 | 0016 | 0031 | 0062 | 0125 | 0250 |
|---|---|---|---|---|---|---|---|
| | | Compound 35 | | | | | |
| POSTEMERGENCE | | | | | | | |
| CORN | 0 | 0 | 0 | 0 | 25 | 45 | — |
| SOYBEAN | 45 | 70 | 85 | 100 | 100 | 100 | — |
| GREEN FXTL | 45 | 55 | 70 | 85 | 95 | 100 | — |
| GIANT FXTL | 40 | 45 | 60 | 75 | 95 | 100 | — |
| PANICUM | 90 | 100 | 100 | 100 | 100 | 100 | — |
| CRABGRASS | 0 | 0 | 0 | 30 | 45 | 55 | — |
| BARNYARDGRASS | 85 | 95 | 100 | 100 | 100 | 100 | — |
| JOHNSONGRASS | 100 | 100 | 100 | 100 | 100 | 100 | — |
| SORGHUM | 100 | 100 | 100 | 100 | 100 | 100 | — |
| NUTSEDGE | 30 | 50 | 85 | 90 | 100 | 100 | — |
| VELVETLEAF | 25 | 55 | 75 | 90 | 100 | 100 | — |
| COCKLEBUR | 100 | 100 | 100 | 100 | 100 | 100 | — |
| SMARTWEED | 60 | 80 | 85 | 90 | 100 | 100 | — |
| LAMBSQUARTER | 0 | 30 | 60 | 75 | 85 | 100 | — |
| PIGWEED | 50 | 85 | 100 | 100 | 100 | 100 | — |
| MORNINGGLORY | 60 | 75 | 95 | 100 | 100 | 100 | — |
| JIMSONWEED | 65 | 100 | 100 | 100 | 100 | 100 | — |
| PREEMERGENCE | | | | | | | |
| CORN | — | — | 0 | 0 | 0 | 0 | 35 |
| SOYBEAN | — | — | 0 | 20 | 30 | 45 | 65 |
| GREEN FXTL | — | — | 55 | 85 | 95 | 95 | 100 |
| GIANT FXTL | — | — | 55 | 85 | 95 | 100 | 100 |
| PANICUM | — | — | 80 | 100 | 100 | 100 | 100 |
| CRABGRASS | — | — | 0 | 20 | 25 | 60 | 70 |
| BARNYARDGRASS | — | — | 85 | 100 | 100 | 100 | 100 |
| JOHNSONGRASS | — | — | 100 | 100 | 100 | 100 | 100 |
| SORGHUM | — | — | 100 | 100 | 100 | 100 | 100 |
| NUTSEDGE | — | — | 60 | 95 | 100 | 100 | 100 |
| VELVETLEAF | — | — | 0 | 0 | 0 | 35 | 60 |
| COCKLEBUR | — | — | 0 | 0 | 0 | 30 | 65 |
| SMARTWEED | — | — | 0 | 0 | 30 | 80 | 100 |
| LAMBSQUARTER | — | — | 0 | 50 | 80 | 100 | 100 |
| PIGWEED | — | — | 0 | 35 | 70 | 95 | 100 |
| MORNINGGLORY | — | — | 0 | 0 | 0 | 30 | 55 |
| JIMSONWEED | — | — | 0 | 30 | 45 | 70 | 100 |
| | | Compound 53 | | | | | |
| POSTEMERGENCE | | | | | | | |
| CORN | 0 | 0 | 0 | 0 | 25 | 45 | — |
| SOYBEAN | 100 | 100 | 100 | 100 | 100 | 100 | — |
| GREEN FXTL | 30 | 40 | 55 | 75 | 85 | 95 | — |
| GIANT FXTL | 35 | 50 | 75 | 90 | 100 | 100 | — |
| PANICUM | 80 | 100 | 100 | 100 | 100 | 100 | — |

TABLE C-continued

| RATE RATE GM | 0004 | 0008 | 0016 | 0031 | 0062 | 0125 | 0250 |
|---|---|---|---|---|---|---|---|
| CRABGRASS | 0 | 0 | 0 | 30 | 45 | 60 | — |
| BARNYARDGRASS | 75 | 100 | 100 | 100 | 100 | 100 | — |
| JOHNSONGRASS | 95 | 100 | 100 | 100 | 100 | 100 | — |
| SORGHUM | 95 | 100 | 100 | 100 | 100 | 100 | — |
| NUTSEDGE | 70 | 95 | 100 | 100 | 100 | 100 | — |
| VELVETLEAF | 65 | 95 | 100 | 100 | 100 | 100 | — |
| COCKLEBUR | 75 | 90 | 100 | 100 | 100 | 100 | — |
| SMARTWEED | 55 | 75 | 90 | 100 | 100 | 100 | — |
| LAMBSQUARTER | 25 | 50 | 70 | 90 | 95 | 100 | — |
| PIGWEED | 70 | 95 | 100 | 100 | 100 | 100 | — |
| MORNINGGLORY | 60 | 80 | 90 | 100 | 100 | 100 | — |
| JIMSONWEED | 70 | 95 | 100 | 100 | 100 | 100 | — |
| PREEMERGENCE | | | | | | | |
| CORN | — | — | 0 | 0 | 0 | 20 | 40 |
| SOYBEAN | — | — | 0 | 35 | 60 | 80 | 100 |
| GREEN FXTL | — | — | 35 | 50 | 70 | 90 | 95 |
| GIANT FXTL | — | — | 35 | 50 | 65 | 85 | 95 |
| PANICUM | — | — | 65 | 85 | 100 | 100 | 100 |
| CRABGRASS | — | — | 0 | 0 | 0 | 30 | 40 |
| BARNYARDGRASS | — | — | 30 | 70 | 85 | 100 | 100 |
| JOHNSONGRASS | — | — | 70 | 100 | 100 | 100 | 100 |
| SORGHUM | — | — | 80 | 100 | 100 | 100 | 100 |
| NUTSEDGE | — | — | 70 | 85 | 100 | 100 | — |
| VELVETLEAF | — | — | 0 | 0 | 30 | 45 | — |
| COCKLEBUR | — | — | 0 | 0 | 0 | 0 | — |
| SMARTWEED | — | — | 30 | 60 | 80 | 100 | — |
| LAMBSQUARTER | — | — | 25 | 60 | 85 | 100 | — |
| PIGWEED | — | — | 0 | 40 | 75 | 95 | — |
| MORNINGGLORY | — | — | 0 | 0 | 25 | 35 | — |
| JIMSONWEED | — | — | 0 | 30 | 55 | 80 | — |
| Compound 163 | | | | | | | |
| POSTEMERGENCE | | | | | | | |
| CORN | 0 | 0 | 0 | 20 | 55 | 65 | — |
| SOYBEAN | 100 | 100 | 100 | 100 | 100 | 100 | — |
| GREEN FXTL | 60 | 80 | 90 | 100 | 100 | 100 | — |
| GIANT FXTL | 60 | 80 | 95 | 100 | 100 | 100 | — |
| PANICUM | 90 | 100 | 100 | 100 | 100 | 100 | — |
| CRABGRASS | 0 | 25 | 40 | 85 | 100 | 100 | — |
| BARNYARDGRASS | 80 | 100 | 100 | 100 | 100 | 100 | — |
| JOHNSONGRASS | 100 | 100 | 100 | 100 | 100 | 100 | — |
| SORGHUM | 100 | 100 | 100 | 100 | 100 | 100 | — |
| NUTSEDGE | 60 | 75 | 90 | 100 | 100 | 100 | — |
| VELVETLEAF | 100 | 100 | 100 | 100 | 100 | 100 | — |
| COCKLEBUR | 0 | 30 | 60 | 80 | 100 | 100 | — |
| SMARTWEED | 60 | 80 | 100 | 100 | 100 | 100 | — |
| LAMBSQUARTER | 65 | 80 | 100 | 100 | 100 | 100 | — |
| PIGWEED | 65 | 95 | 100 | 100 | 100 | 100 | — |
| MORNINGGLORY | 85 | 95 | 100 | 100 | 100 | 100 | — |
| JIMSONWEED | 90 | 100 | 100 | 100 | 100 | 100 | — |
| PREEMERGENCE | | | | | | | |
| CORN | — | — | 0 | 0 | 0 | 0 | 20 |
| SOYBEAN | — | — | 20 | 30 | 40 | 60 | 80 |
| GREEN FXTL | — | — | 25 | 60 | 75 | 100 | 100 |
| GIANT FXTL | — | — | 20 | 40 | 70 | 100 | 100 |
| PANICUM | — | — | 30 | 70 | 95 | 100 | 100 |
| CRABGRASS | — | — | 0 | 25 | 55 | 70 | 100 |
| BARNYARDGRASS | — | — | 0 | 35 | 65 | 100 | 100 |
| JOHNSONGRASS | — | — | 40 | 95 | 100 | 100 | 100 |
| SORGHUM | — | — | 70 | 95 | 100 | 100 | 100 |
| NUTSEDGE | — | — | 60 | 80 | 95 | 100 | 100 |
| VELVETLEAF | — | — | 0 | 0 | 25 | 45 | 80 |
| COCKLEBUR | — | — | 0 | 0 | 30 | 55 | 70 |
| SMARTWEED | — | — | 0 | 35 | 60 | 85 | 100 |
| LAMBSQUARTER | — | — | 20 | 60 | 95 | 100 | 100 |
| PIGWEED | — | — | 30 | 70 | 100 | 100 | 100 |
| MORNINGGLORY | — | — | 0 | 0 | 20 | 35 | 70 |
| JIMSONWEED | — | — | 0 | 30 | 70 | 90 | 100 |
| Compound 165 | | | | | | | |
| POSTEMERGENCE | | | | | | | |
| CORN | 0 | 20 | 45 | 85 | 100 | — | — |
| SOYBEAN | 100 | 100 | 100 | 100 | 100 | — | — |
| GREEN FXTL | 25 | 70 | 75 | 95 | 95 | — | — |
| GIANT FXTL | 40 | 90 | 95 | 100 | 100 | — | — |
| PANICUM | 100 | 100 | 100 | 70 | 100 | — | — |
| CRABGRASS | 20 | 40 | 60 | 70 | 100 | — | — |
| BARNYARDGRASS | 100 | 100 | 100 | 100 | 100 | — | — |
| JOHNSONGRASS | 100 | 100 | 100 | 70 | 100 | — | — |
| SORGHUM | 100 | 100 | 100 | 100 | 100 | — | — |
| NUTSEDGE | 100 | 100 | 100 | 100 | 100 | — | — |

TABLE C-continued

| RATE RATE GM | 0004 | 0008 | 0016 | 0031 | 0062 | 0125 | 0250 |
|---|---|---|---|---|---|---|---|
| VELVETLEAF | 90 | 100 | 100 | 100 | 100 | — | — |
| COCKLEBUR | 25 | 50 | 80 | 100 | 100 | — | — |
| SMARTWEED | 65 | 80 | 90 | 100 | 100 | — | — |
| LAMBSQUARTER | 40 | 70 | 85 | 100 | 100 | — | — |
| PIGWEED | 95 | 100 | 100 | 100 | 100 | — | — |
| MORNINGGLORY | 80 | 95 | 100 | 100 | 100 | — | — |
| JIMSONWEED | 80 | 95 | 100 | 100 | 100 | — | — |
| PREEMERGENCE | | | | | | | |
| CORN | — | 0 | 0 | 0 | 0 | 15 | — |
| SOYBEAN | — | 20 | 35 | 60 | 85 | 100 | — |
| GREEN FXTL | — | 20 | 50 | 85 | 100 | 100 | — |
| GIANT FXTL | — | 30 | 70 | 90 | 100 | 100 | — |
| PANICUM | — | 50 | 85 | 100 | 100 | 100 | — |
| CRABGRASS | — | 0 | 30 | 65 | 90 | 100 | — |
| BARNYARDGRASS | — | 0 | 20 | 50 | 90 | 100 | — |
| JOHNSONGRASS | — | 40 | 85 | 100 | 100 | 100 | — |
| SORGHUM | — | 40 | 75 | 100 | 100 | 100 | — |
| NUTSEDGE | — | 30 | 60 | 80 | 100 | 100 | — |
| VELVETLEAF | — | 0 | 0 | 25 | 50 | 85 | — |
| COCKLEBUR | — | 0 | 0 | 0 | 35 | 70 | — |
| SMARTWEED | — | 25 | 50 | 75 | 95 | 100 | — |
| LAMBSQUARTER | — | 20 | 55 | 70 | 90 | 100 | — |
| PIGWEED | — | 30 | 65 | 90 | 100 | 100 | — |
| MORNINGGLORY | — | 0 | 0 | 20 | 40 | 85 | — |
| JIMSONWEED | — | 0 | 0 | 30 | 70 | 90 | — |
| | | Compound 166 | | | | | |
| POSTEMERGENCE | | | | | | | |
| CORN | 0 | 0 | 0 | 0 | 0 | 25 | 60 |
| SOYBEAN | 95 | 100 | 100 | 100 | 100 | 100 | 100 |
| GREEN FXTL | 70 | 80 | 85 | 90 | 95 | 100 | 100 |
| GIANT FXTL | 70 | 85 | 95 | 100 | 100 | 100 | 100 |
| PANICUM | 90 | 95 | 100 | 100 | 100 | 100 | 100 |
| CRABGRASS | 0 | 0 | 20 | 40 | 50 | 65 | 80 |
| BARNYARDGRASS | 95 | 100 | 100 | 100 | 100 | 100 | 100 |
| JOHNSONGRASS | 100 | 100 | 100 | 100 | 100 | 100 | 100 |
| SORGHUM | 100 | 100 | 100 | 100 | 100 | 100 | 100 |
| NUTSEDGE | 85 | 100 | 100 | 100 | 100 | 100 | 100 |
| VELVETLEAF | 80 | 90 | 100 | 100 | 100 | 100 | 100 |
| COCKLEBUR | 95 | 100 | 100 | 100 | 100 | 100 | 100 |
| SMARTWEED | 45 | 80 | 90 | 95 | 100 | 100 | 100 |
| LAMBSQUARTER | 65 | 65 | 85 | 95 | 95 | 100 | 100 |
| PIGWEED | 90 | 70 | 100 | 100 | 100 | 100 | 100 |
| MORNINGGLORY | 95 | 100 | 100 | 100 | 100 | 100 | 100 |
| JIMSONWEED | 85 | 95 | 100 | 100 | 100 | 100 | 100 |
| PREEMERGENCE | | | | | | | |
| CORN | — | 0 | 0 | 0 | 0 | 0 | 45 |
| SOYBEAN | — | 0 | 0 | 30 | 50 | 65 | 70 |
| GREEN FXTL | — | 0 | 65 | 85 | 100 | 100 | 100 |
| GIANT FXTL | — | 0 | 45 | 85 | 100 | 100 | 100 |
| PANICUM | — | 20 | 75 | 100 | 100 | 100 | 100 |
| CRABGRASS | — | 0 | 20 | 35 | 50 | 65 | 70 |
| BARNYARDGRASS | — | 0 | 75 | 100 | 100 | 100 | 100 |
| JOHNSONGRASS | — | 70 | 100 | 100 | 100 | 100 | 100 |
| SORGHUM | — | 70 | 100 | 100 | 100 | 100 | 100 |
| NUTSEDGE | — | 25 | 85 | 100 | 100 | 100 | 100 |
| VELVETLEAF | — | 0 | 0 | 0 | 35 | 60 | 80 |
| COCKLEBUR | — | 0 | 0 | 0 | 0 | 30 | 65 |
| SMARTWEED | — | 30 | 0 | 20 | 30 | 50 | 100 |
| LAMBSQUARTER | — | 25 | 25 | 75 | 100 | 100 | 100 |
| PIGWEED | — | 45 | 30 | 80 | 100 | 100 | 100 |
| MORNINGGLORY | — | 0 | 0 | 0 | 20 | 65 | 75 |
| JIMSONWEED | — | 0 | 25 | 50 | 75 | 95 | 100 |

Test D

Sixteen cm diameter Wagner pots, equipped with a stoppered drain opening near the bottom of the side wall, were partially filled with Woodstown sandy loam. About 1500 mls of water were added to each pot to bring the water level to a point 3 cm above the soil surface. Japonica and Indica rice seedlings were hand transplanted into the pots. Also, a number of barnyardgrass Echinochloa crus-*galli*) seeds were added to each pot. At the same time, seedlings or tubers of the following species were transplanted into the muddy soil: water plantain (*Alisma trivale*), Scirpus (*Scirpus mucranatus*), and Cyperus (*Cyperus difformis*). The weed species selected for this test are of economic importance in major rice-growing areas. The chemical treatments were applied directly to the paddy water after being formulated in a non-phytotoxic solvent within hours after transplanting of two additional species: water chestnut (*Eleocharis* spp.) and arrowhead (*Sagittaria latifolia*). Shortly after treatment, the drain hole was opened to drop the water level by two cm. Water was then added to restore the water level to its original height. The following day the draining and refilling process was repeated. The pots were then maintained in the greenhouse.

Rates of application and plant response ratings made 21 days after treatment are summarized in Table D. Response ratings are based on a scale of 0 to 100 where 0=no effect and 100=complete control.

TABLE D

| | Compound 188 | | | Compound 189 | | |
|---|---|---|---|---|---|---|
| Rate g/ha | 0016 | 0008 | 0004 | 0016 | 0008 | 0004 |
| Japonica Rice | 0 | 0 | 0 | 15 | 15 | 0 |
| Indica Rice | 0 | 0 | 0 | 15 | 0 | 0 |
| Barnyardgrass | 77 | 22 | 0 | 95 | 77 | 30 |
| Water Chestnut | 82 | 87 | 85 | 90 | 85 | 70 |
| Arrowhead | 95 | 90 | 80 | 92 | 95 | 87 |
| Scirpus | 77 | 80 | 60 | 87 | 85 | 67 |
| Cyperus | 82 | 55 | 32 | 95 | 95 | 92 |
| Water Plantain | 75 | 75 | 60 | 85 | 72 | 67 |

Test E

The weed species used in this test are all of major economic importance in soybean-growing regions. The following species are included in the screen:

| Plant Species | Scientific Name | GROWTH STAGE AT APPLICATION (POST-EMERGENCE PHASE) |
|---|---|---|
| Grass Weeds: | | |
| barnyardgrass | *Echinochloa crus-galli* | 2-3 leaves |
| giant foxtail | *Setaria faberi* | 2-3 leaves |
| green foxtail | *Setaria viridis* | 2-3 leaves |
| johnsongrass | *Sorghum halepense* | 2-3 leaves |
| fall panicum | *Panicum dichotomiflorum* | 2-3 leaves |
| broadleaf signalgrass | *Brachiaria platyphylla* | 2-3 leaves |
| large crabgrass | *Digitaria sanguinalis* | 2-3 leaves |
| Broadleaf Weeds: | | |
| velvetleaf | *Abutilon theophrasti* | 2-3 leaves |
| jimsonweed | *Datura stramonium* | 1-2 true leaves |
| hemp sesbania | *Sesbania exaltata* | 1st true leaf |
| sicklepod | *Cassia obtusifolia* | 1st true leaf |
| cocklebur | *Xanthium pensylvanicum* | 2nd true leaf |
| morningglory | *Ipomoea hederacea* | 1-2 true leaves |
| ladysthumb smartweed | *Polygonum persicaria* | 3-4 leaves |
| pigweed | *Amaranthus retroflexus* | 4-5 leaves |
| lambsquarters | *Chenopodium album* | 4-5 leaves |
| teaweed | *Sida spinosa* | 2-3 leaves |
| black nightshade | *Solanum nigrum* | 2nd true leaf |
| purple nutsedge | *Cyperus rotundus* | 5-6 leaves |
| corn | *Zea mays* | 2-3 leaves |
| soybeans | *Glycine max* | 1st trifoliate |

For the preemergence phase of the test, crop and weed species are planted in a Tama silt loam soil (approximately 3% organic matter). Approximate planting depths are: corn and soybeans—3 to 4 cm; morningglory, cocklebur, and nutsedge—2.5 to 3 cm; velvetleaf, sicklepod, and sesbania—2 cm; all other species—0.5 cm.

For the postemergence phase of the test, crop and weed species are planted in a Sassafras sandy loam soil (approximately 1% organic matter) one to three weeks before application so that they will be present as young plants at the time of treatment. Alternatively, for postemergence tests, plants are grown in a 50:50 mixture of commercially available potting mix and Sassafras soil. Approximate planting depths are: corn and soybeans—3 to 4 cm; morningglory, cocklebur, and nutsedge—2.5 to 3 cm; velvetleaf, sicklepod, and sesbania—2 cm; all other species—0.5 cm.

Treated plants and controls were maintained in a greenhouse for 3 to 4 weeks, after which all species were compared to controls and visually rated for response to treatment. The ratings, summarized in Table E, are based on a numerical scale extending from 0=no injury to 100=complete kill.

TABLE E

| Rate = gm/h Postemergence | 0004 | 0008 | 0016 | 0032 | 0064 | 0125 |
|---|---|---|---|---|---|---|
| | | CMPD 206 | | | | |
| Soil type | Mix | Mix | Mix | Mix | Mix | Mix |
| Soybeans | 0 | 0 | 10 | 15 | 20 | 25 |
| Corn | 40 | 70 | 90 | 100 | 100 | 100 |
| Velvetleaf | 50 | 75 | 100 | 100 | 100 | 100 |
| Jimsonweed | 30 | 40 | 40 | 50 | 85 | 95 |
| Sicklepod | 10 | 20 | 30 | 40 | 40 | 50 |
| Hemp sesbania | 20 | 40 | 50 | 75 | 85 | 95 |
| Cocklebur | 50 | 60 | 80 | 100 | 100 | 100 |
| Ivy morningglory | 75 | 85 | 90 | 95 | 100 | 100 |
| Redroot pigweed | 20 | 40 | 45 | 50 | 50 | 60 |
| Lambsquarter | 50 | 50 | 60 | 90 | 90 | 90 |
| Prickly sida | 30 | 45 | 50 | 65 | 75 | 85 |
| Barnyardgrass | 20 | 30 | 50 | 75 | 95 | 100 |
| Giant foxtail | 0 | 0 | 20 | 30 | 50 | 80 |
| Green foxtail | 0 | 30 | 40 | 50 | 60 | 70 |
| Johsongrass | 20 | 30 | 40 | 50 | 60 | 70 |
| Fall panicum | 0 | 0 | 20 | 30 | 40 | 50 |
| Large crabgrass | 0 | 0 | 0 | 0 | 0 | 0 |
| Brdlf sgnlgrass | 20 | 30 | 40 | 50 | 50 | 70 |
| Purple nutsedge | 0 | 20 | 30 | 40 | 50 | 80 |
| Lady smartweed | 0 | 0 | 0 | 20 | 30 | 50 |
| Black nightshad | 50 | 60 | 70 | 95 | 100 | 100 |
| | | CMPD 207 | | | | |
| Soil type | Mix | Mix | Mix | Mix | Mix | Mix |
| Soybeans | 0 | 0 | 0 | 0 | 10 | 15 |
| Corn | 10 | 20 | 50 | 75 | 80 | 80 |
| Velvetleaf | 50 | 75 | 95 | 100 | 100 | 100 |
| Jimsonweed | 30 | 40 | 50 | 60 | 80 | 100 |
| Sicklepod | 0 | 20 | 30 | 40 | 50 | 80 |
| Hemp sesbania | 20 | 40 | 50 | 60 | 70 | 80 |
| Cocklebur | 50 | 60 | 70 | 100 | 100 | 100 |
| Ivy morningglory | 50 | 75 | 80 | 80 | 95 | 95 |
| Redroot pigweed | 20 | 30 | 50 | 60 | 70 | 95 |
| Lambsquarter | 50 | 50 | 70 | 80 | 80 | 95 |
| Prickly sida | 30 | 40 | 60 | 60 | 75 | 90 |
| Barnyardgrass | 0 | 0 | 20 | 40 | 65 | 100 |
| Giant foxtail | 0 | 30 | 40 | 50 | 60 | 80 |
| Green foxtail | 0 | 30 | 30 | 40 | 50 | 60 |
| Johsongrass | 20 | 30 | 40 | 50 | 60 | 70 |
| Fall panicum | 0 | 0 | 0 | 0 | 0 | 0 |
| Large crabgrass | 0 | 0 | 0 | 0 | 0 | 0 |
| Brdlf sgnlgrass | 0 | 0 | 20 | 50 | 60 | 70 |
| Purple nutsedge | 0 | 20 | 30 | 40 | 100 | 80 |
| Lady smartweed | 0 | 20 | 30 | 40 | 50 | 65 |
| Black nightshad | 50 | 80 | 100 | 100 | 100 | 100 |

What is claimed is:

1. A compound of the formula:

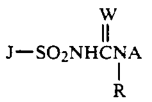

I wherein

J is 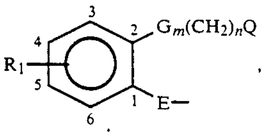, 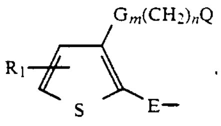

J-1 J-2

-continued

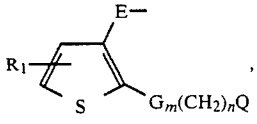, 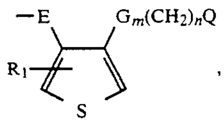,

J-3 J-4

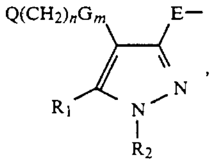, 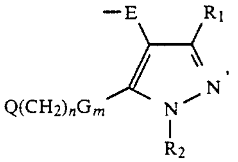,

J-5 J-6

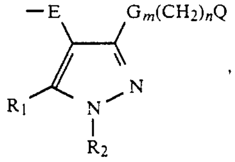, 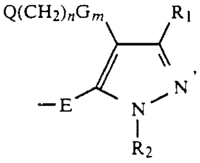,

J-7 J-8

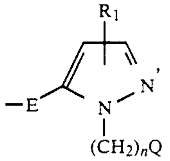, 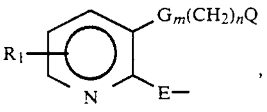,

J-9 J-10

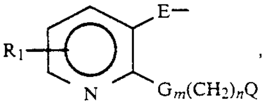, 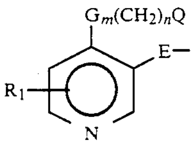 or

J-11 J-12

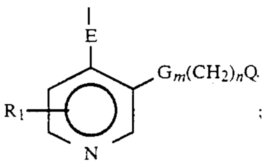;

J-13

W is O or $NR_X$;

$R_X$ is H, OH, $C_1$–$C_3$ alkoxy, allyloxy, propargyloxy, $C_1$–$C_3$ haloalkyl, $C_1$–$C_3$ haloalkoxy or $NR_YR_Z$;

$R_Y$ is H or $C_1$–$C_3$ alkyl;

$R_Z$ is $C_1$–$C_3$ alkyl;

G is O, S, SO or $SO_2$;

m is 0 or 1;

n is 0, 1 or 2;

R is H or $CH_3$;

E is a single bond, $CH_2$ or O;

Q is 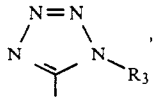, 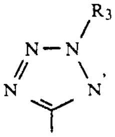, 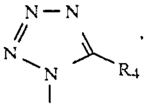,

Q-1 Q-2 Q-3

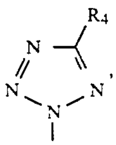, 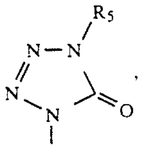, 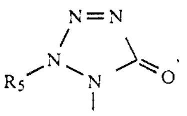,

Q-4 Q-5 Q-6

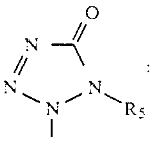;

Q-7

$R_1$ is H, $C_1$–$C_3$ haloalkyl, halogen, nitro, $C_1$–$C_3$ alkoxy, $SO_2NR_aR_b$, $C_1$–$C_3$ alkylthio, $C_1$–$C_3$ alkylsulfinyl, $C_1$–$C_3$ alkylsulfonyl, CN, SCN, $CO_2R_c$, $C_1$–$C_3$ haloalkoxy, $C_1$–$C_3$ haloalkylthio, amino, $C_1$–$C_3$ alkylamino, di($C_1$–$C_3$ alkyl)amino or $C_1$–$C_2$ alkyl substituted with $C_1$–$C_2$ alkoxy, $C_1$–$C_2$ haloalkoxy, $C_1$–$C_2$ alkylthio, $C_1$–$C_2$ haloalkylthio or CN;

$R_2$ is H, $C_1$–$C_3$ alkyl, allyl or phenyl;

$R_3$ is H, $C_1$–$C_6$ alkyl, $C_3$–$C_6$ cycloalkyl, $C_1$–$C_6$ haloalkyl, $CH_2$-($C_2$–$C_5$ alkenyl), $CH_2$($C_2$–$C_5$ haloalkenyl), $CH_2$($C_2$–$C_5$ alkynyl), $CH_2$($C_2$–$C_5$ haloalkynyl), $C_6H_5$ or $C_1$–$C_4$ alkyl substituted with $C_1$–$C_2$ alkoxy, $C_1$–$C_2$ alkylthio, $C_1$–$C_2$ alkylsulfinyl or $C_1$–$C_2$ alkylsulfonyl;

$R_4$ is H, halogen, $C_1$–$C_6$ alkyl, $C_3$–$C_6$ cycloalkyl, $C_1$–$C_6$ haloalkyl, $C_2$–$C_6$ alkenyl, $C_2$–$C_6$ haloalkenyl, $C_2$–$C_6$ alkynyl, $C_3$–$C_6$ haloalkynyl, $C_6H_5$, $C_1$–$C_4$ haloalkoxy, $C_1$–$C_4$ alkylthio, $C_1$–$C_4$ alkylsulfinyl, $C_1$–$C_4$ alkylsulfonyl, $OCH_2CH_2O$-($C_1$–$C_2$ alkyl) or di($C_1$–$C_3$ alkyl)amino;

$R_5$ is H, $C_1$–$C_3$ alkyl, $C_1$–$C_3$ haloalkyl, allyl or propargyl;

$R_a$ is H, $C_1$–$C_4$ alkyl, $C_2$–$C_3$ cyanoalkyl, methoxy or ethoxy;

$R_b$ is H, $C_1$–$C_4$ alkyl or $C_3$–$C_4$ alkenyl; or $R_a$ and $R_b$ may be taken together as $-(CH_2)_3-$, $-(CH_2)_4-$, $-(CH_2)_5-$ or $-CH_2CH_2OCH_2CH_2-$;

$R_c$ is $C_1$–$C_4$ alkyl, $C_3$–$C_4$ alkenyl, $C_3$–$C_4$ alkynyl, $C_2$–$C_4$ haloalkyl, $C_1$–$C_2$ cyanoalkyl, $C_5$–$C_6$ cycloalkyl, $C_4$–$C_7$ cycloalkylalkyl or $C_2$–$C_4$ alkoxyalkyl;

A is 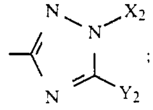;

A-5

$X_2$ is $CH_3$, $C_2H_5$ or $CH_2CF_3$; and $Y_2$ is $OCH_3$, $OC_2H_5$, $SCH_3$, $SC_2H_5$, $CH_3$ or $CH_2CH_3$; and their agriculturally suitable salts; provided that (a) when J is J-9 and n is 0, then Q is Q-1 or Q-2;

(b) when E is 0, then J is J-1;
(c) when J is J-1 and m is 0, then n is 0; and
(d) when n is 0 and m is 1, then Q is Q-1 or Q-2.

2. A compound of claim 1 where E is a single bond.

3. A compound of claim 1 where E is $CH_2$.

4. A compound of claim 1 where E is O.

5. A compound of claim 2 where m is O; and W is O.

6. A compound of claim 5 where $R_1$ i H, $CH_3$, F, Cl, Br, $OCH_3$, $SCH_3$, $CH_2CN$, $CH_2OCH_3$, $CF_3$ or $OCF_2H$; and n is O.

7. A compound of claim 6 where $R_3$ is H, $C_1$-$C_3$ alkyl, $C_1$-$C_2$ alkyl substituted with $C_1$-$C_2$ alkoxy, $CH_2CH_2Cl$, $CH_2CH_2F$, $CH_2CHF_2$, $CH_2CF_3$, allyl or propargyl; and $R_4$ is H, $C_1$-$C_3$ alkyl, $C_1$-$C_2$ alkoxy, $C_1$-$C_2$ alkylthio, $N(CH_3)_2$, allyl, propargyl or $C_1$-$C_2$ alkyl substituted with 1-3 atoms of F, Cl or Br.

8. A compound of claim 7 where J is J-1.

9. C compound of claim 8 where Q is $Q_1$.

10. A compound of claim 8 where Q is $Q_2$.

11. A compound of claim 8 where Q is $Q_3$.

12. A compound of claim 8 where Q is $Q_4$.

13. A compound of claim 8 where Q is $Q_5$.

14. A compound of claim 8 where Q is $Q_6$.

15. A compound of claim 8 where Q is $Q_7$.

16. A compound of claim 7 where J is J-2.

17. A compound of claim 16 where Q is $Q_1$.

18. A compound of claim 7 where J is J-3.

19. A compound of claim 18 where Q is $Q_1$.

20. A compound of claim 7 where J is J-4.

21. A compound of claim 20 where Q is $Q_1$.

22. A compound of claim 7 where J is J-5.

23. A compound of claim 22 where Q is $Q_1$.

24. A compound of claim 7 where J is J-6.

25. A compound of claim 24 where Q is $Q_1$.

26. A compound of claim 7 where J is J-7.

27. A compound of claim 26 where Q is $Q_1$.

28. A compound of claim 7 where J is J-8.

29. A compound of claim 28 where Q is $Q_1$.

30. A compound of claim 28 where Q is $Q_2$.

31. A compound of claim 28 where Q is $Q_3$.

32. A compound of claim 28 where Q is $Q_4$.

33. A compound of claim 28 where Q is $Q_5$.

34. A compound of claim 28 where Q is $Q_6$.

35. A compound of claim 28 where Q is $Q_7$.

36. A compound of claim 7 where J is J-9.

37. A compound of claim 36 where Q is $Q_1$.

38. A compound of claim 7 where J is J-10.

39. A compound of claim 38 where Q is $Q_1$.

40. A compound of claim 7 where J is J-11.

41. A compound of claim 40 where Q is $Q_1$.

42. A compound of claim 7 where J is J-12.

43. A compound of claim 42 where Q is $Q_1$.

44. A compound of claim 7 where J is J-13.

45. A compound of claim 44 where Q is $Q_1$.

46. A compound of claim 3 where m is 0;

n is 0;

J is J-1, J-2, J-3, J-8, J-10 or J-11;

W is O;

R is H;

$R_1$ is H, $CH_3$, F, Cl, Br, $OCH_3$, $SCH_3$, $CH_2CN$, $CH_2OCH_3$, $CF_3$ or $OCF_2H$;

$R_3$ is H, $C_1$-$C_3$ alkyl, $CH_2CH_2OCH_3$, $CH_2CH_2Cl$, $CH_2CH_2F$, $CH_2CHF_2$, $CH_2CF_3$, allyl or propargyl; and $R_4$ is H or $C_1$-$C_3$ alkyl.

47. A compound of claim 4 where m is O;

R is H;

$R_1$ is H;

$R_3$ is H or $C_1$-$C_3$ alkyl; and $R_4$ is H or $C_1$-$C_3$ alkyl.

48. A composition suitable for controlling the growth of undesired vegetation which comprises an effective amount of a compound of claim 1 and at least one of the following: surfactant, solid or liquid diluent.

49. A composition suitable for controlling the growth of undesired vegetation which comprises an effective amount of a compound of claim 2 and at least one of the following: surfactant solid or liquid diluent.

50. A composition suitable for controlling the growth of undesired vegetation which comprises an effective amount of a compound of claim 3 and at least one of the following: surfactant, solid or liquid diluent.

51. A composition suitable for controlling the growth of undesired vegetation which comprises an effective amount of a compound of claim 4 and at least one of the following: surfactant, solid or liquid diluent.

52. A composition suitable for controlling the growth of undesired vegetation which comprises an effective amount of a compound of claim 5 and at least one of the following: surfactant, solid or liquid diluent.

53. A method for controlling the growth of undesired vegetation which comprises applying to the locus to be protected an effective amount of a compound of claim 1.

54. A method for controlling the growth of undesired vegetation which comprises applying to the locus to be protected an effective amount of a compound of claim 2.

55. A method for controlling the growth of undesired vegetation which comprises applying to the locus to be protected an effective amount of a compound of claim 3.

56. A method for controlling the growth of undesired vegetation which comprises applying to the locus to be protected an effective amount of a compound of claim 4.

57. A method for controlling the growth of undesired vegetation which comprises applying to the locus to be protected an effective amount of a compound of claim 5.

* * * * *

UNITED STATES PATENT AND TRADEMARK OFFICE
CERTIFICATE OF CORRECTION

PATENT NO. : 5,017,214

DATED : May 21, 1991

INVENTOR(S) : George Levitt

It is certified that error appears in the above-identified patent and that said Letters Patent is hereby corrected as shown below:

Claim 1, Column 187, Line 56, change "OH" to -- --OH,$C_1$-$C_3$ alkyl --

Claim 1, Column 188, Line 25, change "$R_1$ is H, $C_1$-$C_3$" to -- $R_1$ is H, $C_1$-$C_3$ alkyl, $C_1$-$C_3$--.

Claim 1, Column 188, Line 42, change "$C_6H_5$," to -- $C_6H_5$, $C_1$-$C_4$ alkoxy, --.

Signed and Sealed this

Eighth Day of December, 1992

*Attest:*

DOUGLAS B. COMER

*Attesting Officer*

*Acting Commissioner of Patents and Trademarks*